(12) United States Patent
Berthel et al.

(10) Patent No.: US 8,222,416 B2
(45) Date of Patent: Jul. 17, 2012

(54) AZAINDOLE GLUCOKINASE ACTIVATORS

(75) Inventors: Steven Joseph Berthel, Mendham Township, NJ (US); Li Chen, Shanghai (CN); Wendy Lea Corbett, Lebanon, NJ (US); Lichun Feng, Shanghai (CN); Nancy-Ellen Haynes, Cranford, NJ (US); Robert Francis Kester, West Orange, NJ (US); Sung-Sau So, Verona, NJ (US); Jefferson Wright Tilley, North Caldwell, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 12/943,539

(22) Filed: Nov. 10, 2010

(65) Prior Publication Data

US 2011/0144105 A1    Jun. 16, 2011

Related U.S. Application Data

(60) Provisional application No. 61/286,116, filed on Dec. 14, 2009.

(51) Int. Cl.
*C07D 471/02* (2006.01)
*A61K 31/545* (2006.01)

(52) U.S. Cl. ......................... 546/113; 514/200

(58) Field of Classification Search .................. 546/113; 514/200
See application file for complete search history.

(56) References Cited

U.S. PATENT DOCUMENTS

| | | | |
|---|---|---|---|
| 2005/0261272 A1* | 11/2005 | Bradley et al. ............ | 514/210.21 |
| 2006/0167053 A1 | 7/2006 | Ilno et al. | |
| 2006/0258701 A1 | 11/2006 | Mitsuya et al. | |
| 2007/0123535 A1 | 5/2007 | Greenhouse et al. | |

FOREIGN PATENT DOCUMENTS

| | | |
|---|---|---|
| EP | 1 600 442 | 11/2005 |
| WO | 00/58293 | 10/2000 |
| WO | 01/83465 | 11/2001 |
| WO | 01/85706 | 11/2001 |
| WO | 01/85707 | 11/2001 |
| WO | 02/46173 | 6/2002 |
| WO | 03/015774 | 2/2003 |
| WO | 03/095438 | 11/2003 |
| WO | 2004/050645 | 6/2004 |
| WO | 2004/052869 | 6/2004 |
| WO | 2004/072031 | 8/2004 |
| WO | 2004/072066 | 8/2004 |
| WO | 2004/076420 | 9/2004 |
| WO | 2004/081001 | 9/2004 |
| WO | 2005/080359 | 9/2005 |
| WO | 2005/080360 | 9/2005 |
| WO | 2005/090332 | 9/2005 |
| WO | 2005/095417 | 10/2005 |
| WO | 2005/095418 | 10/2005 |
| WO | 2005/103021 | 11/2005 |
| WO | 2005/121110 | 12/2005 |
| WO | 2006016178 | 2/2006 |
| WO | 2006016194 | 2/2006 |
| WO | 2006/040529 | 4/2006 |
| WO | 2006/058923 | 6/2006 |
| WO | 2006/125972 | 11/2006 |
| WO | 2007/007040 | 1/2007 |
| WO | 2007/007041 | 1/2007 |
| WO | 2007/007042 | 1/2007 |
| WO | 2007/007886 | 1/2007 |
| WO | 2007/017649 | 2/2007 |
| WO | 2007/026761 | 3/2007 |
| WO | 2007/031739 | 3/2007 |
| WO | 2007/041365 | 4/2007 |
| WO | 2007/051845 | 5/2007 |
| WO | 2007/051846 | 5/2007 |
| WO | 2007/051847 | 5/2007 |
| WO | 2007/104034 | 9/2007 |
| WO | 2007/122482 | 11/2007 |
| WO | 2008/136428 | 11/2008 |
| WO | 2007/041366 | 2/2011 |

OTHER PUBLICATIONS

International Search Report for PCT/EP2010/069455 dated Mar. 15, 2011.

* cited by examiner

*Primary Examiner* — Robert Havlin

(74) *Attorney, Agent, or Firm* — George W. Johnston; Dennis P. Tramaloni; Samuel H. Megerditchian

(57) ABSTRACT

Provided herein are compounds of the formula (I):

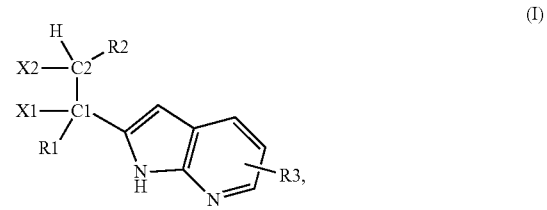

as well as pharmaceutically acceptable salts thereof, wherein the substituents are as those disclosed in the specification. These compounds, and the pharmaceutical compositions containing them, are useful for the treatment of metabolic diseases and disorders such as, for example, type II diabetes mellitus.

30 Claims, No Drawings

AZAINDOLE GLUCOKINASE ACTIVATORS

PRIORITY TO RELATED APPLICATION(S)

This application claims the benefit of U.S. Provisional Application No. 61/286,116, filed Dec. 14, 2009, which is hereby incorporated by reference in its entirety.

FIELD OF THE INVENTION

The invention is directed to compounds, salts and pharmaceutical compositions useful as glucokinase activators for the treatment of metabolic diseases and disorders, preferably diabetes mellitus, more preferably type II diabetes mellitus.

All documents cited or relied upon below are expressly incorporated herein by reference.

BACKGROUND OF THE INVENTION

Glucokinase (GK) is one of four hexokinases that are found in mammals (Colowick, S. P., in *The Enzymes*, Vol. 9 (P. Boyer, ed). Academic Press, New York, N.Y., pages 1-48, 1973). The hexokinases catalyze the first step in the metabolism of glucose, i.e., the conversion of glucose to glucose-6-phosphate. Glucokinase has a limited cellular distribution, being found principally in pancreatic β-cells and liver parenchymal cells. In addition, GK is a rate-controlling enzyme for glucose metabolism in these two cell types that are known to play critical roles in whole-body glucose homeostasis (Chipkin, S. R., Kelly, K. L., and Ruderman, N. B. in *Joslin's Diabetes* (C. R. Khan and G. C. Wier, eds), Lea and Febiger, Philadelphia, Pa., pages 97-115, 1994). The concentration of glucose at which GK demonstrates half-maximal activity is approximately 8 mM. The other three hexokinases are saturated with glucose at much lower concentrations (<1 mM). Therefore, the flux of glucose through the GK pathway rises as the concentration of glucose in the blood increases from fasting (5 mM) to postprandial (≈10-15 mM) levels following a carbohydrate-containing meal (Printz, R. G., Magnuson, M. A., and Granner, D. K. in *Ann. Rev. Nutrition Vol.* 13 (R. E. Olson, D. M. Bier, and D. B. McCormick, eds), Annual Review, Inc., Palo Alto, Calif., pages 463-496, 1993). These findings contributed over a decade ago to the hypothesis that GK functions as a glucose sensor in β-cells and hepatocytes (Meglasson, M. D. and Matschinsky, F. M. *Amer. J. Physiol.* 246, E1-E13, 1984). In recent years, studies in transgenic animals have confirmed that GK does indeed play a critical role in whole-body glucose homeostasis. Animals that do not express GK die within days of birth with severe diabetes while animals overexpressing GK have improved glucose tolerance (Grupe, A., Hultgren, B., Ryan, A. et al., *Cell* 83, 69-78, 1995; Ferrie, T., Riu, E., Bosch, F. et al., *FASEB J.*, 10, 1213-1218, 1996). An increase in glucose exposure is coupled through GK in β-cells to increased insulin secretion and in hepatocytes to increased glycogen deposition and perhaps decreased glucose production.

The finding that type II maturity-onset diabetes of the young (MODY-2) is caused by loss of function mutations in the GK gene suggests that GK also functions as a glucose sensor in humans (Liang, Y., Kesavan, P., Wang, L. et al., *Biochem. J.* 309, 167-173, 1995). Additional evidence supporting an important role for GK in the regulation of glucose metabolism in humans was provided by the identification of patients that express a mutant form of GK with increased enzymatic activity. These patients exhibit a fasting hypoglycemia associated with an inappropriately elevated level of plasma insulin (Glaser, B., Kesavan, P., Heyman, M. et al., *New England J. Med.* 338, 226-230, 1998). While mutations of the GK gene are not found in the majority of patients with type II diabetes, compounds that activate GK and, thereby, increase the sensitivity of the GK sensor system will still be useful in the treatment of the hyperglycemia characteristic of all type II diabetes. Glucokinase activators will increase the flux of glucose metabolism in β-cells and hepatocytes, which will be coupled to increased insulin secretion. Such agents would be useful for treating type II diabetes.

SUMMARY OF THE INVENTION

The present invention is directed to compounds of the formula I:

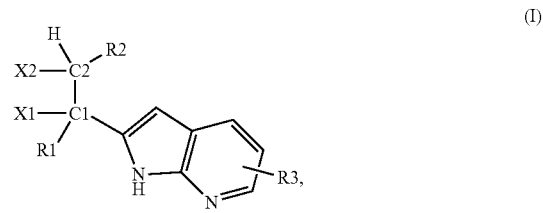

as well as pharmaceutically acceptable salts thereof, pharmaceutical compositions containing them and to methods of treating diseases and disorders. The compounds and compositions disclosed herein are glucokinase activators useful for the treatment of metabolic diseases and disorders, preferably diabetes mellitus, more preferably type II diabetes mellitus.

DETAILED DESCRIPTION OF THE INVENTION

In an embodiment of the present invention, provided are compound of formula (I):

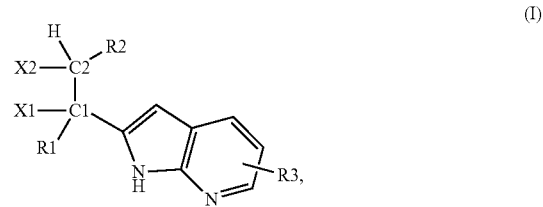

wherein:
R1 is -phenyl, unsubstituted or mono- or bi-substituted independently with halogen, -cyano, -lower alkyl, -alkoxy, —SO$_2$CH$_3$, —CF$_3$, —C(CH$_3$)$_2$OH, —CH(CH$_3$)OH, —C(CH$_3$)(C(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole or —SO$_2$(CH$_2$)$_2$-morpholine,
-heteroaryl, unsubstituted or substituted with lower alkyl, alkoxy or —SO$_2$CH$_3$, or
-2,3-dihydrobenzo[1,4]dioxin-6-yl;
R2 is -lower alkyl,
-heterocycloalkyl, or
-cycloalkyl, unsubstituted or substituted with (═O);
R3 is -hydrogen,
-halogen,
-an acyl group,
-cyano, -lower alkyl, unsubstituted or mono-, bi- or tri-substituted independently with hydroxy, alkoxy, halogen, lower alkyl, cyano, (=O), or —N(CH$_3$)$_2$,
—OCH$_3$,
—OCH$_2$C(O)N(CH$_3$)$_2$,
—O(CH$_2$)$_2$OCH$_3$,
—O(CH$_2$)$_2$N(CH$_3$)$_2$,
—OCH(CH$_3$)$_2$,
—OC(CH$_3$)$_2$CH$_2$OH,
—OCH$_2$CH$_2$OH,
—OC(CH$_3$)$_2$C(O)OCH$_2$CH$_3$,
—OC(CH$_3$)$_2$C(O)OH,
—CH$_2$OC(O)CH$_2$N(CH$_3$)$_2$,
—NHC(O)CH$_2$N(CH$_3$)$_2$, or
—SO$_2$-lower alkyl;
the bond between C$_1$ and C$_2$ is a single or double bond;
X1 is -hydrogen,
-hydroxy,
-alkoxy, or
-absent if the bond between C$_1$ and C$_2$ is a double bond; and
X2 is -hydrogen, or
-absent if the bond between C$_1$ and C$_2$ is a double bond,
or a pharmaceutically acceptable salt thereof.

In another embodiment of the present invention, provided is a compound according to formula (I), wherein:
R1 is -phenyl, unsubstituted or mono- or bi-substituted independently with halogen, -cyano, -lower alkyl, -alkoxy, —SO$_2$CH$_3$, —CF$_3$, —C(CH$_3$)$_2$OH, —CH(CH$_3$)OH, —C(CH$_3$)(C(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole or —SO$_2$(CH$_2$)$_2$-morpholine;
R2 is -lower alkyl;
R3 is -hydrogen,
-halogen,
-an acyl group,
-cyano, or
-lower alkyl, unsubstituted or mono-, bi- or tri-substituted independently with hydroxy, alkoxy, halogen, lower alkyl, cyano, (=O), or —N(CH$_3$)$_2$;
the bond between C$_1$ and C$_2$ is a single bond;
X1 is -hydrogen,
-hydroxy, or
-alkoxy; and
X2 is -hydrogen.

In another embodiment of the present invention, provided is a compound according to formula (I), wherein:
R1 is -phenyl, unsubstituted or mono- or bi-substituted independently with halogen, -cyano, -lower alkyl, -alkoxy, —SO$_2$CH$_3$, —CF$_3$, —C(CH$_3$)$_2$OH, —CH(CH$_3$)OH, —C(CH$_3$)(C(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole or —SO$_2$(CH$_2$)$_2$-morpholine;
R2 is -lower alkyl;
R3 is —OCH$_3$,
—OCH$_2$C(O)N(CH$_3$)$_2$,
—O(CH$_2$)$_2$OCH$_3$,
—O(CH$_2$)$_2$N(CH$_3$)$_2$,
—OCH(CH$_3$)$_2$,
—OC(CH$_3$)$_2$CH$_2$OH,
—OCH$_2$CH$_2$OH,
—OC(CH$_3$)$_2$C(O)OCH$_2$CH$_3$,
—OC(CH$_3$)$_2$C(O)OH,
—CH$_2$OC(O)CH$_2$N(CH$_3$)$_2$,
—NHC(O)CH$_2$N(CH$_3$)$_2$, or
—SO$_2$-lower alkyl;
the bond between C$_1$ and C$_2$ is a single bond;
X1 is -hydrogen,
-hydroxy, or
-alkoxy; and
X2 is -hydrogen.

In another embodiment of the present invention, provided is a compound according to formula (I), wherein:
R1 is -phenyl, unsubstituted or mono- or bi-substituted independently with halogen, -cyano, -lower alkyl, -alkoxy, —SO$_2$CH$_3$, —CF$_3$, —C(CH$_3$)$_2$OH, —CH(CH$_3$)OH, —C(CH$_3$)(C(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole or —SO$_2$(CH$_2$)$_2$-morpholine;
R2 is -heterocycloalkyl, or
-cycloalkyl, unsubstituted or substituted with (=O);
R3 is -hydrogen,
-halogen,
-an acyl group,
-cyano, or
-lower alkyl, unsubstituted or mono-, bi- or tri-substituted independently with hydroxy, alkoxy, halogen, lower alkyl, cyano, (=O), or —N(CH$_3$)$_2$;
the bond between C$_1$ and C$_2$ is a single bond;
X1 is -hydrogen,
-hydroxy, or
-alkoxy; and
X2 is -hydrogen.

In another embodiment of the present invention, provided is a compound according to formula (I), wherein:
R1 is -phenyl, unsubstituted or mono- or bi-substituted independently with halogen, -cyano, -lower alkyl, -alkoxy, —SO$_2$CH$_3$, —CF$_3$, —C(CH$_3$)$_2$OH, —CH(CH$_3$)OH, —C(CH$_3$)(C(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole or —SO$_2$(CH$_2$)$_2$-morpholine;
R2 is -heterocycloalkyl, or
-cycloalkyl, unsubstituted or substituted with (=O);
R3 is —OCH$_3$,
—OCH$_2$C(O)N(CH$_3$)$_2$,
—O(CH$_2$)$_2$OCH$_3$,
—O(CH$_2$)$_2$N(CH$_3$)$_2$,
—OCH(CH$_3$)$_2$,
—OC(CH$_3$)$_2$CH$_2$OH,
—OCH$_2$CH$_2$OH,
—OC(CH$_3$)$_2$C(O)OCH$_2$CH$_3$,
—OC(CH$_3$)$_2$C(O)OH,
—CH$_2$OC(O)CH$_2$N(CH$_3$)$_2$,
—NHC(O)CH$_2$N(CH$_3$)$_2$, or
—SO$_2$-lower alkyl;
the bond between C$_1$ and C$_2$ is a single bond;
X1 is -hydrogen,
-hydroxy, or
-alkoxy; and
X2 is -hydrogen.

In another embodiment of the present invention, provided is a compound according to formula (I), wherein:
R1 is -heteroaryl, unsubstituted or substituted with lower alkyl, alkoxy or —SO$_2$CH$_3$;
R2 is -lower alkyl;
R3 is -hydrogen,
-halogen,
-an acyl group,
-cyano, or -lower alkyl, unsubstituted or mono-, bi- or tri-substituted independently with hydroxy, alkoxy, halogen, lower alkyl, cyano, (=O), or —N(CH₃)₂;
the bond between $C_1$ and $C_2$ is a single bond;
X1 is -hydrogen,
  -hydroxy, or
  -alkoxy; and
X2 is -hydrogen.

In another embodiment of the present invention, provided is a compound according to formula (I), wherein:
R1 is -heteroaryl, unsubstituted or substituted with lower alkyl, alkoxy or —SO₂CH₃;
R2 is -lower alkyl;
R3 is —OCH₃,
  —OCH₂C(O)N(CH₃)₂,
  —O(CH₂)₂OCH₃,
  —O(CH₂)₂N(CH₃)₂,
  —OCH(CH₃)₂,
  —OC(CH₃)₂CH₂OH,
  —OCH₂CH₂OH,
  —OC(CH₃)₂C(O)OCH₂CH₃,
  —OC(CH₃)₂C(O)OH,
  —CH₂OC(O)CH₂N(CH₃)₂,
  —NHC(O)CH₂N(CH₃)₂, or
  —SO₂-lower alkyl;
the bond between $C_1$ and $C_2$ is a single bond;
X1 is -hydrogen,
  -hydroxy, or
  -alkoxy; and
X2 is -hydrogen.

In another embodiment of the present invention, provided is a compound according to formula (I), wherein:
R1 is -heteroaryl, unsubstituted or substituted with lower alkyl, alkoxy or —SO₂CH₃, or
  -2,3-dihydrobenzo[1,4]dioxin-6-yl;
R2 is -heterocycloalkyl, or
  -cycloalkyl, unsubstituted or substituted with (=O);
R3 is -hydrogen,
  -halogen,
  -an acyl group,
  -cyano, or
  -lower alkyl, unsubstituted or mono-, bi- or tri-substituted independently with hydroxy, alkoxy, halogen, lower alkyl, cyano, (=O), or —N(CH₃)₂;
the bond between $C_1$ and $C_2$ is a single bond;
X1 is -hydrogen,
  -hydroxy,
  -alkoxy; and
X2 is -hydrogen.

In another embodiment of the present invention, provided is a compound according to formula (I), wherein:
R1 is -heteroaryl, unsubstituted or substituted with lower alkyl, alkoxy or —SO₂CH₃, or
  -2,3-dihydrobenzo[1,4]dioxin-6-yl;
R2 is -heterocycloalkyl, or
  -cycloalkyl, unsubstituted or substituted with (=O);
R3 is —OCH₃,
  —OCH₂C(O)N(CH₃)₂,
  —O(CH₂)₂OCH₃,
  —O(CH₂)₂N(CH₃)₂,
  —OCH(CH₃)₂,
  —OC(CH₃)₂CH₂OH,
  —OCH₂CH₂OH,
  —OC(CH₃)₂C(O)OCH₂CH₃,
  —OC(CH₃)₂C(O)OH,
  —CH₂OC(O)CH₂N(CH₃)₂,
  —NHC(O)CH₂N(CH₃)₂, or
  —SO₂-lower alkyl;
the bond between $C_1$ and $C_2$ is a single bond;
X1 is -hydrogen,
  -hydroxy,
  -alkoxy; and
X2 is -hydrogen.

In another embodiment of the present invention, provided is a compound according to formula (I), wherein R1 is phenyl, unsubstituted or mono- or bi-substituted independently with halogen, -cyano, -lower alkyl, -alkoxy, —SO₂CH₃, —CF₃, —C(CH₃)₂OH, —CH(CH₃)OH, —C(CH₃)(C(CH₃)₂)OH, —SO₂(CH₂)₂OH, —NH(SO₂CH₃), —C(O)CH₃, —C(CH₂CH₃)₂OH, —N(CH₃)₂, —SO₂CH(CH₃)₂, —SO₂(CH₂)₂OCH₂CH₃, —SO₂(CH₂)₂N(CH₃)₂, pyrazole or —SO₂(CH₂)₂-morpholine.

In another embodiment of the present invention, provided is a compound according to formula (I), wherein R1 is heteroaryl, unsubstituted or substituted with lower alkyl, alkoxy or —SO₂CH₃, or -2,3-dihydrobenzo[1,4]dioxin-6-yl.

In another embodiment of the present invention, provided is a compound according to formula (I), wherein R1 is 4-methanesulfonyl-3-trifluoromethyl-phenyl, 3-fluoro-4-(1-hydroxy-1-methyl-ethyl)-phenyl, 4-(1-hydroxy-1,2-dimethyl-propyl)-phenyl, 4-(1-ethyl-1-hydroxy-propyl)-phenyl, 4-(propane-2-sulfonyl)-phenyl, 4-(2-dimethylamino-ethanesulfonyl)-phenyl, 4-(2-morpholin-4-yl-ethanesulfonyl)-phenyl, 4-(2-hydroxy-ethanesulfonyl)-phenyl, 4-(2-ethoxy-ethanesulfonyl)-phenyl, 2-fluoro-4-(1-hydroxy-1-methyl-ethyl)-phenyl, 4-methanesulfonylamino-phenyl, 3-pyrazol-1-yl-phenyl, 2,3-dihydro-benzo[1,4]dioxin-6-yl, 3,4-dichloro-phenyl, 3,5-dimethyl-phenyl, 3-acetyl-phenyl, 3-chloro-phenyl, 3-dimethylamino-phenyl, 3-ethoxy-phenyl, 3-fluoro-phenyl, 3-methoxy-phenyl, 4-(1-hydroxy-1-methyl-ethyl)-phenyl, 4-(1-hydroxy-ethyl)-phenyl, 4-acetyl-phenyl, 4-cyano-phenyl, 4-dimethylamino-phenyl, 4-isopropyl-phenyl, 4-methanesulfonyl-phenyl, 4-trifluoromethyl-phenyl, 5-methanesulfonyl-pyridin-2-yl, 6-ethoxy-pyridin-3-yl, 6-methanesulfonyl-pyridin-3-yl, 6-methoxy-pyridin-3-yl, 6-methyl-pyridin-3-yl, m-tolyl or pyridin-3-yl.

In another embodiment of the present invention, provided is a compound according to formula (I), wherein R2 is lower alkyl.

In another embodiment of the present invention, provided is a compound according to formula (I), wherein R2 is heterocycloalkyl, or cycloalkyl, unsubstituted or substituted with (=O).

In another embodiment of the present invention, provided is a compound according to formula (I), wherein R2 is cyclobutyl, cyclohexyl, cyclopentyl, isopropyl, tert-butyl, tetrahydro-furan-2-yl, tetrahydro-pyran-4-yl, tetrahydro-pyran-2-yl or 3-oxo-cyclopentyl.

In another embodiment of the present invention, provided is a compound according to formula (I), wherein R3 is hydrogen, halogen, an acyl group, cyano, or lower alkyl, unsubstituted or mono-, bi- or tri-substituted independently with hydroxy, alkoxy, halogen, lower alkyl, cyano, (=O), or —N(CH₃)₂.

In another embodiment of the present invention, provided is a compound according to formula (I), wherein R3 is hydrogen, 2-hydroxyethyl-carbamoyl, 1,2-dihydroxy-ethyl, methoxycarbonyl, 1-carboxy-1-methyl-ethoxy, 1-ethoxycarbonyl-1-methyl-ethoxy, 1-hydroxy-ethyl, 2,3-dihydroxy-propyl, 2-dimethylamino-acetoxymethyl, 2-dimethylamino-acetoxyamino, 2-dimethylamino-ethoxy, 2-dimethylamino-ethyl, 2-hydroxy-1,1-dimethyl-ethoxy, 2-hydroxy-ethoxy, 2-hydroxy-ethyl, 2-methoxy-ethoxy, 3-hydroxy-propyl, 3-methoxy-propyl, carboxy, chloro, cyano, cyanomethyl, dimethylcarbamoylmethoxy, dimethylcarbamoylmethyl, ethanesulfonyl, fluoro, hydroxymethyl, isopropoxy, isopropylcarbamoyl, methoxy, methoxymethyl, methyl, methylcarbamoyl, morpholine-4-carbonyl or trifluoromethyl.

In another embodiment of the present invention, provided is a compound according to formula (I), wherein the bond between $C_1$ and $C_2$ is a single bond.

In another embodiment of the present invention, provided is a compound according to formula (I), wherein the bond between $C_1$ and $C_2$ is a double bond.

In another embodiment of the present invention, provided is a compound according to formula (I), wherein X1 is hydrogen, hydroxy or alkoxy.

In another embodiment of the present invention, provided is a compound according to formula (I), wherein X2 is hydrogen.

Preferably, provided is a compound according to formula (I), wherein said compound is:

2-[1-(4-Methanesulfonyl-phenyl)-3-methyl-butyl]-1H-pyrrolo[2,3-b]pyridin-5-carboxylic acid isopropylamide,
2-[1-(4-M ethanesulfonyl-phenyl)-3-methyl-butyl]-1H-pyrrolo[2,3-b]pyridin-5-carboxylic acid methylamide,
2-[2-Cyclopentyl-1-(4-methanesulfonyl-phenyl)-ethyl]-1H-pyrrolo[2,3-b]pyridin-5-carboxylic acid isopropylamide,
{2-[2-Cyclopentyl-1-(4-methanesulfonyl-phenyl)-ethyl]-1H-pyrrolo[2,3-b]pyridin-5-yl}-morpholin-4-yl-methanone,
2-[2-Cyclopentyl-1-(4-methanesulfonyl-phenyl)-ethyl]-1H-pyrrolo[2,3-b]pyridin-5-carboxylic acid methylamide,
2-[2-Cyclopentyl-1(R)-(4-methanesulfonyl-phenyl)-ethyl]-1H-pyrrolo[2,3-b]pyridin-5-carboxylic acid methylamide,
1-{2-[2-Cyclopentyl-1-(4-methanesulfonyl-phenyl)-ethyl]-1H-pyrrolo[2,3-b]pyridin-5-yl}-ethane-1,2-diol,
{2-[2-Cyclopentyl-1-(4-methanesulfonyl-phenyl)-ethyl]-1H-pyrrolo[2,3-b]pyridin-5-yl}-methanol,
1-{2-[2-Cyclopentyl-1-(4-methanesulfonyl-phenyl)-ethyl]-1H-pyrrolo[2,3-b]pyridin-5-yl}-ethanol,
2-[2-Cyclohexyl-1(R)-(4-methanesulfonyl-phenyl)-ethyl]-5-methoxy-1H-pyrrolo[2,3-b]pyridine,
3-{2-[2-Cyclopentyl-1-(4-methanesulfonyl-phenyl)-ethyl]-1H-pyrrolo[2,3-b]pyridin-5-yl}-propane-1,2-diol,
2-[2-Cyclopentyl-1-(4-methanesulfonyl-phenyl)-ethyl]-5-methoxy-1H-pyrrolo[2,3-b]pyridine,
2-{2-[2-Cyclopentyl-1-(4-methanesulfonyl-phenyl)-ethyl]-1H-pyrrolo[2,3-b]pyridin-5-yloxy}-N,N-dimethyl-acetamide,
2-{2-[2-Cyclopentyl-1(R)-(4-methanesulfonyl-phenyl)-ethyl]-1H-pyrrolo[2,3-b]pyridin-5-yloxy}-N,N-dimethyl-acetamide,
2-[2-Cyclopentyl-1-(4-methanesulfonyl-phenyl)-ethyl]-5-(2-methoxy-ethoxy)-1H-pyrrolo[2,3-b]pyridine,
2-[2-Cyclopentyl-1(R)-(4-methanesulfonyl-phenyl)-ethyl]-5-(2-methoxy-ethoxy)-1H-pyrrolo[2,3-b]pyridine,
(2-{2-[2-Cyclopentyl-1-(4-methanesulfonyl-phenyl)-ethyl]-1H-pyrrolo[2,3-b]pyridin-5-yloxy}-ethyl)-dimethyl-amine,
2-[2-Cyclopentyl-1-(4-methanesulfonyl-phenyl)-ethyl]-5-isopropoxy-1H-pyrrolo[2,3-b]pyridine,
2-[2-Cyclopentyl-1(R)-(4-methanesulfonyl-phenyl)-ethyl]-5-isopropoxy-1H-pyrrolo[2,3-b]pyridine,
2-[2-Cyclopentyl-1-(4-trifluoromethyl-phenyl)-ethyl]-5-methoxy-1H-pyrrolo[2,3b]pyridine,
2-[(E)-1-(4-Methanesulfonyl-phenyl)-2-(tetrahydro-furan-2-yl)-vinyl]-5-methoxy-1H-pyrrolo[2,3-b]pyridine,
2-[1-(4-Methanesulfonyl-phenyl)-2-(tetrahydro-furan-2-yl)-ethyl]-5-methoxy-1H-pyrrolo[2,3-b]pyridine,
2-[1-(4-Methanesulfonyl-phenyl)-2-(tetrahydro-furan-2-yl)-ethyl]-5-methoxy-1H-pyrrolo[2,3-b]pyridine,
2-[1-(4-Methanesulfonyl-phenyl)-2-(tetrahydro-furan-2-yl)-ethyl]-5-methoxy-1H-pyrrolo[2,3-b]pyridine,
2-[1-(4-Methanesulfonyl-phenyl)-2-(tetrahydro-furan-2-yl)-ethyl]-5-methoxy-1H-pyrrolo[2,3-b]pyridine, diastereomer 4,
2-{2-[2-Cyclopentyl-1-(4-methanesulfonyl-phenyl)-ethyl]-1H-pyrrolo[2,3-b]pyridin-5-yloxy}-2-methyl-propionic acid ethyl ester,
2-{2-[2-Cyclopentyl-1-(4-methanesulfonyl-phenyl)-ethyl]-1H-pyrrolo[2,3-b]pyridin-5-yloxy}-2-methyl-propionic acid,
2-{2-[2-Cyclopentyl-1-(4-methanesulfonyl-phenyl)-ethyl]-1H-pyrrolo[2,3-b]pyridin-5-yloxy}-2-methyl-propan-1-ol,
2-{2-[2-Cyclopentyl-1(R)-(4-methanesulfonyl-phenyl)-ethyl]-1H-pyrrolo[2,3-b]pyridin-5-yloxy}-2-methyl-propan-1-ol,
2-{2-[2-Cyclopentyl-1-(4-methanesulfonyl-phenyl)-ethyl]-1H-pyrrolo[2,3-b]pyridin-5-yloxy}-ethanol,
2-[1-(4-Methanesulfonyl-phenyl)-2-(tetrahydro-pyran-4-yl)-5-methoxy-1H-pyrrolo[2,3-b]pyridine,
2-[1(R)-(4-Methanesulfonyl-phenyl)-2-(tetrahydro-pyran-4-yl)-5-methoxy-1H-pyrrolo[2,3-b]pyridine,
5-Methoxy-2-[2-(tetrahydro-pyran-4-yl)-1-(4-trifluoromethyl-phenyl)-ethyl]-1H-pyrrolo[2,3-b]pyridine,
5-Methoxy-2-[2-(tetrahydro-pyran-4-yl)-1(R)-(4-trifluoromethyl-phenyl)-ethyl]-1H-pyrrolo[2,3-b]pyridine,
2-{4-[2-Cyclopentyl-1-(5-methoxy-1H-pyrrolo[2,3-b]pyridin-2-yl)-ethyl]-phenyl}-propan-2-ol,
2-{2-[2-Cyclopentyl-1-(4-methanesulfonyl-phenyl)-ethyl]-1H-pyrrolo[2,3-b]pyridin-5-yl}-ethanol,
Dimethylamino-acetic acid 2-[2-cyclopentyl-1-(4-methanesulfonyl-phenyl)-ethyl]-1H-pyrrolo[2,3-b]pyridin-5-ylmethyl-ester,
{2-[2-Cyclopentyl-1-(4-methanesulfonyl-phenyl)-ethyl]-1H-pyrrolo[2,3-b]pyridin-5-yl}-acetonitrile,
2-{2-[2-Cyclopentyl-1-(4-methanesulfonyl-phenyl)-ethyl]-1H-pyrrolo[2,3-b]pyridin-5-yl}-N,N-dimethyl-acetamide,
(2-{2-[2-Cyclopentyl-1-(4-methanesulfonyl-phenyl)-ethyl]-1H-pyrrolo[2,3-b]pyridin-5-yl}-ethyl)-dimethyl-amine,
2-[2-Cyclopentyl-1-(4-methanesulfonyl-phenyl)-ethyl]-5-methoxymethyl-1H-pyrrolo[2,3-b]pyridine,
2-[2-Cyclopentyl-1(R)-(4-methanesulfonyl-phenyl)-ethyl]-5-methoxymethyl-1H-pyrrolo[2,3-b]pyridine,
4-[2-Cyclopentyl-1-(1H-pyrrolo[2,3-b]pyridin-2-yl)-ethyl]-benzonitrile,
2-[2-Cyclopentyl-1-(4-methanesulfonyl-phenyl)-ethyl]-5-(3-methoxy-propyl)-1H-pyrrolo[2,3-b]pyridine,
3-{2-[2-Cyclopentyl-1-(4-methanesulfonyl-phenyl)-ethyl]-1H-pyrrolo[2,3-b]pyridin-5-yl}-propan-1-ol,
2-[(E)-2-Cyclobutyl-1-(4-methanesulfonyl-phenyl)-vinyl]-5-fluoro-1H-pyrrolo[2,3-b]pyridine,
2-[2-Cyclobutyl-1-(4-methanesulfonyl-phenyl)-ethyl]-5-fluoro-1H-pyrrolo[2,3-b]pyridine,
2-Cyclopentyl-1-(5-fluoro-1H-pyrrolo[2,3-b]pyridin-2-yl)-1-(4-methanesulfonyl-phenyl)-ethanol,
2-Cyclopentyl-1-(5-fluoro-1H-pyrrolo[2,3-b]pyridin-2-yl)-1-(4-methanesulfonyl-phenyl)-ethanol,
4-[2-Cyclopentyl-1-(5-fluoro-1H-pyrrolo[2,3-b]pyridin-2-yl)-ethyl]-benzonitrile,
4-[2-Cyclopentyl-1(R)-(5-fluoro-1H-pyrrolo[2,3-b]pyridin-2-yl)-ethyl]-benzonitrile, 2-[2-Cyclopentyl-1-(4-methanesulfonyl-phenyl)-ethyl]-1H-pyrrolo[2,3-b]pyridin-5-carbonitrile,
2-[2-Cyclopentyl-1(R)-(4-methanesulfonyl-phenyl)-ethyl]-1H-pyrrolo[2,3-b]pyridin-5-carbonitrile,
2-[2-Cyclopentyl-1-(4-methanesulfonyl-phenyl)-ethyl]-1H-pyrrolo[2,3-b]pyridin-5-carboxylic acid methyl Ester,
2-[2-Cyclopentyl-1(R)-(4-methanesulfonyl-phenyl)-ethyl]-1H-pyrrolo[2,3-b]pyridin-5-carboxylic acid methyl ester,
2-[2-Cyclopentyl-1(R)-(4-methanesulfonyl-phenyl)-ethyl]-1H-pyrrolo[2,3-b]pyridin-5-carboxylic acid,
2-{2-Cyclopentyl-1-[3-fluoro-4-(1-hydroxy-1-methyl-ethyl)-phenyl]-ethyl}-1H-pyrrolo[2,3-b]pyridin-5-carboxylic acid,
2-{2-Cyclopentyl-1(R)-[3-fluoro-4-(1-hydroxy-1-methyl-ethyl)-phenyl]-ethyl}-1H-pyrrolo[2,3-b]pyridin-5-carboxylic acid,
2-[2-Cyclopentyl-1-(6-methanesulfonyl-pyridin-3-yl)-ethyl]-1H-pyrrolo[2,3-b]pyridin-5-carboxylic acid(2-hydroxy-ethyl)-amide,
2-[1-(4-Methanesulfonyl-phenyl)-2-(tetrahydro-pyran-2-yl)-ethyl-]-1H-pyrrolo[2,3-b]pyridine,
2-[2-Cyclopentyl-1-(6-methoxy-pyridin-3-yl))-ethyl]-1H-pyrrolo[2,3-b]pyridine,
2-[2-Cyclopentyl-1-(2,3-dihydro-benzo[1,4]dioxin-6-yl)-ethyl]-1H-pyrrolo[2,3-b]pyridine,
2-[2-Cyclopentyl-1-(6-methyl-pyridin-3-yl))-ethyl]-1H-pyrrolo[2,3-b]pyridine,
1-{4-[2-Cyclopentyl-1-(1H-pyrrolo[2,3-b]pyridin-2-yl)-ethyl]-phenyl}-ethanol,
{4-[2-Cyclopentyl-1-(1H-pyrrolo[2,3-b]pyridin-2-yl)-ethyl]-phenyl}-dimethyl-amine,
2-[2-Cyclopentyl-1-(3.5-dimethyl-phenyl)-ethyl]-1H-pyrrolo[2,3-b]pyridine,
2-[1(R)-(4-Methanesulfonyl-phenyl)-2-(tetrahydro-pyran-4-yl)-ethyl]-1H-pyrrolo[2,3-b]pyridine,
2-[2-(Tetrahydro-pyran-4-yl)-1-(4-trifluoromethyl-phenyl)-ethyl]-1H-pyrrolo[2,3-b]pyridine,
2-[2-Cyclopentyl-1-[4-(propane-2-sulfonyl-phenyl)-ethyl]-1H-pyrrolo[2,3-b]pyridine,
(E)-2-[1-(4-Methanesulfonyl-phenyl)-2-(tetrahydro-furan-2-yl)-vinyl]-1H-pyrrolo[2,3-b]pyridine,
2-[1-(4-Methanesulfonyl-phenyl)-2-(tetrahydro-furan-2-yl)-ethyl]-1H-pyrrolo[2,3-b]pyridine,
2-Cyclobutyl-1-(4-methanesulfonyl-3-trifluoromethyl-phenyl)-1-(5-methoxy-1H-pyrrolo[2,3-b]pyridin-2-yl)-ethanol,
2-[(E)-1-(4-Methanesulfonyl-phenyl)-3,3-dimethyl-but-1-enyl]-1H-pyrrolo[2,3-b]pyridine,
2-[1-(4-Methanesulfonyl-phenyl)-3,3-dimethyl-butyl]-1H-pyrrolo[2,3-b]pyridine,
N-{4-[2-Cyclopentyl-1-(1H-pyrrolo[2,3-b]pyridin-2-yl)-ethyl]-phenyl}-methanesulfonamide,
2-Cyclobutyl-1-(4-methanesulfonyl-3-trifluoromethyl-phenyl)-1-(1H-pyrrolo[2,3-b]pyridin-2-yl)-ethanol,
2-[2-Cyclobutyl-1-(4-methanesulfonyl-3-trifluoromethyl-phenyl)-ethyl]-1H-pyrrolo[2,3-b]pyridine,
3-[2-(4-Methanesulfonyl-phenyl)-2-(1H-pyrrolo[2,3-b]pyridin-2-yl)-ethyl]-cyclopentanone,
3-[2-(4-Methanesulfonyl-phenyl)-2-(1H-pyrrolo[2,3-b]pyridin-2-yl)-ethyl]-cyclopentanone,
1-{4-[2-Cyclopentyl-1-(1H-pyrrolo[2,3-b]pyridin-2-yl)-ethyl]-phenyl}-ethanone,
2-{4-[2-Cyclopentyl-1-(1H-pyrrolo[2,3-b]pyridin-2-yl)-ethyl]-phenyl}-propan-2-ol,
2-{4-[2-Cyclopentyl-1(R)-(1H-pyrrolo[2,3-b]pyridin-2-yl)-ethyl]-phenyl}-propan-2-ol,
3-{4-[2-Cyclopentyl-1-(1H-pyrrolo[2,3-b]pyridin-2-yl)-ethyl]-phenyl}-pentan-3-ol,
3-{4-[2-Cyclopentyl-1(R)-(1H-pyrrolo[2,3-b]pyridin-2-yl)-ethyl]-phenyl}-pentan-3-ol,
2-{4-[2-Cyclopentyl-1-(1H-pyrrolo[2,3-b]pyridin-2-yl)-ethyl]-phenyl}-3-methyl-butan-2-ol,
2-Cyclopentyl-1-(4-methanesulfonyl-phenyl)-1-(1H-pyrrolo[2,3-b]pyridin-2-yl)-ethanol,
2-[2-Cyclopentyl-1-ethoxy-1-(4-methanesulfonyl-phenyl)-ethyl]-1H-pyrrolo[2,3-b]pyridine,
2-{4-[2-Cyclopentyl-1-(5-fluoro-1H-pyrrolo[2,3-b]pyridin-2-yl)-ethyl]-benzenesulfonyl}-ethanol,
(2-{4-[1-(5-Fluoro-1H-pyrrolo[2,3-b]pyridin-2-yl)-2-(tetrahydro-pyran-4-yl)-ethyl]-benzenesulfonyl}-ethanol,
2-{2-Cyclopentyl-1-[4-(2-ethoxy-ethanesulfonyl)-phenyl]-ethyl}-1H-pyrrolo[2,3-b]pyridine,
(2-{4-[2-Cyclopentyl-1-(1H-pyrrolo[2,3-b]pyridin-2-yl)-ethyl]-benzenesulfonyl}-ethanol,
(2-{4-[2-Cyclopentyl-1-(1H-pyrrolo[2,3-b]pyridin-2-yl)-ethyl]-benzenesulfonyl}-ethyl)-dimethyl-amine,
2-{2-Cyclopentyl-1-[4-(2-morpholin-4-yl-ethanesulfonyl)-phenyl]-ethyl}-1H-pyrrolo[2,3-b]pyridine,
2-{4-[2-Cyclopentyl-1-(1H-pyrrolo[2,3-b]pyridin-2-yl)-ethyl]-3-fluoro-phenyl}-propan-2-ol,
2-{4-[2-Cyclopentyl-1-(1H-pyrrolo[2,3-b]pyridin-2-yl)-ethyl]-2-fluoro-phenyl}-propan-2-ol,
2-{4-[2-Cyclopentyl-1(R)-(1H-pyrrolo[2,3-b]pyridin-2-yl)-ethyl]-2-fluoro-phenyl}-propan-2-ol,
2-{2-Fluoro-4-[1-(5-fluoro-1H-pyrrolo[2,3-b]pyridin-2-yl)-2-(tetrahydro-pyran-4-yl)-ethyl]-phenyl}-propan-2-ol,
2-{2-Fluoro-4-[1(R)-(5-fluoro-1H-pyrrolo[2,3-b]pyridin-2-yl)-2-(tetrahydro-pyran-4-yl)-ethyl]-phenyl}-propan-2-ol,
5-Fluoro-2-[1-(4-methanesulfonyl-phenyl)-3-methyl-butyl]-1H-pyrrolo[2,3-b]pyridine,
5-Fluoro-2-[1(R)-(4-methanesulfonyl-phenyl)-3-methyl-butyl]-1H-pyrrolo[2,3-]pyridine,
(2-{4-[1-(5-Fluoro-(1H-pyrrolo[2,3-b]pyridin-2-yl)-3-methyl-butyl]-benzenesulfonyl}-ethanol,
(2-{4-[1(R)-(5-Fluoro-(1H-pyrrolo[2,3-b]pyridin-2-yl)-3-methyl-butyl]-benzenesulfonyl}-ethanol,
2-{4-[2-Cyclopentyl-1-(5-fluoro-1H-pyrrolo[2,3-b]pyridin-2-yl)-ethyl]-2-fluoro-phenyl}-propan-2-ol,
2-{4-[2-Cyclopentyl-1(R)-(5-fluoro-1H-pyrrolo[2,3-b]pyridin-2-yl)-ethyl]-2-fluoro-phenyl}-propan-2-ol,
2-{2-Fluoro-4-[1-(5-fluoro-1H-pyrrolo[2,3-b]pyridin-2-yl)-3-methyl-butyl]-phenyl}-propan-2-ol,
2-{2-Fluoro-4-[1(R)-(5-fluoro-1H-pyrrolo[2,3-b]pyridin-2-yl)-3-methyl-butyl]-phenyl}-propan-2-ol,
N-{2-[2-Cyclopentyl-1-(4-methanesulfonyl-phenyl)-ethyl]-1H-pyrrolo[2,3-b]pyridin-5-yl}-2-dimethylamino-acetamide,
2-[2-Cyclopentyl-1-(6-ethoxy-pyridin-3-yl)-ethyl]-1H-pyrrolo[2,3-b]pyridine,
2-[2-Cyclopentyl-1-(6-methanesulfonyl-pyridin-3-yl)-ethyl]-1H-pyrrolo[2,3-b]pyridine,
2-(2-Cyclopentyl-1-pyridin-3-yl-ethyl)-1H-pyrrolo[2,3-b]pyridine,
5-Chloro-2-[2-cyclopentyl-1-(4-methanesulfonyl-phenyl)-ethyl]-1H-pyrrolo[2,3-b]pyridine,
2-[2-Cyclopentyl-1-(5-methanesulfonyl-pyridin-2-yl)-ethyl]-1H-pyrrolo[2,3-b]pyridine,
2-[2-Cyclopentyl-1-(4-methanesulfonyl-phenyl)-ethyl]-6-methoxy-1H-pyrrolo[2,3-b]pyridine,
5-Chloro-2-[1-(4-methanesulfonyl-phenyl)-2-(tetrahydro-pyran-4-yl)-ethyl]-1H-pyrrolo[2,3-b]pyridine, 2-Cyclobutyl-1-(4-methanesulfonyl-phenyl)-1-(1H-pyrrolo[2,3-b]pyridin-2-yl)-ethanol, 2-[(E)-2-cyclopentyl-1-(4-methanesulfonyl-phenyl)-vinyl]-5-fluoro-1H-pyrrolo[2,3-b]pyridine, 2-[2-Cyclopentyl-1-(4-methanesulfonyl-phenyl)-ethyl]-5-fluoro-1H-pyrrolo[2,3-b]pyridine, 2-[2-Cyclopentyl-1(R)-(4-methanesulfonyl-phenyl)-ethyl]-5-fluoro-1H-pyrrolo[2,3-b]pyridine, 2-{4-[2-Cyclopentyl-1-(5-fluoro-1H-pyrrolo[2,3-b]pyridin-2-yl)-ethyl]-phenyl}-propan-2-ol, 2-{4-[2-Cyclopentyl-1(R)-(5-fluoro-1H-pyrrolo[2,3-b]pyridin-2-yl)-ethyl]-phenyl}-propan-2-ol, 2-[2-Cyclopentyl-1-(4-isopropyl-phenyl)-ethyl]-5-fluoro-1H-pyrrolo[2,3-b]pyridine, 5-Fluoro-2-[(E)-1-(4-methanesulfonyl-phenyl)-2-(tetrahydro-pyran-4-yl)-vinyl]-1H-pyrrolo[2,3-b]pyridine, 5-Fluoro-2-[1-(4-methanesulfonyl-phenyl)-2-(tetrahydro-pyran-4-yl)-ethyl]-1H-pyrrolo[2,3-b]pyridine, 5-Fluoro-2-[1(R)-(4-methanesulfonyl-phenyl)-2-(tetrahydro-pyran-4-yl)-ethyl]-1H-pyrrolo[2,3-b]pyridine, 2-[2-Cyclopentyl-1-(4-methanesulfonyl-phenyl)-ethyl]-5-ethanesulfonyl-1H-pyrrolo[2,3-b]pyridine, 2-[2-Cyclopentyl-1-(4-methanesulfonyl-phenyl)-ethyl]-5-trifluoromethyl-1H-pyrrolo[2,3-b]pyridine, 2-[2-Cyclopentyl-1(R)-(4-methanesulfonyl-phenyl)-ethyl]-5-trifluoromethyl-1H-pyrrolo[2,3-b]pyridine, 2-[2-Cyclopentyl-1-(4-methanesulfonyl-phenyl)-ethyl]-5-methyl-1H-pyrrolo[2,3-b]pyridine, 2-{4-[2-Cyclopentyl-1(R)-(5-methyl-1H-pyrrolo[2,3-b]pyridin-2-yl)-ethyl]-2-fluoro-phenyl}-propan-2-ol, 2-(3-Methyl-1-m-tolyl-butyl)-1H-pyrrolo[2,3-b]pyridine, 2-(1-(3-Chloro-phenyl)-3-methyl-butyl)-1H-pyrrolo[2,3-b]pyridine, 2-(1-(3-Fluoro-phenyl)-3-methyl-butyl)-1H-pyrrolo[2,3-b]pyridine, 2-(1-(3-Ethoxy-phenyl)-3-methyl-butyl)-1H-pyrrolo[2,3-b]pyridine, 2-(1-(3-Methoxy-phenyl)-3-methyl-butyl)-1H-pyrrolo[2,3-b]pyridine, 1-{3-[3-Methyl-1-(1H-pyrrolo[2,3-b]pyridin-2-yl)-butyl]-phenyl}-ethanone, N,N-Dimethyl-3-(3-methyl-1-(1H-pyrrolo[2,3-b]pyridine-2-yl)butyl)benzenamine, 2-(1-(3-(1H-Pyrazol-1-yl)phenyl)-3-methylbutyl)-1H-pyrrolo[2,3-b]pyridine, 2-[2-Cyclopentyl-1-(4-methanesulfonyl-phenyl)-ethyl]-1H-pyrrolo[2,3-b]pyridine, or 2-[2-Cyclopentyl-1-(3,4-dichloro-phenyl)-ethyl]-1H-pyrrolo[2,3-b]pyridine.

In a still further embodiment of the present invention, provided is a pharmaceutical composition, comprising a therapeutically effective amount of a compound according to formula (I) or a pharmaceutically acceptable salt thereof and a pharmaceutically acceptable carrier.

It is to be understood that the terminology employed herein is for the purpose of describing particular embodiments, and is not intended to be limiting. Further, although any methods, devices and materials similar or equivalent to those described herein can be used in the practice or testing of the invention, the preferred methods, devices and materials are now described.

As used herein, the term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms.

As used herein, the term "acyl" means an optionally substituted alkyl, alkoxy, amino, cycloalkyl, heterocyclic, aryl or heteroaryl group bound via a carbonyl group and includes groups such as acetyl, —C(O)-lower alkyl, branched or unbranched, unsubstituted or substituted with alkoxy or cycloalkyl, —C(O)-cycloalkyl, —C(O)-heterocycloalkyl, unsubstituted or substituted with methyl, —C(O)-aryl, —C(O)-alkoxy, —C(O)—N-alkyl and —C(O)-heteroaryl, unsubstituted or substituted with methyl, and the like.

The term "cycloalkyl" refers to a monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, adamantyl, indanyl and the like. In a preferred embodiment, the "cycloalkyl" moieties can optionally be substituted with one, two, three or four substituents, with the understanding that said substituents are not, in turn, substituted further unless indicated otherwise in the Examples or claims below. An example of said substituent is (=O).

The term "heterocycloalkyl" denotes a mono- or polycyclic alkyl ring, wherein one, two or three of the carbon ring atoms is replaced by a heteroatom such as N, O or S. Examples of heterocycloalkyl groups include, but are not limited to, morpholinyl, thiomorpholinyl, piperazinyl, piperidinyl, pyrrolidinyl, tetrahydropyranyl, tetrahydrofuranyl, 1,3-dioxanyl and the like. The heterocycloalkyl groups may be unsubstituted or substituted and attachment may be through their carbon frame or through their heteroatom(s) where appropriate, with the understanding that said substituents are not, in turn, substituted further unless indicated otherwise in the Examples or claims below.

The term "lower alkyl", alone or in combination with other groups, refers to a branched or straight-chain alkyl radical of one to nine carbon atoms, preferably one to six carbon atoms, more preferably one to four carbon atoms. This term is further exemplified by radicals such as methyl, ethyl, n-propyl, isopropyl, n-butyl, s-butyl, isobutyl, t-butyl, n-pentyl, 3-methylbutyl, n-hexyl, 2-ethylbutyl and the like.

The term "aryl" refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthalene, 1,2-dihydronaphthalene, indanyl, 1H-indenyl and the like.

The alkyl, lower alkyl and aryl groups may be substituted or unsubstituted. When substituted, there will generally be, for example, 1 to 4 substituents present, with the understanding that said substituents are not, in turn, substituted further unless indicated otherwise in the Examples or claims below. These substituents may optionally form a ring with the alkyl, loweralkyl or aryl group with which they are connected. Substituents may include, for example, —N(CH$_3$)$_2$, halogen, -cyano, -lower alkyl, -alkoxy, —SO$_2$CH$_3$, —CF$_3$, —C(CH$_3$)$_2$OH, —CH(CH$_3$)OH, —C(CH$_3$)(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole and —SO$_2$(CH$_2$)$_2$-morpholine.

The term "heteroaryl," refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group.

The heteroaryl group described above may be substituted independently with one, two, or three substituents, with the understanding that said substituents are not, in turn, substituted further unless indicated otherwise in the Examples or claims below. These substituents may optionally form a ring with the heteroaryl group to which they are connected. Substituents may include, for example, lower alkyl, alkoxy and $SO_2CH_3$.

As used herein, the term "alkoxy" means alkyl-O—; and "alkoyl" means alkyl-CO—. Alkoxy substituent groups or alkoxy-containing substituent groups may be substituted by, for example, one or more alkyl groups, with the understanding that said substituents are not, in turn, substituted further unless indicated otherwise in the Examples or claims below.

As used herein, the term "halogen" means a fluorine, chlorine, bromine or iodine radical, preferably a fluorine, chlorine or bromine radical, and more preferably a fluorine or chlorine radical.

Compounds of formula (I) can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). The invention embraces all of these forms.

The preferred stereochemistry at carbon C1 is R unless R1 is a heterocycle attached to the carbon adjacent to a ring nitrogen thereby making the R1 group have a higher priority then the azaindole. In this case, the preferred stereochemistry at carbon C1 is "S."

The preferred stereochemistry for the double bond between C1 and C2 is E unless R1 is a heterocycle attached to the carbon adjacent to a ring nitrogen thereby making the R1 group have a higher priority then the azaindole. In this case the preferred stereochemistry for the double bond between C1 and C2 is Z.

As used herein, the term "pharmaceutically acceptable salt" means any pharmaceutically acceptable salt of the compound of formula (I). Salts may be prepared from pharmaceutically acceptable non-toxic acids and bases including inorganic and organic acids and bases. Such acids include, for example, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfuric, tartaric, oxalic, p-toluenesulfonic and the like. Particularly preferred are fumaric, hydrochloric, hydrobromic, phosphoric, succinic, sulfuric and methanesulfonic acids. Acceptable base salts include alkali metal (e.g. sodium, potassium), alkaline earth metal (e.g. calcium, magnesium) and aluminum salts.

In the practice of the method of the present invention, an effective amount of any one of the compounds of this invention or a combination of any of the compounds of this invention or a pharmaceutically acceptable salt thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form or solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

Useful pharmaceutical carriers for the preparation of the compositions hereof, can be solids, liquids or gases. Thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

The dose of a compound of the present invention depends on a number of factors, such as, for example, the manner of administration, the age and the body weight of the subject, and the condition of the subject to be treated, and ultimately will be decided by the attending physician or veterinarian. Such an amount of the active compound as determined by the attending physician or veterinarian is referred to herein, and in the claims, as a "therapeutically effective amount". For example, the dose of a compound of the present invention is typically in the range of about 1 to about 1000 mg per day. Preferably, the therapeutically effective amount is in an amount of from about 1 mg to about 500 mg per day.

It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

Compounds of the present invention can be prepared beginning with commercially available starting materials and utilizing general synthetic techniques and procedures known to those skilled in the art. Chemicals may be purchased from companies such as for example Aldrich, Argonaut Technologies, VWR and Lancaster. Chromatography supplies and equipment may be purchased from such companies as for example AnaLogix, Inc, Burlington, Wis.; Biotage AB, Charlottesville, Va.; Analytical Sales and Services, Inc., Pompton Plains, N.J.; Teledyne Isco, Lincoln, Nebr.; VWR International, Bridgeport, N.J.; Varian Inc., Palo Alto, Calif., and Multigram II Mettler Toledo Instrument Newark, Del. Biotage, ISCO and Analogix columns are pre-packed silica gel columns used in standard chromatography.

General Reaction Scheme
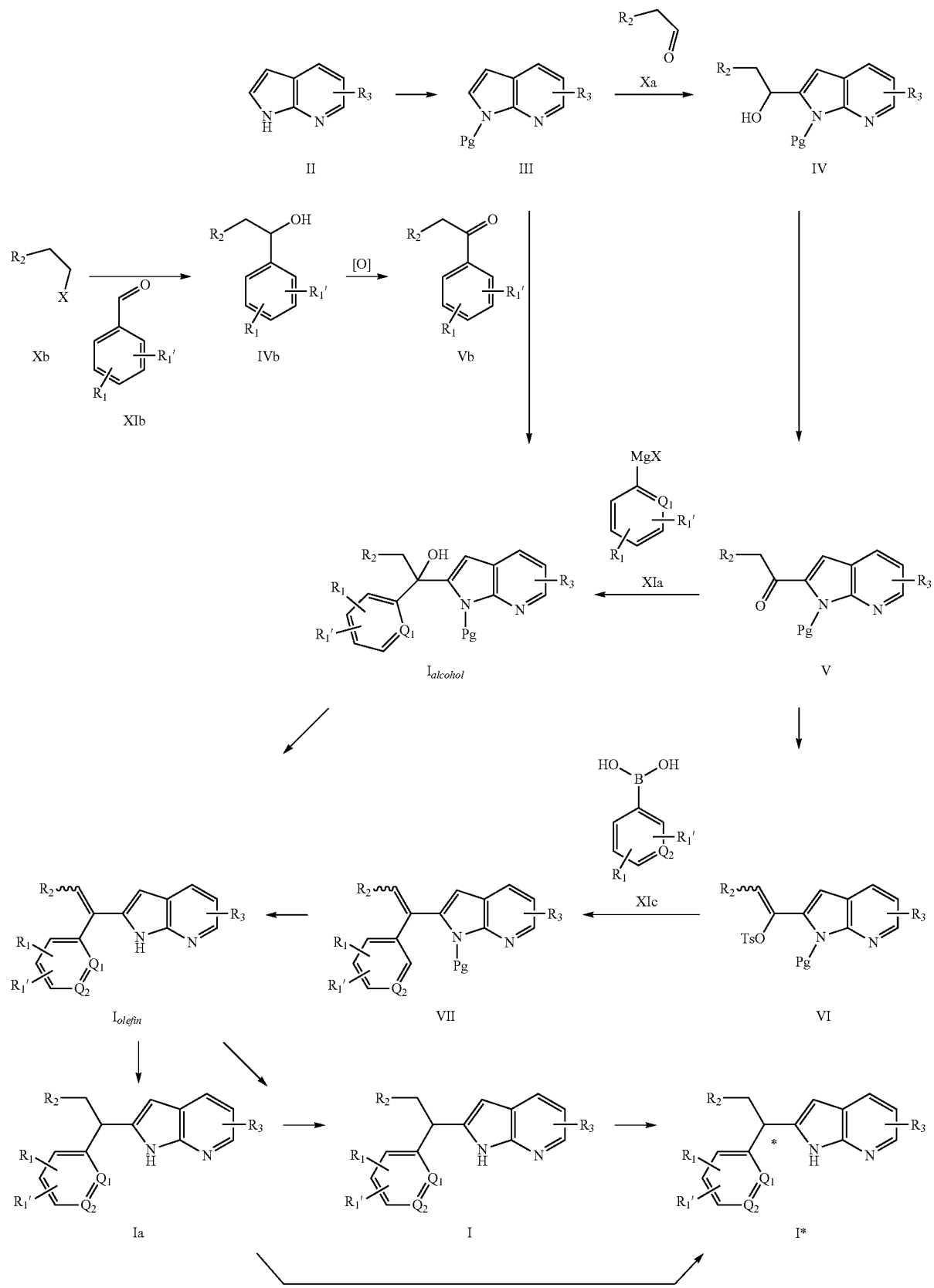

The majority of compounds of formula I can be prepared as outlined in the general reaction scheme.

Compounds of formula II, where $R_3$ is hydrogen, halo, lower alkyl, lower alkoxy, carboxy, carboalkoxy, cyano, perfluoroalkyl, mono or dialkylcarbamoyl, or heterocyclic carbamoyl, are commerically available or can be prepared using standard procedures.

Compounds of formula III, where $R_3$ is hydrogen, halo, lower alkyl, lower alkoxy, carboxy, carboalkoxy, cyano, perfluoroalkyl, mono or dialkylcarbamoyl, or heterocyclic carbamoyl, and Pg is a protecting group such as 2-trimethylsilylethyoxymethyl or phenylsulfonyl, can be prepared from the corresponding compounds of formula II where $R_3$ is hydrogen, halo, lower alkyl, lower alkoxy, carboxy, carboalkoxy, cyano, perfluoroalkyl, mono or dialkylcarbamoyl, or heterocyclic carbamoyl, using standard protecting group procedures (see for example, Greene, T. W. *Protective Groups in Organic Synthesis*; John Wiley & Sons, Inc.: New York, 1991).

Compounds of formula IV, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, and $R_2$ is alkyl, cycloalkyl or heterocyclic can be prepared by treatment of compounds of formula III where $R_3$ is hydrogen, halo, lower alkyl, lower alkoxy, carboxy, carboalkoxy, cyano, perfluoroalkyl, mono or dialkylcarbamoyl, or heterocyclic carbamoyl, and Pg is a protecting group such as 2-trimethylsilylethyoxymethyl or phenylsulfonyl with base, such as lithium diisopropylamide, followed by addition of compounds of formula Xa, where $R_2$ is alkyl, cycloalkyl or heterocyclic. Compounds of formula Xa are commerically available or readily prepared using standard procedures.

Compounds of formula V, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, and $R_2$ is alkyl, cycloalkyl or heterocyclic can be prepared from the corresponding compounds of formula IV where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, and $R_2$ is alkyl, cycloalkyl or heterocyclic by treating with an oxidizing agent such as Dess-Martin periodinate.

Compounds of formula VI, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, and $R_2$ is alkyl, cycloalkyl or heterocyclic can be prepared from the corresponding compounds of formula V where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, and $R_2$ is alkyl, cycloalkyl or heterocyclic by treatment with base such as n-butyl lithium, lithium diisopropylamide or lithium bis(trimethylsilyl)amide followed by p-toluenesulfonic anhydride.

Compounds of formula VII, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, $R_2$ is alkyl, cycloalkyl or heterocyclic, $Q_2$ is carbon or nitrogen, and $R_1$, $R_1'$ are hydrogen, alkyl, cyano, perfluoroalkyl, alkoxy, aryloxy, carboxy, carboalkoxy, alkylamino, or alkylsulfonyl, can be prepared by coupling the corresponding compounds of formula VI where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, and $R_2$ is alkyl, cycloalkyl or heterocyclic with boronic acids of formula XIc, where $R_1$, $R_1'$ are hydrogen, alkyl, cyano, perfluoroalkyl, alkoxy, aryloxy, carboxy, carboalkoxy, alkylamino, or alkylsulfonyl and $Q_2$ is carbon or nitrogen, under standard palladium catalyzed conditions. Boronic acids of formula XIc are commerically available or can be made using standard methods.

Compounds of formula $I_{olefin}$, where $R_3$ is hydrogen, halo, lower alkyl, lower alkoxy, carboxy, carboalkoxy, cyano, perfluoroalkyl, mono or dialkylcarbamoyl, or heterocyclic carbamoyl, $R_2$ is alkyl, cycloalkyl or heterocyclic, $Q_2$ is carbon or nitrogen, and $R_1$, $R_1'$ are hydrogen, alkyl, cyano, perfluoroalkyl, alkoxy, aryloxy, carboxy, carboalkoxy, alkylamino, or alkylsulfonyl, can be prepared by deprotecting the corresponding compounds of formula VII where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, $R_2$ is alkyl, cycloalkyl or heterocyclic, $Q_1$ and $Q_2$ are both carbon or $Q_1$ is carbon and $Q_2$ is nitrogen or $Q_1$ is nitrogen and $Q_2$ is carbon, and $R_1$, $R_1'$ are hydrogen, alkyl, cyano, perfluoroalkyl, alkoxy, aryloxy, carboxy, carboalkoxy, alkylamino, or alkylsulfonyl using standard condition such as aqueous base.

Compounds of formula IVb, where $R_2$ is alkyl, cycloalkyl or heterocyclic, and $R_1$, $R_1'$ are hydrogen, alkyl, cyano, perfluoroalkyl, alkoxy, aryloxy, carboxy, carboalkoxy, alkylamino, or alkylsulfonyl, can be prepared by treating the corresponding compounds of formula Xb, where $R_2$ is alkyl, cycloalkyl or heterocyclic and X is a halogen with base, such as butyl lithium, followed by treatment with aldehydes of formula XIb where $R_1$, $R_1'$ are hydrogen, alkyl, cyano, perfluoroalkyl, alkoxy, aryloxy, carboxy, carboalkoxy, alkylamino, or alkylsulfonyl. Compounds of formula Xb and compounds of formula XIb are commerically available or can be prepared using standard methods.

Compounds of formula Vb, where $R_2$ is alkyl, cycloalkyl or heterocyclic, and $R_1$, $R_1'$ are hydrogen, alkyl, cyano, perfluoroalkyl, alkoxy, aryloxy, carboxy, carboalkoxy, alkylamino, or alkylsulfonyl, can be prepared by treating the corresponding compounds of formula IVb where $R_2$ is alkyl, cycloalkyl or heterocyclic, and $R_1$, $R_1'$ are hydrogen, alkyl, cyano, perfluoroalkyl, alkoxy, aryloxy, carboxy, carboalkoxy, alkylamino, or alkylsulfonyl with an oxidizing agent such as pyridinium chlorochromate using standard methods.

Compounds of formula $I_{alcohol}$, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, $R_2$ is alkyl, cycloalkyl or heterocyclic, $Q_1$ is carbon and $R_1$, $R_1'$ are hydrogen, alkyl, cyano, perfluoroalkyl, alkoxy, aryloxy, carboxy, carboalkoxy, alkylamino, or alkylsulfonyl, can be prepared by treating the corresponding compounds of formula III where $R_3$ is hydrogen, halo, lower alkyl, lower alkoxy, carboxy, carboalkoxy, cyano, perfluoroalkyl, mono or dialkylcarbamoyl, or heterocyclic carbamoyl, and Pg is a protecting group such as 2-trimethylsilylethyoxymethyl or phenylsulfonyl with base, such as butyl lithium, followed by the corresponding compound of formula Vb where $R_2$ is alkyl, cycloalkyl or heterocyclic, and $R_1$, $R_1'$ are hydrogen, alkyl, cyano, perfluoroalkyl, alkoxy, aryloxy, carboxy, carboalkoxy, alkylamino, or alkylsulfonyl.

Alternatively, compounds of $I_{alcohol}$, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, $R_2$ is alkyl, cycloalkyl or heterocyclic, $Q_1$ is carbon or nitrogen and $R_1$, $R_1'$ are hydrogen, alkyl, cyano, perfluoroalkyl, alkoxy, aryloxy, carboxy, carboalkoxy, alkylamino, or alkylsulfonyl, can be prepared by treating the corresponding compounds of formula V where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, and $R_2$ is alkyl, cycloalkyl or heterocyclic with Grignard reagents of formula XIa, where $R_1$, $R_1'$ are hydrogen, alkyl, cyano, perfluoroalkyl, alkoxy, aryloxy, carboxy, carboalkoxy, alkylamino, or alkylsulfonyl and $Q_1$ is carbon or nitrogen, using standard procedures.

Alternatively, compounds of formula $I_{olefin}$, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, $R_2$ is alkyl, cycloalkyl or heterocyclic, $Q_1$ and $Q_2$ are both carbon or $Q_1$ is carbon and $Q_2$ is nitrogen or $Q_1$ is nitrogen and $Q_2$ is carbon, and $R_1$, $R_1'$ are hydrogen, alkyl, cyano, perfluoroalkyl, alkoxy, aryloxy, carboxy, carboalkoxy, alkylamino, or alkylsulfonyl, can be prepared from the corresponding compounds of formula $I_{alcohol}$, where $R_3$ is hydrogen, halo, lower alkyl, lower alkoxy, carboxy, carboalkoxy, cyano, perfluoroalkyl, mono or dialkylcarbamoyl, or heterocyclic carbamoyl, Pg is a protecting group such as 2-trimethylsilylethyoxymethyl or phenylsulfonyl, $R_2$ is alkyl, cycloalkyl or heterocyclic, and $R_1$, $R_1'$ are hydrogen, alkyl, cyano, perfluoroalkyl, alkoxy, aryloxy, carboxy, carboalkoxy, alkylamino, or alkylsulfonyl, by treatment with reagents such as boron trifluoride etherate or tetra-n-butylammonium fluoride using standard procedures.

Compounds of formula I or Ia, where $R_3$ is hydrogen, halo, lower alkyl, lower alkoxy, carboxy, carboalkoxy, cyano, perfluoroalkyl, mono or dialkylcarbamoyl, or heterocyclic carbamoyl, $R_2$ is alkyl, cycloalkyl or heterocyclic, $Q_1$ and $Q_2$ are both carbon or $Q_1$ is carbon and $Q_2$ is nitrogen or $Q_1$ is nitrogen and $Q_2$ is carbon and $R_1$, $R_1'$ are hydrogen, alkyl, cyano, perfluoroalkyl, alkoxy, aryloxy, carboxy, carboalkoxy, alkylamino, or alkylsulfonyl, can be prepared from the corresponding compounds of formula $I_{olefin}$ where $R_3$ is hydrogen, halo, lower alkyl, lower alkoxy, carboxy, carboalkoxy, cyano, perfluoroalkyl, mono or dialkylcarbamoyl, or heterocyclic carbamoyl, $R_2$ is alkyl, cycloalkyl or heterocyclic, $Q_1$ and $Q_2$ are both carbon or $Q_1$ is carbon and $Q_2$ is nitrogen or $Q_1$ is nitrogen and $Q_2$ is carbon and $R_1$, $R_1'$ are hydrogen, alkyl, cyano, perfluoroalkyl, alkoxy, aryloxy, carboxy, carboalkoxy, alkylamino, or alkylsulfonyl, by reduction with hydrogen gas and palladium catalyst using standard conditions.

Alternatively, compounds of formula I, having functional groups typically needing transformation, conversion or deprotection can be prepared from the corresponding compounds of formula Ia by transforming, converting or deprotecting the desired functionality using conventional methods (see for example, Greene, T. W. *Protective Groups in Organic Synthesis*; John Wiley & Sons, Inc.: New York, 1991). Such conversions include saponification of an ester to an acid under basic conditions or removal of a silyl protecting group from an alcohol. Such conversions also include formation of a carboxylic acid ester or amide from the corresponding acid or acid chloride using conventional methods. Such conversions also include displacement of an alkyl halide, triflate or mesylate with nucleophiles such as alcohols, thiols or amines using conventional methods. Such conversions also include hydrogenation of alkenes or coupling of aryl halides or triflates with alkyl or aryl coupling partners such as but not limited to boronic acids, amines, alkynes, vinyl or alkyl halides (see for example Doucet, H.; Hierso, J.-C. *Curr. Opin. Drug Discovery Dev.* 2007, 10, 672-690; Beccalli, E. M.; Broggini, G.; Martinelli, M.; Sottocornola, S. *Chem. Rev.* 2007, 107, 5318-5365; Kienle, M.; Dubbaka, S. R.; Brade, K.; Knochel, P. *Eur. J. Org. Chem.* 2007, 4166-4176; Chinchilla, R.; Najera, C. *Chem. Rev* 2007, 107, 874-922; Yin, L.; Liebscher, *J. Chem. Rev.* 2007, 107, 133-173).

Compounds of formula I* which are chirally pure or chirally enriched enantiomers or diastereomers can be derived from the corresponding enantiomeric or diastereomeric mixtures of compounds of formula I using standard chromatographic techniques, such as supercritical fluid chromatography or high pressure liquid chromatography on chiral supports.

The invention will now be further described in the Examples below, which are intended as an illustration only and do not limit the scope of the invention.

EXAMPLES

Example 1

2-[1-(4-Methanesulfonyl-phenyl)-3-methyl-butyl]-1H-pyrrolo[2,3-b]pyridin-5-carboxylic acid isopropylamide

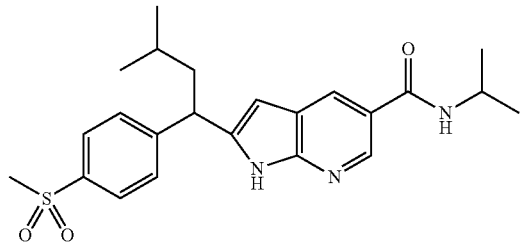

To a stirred suspension of methyl 6-aminonicotinate (10 g, 65.7 mmol) and trifluoroacetic acid silver salt (36.3 g, 164.3 mmol) in methanol (250 mL) was added iodine (41.7 g, 164.3 mmol) at 25° C. and the reaction mixture was stirred at 25° C. for 72 h. The mixture was filtered, washed with methanol and concentrated in vacuo. The residue was dissolved in ethyl acetate and washed consecutively with a saturated sodium thiosulfate solution, brine and dried over anhydrous sodium sulfate. The solvent was evaporated in vacuo to afford 6-amino-5-iodo-nicotinic acid methyl ester (13.8 g, 77%) as a light yellow solid: $^1$H NMR (400 MHz, CDCl$_3$) δ ppm 3.89 (s, 3H), 5.46 (br. s., 2H), 8.47 (br. s., 1H), 8.67 (br. s., 1H).

Trimethylsilyl acetylene (10.5 mL, 79.1 mmol) was added to a solution of 6-amino-5-iodo-nicotinic acid methyl ester (11 g, 39.6 mmol), copper (I) iodide (754 mg, 4.0 mmol), tetrakis(triphenylphosphine)palladium(0) (2.3 g, 2.0 mmol) and diisopropylethylamine (21 mL, 118.7 mmol) in N,N-dimethyl formamide (80 mL) at 0° C. After addition, the reaction mixture was allowed to warm up to 25° C. and stirred for 2 h. The mixture was extracted with ethyl acetate, washed with brine and dried over sodium sulfate. The solvent was evaporated in vacuo and the residue was purified by flash column chromatography (QingDao silica gel, 200-300 mesh, 5% dichloromethane/hexanes to 60% dichloromethane/hexanes) to afford 6-amino-5-trimethylsilanylethynyl-nicotinic acid methyl ester (7.1 g, 72%) as a light yellow solid: $^1$H NMR (400 MHz, CDCl$_3$) δ ppm 0.28 (s, 9H), 3.88 (s, 3H), 5.58 (br. s., 2H), 8.14 (d, J=2.2 Hz, 1H), 8.66 (d, J=2.2 Hz, 1H).

To a solution of 6-amino-5-trimethylsilanylethynyl-nicotinic acid methyl ester (6.05 g, 24.4 mmol) and pyridine (4 mL, 49.4 mmol) in dichloromethane (80 mL) was added acetyl chloride (2.6 mL, 35.6 mmol) at 0° C. The mixture was allowed to warm up to 25° C. and stirred for 12 h. The reaction mixture was extracted with ethyl acetate, washed with brine and dried over sodium sulfate. The solvent was evaporated in vacuo to afford 6-acetylamino-5-trimethylsilanylethynyl nicotinic acid methyl ester which was used without further purification.

To a stirred solution of 6-acetylamino-5-trimethylsilanylethynyl-nicotinic acid methyl ester (24.4 mmol theoretical from previous step) in tetrahydrofuran (15 mL) was added tetrabutylammonium fluoride (1 M solution in tetrahydrofuran, 100 mL, 100 mmol) at 25° C. The mixture was heated at reflux at 80° C. for 2 h and then cooled to 25° C. The resulting mixture was extracted with ethyl acetate, washed with brine and dried over sodium sulfate. The solvent was evaporated in vacuo to afford 1H-pyrrolo[2,3-b]pyridin-5-carboxylic acid methyl ester (3.4 g, 79% over two steps) as a light yellow solid: $^1$H NMR (400 MHz, CDCl$_3$) δ ppm 4.01 (s, 3H), 6.71 (d, J=3.6 Hz, 1H), 7.53 (d, J=3.6 Hz, 1H), 8.77 (s, 1H), 9.04 (s, 1H).

To a solution of tetrabutylammonium bromide (154 mg, 0.48 mmol) and 1H-pyrrolo[2,3-b]pyridin-5-carboxylic acid methyl ester (2.8 g, 15.9 mmol) in dichloromethane (40 mL) was added sodium hydroxide powder (1.9 g, 47.7 mmol) at 0° C. The mixture was stirred at 0° C. for 5 min. Benzene sulfonyl chloride (3 mL, 23.8 mmol) was added slowly to the above mixture at 0° C. and the resulting mixture was stirred at 0° C. for another 15 min before it was warmed to 25° C. and kept at that temperature for 12 h. The reaction mixture was filtered and then concentrated in vacuo to afford 1-benzenesulfonyl-1H-pyrrolo[2,3-b]pyridin-5-carboxylic acid methyl ester as a light yellow solid which was washed with hexane to give a white solid (4.6 g, 90%): $^1$H NMR (400 MHz, CDCl$_3$) δ ppm 3.95 (s, 3H), 6.69 (d, J=4.0 Hz, 1H), 7.51 (m, 2H), 7.61 (m, 1H), 7.82 (d, J=4.0 Hz, 1H), 8.22 (m, 2H), 8.51 (d, J=2.0 Hz, 1H), 9.08 (d, J=2.0 Hz, 1H).

To a suspension of 1-benzenesulfonyl-1H-pyrrolo[2,3-b]pyridin-5-carboxylic acid methyl ester (2.0 g, 6.33 mmol) in dry tetrahydrofuran (15 mL) at −78° C. was added freshly prepared lithium diisopropylamide [prepared by adding 1.6 M n-butyllithium in n-hexane (5.3 mL, 8.55 mmol) to a 0° C. solution of diisopropylamine (1.3 mL, 9.2 mmol) in dry tetrahydrofuran (40 mL)] dropwise. The mixture was stirred at −78° C. for 5 min and then treated with isovaleraldehyde (1.4 mL, 13.3 mmol) dropwise. The resulting mixture was stirred at −78° C. for 1 h and then quenched with brine. The mixture was extracted with ethyl acetate (2×150 mL), washed with brine, dried over anhydrous sodium sulfate and concentrated in vacuo. Purification by flash column chromatography (QingDao silica gel, 200-300 mesh, 15% ethyl acetate/hexanes) afforded 1-benzenesulfonyl-2-(1-hydroxy-3-methyl-butyl)-1H-pyrrolo[2,3-b]pyridin-5-carboxylic acid methyl ester as a colorless oil (938 mg, 35%): LC/MS m/e calcd for C$_{20}$H$_{23}$N$_2$O$_5$S [M+H]$^+$ 403.47, observed 403.3; $^1$H NMR (400 MHz, CDCl$_3$) δ ppm 1.04 (d, J=6.4 Hz, 3H), 1.06 (d, J=6.4 Hz, 3H), 1.82 (m, 1H), 1.94-2.03 (m, 2H), 3.30 (br, 1H), 3.94 (s, 3H), 5.45 (m, 1H), 6.70 (s, 1H), 7.49 (m, 2H), 7.59 (m, 1H), 8.19 (m, 2H), 8.41 (d, J=2.0 Hz, 1H), 9.01 (d, J=2.0 Hz, 1H).

To a 25 ml, round bottomed flask charged with 1-benzenesulfonyl-2-(1-hydroxy-3-methyl-butyl)-1H-pyrrolo[2,3-b]pyridin-5-carboxylic acid methyl ester (938 mg, 2.33 mmol) was added a solution of Dess-Martin periodinane in dichloromethane (0.3M, 15 mL, 4.5 mmol) at 25° C. The reaction mixture was stirred at 25° C. for 1 h and then quenched with a saturated aqueous sodium bicarbonate solution (10 mL). The mixture was extracted with ethyl acetate (150 mL), washed with a saturated aqueous sodium bicarbonate solution (3×20 mL), brine, dried over anhydrous sodium sulfate and then concentrated in vacuo to give 1-benzenesulfonyl-2-(3-methyl-butyryl)-1H-pyrrolo[2,3-b]pyridin-5-carboxylic acid methyl ester (613 mg, 66%) as a light yellow solid which was used without further purification: LC/MS m/e calcd for C$_{20}$H$_{21}$N$_2$O$_5$S [M+H]$^+$ 401.46, observed 401.3; $^1$H NMR (400 MHz, CDCl$_3$) δ ppm 1.07 (d, J=6.6 Hz, 6H), 2.36 (m, 1H), 2.89 (d, J=7.0 Hz, 2H), 3.97 (s, 3H), 7.00 (s, 1H), 7.57 (brt, 2H), 7.64 (brt, 1H), 8.44 (br. d., 2H), 8.58 (d, J=2.0 Hz, 1H), 9.20 (d, J=2.0 Hz, 1H).

To a solution of 1-benzenesulfonyl-2-(3-methyl-butyryl)-1H-pyrrolo[2,3-b]pyridin-5-carboxylic acid methyl ester (613 mg, 1.53 mmol) in dry tetrahydrofuran (15 mL) at −78° C. was added lithium bis(trimethylsilyl)amide (1.0 M in tetrahydrofuran, 2.3 mL, 2.3 mmol) dropwise. After stirring at −78° C. for 1 h, a solution of p-toluenesulfonic anhydride (816 mg, 2.5 mmol) in tetrahydrofuran (5 mL) was added dropwise. The resulting solution was kept at −78° C. for another 1.5 h. The reaction was quenched with water, extracted with ethyl acetate (200 mL), washed with brine, dried over sodium sulfate and then concentrated in vacuo. Purification by flash column chromatography (QingDao silica gel, 200-300 mesh, 5% ethyl acetate/hexanes) afforded 1-benzenesulfonyl-2-[3-methyl-1-(toluene-4-sulfonyloxy)-but-1-enyl]-1H-pyrrolo[2,3-b]pyridin-5-carboxylic acid methyl ester (721 mg, 85%) as a white solid: LC/MS m/e calcd for C$_{27}$H$_{27}$N$_2$O$_7$S$_2$ [M+H]$^+$ 555.65, observed 555.3; $^1$H NMR (400 MHz, CDCl$_3$) δ ppm 1.12 (d, J=6.6 Hz, 6H), 2.13 (s, 3H), 3.03 (m, 1H), 3.98 (s, 3H), 5.62 (d, J=10.2 Hz, 1H), 6.52 (s, 1H), 6.85 (d, J=8.0 Hz, 2H), 7.28 (d, J=8.0 Hz, 2H), 7.52 (m, 2H), 7.62 (m, 1H), 8.29 (m, 2H), 8.35 (d, J=2.0 Hz, 1H), 9.07 (d, J=2.0 Hz, 1H).

To a mixture of 1-benzenesulfonyl-2-[3-methyl-1-(toluene-4-sulfonyloxy)-but-1-enyl]-1H-pyrrolo[2,3-b]pyridin-5-carboxylic acid methyl ester (1.2 g, 2.1 mmol), 4-(methanesulfonyl)phenylboronic acid (1.0 g, 5.2 mmol), dichlorobis(triphenylphosphine)palladium (II) (150 mg, 0.21 mmol) in dioxane (10 mL) was added an aqueous sodium carbonate solution (2 M, 5.2 mL). The resulting mixture was subjected to microwave irradiation for 120 min at 100° C. The mixture was diluted with ethyl acetate (150 mL), washed with a saturated aqueous sodium bicarbonate solution (2×30 mL), brine, dried over anhydrous sodium sulfate and then concentrated in vacuo. Purification by flash column chromatography (QingDao silica gel, 200-300 mesh, 50% ethyl acetate/hexanes) afforded 1-benzenesulfonyl-2-[1-(4-methanesulfonyl-phenyl)-3-methyl-but-1-enyl]-1H-pyrrolo[2,3-b]pyridin-5-carboxylic acid methyl ester (820 mg, 73%) as a light yellow solid: LC/MS m/e calcd for C$_{27}$H$_{26}$N$_2$O$_6$S$_2$ [M+H]$^+$ 539.65, observed 539.3; $^1$H NMR (400 MHz, CDCl$_3$) δ ppm 1.16 (d, J=6.6 Hz, 3H), 1.18 (d, J=6.6 Hz, 3H), 2.68 (m, 1H), 3.08 (s, 3H), 3.99 (s, 3H), 6.27 (d, J=10.2 Hz, 1H), 6.67 (s, 1H), 7.28

(m, 2H), 7.36 (m, 2H), 7.49 (m, 1H), 7.67 (m, 2H), 7.78 (m, 2H), 8.55 (d, J=2.0 Hz, 1H), 9.14 (d, J=2.0 Hz, 1H).

A mixture of 1-benzenesulfonyl-2-[1-(4-methanesulfonyl-phenyl)-3-methyl-but-1-enyl]-1H-pyrrolo[2,3-b]pyridin-5-carboxylic acid methyl ester (800 mg, 1.48 mmol) in ethanol (4 mL) and an aqueous sodium hydroxide solution (10%, 1.5 mL) was heated at 100° C. for 1 h. The mixture was acidified to pH 4-5 with a 2N aqueous hydrochloric acid solution, diluted with dichloromethane (150 mL), washed with water, dried over anhydrous sodium sulfate and then concentrated in vacuo to afford 2-[1-(4-methanesulfonyl-phenyl)-3-methyl-but-1-enyl]-1H-pyrrolo[2,3-b]pyridin-5-carboxylic acid (540 mg, 95%) as a light yellow solid which was used without further purification: LC/MS m/e calcd for $C_{20}H_{20}N_2O_4S$ [M+H]$^+$ 385.46, observed 385.3.

A mixture of 2-[1-(4-methanesulfonyl-phenyl)-3-methyl-but-1-enyl]-1H-pyrrolo[2,3-b]pyridin-5-carboxylic acid (540 mg, 1.40 mmol) and 10% palladium on activated carbon (162 mg) in methanol (300 mL) was heated at 50° C. under 50 bar of hydrogen in a steel bomb and kept for 5 h. The mixture was cooled to 25° C., filtered off solids and washed with ethyl acetate. The filtrate was concentrated in vacuo to afford 2-[1-(4-methanesulfonyl-phenyl)-3-methyl-butyl]-1H-pyrrolo[2,3-b]pyridin-5-carboxylic acid (400 mg, 73%) which was used without further purification.

To a solution of 2-[1-(4-methanesulfonyl-phenyl)-3-methyl-butyl]-1H-pyrrolo[2,3-b]pyridin-5-carboxylic acid (200 mg, 0.52 mmol) and isopropylamine (54 μL, 0.62 mmol) in dichloromethane (1 mL), N,N-dimethylformamide (500 μL) and N-methylmorpholine (200 μL, 1.56 mmol) was added 1-hydroxybenzotriazole hydrate (141 mg, 1.04 mmol) followed by N-(3-dimethylaminopropyl)-N'-ethylcarbodiimide hydrochloride (199 mg, 1.04 mmol) in one portion. The mixture was then stirred at 25° C. for 14 h. The mixture was diluted with ethyl acetate (100 mL), washed with a 1 N aqueous sodium bicarbonate solution, 1 N aqueous hydrochloric acid solution, brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[1-(4-methanesulfonyl-phenyl)-3-methyl-butyl]-1H-pyrrolo[2,3-b]pyridin-5-carboxylic acid isopropylamide (45 mg, 20%) as a white solid: LC/MS m/e calcd for $C_{23}H_{29}N_3O_3S$ [M+H]$^+$ 428.57, observed 428.2; $^1$H NMR (400 MHz, CDCl$_3$) δ ppm 0.94 (d, J=6.7 Hz, 3H), 0.97 (d, J=6.7 Hz, 3H), 1.29 (d, J=6.6 Hz, 6H), 1.49 (m, 1H), 1.96 (m, 1H), 2.08 (m, 1H), 3.03 (s, 3H), 4.24-4.37 (m, 2H), 6.17 (d, J=7.9 Hz, 1H), 6.38 (s, 1H), 7.43 (d, J=8.3 Hz, 2H), 7.84 (d, J=8.3 Hz, 2H), 8.24 (d, J=2.0 Hz, 1H), 8.55 (d, J=2.0 Hz, 1H), 10.31 (br, 0.3H).

Example 2

2-[1-(4-Methanesulfonyl-phenyl)-3-methyl-butyl]-1H-pyrrolo[2,3-b]pyridin-5-carboxylic acid methylamide

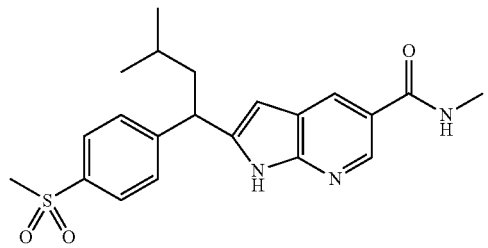

To a solution of 2-[1-(4-methanesulfonyl-phenyl)-3-methyl-butyl]-1H-pyrrolo[2,3-b]pyridin-5-carboxylic acid (prepared as in Example 1, 432 mg, 1.12 mmol) and methylamine hydrochloride (151 mg, 2.23 mmol) in dichloromethane (8 mL), N,N-dimethylformamide (2 mL) and N-methylmorpholine (370 μL, 3.36 mmol) was added 1-hydroxybenzotriazole hydrate (380 mg, 2.8 mmol) followed by N-(3-dimethylaminopropyl)-N'-ethylcarbodiimide hydrochloride (540 mg, 2.8 mmol) in one portion. The mixture was then stirred at 25° C. for 14 h. The mixture was diluted with ethyl acetate (200 mL), washed with a 1 N aqueous sodium bicarbonate solution, 1 N aqueous hydrochloric acid solution, brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[1-(4-methanesulfonyl-phenyl)-3-methyl-butyl]-1H-pyrrolo[2,3-b]pyridin-5-carboxylic acid methylamide (53 mg, 12%) as a white solid: LC/MS m/e calcd for $C_{21}H_{26}N_3O_3S$ [M+H]$^+$ 400.52, observed 400.2; $^1$H NMR (400 MHz, CDCl$_3$) δ ppm 0.97 (d, J=6.9 Hz, 3H), 0.99 (d, J=6.9 Hz, 3H), 1.52 (m, 1H), 1.96 (m, 1H), 2.11 (m, 1H), 3.04 (s, 3H), 3.08 (d, J=4.4 Hz, 3H), 4.31 (m, 1H), 6.35 (m, 1H), 6.42 (s, 1H), 7.41 (d, J=8.3 Hz, 2H), 7.82 (d, J=8.3 Hz, 2H), 8.25 (s, 1H), 8.50 (s, 1H), 10.84 (br. s., 1H).

Example 3

2-[2-Cyclopentyl-1-(4-methanesulfonyl-phenyl)-ethyl]-1H-pyrrolo[2,3-b]pyridin-5-carboxylic acid isopropylamide

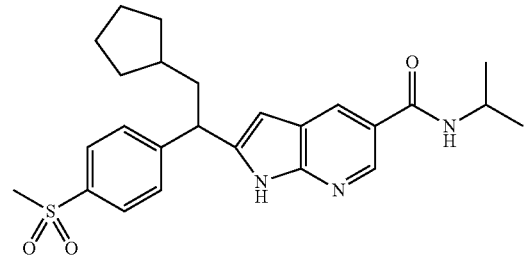

To a suspension of lithium aluminium hydride (8.3 g, 218.4 mmol) in dry tetrahydrofuran (300 mL) at 0° C. was added a solution of cyclopentylacetic acid (20 g, 156 mmol) in tetrahydrofuran (15 mL) dropwise. The mixture was then heated at 80° C. for 14 h. The reaction was quenched with a 10% sodium hydroxide solution. The solid formed was filtered off and washed with tetrahydrofuran (3×100 mL). The combined filtrate was dried over anhydrous sodium sulfate, concentrated in vacuo to give 2-cyclopentyl-ethanol as a colorless oil (15.7 g, 80%) which was used without further purification.

To a solution of 2-cyclopentyl-ethanol (15.7 g, 137.7 mmol) in dichloromethane (500 mL) was added pyridinium chlorochromate (59.4 g, 275.4 mmol) in a few portions at 25° C. The dark suspension was stirred at 25° C. for 3 h. The mixture was filtered through a short pad of silica gel. The filtrate was concentrated in vacuo and the residue was diluted with n-hexanes (100 mL). The mixture was filtered through a short pad of silica gel and the filtrate was concentrated in vacuo to afford cyclopentyl acetaldehyde as a colorless oil (10 g, 65%): $^1$H NMR (400 MHz, CDCl$_3$) δ ppm 1.15-1.20 (m, 2H), 1.56-1.70 (m, 4H), 1.85-1.92 (m, 2H), 2.47-2.31 (m, 1H), 2.47 (d, J=2.4 Hz, 2H); 9.78 (s, 1H).

To a suspension of 1-benzenesulfonyl-1H-pyrrolo[2,3-b]pyridin-5-carboxylic acid methyl ester (prepared as in Example 1, 2.6 g, 8.3 mmol) in dry tetrahydrofuran (60 mL) at −78° C. was added freshly prepared lithium diisopropylamide [prepared by adding 1.6 M n-butyllithium in n-hexane (6.7 mL, 10.7 mmol) to a solution of diisopropylamine (1.6 mL, 11.3 mmol) in dry tetrahydrofuran (15 mL) at 0° C.] dropwise. The mixture was stirred at −78° C. for 5 min and then treated with cyclopentyl acetaldehyde (1.2 g, 10.7 mmol) dropwise. The resulting mixture was stirred at −78° C. for 1 h and then quenched with brine. The mixture was extracted with ethyl acetate (2×150 mL), washed with brine, dried over anhydrous sodium sulfate and concentrated in vacuo. Purification by flash column chromatography (QingDao silica gel, 200-300 mesh, 15% ethyl acetate/hexanes) afforded 1-benzenesulfonyl-2-(2-cyclopentyl-1-hydroxy-ethyl)-1H-pyrrolo[2,3-b]pyridin-5-carboxylic acid methyl ester as a colorless oil (730 mg, 21%): $^1$H NMR (400 MHz, CDCl$_3$) δ ppm 1.26 (m, 2H), 1.53-1.68 (m, 4H), 1.73-2.16 (m, 5H, H), 3.50 (br, 1H), 3.89 (s, 3H), 5.41 (dd, J=5.0 Hz, 8.1 Hz, 1H), 6.67 (s, 1H), 7.42 (brt, 2H), 7.53 (brt, 1H), 8.14 (br. d., 2H), 8.33 (m, 1H), 8.96 (m, 1H).

To a 25 mL round bottomed flask charged with 1-benzenesulfonyl-2-(2-cyclopentyl-1-hydroxy-ethyl)-1H-pyrrolo[2,3-b]pyridin-5-carboxylic acid methyl ester (730 mg, 1.7 mmol) was added a solution of Dess-Martin periodinane in dichloromethane (0.3M, 12 mL, 3.6 mmol) at 25° C. The reaction mixture was stirred at 25° C. for 1 h and then quenched with a saturated aqueous sodium bicarbonate solution (10 mL). The mixture was extracted with ethyl acetate (100 mL), washed with a saturated aqueous sodium bicarbonate solution (3×20 mL), brine, dried over anhydrous sodium sulfate and then concentrated in vacuo to give 1-benzenesulfonyl-2-(2-cyclopentyl-acetyl)-1H-pyrrolo[2,3-b]pyridin-5-carboxylic acid methyl ester (670 mg, 93%) as a light yellow solid which was used without further purification: $^1$H NMR (400 MHz, CDCl$_3$) δ ppm 1.26 (m, 2H), 1.52-1.74 (m, 4H), 1.97 (m, 2H), 2.45 (m, 1H), 3.04 (d, J=7.2 Hz, 2H), 3.98 (s, 3H), 6.99 (s, 1H), 7.57 (m, 2H), 7.65 (m, 1H), 8.43 (m, 2H), 8.55 (d, J=2.0 Hz, 1H), 9.21 (d, J=2.0 Hz, 1H).

To a solution of 1-benzenesulfonyl-2-(2-cyclopentyl-acetyl)-1H-pyrrolo[2,3-b]pyridin-5-carboxylic acid methyl ester (670 mg, 1.6 mmol) in dry tetrahydrofuran (30 mL) at −78° C. was added lithium bis(trimethylsilyl)amide (1.0 M in tetrahydrofuran, 2.4 mL, 2.4 mmol) dropwise. After stirring at −78° C. for 1 h, a solution of p-toluenesulfonic anhydride (783 mg, 2.4 mmol) in tetrahydrofuran (5 mL) was added dropwise. The resulting mixture was kept at −78° C. for another 1.5 h. The reaction was quenched with water, extracted with ethyl acetate (200 mL), washed with brine, dried over anhydrous sodium sulfate and then concentrated in vacuo. Purification by flash column chromatography (QingDao silica gel, 200-300 mesh, 5% ethyl acetate/hexanes) afforded 1-benzenesulfonyl-2-[2-cyclopentyl-1-(toluene-4-sulfonyloxy)-vinyl]-1H-pyrrolo[2,3-b]pyridin-5-carboxylic acid methyl ester (850 mg, 94%) as a light yellow solid.

To a mixture of 1-benzenesulfonyl-2-[2-cyclopentyl-1-(toluene-4-sulfonyloxy)-vinyl]-1H-pyrrolo[2,3-b]pyridin-5-carboxylic acid methyl ester (0.9 g, 1.55 mmol), 4-(methanesulfonyl)phenylboronic acid (930 mg, 4.6 mmol) and dichlorobis(triphenylphosphine)palladium (II) (110 mg, 0.15 mmol) in dioxane (8 mL) was added an aqueous sodium carbonate solution (2 M, 2.3 mL). The resulting mixture was subjected to microwave irradiation for 120 min at 100° C. The mixture was diluted with ethyl acetate (150 mL), washed with a saturated aqueous sodium bicarbonate solution (2×30 mL), brine, dried over anhydrous sodium sulfate and then concentrated in vacuo. Purification by flash column chromatography (QingDao silica gel, 200-300 mesh, 50% ethyl acetate/hexanes) afforded 1-benzenesulfonyl-2-[2-cyclopentyl-1-(4-methanesulfonyl-phenyl)-vinyl]-1H-pyrrolo[2,3-b]pyridin-5-carboxylic acid methyl ester (815 mg, 73%) as a white solid: LC/MS m/e calcd for $C_{29}H_{28}N_2O_6S_2$ [M+H]$^+$ 565.68, observed 565.1.

A mixture of 1-benzenesulfonyl-2-[2-cyclopentyl-1-(4-methanesulfonyl-phenyl)-vinyl]-1H-pyrrolo[2,3-b]pyridin-5-carboxylic acid methyl ester (950 mg, 1.69 mmol) in ethanol (10 mL), tetrahydrofuran (2 mL) and 10% aqueous sodium hydroxide solution (1.5 mL) was heated at 100° C. for 1 h. The mixture was neutralized with a 3 N aqueous hydrochloric acid solution, diluted with ethyl acetate (150 mL), washed with brine, dried over anhydrous sodium sulfate and then concentrated in vacuo to afford 2-[2-cyclopentyl-1-(4-methanesulfonyl-phenyl)-vinyl]-1H-pyrrolo[2,3-b]pyridin-5-carboxylic acid (680 mg, 98%) as a solid which was used without further purification.

A mixture of 2-[2-cyclopentyl-1-(4-methanesulfonyl-phenyl)-vinyl]-1H-pyrrolo[2,3-b]pyridin-5-carboxylic acid (680 mg, 1.24 mmol) and 10% palladium on activated carbon (204 mg) in methanol (300 mL) was heated at 50° C. under 50 bar of hydrogen in a steel bomb and kept for 5 h. The mixture was cooled to 25° C., the solids were filtered off, washed with ethyl acetate and the filtrate concentrated in vacuo to afford 2-[2-cyclopentyl-1-(4-methanesulfonyl-phenyl)-ethyl]-1H-pyrrolo[2,3-b]pyridin-5-carboxylic acid (600 mg, 87%) which was used without further purification.

To a solution of 2-[2-cyclopentyl-1-(4-methanesulfonyl-phenyl)-ethyl]-1H-pyrrolo[2,3-b]pyridin-5-carboxylic acid (200 mg, 0.48 mmol) and isopropylamine (50 µL, 0.62 mmol) in dichloromethane (1 mL), N,N-dimethylformamide (500 µL) and N-methylmorpholine (150 µL, 1.45 mmol) was added 1-hydroxybenzotriazole hydrate (132 mg, 0.97 mmol) followed by N-(3-dimethylaminopropyl)-N'-ethylcarbodiimide hydrochloride (186 mg, 0.97 mmol) in one portion. The mixture was then stirred at 25° C. for 14 h. The mixture was diluted with ethyl acetate (100 mL), washed with a 1 N aqueous sodium bicarbonate solution, 1 N aqueous hydrochloric acid solution, brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(4-methanesulfonyl-phenyl)-ethyl]-1H-pyrrolo[2,3-b]pyridin-5-carboxylic acid isopropylamide (80 mg, 36%) as a white solid: LC/MS m/e calcd for $C_{25}H_{31}N_3O_3S$ [M+H]$^+$ 454.61, observed 454.4; $^1$H NMR (400 MHz, CDCl$_3$) δ ppm 1.12 (m, 2H), 1.24 (d, J=6.7 Hz, 6H), 1.43 (m, 2H), 1.52-1.81 (m, 5H, H), 2.04 (m, 1H), 2.17 (m, 1H), 2.99 (s, 3H), 4.18 (t, J=7.9 Hz, 1H), 4.25 (m, 1H), 6.34 (s, 1H), 6.60 (d, J=7.6 Hz, 1H), 7.41 (d, J=8.1 Hz, 2H), 7.78 (d, J=8.1 Hz, 2H), 8.23 (d, J=1.8 Hz, 1H), 8.53 (d, J=1.8 Hz, 1H), 10.72 (br, 1H).

Example 4

{2-[2-Cyclopentyl-1-(4-methanesulfonyl-phenyl)-ethyl]-1H-pyrrolo[2,3-b]pyridin-5-yl}-morpholin-4-yl-methanone

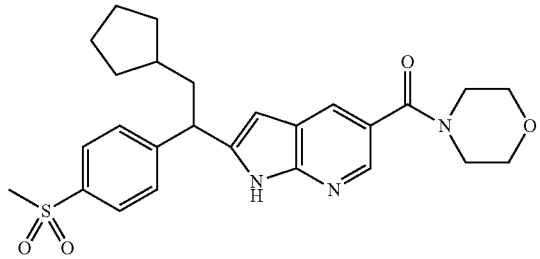

To a solution of 2-[2-cyclopentyl-1-(4-methanesulfonyl-phenyl)-ethyl]-1H-pyrrolo[2,3-b]pyridin-5-carboxylic acid (prepared as in Example 3, 200 mg, 0.48 mmol) and morpholine (51 µL, 0.58 mmol) in dichloromethane (1 mL), N,N-dimethylformamide (500 µL) and N-methylmorpholine (152 µL, 1.45 mmol) was added 1-hydroxybenzotriazole hydrate (132 mg, 0.97 mmol) followed by N-(3-dimethylaminopropyl)-N'-ethylcarbodiimide hydrochloride (186 mg, 0.97 mmol) in one portion. The mixture was then stirred at 25° C. for 14 h. The mixture was diluted with ethyl acetate (100 mL), washed with a 1 N aqueous sodium bicarbonate solution, 1 N aqueous hydrochloric acid solution, brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded {2-[2-cyclopentyl-1-(4-methanesulfonyl-phenyl)-ethyl]-1H-pyrrolo[2,3-b]pyridin-5-yl}-morpholin-4-yl-methanone (85 mg, 36%) as a yellow solid: LC/MS m/e calcd for $C_{26}H_{31}N_3O_4S$ [M+H]$^+$ 482.62, observed 482.2; $^1$H NMR (400 MHz, CDCl$_3$) δ ppm 1.17 (m, 2H), 1.47 (m, 2H), 1.55-1.85 (m, 5H, H), 2.09 (m, 1H), 2.25 (m, 1H), 3.02 (s, 3H), 3.72 (br. s., 8H), 4.27 (t, J=7.9 Hz, 1H), 6.41 (s, 1H), 7.46 (d, J=8.4 Hz, 2H), 7.83 (d, J=8.4 Hz, 2H), 7.93 (d, J=1.9 Hz, 1H), 8.20 (d, J=1.9 Hz, 1H), 11.01 (br, 1H).

Example 5

2-[2-Cyclopentyl-1-(4-methanesulfonyl-phenyl)-ethyl]-1H-pyrrolo[2,3-b]pyridin-5-carboxylic acid methylamide

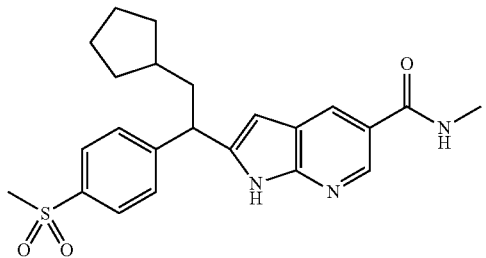

To a solution of 2-[2-cyclopentyl-1-(4-methanesulfonyl-phenyl)-ethyl]-1H-pyrrolo[2,3-b]pyridin-5-carboxylic acid (prepared as in Example 3, 200 mg, 0.48 mmol) and methylamine hydrochloride (39.4 mg, 0.58 mmol) in dichloromethane (1 mL), N,N-dimethylformamide (500 µL) and N-methylmorpholine (152 µL, 1.45 mmol) was added 1-hydroxybenzotriazole hydrate (132 mg, 0.97 mmol) followed by N-(3-dimethylaminopropyl)-N'-ethylcarbodiimide hydrochloride (186 mg, 0.97 mmol) in one portion. The mixture was then stirred at 25° C. for 14 h. The mixture was diluted with ethyl acetate (100 mL), washed with a 1 N sodium bicarbonate solution, 1 N aqueous hydrochloric acid solution, brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(4-methanesulfonyl-phenyl)-ethyl]-1H-pyrrolo[2,3-b]pyridin-5-carboxylic acid methylamide (63 mg, 30%) as a light yellow solid: LC/MS m/e calcd for $C_{23}H_{27}N_3O_3S$ [M+H]$^+$ 426.55, observed 426.4; $^1$H NMR (400 MHz, CDCl$_3$) δ ppm 1.18 (m, 2H), 1.49 (m, 2H), 1.55-1.84 (m, 5H, H), 2.10 (m, 1H), 2.23 (m, 1H), 3.02 (s, 3H), 3.07 (d, J=4.8 Hz, 3H), 4.23 (t, J=8.0 Hz, 1H), 6.36 (q, J=4.8 Hz, 1H), 6.42 (s, 1H), 7.40 (d, J=8.4 Hz, 2H), 7.81 (d, J=8.4 Hz, 2H), 8.21 (d, J=2.1 Hz, 1H), 8.49 (d, J=2.1 Hz, 1H), 10.89 (br. s., 1H).

Example 6

2-[2-Cyclopentyl-1(R)-(4-methanesulfonyl-phenyl)-ethyl]-1H-pyrrolo[2,3-b]pyridin-5-carboxylic acid methylamide

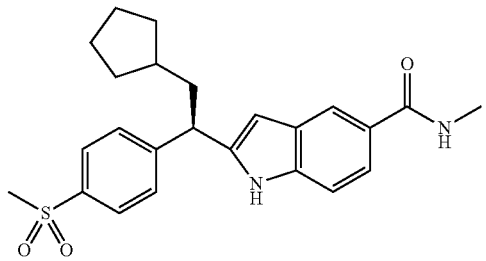

The 1:1 mixture of enantiomers of 2-[2-cyclopentyl-1-(4-methanesulfonyl-phenyl)-ethyl]-1H-pyrrolo[2,3-b]pyridin-5-carboxylic acid methylamide (from example 5) were separated by Agilent high performance liquid chromatography (chiral column: Daicel IA-H, 250 mm×20 mm i. d., 5 µm-particle size, temperature: 25° C., flow rate of 14 mL/min, 50% isopropyl alcohol/hexanes as mobile phase and UV detection: 214 and 254 nm) to afford the two pure enantiomers. The second peak to elute was the more active 2-[2-cyclopentyl-1(R)-(4-methanesulfonyl-phenyl)-ethyl]-1H-pyrrolo[2,3-b]pyridin-5-carboxylic acid methylamide which was isolated as white solid: $^1$H NMR (400 MHz, CDCl$_3$) δ ppm 10.07 (br. s., 2H), 8.54 (s, 1H), 8.27 (s, 1H), 7.86 (d, J=8.1 Hz, 1H), 7.44 (d, J=8.3 Hz, 1H), 7.28 (s, 2H), 6.46 (s, 1H), 6.24 (d, J=4.3 Hz, 1H), 4.25 (t, J=7.7 Hz, 1H), 3.08 (d, 3H) 3.06 (s, 3H), 2.07-2.28 (m, 1H), 1.63-1.84 (m, 7H), 1.47-1.63 (m, 2H).

Example 7

1-{2-[2-Cyclopentyl-1-(4-methanesulfonyl-phenyl)-ethyl]-1H-pyrrolo[2,3-b]pyridin-5-yl}-ethane-1,2-diol

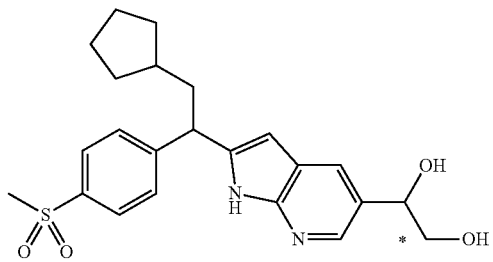

Formic acid (98%, 37.5 mL, 0.97 mol) was added to cooled (ice bath) triethylamine (150 mL, 1.08 mol) and stirred for 20 min. The resulting two-phase system was added to a mixture of 7-azaindole (50.0 g, 0.42 mol), formic acid (750 mL), and 10% palladium on activated carbon (30.0 g) at 0° C. and the resulting mixture was then heated at 80° C. for 5 days. The mixture was then cooled to room temperature, the catalyst was removed by filtration and washed with formic acid. The filtrate and washings were combined and concentrated in vacuo. The residual liquid was cooled (ice bath) and basified to pH=13 by slow addition of a 50% aqueous solution of sodium hydroxide. The resulting solution was refluxed for 1 h and then cooled to room temperature. The precipitate formed was filtered and washed with hexane to give 2,3-dihydro-1H-pyrrolo[2,3-b]pyridine (31 g) as a light yellow solid. The filtrate was then extracted with ethyl acetate, washed with brine, dried over anhydrous sodium sulfate and concentrated in vacuo. Purification by flash silica gel chromatography (silica gel from QingDao, 200-300 mesh, glass column from Shanghai SD company, hexanes) afforded another batch of 2,3-dihydro-1H-pyrrolo[2,3-b]pyridine (9.5 g) as a light yellow solid (total yield 40.5 g, 81%): $^1$H NMR (400 MHz, CDCl$_3$) δ ppm 3.06 (t, J=8.3 Hz, 2H), 3.61 (t, J=8.3 Hz, 2H), 4.50 (br, 1H), 6.50 (m, 1H), 7.24 (m, 1H), 7.81 (d, J=5.2 Hz, 1H).

To a 0° C. solution of 2,3-dihydro-1H-pyrrolo[2,3-b]pyridine (24.0 g, 200 mmol) in N,N-dimethylformamide (68 mL) was added a 60% dispersion of sodium hydride in mineral oil (12.0 g, 300 mmol) portionwise. The mixture was stirred at 0° C. for 30 min and then a solution of tert-butyldimethylsilyl chloride (46 g, 300 mmol) in N,N-dimethylformamide (100 mL) was added to the above mixture dropwise at 0° C. The mixture was stirred at 0° C. for 3 h and then extracted with ethyl acetate, washed with brine, dried over anhydrous sodium sulfate and concentrated in vacuo. The yellowish residue was purified by flash silica gel chromatography (silica gel from QingDao, 200-300 mesh, glass column from Shanghai SD company, 5% ethyl acetate/hexanes) to afford 1-(tert-butyl-dimethyl-silanyl)-2,3-dihydro-1H-pyrrolo[2,3-b]pyridine (31 g, 66%) as a yellow oil: LC/MS m/e calcd for C$_{13}$H$_{23}$N$_2$Si [M+H]$^+$ 235.42, observed 235.3; $^1$H NMR (400 MHz, CDCl$_3$) δ ppm 0.35 (s, 6H), 0.98 (s, 9H, 3×CH$_3$), 3.02 (t, J=8.6 Hz, 2H), 3.68 (t, J=8.6 Hz, 2H), 6.40 (dd, J=5.2 Hz, 7.0 Hz, 1H), 7.15 (d, J=7.0 Hz, 1H), 7.80 (d, J=5.2 Hz, 1H).

To a 0° C. solution of 1-(tert-butyl-dimethyl-silanyl)-2,3-dihydro-1H-pyrrolo[2,3-b]pyridine (20 g, 85.6 mmol) and pyridine (8.4 mL) in dichloromethane (500 mL) was added dropwise to a solution of bromine (5.6 mL, 111.4 mmol) in dichloromethane (400 mL) over a period of 1 h. After stirring for 1 h at 0° C., the mixture was diluted with a mixture of saturated solutions of sodium thiosulfate-sodium bicarbonate (1:1 v/v) and stirred vigorously for 30 min. The resulting mixture was partitioned and the aqueous layer was extracted with dichloromethane. The combined organic extracts were dried over anhydrous sodium sulfate and concentrated in vacuo. The residue was purified by flash silica gel chromatography (silica gel from QingDao, 200-300 mesh, glass column from Shanghai SD company, 2% ethyl acetate/hexanes) to afford 5-bromo-1-(tert-butyl-dimethyl-silanyl)-2,3-dihydro-1H-pyrrolo[2,3-b]pyridine (22.5 g, 84%) as a light yellow oil: LC/MS m/e calcd for C$_{13}$H$_{22}$BrN$_2$Si [M+H]$^+$ 314.32, observed 313.1, 315.1; $^1$H NMR (400 MHz, CDCl$_3$) δ ppm 0.32 (s, 6H), 0.96 (s, 9H, 3×CH$_3$), 3.01 (t, J=8.7 Hz, 2H), 3.68 (t, J=8.7 Hz, 2H), 7.21 (br. s., 1H), 7.81 (br. s., 1H).

To a stirred solution of 5-bromo-1-(tert-butyl-dimethyl-silanyl)-2,3-dihydro-1H-pyrrolo[2,3-b]pyridine (17.0 g, 54.3 mmol) in dichloromethane (700 mL) was added 2,3-dichloro-5,6-dicyano-1,4-benzoquinone (12.3 g, 54.3 mmol) in one portion. After 1 h, the resulting black mixture was diluted with a saturated aqueous sodium bicarbonate solution and stirred vigorously for 30 min. The solids were filtered off and the filtrate was separated. The aqueous layer was extracted with ethyl acetate. The combined organic solutions were dried over anhydrous sodium sulfate, concentrated in vacuo to afford 5-bromo-1-(tert-butyl-dimethyl-silanyl)-1H-pyrrolo[2,3-b]pyridine (16.5 g, 97%) which was used in the next step without further purification: $^1$H NMR (400 MHz, CDCl$_3$) δ ppm 0.64 (s, 6H), 0.94 (s, 9H), 6.49 (d, J=3.4 Hz, 1H), 7.27 (d, J=3.4 Hz, 1H), 8.00 (d, J=2.3 Hz, 1H), 8.31 (d, J=2.3 Hz, 1H).

Tetrabutylammonium fluoride (1 M solution in tetrahydrofuran) (58.5 mL, 58.5 mmol) was added to a solution of 5-bromo-1-(tert-butyl-dimethyl-silanyl)-1H-pyrrolo[2,3-b] pyridine (16.5 g, 53 mmol) in tetrahydrofuran (15 mL) at 25° C. The mixture was stirred at 25° C. for 30 min and then extracted with ethyl acetate, washed with water, brine, dried over anhydrous sodium sulfate. The solvent was evaporated in vacuo to afford 5-bromo-1H-pyrrolo[2,3-b]pyridine (7.4 g, 71%) as a light yellow solid: LC/MS m/e calcd for C$_7$H$_6$BrN [M+H]$^+$ 198.04, observed 197.1, 199.1; $^1$H NMR (400 MHz, CDCl$_3$) δ ppm 6.49 (m, 1H), 7.39 (m, 1H), 8.10 (s, 1H), 8.38 (s, 1H), 10.48 (br. s., 1H).

Sodium hydroxide (4.1 g, 102.8 mmol) was added to a solution of tetrabutylammonium bromide (331 mg, 1.0 mmol) and 5-bromo-1H-pyrrolo[2,3-b]pyridine (6.7 g, 34.7 mmol) in dichloromethane (80 mL) at 0° C. The mixture was stirred at 0° C. for 5 min. Benzene sulfonyl chloride (5.7 mL, 44.5 mmol) was added to the above mixture slowly at 0° C. The resulting mixture was stirred at 0° C. for 15 min before it was warmed to 25° C. and kept stirring at that temperature for 12 h. The reaction mixture was filtered and the filtrate was concentrated in vacuo and then washed with hexanes to afford 1-benzenesulfonyl-5-bromo-1H-pyrrolo[2,3-b]pyridine as a white solid (11.8 g, 100%): LC/MS m/e calcd for C$_{13}$H$_{10}$BrN$_2$O$_2$S [M+H]$^+$ 338.20, observed 337.1, 339.1; $^1$H NMR (400 MHz, CDCl$_3$) δ ppm 6.56 (d, J=4.0 Hz, 1H), 7.51 (m, 2H), 7.60 (m, 1H), 7.75 (d, J=4.0 Hz, 1H), 7.98 (d, J=2.1 Hz, 1H), 8.18 (m, 2H), 8.45 (d, J=2.0 Hz, 1H).

A mixture of 1-benzenesulfonyl-5-bromo-1H-pyrrolo[2,3-b]pyridine (3.0 g, 8.9 mmol), tributyl-vinyl-stannane (3.9 mL, 13.55 mmol) and tetrakis(triphenylphosphine)palladium (0) (514 mg, 0.445 mmol) in N,N-dimethylformamide (10 mL) was stirred at 85° C. for 15 h. The mixture was cooled to 25° C., extracted with ethyl acetate, washed with brine, dried over anhydrous sodium sulfate and concentrated in vacuo. The residue was purified by flash silica gel chromatography (silica gel from QingDao, 200-300 mesh, glass column from Shanghai SD company, hexanes to 15% ethyl acetate/hexanes) to afford 1-benzenesulfonyl-5-vinyl-1H-pyrrolo[2,3-b] pyridine (2.2 g, 87%) as a white solid: LC/MS m/e calcd for C$_{15}$H$_{13}$N$_2$SO$_2$ [M+H]$^+$ 285.34, observed 285.2; $^1$H NMR (400 MHz, CDCl$_3$) δ ppm 5.32 (d, J=11.0 Hz, 1H), 5.78 (d, J=17.6 Hz, 1H), 6.59 (d, J=4.0 Hz, 1H), 6.77 (dd, J=11.0 Hz, J=17.6 Hz, 1H), 7.49 (m, 2H), 7.58 (m, 1H), 7.74 (d, J=4.0 Hz, 1H), 7.88 (d, J=2.0 Hz, 1H), 8.19 (m, 2H), 8.46 (d, J=2.0 Hz, 1H).

A mixture of AD-mix-β (9.9 g) and methanesulfonylamide (670 mg, 7.04 mmol) in tert-butyl alcohol/water (1:1 v/v, 120 mL) was stirred at 25° C. until it became a clear solution. The solution was then cooled to 0° C. and a solution of 1-benzenesulfonyl-5-vinyl-1H-pyrrolo[2,3-b]pyridine (2.0 g, 7.04 mmol) in tert-butyl alcohol/water (1:1 v/v, 40 mL) was slowly added. The mixture was stirred at 0° C. for 12 h. Sodium sulfite (11.2 g, 88.2 mmol) was then added at 25° C. and the mixture was stirred for 30 min until all of the salt dissolved. The mixture was then extracted with ethyl acetate, washed with brine, dried over anhydrous sodium sulfate and concentrated in vacuo to afford a single stereoisomer of 1-(1-benzenesulfonyl-pyrrolo[2,3-b]pyridine-5-yl)-ethane-1,2-diol as a colorless oil (2.1 g, 94%) which was used in the next step without purification.

A solution of 1-(1-benzenesulfonyl-pyrrolo[2,3-b]pyridine-5-yl)-ethane-1,2-diol (2.1 g, 6.61 mmol), p-toluene sulfonic acid (134 mg, 0.71 mmol) and 2,2-dimethoxy-propane (10 mL) in dichloromethane (20 mL) was stirred at 25° C. for 12 h. The solution was then concentrated in vacuo. The residue was diluted with ethyl acetate, washed with a saturated aqueous sodium bicarbonate solution, brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-benzenesulfonyl-5-(2,2-dimethyl-[1,3]dioxolan-4-yl)-1H-pyrrolo[2,3-b]pyridine (2.0 g, 85%) as a white solid: LC/MS m/e calcd for $C_{18}H_{19}N_2SO_4$ [M+H]$^+$ 359.42, observed 359.3; $^1$H NMR (400 MHz, CDCl$_3$) δ ppm 1.49 (s, 3H), 1.56 (s, 3H), 3.73 (dd, J=7.5 Hz, 8.3 Hz, 1H), 4.35 (dd, J=6.4 Hz, 8.3 Hz, 1H), 5.16 (dd, J=6.4 Hz, 7.5 Hz, 1H), 6.60 (d, J=4.0 Hz, 1H), 7.49 (m, 2H), 7.58 (m, 1H), 7.75 (d, J=4.0 Hz, 1H), 7.89 (d, J=2.0 Hz, 1H), 8.19 (d, J=7.6 Hz, 2H), 8.42 (d, J=2.0 Hz, 1H).

To a stirred solution of 1-benzenesulfonyl-5-(2,2-dimethyl-[1,3]dioxolan-4-yl)-1H-pyrrolo[2,3-b]pyridine (1.23 g, 3.44 mmol) in dry tetrahydrofuran (20 mL) at −78° C. was added freshly prepared lithium diisopropylamide [prepared by adding 1.6 M n-butyllithium in n-hexane (3.2 mL, 5.12 mmol) to a 0° C. solution of diisopropylamine (780 uL, 5.12 mmol) in dry tetrahydrofuran (10 mL)] dropwise. The mixture was stirred at −78° C. for 15 min before a solution of cyclopentanecarbaldehyde (580 mg, 5.15 mmol) was added dropwise. The mixture was stirred at −78° C. for 1 h and then quenched with brine. The mixture was extracted with ethyl acetate, washed with brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded 14'-benzenesulfonyl-5-(2,2-dimethyl-[1,3]dioxolan-4-yl)-1H-pyrrolo[2,3-b]pyridin-2-yl]-2-cyclopentyl-ethanol (610 mg, 65%) as a light yellow solid: LC/MS m/e calcd for $C_{25}H_{31}N_2SO_5$ [M+H]$^+$ 471.59, observed 471.3; $^1$H NMR (400 MHz, CDCl$_3$) δ ppm 1.25 (m, 2H), 1.48-1.75 (m, 4H), 1.49 (s, 3H), 1.56 (s, 3H), 1.80-2.17 (m, 5H, H), 3.30 (br. s., 1H), 3.71 (dd, J=7.6 Hz, 8.3 Hz, 1H), 4.33 (dd, J=6.3 Hz, 8.3 Hz, 1H), 5.14 (dd, J=6.3 Hz, 7.6 Hz, 1H), 5.36 (br, 1H), 6.63 (s, 1H), 7.47 (m, 2H), 7.57 (m, 1H), 7.81 (d, J=2.0 Hz, 1H), 8.15 (d, J=8.2 Hz, 2H), 8.37 (d, J=2.0 Hz, 1H).

A Dess-Martin periodinane solution in dichloromethane (0.3 M, 9 mL, 2.7 mmol) was added to 1-[1-benzenesulfonyl-5-(2,2-dimethyl-[1,3]dioxolan-4-yl)-1H-pyrrolo[2,3-b]pyridin-2-yl]-2-cyclopentyl-ethanol (610 mg, 1.3 mmol) at 25° C. and then stirred for 1 h. The reaction was quenched with saturated aqueous sodium bicarbonate. The mixture was extracted with ethyl acetate, washed with a saturated aqueous sodium bicarbonate solution (3×20 mL), brine, dried over anhydrous sodium sulfate and concentrated in vacuo to afford 1-[1-benzenesulfonyl-5-(2,2-dimethyl-[1,3]dioxolan-4-yl)-1H-pyrrolo[2,3-b]pyridin-2-yl]-2-cyclopentyl-ethanone (600 mg crude) as a light yellow solid which was used in the next step without further purification: $^1$H NMR (400 MHz, CDCl$_3$) δ ppm 1.26 (m, 2H), 1.57-1.73 (m, 4H), 1.52 (s, 3H), 1.59 (s, 3H), 1.96 (m, 2H), 2.44 (m, 1H), 3.03 (d, J=7.2 Hz, 2H), 3.74 (dd, J=7.6 Hz, 8.4 Hz, 1H), 4.39 (dd, J=6.4 Hz, 8.4 Hz, 1H), 5.19 (dd, J=6.4 Hz, 7.6 Hz, 1H), 6.94 (s, 1H), 7.55 (m, 2H), 7.62 (m, 1H), 7.93 (d, J=2.0 Hz, 1H), 8.39 (d, J=7.6 Hz, 2H), 8.56 (d, J=2.0 Hz, 1H).

To a −78° C. solution of 1-[1-benzenesulfonyl-5-(2,2-dimethyl-[1,3]dioxolan-4-yl)-1H-pyrrolo[2,3-b]pyridin-2-yl]-2-cyclopentyl-ethanone (600 mg, 1.28 mmol) in dry tetrahydrofuran (30 mL) was added lithium bis(trimethylsilyl)amide (2.0 ml, 1.9 mmol) and the mixture was stirred for 45 min at −78° C. before a solution of p-toluenesulfonic anhydride (775 mg, 2.37 mmol) in dry tetrahydrofuran (5 mL) was added. The mixture was stirred at −78° C. for 1 h and then quenched with brine. The mixture was extracted with ethyl acetate, washed with brine, dried over anhydrous sodium sulfate and concentrated in vacuo to afford toluene-4-sulfonic acid 1-[1-benzenesulfonyl-5-(2,2-dimethyl-[1,3]dioxolan-4-yl)-1H-pyrrolo[2,3-b]pyridin-2-yl]-2-cyclopentyl-vinyl ester (621 mg, 78% two steps) as a light yellow solid which was used in the next step without purification.

To a mixture of toluene-4-sulfonic acid 1-[1-benzenesulfonyl-5-(2,2-dimethyl-[1,3]dioxolan-4-yl)-1H-pyrrolo[2,3-b]pyridin-2-yl]-2-cyclopentyl-vinyl ester (620 mg, 1 mmol), bis(triphenylphosphine)palladium(II) chloride (70.1 mg, 0.1 mmol) and 4-(methanesulfonyl)phenylboronic acid (460 mg, 2.3 mmol) in dioxane (6 mL) was added a 2M sodium carbonate solution (1.5 mL) at 25° C. The mixture was subjected to microwave irradiation for 1.5 h at 100° C. The mixture was cooled to 25° C., extracted with ethyl acetate, washed with brine and dried over anhydrous sodium sulfate. Purification by flash silica gel chromatography (silica gel from QingDao, 200-300 mesh, glass column from Shanghai SD company, 30% ethyl acetate/hexanes) afforded 1-benzenesulfonyl-2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (510 mg, 85%) as a light yellow solid: LC/MS m/e calcd for $C_{32}H_{35}N_2S_2O_6$ [M+H]$^+$ 607.77, observed 607.3; $^1$H NMR (400 MHz, CDCl$_3$) δ ppm 1.47-1.62 (m, 4H), 1.52 (s, 3H), 1.60 (s, 3H), 1.71-1.98 (m, 4H), 2.68 (m, 1H), 3.07 (s, 3H), 3.80 (m, 1H), 4.40 (dd, J=6.3 Hz, 8.3 Hz, 1H), 5.22 (m, 1H), 6.35 (d, J=10.1 Hz, 1H), 6.58 (s, 1H), 7.29 (m, 2H), 7.37, 7.39 (2d, J=8.6 Hz, 2H), 7.49 (t, J=7.5 Hz, 1H), 7.74 (m, 2H), 7.78, 7.79 (2d, J=8.6 Hz, 2H), 7.96, 7.97 (2d, J=2.1 Hz, 1H), 8.50, 8.51 (2d, J=2.1 Hz, 1H).

A mixture of 1-benzenesulfonyl-2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (510 mg, 0.85 mmol), a 10% aqueous sodium hydroxide solution (1 mL) and ethanol (8 mL) was heated at 100° C. for 1 h. The mixture was cooled to 25° C., extracted with ethyl acetate, washed with water, brine, dried over anhydrous sodium sulfate and concentrated in vacuo to afford 2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (320 mg, 81%) as a light yellow oil which was used in the next step without purification.

A mixture of 2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (320 mg, 0.69 mmol) and 10% palladium on activated carbon (100 mg) in methanol (250 mL) was heated at 50° C. under 50 bar of hydrogen in a steel bomb for 12 h. The mixture was cooled to 25° C., the solids were removed by filtration, and then washed with ethyl acetate and the filtrate concentrated in vacuo to afford a diastereomeric mixture of 2-[2-cyclopentyl-1-(4-methanesulfonyl-phenyl)-ethyl]-5-(2,2-dimethyl-[1,3]dioxolan-4-yl)-1H-pyrrolo[2,3-b]pyridine (260 mg, 81%) which was used in the next step without purification.

A diastereomeric mixture of 2-[2-cyclopentyl-1-(4-methanesulfonyl-phenyl)-ethyl]-5-(2,2-dimethyl-[1,3]dioxolan-4-yl)-1H-pyrrolo[2,3-b]pyridine (260 mg, 0.56 mmol) and 6N hydrochloric acid (1 mL) in tetrahydrofuran (10 mL) was heated at 80° C. for 1 h. The mixture was cooled to 25° C., extracted with ethyl acetate, washed with a saturated aqueous sodium bicarbonate solution, brine, dried over anhydrous sodium sulfate and concentrated in vacuo. Purification using a Waters autopurification system (column: Xterra 30 mm×100 mm) afforded a diastereomeric mixture of 1-{2-[2-cyclopentyl-1-(4-methanesulfonyl-phenyl)-ethyl]-1H-pyrrolo[2,3-b]pyridin-5-yl}-ethane-1,2-diol (140 mg, 59%) as a white solid: LC/MS m/e calcd for $C_{23}H_{29}N_2SO_4$ $[M+H]^+$ 428.55, observed 429.2; $^1$H NMR (400 MHz, CDCl$_3$) δ ppm 1.22 (m, 2 H), 1.47 (m, 2H), 1.57-1.86 (m, 5H, H), 2.10 (m, 1H), 2.26 (m, 1H), 3.07 (s, 3H), 3.68 (m, 2 H), 4.30 (t, J=7.9 Hz, 1H), 4.79 (dd, J=5.1 Hz, 7.0 Hz, 1H), 6.38 (s, 1H), 7.58 (d, J=8.3 Hz, 2 H), 7.88 (d, J=8.3 Hz, 2H), 7.92 (s, 1H), 8.12 (s, 1H).

Example 8

{2-[2-Cyclopentyl-1-(4-methanesulfonyl-phenyl)-ethyl]-1H-pyrrolo[2,3-b]pyridin-5-yl}-methanol

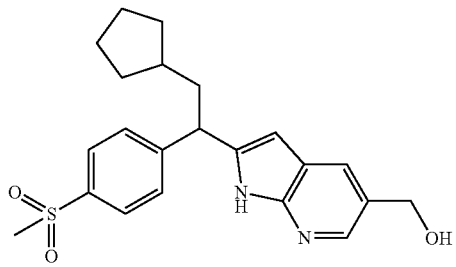

A mixture of AD-mix-α (14.9 g) and methanesulfonyl amide (1 g, 10.6 mmol) in tert-butyl alcohol/water (1:1 v/v, 160 mL) was stirred at 25° C. until it became a clear solution. The solution was stirred and cooled to 0° C. and a solution of 1-benzenesulfonyl-5-vinyl-1H-pyrrolo[2,3-b]pyridine (prepared as in Example 7, 3 g, 10.6 mmol) in tert-butyl alcohol/water (1:1 v/v, 80 mL) was slowly added. The mixture was stirred at 0° C. for 12 h. Sodium sulfite (16 g, 126.8 mmol) was then added at 25° C. and the mixture was stirred for 30 min until all of salt was dissolved. The mixture was extracted with ethyl acetate, washed with brine, dried over anhydrous sodium sulfate and concentrated in vacuo to afford a single stereoisomer of 1-(1-benzenesulfonyl-pyrrolo[2,3-b]pyridine-5-yl)-ethane-1,2-diol as a colorless oil (3 g, 89%) which was used in the next step without purification: $^1$H NMR (400 MHz, CDCl$_3$) δ ppm 2.72 (br, 2H), 3.69 (dd, J=8.0 Hz, 11.2 Hz, 1H), 3.81 (dd, J=3.4 Hz, 11.2 Hz, 1H), 4.94 (dd, J=3.4 Hz, 8.0 Hz, 1H), 6.60 (d, J=4.0 Hz, 1H), 7.49 (m, 2H), 7.58 (m, 1H), 7.74 (d, J=4.0 Hz, 1H), 7.91 (d, J=1.9 Hz, 1H), 8.19 (d, J=7.8 Hz, 2H), 8.40 (d, J=1.9 Hz, 1H).

A solution of 1-(1-benzenesulfonyl-pyrrolo[2,3-b]pyridine-5-yl)-ethane-1,2-diol (3 g, 9.43 mmol), p-toluene sulfonic acid (160 mg, 0.84 mmol) and 2,2-dimethoxy-propane (10 mL) in dichloromethane (20 mL) was stirred at 25° C. for 12 h. The solution was concentrated in vacuo. The residue was diluted with ethyl acetate, washed with a saturated aqueous sodium bicarbonate solution, brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-benzenesulfonyl-5-(2,2-dimethyl-[1,3]dioxolan-4-yl)-1H-pyrrolo[2,3-b]pyridine (2.8 g, 83%) as a white solid: LC/MS m/e calcd for $C_{18}H_{19}N_2SO_4$ $[M+H]^+$ 359.42, observed 359.3; $^1$H NMR (400 MHz, CDCl$_3$) δ ppm 1.49 (s, 3H), 1.56 (s, 3H), 3.73 (dd, J=7.5 Hz, 8.3 Hz, 1H), 4.35 (dd, J=6.4 Hz, 8.3 Hz, 1H), 5.16 (dd, J=6.4 Hz, 7.5 Hz, 1H), 6.60 (d, J=4.0 Hz, 1H), 7.49 (m, 2H), 7.58 (m, 1H), 7.75 (d, J=4.0 Hz, 1H), 7.89 (d, J=2.0 Hz, 1H), 8.19 (d, J=7.6 Hz, 2H), 8.42 (d, J=2.0 Hz, 1H).

To a stirred solution of 1-benzenesulfonyl-5-(2,2-dimethyl-[1,3]dioxolan-4-yl)-1H-pyrrolo[2,3-b]pyridine (2 g, 5.59 mmol) in dry tetrahydrofuran (30 mL) at −78° C. was added freshly prepared lithium diisopropylamide [prepared by adding 1.6 M n-butyllithium in n-hexane (5.24 mL, 8.39 mmol) to a 0° C. solution of diisopropylamine (1.3 mL, 9.2 mmol) in dry tetrahydrofuran (15 mL)] dropwise. The mixture was stirred at −78° C. for 15 min and then a solution of cyclopentanecarbaldehyde (940 mg, 8.38 mmol) was added dropwise. The mixture was stirred at −78° C. for 1 h then quenched with brine. The mixture was extracted with ethyl acetate, washed with brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded 1-[1-benzenesulfonyl-5-(2,2-dimethyl-[1,3]dioxolan-4-yl)-1H-pyrrolo[2,3-b]pyridin-2-yl]-2-cyclopentyl-ethanol (1.7 g, 66%) as a white solid: LC/MS m/e calcd for $C_{25}H_{31}N_2SO_5$ $[M+H]^+$ 471.59, observed 471.3; $^1$H NMR (400 MHz, CDCl$_3$) δ ppm 1.25 (m, 2H), 1.48-1.75 (m, 4H), 1.49 (s, 3H), 1.56 (s, 3H), 1.80-2.17 (m, 5H, H), 3.30 (br. s., 1H), 3.71 (dd, J=7.6 Hz, 8.3 Hz, 1H), 4.33 (dd, J=6.3 Hz, 8.3 Hz, 1H), 5.14 (dd, J=6.3 Hz, 7.6 Hz, 1H), 5.36 (br, 1H), 6.63 (s, 1H), 7.47 (m, 2H), 7.57 (m, 1H), 7.81 (d, J=2.0 Hz, 1H), 8.15 (d, J=8.2 Hz, 2H), 8.37 (d, J=2.0 Hz, 1H).

A Dess-Martin periodinane solution in dichloromethane (0.3 M, 35 mL, 10.5 mmol) was added to 1-[1-benzenesulfonyl-5-(2,2-dimethyl-[1,3]dioxolan-4-yl)-1H-pyrrolo[2,3-b]pyridin-2-yl]-2-cyclopentyl-ethanol (1.7 g, 4.62 mmol) at 25° C. and then stirred for 1 h. The reaction was quenched with saturated aqueous sodium bicarbonate. The mixture was extracted with ethyl acetate, washed with a saturated aqueous sodium bicarbonate (3×30 mL), brine, dried over anhydrous sodium sulfate and concentrated in vacuo to afford 1-[1-benzenesulfonyl-5-(2,2-dimethyl-[1,3]dioxolan-4-yl)-1H-pyrrolo[2,3-b]pyridin-2-yl]-2-cyclopentyl-ethanone (2.3 g crude) as a light yellow solid which was used in the next step without further purification: LC/MS m/e calcd for $C_{25}H_{28}N_2O_5S$ $[M+H]^+$ 469.58, observed 469.2; $^1$H NMR (400 MHz, CDCl$_3$) δ ppm 1.26 (m, 2H), 1.57-1.73 (m, 4H), 1.52 (s, 3H), 1.59 (s, 3H), 1.96 (m, 2H), 2.44 (m, 1 H), 3.03 (d, J=7.2 Hz, 2H), 3.74 (dd, J=7.6 Hz, 8.4 Hz, 1H), 4.39 (dd, J=6.4 Hz, 8.4 Hz, 1H), 5.19 (dd, J=6.4 Hz, 7.6 Hz, 1H), 6.94 (s, 1H), 7.55 (m, 2H), 7.62 (m, 1H), 7.93 (d, J=2.0 Hz, 1H), 8.39 (d, J=7.6 Hz, 2H), 8.56 (d, J=2.0 Hz, 1H).

To a −78° C. solution of 1-[1-benzenesulfonyl-5-(2,2-dimethyl-[1,3]dioxolan-4-yl)-1H-pyrrolo[2,3-b]pyridin-2-yl]-2-cyclopentyl-ethanone (2.3 g, 4.92 mmol) in dry tetrahydrofuran (50 mL) was added lithium bis(trimethylsilyl)amide (7.7 ml, 7.7 mmol) and the mixture was stirred for 45 min at −78° C. then a solution of p-toluenesulfonic anhydride (3 g, 9.2 mmol) in dry tetrahydrofuran (15 mL) was added. The mixture was stirred at −78° C. for 1 h and then quenched with brine. The mixture was extracted with ethyl acetate, washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afford toluene-4-sulfonic acid 1-[1-benzenesulfonyl-5-(dimethyl-[1,3]dioxolan-4-yl)-1H-pyrrolo[2,3-b]pyridin-2-yl]-2-cyclopentyl-vinyl ester (2.4 g, 76%) as a white solid: LC/MS m/e calcd for $C_{32}H_{34}N_2O_7S_2$ $[M+H]^+$ 623.76, observed 623.3.

To a mixture of toluene-4-sulfonic acid 1-[1-benzenesulfonyl-5-(2,2-dimethyl-[1,3]dioxolan-4-yl)-1H-pyrrolo[2,3-b]pyridin-2-yl]-2-cyclopentyl-vinyl ester (1.7 g, 2.7 mmol), bis(triphenylphosphine)palladium(II) chloride (190 mg, 0.27 mmol) and 4-(methanesulfonyl)phenylboronic acid (1.1 g, 5.5 mmol) in dioxane (10 mL) was added a 2M sodium carbonate solution (3.4 mL) at 25° C. The mixture was subjected to microwave irradiation for 1.5 h at 100° C. The mixture was cooled to 25° C., extracted with ethyl acetate, washed with brine and dried over anhydrous sodium sulfate. Purification by flash silica gel chromatography (silica gel from QingDao, 200-300 mesh, glass column from Shanghai SD company, 30% ethyl acetate/hexanes) afforded 1-benzenesulfonyl-2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (1.1 g, 67.2%) as a yellow solid: LC/MS m/e calcd for $C_{32}H_{35}N_2S_2O_6$ [M+H]$^+$ 607.77, observed 607.3; $^1$H NMR (400 MHz, CDCl$_3$) δ ppm 1.47-1.62 (m, 4H), 1.52 (s, 3H), 1.60 (s, 3H), 1.71-1.98 (m, 4H), 2.68 (m, 1H), 3.07 (s, 3H), 3.80 (m, 1H), 4.40 (dd, J=6.3 Hz, 8.3 Hz, 1H), 5.22 (m, 1H), 6.35 (d, J=10.1 Hz, 1H), 6.58 (s, 1H), 7.29 (m, 2H), 7.37, 7.39 (2d, J=8.6 Hz, 2H), 7.49 (t, J=7.5 Hz, 1H), 7.74 (m, 2H), 7.78, 7.79 (2d, J=8.6 Hz, 2H), 7.96, 7.97 (2d, J=2.1 Hz, 1H), 8.50, 8.51 (2d, J=2.1 Hz, 1H).

A mixture of 1-benzenesulfonyl-2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (950 mg, 1.57 mmol), ethanol (3 mL), and a 10% aqueous sodium hydroxide solution (1.5 mL) was heated at 100° C. for 1 h. The mixture was acidified to pH 4-5 with a 2N aqueous hydrochloric acid solution, diluted with ethyl acetate (150 mL), washed with brine, dried over anhydrous sodium sulfate and then concentrated in vacuo to give 2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (700 mg, 96%) as a light yellow solid: LC/MS m/e calcd for $C_{26}H_{30}N_2O_4S$ [M+H]$^+$ 467.6, observed 467.1.

A mixture of 2-[2-cyclopentyl-1-(4-methanesulfonyl-phenyl)-vinyl]-5-(2,2-dimethyl-[1,3]dioxolan-4-yl)-1H-pyrrolo[2,3-b]pyridine (700 mg, 1.54 mmol) and 10% palladium on activated carbon (200 mg) in methanol (250 mL) was heated at 50° C. under hydrogen (50 psi) for 8 h. The mixture was cooled to room temperature, the catalyst was removed by filtration and washed with ethyl acetate. The filtrate was concentrated in vacuo to afford a diastereomeric mixture of 2-[2-cyclopentyl-1-(4-methanesulfonyl-phenyl)-ethyl]-5-(2,2-dimethyl-[1,3]dioxolan-4-yl)-1H-pyrrolo[2,3-b]pyridine (400 mg, 57%) as a white solid which was used without further purification: LC/MS m/e calcd for $C_{26}H_{32}N_2O_4S$ [M+H]$^+$ 469.62, observed 469.5.

The diastereomeric mixture of 2-[2-cyclopentyl-1-(4-methanesulfonyl-phenyl)-ethyl]-5-(2,2-dimethyl-[1,3]dioxolan-4-yl)-1H-pyrrolo[2,3-b]pyridine (400 mg, 0.86 mmol) and 6N HCl (1 mL) in tetrahydrofuran (5 mL) was heated at reflux for 1 h, cooled to room temperature and extracted with ethyl acetate and then washed with a saturated aqueous sodium bicarbonate solution, brine, and dried over anhydrous sodium sulfate. The mixture was filtered and the solvent was evaporated in vacuo to afford a diastereomeric mixture of 1-{2-[2-cyclopentyl-1-(4-methanesulfonyl-phenyl)-ethyl]-1H-pyrrolo[2,3-b]pyridin-5-yl}-ethane-1,2-diol (366 mg, quant.) as white solid: LC/MS m/e calcd for $C_{23}H_{29}N_2SO_4$ [M+H]$^+$ 429.55, observed 429.2; $^1$H NMR (400 MHz, CDCl$_3$) δ ppm 1.16 (m, 2H), 1.46 (m, 2H), 1.55-1.82 (m, 5H, H), 1.95-2.28 (brm, 4 H), 3.02 (s, 3H), 3.61-3.76 (m, 2H), 4.21 (t, J=7.8 Hz, 1H), 4.86 (dd, J=3.6 Hz, 8.1 Hz, 1H), 6.32 (s, 1H), 7.47 (d, J=8.2 Hz, 2H), 7.84 (d, J=8.2 Hz, 2H), 7.89 (s, 1H), 8.05 (br. s., 1H), 10.40 (br, 1H).

To a stirred solution of a diastereomeric mixture of 1-{2-[2-cyclopentyl-1-(4-methanesulfonyl-phenyl)-ethyl]-1H-pyrrolo[2,3-b]pyridin-5-yl}-ethane-1,2-diol (366 mg, 0.86 mmol) in 50% aqueous tetrahydrofuran (10 mL) was added sodium metaperiodate (366 mg, 1.71 mmol) at 0° C. The resulting mixture was stirred at room temperature for 2 h and extracted with ethyl acetate and washed with brine, dried over anhydrous sodium sulfate. The solvent was evaporated in vacuo to give 2-[2-cyclopentyl-1-(4-methanesulfonyl-phenyl)-ethyl]-1H-pyrrolo[2,3-b]pyridin-5-carbaldehyde (340 mg, quant.) as a light yellow solid: LC/MS m/e calcd for $C_{22}H_{24}N_2OS$ [M+H]$^+$ 397.51, observed 397.0.

To a stirred solution of 2-[2-cyclopentyl-1-(4-methanesulfonyl-phenyl)-ethyl]-1H-pyrrolo[2,3-b]pyridin-5-carbaldehyde (104 mg, 0.26 mmol) in dry methanol (5 mL) was added sodium borohydride (40 mg, 1.05 mmol) at 0° C. The resulting mixture was stirred at room temperature for 2 h and then quenched with a saturated ammonium chloride solution, extracted with ethyl acetate and washed with brine, dried over anhydrous sodium sulfate. The solvent was evaporated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded {2-[2-cyclopentyl-1-(4-methanesulfonyl-phenyl)-ethyl]-1H-pyrrolo[2,3-b]pyridin-5-yl}-methanol (85 mg, 81%) as a white solid: LC/MS m/e calcd for $C_{22}H_{26}N_2O_3S$ [M+H]$^+$ 399.53, observed 399.1; $^1$H NMR (400 MHz, CDCl$_3$) δ ppm 1.18 (m, 2H), 1.48 (m, 2H), 1.56-1.87 (m, 5H, H), 2.13 (m, 1H), 2.24 (m, 1H), 3.04 (s, 3H), 3.59 (br, 1H), 4.30 (t, J=7.7 Hz, 1H), 4.08 (s, 2H), 6.41 (s, 1H), 7.50 (d, J=8.2 Hz, 2H), 7.87 (d, J=8.2 Hz, 2H), 8.02 (s, 1H), 8.14 (br. s., 1H), 10.80 (br, 1H).

Example 9

1-{2-[2-Cyclopentyl-1-(4-methanesulfonyl-phenyl)-ethyl]-1H-pyrrolo[2,3-b]pyridin-5-yl}-ethanol diastereomer 1

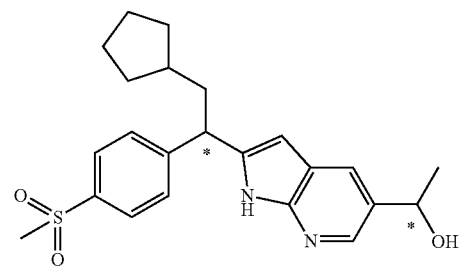

To a stirred solution of 2-[2-cyclopentyl-1-(4-methanesulfonyl-phenyl)-ethyl]-1H-pyrrolo[2,3-b]pyridin-5-carbaldehyde (prepared as in Example 8, 240 mg, 0.61 mmol) in dry tetrahydrofuran (5 mL) was added methylmagnesium chloride (3 M, 0.3 mL, 0.9 mmol) at 0° C. The resulting mixture was stirred at room temperature for 2 h and quenched with a saturated aqueous ammonium chloride solution, extracted with ethyl acetate and washed with brine, and dried over anhydrous sodium sulfate. The solvent was evaporated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded a mixture of four stereoisomers of 1-{2-[2-cyclopentyl-1-(4-methanesulfonyl-phenyl)-ethyl]-1H-pyrrolo[2,3-b]pyridin-5-yl}-ethanol (125 mg, 50%) as a white solid: LC/MS m/e calcd for $C_{23}H_{28}N_2O_3S$ [M+H]$^+$ 413.58, observed 413.3

The mixture of four stereoisomers of 1-{2-[2-cyclopentyl-1-(4-methanesulfonyl-phenyl)-ethyl]-1H-pyrrolo[2,3-b]pyridin-5-yl}-ethanol (100 mg) were separated by Agilent high performance liquid chromatography (chiral column: Daicel IA-H, 250 mm×20 mm i. d., 5 μm-particle size, temperature: 25° C., flow rate of 15 mL/min, 60% ethanol/hexanes as mobile phase and UV detection: 214 and 254 nm) to afford the pure stereoisomers of 1-{2-[2-cyclopentyl-1-(4-methanesulfonyl-phenyl)-ethyl]-1H-pyrrolo[2,3-b]pyridin-5-yl}-ethanol. The first peak, diastereomer 1 (8 mg) was isolated as a white solid: $^1$H NMR (400 MHz, CDCl$_3$) δ ppm 1.14-1.26 (m, 2H), 1.43-1.86 (m, 7H), 1.59 (d, J=6.5 Hz, 3H), 2.13 (m, 1H), 2.27 (m, 1H), 2.39 (br, 1H), 3.05 (s, 3H), 4.28 (t, J=7.8 Hz, 1H), 5.06 (q, J=6.5 Hz, 1H), 6.39 (s, 1H), 7.49 (d, J=8.3 Hz, 2H), 7.88 (d, J=8.3 Hz, 2H), 7.94 (d, J=1.9 Hz, 1H), 8.13 (d, J=1.9 Hz, 1H), 10.30 (br, 1H).

Example 10

2-[2-Cyclohexyl-1(R)-(4-methanesulfonyl-phenyl)-ethyl]-5-methoxy-1H-pyrrolo[2,3-b]pyridine

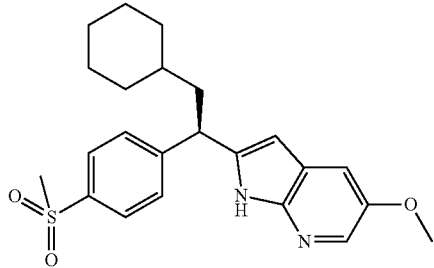

To a solution of 5-bromo-1H-pyrrolo[2,3-b]pyridine (prepared as in Example 7, 10 g, 50.8 mmol) in N,N-dimethylformamide (200 mL) and methanol (150 mL) at 25° C. was added sodium (100 g, 185.1 mmol) and copper(I) bromide (14.56 g, 101.5 mmol) under a nitrogen atmosphere. The mixture was then heated at reflux for 5 h. After cooling, the solvent was removed under reduced pressure and the residue was extracted with ethyl acetate (3×300 mL), and washed with a saturated aqueous ammonium chloride solution, brine, and dried over anhydrous sodium sulfate. The solvent was evaporated in vacuo to afford 5-methoxy-1H-pyrrolo[2,3-b]pyridine (5.8 g, 77.3%) as a light yellow solid: LC/MS m/e calcd for $C_8H_8N_2O$ [M+H]$^+$ 149.17, observed 149.3.

To a solution of tetrabutylammonium bromide (1.05 g, 3.24 mmol) and 5-methoxy-1H-pyrrolo[2,3-b]pyridine (16 g, 108.1 mmol) in dichloromethane (300 mL) at 0° C. was added powdered sodium hydroxide (13 g, 324.3 mmol). The mixture was then stirred at 0° C. for 5 min. Then benzene sulfonyl chloride (18 mL, 140.54 mmol) was added to the above mixture slowly and the resulting mixture was stirred at 0° C. for 15 min before it was warmed to room temperature and stirred for 12 h. The mixture was filtered and the filtrate concentrated in vacuo and then washed with hexane to afford 1-benzenesulfonyl-5-methoxy-1H-pyrrolo[2,3-b]pyridine (28.8 g, 93%) as a white solid: LC/MS m/e calcd for $C_{14}H_{12}N_2O_3S$ [M+H]$^+$ 289.33, observed 289.0.

To a suspension of 1-benzenesulfonyl-5-methoxy-1H-pyrrolo[2,3-b]pyridine (0.45 g, 1.56 mmol) in dry tetrahydrofuran (20 mL) at −78° C. was added freshly prepared lithium diisopropylamide [prepared by adding 1.6 M n-butyllithium in n-hexane (1.5 mL, 2.34 mmol) to a 0° C. solution of diisopropylamine (0.35 mL, 2.48 mmol) in dry tetrahydrofuran (10 mL)] dropwise. The mixture was stirred at −78° C. for 5 min and then treated with cyclohexanecarbaldehyde (353.8 mg, 2.81 mmol) dropwise. The resulting mixture was stirred at −78° C. for 1 h and then quenched with brine. The mixture was extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded 1-(1-benzenesulfonyl-5-methoxy-1H-pyrrolo[2,3-b]pyridin-2-yl)-2-cyclohexyl-ethanol (240 mg, 37.2%) as a white solid: LC/MS m/e calcd for $C_{22}H_{26}N_2O_4S$ [M+H]$^+$ 415.53, observed 415.3.

To a 250 mL round bottomed flask charged with 1-(1-benzenesulfonyl-5-methoxy-1H-pyrrolo[2,3-b]pyridin-2-yl)-2-cyclohexyl-ethanol (240 mg, 0.58 mmol) was added a solution of Dess-Martin periodinane in dichloromethane (0.3 M, 3.86 mL, 1.16 mmol) at 25° C. The reaction mixture was stirred at 25° C. for 1 h and then quenched with a saturated aqueous sodium bicarbonate solution (60 mL). The mixture was extracted with ethyl acetate (250 mL), washed with a saturated aqueous sodium bicarbonate solution (3×50 mL), brine, dried over anhydrous sodium sulfate and then concentrated in vacuo to give 1-(1-benzenesulfonyl-5-methoxy-1H-pyrrolo[2,3-b]pyridin-2-yl)-2-cyclohexyl-ethanone (240 mg, quant.) as a light yellow solid which was used in the next step without further purification: LC/MS m/e calcd for $C_{22}H_{24}N_2O_4S$ [M+H]$^+$ 413.51, observed 413.1.

To a solution of 1-(1-benzenesulfonyl-5-methoxy-1H-pyrrolo[2,3-b]pyridin-2-yl)-2-cyclohexyl-ethanone (240 mg, 0.58 mmol) in dry tetrahydrofuran (20 mL) at −78° C. was added lithium bis(trimethylsilyl)amide (1 M in tetrahydrofuran, 0.9 mL, 0.9 mmol) dropwise. After stirring at −78° C. for 1 h, a solution of p-toluenesulfonic anhydride (322 mg, 0.98 mmol) in tetrahydrofuran (10 mL) was added dropwise. The resulting mixture was kept at −78° C. for another 1.5 h. The reaction was quenched with water, extracted with ethyl acetate (300 mL), washed with brine, dried over anhydrous sodium sulfate and then concentrated in vacuo to afford toluene-4-sulfonic acid 1-(1-benzenesulfonyl-5-methoxy-1H-pyrrolo[2,3-b]pyridin-2-yl)-2-cyclohexyl-vinyl ester as a light yellow solid (330 mg, quant.) which was used in the next step without further purification: LC/MS m/e calcd for $C_{29}H_{30}N_2O_6S_2$ [M+H]$^+$ 567.7, observed 567.4.

To a mixture of 1-(1-benzenesulfonyl-5-methoxy-1H-pyrrolo[2,3-b]pyridin-2-yl)-2-cyclohexyl-vinyl ester (330 mg, 0.58 mmol), 4-(methanesulfonyl)phenylboronic acid (232 mg, 1.16 mmol), dichlorobis(triphenylphosphine)palladium (II) (41 mg, 0.06 mmol) in dioxane (2 mL) was added a aqueous sodium carbonate solution (2 M, 0.6 mL, 1.2 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 33% ethyl acetate/hexanes) afforded 1-benzenesulfonyl-2-[2-cyclohexyl-1-(4-methanesulfonyl-phenyl)-vinyl]-5-methoxy-1H- pyrrolo[2,3-b]pyridine (130 mg, 33.3%) as a light yellow solid: LC/MS m/e calcd for $C_{29}H_{30}N_2O_5S_2$ [M+H]+ 551.70, observed 551.3.

A solution of 1-benzenesulfonyl-2-[2-cyclohexyl-1-(4-methanesulfonyl-phenyl)-vinyl]-5-methoxy-1H-pyrrolo[2,3-b]pyridine (130 mg, 0.24 mmol) in tetrahydrofuran (0.5 mL) and a tetrabutylammonium fluoride solution in tetrahydrofuran (1 M, 2 mL, 2 mmol) was stirred at room temperature for 12 h. The mixture was then diluted with ethyl acetate (150 mL) and washed with a saturated aqueous ammonium chloride solution, brine, dried over anhydrous sodium sulfate and then concentrated in vacuo to afford 2-[2-cyclohexyl-1-(4-methanesulfonyl-phenyl)-vinyl]-5-methoxy-1H-pyrrolo[2,3-b]pyridine (80 mg, 82.6%) as a white solid: LC/MS m/e calcd for $C_{23}H_{26}N_2O_3S$ [M+H]+ 411.54, observed 411.2.

A mixture of 2-[2-cyclohexyl-1-(4-methanesulfonyl-phenyl)-vinyl]-5-methoxy-1H-pyrrolo[2,3-b]pyridine (80 mg, 0.19 mmol) and 10% palladium on activated carbon (50 mg) in methanol (200 mL) was heated at 50° C. under hydrogen (50 psi) for 6 h. The mixture was cooled to room temperature, the catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclohexyl-1-(4-methanesulfonyl-phenyl)-ethyl]-5-methoxy-1H-pyrrolo[2,3-b]pyridine (60 mg, 75%) as a light yellow solid: LC/MS m/e calcd for $C_{23}H_{28}N_2O_3S$ [M+H]+ 413.56, observed 413.3.

The 1:1 mixture of enantiomers of 2-[2-cyclohexyl-1-(4-methanesulfonyl-phenyl)-ethyl]-5-methoxy-1H-pyrrolo[2,3-b]pyridine (50 mg) were separated by Agilent high performance liquid chromatography (chiral column: Daicel OJ-H, 250 mm×20 mm i. d., 5 μm-particle size, temperature: 25° C., flow rate of 20 mL/min, 30% isopropanol/hexanes as mobile phase and UV detection: 214 and 254 nm) to afford two separate enantiomers. The first peak, 2-[2-cyclohexyl-1(R)-(4-methanesulfonyl-phenyl)-ethyl]-5-methoxy-1H-pyrrolo[2,3-b]pyridine (10 mg), was isolated as light yellow solid: $^1$H NMR (400 MHz, CDCl$_3$) δ ppm 0.92-1.05 (m, 2H), 1.06-1.23 (m, 4H), 1.60-1.76 (m, 4H, CH and 3×CH of 2×CH$_2$), 1.82 (m, 1H), 1.86-1.96 (m, 1H), 2.05-2.15 (m, 1H), 3.04 (s, 3H), 3.88 (s, 3H), 4.33 (t, J=7.7 Hz, 1H), 6.29 (s, 1H), 7.41 (s, 1H), 7.46 (d, J=8.3 Hz, 2H), 7.87 (d, J=8.3 Hz, 2H), 7.90 (s, 1H), 9.69 (s, 1H).

Example 11

3-{2-[2-Cyclopentyl-1-(4-methanesulfonyl-phenyl)-ethyl]-1H-pyrrolo[2,3-b]pyridin-5-yl}-propane-1,2-diol

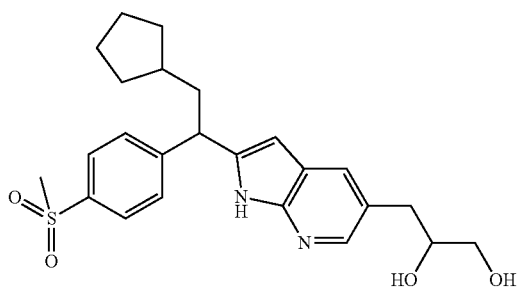

To a solution of 1-benzenesulfonyl-5-bromo-1H-pyrrolo[2,3-b]pyridine (prepared as in Example 7) (10 g, 29.7 mmol) in N,N-dimethylformamide (20 mL) was added allyltributylstannane (14 mL, 44.51 mmol), and tetrakis(triphenylphosphine)palladium(0) (1.72 g, 1.49 mmol) at room temperature and then stirred at 80° C. for 12 h. The mixture was cooled to room temperature and extracted with ethyl acetate (2×250 mL), washed with brine, dried over anhydrous sodium sulfate and concentrated in vacuo. Purification by flash silica gel chromatography (silica gel from QingDao, 200-300 mesh, glass column from Shanghai SD company, 33% ethyl acetate/hexanes) afforded 5-allyl-1-benzenesulfonyl-1H-pyrrolo[2,3-b]pyridine as a white solid (5.3 g, 60%): LC/MS m/e calcd for $C_{16}H_{14}N_2O_2S$ [M+H]+ 299.37, observed 299.1.

A mixture of AD-mix-α (7.06 g) and methanesulfonyl amide (479 mg, 5.03 mmol) in tert-butyl alcohol/water (1:1 v/v, 160 mL) was stirred at 25° C. until it became a clear solution. The solution was then cooled to 0° C. and then a solution of 5-allyl-1-benzenesulfonyl-1H-pyrrolo[2,3-b]pyridine (1.5 g, 5.03 mmol) in tert-butyl alcohol/water (1:1 v/v, 80 mL) was slowly added. The mixture was stirred at 0° C. for 12 h. Sodium sulfite (7.6 g, 60.4 mmol) was then added at 25° C. and the mixture was stirred for 30 min until all of the salt was dissolved. The mixture was extracted with ethyl acetate, washed with brine, dried over anhydrous sodium sulfate and concentrated in vacuo to afford a stereoisomeric mixture 3-(1-benzenesulfonyl-pyrrolo[2,3-b]pyridine-5-yl)-propane-1,2-diol as a white solid (1.68 g, quant.) which was used in the next step without purification: LC/MS m/e calcd for $C_{16}H_{16}N_2O_4S_2$ [M+H]+ 333.38, observed 333.0.

A solution of 3-(1-benzenesulfonyl-pyrrolo[2,3-b]pyridine-5-yl)-propane-1,2-diol (1.67 g, 5.03 mmol), p-toluene sulfonic acid (96 mg, 0.5 mmol) and 2,2-dimethoxy-propane (3.1 mL, 25.2 mmol) in dichloromethane (20 mL) was stirred at 25° C. for 12 h. The solution was concentrated in vacuo. The residue was diluted with ethyl acetate, washed with a saturated aqueous sodium bicarbonate solution, brine, dried over anhydrous sodium sulfate and concentrated in vacuo. Purification by flash silica gel chromatography (silica gel from QingDao, 200-300 mesh, glass column from Shanghai SD company, 33% ethyl acetate/hexanes) afforded 1-benzenesulfonyl-5-(2,2-dimethyl-[1,3]dioxolan-4-ylmethyl)-1H-pyrrolo[2,3-b]pyridine (1.51 g, 81%) as a white solid: LC/MS m/e calcd for $C_{19}H_{20}N_2O_4S$ [M+H]+ 373.45, observed 373.0.

To a suspension of 1-benzenesulfonyl-5-(2,2-dimethyl-[1,3]dioxolan-4-ylmethyl)-1H-pyrrolo[2,3-b]pyridine (3 g, 8.06 mmol) in dry tetrahydrofuran (40 mL) at −78° C. was added freshly prepared lithium diisopropylamide [prepared by adding 1.6 M n-butyllithium in n-hexane (8.1 mL, 13.0 mmol) to a 0° C. solution of diisopropylamine (2 mL, 13.8 mmol) in dry tetrahydrofuran (20 mL)] dropwise. The mixture was stirred at −78° C. for 5 min and then cyclopentanecarbaldehyde (1.35 g, 13.0 mmol) was added dropwise. The resulting mixture was stirred at −78° C. for 1 h and quenched with brine. The mixture was extracted with ethyl acetate (2×150 mL), washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-[1-benzenesulfonyl-5-(2,2-dimethyl-[1,3]dioxolan-4-ylmethyl)-1H-pyrrolo[2,3-b]pyridin-2-yl]-2-cyclopentyl-ethanol as a light yellow solid (850 mg, 22%): LC/MS m/e calcd for $C_{26}H_{32}N_2O_5S$ [M+H]+ 485.62, observed 485.1.

To a 50 mL round bottomed flask charged with 1-[1-benzenesulfonyl-5-(2,2-dimethyl-[1,3]dioxolan-4-yl)-1H-pyrrolo[2,3-b]pyridin-2-ylmethyl]-2-cyclopentyl-ethanol (850 mg, 1.75 mmol) was added a solution of Dess-Martin periodinane in dichloromethane (0.3 M, 12 mL, 3.51 mmol) at 25° C. The reaction mixture was stirred at 25° C. for 1 h and then quenched with a saturated aqueous sodium bicarbonate solution (200 mL). The mixture was extracted with ethyl acetate (150 mL), washed with a saturated aqueous sodium bicarbonate solution (3×300 mL), brine, dried over anhydrous sodium sulfate and then concentrated in vacuo to give 1-[1-benzenesulfonyl-5-(2,2-dimethyl-[1,3]dioxolan-4-ylmethyl)-1H-pyrrolo[2,3-b]pyridin-2-yl]-2-cyclopentyl-ethanone (852 mg, quant.) as a light yellow solid which was used in the next step without further purification: LC/MS m/e calcd for $C_{26}H_{30}N_2O_5S$ [M+H]$^+$ 483.6, observed 483.1.

a solution of 1-[1-benzenesulfonyl-5-(2,2-dimethyl-[1,3]dioxolan-4-ylmethyl)-1H-pyrrolo[2,3-b]pyridin-2-yl]-2-cyclopentyl-ethanone (852 g, 1.76 mmol) in dry tetrahydrofuran (40 mL) at −78° C. was treated with lithium bis(trimethylsilyl)amide solution in tetrahydrofuran (1 M, 2.64 mL, 2.64 mmol) dropwise. After stirring at −78° C. for 1 h, a solution of p-toluenesulfonic anhydride (1.15 g, 3.52 mmol) in tetrahydrofuran (15 mL) was added dropwise. The resulting mixture was kept at −78° C. for another 1.5 h. The reaction was quenched with water, extracted with ethyl acetate (200 mL), washed with brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded toluene-4-sulfonic acid 1-{1-benzenesulfonyl-5-[2-(1-methyloxy-1-methyl-ethoxy)-propyl]-1H-pyrrolo[2,3-b]pyridin-2-yl}-2-cyclopentyl-vinyl ester (1.12 g, quant.) as a white solid: LC/MS m/e calcd for $C_{33}H_{36}N_2O_7S_2$ [M+H]$^+$ 637.79, observed 637.1.

To a mixture of toluene-4-sulfonic acid 1-{1-benzenesulfonyl-5-[2-(1-methyloxy-1-methyl-ethoxy)-propyl]-1H-pyrrolo[2,3-b]pyridin-2-yl}-2-cyclopentyl-vinyl ester (1.12 g, 1.76 mmol), 4-(methanesulfonyl)phenylboronic acid (704 mg, 3.52 mmol), dichlorobis(triphenylphosphine)palladium (II) (124 mg, 0.17 mmol) in dioxane (5 mL) was added an aqueous sodium carbonate solution (2 M, 2.2 mL). The resulting mixture was subjected to microwave irradiation for 1 h at 100° C. The mixture was diluted with ethyl acetate (150 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 33% ethyl acetate/hexanes) afforded 1-benzenesulfonyl-2-[2-cyclopentyl-1-(4-methanesulfonyl-phenyl)-vinyl]-5-(2,2-dimethyl-[1,3]dioxolan-4-ylmethyl)-1H-pyrrolo[2,3-b]pyridine (480 mg, 44%) as a light yellow solid: LC/MS m/e calcd for $C_{33}H_{36}N_2O_6S_2$ [M+H]$^+$ 621.79, observed 621.0.

A solution of 1-benzenesulfonyl-2-[2-cyclopentyl-1-(4-methanesulfonyl-phenyl)-vinyl]-5-(2,2-dimethyl-[1,3]dioxolan-4-ylmethyl)-1H-pyrrolo[2,3-b]pyridine (460 mg, 0.74 mmol) in tetrahydrofuran (0.5 mL) and a tetrabutylammonium fluoride solution in tetrahydrofuran (1 M, 4 mL, 4 mmol) was stirred at room temperature for 12 h. The mixture was diluted with ethyl acetate (150 mL) and then washed with a saturated aqueous ammonium chloride solution, brine, dried over anhydrous sodium sulfate and then concentrated in vacuo to afford 2-[2-cyclopentyl-1-(4-methanesulfonyl-phenyl)-vinyl]-5-(2,2-dimethyl-[1,3]dioxolan-4-ylmethyl)-1H-pyrrolo[2,3-b]pyridine (315 mg, 88.5%) as a light yellow solid: LC/MS m/e calcd for $C_{27}H_{32}N_2O_4S$ [M+H]$^+$ 481.63, observed 481.1.

A mixture of 2-[2-cyclopentyl-1-(4-methanesulfonyl-phenyl)-vinyl]-5-(2,2-dimethyl-[1,3]dioxolan-4-ylmethyl)-1H-pyrrolo[2,3-b]pyridine (310 mg, 0.65 mmol) and 10% palladium on activated carbon (100 mg) in methanol (250 mL) was heated at 50° C. under 50 bar of hydrogen in a steel bomb pressure for 8 h. The mixture was cooled to room temperature. The catalyst was removed by filtration and washed with ethyl acetate. The filtrate was concentrated in vacuo to afford 2-[2-cyclopentyl-1-(4-methanesulfonyl-phenyl)-ethyl]-5-(2,2-dimethyl-[1,3]dioxolan-4-ylmethyl)-1H-pyrrolo[2,3-b]pyridine (270 mg, 86.8%) as a white solid: LC/MS m/e calcd for $C_{27}H_{34}N_2O_4S$ [M+H]$^+$ 483.65, observed 483.3.

A mixture of 2-[2-cyclopentyl-1-(4-methanesulfonyl-phenyl)-ethyl]-5-(2,2-dimethyl-[1,3]dioxolan-4-ylmethyl)-1H-pyrrolo[2,3-b]pyridine (260 mg, 0.54 mmol) and 6N HCl (1.0 mL) in tetrahydrofuran (5 mL) was heated at reflux for 1 h. The mixture was cooled to room temperature and extracted with ethyl acetate and then washed with a saturated aqueous sodium bicarbonate solution, brine, dried over anhydrous sodium sulfate. The solvent was evaporated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 3-{2-[2-cyclopentyl-1-(4-methanesulfonyl-phenyl)-ethyl]-1H-pyrrolo[2,3-b]pyridin-5-yl}-propane-1,2-diol (100 mg, 41.9%) as a white solid: LC/MS m/e calcd for $C_{24}H_{30}N_2O_4S$ [M+H]$^+$ 443.58, observed 443.2; $^1$H NMR (400 MHz, CDCl$_3$) δ ppm 1.15 (m, 2H), 1.45 (m, 2H), 1.54-1.82 (m, 5H, H), 2.06 (m, 1H), 2.23 (m, 1H), 2.74 (dd, J=8.1, J=13.8 Hz, 1H), 2.82 (dd, J=4.8, J=13.8 Hz, 1H), 2.90 (br, 2H), 2.98 (s, 3H), 3.53 (dd, J=7.3, J=11.4 Hz, 1H), 3.68 (dd, J=3.0, J=11.4 Hz, 1H), 3.93 (m, 1H), 4.22 (t, J=7.7 Hz, 1H), 6.29 (s, 1H), 7.75 (d, J=8.3 Hz, 2H), 7.71 (s, 1H), 7.76 (s, 1H), 7.77 (d, J=8.3 Hz, 2 H), 10.82 (s, 1H).

Example 12

2-[2-Cyclopentyl-1-(4-methanesulfonyl-phenyl)-ethyl]-5-methoxy-1H-pyrrolo[2,3-b]pyridine

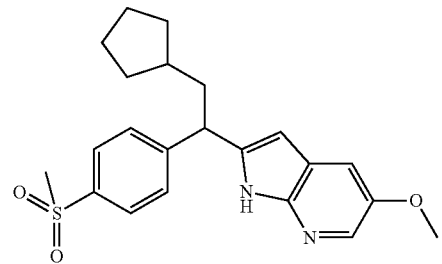

To a solution of 1-benzenesulfonyl-5-methoxy-1H-pyrrolo[2,3-b]pyridine (prepared as in Example 10, 2.5 g, 8.68 mmol) in dry tetrahydrofuran (40 mL) at −78° C. was added freshly prepared lithium diisopropylamide [prepared by adding 1.6 M n-butyllithium in n-hexane (8.13 mL, 13.0 mmol) to a 0° C. solution of diisopropylamine (13.7 mmol, 1.96 mL) in dry tetrahydrofuran (20 mL)] dropwise. The mixture was stirred at −78° C. for 5 min and then cyclopentanecarbaldehyde (13.0 mmol, 1.46 g) was added dropwise. The resulting mixture was stirred at −78° C. for 1 h and quenched with brine. The mixture was extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded 1-(-benzenesulfonyl-5-methoxy-1H-pyrrolo[2,3-b]pyridin-2-yl]-2-cyclopentyl-ethanol (2.3 g, 68%) as a white solid: LC/MS m/e calcd for $C_{21}H_{24}N_2O_4S$ [M+H]$^+$ 401.50, observed 401.0.

To a 250 mL round bottomed flask charged with 1-(-benzenesulfonyl-5-methoxy-1H-pyrrolo[2,3-b]pyridin-2-yl]-2-cyclopentyl-ethanol (2.3 g, 5.75 mmol) was added a solution of Dess-Martin periodinane in dichloromethane (0.3 M, 30 mL, 9 mmol) at 25° C. The reaction mixture was stirred at 25° C. for 1 h and then quenched with a saturated aqueous sodium bicarbonate solution (60 mL). The mixture was extracted with ethyl acetate (250 mL), washed with a saturated aqueous sodium bicarbonate solution (3×50 mL), brine, dried over anhydrous sodium sulfate and then concentrated in vacuo to give 1-(-benzenesulfonyl-5-methoxy-1H-pyrrolo[2,3-b]pyridin-2-yl]-2-cyclopentyl-ethanone (2.28 g, 99%) as a light yellow solid which was used in the next step without further purification: LC/MS m/e calcd for $C_{21}H_{22}N_2O_4S$ [M+H]$^+$ 399.48, observed 399.0.

To a solution of 1-(-benzenesulfonyl-5-methoxy-1H-pyrrolo[2,3-b]pyridin-2-yl]-2-cyclopentyl-ethanone (2.28 g, 5.73 mmol) in dry tetrahydrofuran (50 mL) at −78° C. was added lithium bis(trimethylsilyl)amide in tetrahydrofuran (1 M, 8.6 mL, 8.6 mmol) dropwise. After stirring at −78° C. for 1 h, a solution of p-toluenesulfonic anhydride (3.8, 11.5 mmol) in tetrahydrofuran (30 mL) was added dropwise. The resulting mixture was kept at −78° C. for another 1.5 h. The reaction was quenched with water, extracted with ethyl acetate (300 mL), washed with brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded toluene-4-sulfonic acid-1-(benzenesulfonyl-5-methoxy-1H-pyrrolo[2,3-b]pyridin-2-yl)-2-cyclopentyl-vinyl ester as a light yellow solid (1.8 g, 58.0%): LC/MS m/e calcd for $C_{28}H_{28}N_2O_6S_2$ [M+H]$^+$ 553.67, observed 553.3.

To a mixture of toluene-4-sulfonic acid-1-benzenesulfonyl-5-methoxy-1H-pyrrolo[2,3-b]pyridin-2-yl)-2-cyclopentyl-vinyl ester (1.1 g, 2 mmol), 4-(methanesulfonyl)phenylboronic acid (800 mg, 4.0 mmol), and dichlorobis(triphenylphosphine)palladium (II) (141 mg, 0.2 mmol) in dioxane (5 mL) was added an aqueous sodium carbonate solution (2 M, 2.5 mL, 5 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 33% ethyl acetate/hexanes) afforded 1-benzenesulfonyl-2-[2-cyclopentyl-1-(4-methanesulfonyl-phenyl)-vinyl]-5-methoxy-1H-pyrrolo[2,3-b]pyridine (860 mg, 86%) as a light yellow solid: LC/MS m/e calcd for $C_{28}H_{28}N_2O_5S_2$ [M+H]$^+$ 537.67, observed 537.0.

A solution of 1-benzenesulfonyl-2-[2-cyclopentyl-1-(4-methanesulfonyl-phenyl)-vinyl]-5-methoxy-1H-pyrrolo[2,3-b]pyridine (536 mg, 1 mmol) in tetrahydrofuran (0.5 mL) and a tetrabutylammonium fluoride solution in tetrahydrofuran (1 M, 2 mL, 2 mmol) was stirred at room temperature for 12 h. The mixture was then diluted with ethyl acetate (150 mL), and washed with a saturated aqueous ammonium chloride solution, brine, dried over anhydrous sodium sulfate and concentrated in vacuo to afford 2-[2-cyclopentyl-1-(4-methanesulfonyl-phenyl)-vinyl]-5-methoxy-1H-pyrrolo[2,3-b]pyridine (390 mg, 98.5%) as a white solid: LC/MS m/e calcd for $C_{22}H_{24}N_2O_3S$ [M+H]$^+$ 397.51, observed 397.2.

A mixture of 2-[2-cyclopentyl-1-(4-methanesulfonyl-phenyl)-vinyl]-5-methoxy-1H-pyrrolo[2,3-b]pyridine (390 mg, 0.98 mmol) and 10% palladium on activated carbon (50 mg) in methanol (200 mL) was heated at 50° C. under 50 bar of hydrogen in a steel bomb pressure for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-5-methoxy-1H-pyrrolo[2,3-b]pyridine (240 mg, 61.4%) as a white solid: LC/MS m/e calcd for $C_{22}H_{26}N_2O_3S$ [M+H]$^+$ 399.53; observed 399.2. $^1$H NMR (400 MHz, CDCl$_3$) δ ppm 11.86 (s, 1H), 7.92 (d, J=8.6 Hz, 3H), 7.55 (d, J=7.8 Hz, 1H), 7.28 (s, 3H), 6.49 (s, 1H), 4.37 (t, J=7.6 Hz, 1H), 3.97 (s, 3H), 3.07 (s, 3H), 2.13-2.29 (m, 2H), 1.79 (d, J=20.0 Hz, 2H), 1.65 (m, 2H), 1.45-1.56 (m, 2H), 1.14-1.25 (m, 2H).

Example 13

2-{2-[2-Cyclopentyl-1-(4-methanesulfonyl-phenyl)-ethyl]-1H-pyrrolo[2,3-b]pyridin-5-yloxy}-N,N-dimethyl-acetamide

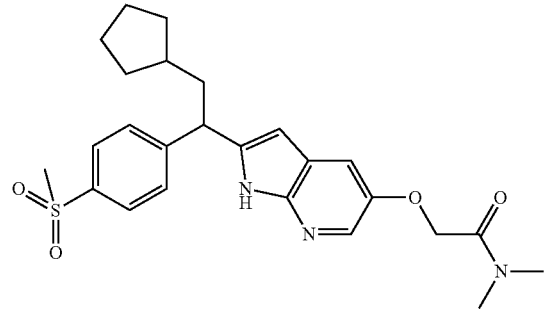

To a stirred solution of 1-benzenesulfonyl-2-[2-cyclopentyl-1-(4-methanesulfonyl-phenyl)-vinyl]-5-methoxy-1H-pyrrolo[2,3-b]pyridine (prepared as in Example 12, 950 mg, 1.77 mmol) in dry dichloromethane (30 mL) at −78° C. was added a solution of boron tribromide (1.7 mL, 17.7 mmol) in dry dichloromethane (10 mL). The mixture was then warmed to room temperature and stirred for 1 h. The solution was poured into ice-water and neutralized with a 2.5M aqueous sodium hydroxide solution (pH ~6). The mixture was extracted with ethyl acetate (2×250 mL), washed with brine, dried over anhydrous sodium sulfate and then concentrated in vacuo to give 1-benzenesulfonyl-2-[2-cyclopentyl-1-(4-methanesulfonyl-phenyl)-vinyl]-1H-pyrrolo[2,3-b]pyridin-5-ol (925 mg, 100%) as a light yellow solid which was used in the next step without further purification: LC/MS m/e calcd for $C_{27}H_{26}N_2O_5S_2$ [M+H]$^+$ 523.65, observed 523.1.

Potassium carbonate (246 mg, 1.78 mmol) was added to a solution of 1-benzenesulfonyl-2-[2-cyclopentyl-1-(4-methanesulfonyl-phenyl)-vinyl]-1H-pyrrolo[2,3-b]pyridin-5-ol (310 mg, 0.59 mmol) in N,N-dimethylformamide (2 mL) at room temperature and stirred for 30 min. 2-Chloro-N,N-dimethyl-acetamide (0.061 mL, 0.59 mmol) was then added to the above mixture and stirred at room temperature for 13 h.

The mixture was diluted with ethyl acetate (150 mL), washed with brine, dried over anhydrous sodium sulfate and then concentrated in vacuo to afford 2-{1-benzenesulfonyl-2-[2-cyclopentyl-1-(4-methanesulfonyl-phenyl)-vinyl]-1H-pyrrolo[2,3-b]pyridin-5-yloxy}-N,N-dimethyl-acetamide (340 mg, quant.) as a light yellow solid which was used in the next step without further purification: LC/MS m/e calcd for $C_{31}H_{33}N_3O_6S_2$ [M+H]$^+$ 608.75, observed 608.1.

A solution of 2-{1-benzenesulfonyl-2-[2-cyclopentyl-1-(4-methanesulfonyl-phenyl)-vinyl]-1H-pyrrolo[2,3-b]pyridin-5-yloxy}-N,N-dimethyl-acetamide (340 mg, 0.59 mmol) in tetrahydrofuran (0.5 mL) and a tetrabutylammonium fluoride solution in tetrahydrofuran (1 M, 4 mL, 4 mmol) was stirred at room temperature for 12 h. The mixture was diluted with ethyl acetate (150 mL), and washed with a saturated aqueous ammonium chloride solution, brine, dried over anhydrous sodium sulfate and then concentrated in vacuo to afford 2-{2-[2-cyclopentyl-1-(4-methanesulfonyl-phenyl)-vinyl]-1H-pyrrolo[2,3-b]pyridin-5-yloxy}-N,N-dimethyl-acetamide (276 mg, quant.) as a white solid: LC/MS m/e calcd for $C_{25}H_{29}N_3O_4S$ [M+H]$^+$ 468.59, observed 468.2.

A mixture of 2-{2-[2-cyclopentyl-1-(4-methanesulfonyl-phenyl)-vinyl]-1H-pyrrolo[2,3-b]pyridin-5-yloxy}-N,N-dimethyl-acetamide (276 mg, 0.59 mmol) and 10% palladium on activated carbon (50.0 mg) in methanol (200 mL) was heated at 50° C. under 50 bar of hydrogen in a steel bomb pressure for 6 h. The mixture was then cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-{2-[2-cyclopentyl-1-(4-methanesulfonyl-phenyl)-ethyl]-1H-pyrrolo[2,3-b]pyridin-5-yloxy}-N,N-dimethyl-acetamide (140 mg, 50.7%) as a white solid: LC/MS m/e calcd for $C_{25}H_{31}N_3O_4S$ [M+H]$^+$ 470.61, observed 470.2. solid $^1$H NMR (400 MHz, CD$_3$OD) δ ppm 7.86-7.93 (m, 4H), 7.59 (d, J=8.1 Hz, 3H), 7.52 (s, 1H), 6.32 (s, 1H), 4.84 (s, 2H), 4.28 (t, J=7.8 Hz, 1H), 3.08 (s, 3H), 3.10 (s, 3H), 2.98 (s, 3H), 2.22-2.30 (m, 1H), 2.03-2.13 (m, 2H), 1.61-1.79 (m, 4H), 1.48 (br. s., 1H), 1.21-1.23 (m, 1H).

Example 14

2-{2-[2-Cyclopentyl-1(R)-(4-methanesulfonyl-phenyl)-ethyl]-1H-pyrrolo[2,3-b]pyridin-5-yloxy}-N,N-dimethyl-acetamide

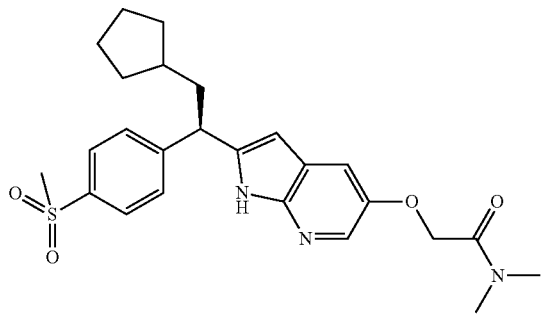

The 1:1 mixture of enantiomers of 2-{2-[2-cyclopentyl-1-(4-methanesulfonyl-phenyl)-ethyl]-1H-pyrrolo[2,3-b]pyridin-5-yloxy}-N,N-dimethyl-acetamide (prepared as in Example 13, 120 mg) were separated by Agilent high performance liquid chromatography (chiral column: Daicel OJ-H, 250 mm×20 mm i. d., 5 μm-particle size, temperature: 25° C., flow rate of 15 mL/min, 65% ethanol/hexanes as mobile phase and UV detection: 214 and 254 nm) to afford two separate pure enantiomers. The first peak was 2-{2-[2-cyclopentyl-1(R)-(4-methanesulfonyl-phenyl)-ethyl]-1H-pyrrolo[2,3-b]pyridin-5-yloxy}-N,N-dimethyl-acetamide (29 mg) as a white solid: $^1$H NMR (400 MHz, CD$_3$OD) δ ppm 1.21 (m, 2H), 1.49 (m, 2H), 1.57-1.88 (m, 5H, H), 2.08 (m, 1H), 2.25 (m, 1H), 2.98 (s, 3H), 3.08 (s, 3H), 3.11 (s, 3H), 4.28 (t, J=8.0 Hz, 1H), 4.84 (s, 2H), 6.32 (s, 1H), 7.52 (d, J=2.5 Hz, 1H), 7.59 (d, J=8.3 Hz, 2H), 7.88 (d, J=8.3 Hz, 2 H), 7.92 (d, J=2.5 Hz, 1H).

Example 15

2-[2-Cyclopentyl-1-(4-methanesulfonyl-phenyl)-ethyl]-5-(2-methoxy-ethoxy)-1H-pyrrolo[2,3-b]pyridine

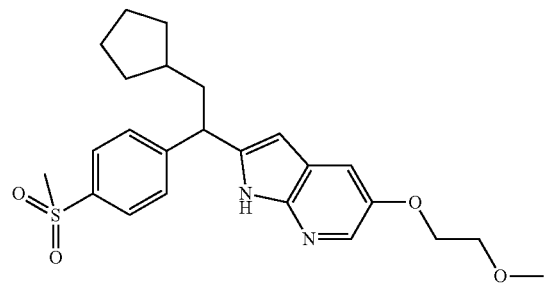

Potassium carbonate (246 mg, 1.78 mmol) was added to a solution of 1-benzenesulfonyl-2-[2-cyclopentyl-1-(4-methanesulfonyl-phenyl)-vinyl]-1H-pyrrolo[2,3-b]pyridin-5-ol (prepared as in Example 13, 310 mg, 0.59 mmol) in N,N-dimethylformamide (2 mL) at room temperature and the mixture was then stirred at room temperature for 30 min and then treated with 2-bromoethyl methyl ether (0.06 mL, 0.59 mmol). The mixture was then heated at 80° C. for 1 h. The resulting reaction mixture was diluted with ethyl acetate (150 mL), washed with brine, dried over anhydrous sodium sulfate and then concentrated in vacuo to afford 1-benzenesulfonyl-2-[2-cyclopentyl-1-(4-methanesulfonyl-phenyl)-vinyl]-5-(2-methoxy-ethoxy)-1H-pyrrolo[2,3-b]pyridine (343 mg, quant.) as a light yellow solid which was used in the next step without further purification: LC/MS m/e calcd for $C_{30}H_{32}N_2O_6S_2$ [M+H]$^+$ 581.73, observed 581.1.

A solution of 1-benzenesulfonyl-2-[2-cyclopentyl-1-(4-methanesulfonyl-phenyl)-vinyl]-5-(2-methoxy-ethoxy)-1H-pyrrolo[2,3-b]pyridine (343 mg, 0.59 mmol) in tetrahydrofuran (0.5 mL) and a tetrabutylammonium fluoride solution in tetrahydrofuran (1 M, 4 mL, 4 mmol) was stirred at room temperature for 12 h. The mixture was diluted with ethyl acetate (150 mL), and washed with a saturated aqueous ammonium chloride solution, brine, dried over anhydrous sodium sulfate and concentrated in vacuo to afford 2-[2-cyclopentyl-1-(4-methanesulfonyl-phenyl)-vinyl]-5-(2-methoxy-ethoxy)-1H-pyrrolo[2,3-b]pyridine (260 mg, quant.) as a white solid: LC/MS m/e calcd for $C_{24}H_{28}N_2O_4S$ [M+H]$^+$ 441.57, observed 441.2.

A mixture of 2-[2-cyclopentyl-1-(4-methanesulfonyl-phenyl)-vinyl]-5-(2-methoxy-ethoxy)-1H-pyrrolo[2,3-b]pyridine (260 mg, 0.59 mmol) and 10% palladium on activated carbon (40 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-5-(2-methoxy-ethoxy)-1H-pyrrolo[2,3-b]pyridine (100 mg, 38.5%) as a white solid: LC/MS m/e calcd for $C_{24}H_{30}N_2O_4S$ [M+H]$^+$ 443.58, observed 443.3; $^1$H NMR (400 MHz, CDCl$_3$) δ ppm 10.76 (br. s., 1H), 7.96 (br. s., 1H), 7.86-7.93 (m, 2H), 7.72 (s, 1H), 7.50-7.60 (m, 2H), 6.40 (br. s., 1H), 4.30 (t, J=7.6 Hz, 1H), 4.22 (br. s., 2H), 3.80 (br. s., 2H), 3.48 (s, 3H), 3.02-3.08 (m, 3H), 2.09-2.29 (m, 2H), 1.59-1.85 (m, 5H), 1.44-1.56 (m, 2H), 1.13-1.28 (m, 2H).

Example 16

2-[2-Cyclopentyl-1(R)-(4-methanesulfonyl-phenyl)-ethyl]-5-(2-methoxy-ethoxy)-1H-pyrrolo[2,3-b]pyridine

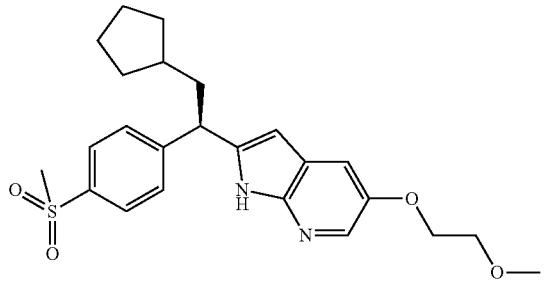

The 1:1 mixture of enantiomers of 2-[2-cyclopentyl-1-(4-methanesulfonyl-phenyl)-ethyl]-5-(2-methoxy-ethoxy)-1H-pyrrolo[2,3-b]pyridine (prepared as in Example 15, 60 mg) were separated by Agilent high performance liquid chromatography (chiral column: Daicel IB-H, 250 mm×20 mm i. d., 5 μm-particle size, temperature: 25° C., flow rate of 15 mL/min, 50% ethanol/hexanes as mobile phase and UV detection: 214 and 254 nm) to afford two pure enantiomers. The second peak, 2-[2-cyclopentyl-1(R)-(4-methanesulfonyl-phenyl)-ethyl]-5-(2-methoxy-ethoxy)-1H-pyrrolo[2,3-b]pyridine (18 mg) was isolated as a colorless oil: $^1$H NMR (400 MHz, CD$_3$OD) δ ppm 7.87-7.92 (m, 3H), 7.60 (d, J=8.3 Hz, 2H), 7.53 (d, J=2.5 Hz, 1H), 6.33 (s, 1H), 4.30 (t, J=7.8 Hz, 1H), 4.15-4.20 (m, 2H), 3.74-3.79 (m, 2H), 3.45 (s, 3H), 3.10 (s, 3H), 2.22-2.32 (m, 1H), 2.03-2.15 (m, 1H), 1.61-1.87 (m, 5H), 1.44-1.57 (m, 2H), 1.15-1.37 (m, 2H).

Example 17

(2-{2-[2-Cyclopentyl-1-(4-methanesulfonyl-phenyl)-ethyl]-1H-pyrrolo[2,3-b]pyridin-5-yloxy}-ethyl)-dimethyl-amine

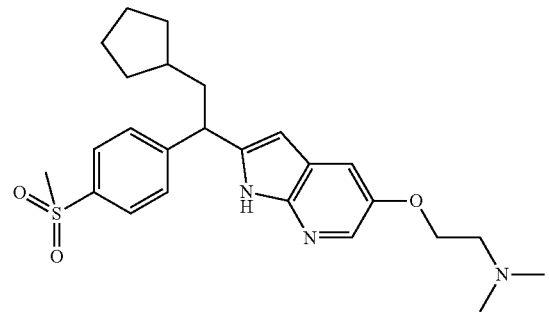

Potassium carbonate (410 mg, 2.97 mmol) was added to a solution of 1-benzenesulfonyl-2-[2-cyclopentyl-1-(4-methanesulfonyl-phenyl)-vinyl]-1H-pyrrolo[2,3-b]pyridin-5-ol (prepared as in Example 13, 310 mg, 0.59 mmol) in N,N-dimethylformamide (2 mL) at room temperature for 30 min. 2-Dimethylaminoethyl chloride hydrochloride (85.6 mg, 0.59 mmol) was then added. The mixture was heated at 80° C. for 1 h. The resulting reaction mixture was diluted with ethyl acetate (150 mL), washed with brine, dried over anhydrous sodium sulfate and then concentrated in vacuo to afford (2-{1-benzenesulfonyl-2-[2-cyclopentyl-1-(4-methanesulfonyl-phenyl)-vinyl]-1H-pyrrolo[2,3-b]pyridin-5-yloxy}-ethyl)-dimethyl-amine (350 mg, quant.) as a light yellow solid which was used in the next step without further purification: LC/MS m/e calcd for $C_{31}H_{35}N_3O_5S_2$ [M+H]$^+$ 594.77, observed 594.2.

A solution of (2-{1-benzenesulfonyl-2-[2-cyclopentyl-1-(4-methanesulfonyl-phenyl)-vinyl]-1H-pyrrolo[2,3-b]pyridin-5-yloxy}-ethyl)-dimethyl-amine (350 mg, 0.59 mmol) in tetrahydrofuran (0.5 mL) and a tetrabutylammonium fluoride solution in tetrahydrofuran (1 M, 4 mL, 4 mmol) was stirred at room temperature for 12 h. The mixture was diluted with ethyl acetate (150 mL), and washed with a saturated aqueous ammonium chloride solution, brine, dried over anhydrous sodium sulfate and then concentrated in vacuo to afford (2-{2-[2-cyclopentyl-1-(4-methanesulfonyl-phenyl)-vinyl]-1H-pyrrolo[2,3-b]pyridin-5-yloxy}-ethyl)-dimethyl-amine (200 mg, 75%) as a white solid: LC/MS m/e calcd for $C_{25}H_{31}N_3O_3S$ [M+H]$^+$ 454.61, observed 454.1.

A mixture of (2-{2-[2-cyclopentyl-1-(4-methanesulfonyl-phenyl)-vinyl]-1H-pyrrolo[2,3-b]pyridin-5-yloxy}-ethyl)-dimethyl-amine (200 mg, 0.44 mmol) and 10% palladium on activated carbon (40 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford (2-{2-[2-cyclopentyl-1-(4-methanesulfonyl-phenyl)-ethyl]-1H-pyrrolo[2,3-b]pyridin-5-yloxy}-ethyl)-dimethyl-amine (20 mg, 10%) as a white solid: LC/MS m/e calcd for $C_{25}H_{33}N_3O_3S$ [M+H]$^+$ 456.62, observed 456.3; $^1$H NMR (400 MHz, CD$_3$OD) δ ppm 1.26 (m, 2 H), 1.51 (m, 2H), 1.58-1.90 (m, 5H, H), 2.11 (m, 1H), 2.27 (m, 1H), 2.44 (s, 6H), 2.89 (t, J=5.4 Hz, 2H), 3.10 (s, 3H), 4.19 (t, J=5.4 Hz, 2H), 4.30 (t, J=8.0 Hz, 1H), 6.35 (s, 1H), 7.55 (d, J=2.8 Hz, 1H), 7.61 (d, J=8.3 Hz, 2H), 7.9 (m, 3H).

Example 18

2-[2-Cyclopentyl-1-(4-methanesulfonyl-phenyl)-ethyl]-5-isopropoxy-1H-pyrrolo[2,3-b]pyridine

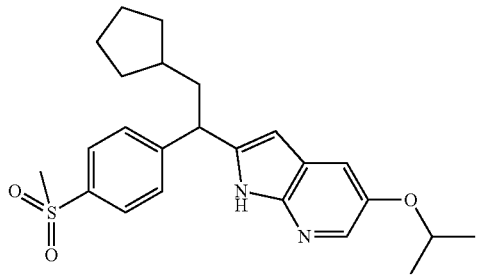

Potassium carbonate (430 mg, 3.11 mmol) was added to a solution of 1-benzenesulfonyl-2-[2-cyclopentyl-1-(4-methanesulfonyl-phenyl)-vinyl]-1H-pyrrolo[2,3-b]pyridin-5-ol (prepared as in Example 13, 325 mg, 0.62 mmol) in N,N-dimethylformamide (2 mL) at room temperature and stirred for 30 min and then 2-bromopropane (0.13 mL, 1.24 mmol) was added. The mixture was then heated to 60° C. and stirred for 3 h. The resulting mixture was diluted with ethyl acetate (150 mL), washed with brine, dried over anhydrous sodium sulfate and then concentrated in vacuo to afford 1-benzenesulfonyl-2-[2-cyclopentyl-1-(4-methanesulfonyl-phenyl)-vinyl]-5-isopropoxy-1H-pyrrolo[2,3-b]pyridine (310 mg, 100%) as a light yellow solid which was used in the next step without further purification: LC/MS m/e calcd for $C_{30}H_{32}N_2O_5S_2$ [M+H]$^+$ 565.73, observed 565.2.

A solution of 1-benzenesulfonyl-2-[2-cyclopentyl-1-(4-methanesulfonyl-phenyl)-vinyl]-5-isopropoxy-1H-pyrrolo[2,3-b]pyridine (310 mg, 0.55 mmol) in tetrahydrofuran (0.5 mL) and a tetrabutylammonium fluoride solution in tetrahydrofuran (1 M, 4 mL, 4 mmol) was stirred at room temperature for 12 h. The reaction mixture was then diluted with ethyl acetate (150 mL), and washed with a saturated aqueous ammonium chloride solution, brine, dried over anhydrous sodium sulfate and concentrated in vacuo to afford 2-[2-cyclopentyl-1-(4-methanesulfonyl-phenyl)-vinyl]-5-isopropoxy-1H-pyrrolo[2,3-b]pyridine (236 mg, quant.) as a white solid: LC/MS m/e calcd for $C_{24}H_{28}N_2O_3S$ [M+H]$^+$ 425.57, observed 425.2.

A mixture of 2-[2-cyclopentyl-1-(4-methanesulfonyl-phenyl)-vinyl]-5-isopropoxy-1H-pyrrolo[2,3-b]pyridine (236 mg, 0.55 mmol) and 10% palladium on activated carbon (40 mg) in methanol (200 mL) was heated at 50° C. under 50 bar of hydrogen in a steel bomb pressure for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-5-isopropoxy-1H-pyrrolo[2,3-b]pyridine (180 mg, 76%) as a white solid: LC/MS m/e calcd for $C_{24}H_{30}N_2O_3S$ [M+H]$^+$ 427.58, observed 427.2; $^1$H NMR (400 MHz, CD$_3$OD) δ ppm 7.88-7.92 (m, J=8.3 Hz, 2H), 7.81 (d, J=2.3 Hz, 1H), 7.58-7.63 (m, J=8.3 Hz, 2H), 7.51 (d, J=2.5 Hz, 1H), 6.33 (s, 1H), 4.53 (dt, J=12.1, 6.1 Hz, 1H), 4.30 (t, J=7.8 Hz, 1H), 3.10 (s, 3H), 2.24-2.32 (m, 1H), 2.07-2.15 (m, 1H), 1.61-1.88 (m, 5H), 1.46-1.57 (m, 2H), 1.18-1.35 (m, 8H).

Example 19

2-[2-Cyclopentyl-1(R)-(4-methanesulfonyl-phenyl)-ethyl]-5-isopropoxy-1H-pyrrolo[2,3-b]pyridine

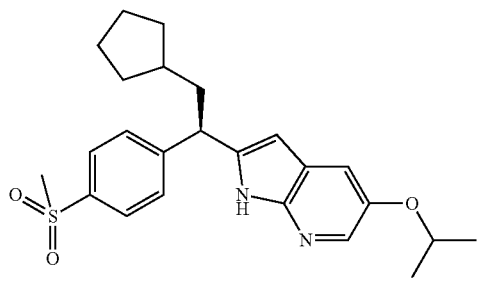

The 1:1 mixture of enantiomers of 2-[2-cyclopentyl-1-(4-methanesulfonyl-phenyl)-ethyl]-5-isopropoxy-1H-pyrrolo[2,3-b]pyridine (prepared as in Example 18, 120 mg) were separated by Agilent high performance liquid chromatography (chiral column: Daicel OJ-H, 250 mm×20 mm i. d., 5 μm-particle size, temperature: 25° C., flow rate of 15 mL/min, 50% ethanol/hexanes as mobile phase and UV detection: 214 and 254 nm) to afford two pure enantiomers. The first peak, 2-[2-cyclopentyl-1(R)-(4-methanesulfonyl-phenyl)-ethyl]-5-isopropoxy-1H-pyrrolo[2,3-b]pyridine (17 mg) was isolated as a colorless oil: $^1$H NMR (400 MHz, CD$_3$OD) δ ppm 1.21 (m, 2H), 1.31 (d, J=6.1 Hz, 6H), 1.49 (m, 2H), 1.57-1.89 (m, 5H, H), 2.09 (m, 1H), 2.26 (m, 1H), 3.08 (s, 3H), 4.28 (t, J=8.0 Hz, 1H), 4.52 (m, 1H), 6.31 (s, 1H), 7.49 (d, J=2.5 Hz, 1H), 7.59 (d, J=8.3 Hz, 2H), 7.79 (d, J=2.5 Hz, 1H), 7.88 (d, J=8.3 Hz, 2H).

Example 20

2-[2-Cyclopentyl-1-(4-trifluoromethyl-phenyl)-ethyl]-5-methoxy-1H-pyrrolo[2,3b]pyridine

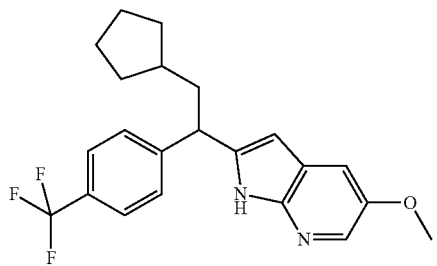

To a mixture of toluene-4-sulfonic acid-1-benzenesulfonyl-5-methoxy-1H-pyrrolo[2,3-b]pyridin-2-yl]-2-cyclopentyl-vinyl ester (prepared as in Example 12, 350 mg, 0.63 mmol), 4-(trifluormethyl)phenylboronic acid (301 mg, 1.59 mmol) and dichlorobis(triphenylphosphine)palladium (II) (45 mg, 0.06 mmol) in dioxane (3 mL) was added an aqueous sodium carbonate solution (2 M, 0.8 mL, 1.59 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 10% ethyl acetate/hexanes) afforded 1-benzenesulfonyl-2-[2-cyclopentyl-1-(4-trifluoromethyl-phenyl)-vinyl]-5-methoxy-1H-pyrrolo[2,3-b]pyridine (260 mg, 77.6%) as a light yellow solid: LC/MS m/e calcd for $C_{28}H_{25}F_3N_2O_3S$ [M+H]$^+$ 527.58, observed 527.2.

A solution of 1-benzenesulfonyl-2-[2-cyclopentyl-1-(4-trifluoromethyl-phenyl)-vinyl]-5-methoxy-1H-pyrrolo[2,3-b]pyridine (260 mg, 0.49 mmol) in tetrahydrofuran (0.5 mL) and a tetrabutylammonium fluoride solution in tetrahydrofuran (1 M, 2 mL, 2 mmol) were stirred at room temperature for 12 h. The mixture was diluted with ethyl acetate (150 mL), and washed with a saturated aqueous ammonium chloride solution, brine, dried over anhydrous sodium sulfate and concentrated in vacuo to afford 2-[2-cyclopentyl-1-(4-trifluoromethyl-phenyl)-vinyl]-5-methoxy-1H-pyrrolo[2,3-b]pyridine (191 mg, quant.) as a white solid: LC/MS m/e calcd for $C_{22}H_{21}F_3N_2O$ [M+H]$^+$ 387.42, observed 387.2.

A mixture of 2-[2-cyclopentyl-1-(4-trifluoromethyl-phenyl)-vinyl]-5-methoxy-1H-pyrrolo[2,3-b]pyridine (191 mg, 0.49 mmol) and 10% palladium on activated carbon (50 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-trifluoromethyl-phenyl)-ethyl]-5-methoxy-1H-pyrrolo[2,3-b]pyridine (80 mg, 41.9%) as a white solid: LC/MS m/e calcd for $C_{22}H_{23}F_3N_2O$ [M+H]$^+$ 389.54, observed 389.3; $^1$H NMR (400 MHz, CD$_3$OD) δ ppm 7.84 (d, J=2.5 Hz, 1H), 7.61 (d, J=8.1 Hz, 2H), 7.52 (d, J=8.6 Hz, 3H), 6.31 (s, 1H), 4.25 (t, J=8.0 Hz, 1H), 3.86 (s, 3H), 2.22-2.30 (m, 1H), 2.05-2.13 (m, 1H), 1.60-1.87 (m, 6H), 1.44-1.57 (m, 2H), 1.17-1.29 (m, 2H).

Example 21

2-[(E)-1-(4-Methanesulfonyl-phenyl)-2-(tetrahydro-furan-2-yl)-vinyl]-5-methoxy-1H-pyrrolo[2,3-b]pyridine

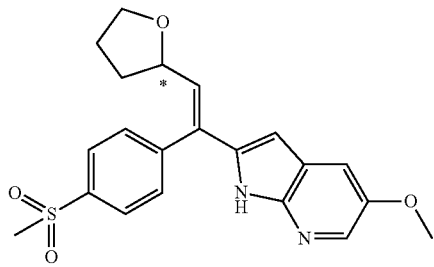

To a solution of 1-benzenesulfonyl-5-methoxy-1H-pyrrolo[2,3-b]pyridine (prepared as in Example 10, 6 g, 20.8 mmol) in dry tetrahydrofuran (40 mL) at −78° C. was added freshly prepared lithium diisopropylamide [prepared by adding 1.6 M n-butyllithium in n-hexane (19.5 mL, 31.2 mmol) to a 0° C. solution of diisopropylamine (4.7 mL, 32.8 mmol) in dry tetrahydrofuran (20 mL)] dropwise. The mixture was stirred at −78° C. for 5 min and then treated with (tetrahydro-furan-2-yl)-acetaldehyde (3.5 g, 30.7 mmol) dropwise. The resulting mixture was stirred at −78° C. for 1 h and quenched with brine. The mixture was extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-(1-benzenesulfonyl-5-methoxy-1H-pyrrolo[2,3-b]pyridin-2-yl)-2-(tetrahydro-furan-2-yl)-ethanol (2.5 g, 30%) as a white solid: LC/MS m/e calcd for $C_{21}H_{22}N_2O_5S$ [M+H]$^+$ 403.47, observed 403.2.

To a 250 mL round bottomed flask charged with 1-(1-benzenesulfonyl-5-methoxy-1H-pyrrolo[2,3-b]pyridin-2-yl)-2-(tetrahydro-furan-2-yl)-ethanol (2.5 g, 6.2 mmol) in dichloromethane (200 mL) was added Dess-Martin periodinane (6.6 g, 15.5 mmol) at 25° C. The reaction mixture was stirred at 25° C. for 1 h and then quenched with a saturated aqueous sodium bicarbonate solution (60 mL). The mixture was extracted with ethyl acetate (250 mL), washed with a saturated aqueous sodium bicarbonate solution (3×50 mL), brine, dried over anhydrous sodium sulfate and then concentrated in vacuo to give 1-(1-benzenesulfonyl-5-methoxy-1H-pyrrolo[2,3-b]pyridin-2-yl)-2-(tetrahydro-furan-2-yl)-ethanone (1.7 g, 71%) as a light yellow solid which was used in the next step without further purification: LC/MS m/e calcd for $C_{20}H_{20}N_2O_5S$ [M+H]$^+$ 401.46, observed 401.2.

The 1:1 mixture of enantiomers of 1-(1-benzenesulfonyl-5-methoxy-1H-pyrrolo[2,3-b]pyridin-2-yl)-2-(tetrahydro-furan-2-yl)-ethanone (1.7 g) were separated by Agilent high performance liquid chromatography (chiral column: Daicel OJ-H, 250 mm×20 mm i. d., 5 μm-particle size, temperature: 25° C., flow rate of 16 mL/min, 65% ethanol/hexanes as mobile phase and UV detection: 214 and 254 nm) to afford two pure enantiomers of 1-(1-benzenesulfonyl-5-methoxy-1H-pyrrolo[2,3-b]pyridin-2-yl)-2-(tetrahydro-furan-2-yl)-ethanone. The first peak, enantiomer 1 (655.0 mg) was isolated as a white solid, and the second peak, enantiomer 2 (658 mg) was isolated as a white solid.

To a solution of 1-(1-benzenesulfonyl-5-methoxy-1H-pyrrolo[2,3-b]pyridin-2-yl)-2-(tetrahydro-furan-2-yl)-ethanone (enantiomer 1, 620 mg, 1.55 mmol) in dry tetrahydrofuran (5 mL) at 0° C. was added a solution of 4-thioanisolemagnesium bromide in tetrahydrofuran (0.5M, 15.5 mL, 7.75 mmol) dropwise. After stirring at 0° C. for 1 h, the reaction was quenched with water, extracted with ethyl acetate (300 mL), washed with brine, dried over anhydrous sodium sulfate and concentrated in vacuo. Purification by flash silica gel chromatography (silica gel from QingDao, 200-300 mesh, glass column from Shanghai SD company, 50% ethyl acetate/hexanes) afforded 1-(1-benzenesulfonyl-5-methoxy-1H-pyrrolo[2,3-b]pyridin-2-yl)-1-(4-methylsulfanyl)-2-(tetrahydro-furan-2-yl)-ethanol as a light yellow solid (770 mg, 94.8%). LC/MS m/e calcd for $C_{27}H_{28}N_2O_5S_2$ [M+H]$^+$ 525.66, observed 525.4.

To a stirred solution of 1-(1-benzenesulfonyl-5-methoxy-1H-pyrrolo[2,3-b]pyridin-2-yl)-1-(4-methylsulfanyl)-2-(tetrahydro-furan-2-yl)-ethanol (130 mg, 0.248 mmol) in methanol (10 mL) and water (3 mL) was added sodium metaperiodate (159 mg, 0.743 mmol) at room temperature and the mixture was stirred for 8 h. The resulting mixture was extracted with ethyl acetate, washed with brine, dried over anhydrous sodium sulfate. The solvent was evaporated in vacuo to give 1-(1-benzenesulfonyl-5-methoxy-1H-pyrrolo[2,3-b]pyridin-2-yl)-1-(4-methaneylsulfinyl)-2(R)-(tetrahydro-furan-2-yl)-ethanol (134 mg, quant.) as a light yellow solid: LC/MS m/e calcd for $C_{27}H_{28}N_2O_6S_2$ $[M+H]^+$ 541.66, observed 541.4.

To a stirred solution of 1-(1-benzenesulfonyl-5-methoxy-1H-pyrrolo[2,3-b]pyridin-2-yl)-1-(4-methaneylsulfinyl)-2-(tetrahydro-furan-2-yl)-ethanol (134 mg, 0.25 mmol) in methanol (15 mL) and water (3 mL) was added potassium permanganate (31 mg, 0.20 mmol) at room temperature and the mixture was stirred at room temperature for 2 h. The resulting mixture was diluted with ethyl acetate (150 mL), washed with brine, dried over anhydrous sodium sulfate and concentrated in vacuo to afford 1-(1-benzenesulfonyl-5-methoxy-1H-pyrrolo[2,3-b]pyridin-2-yl)-1-(4-methanesulfonyl-phenyl)-2-(tetrahydro-furan-2-yl)-ethanol (110 mg, 80%) as a light yellow solid: LC/MS m/e calcd for $C_{27}H_{28}N_2O_7S_2$ $[M+H]^+$ 557.68, observed 557.3.

A solution of 1-(1-benzenesulfonyl-5-methoxy-1H-pyrrolo[2,3-b]pyridin-2-yl)-1-(4-methanesulfonyl-phenyl)-2-(tetrahydro-furan-2-yl)-ethanol (110 mg, 0.20 mmol) in tetrahydrofuran (0.5 mL) and a tetrabutylammonium fluoride solution in tetrahydrofuran (1 M, 2.0 mL, 2.0 mmol) was stirred at room temperature for 2 h. The reaction mixture was diluted with ethyl acetate (150 mL), and washed with a saturated aqueous ammonium chloride solution, brine, dried over anhydrous sodium sulfate and concentrated in vacuo the residue was treated with methanol to afford 2-[(E)-1-(4-methanesulfonyl-phenyl)-2-(tetrahydro-furan-2-yl)-vinyl]-5-methoxy-1H-pyrrolo[2,3-b]pyridine (50 mg, 64.1%) as a light yellow solid: LC/MS m/e calcd for $C_{21}H_{22}N_2O_4S$ $[M+H]^+$ 399.48, observed 399.3; $^1$H NMR (400 MHz, $CD_3OD$) δ ppm 8.05-8.09 (m, J=8.1 Hz, 2H), 7.94 (d, J=2.5 Hz, 1H), 7.60-7.64 (m, J=8.1 Hz, 2H), 7.43 (d, J=2.5 Hz, 1H), 6.46 (d, J=9.1 Hz, 1H), 5.86 (s, 1H), 4.11-4.24 (m, 1H), 3.97 (q, J=7.0 Hz, 1H), 3.85 (s, 3H), 3.73-3.81 (m, 1H), 3.22 (s, 3H), 2.03-2.13 (m, 2H), 1.79-1.97 (m, 2H).

Example 22

2-[1-(4-Methanesulfonyl-phenyl)-2-(tetrahydro-furan-2-yl)-ethyl]-5-methoxy-1H-pyrrolo[2,3-b]pyridine diastereomer 1

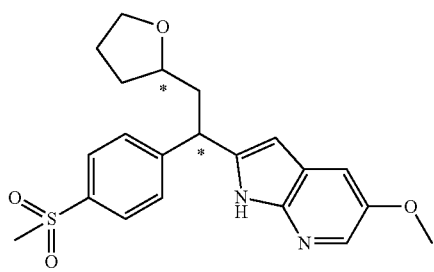

A mixture of 2-[(E)-1-(4-methanesulfonyl-phenyl)-2-(tetrahydro-furan-2-yl)-vinyl]-5-methoxy-1H-pyrrolo[2,3-b]pyridine (304 mg, 0.76 mmol) and 10% palladium on activated carbon (80 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford a mixture of diastereomers of 2-[1-(4-methanesulfonyl-phenyl)-2-(tetrahydro-furan-2-yl)-ethyl]-5-methoxy-1H-pyrrolo[2,3-b]pyridine (80 mg, 26.1%) as a light yellow solid: LC/MS m/e calcd for $C_{21}H_{24}N_2O_4S$ $[M+H]^+$ 401.5, observed 401.3.

The mixture of diastereomers of 2-[1-(4-methanesulfonyl-phenyl)-2-(tetrahydro-furan-2-yl)-ethyl]-5-methoxy-1H-pyrrolo[2,3-b]pyridine (70 mg) were separated by Agilent high performance liquid chromatography (chiral column: Daicel OJ-H, 250 mm×20 mm i. d., 5 μm-particle size, temperature: 25° C., flow rate of 17 mL/min, 60% ethanol/hexanes as mobile phase and UV detection: 214 and 254 nm) to afford two pure diastereomers of 2-[1-(4-methanesulfonyl-phenyl)-2-(tetrahydro-furan-2-yl)-ethyl]-5-methoxy-1H-pyrrolo[2,3-b]pyridine. The first peak, diastereomer 1 (19 mg) was isolated as a white solid: $^1$H NMR (400 MHz, $CD_3OD$) δ ppm 1.52-1.63 (m, 1H), 1.80-2.08 (m, 3H), 2.13-2.22 (m, 1H), 2.41-2.50 (m, 1H), 3.07 (s, 3H), 3.69 (m, 1H), 379 (m, 1H), 3.85 (s, 3H), 3.86 (m, 1H), 4.47 (dd, J=5.7, 9.9 Hz, 1H), 6.36 (s, 1H), 7.50 (d, J=2.5 Hz, 1H), 7.59 (d, J=8.3 Hz, 2H), 7.84 (d, J=2.5 Hz, 1H), 7.88 (d, J=8.3 Hz, 2H).

Example 23

2-[1-(4-Methanesulfonyl-phenyl)-2-(tetrahydro-furan-2-yl)-ethyl]-5-methoxy-1H-pyrrolo[2,3-b]pyridine diastereomer 2

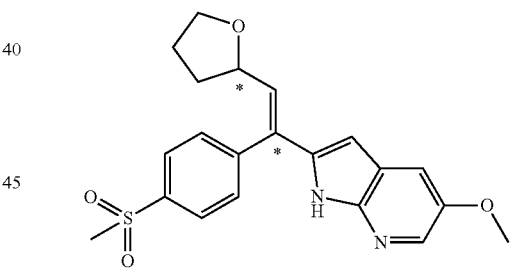

The mixture of diastereomers of 2-[1-(4-methanesulfonyl-phenyl)-2-(tetrahydro-furan-2-yl)-ethyl]-5-methoxy-1H-pyrrolo[2,3-b]pyridine (70 mg) were separated by Agilent high performance liquid chromatography (chiral column: Daicel OJ-H, 250 mm×20 mm i. d., 5 μm-particle size, temperature: 25° C., flow rate of 17 mL/min, 60% ethanol/hexanes as mobile phase and UV detection: 214 and 254 nm) to afford two pure diastereomers of 2-[1-(4-methanesulfonyl-phenyl)-2-(tetrahydro-furan-2-yl)-ethyl]-5-methoxy-1H-pyrrolo[2,3-b]pyridine. The second peak, diastereomer 2 (9 mg) was isolated as a white solid: $^1$H NMR (400 MHz, $CD_3OD$) δ ppm 1.52-1.63 (m, 1H), 1.80-2.08 (m, 3H), 2.13-2.30 (m, 1H), 2.37-2.50 (m, 1H), 3.07, 3.08 (2×s, 3H), 3.59-3.92 (m, 3H, $OCH_2$ and OCH), 3.85 (s, 3H), 4.46 (m, 1H), 6.32, 6.36 (2×s, 1H), 7.49 (m, 1H), 7.59 (m, 2H), 7.84 (m, 1H), 7.88 (m, 2H).

Example 24

2-[1-(4-Methanesulfonyl-phenyl)-2-(tetrahydro-furan-2-yl)-ethyl]-5-methoxy-1H-pyrrolo[2,3-b]pyridine diastereomer 3

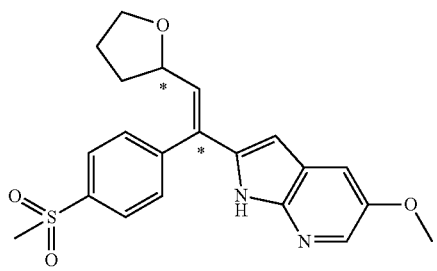

To a solution of 1-(1-benzenesulfonyl-5-methoxy-1H-pyrrolo[2,3-b]pyridin-2-yl)-2-(tetrahydro-furan-2-yl)-ethanone (enantiomer 2, prepared as in Example 21, 600 mg, 1.5 mmol) in dry tetrahydrofuran (5 mL) at 0° C. was added a 4-thioanisolemagnesium bromide solution in tetrahydrofuran (0.5M, 15 mL, 7.5 mmol) dropwise. After stirring at 0° C. for 1 h, the reaction was quenched with water, extracted with ethyl acetate (300 mL), washed with brine, dried over anhydrous sodium sulfate and concentrated in vacuo. Purification by flash silica gel chromatography (silica gel from QingDao, 200-300 mesh, glass column from Shanghai SD company, 50% ethyl acetate/hexanes) afforded 1-(1-benzenesulfonyl-5-methoxy-1H-pyrrolo[2,3-b]pyridin-2-yl)-1-(4-methylsulfanyl)-2-(tetrahydro-furan-2-yl)-ethanol as a light yellow solid (730 mg, 93%). LC/MS m/e calcd for $C_{27}H_{28}N_2O_5S_2$ [M+H]$^+$ 525.66, observed 525.4.

To a stirred solution of 1-(1-benzenesulfonyl-5-methoxy-1H-pyrrolo[2,3-b]pyridin-2-yl)-1-(4-methylsulfanyl)-2-(tetrahydro-furan-2-yl)-ethanol (174 mg, 0.33 mmol) in methanol (10 mL) and water (3 mL) was added sodium metaperiodate (213 mg, 1.0 mmol) at room temperature and the mixture was stirred at room temperature for 8 h. The resulting mixture was extracted with ethyl acetate, washed with brine, dried over anhydrous sodium sulfate. The solvent was evaporated in vacuo to give 1-(1-benzenesulfonyl-5-methoxy-1H-pyrrolo[2,3-b]pyridin-2-yl)-1-(4-methaneylsulfinyl)-2-(tetrahydro-furan-2-yl)-ethanol (180 mg, quant.) as a light yellow solid: LC/MS m/e calcd for $C_{27}H_{28}N_2O_6S_2$ [M+H]$^+$ 541.66, observed 541.4.

To a stirred solution of 1-(1-benzenesulfonyl-5-methoxy-1H-pyrrolo[2,3-b]pyridin-2-yl)-1-(4-methaneylsulfinyl)-2-(tetrahydro-furan-2-yl)-ethanol (180 mg, 0.33 mmol) in methanol (15 mL) and water (3 mL) was added potassium permanganate (41 mg, 0.27 mmol) at room temperature and the mixture was stirred at room temperature for 2 h. The resulting mixture was diluted with ethyl acetate (150 mL), washed with brine, dried over anhydrous sodium sulfate and concentrated in vacuo to afford 1-(1-benzenesulfonyl-5-methoxy-1H-pyrrolo[2,3-b]pyridin-2-yl)-1-(4-methanesulfonyl-phenyl)-2-(tetrahydro-furan-2-yl)-ethanol (184 mg, quant.) as a light yellow solid: LC/MS m/e calcd for $C_{27}H_{28}N_2O_7S_2$ [M+H]$^+$ 557.68, observed 557.3.

A solution of 1-(1-benzenesulfonyl-5-methoxy-1H-pyrrolo[2,3-b]pyridin-2-yl)-1-(4-methanesulfonyl-phenyl)-2-(tetrahydro-furan-2-yl)-ethanol (184 mg, 0.33 mmol) in tetrahydrofuran (0.5 mL) and a tetrabutylammonium fluoride solution in tetrahydrofuran (1 M, 2 mL, 2 mmol) was stirred at room temperature for 2 h. The mixture was diluted with ethyl acetate (150 mL), washed with a saturated aqueous ammonium chloride solution and brine, dried over anhydrous sodium sulfate and concentrated in vacuo and the residue was washed with methanol to afford 2-[1-(4-methanesulfonyl-phenyl)-2-(tetrahydro-furan-2-yl)-vinyl]-5-methoxy-1H-pyrrolo[2,3-b]pyridine (50 mg, 64.1%) as a light yellow solid: LC/MS m/e calcd for $C_{21}H_{22}N_2O_4S$ [M+H]$^+$ 399.48, observed 399.3.

A mixture of 2-[1-(4-methanesulfonyl-phenyl)-2-(tetrahydro-furan-2-yl)-vinyl]-5-methoxy-1H-pyrrolo[2,3-b]pyridine (315 mg, 0.79 mmol) and 10% palladium on activated carbon (100 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[1-(4-methanesulfonyl-phenyl)-2-(tetrahydro-furan-2-yl)-ethyl]-5-methoxy-1H-pyrrolo[2,3-b]pyridine (60 mg, 18.9%) as a light yellow solid: LC/MS m/e calcd for $C_{21}H_{24}N_2O_4S$ [M+H]$^+$ 401.5, observed 401.3.

The mixture of diastereomers of 2-[1-(4-methanesulfonyl-phenyl)-2-(tetrahydro-furan-2-yl)-ethyl]-5-methoxy-1H-pyrrolo[2,3-b]pyridine (70 mg) were separated by Agilent high performance liquid chromatography (chiral column: Daicel OJ-H, 250 mm×20 mm i. d., 5 μm-particle size, temperature: 25° C., flow rate of 17 mL/min, 60% ethanol/hexanes as mobile phase and UV detection: 214 and 254 nm) to afford two pure diastereomers of 2-[1-(4-methanesulfonyl-phenyl)-2-(tetrahydro-furan-2-yl)-ethyl]-5-methoxy-1H-pyrrolo[2,3-b]pyridine. The first peak, diastereomer 3 (6 mg) was isolated as a white solid: $^1$H NMR (400 MHz, CD$_3$OD) δ ppm 1.52-1.63 (m, 1H), 1.80-2.08 (m, 3H), 2.13-2.30 (m, 1H), 2.37-2.50 (m, 1H), 3.07, 3.08 (2×s, 3H), 3.59-3.92 (m, 3H), 3.85 (s, 3H), 4.46 (m, 1H), 6.32, 6.36 (2×s, 1H), 7.49 (m, 1H), 7.59 (m, 2H), 7.84 (m, 1H), 7.88 (m, 2H).

Example 25

2-[1-(4-Methanesulfonyl-phenyl)-2-(tetrahydro-furan-2-yl)-ethyl]-5-methoxy-1H-pyrrolo[2,3-b]pyridine, diastereomer 4

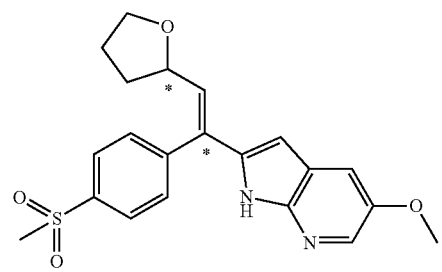

The mixture of diastereomers of 2-[1-(4-methanesulfonyl-phenyl)-2-(tetrahydro-furan-2-yl)-ethyl]-5-methoxy-1H-pyrrolo[2,3-b]pyridine (70 mg) were separated by Agilent high performance liquid chromatography (chiral column: Daicel OJ-H, 250 mm×20 mm i. d., 5 μm-particle size, temperature: 25° C., flow rate of 17 mL/min, 60% ethanol/hexanes as mobile phase and UV detection: 214 and 254 nm) to afford two pure diastereomers of 2-[1-(4-methanesulfonyl-phenyl)-2-(tetrahydro-furan-2-yl)-ethyl]-5-methoxy-1H-pyrrolo[2,3-b]pyridine. The second peak, diastereomer 4 (7 mg), was isolated as a white solid: $^1$H NMR (400 MHz, CD$_3$OD) δ ppm 1.52-1.63 (m, 1H), 1.80-2.08 (m, 3H), 2.13-2.22 (m, 1H), 2.41-2.50 (m, 1H), 3.07 (s, 3H), 3.69 (m, 1H), 379 (m, 1H), 3.85 (s, 3H), 3.86 (m, 1H), 4.47 (dd, J=5.7, 9.9 Hz, 1H), 6.36 (s, 1H), 7.50 (d, J=2.5 Hz, 1H), 7.59 (d, J=8.3 Hz, 2H), 7.84 (d, J=2.5 Hz, 1H), 7.88 (d, J=8.3 Hz, 2H).

Example 26

2-{2-[2-Cyclopentyl-1-(4-methanesulfonyl-phenyl)-ethyl]-1H-pyrrolo[2,3-b]pyridin-5-yloxy}-2-methyl-propionic acid ethyl ester

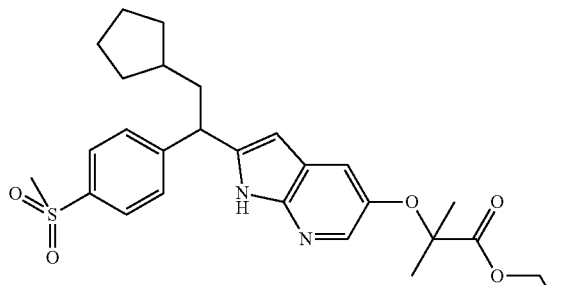

Potassium carbonate (828 mg, 5.99 mmol) was added to a solution of 1-benzenesulfonyl-2-[2-cyclopentyl-1-(4-methanesulfonyl-phenyl)-vinyl]-1H-pyrrolo[2,3-b]pyridin-5-ol (prepared as in Example 13, 1.6 g, 3.07 mmol) in N,N-dimethylformamide (4.0 mL) at room temperature. The mixture was stirred for 30 min at room temperature and then 2-bromo-2-methyl-propionic acid ethyl ester (0.48 mL, 3.21 mmol) was added. The mixture was heated at 80° C. for 1 h. The resulting mixture was diluted with ethyl acetate (150 mL), washed with brine, dried over anhydrous sodium sulfate and then concentrated in vacuo. Purification by flash silica gel chromatography (silica gel from QingDao, 200-300 mesh, glass column from Shanghai SD company, 33% ethyl acetate/hexanes) afforded 2-{1-benzenesulfonyl-2-[2-cyclopentyl-1-(4-methanesulfonyl-phenyl)-vinyl]-1H-pyrrolo[2,3-b]pyridin-5-yloxy}-2-methyl-propionic acid ethyl ester (1.34 g, 68.7%) as a light yellow solid: LC/MS m/e calcd for C$_{33}$H$_{36}$N$_2$O$_7$S$_2$ [M+H]$^+$ 637.79, observed 637.5.

A solution of 2-{1-benzenesulfonyl-2-[2-cyclopentyl-1-(4-methanesulfonyl-phenyl)-vinyl]-1H-pyrrolo[2,3-b]pyridin-5-yloxy}-2-methyl-propionic acid ethyl ester (1.34 g, 2.11 mmol) in tetrahydrofuran (0.5 mL) and a tetrabutylammonium fluoride solution in tetrahydrofuran (1 M, 8.0 mL, 8.0 mmol) was stirred at room temperature for 12 h. The resulting mixture was diluted with ethyl acetate (150 mL), washed with a saturated aqueous ammonium chloride solution and brine, dried over anhydrous sodium sulfate and then concentrated in vacuo to afford 2-{2-[2-cyclopentyl-1-(4-methanesulfonyl-phenyl)-vinyl]-1H-pyrrolo[2,3-b]pyridin-5-yloxy}-2-methyl-propionic acid ethyl ester (1.04 g, quant.) as a white solid: LC/MS m/e calcd for C$_{27}$H$_{32}$N$_2$O$_5$S [M+H]$^+$ 497.63, observed 497.4.

A mixture of 2-{2-[2-cyclopentyl-1-(4-methanesulfonyl-phenyl)-vinyl]-1H-pyrrolo[2,3-b]pyridin-5-yloxy}-2-methyl-propionic acid ethyl ester (1.04 g, 2.1 mmol) and 10% palladium on activated carbon (200 mg) in methanol (300 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-{2-[2-cyclopentyl-1-(4-methanesulfonyl-phenyl)-ethyl]-1H-pyrrolo[2,3-b]pyridin-5-yloxy}-2-methyl-propionic acid ethyl ester (700 mg, 70%) as a white solid: LC/MS m/e calcd for C$_{27}$H$_{34}$N$_2$O$_5$S [M+H]$^+$ 499.65, observed 499.7; $^1$H NMR (400 MHz, CD$_3$OD) δ ppm 1.24 (m, 2H), 1.30 (t, J=7.2 Hz, 3H), 1.51 (m, 2H), 1.57 (s, 6H), 1.60-1.90 (m, 5H, H), 2.13 (m, 1H), 2.29 (m, 1H), 3.10 (s, 3H), 4.26 (q, J=7.2 Hz, 2H), 4.33 (t, J=7.9 Hz, 1H), 6.46 (s, 1H), 7.61 (d, J=8.3 Hz, 2H), 7.71 (d, J=2.4 Hz, 1H), 7.91 (d, J=8.3 Hz, 2H), 7.92 (br, 1H).

Example 27

2-{2-[2-Cyclopentyl-1-(4-methanesulfonyl-phenyl)-ethyl]-1H-pyrrolo[2,3-b]pyridin-5-yloxy}-2-methyl-propionic acid

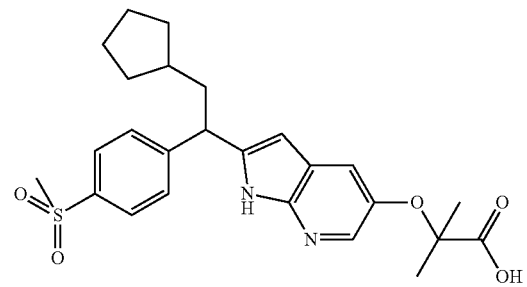

To a stirred solution of 2-{2-[2-cyclopentyl-1-(4-methanesulfonyl-phenyl)-ethyl]-1H-pyrrolo[2,3-b]pyridin-5-yloxy}-2-methyl-propionic acid ethyl ester (prepared as in Example 26, 120 mg, 0.24 mmol) in tetrahydrofuran (10 mL) and water (2.5 mL) was added lithium hydroxide (48 mg, 2 mmol) at room temperature and the mixture was stirred for 12 h. The resulting mixture was extracted with ethyl acetate, washed with brine, dried over anhydrous sodium sulfate and then concentrated in vacuo to afford 2-{2-[2-cyclopentyl-1-(4-methanesulfonyl-phenyl)-vinyl]-1H-pyrrolo[2,3-b]pyridin-5-yloxy}-2-methyl-propionic acid (60 mg, 92.3%) as a white solid: LC/MS m/e calcd for C$_{25}$H$_{30}$N$_2$O$_5$S [M+H]$^+$ 471.59, observed 471.6; $^1$H NMR (400 MHz, CD$_3$OD) δ ppm 1.24 (m, 2H), 1.51 (m, 2H), 1.57 (s, 6H), 1.60-1.88 (m, 5 H, H), 2.13 (m, 1H), 2.27 (m, 1H), 3.08 (s, 3H), 4.32 (t, J=7.8 Hz, 1H), 6.50 (s, 1H), 7.59 (d, J=8.3 Hz, 2H), 7.85 (d, J=2.3 Hz, 1H), 7.89 (d, J=8.3 Hz, 2H), 7.97 (br. d., 1H).

Example 28

2-{2-[2-Cyclopentyl-1-(4-methanesulfonyl-phenyl)-ethyl]-1H-pyrrolo[2,3-b]pyridin-5-yloxy}-2-methyl-propan-1-ol

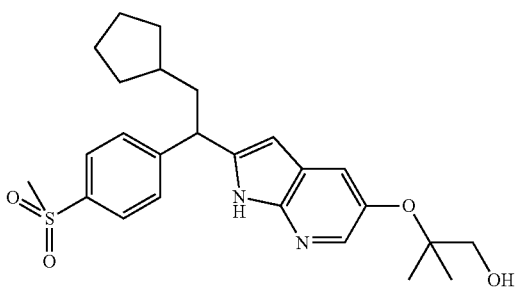

To a stirred solution of 2-{2-[2-cyclopentyl-1-(4-methanesulfonyl-phenyl)-ethyl]-1H-pyrrolo[2,3-b]pyridin-5-yloxy}-2-methyl-propionic acid ethyl ester (prepared as in Example 26, 300 mg, 0.6 mmol) in dry tetrahydrofuran (10 mL) at −78° C. was added diisobutylaluminum hydride (3.0 mL, 3.01 mmol). The mixture was then warmed to room temperature and stirred for 1 h. The reaction was quenched with a saturated aqueous potassium sodium tartrate solution at 0° C. After stirring at 0° C. for 30 min, the mixture was filtered and washed with tetrahydrofuran (100 mL). The combined organic layers were washed with brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-[2-cyclopentyl-1-(4-methanesulfonyl-phenyl)-ethyl]-1H-pyrrolo[2,3-b]pyridin-5-yloxy}-2-methyl-propan-1-ol (236 mg, 86.1%) as a white solid: LC/MS m/e calcd for $C_{25}H_{32}N_2O_4S$ [M+H]$^+$ 457.61, observed 457.1; $^1$H NMR (400 MHz, CD$_3$OD) δ ppm 7.87-7.92 (m, 3H), 7.59-7.64 (m, 3H), 6.36 (s, 1H), 4.31 (t, J=7.8 Hz, 1H), 3.56 (s, 2H), 3.10 (s, 3H), 2.25-2.34 (m, 1H), 2.07-2.15 (m, 1H), 1.62-1.89 (m, 6H), 1.45-1.57 (m, 2H), 1.02-1.42 (m, 6H).

Example 29

2-{2-[2-Cyclopentyl-1(R)-(4-methanesulfonyl-phenyl)-ethyl]-1H-pyrrolo[2,3-b]pyridin-5-yloxy}-2-methyl-propan-1-ol

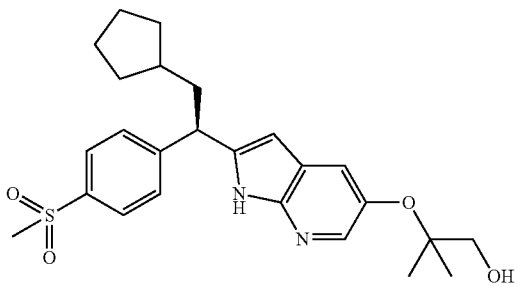

The 1:1 mixture of enantiomers of 2-{2-[2-cyclopentyl-1-(4-methanesulfonyl-phenyl)-ethyl]-1H-pyrrolo[2,3-b]pyridin-5-yloxy}-2-methyl-propan-1-ol (prepared in Example 28, 210 mg) were separated by Agilent high performance liquid chromatography (chiral column: Daicel IB-H, 250 mm×20 mm i.d., 5 μm-particle size, temperature: 25° C., flow rate of 15 mL/min, 15% ethanol/hexanes as mobile phase and UV detection: 214 and 254 nm) to afford two pure enantiomers. The second peak, 2-{2-[2-cyclopentyl-1(R)-(4-methanesulfonyl-phenyl)-ethyl]-1H-pyrrolo[2,3-b]pyridin-5-yloxy}-2-methyl-propan-1-ol (20 mg) was isolated as a white solid: $^1$H NMR (400 MHz, CD$_3$OD) δ ppm 1.24 (s, 6H), 1.24 (m, 2H), 1.50 (m, 2H), 1.59-1.89 (m, 5H, H), 2.10 (m, 1H), 2.28 (m, 1H), 3.08 (s, 3H), 3.54 (s, 2H), 4.29 (t, J=7.8 Hz, 1H), 6.35 (s, 1H), 7.60 (m, 3H), 7.78 (d, J=2.5 Hz, 1H), 7.89 (d, J=8.3 Hz, 2H).

Example 30

2-{2-[2-Cyclopentyl-1-(4-methanesulfonyl-phenyl)-ethyl]-1H-pyrrolo[2,3-b]pyridin-5-yloxy}-ethanol

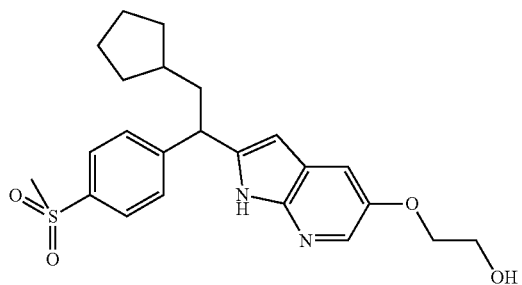

To a stirred solution of 2-bromoethanol (25 g, 200 mmol) and imidazole (41 g, 600 mmol) in dichloromethane (300 mL) was added tert-butyldiphenylchlorosilane (55 mL, 210 mmol) at room temperature and the mixture was stirred for 24 h. The resulting mixture was poured into ice-water, extracted with dichloromethane (2×250 mL), washed with brine, dried over anhydrous sodium sulfate and then concentrated in vacuo. Purification by flash silica gel chromatography (silica gel from QingDao, 200-300 mesh, glass column from Shanghai SD company, hexanes) afforded (2-bromo-ethoxy)-tert-butyl-diphenyl-silane (60 g, 83%) as a colorless oil.

Potassium carbonate (722 mg, 5.23 mmol) was added to a solution of 1-benzenesulfonyl-2-[2-cyclopentyl-1-(4-methanesulfonyl-phenyl)-vinyl]-1H-pyrrolo[2,3-b]pyridin-5-ol (prepared as in Example 13, 900 mg, 1.72 mmol) in N,N-dimethylformamide (2 mL) at room temperature. The mixture was stirred for 30 min and then treated with (2-bromo-ethoxy)-tert-butyl-diphenyl-silane (658 mg, 1.81 mmol) at room temperature. The mixture was heated at 80° C. and stirred for 3 h. The resulting mixture was diluted with ethyl acetate (150 mL), washed with brine, dried over anhydrous sodium sulfate and then concentrated in vacuo. Purification by flash silica gel chromatography (silica gel from QingDao, 200-300 mesh, glass column from Shanghai SD company, 33% ethyl acetate/hexanes) afforded 1-benzenesulfonyl-5-[2-(tert-butyl-diphenyl-silanyloxy)-ethoxy]-2-[2-cyclopentyl-1-(4-methanesulfonyl-phenyl)-vinyl]-1H-pyrrolo[2,3-b]pyridine (870 mg, 62.8%) as a white solid.

A solution of 1-benzenesulfonyl-5-[2-(tert-butyl-diphenyl-silanyloxy)-ethoxy]-2-[2-cyclopentyl-1-(4-methanesulfonyl-phenyl)-vinyl]-1H-pyrrolo[2,3-b]pyridine (870 mg, 1.08 mmol) in tetrahydrofuran (0.5 mL) and a tetrabutylammonium fluoride solution in tetrahydrofuran (1 M, 10 mL, 10 mmol) was stirred at room temperature for 12 h. The resulting mixture was diluted with ethyl acetate (150 mL), washed with a saturated aqueous ammonium chloride solution and brine, dried over anhydrous sodium sulfate and then concentrated in vacuo to afford 2-{2-[2-cyclopentyl-1-(4-methanesulfonyl-phenyl)-vinyl]-1H-pyrrolo[2,3-b]pyridin-5-yloxy}-ethanol (460 mg, quant.) as a white solid: LC/MS m/e calcd for $C_{23}H_{26}N_2O_4S$ [M+H]$^+$ 427.54, observed 427.4.

A mixture of 2-{2-[2-cyclopentyl-1-(4-methanesulfonyl-phenyl)-vinyl]-1H-pyrrolo[2,3-b]pyridin-5-yloxy}-ethanol (460 mg, 1.08 mmol) and 10% palladium on activated carbon (100 mg) in methanol (200 mL) was heated at 50° C. under hydrogen (50 psi) for 6 h. The mixture was cooled to room temperature before the catalyst was removed by filtration. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-{2-[2-cyclopentyl-1-(4-methanesulfonyl-phenyl)-ethyl]-1H-pyrrolo[2,3-b]pyridin-5-yloxy}-ethanol (236 mg, 55.1%) as a white solid: LC/MS m/e calcd for $C_{23}H_{28}N_2O_4S$ [M+H]$^+$ 429.55, observed 429.5; $^1$H NMR (400 MHz, CD$_3$OD) δ ppm 7.98 (br. s., 1H), 7.90 (d, J=8.3 Hz, 3H), 7.60 (d, J=8.1 Hz, 2H), 6.53 (s, 1H), 4.33 (t, J=7.8 Hz, 1H), 4.16 (t, J=4.5 Hz, 2H), 3.90 (t, J=4.5 Hz, 2H), 3.09 (s, 3H), 2.23-2.31 (m, 1H), 2.09-2.18 (m, 1H), 1.60-1.87 (m, 5H), 1.44-1.56 (m, 2H), 1.17-1.30 (m, 2H).

Example 31

2-[1-(4-Methanesulfonyl-phenyl)-2-(tetrahydro-pyran-4-yl)-5-methoxy-1H-pyrrolo[2,3-b]pyridine

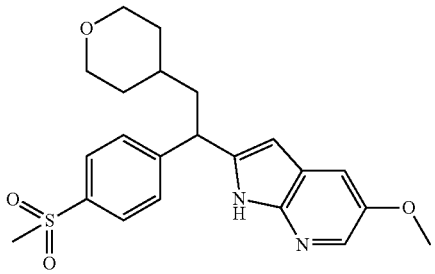

To a suspension of 1-benzenesulfonyl-5-methoxy-1H-pyrrolo[2,3-b]pyridine (prepared as in Example 10, 4 g, 13.9 mmol) in dry tetrahydrofuran (60 mL) at −78° C. was added freshly prepared lithium diisopropylamide [prepared by adding 1.6 M n-butyllithium in n-hexane (13 mL, 20.83 mmol) to a 0° C. solution of diisopropylamine (3.2 mL, 22.1 mmol) in dry tetrahydrofuran (20 mL)] dropwise. The mixture was stirred at −78° C. for 5 min and then treated with (tetrahydro-pyran-4-yl)-acetaldehyde (2.67 g, 20.8 mmol) dropwise. The resulting mixture was stirred at −78° C. for 1 h and quenched with brine. The mixture was extracted with ethyl acetate (2×300 mL), washed with brine, dried over anhydrous sodium sulfate and concentrated in vacuo. Purification by flash silica gel chromatography (silica gel from QingDao, 200-300 mesh, glass column from Shanghai SD company, 33% ethyl acetate/hexanes) afforded 1-(1-benzenesulfonyl-5-methoxy-1H-pyrrolo[2,3-b]pyridin-2-yl)-2-(tetrahydro-pyran-4-yl)-ethanol as a white solid (4.4 g, 77.2%): LC/MS m/e calcd for $C_{21}H_{24}N_2O_5S$ [M+H]$^+$ 417.50, observed 417.1.

To a 250 mL round bottomed flask charged with 1-(1-benzenesulfonyl-5-methoxy-1H-pyrrolo[2,3-b]pyridin-2-yl)-2-(tetrahydro-pyran-4-yl)-ethanol (4.4 g, 10.6 mmol) was added a solution of Dess-Martin periodinane in dichloromethane (0.3M, 106 mL, 31.7 mmol) at 25° C. The reaction mixture was stirred at 25° C. for 1 h and then quenched with a saturated aqueous sodium bicarbonate solution (60 mL). The mixture was extracted with ethyl acetate (350 mL), washed with a saturated aqueous sodium bicarbonate solution (3×50 mL), brine, dried over anhydrous sodium sulfate and then concentrated in vacuo to give 1-(1-benzenesulfonyl-5-methoxy-1H-pyrrolo[2,3-b]pyridin-2-yl)-2-(tetrahydro-pran-4-yl)-ethanone (4 g, 91%) as a light yellow solid which was used in the next step without further purification: LC/MS m/e calcd for $C_{21}H_{22}N_2O_5S$ [M+H]$^+$ 415.48, observed 415.1.

To a solution of 1-(1-benzenesulfonyl-5-methoxy-1H-pyrrolo[2,3-b]pyridin-2-yl)-2-(tetrahydro-pran-4-yl)-ethanone (2.9 g, 7 mmol) in dry tetrahydrofuran (50 mL) at −78° C. was added lithium bis(trimethylsilyl)amide solution in tetrahydrofuran (1 M, 10.5 mL, 10.5 mmol) dropwise. After stirring at −78° C. for 1 h, a solution of p-toluenesulfonic anhydride (3.16 g, 9.68 mmol) in tetrahydrofuran (20 mL) was added dropwise. The resulting mixture was kept at −78° C. for another 1.5 h. The reaction was quenched with water, extracted with ethyl acetate (300 mL), washed with brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded toluene-4-sulfonic acid-1-(1-benzenesulfonyl-5-methoxy-1H-pyrrolo[2,3-b]pyridin-2-yl)-2-(tetrahydro-pyran-4-yl)-vinyl ester (2.81 g, 72.1%) as a light yellow solid; LC/MS m/e calcd for $C_{28}H_{28}N_2O_7S_2$ [M+H]$^+$ 569.67, observed 569.13.

To a mixture of toluene-4-sulfonic acid-1-(1-benzenesulfonyl-5-methoxy-1H-pyrrolo[2,3-b]pyridin-2-yl)-2-(tetrahydro-pyran-4-yl)-vinyl ester (1.1 g, 1.94 mmol), 4-(methanesulfonyl)phenylboronic acid (775 mg, 3.88 mmol), dichlorobis(triphenylphosphine)palladium (II) (136 mg, 0.194 mmol) in dioxane (5 mL) was added an aqueous sodium carbonate solution (2 M, 2.5 mL, 5 mmol). The resulting mixture was subjected to microwave irradiation for 2 h at 100° C. The resulting mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-2-[1-(4-methanesulfonyl-phenyl)-2-(tetrahydro-pyran-4-yl)-vinyl]-5-methoxy-1H-pyrrolo[2,3-b]pyridine (540 mg, 54%) as a light yellow solid: LC/MS m/e calcd for $C_{28}H_{28}N_2O_6S_2$ [M+H]$^+$ 553.67, observed 553.2.

A solution of 1-benzenesulfonyl-2-[1-(4-methanesulfonyl-phenyl)-2-(tetrahydro-pyran-4-yl)-vinyl]-5-methoxy-1H-pyrrolo[2,3-b]pyridine (300 mg, 0.54 mmol) in tetrahydrofuran (0.5 mL) and a tetrabutylammonium fluoride solution in tetrahydrofuran (1 M, 2 mL, 2 mmol) was stirred at room temperature for 12 h. The resulting mixture was diluted with ethyl acetate (150 mL), washed with a saturated aqueous ammonium chloride solution and brine, dried over anhydrous sodium sulfate and then concentrated in vacuo to afford 2-[1-(4-methanesulfonyl-phenyl)-2-(tetrahydro-pyran-4-yl)-vinyl]-5-methoxy-1H-pyrrolo[2,3-b]pyridine (180 mg, 80.7%) as a white solid: LC/MS m/e calcd for $C_{22}H_{24}N_2O_4S$ [M+H]$^+$ 413.54, observed 413.1.

A mixture of 2-[1-(4-methanesulfonyl-phenyl)-2-(tetrahydro-pyran-4-yl)-vinyl]-5-methoxy-1H-pyrrolo[2,3-b]pyridine (180 mg, 0.44 mmol) and 10% palladium on activated carbon (50 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[1-(4-methanesulfonyl-phenyl)-2-(tetrahydro-pyran-4-yl)-ethyl]-5-methoxy-1H-pyrrolo[2,3-b]pyridine (80 mg, 44.4%) as a white solid: LC/MS m/e calcd for $C_{22}H_{26}N_2O_4S$ [M+H]$^+$ 415.53, observed 415.2; $^1$H NMR (400 MHz, CD$_3$OD) δ ppm 7.84-7.92 (m, 3H), 7.61 (d, J=8.3 Hz, 2H), 7.50 (d, J=2.5 Hz, 1H), 6.34 (s, 1H), 4.42 (t, J=8.0 Hz, 1H), 3.84-3.93 (m, 5H), 3.32-3.26 (m, 2H), 3.09 (s, 3H), 2.18-2.27 (m, 1H), 1.97-2.05 (m, 1H), 1.69-1.76 (m, 2H), 1.50 (ddt, J=10.8, 7.1, 3.5 Hz, 1H), 1.31-1.42 (m, 2H).

Example 32

2-[1(R)-(4-Methanesulfonyl-phenyl)-2-(tetrahydro-pyran-4-yl)-5-methoxy-1H-pyrrolo[2,3-b]pyridine

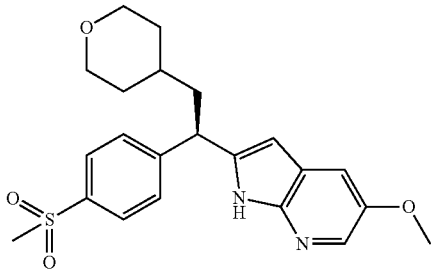

The 1:1 mixture of enantiomers of 2-[1-(4-methanesulfonyl-phenyl)-2-(tetrahydro-pyran-4-yl)-ethyl]-5-methoxy-1H-pyrrolo[2,3-b]pyridine (prepared as in Example 31, 50 mg) were separated by Agilent high performance liquid chromatography (chiral column: Daicel IA-H, 250 mm×20 mm i. d., 5 μm-particle size, temperature: 25° C., flow rate of 6.5 mL/min, 98% isopropanol/hexane as mobile phase and UV detection: 214 and 254 nm) to afford two pure enantiomers. The second peak, 2-[1(R)-(4-methanesulfonyl-phenyl)-2-(tetrahydro-pyran-4-yl)-ethyl]-5-methoxy-1H-pyrrolo[2,3-b]pyridine (14 mg) was isolated as a colorless oil: HR-ES-MS m/z calculated for $C_{22}H_{26}N_2O_4S_1$ [M+H]$^+$ 415.1683 observed 415.1686.

Example 33

5-Methoxy-2-[2-(tetrahydro-pyran-4-yl)-1-(4-trifluoromethyl-phenyl)-ethyl]-1H-pyrrolo[2,3-b]pyridine

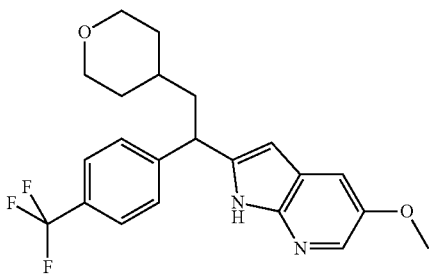

To a mixture of toluene-4-sulfonic acid-1-(1-benzenesulfonyl-5-methoxy-1H-pyrrolo[2,3-b]pyridin-2-yl)-2-(tetrahydro-pyran-4-yl)-vinyl ester (prepared as in Example 31, 350 mg, 0.62 mmol), 4-(trifluoromethyl)phenylboronic acid (293 mg, 1.54 mmol) and dichlorobis(triphenylphosphine) palladium (II) (43 mg, 0.06 mmol) in dioxane (5 mL) was added an aqueous sodium carbonate solution (2 M, 0.8 mL, 1.6 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-5-methoxy-2-[2-(tetrahydro-pyran-4-yl)-1-(trifluoromethyl-phenyl)-vinyl]-1H-pyrrolo[2,3-b]pyridine (272 mg, 82%) as a light yellow solid: LC/MS m/e calcd for $C_{28}H_{25}F_3N_2O_4S$ [M+H]$^+$ 543.58, observed 543.2.

A solution of 1-benzenesulfonyl-5-methoxy-2-[2-(tetrahydro-pyran-4-yl)-1-(4-trifluoromethyl-phenyl)-vinyl]-1H-pyrrolo[2,3-b]pyridine (260 mg, 0.48 mmol) in tetrahydrofuran (0.5 mL) and a tetrabutylammonium fluoride solution in tetrahydrofuran (1 M, 2 mL, 2 mmol) was stirred at room temperature for 12 h. The resulting mixture was diluted with ethyl acetate (150 mL), washed with a saturated aqueous ammonium chloride solution and brine, dried over anhydrous sodium sulfate and then concentrated in vacuo to afford 5-methoxy-2-[2-(tetrahydro-pyran-4-yl)-1-(4-trifluoromethyl-phenyl)-vinyl]-1H-pyrrolo[2,3-b]pyridine (193 mg, quant.) as a white solid: LC/MS m/e calcd for $C_{22}H_{21}F_3N_2O_2$ [M+H]$^+$ 403.42, observed 403.2.

A mixture of 5-methoxy-2-[2-(tetrahydro-pyran-4-yl)-1-(4-trifluoromethyl-phenyl)-vinyl]-1H-pyrrolo[2,3-b]pyridine (180 mg, 0.45 mmol) and 10% palladium on activated carbon (50 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 5-methoxy-2-[2-(tetrahydro-pyran-4-yl)-1-(4-trifluoromethyl-phenyl)-ethyl]-1H-pyrrolo[2,3-b]pyridine (120 mg, 66.7%) as a white solid: LC/MS m/e calcd for $C_{22}H_{23}F_3N_2O_2$ [M+H]$^+$ 405.44, observed 405.2; $^1$H NMR (400 MHz, CD$_3$OD) δ ppm 7.84 (d, J=2.5 Hz, 1H), 7.59 (d, J=8.3 Hz, 2H), 7.51 (d, J=8.3 Hz, 2H), 7.48 (d, J=2.5 Hz, 1H), 6.30 (s, 1H), 4.36 (t, J=8.1 Hz, 1H), 3.86-3.95 (m, 2H), 3.20-3.30 (m, 2H), 2.16-2.27 (m, 1H), 1.98 (ddd, J=13.9, 7.3, 7.1 Hz, 1H), 1.70 (t, J=14.5 Hz, 2H), 1.48 (dddd, J=14.5, 10.8, 7.2, 3.7 Hz, 1H), 1.26-1.42 (m, 2H).

Example 34

5-Methoxy-2-[2-(tetrahydro-pyran-4-yl)-1(R)-(4-trifluoromethyl-phenyl)-ethyl]-1H-pyrrolo[2,3-b]pyridine

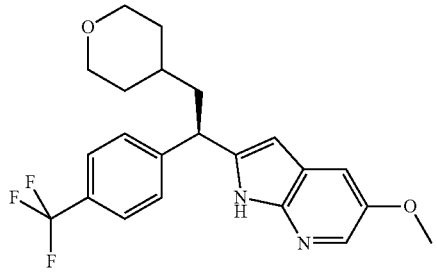

The 1:1 mixture of enantiomers of 5-methoxy-2-[2-(tetrahydro-pyran-4-yl)-1-(4-trifluoromethyl-phenyl)-ethyl]-

1H-pyrrolo[2,3-b]pyridine (prepared as in Example 33, 100 mg) were separated by Agilent high performance liquid chromatography (chiral column: Daicel IB-H, 250 mm×20 mm i. d., 5 μm-particle size, temperature: 25° C., flow rate of 15 mL/min, 20% ethanol/hexanes as mobile phase and UV detection: 214 and 254 nm) to afford two pure enantiomers. The second peak, 5-methoxy-2-[2-(tetrahydro-pyran-4-yl)-1 (R)-(4-trifluoromethyl-phenyl)-ethyl]-1H-pyrrolo[2,3-b]pyridine (18 mg) was isolated as a white solid: $^1$H NMR (400 MHz, CD$_3$OD) δ ppm 1.36 (m, 2H), 1.49 (m, 1H), 1.71 (m, 2H), 1.99 (m, 1H), 2.22 (m, 1H), 3.31 (m, 2H), 3.87 (s, 3H), 3.90 (m, 2H), 4.39 (t, J=8.1 Hz, 1H), 6.32 (s, 1H), 7.51 (d, J=2.8 Hz, 1H), 7.53 (d, J=8.1 Hz, 2H), 7.62 (d, J=8.1 Hz, 2H), 7.85 (d, J=2.8 Hz, 1H).

Example 35

2-{4-[2-Cyclopentyl-1-(5-methoxy-1H-pyrrolo[2,3-b]pyridin-2-yl)-ethyl]-phenyl}-propan-2-ol

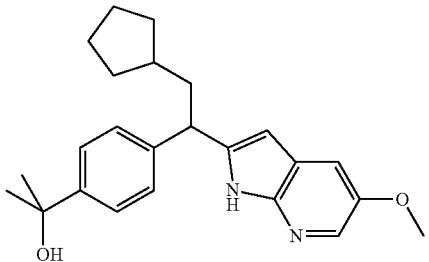

To a mixture of toluene-4-sulfonic acid-1-(benzenesulfonyl-5-methoxy-1H-pyrrolo[2,3-b]pyridin-2-yl)-2-cyclopentyl-vinyl ester (prepared as in Example 12, 1 g, 1.81 mmol), 4-acetylphenylboronic acid (743 mg, 4.53 mmol), and dichlorobis(triphenylphosphine)palladium (II) (127 mg, 0.18 mmol) in dioxane (5 mL) was added an aqueous sodium carbonate solution (2 M, 2.3 mL, 4.6 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 20% ethyl acetate/hexanes) afforded 1-{4-[1-(1-benzenesulfonyl-5-methoxy-1H-pyrrolo[2,3-b]pyridin-2-yl)-2-cyclopentyl-vinyl]-phenyl}-ethanone (850 mg, 93.9%) as a light yellow solid: LC/MS m/e calcd for C$_{29}$H$_{28}$N$_2$O$_4$S [M+H]$^+$ 501.62, observed 501.2.

To a stirred solution of 1-{4-[1-(1-benzenesulfonyl-5-methoxy-1H-pyrrolo[2,3-b]pyridin-2-yl)-2-cyclopentyl-vinyl]-phenyl}-ethanone (300 mg, 0.6 mmol) in dry tetrahydrofuran (5 mL) was added a methylmagnesium chloride solution in tetrahydrofuran (3 M, 2 mL, 6 mmol) at 0° C. The resulting mixture was stirred at room temperature for 2 h, quenched with an ammonium chloride solution, extracted with ethyl acetate, washed with brine, dried over anhydrous sodium sulfate. The solvent was evaporated in vacuo. Purification by flash silica gel chromatography (silica gel from QingDao, 200-300 mesh, glass column from Shanghai SD company, 25% ethyl acetate/hexanes) afforded 2-{4-[1-(1-benzenesulfonyl-5-methoxy-1H-pyrrolo[2,3-b]pyridin-2-yl)-2-cyclopentyl-vinyl]-phenyl}-propan-2-ol (160 mg, 51.8%) as a light yellow solid: LC/MS m/e calcd for C$_{30}$H$_{32}$N$_2$O$_4$S [M+H]$^+$ 517.66, observed 517.1.

A mixture of 2-{4-[1-(1-benzenesulfonyl-5-methoxy-1H-pyrrolo[2,3-b]pyridin-2-yl)-2-cyclopentyl-vinyl]-phenyl}-propan-2-ol (160 mg, 0.31 mmol) in ethanol (3 mL) and an aqueous sodium hydroxide solution (10%, 1.5 mL) was heated at reflux for 5 h. The mixture was acidified to pH 4-5 with a 2 N aqueous hydrochloric acid solution, diluted with ethyl acetate (150 mL), washed with brine, dried over anhydrous sodium sulfate and then concentrated in vacuo to give 2-{4-[2-cyclopentyl-1-(5-methoxy-1H-pyrrolo[2,3-b]pyridin-2-yl)-vinyl]-phenyl}-propan-2-ol (100 mg, 86.2%) as a light yellow solid: LC/MS m/e calcd for C$_{24}$H$_{28}$N$_2$O$_2$ [M+H]$^+$ 377.5, observed 377.2.

A mixture of 2-{4-[2-cyclopentyl-1-(5-methoxy-1H-pyrrolo[2,3-b]pyridin-2-yl)-vinyl]-phenyl}-propan-2-ol (100 mg, 0.266 mmol) and 10% palladium on activated carbon (50 mg) in methanol (200 mL) was heated at 50° C. under hydrogen (50 psi) for 6 h. The mixture was cooled to room temperature. The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-{4-[2-cyclopentyl-1-(5-methoxy-1H-pyrrolo[2,3-b]pyridin-2-yl)-ethyl]-phenyl}-propan-2-ol (24 mg, 24%) as a white solid: LC/MS m/e calcd for C$_{24}$H$_{30}$N$_2$O$_2$ [M+H]$^+$ 379.52, observed 379.2; $^1$H NMR (400 MHz, CD$_3$OD) δ ppm 1.21 (m, 2H), 1.48 (m, 2H), 1.50 (s, 6H), 1.57-1.91 (m, 5H, H), 2.08 (m, 1H), 2.17 (m, 1H), 3.86 (s, 3H), 4.12 (t, J=7.8 Hz, 1H), 6.30 (s, 1H), 7.27 (d, J=8.3 Hz, 2H), 7.42 (d, J=8.3 Hz, 2H), 7.58 (d, J=2.5 Hz, 1H), 7.82 (br, 1H).

Example 36

2-{2-[2-Cyclopentyl-1-(4-methanesulfonyl-phenyl)-ethyl]-1H-pyrrolo[2,3-b]pyridin-5-yl}-ethanol

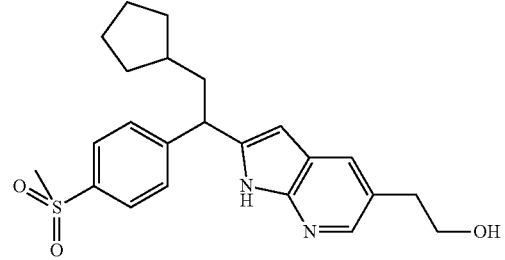

To a stirred solution of 3-{2-[2-cyclopentyl-1-(4-methanesulfonyl-phenyl)-ethyl]-1H-pyrrolo[2,3-b]pyridin-5-yl}-propane-1,2-diol (prepared as in Example 11, 70 mg, 0.16 mmol) in 50% aqueous tetrahydrofuran (10 mL) was added sodium metaperiodate (40 mg, 0.19 mmol) at 0° C. The resulting mixture was stirred at room temperature for 2 h, extracted with ethyl acetate, washed with brine, dried over anhydrous sodium sulfate. The solvent was evaporated in vacuo to give {2-[2-cyclopentyl-1-(4-methanesulfonyl-phenyl)-ethyl]-1H-pyrrolo[2,3-b]pyridin-5-yl}-acetaldehyde (65 mg, quant.) as a light yellow solid: LC/MS m/e calcd for C$_{23}$H$_{26}$N$_2$O$_3$S [M+H]$^+$ 411.54, observed 411.1.

To a stirred solution of {2-[2-cyclopentyl-1-(4-methanesulfonyl-phenyl)-ethyl]-1H-pyrrolo[2,3-b]pyridin-5-yl}-acetaldehyde (65 mg, 0.158 mmol) in dry methanol at 0° C. (5 mL) was added sodium borohydride (60 mg, 1.58 mmol). The resulting mixture was stirred at room temperature for 2 h, quenched with a saturated aqueous ammonium chloride solution, extracted with ethyl acetate, washed with brine, and dried over anhydrous sodium sulfate. The solvent was evaporated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-[2-cyclopentyl-1-(4-methanesulfonyl-phenyl)-ethyl]-1H-pyrrolo[2,3-b]pyridin-5-yl}-ethanol (20 mg, 30.7%) as a white solid: LC/MS m/e calcd for $C_{23}H_{28}N_2O_3S$ [M+H]$^+$ 413.56, observed 413.2; $^1$H NMR (400 MHz, CD$_3$OD) δ ppm 7.99 (s, 1H), 7.87-7.92 (m, J=8.3 Hz, 2H), 7.79 (s, 1H), 7.58-7.63 (m, J=8.3 Hz, 2H), 6.36 (s, 1H), 4.31 (t, J=7.8 Hz, 1H), 3.78 (t, J=6.8 Hz, 2H), 3.10 (s, 3H), 2.90 (t, J=6.8 Hz, 2H), 2.25-2.33 (m, 1H), 2.07-2.15 (m, 1H), 1.62-1.87 (m, 5H), 1.46-1.56 (m, 2H), 1.19-1.31 (m, 2H).

Example 37

Dimethylamino-acetic acid 2-[2-cyclopentyl-1-(4-methanesulfonyl-phenyl)-ethyl]-1H-pyrrolo[2,3-b]pyridin-5-ylmethyl-ester

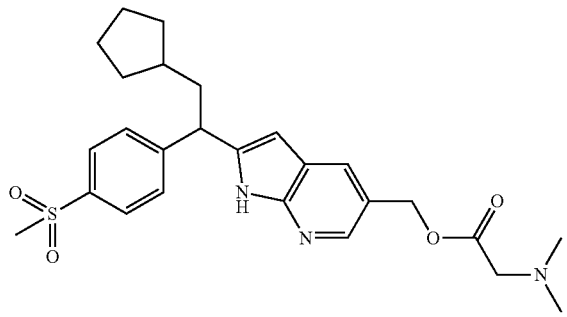

To a solution of {2-[2-cyclopentyl-1-(4-methanesulfonyl-phenyl)-ethyl]-1H-pyrrolo[2,3-b]pyridin-5-yl}-methanol (prepared as in Example 8, 30 mg, 0.075 mmol), dimethylamino-acetic acid (21 mg, 0.11 mmol) in N,N-dimethylformamide (1.0 mL) and N-methylmorpholine (33 uL, 0.23 mmol) was added 1-hydroxybenzotriazole hydrate (20 mg, 0.113 mmol) followed by N-(3-dimethylaminopropyl)-N'-ethylcarbodiimide hydrochloride (29 mg, 0.11 mmol) in one portion. The mixture was stirred at 25° C. for 6 h, diluted with ethyl acetate (100 mL), washed with a 1 N sodium bicarbonate solution, 1 N aqueous hydrochloric acid solution, brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded dimethylamino-acetic acid 2-[2-cyclopentyl-1-(4-methanesulfonyl-phenyl)-ethyl]-1H-pyrrolo[2,3-b]pyridin-5-ylmethyl-ester (20 mg, 54.9%) as a light yellow solid: LC/MS m/e calcd for $C_{26}H_{33}N_3O_4S_1$ [M+H]$^+$ 484.63, observed 484.3; $^1$H NMR (400 MHz, CDCl$_3$) δ ppm 1.19 (m, 2H), 1.48 (m, 2H), 1.56-1.86 (m, 5H, H), 2.12 (m, 1H), 2.27 (m, 1H), 2.43 (s, 6H, 2×NCH$_3$), 3.02 (s, 3H), 3.29 (s, 2H, NCH$_2$), 4.28 (t, J=7.8 Hz, 1H), 5.28 (s, 2H), 6.38 (s, 1H), 7.50 (d, J=8.0 Hz, 2H), 7.87 (d, J=8.0 Hz, 2H), 7.39 (s, 1H), 8.16 (s, 1H), 10.87 (s, 1H).

Example 38

{2-[2-Cyclopentyl-1-(4-methanesulfonyl-phenyl)-ethyl]-1H-pyrrolo[2,3-b]pyridin-5-yl}-acetonitrile

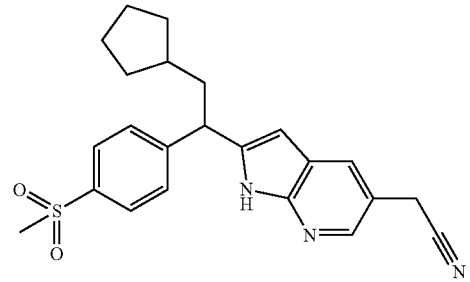

To a stirred solution of {2-[2-cyclopentyl-1-(4-methanesulfonyl-phenyl)-ethyl]-1H-pyrrolo[2,3-b]pyridin-5-yl}-methanol (prepared as in Example 8, 800 mg, 1.92 mmol) in dichloromethane (20 mL) at 0° C. was added a solution of thionyl chloride (0.36 mL, 4.89 mmol) in dichloromethane (2 mL) and the mixture was stirred for 2 h. The resulting mixture was concentrated in vacuo and the residue was extracted with ethyl acetate, washed with a saturated aqueous sodium bicarbonate solution (2×50 mL), brine, dried over anhydrous sodium sulfate and then concentrated in vacuo to afford 5-chloromethyl-2-[2-cyclopentyl-1-(4-methanesulfonyl-phenyl)-ethyl]-1H-pyrrolo[2,3-b]pyridine (798 mg, quant.) as a light yellow solid which was used in the next step without further purification: LC/MS m/e calcd for $C_{22}H_{25}ClN_2O_2S$ [M+H]$^+$ 417.97, observed 417.0.

A mixture of 5-chloromethyl-2-[2-cyclopentyl-1-(4-methanesulfonyl-phenyl)-ethyl]-1H-pyrrolo[2,3-b]pyridine (798 mg, 1.92 mmol) and sodium cyanide (500 mg, 10.87 mmol) in N,N-dimethylformamide (3 mL) was subjected to microwave irradiation for 0.5 h at 100° C. The mixture was diluted with ethyl acetate (250 mL), washed with brine, dried over anhydrous sodium sulfate and then concentrated in vacuo. Purification by flash silica gel chromatography (silica gel from QingDao, 200-300 mesh, glass column from Shanghai SD company, 5% methanol/dichloromethane) afforded {2-[2-cyclopentyl-1-(4-methanesulfonyl-phenyl)-ethyl]-1H-pyrrolo[2,3-b]pyridin-5-yl}-acetonitrile (140 mg, 18%) as a light yellow solid: LC/MS m/e calcd for $C_{23}H_{25}N_3O_2S$ [M+H]$^+$ 408.54, observed 408.0; $^1$H NMR (400 MHz, CDCl$_3$) δ ppm 1.21 (m, 2H), 1.48 (m, 2H), 1.57-1.90 (m, 5H, H), 2.18 (m, 1H), 2.26 (m, 1H), 3.06 (s, 3H), 3.99 (s, 2H), 4.43 (m, 1H), 6.59 (s, 1H), 7.56 (d, J=8.2 Hz, 2H), 7.90 (d, J=8.2 Hz, 2H), 8.24 (s, 1H), 8.32 (s, 1H), 12.48 (br, 1H).

Example 39

2-{2-[2-Cyclopentyl-1-(4-methanesulfonyl-phenyl)-ethyl]-1H-pyrrolo[2,3-b]pyridin-5-yl}-N,N-dimethyl-acetamide

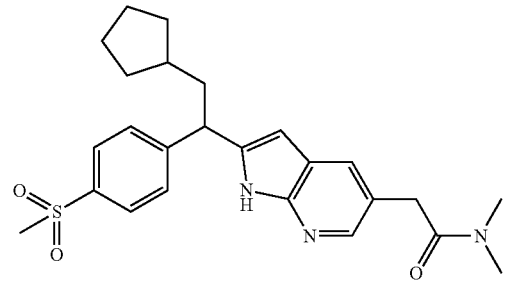

A mixture of {2-[2-cyclopentyl-1-(4-methanesulfonyl-phenyl)-ethyl]-1H-pyrrolo[2,3-b]pyridin-5-yl}-acetonitrile (as prepared in Example 38, 140 mg, 0.34 mmol) in 36% hydrochloric acid (1 mL) and acetic acid (5 mL) was refluxed for 2 h. The mixture was concentrated in vacuo, extracted with ethyl acetate (250 mL), washed with brine, dried over anhydrous sodium sulfate and then concentrated in vacuo to afford {2-[2-cyclopentyl-1-(4-methanesulfonyl-phenyl)-ethyl]-1H-pyrrolo[2,3-b]pyridin-5-yl}-acetic acid (150 mg, quant.) as a light yellow solid which was used in the next step without further purification: LC/MS m/e calcd for $C_{23}H_2N_2O_4S$ [M+H]$^+$ 427.54, observed 427.0.

To a solution of {2-[2-cyclopentyl-1-(4-methanesulfonyl-phenyl)-ethyl]-1H-pyrrolo[2,3-b]pyridin-5-yl}-acetic acid (75 mg, 0.17 mmol) and dimethylamine hydrochloride (43 mg, 0.53 mmol) in N,N-dimethylformamide (2 mL) and N-methylmorpholine (97 uL, 0.88 mmol) was added 1-hydroxybenzotriazole hydrate (110 mg, 0.81 mmol) followed by N-(3-dimethylaminopropyl)-N'-ethylcarbodiimide hydrochloride (68 mg, 0.35 mmol) in one portion. The mixture was stirred at 25° C. for 6 h. The mixture was diluted with ethyl acetate (100 mL), washed with a 1 N aqueous sodium bicarbonate solution, 1N aqueous hydrochloric acid solution, brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-[2-cyclopentyl-1-(4-methanesulfonyl-phenyl)-ethyl]-1H-pyrrolo[2,3-b]pyridin-5-yl}-N,N-dimethyl-acetamide (45 mg, 56%) as a light yellow solid: LC/MS m/e calcd for $C_{25}H_{31}N_3O_3S$ [M+H]$^+$ 454.61, observed 454.1; $^1$H NMR (400 MHz, CDCl$_3$) δ ppm 1.18 (m, 2H), 1.48 (m, 2H), 1.56-1.85 (m, 5H, H), 2.10 (m, 1H), 2.23 (m, 1H), 2.99 (s, 3H), 3.04 (s, 3H), 3.10 (s, 3H), 3.81 (s, 2H), 4.29 (t, J=7.8 Hz, 1H), 6.35 (s, 1H), 7.50 (d, J=8.3 Hz, 2H), 7.86 (d, J=8.3 Hz, 2H), 7.96 (s, 1H), 8.02 (s, 1H), 10.99 (br, 1H).

Example 40

(2-{2-[2-Cyclopentyl-1-(4-methanesulfonyl-phenyl)-ethyl]-1H-pyrrolo[2,3-b]pyridin-5-yl}-ethyl)-dimethyl-amine

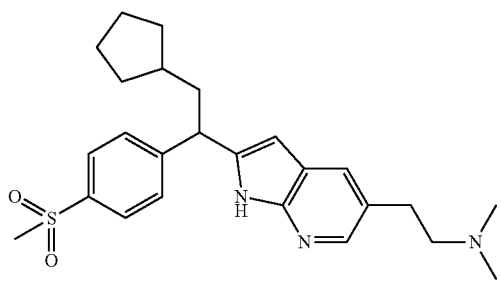

A mixture of 2-{2-[2-cyclopentyl-1-(4-methanesulfonyl-phenyl)-ethyl]-1H-pyrrolo[2,3-b]pyridin-5-yl}-N,N-dimethyl-acetamide (as prepared in Example 39, 30 mg, 0.066 mmol) and lithium aluminum hydride (5 mg, 0.13 mmol) in dry tetrahydrofuran (3 mL) was refluxed for 4 h. The mixture was then cooled to room temperature, quenched with a 15% aqueous sodium hydroxide solution, extracted with ethyl acetate, washed with brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded (2-{2-[2-cyclopentyl-1-(4-methanesulfonyl-phenyl)-ethyl]-1H-pyrrolo[2,3-b]pyridin-5-yl}-ethyl)-dimethyl-amine (15 mg, 50%) as a colorless oil: LC/MS m/e calcd for $C_{25}H_{33}N_3O_2S$ [M+H]$^+$ 440.62, observed 440.2; $^1$H NMR (400 MHz, CDCl$_3$) δ ppm 1.20 (m, 2H), 1.49 (m, 2H), 1.64 (m, 2H), 1.67-1.86 (m, 3H), 2.09 (m, 1H), 2.26 (m, 1H), 2.56 (br. s., 6H), 2.81 (s, 2H), 3.03 (s, 2H), 3.05 (s, 3H), 4.27 (t, J=7.8 Hz, 1H), 6.33 (s, 1H), 7.49 (d, J=8.3 Hz, 2H), 7.74 (d, J=1.8 Hz, 1H), 7.84 (br. s., 1H), 7.90 (d, J=8.3 Hz, 2H), 10.38 (br. s., 1H).

Example 41

2-[2-Cyclopentyl-1-(4-methanesulfonyl-phenyl)-ethyl]-5-methoxymethyl-1H-pyrrolo[2,3-b]pyridine

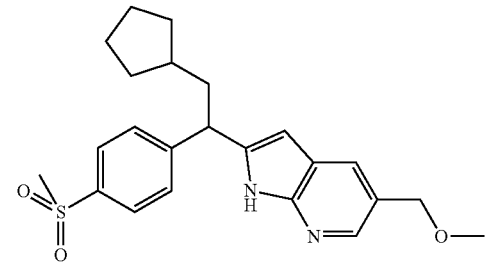

To a stirred solution of 1-benzenesulfonyl-1H-pyrrolo[2,3-b]pyridin-5-carboxylic acid methyl ester (prepared as in Example 1, 8 g, 25.3 mmol) in dry tetrahydrofuran (100 mL) was added diisobutylaluminum hydride (126 mL, 126 mmol) at −78° C. The mixture was warmed to room temperature and stirred for 1 h. The mixture was cooled to 0° C. and quenched with a saturated aqueous potassium sodium tartrate solution, and then stirred for 30 min. The resulting mixture was filtered, washed with tetrahydrofuran (300 mL). The combined organic layers were washed with brine, dried over anhydrous sodium sulfate and then concentrated in vacuo to afford (1-benzenesulfonyl-1H-pyrrolo[2,3-b]pyridin-5-yl)-methanol (6.5 g, 89.2%) as a light yellow solid: LC/MS m/e calcd for $C_{14}H_{12}N_2O_3S$ [M+H]$^+$ 289.33, observed 289.1.

To a stirred solution of (1-benzenesulfonyl-1H-pyrrolo[2,3-b]pyridin-5-yl)-methanol (4.2 g, 14.6 mmol) in dichloromethane (20 mL) at 0° C. was added a solution of thionyl chloride (1.6 mL, 21.9 mmol) in dichloromethane (5 mL) and then stirred for 2 h. The reaction mixture was concentrated in vacuo and the residue was extracted with ethyl acetate, washed with a saturated aqueous sodium bicarbonate solution (2×100 mL), brine, dried over anhydrous sodium sulfate and then concentrated in vacuo to afford 1-benzenesulfonyl-5-chloromethyl-1H-pyrrolo[2,3-b]pyridine (3.3 g, 75%) as a light yellow solid which was used in the next step without further purification: LC/MS m/e calcd for $C_{14}H_{11}ClN_2O_2S$ [M+H]$^+$ 307.77, observed 307.1.

To a mixture of 1-benzenesulfonyl-5-chloromethyl-1H-pyrrolo[2,3-b]pyridine (3.3 g, 10.76 mmol) in methanol (15 mL) was added sodium methoxide (1.74 g, 32.3 mmol) at room temperature and the resulting mixture was stirred for 12 h. The mixture was diluted with ethyl acetate (250 mL), washed with brine, dried over anhydrous sodium sulfate and then concentrated in vacuo to afford 5-methoxymethyl-1H- pyrrolo[2,3-b]pyridine (1.74 g, quant.) as a light yellow solid which was used in the next step without further purification: LC/MS m/e calcd for $C_9H_{10}N_2O$ [M+H]$^+$ 163.19, observed 162.9.

To a solution of tetrabutylammonium bromide (104 mg, 0.32 mmol) and 5-methoxymethyl-1H-pyrrolo[2,3-b]pyridine (1.74 g, 10.76 mmol) in dichloromethane (100 mL) was added sodium hydroxide powder (1.3 g, 32.4 mmol) at 0° C. The mixture was stirred at 0° C. for 5 min and then treated with benzene sulfonyl chloride (1.7 mL, 14.0 mmol). The mixture was stirred at 0° C. for another 15 min before it was warmed to 25° C. and stirred for 12 h. The resulting mixture was filtered and then concentrated in vacuo. Purification by flash silica gel chromatography (silica gel from QingDao, 200-300 mesh, glass column from Shanghai SD company, 25% ethyl acetate/hexanes) afforded 1-benzenesulfonyl-5-methoxymethyl-1H-pyrrolo[2,3-b]pyridine (1.54 g, 47.5%) as a white solid: LC/MS m/e calcd for $C_{15}H_{14}N_2O_3S$ [M+H]$^+$ 303.35, observed 302.9.

To a suspension of 1-benzenesulfonyl-5-methoxymethyl-1H-pyrrolo[2,3-b]pyridine (1.54 g, 5.1 mmol) in dry tetrahydrofuran (40 mL) at −78° C. was added n-butyllithium in n-hexane (1.6 M, 6.63 mmol, 4.14 mL) dropwise. The mixture was stirred at −78° C. for 5 min and then treated with cyclopentanecarbaldehyde (9.2 mmol, 1.03 g) dropwise. The resulting mixture was stirred at −78° C. for 1 h and quenched with brine. The mixture was extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-(1-benzenesulfonyl-5-methoxymethyl-1H-pyrrolo[2,3-b]pyridin-2-yl]-2-cyclopentyl-ethanol as a light yellow solid (710 mg, 33.6%): LC/MS m/e calcd for $C_{22}H_{26}N_2O_4S$ [M+H]$^+$ 415.53, observed 415.0.

To a solution of 1-(1-benzenesulfonyl-5-methoxymethyl-1H-pyrrolo[2,3-b]pyridin-2-yl]-2-cyclopentyl-ethanol (710 mg, 1.71 mmol) in dichloromethane (50 mL) was added Dess-Martin periodinane (1.8 g, 4.2 mmol) at 25° C. The reaction mixture was stirred at 25° C. for 1 h and then quenched with a saturated aqueous sodium bicarbonate solution (60 mL). The mixture was extracted with ethyl acetate (250 mL), washed with a saturated aqueous sodium bicarbonate solution (3×50 mL), brine, dried over anhydrous sodium sulfate and then concentrated in vacuo to give 1-(1-benzenesulfonyl-5-methoxymethyl-1H-pyrrolo[2,3-b]pyridin-2-yl]-2-cyclopentyl-ethanone (704 mg, quant.) as a light yellow solid which was used in the next step without further purification: LC/MS m/e calcd for $C_{22}H_{24}N_2O_4S$ [M+H]$^+$ 413.51, observed 413.2.

To a solution of 1-(1-benzenesulfonyl-5-methoxymethyl-1H-pyrrolo[2,3-b]pyridin-2-yl]-2-cyclopentyl-ethanone (800 mg, 1.94 mmol) in dry tetrahydrofuran (50 mL) at −78° C. was added a solution of lithium bis(trimethylsilyl)amide in tetrahydrofuran (1 M, 2.9 mL, 2.9 mmol) dropwise. After stirring at −78° C. for 1 h, a solution of p-toluenesulfonic anhydride (1.1 g, 3.3 mmol) in tetrahydrofuran (10 mL) was added dropwise. The resulting mixture was kept at −78° C. for an additional 1.5 h. The reaction was quenched with water, extracted with ethyl acetate (300 mL), washed with brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded toluene-4-sulfonic acid 1-benzenesulfonyl-5-methoxymethyl-1H-pyrrolo[2,3-b]pyridin-2-yl)-2-cyclopentyl-vinyl ester (1.03 g, 93%) as a light yellow solid: LC/MS m/e calcd for $C_{29}H_{30}N_2O_6S_2$ [M+H]$^+$ 567.70, observed 567.0.

To a mixture of toluene-4-sulfonic acid 1-benzenesulfonyl-5-methoxymethyl-1H-pyrrolo[2,3-b]pyridin-2-yl)-2-cyclopentyl-vinyl ester (1.03 g, 1.82 mmol), 4-(methanesulfonyl)phenylboronic acid (910 mg, 4.55 mmol), dichlorobis(triphenylphosphine)palladium (II) (130 mg, 0.18 mmol) in dioxane (5 mL) was added an aqueous sodium carbonate solution (2 M, 2.3 mL, 4.6 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 1-benzenesulfonyl-2-[2-cyclopentyl-1-(4-methanesulfonyl-phenyl)-vinyl]-5-methoxymethyl-1H-pyrrolo[2,3-b]pyridine (600 mg, 60%) as a light yellow solid: LC/MS m/e calcd for $C_{29}H_{30}N_2O_5S_2$ [M+H]$^+$ 551.70, observed 551.2.

A solution of 1-benzenesulfonyl-2-[2-cyclopentyl-1-(4-methanesulfonyl-phenyl)-vinyl]-5-methoxymethyl-1H-pyrrolo[2,3-b]pyridine (600 mg, 1.09 mmol) in tetrahydrofuran (0.5 mL) and a tetrabutylammonium fluoride solution in tetrahydrofuran (1 M, 5 mL, 5 mmol) was stirred at room temperature for 12 h. The mixture was diluted with ethyl acetate (150 mL), washed with a saturated aqueous ammonium chloride solution and brine, dried over anhydrous sodium sulfate and concentrated in vacuo to afford 2-[2-cyclopentyl-1-(4-methanesulfonyl-phenyl)-vinyl]-5-methoxymethyl-1H-pyrrolo[2,3-b]pyridine (411 mg, quant.) as a white solid: LC/MS m/e calcd for $C_{23}H_{26}N_2O_3S$ [M+H]$^+$ 411.54, observed 411.1.

A mixture of 2-[2-cyclopentyl-1-(4-methanesulfonyl-phenyl)-vinyl]-5-methoxymethyl-1H-pyrrolo[2,3-b]pyridine (411 mg, 1.09) and 10% palladium on activated carbon (100 mg) in methanol (250 mL) was heated at 50° C. under hydrogen (50 psi) for 6 h. The mixture was cooled to room temperature before The catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-5-methoxymethyl-1H-pyrrolo[2,3-b]pyridine (80 mg, 19.4%) as a white solid: LC/MS m/e calcd for $C_{23}H_{28}N_2O_3S$ [M+H]$^+$ 413.56, observed 413.1; $^1$H NMR (400 MHz, CD$_3$OD) δ ppm 8.30 (s, 1H), 8.20 (s, 1H), 7.89-7.93 (m, J=8.3 Hz, 2H), 7.55-7.66 (m, 2H), 6.67 (s, 1H), 4.61 (s, 2H), 4.37 (t, J=8.0 Hz, 1H), 3.33-3.48 (m, 3H), 3.08-3.13 (m, 3H), 2.25-2.33 (m, 1H), 2.12-2.20 (m, 1H), 1.61-1.88 (m, 5H), 1.45-1.56 (m, 2H), 1.18-1.31 (m, 2H).

Example 42

2-[2-Cyclopentyl-1(R)-(4-methanesulfonyl-phenyl)-ethyl]-5-methoxymethyl-1H-pyrrolo[2,3-b]pyridine

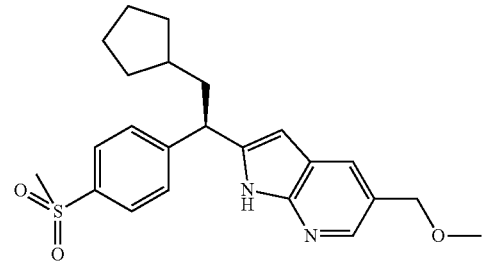

The 1:1 mixture of enantiomers of 2-[2-cyclopentyl-1-(4-methanesulfonyl-phenyl)-ethyl]-5-methoxymethyl-1H-pyrrolo[2,3-b]pyridine (prepared as in Example 41, 70 mg) were separated by Berger SFC-Minigram High performance Liquid chromatography (chiral column: Daicel AD-H, 250 mm×10 mm i. d., 5 μm-particle size, temperature: 25° C., flow rate of 10 mL/min, 30% isopropanol as mobile phase and UV detection: 214 and 254 nm) to afford two pure enantiomers. The second peak, 2-[2-cyclopentyl-1(R)-(4-methanesulfonyl-phenyl)-ethyl]-5-methoxymethyl-1H-pyrrolo[2,3-b]pyridine (20 mg) was isolated as a white solid: $^1$H NMR (400 MHz, CD$_3$OD) δ ppm 1.24 (m, 2H), 1.50 (m, 2H), 1.59-1.90 (m, 5H, H), 2.16 (m, 1H), 2.29 (m, 1H), 3.09 (s, 3H), 3.43 (s, 3H), 4.38 (t, J=7.9 Hz, 1H), 4.61 (s, 2H), 6.67 (s, 1H), 7.61 (d, J=8.3 Hz, 2H), 7.91 (d, J=8.3 Hz, 2H), 8.20 (br. d., 1H), 8.30 (br. d., 1H).

Example 43

4-[2-Cyclopentyl-1-(1H-pyrrolo[2,3-b]pyridin-2-yl)-ethyl]-benzonitrile

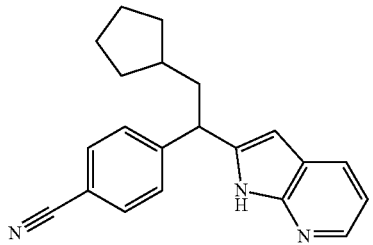

To a solution of 4-carboxyphenylboronic (8 g, 48.2 mmol) and 2-amino-2-methylpropane (10.1 mL, 96.4 mmol) in N,N-dimethylformamide (10 mL), dichloromethane (150 mL) and N-methylmorpholine (10.6 mL, 96.4 mmol) was added 1-hydroxybenzotriazole hydrate (9.77 g, 72.3 mmol) at 0° C. followed by N-(3-dimethylaminopropyl)-N'-ethylcarbodiimide hydrochloride (13.9 g, 72.3 mmol) in one portion. The mixture was then stirred at 25° C. for 6 h, diluted with dichloromethane (100 mL), washed with 1 N aqueous hydrochloric acid solution, brine, dried over anhydrous sodium sulfate and concentrated in vacuo to afford [4-(tert-butylaminocarbonyl)phenyl]boronic acid (7.5 g, 70.7%) as a white solid: LC/MS m/e calcd for C$_{11}$H$_{16}$BNO$_3$ [M+H]$^+$ 222.07, observed 222.1.

To a −78° C. suspension of 1-benzenesulfonyl-1H-pyrrolo[2,3-b]pyridine (800.7 mg, 3.1 mmol) in dry tetrahydrofuran (40 mL) was added 1.6 M n-butyllithium in n-hexane (2.2 mL, 3.5 mmol) dropwise. The mixture was stirred at −78° C. for 5 min before adding cyclopentanecarbaldehyde (516 mg, 4.6 mmol) dropwise. The resulting mixture was stirred at −78° C. for 1 h and quenched by adding brine. The mixture was extracted with ethyl acetate (200 mL×2), washed with brine, dried over anhydrous sodium sulfate and concentrated in vacuo. Purification by flash silica gel chromatography (silica gel from QingDao, 200-300 mesh, glass column from Shanghai SD company) (20% ethyl acetate/hexanes) afforded 1-(1-benzenesulfonyl-1H-pyrrolo[2,3-b]pyridin-2-yl)-2-cyclopentyl-ethanol as colorless oil (690 mg, 60%): LC/MS m/e calcd for C$_{20}$H$_{23}$N$_2$O$_3$S [M+H]$^+$ 371.14, observed 371.0.

To a 250 mL round bottomed flask charged with 1-(1-benzenesulfonyl-1H-pyrrolo[2,3-b]pyridin-2-yl)-2-cyclopentyl-ethanol (690 mg, 1.86 mmol) was added a 0.3 M solution of Dess-Martin periodinane in methylene chloride (12.4 mL, 3.72 mmol) at 25° C. The reaction mixture was stirred at 25° C. for 1 h before quenching with saturated aqueous sodium bicarbonate solution (60 mL). The mixture was extracted with ethyl acetate (250 mL), washed with saturated aqueous sodium bicarbonate solution (50 mL×3), brine, dried over anhydrous sodium sulfate and then concentrated in vacuo to give 1-(1-benzenesulfonyl-1H-pyrrolo[2,3-b]pyridin-2-yl)-2-cyclopentyl-ethanone (685 mg, quant.) as a light yellow solid which was used for the next step without further purification: LC/MS m/e calcd for C$_{20}$H$_{21}$N$_2$O$_3$S [M+H]$^+$ 369.12, observed 369.0.

To a −78° C. solution of 1-(1-benzenesulfonyl-1H-pyrrolo[2,3-b]pyridin-2-yl)-2-cyclopentyl-ethanone (685 mg, 1.86 mmol) in dry tetrahydrofuran (40 mL) was added lithium bis(trimethylsilyl)amide (1 M in tetrahydrofuran, 2.8 mL, 2.8 mmol) dropwise. After stirring at −78° C. for 1 h, a solution of p-toluenesulfonic anhydride (1.1 g, 0.98 3.35 mmol) in tetrahydrofuran (20 mL) was added dropwise. The ultimate solution was kept at −78° C. for another 1.5 h. The reaction was quenched with water, extracted with ethyl acetate (300 mL), washed with brine, dried over anhydrous sodium sulfate and then concentrated in vacuo to afford toluene-4-sulfonic acid 1-(1-benzenesulfonyl-1H-pyrrolo[2,3-b]pyridin-2-yl)-2-cyclopentyl-vinyl ester as a light yellow solid (972 mg, quant.) which was used for the next step without further purification: LC/MS m/e calcd for C$_{27}$H$_{27}$N$_2$O$_5$S$_2$ [M+H]$^+$ 523.13, observed 523.1.

To a mixture of toluene-4-sulfonic acid-1-(1-benzenesulfonyl-1H-pyrrolo[2,3-b]pyridin-2-yl)-2-cyclopentyl-vinyl ester (522 mg, 1 mmol), [4-(tert-butylaminocarbonyl)phenyl]boronic acid (442 mg, 2 mmol), and dichlorobis(triphenylphosphine)palladium (II) (70.2 mg, 0.1 mmol) in dioxane (5 mL) was added an aqueous sodium carbonate solution (2 M, 1.25 mL, 2.5 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 20% ethyl acetate/hexanes) to afford 4-[1-(1-benzenesulfonyl-1H-pyrrolo[2,3-b]pyridin-2-yl)-2-cyclopentyl-vinyl]-N-tert-butyl-benzamide (300 mg, 56.9%) as a light yellow solid: LC/MS m/e calcd for C$_{31}$H$_{33}$N$_3$O$_3$S [M+H]$^+$ 528.69, observed 528.0.

A solution of 4-[1-(1-benzenesulfonyl-1H-pyrrolo[2,3-b]pyridin-2-yl)-2-cyclopentyl-vinyl]-N-tert-butyl-benzamide (300 mg, 0.57 mmol) in tetrahydrofuran (0.5 mL) and a tetrabutylammonium fluoride solution in tetrahydrofuran (1 M, 5 mL, 5 mmol) was stirred at room temperature for 12 h. The mixture was diluted with ethyl acetate (150 mL), washed with a saturated aqueous ammonium chloride solution and brine, dried over anhydrous sodium sulfate and concentrated in vacuo to afford N-tert-butyl-4-[2-cyclopentyl-1H-pyrrolo[2,3-b]pyridin-2-yl)-vinyl]-benzamide (220 mg, quant.) as a white solid: LC/MS m/e calcd for C$_{25}$H$_{29}$N$_3$O [M+H]$^+$ 388.53, observed 388.2.

A mixture of N-tert-butyl-4-[2-cyclopentyl-1H-pyrrolo[2,3-b]pyridin-2-yl)-vinyl]-benzamide (220 mg, 0.57 mmol) and 10% palladium on activated carbon (60 mg) in methanol (250 mL) was heated at 50° C. under hydrogen (50 psi) for 6 h. The mixture was cooled to room temperature. The catalyst was removed by filtration and washed with ethyl acetate. The filtrate was concentrated in vacuo to afford N-tert-butyl-4-[2-cyclopentyl-1H-pyrrolo[2,3-b]pyridin-2-yl)-ethyl]-benzamide (187 mg, 84.6%) as a white solid: LC/MS m/e calcd for C$_{25}$H$_{31}$N$_3$O [M+H]$^+$ 390.55, observed 390.2.

To a stirred solution of N-tert-butyl-4-[2-cyclopentyl-1H-pyrrolo[2,3-b]pyridin-2-yl)-ethyl]-benzamide (150 mg, 0.38 mmol) in dichloromethane (2.0 mL) was added thionyl chloride (0.28 mL, 3.85 mmol). The mixture was heated at 60° C. and then stirred at 60° C. for 4 h. The reaction mixture was concentrated in vacuo and the residue was extracted with ethyl acetate, washed with a saturated aqueous sodium bicarbonate solution (2×50 mL), brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 4-[2-cyclopentyl-1-(1H-pyrrolo[2,3-b]pyridin-2-yl)-ethyl]-benzonitrile (26 mg, 21.5%) as a light yellow solid: LC/MS m/e calcd for $C_{21}H_{21}N_3$ [M+H]$^+$ 316.42, observed 316.1; $^1$H NMR (400 MHz, CD$_3$OD) δ ppm 8.07 (d, J=4.5 Hz, 1H), 7.88 (d, J=7.8 Hz, 1H), 7.59-7.70 (m, 2H), 7.37-7.52 (m, J=8.3 Hz, 2H), 7.03 (dd, J=7.7, 4.9 Hz, 1H), 6.33-6.38 (m, 1H), 4.26 (t, J=7.8 Hz, 1H), 2.20-2.29 (m, 1H), 1.98-2.12 (m, 1H), 1.57-1.84 (m, 5H), 1.40-1.53 (m, 2H), 1.13-1.33 (m, 2H).

Example 44

2-[2-Cyclopentyl-1-(4-methanesulfonyl-phenyl)-ethyl]-5-(3-methoxy-propyl)-1H-pyrrolo[2,3-b]pyridine

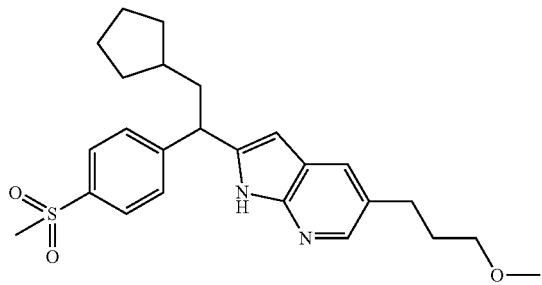

To a solution of 1-benzenesulfonyl-5-bromo-1H-pyrrolo[2,3-b]pyridine (prepared as in Example 7, 6.5 g, 19.3 mmol) in N,N-dimethylformamide (30 mL) was added 3-methoxypropyne (5 mL, 57.9 mmol), tetrakis(triphenylphosphine)palladium(0) (2.2 g, 1.93 mmol), copper (I) iodide (735 mg, 3.85 mmol) and triethylamine (8.1 mL, 57.9 mmol) at room temperature. The mixture was then heated at 85° C. and stirred for 12 h. The resulting mixture was cooled to room temperature, extracted with ethyl acetate (2×250 mL), washed with brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded 1-benzenesulfonyl-5-(3-methoxy-prop-1-ynyl)-1H-pyrrolo[2,3-b]pyridine as a light yellow solid (5 g, 89.1%): LC/MS m/e calcd for $C_{17}H_{14}N_2O_3S$ [M+H]$^+$ 327.38, observed 327.0.

To a suspension of 1-benzenesulfonyl-5-(3-methoxy-prop-1-ynyl)-1H-pyrrolo[2,3-b]pyridine (5 g, 15.3 mmol) in dry tetrahydrofuran (100 mL) at −78° C. was added a solution n-butyllithium in n-hexane (1.6 M, 9.2 mL, 23.0 mmol). The mixture was stirred at −78° C. for 15 min and then treated with cyclopentanecarbaldehyde (3.1 g, 27.6 mmol) dropwise. The resulting mixture was stirred at −78° C. for 1 h and quenched with brine. The mixture was extracted with ethyl acetate (2×150 mL), washed with brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded 1-[1-benzenesulfonyl-5-(3-methoxy-prop-1-ynyl)-1H-pyrrolo[2,3-b]pyridin-2-yl]-2-cyclopentyl-ethanol (1.4 g, 20.9%): LC/MS m/e calcd for $C_{24}H_{26}N_2O_4S$ [M+H]$^+$ 439.55, observed 439.0.

To a 50 mL round bottomed flask charged with 14'-benzenesulfonyl-5-(3-methoxy-prop-1-ynyl)-1H-pyrrolo[2,3-b]pyridin-2-yl]-2-cyclopentyl-ethanol (1.4 g, 3.2 mmol) and dichloromethane (20 mL) was added Dess-Martin periodinane (3.4 g, 8 mmol) at 25° C. The reaction mixture was stirred at 25° C. for 1 h and then quenched with a saturated aqueous sodium bicarbonate solution (200 mL). The mixture was extracted with ethyl acetate (150 mL), washed with a saturated aqueous sodium bicarbonate solution (3×300 mL), brine, dried over anhydrous sodium sulfate and concentrated in vacuo to give 1-[1-benzenesulfonyl-5-(3-methoxy-prop-1-ynyl)-1H-pyrrolo[2,3-b]pyridin-2-yl]-2-cyclopentyl-ethanone (1 g, 71.9%) as an orange oil which was used in the next step without further purification: LC/MS m/e calcd for $C_{24}H_{24}N_2O_4S$ [M+H]$^+$ 437.53, observed 437.0.

To a solution of 1-[1-benzenesulfonyl-5-(3-methoxy-prop-1-ynyl)-1H-pyrrolo[2,3-b]pyridin-2-yl]-2-cyclopentyl-ethanone (1 g, 2.3 mmol) in dry tetrahydrofuran (60 mL) at −78° C. was added lithium bis(trimethylsilyl)amide solution in tetrahydrofuran (1 M, 3.4 mL, 3.4 mmol) dropwise. After stirring at −78° C. for 1 h, a solution of p-toluenesulfonic anhydride (1.3 g, 3.98 mmol) in tetrahydrofuran (25 mL) was added dropwise. The resulting mixture was kept at −78° C. for an additional 1.5 h. The reaction was quenched with water, extracted with ethyl acetate (200 mL), washed with brine, dried over anhydrous sodium sulfate and then concentrated in vacuo. Purification by flash silica gel chromatography (silica gel from QingDao, 200-300 mesh, glass column from Shanghai SD company, 20% ethyl acetate/hexanes) afforded toluene-4-sulfonic acid 1-[1-benzenesulfonyl-5-(3-methoxy-prop-1-ynyl)-1H-pyrrolo[2,3-b]pyridin-2-yl]-2-cyclopentyl-vinyl ester (1 g, 74.1%) as a light yellow solid: LC/MS m/e calcd for $C_{31}H_{30}N_2O_6S_2$ [M+H]$^+$ 591.72, observed 591.1.

To a mixture of toluene-4-sulfonic acid 1-[1-benzenesulfonyl-5-(3-methoxy-prop-1-ynyl)-1H-pyrrolo[2,3-b]pyridin-2-yl]-2-cyclopentyl-vinyl ester (900 mg, 1.53 mmol), 4-(methanesulfonyl)phenylboronic acid (763 mg, 3.81 mmol) and dichlorobis(triphenylphosphine)palladium (II) (107 mg, 0.15 mmol) in dioxane (5 mL) was added an aqueous sodium carbonate solution (2 M, 1.9 mL). The mixture was subjected to microwave irradiation for 1 h at 100° C. The resulting mixture was diluted with ethyl acetate (150 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 33% ethyl acetate/hexanes) afforded 1-benzenesulfonyl-2-[2-cyclopentyl-1-(4-methanesulfonyl-phenyl)-vinyl]-5-(3-methoxy-prop-1-ynyl)-1H-pyrrolo[2,3-b]pyridine (400 mg, 45.6%) as an orange oil: LC/MS m/e calcd for $C_{31}H_{30}N_2O_5S_2$ [M+H]$^+$ 575.72, observed 575.1.

A solution of 1-benzenesulfonyl-2-[2-cyclopentyl-1-(4-methanesulfonyl-phenyl)-vinyl]-5-(3-methoxy-prop-1-ynyl)-1H-pyrrolo[2,3-b]pyridine (400 mg, 0.70 mmol) in tetrahydrofuran (0.5 mL) and a tetrabutylammonium fluoride solution in tetrahydrofuran (1 M, 4 mL, 4 mmol) was stirred at room temperature for 12 h. The mixture was diluted with ethyl acetate (150 mL), washed with a saturated aqueous ammonium chloride solution and brine, dried over anhydrous sodium sulfate and concentrated in vacuo to afford 2-[2-cyclopentyl-1-(4-methanesulfonyl-phenyl)-vinyl]-5-(3-methoxy-prop-1-ynyl)-1H-pyrrolo[2,3-b]pyridine (302 mg, quant.) as a light yellow solid: LC/MS m/e calcd for $C_{25}H_{26}N_2O_3S$ [M+H]$^+$ 435.56, observed 435.0.

A mixture of 2-[2-cyclopentyl-1-(4-methanesulfonyl-phenyl)-vinyl]-5-(3-methoxy-prop-1-ynyl)-1H-pyrrolo[2,3-b]pyridine (302 mg, 0.7 mmol) and 10% palladium on activated carbon (80 mg) in methanol (250 mL) was heated at 50° C. under hydrogen (50 psi) for 8 h. The mixture was cooled to room temperature. The catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(4-methanesulfonyl-phenyl)-ethyl]-5-(3-methoxy-propyl)-1H-pyrrolo[2,3-b]pyridine (100 mg, 32.5%) as a colorless oil: LC/MS m/e calcd for $C_{25}H_{32}N_2O_3S$ [M+H]$^+$ 441.61, observed 441.1; $^1$H NMR (400 MHz, CD$_3$OD) δ ppm 8.25 (s, 1H), 8.10 (br. s., 1H), 7.90-7.95 (m, J=8.1 Hz, 2H), 7.60-7.65 (m, J=8.3 Hz, 2H), 6.65 (s, 1H), 4.39 (t, J=7.8 Hz, 1H), 3.43 (t, J=6.2 Hz, 2H), 3.35 (s, 3H), 3.11 (s, 3H), 2.88 (t, J=7.6 Hz, 2H), 2.26-2.34 (m, 1H), 2.13-2.22 (m, 1H), 1.92-1.99 (m, 2H), 1.63-1.89 (m, 5H), 1.46-1.58 (m, 2H), 1.19-1.34 (m, 2H).

Example 45

3-{2-[2-Cyclopentyl-1-(4-methanesulfonyl-phenyl)-ethyl]-1H-pyrrolo[2,3-b]pyridin-5-yl}-propan-1-ol

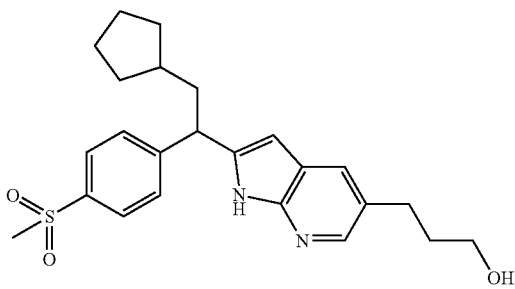

To stirred solution of 2-[2-cyclopentyl-1-(4-methanesulfonyl-phenyl)-ethyl]-5-(3-methoxy-propyl)-1H-pyrrolo[2,3-b]pyridine (prepared as in Example 44, 90 mg, 0.21 mmol) in dry dichloromethane (10 mL) was added a solution of boron tribromide (0.67 mL, 6.95 mmol) in dry dichloromethane (5 mL) at –78° C. The mixture was warmed to room temperature and stirred for 1 h. The mixture was poured into ice-water, neutralized with a 2.5 M aqueous sodium hydroxide solution (pH ~6) and then extracted with ethyl acetate (2×250 mL), washed with brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3-{2-[2-cyclopentyl-1-(4-methanesulfonyl-phenyl)-ethyl]-1H-pyrrolo[2,3-b]pyridin-5-yl}-propan-1-ol (20 mg, 23%) as a white solid: LC/MS m/e calcd for $C_{24}H_{30}N_2O_3S$ [M+H]$^+$ 427.58, observed 427.1; $^1$H NMR (400 MHz, CD$_3$OD) δ ppm 8.35 (s, 1H), 8.14 (br. s., 1H), 7.90-7.95 (m, J=8.1 Hz, 2H), 7.60-7.65 (m, J=8.3 Hz, 2H), 6.67-6.72 (m, 1H), 4.37-4.46 (m, 1H), 3.62 (t, J=6.2 Hz, 2H), 3.11 (s, 3H), 2.92 (t, J=7.7 Hz, 2H), 2.26-2.35 (m, 1H), 2.14-2.23 (m, 1H), 1.83-1.96 (m, 3H), 1.64-1.81 (m, 4H), 1.47-1.58 (m, 2H), 1.20-1.33 (m, 2H).

Example 46

2-[(E)-2-Cyclobutyl-1-(4-methanesulfonyl-phenyl)-vinyl]-5-fluoro-1H-pyrrolo[2,3-b]pyridine

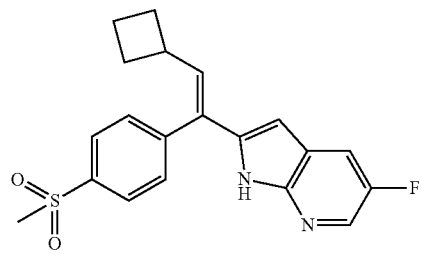

To a solution of 1-benzenesulfonyl-5-fluoro-1H-pyrrolo[2,3-b]pyridine (3 g, 10.87 mmol) in dry tetrahydrofuran (40 mL) at –78° C. was added a solution of n-butyllithium in n-hexane (2.5 M, 6.8 mL 17 mmol). The mixture was stirred at –78° C. for 35 min and then treated with 4-methylsulfanyl-benzaldehyde (2.8 mL, 21.0 mmol) dropwise. The resulting mixture was stirred at –78° C. for 1 h and quenched with brine. The mixture was extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded (1-benzenesulfonyl-5-fluoro-1H-pyrrolo[2,3-b]pyridin-2-yl)-(4-methylsulfanyl-phenyl)-methanol as a white solid (2.1 g, 45.2%): LC/MS m/e calcd for $C_{21}H_{17}FN_2O_3S_2$ [M+H]$^+$ 429.51, observed 428.7.

To a 250 mL round bottomed flask charged with (1-benzenesulfonyl-5-fluoro-1H-pyrrolo[2,3-b]pyridin-2-yl)-(4-methylsulfanyl-phenyl)-methanol (2.1 g, 4.9 mmol) in dichloromethane (200 mL) was added Dess-Martin periodinane (2.5 g, 5.9 mmol) at 25° C. The reaction mixture was stirred at 25° C. for 1 h and then quenched with a saturated aqueous sodium bicarbonate solution (60 mL). The mixture was extracted with ethyl acetate (250 mL), washed with a saturated aqueous sodium bicarbonate solution (3×50 mL), brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded (1-benzenesulfonyl-5-fluoro-1H-pyrrolo[2,3-b]pyridin-2-yl)-(4-methylsulfanyl-phenyl)-methanone (1.9 g, 90%) as a light yellow oil: LC/MS m/e calcd for $C_{21}H_{15}FN_2O_3S_2$ [M+H]$^+$ 427.49, observed 426.7.

To a stirred suspension of magnesium powder (1.6 g, 67.5 mmol) and iodine (3 pieces) in dry tetrahydrofuran (8 mL) was added (bromomethyl)cyclobutane (1.1 mL, 7.5 mmol)

dropwise at room temperature. After the reaction initiated, a solution of (bromomethyl)cyclobutane (5.5 mL, 37.5 mmol) in dry tetrahydrofuran (30 mL) was added dropwise and then heated at reflux for 30 min. The resulting Grignard reagent was added to a solution of (1-benzenesulfonyl-5-fluoro-1H-pyrrolo[2,3-b]pyridin-2-yl)-(4-methylsulfanyl-phenyl)-methanone (1.9 g, 4.5 mmol) at 0° C. and stirred for 1 h. The reaction was quenched with water, extracted with ethyl acetate (300 mL), washed with brine, dried over anhydrous sodium sulfate and concentrated in vacuo. Purification by flash silica gel chromatography (silica gel from QingDao, 200-300 mesh, glass column from Shanghai SD company, 15% ethyl acetate/hexanes) afforded 1-(1-benzenesulfonyl-5-fluoro-1H-pyrrolo[2,3-b]pyridin-2-yl)-2-cyclobutyl-1-(4-methylsulfanyl-phenyl)-ethanol (600 mg, 26.9%) as a light yellow solid; LC/MS m/e calcd for $C_{26}H_{25}FN_2O_3S_2$ $[M+H]^+$ 497.63, observed 496.8.

To a stirred solution of 1-(1-benzenesulfonyl-5-fluoro-1H-pyrrolo[2,3-b]pyridin-2-yl)-2-cyclobutyl-1-(4-methylsulfanyl-phenyl)-ethanol (500 mg, 1 mmol) in methanol (50 mL) and water (10 mL) was added sodium metaperiodate (440 mg, 2 mmol) at room temperature. The resulting mixture was stirred at room temperature for 8 h, extracted with ethyl acetate, washed with brine, dried over anhydrous sodium sulfate. The solvent was evaporated in vacuo to give 1-(1-benzenesulfonyl-5-fluoro-1H-pyrrolo[2,3-b]pyridin-2-yl)-2-cyclobutyl-1-(4-methylsulfinyl-phenyl)-ethanol (512 mg, quant.) as a light yellow solid: LC/MS m/e calcd for $C_{26}H_{25}FN_2O_4S_2$ $[M+H]^+$ 513.63, observed 512.8.

To a stirred solution of 1-(1-benzenesulfonyl-5-fluoro-1H-pyrrolo[2,3-b]pyridin-2-yl)-2-cyclobutyl-1-(4-methylsulfinyl-phenyl)-ethanol (512 mg, 1 mmol) in methanol (50 mL) and water (10 mL) was added potassium permanganate (126 mg, 0.8 mmol) at room temperature. The mixture was stirred at room temperature for 2 h, diluted with ethyl acetate (150 mL), washed with brine, dried over anhydrous sodium sulfate and concentrated in vacuo to afford 1-(1-benzenesulfonyl-5-fluoro-1H-pyrrolo[2,3-b]pyridin-2-yl)-2-cyclobutyl-1-(4-methylsulfonyl-phenyl)-ethanol (520 mg, quant.) as a light yellow solid: LC/MS m/e calcd for $C_{26}H_{25}FN_2O_5S_2$ $[M+H]^+$ 529.63, observed 529.0.

A solution of 1-(1-benzenesulfonyl-5-fluoro-1H-pyrrolo[2,3-b]pyridin-2-yl)-2-cyclobutyl-1-(4-methylsulfonyl-phenyl)-ethanol (520 mg, 1 mmol) in tetrahydrofuran (0.5 mL) and a tetrabutylammonium fluoride solution in tetrahydrofuran (1 M, 5.0 mL, 5.0 mmol) was stirred at room temperature for 2 h. The mixture was diluted with ethyl acetate (150 mL), washed with a saturated aqueous ammonium chloride solution and brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[(E)-2-cyclobutyl-1-(4-methanesulfonyl-phenyl)-vinyl]-5-fluoro-1H-pyrrolo[2,3-b]pyridine (230 mg, 62.1%) as a light yellow solid: LC/MS m/e calcd for $C_{20}H_{19}FN_2O_2S$ $[M+H]^+$ 371.45, observed 371.0; $^1$H NMR (400 MHz, $CD_3OD$) δ ppm 8.06 (d, J=8.3 Hz, 3H), 7.50-7.58 (m, 3H), 6.66 (d, J=9.3 Hz, 1H), 5.86 (s, 1H), 3.22 (s, 3H), 2.99 (m, 1H), 2.04-2.16 (m, 4H), 1.85-1.94 (m, 2H).

Example 47

2-[2-Cyclobutyl-1-(4-methanesulfonyl-phenyl)-ethyl]-5-fluoro-1H-pyrrolo[2,3-b]pyridine

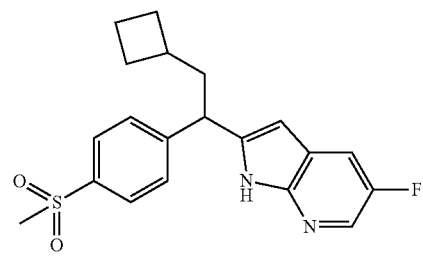

A mixture of [2-(E)-cyclobutyl-1-(4-methanesulfonyl-phenyl)-vinyl]-5-fluoro-1H-pyrrolo[2,3-b]pyridine (prepared as in Example 46, 200 mg, 0.54 mmol) and 10% palladium on activated carbon (70 mg) in methanol (250 mL) was heated at 50° C. under hydrogen (50 psi) for 8 h. The mixture was cooled to room temperature. The catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclobutyl-1-(4-methanesulfonyl-phenyl)-ethyl]-5-fluoro-1H-pyrrolo[2,3-b]pyridine (35 mg, 17.5%) as a light yellow solid: LC/MS m/e calcd for $C_{20}H_{21}FN_2O_2S$ $[M+H]^+$ 373.46, observed 372.8; $^1$H NMR (400 MHz, $CD_3OD$) δ ppm 8.03 (t, J=2.1 Hz, 1H), 7.88-7.93 (m, J=8.3 Hz, 2H), 7.67-7.79 (m, 1H), 7.56-7.61 (m, J=8.3 Hz, 2H), 6.42 (s, 1H), 4.20 (t, J=7.7 Hz, 1H), 3.06-3.19 (m, 3H), 2.16-2.40 (m, 3H), 1.93-2.08 (m, 2H), 1.64-1.90 (m, 4H).

Example 48

2-Cyclopentyl-1-(5-fluoro-1H-pyrrolo[2,3-b]pyridin-2-yl)-1-(4-methanesulfonyl-phenyl)-ethanol

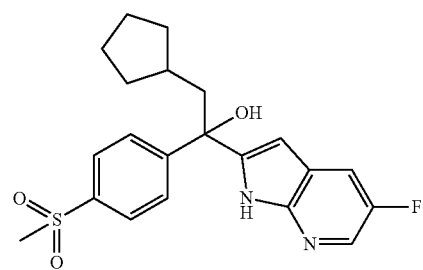

To a suspension of 1-benzenesulfonyl-5-fluoro-1H-pyrrolo[2,3-b]pyridine (10.9 g, 39.5 mmol) in dry tetrahydrofuran (200 mL) at −78° C. was added a solution of n-butyl-lithium in n-hexane (2.5 M, 23 mL, 55.3 mmol) dropwise. The mixture was stirred at −78° C. for 5 min and then treated with cyclopentanecarbaldehyde (8 g, 71.1 mmol) dropwise. The mixture was stirred at −78° C. for 1 h and quenched with brine. The resulting mixture was extracted with ethyl acetate (2×200 mL), washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-(1-benzenesulfonyl-5-fluoro-1H-pyrrolo[2,3-b]pyridin-2-yl)-2-cyclopentyl-ethanol as a white solid (12.5 g, 81.5%): LC/MS m/e calcd for $C_{20}H_{21}FN_2O_3S$ [M+H]$^+$ 389.46, observed 388.9.

To a 250 mL round bottomed flask charged with 1-(1-benzenesulfonyl-5-fluoro-1H-pyrrolo[2,3-b]pyridin-2-yl)-2-cyclopentyl-ethanol (12.5 g, 32.2 mmol) in dichloromethane (300 mL) was added Dess-Martin periodinane (17.8 g, 41.9 mmol) at 25° C. The reaction mixture was stirred at 25° C. for 1 h and then quenched with a saturated aqueous sodium bicarbonate solution (200 mL). The mixture was extracted with ethyl acetate (500 mL), washed with a saturated aqueous sodium bicarbonate solution (3×150 mL), brine, dried over anhydrous sodium sulfate and concentrated in vacuo to give 1-(1-benzenesulfonyl-5-fluoro-1H-pyrrolo[2,3-b]pyridin-2-yl)-2-cyclopentyl-ethanone (9.9 g, 80%) as a light yellow solid which was used in the next step without further purification: LC/MS m/e calcd for $C_{20}H_{19}FN_2O_3S$ [M+H]$^+$ 387.45, observed 387.1.

To a solution of 1-(1-benzenesulfonyl-5-fluoro-1H-pyrrolo[2,3-b]pyridin-2-yl)-2-cyclopentyl-ethanone (4 g, 10.36 mmol) in dry tetrahydrofuran (10 mL) at 0° C. was added a solution of 4-thioanisolemagnesium bromide in tetrahydrofuran (0.5 M, 50 mL, 25 mmol) dropwise. After stirring at 0° C. for 1 h, the reaction was quenched with water, extracted with ethyl acetate (300 mL), washed with brine, dried over anhydrous sodium sulfate and concentrated in vacuo. Purification by flash silica gel chromatography (silica gel from QingDao, 200-300 mesh, glass column from Shanghai SD company, 33% ethyl acetate/hexanes) afforded 1-(1-benzenesulfonyl-5-fluoro-1H-pyrrolo[2,3-b]pyridin-2-yl)-2-cyclopentyl-1-(4-methylsulfanyl-phenyl)-ethanol (5 g, 94.6%) as a light yellow solid; LC/MS m/e calcd for $C_{27}H_{27}FN_2O_3S_2$ [M+H]$^+$ 511.65, observed 510.7.

To a stirred solution of 1-(1-benzenesulfonyl-5-fluoro-1H-pyrrolo[2,3-b]pyridin-2-yl)-2-cyclopentyl-1-(4-methylsulfanyl-phenyl)-ethanol (5 g, 10 mmol) in methanol (100 mL) and water (30 mL) was added sodium metaperiodate (4.3 g, 20 mmol) at room temperature. The resulting mixture was stirred at room temperature for 18 h, extracted with ethyl acetate, washed with brine, dried over anhydrous sodium sulfate. The solvent was evaporated in vacuo to give 1-(1-benzenesulfonyl-5-fluoro-1H-pyrrolo[2,3-b]pyridin-2-yl)-2-cyclopentyl-1-(4-methaneylsulfinyl-phenyl)-ethanol (5.1 g, quant.) as a light yellow solid: LC/MS m/e calcd for $C_{27}H_{27}FN_2O_4S_2$ [M+H]$^+$ 527.65, observed 527.0.

To a stirred solution of 1-(1-benzenesulfonyl-5-fluoro-1H-pyrrolo[2,3-b]pyridin-2-yl)-2-cyclopentyl-1-(4-methaneylsulfinyl-phenyl)-ethanol (5.1 g, 10 mmol) in methanol (150 mL) and water (30 mL) at room temperature was added potassium permanganate (948 mg, 6 mmol). The mixture was stirred at room temperature for 2 h, diluted with ethyl acetate (150 mL), washed with brine, dried over anhydrous sodium sulfate and concentrated in vacuo to afford 1-(1-benzenesulfonyl-5-fluoro-1H-pyrrolo[2,3-b]pyridin-2-yl)-2-cyclopentyl-1-(4-methanesulfonyl-phenyl)-ethanol (5.1 g, 94%) as a light yellow solid: LC/MS m/e calcd for $C_{27}H_{27}FN_2O_5S_2$ [M+H]$^+$ 543.65, observed 542.9.

A solution of 1-(1-benzenesulfonyl-5-fluoro-1H-pyrrolo[2,3-b]pyridin-2-yl)-2-cyclopentyl-1-(4-methanesulfonyl-phenyl)-ethanol (5.1 g, 9.4 mmol) in tetrahydrofuran (0.5 mL) and a tetrabutylammonium fluoride solution in tetrahydrofuran (1 M, 20 mL, 20 mmol) was stirred at room temperature for 2 h. The mixture was diluted with ethyl acetate (150 mL), washed with a saturated aqueous ammonium chloride solution and brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-cyclopentyl-1-(5-fluoro-1H-pyrrolo[2,3-b]pyridin-2-yl)-1-(4-methanesulfonyl-phenyl)-ethanol (100 mg) as a white solid: LC/MS m/e calcd for $C_{21}H_{23}FN_2O_3S$ [M+H]$^+$ 403.49, observed 403.1; $^1$H NMR (400 MHz, CD$_3$OD) δ ppm 8.11 (br. s., 1H), 7.95-8.00 (m, J=8.3 Hz, 2H), 7.88-7.94 (m, J=8.6 Hz, 2H), 7.77 (dd, J=9.1, 2.3 Hz, 1H), 6.60 (s, 1H), 3.16-3.23 (m, 3H), 2.54-2.64 (m, 2H), 1.83-1.98 (m, 2H), 1.43-1.71 (m, 5H), 1.25-1.40 (m, 1H), 1.05-1.15 (m, 1H).

Example 49

2-Cyclopentyl-1-(5-fluoro-1H-pyrrolo[2,3-b]pyridin-2-yl)-1-(4-methanesulfonyl-phenyl)-ethanol

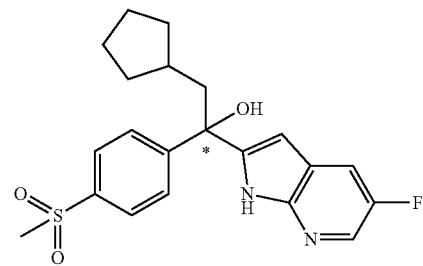

The 1:1 mixture of enantiomers of 2-cyclopentyl-1-(5-fluoro-1H-pyrrolo[2,3-b]pyridin-2-yl)-1-(4-methanesulfonyl-phenyl)-ethanol (prepared as in Example 48, 80 mg) were separated by Agilent high performance liquid chromatography (chiral column: Daicel OJ-H, 250 mm×20 mm i. d., 5 μm-particle size, temperature: 25° C., flow rate of 15 mL/min, 60% ethanol/hexanes as mobile phase and UV detection: 214 and 254 nm) to afford two pure enantiomers. The first peak, 2-cyclopentyl-(5-fluoro-1H-pyrrolo[2,3-b]pyridin-2-yl)-1-(4-methanesulfonyl-phenyl)-ethanol (25 mg) was isolated as a white solid: $^1$H NMR (400 MHz, CD$_3$OD) δ ppm 8.03 (t, J=2.1 Hz, 1H), 7.88-7.93 (m, J=8.6 Hz, 2H), 7.81-7.86 (m, J=8.6 Hz, 2H), 7.68 (dd, J=9.1, 2.5 Hz, 1H), 6.52 (s, 1H), 3.10 (s, 3H), 2.46-2.57 (m, 2H), 1.76-1.90 (m, 2H), 1.36-1.65 (m, 5H), 1.16-1.27 (m, 1H), 0.97-1.07 (m, 1H).

Example 50

4-[2-Cyclopentyl-1-(5-fluoro-1H-pyrrolo[2,3-b]pyridin-2-yl)-ethyl]-benzonitrile

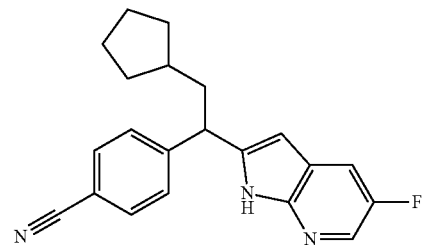

To a solution of 1-(1-benzenesulfonyl-5-fluoro-1H-pyrrolo[2,3-b]pyridin-2-yl)-2-cyclopentyl-ethanone (prepared as in Example 48, 8 g, 20.7 mmol) in dry tetrahydrofuran (150 mL) at −78° C. was added lithium bis(trimethylsilyl)amide solution in tetrahydrofuran (1 M, 31.1 mL, 31.1 mmol) dropwise. After stirring at −78° C. for 1 h, a solution of p-toluenesulfonic anhydride (11.5 g, 35.2 mmol) in tetrahydrofuran (75 mL) was added dropwise. The resulting mixture was kept at −78° C. for an additional 1.5 h. The reaction was quenched with water, extracted with ethyl acetate (200 mL), washed with brine, dried over anhydrous sodium sulfate and then concentrated in vacuo. Purification by flash silica gel chromatography (silica gel from QingDao, 200-300 mesh, glass column from Shanghai SD company, 20% ethyl acetate/hexanes) afforded toluene-4-sulfonic acid 1-(1-benzenesulfonyl-5-fluoro-1H-pyrrolo[2,3-b]pyridin-2-yl)-2-cyclopentyl-vinyl ester (10 g, 89.3%) as a white solid: LC/MS m/e calcd for $C_{27}H_{25}FN_2O_5S_2$ [M+H]$^+$ 541.64, observed 540.9.

To a mixture of toluene-4-sulfonic acid-1-(1-benzenesulfonyl-5-fluoro-1H-pyrrolo[2,3-b]pyridin-2-yl)-2-cyclopentyl-vinyl ester (1.5 g, 2.78 mmol), [4-(tert-butylaminocarbonyl)phenyl]boronic acid (1.3 g, 5.56 mmol) and dichlorobis(triphenylphosphine)palladium (II) (195 mg, 0.28 mmol) in dioxane (8 mL) was added an aqueous sodium carbonate solution (2 M, 3.5 mL, 7 mmol). The resulting mixture was subjected to microwave irradiation for 2 h at 100° C. The mixture was diluted with ethyl acetate (250 mL), washed with a saturated aqueous sodium bicarbonate solution (2×50 mL), brine, dried over anhydrous sodium sulfate and concentrated in vacuo. Purification by flash silica gel chromatography (silica gel from QingDao, 200-300 mesh, glass column from Shanghai SD company, 20% ethyl acetate/hexanes) afforded 4-[1-(1-benzenesulfonyl-5-fluoro-1H-pyrrolo[2,3-b]pyridin-2-yl)-2-cyclopentyl-vinyl]-N-tert-butyl-benzamide (1.2 g, 79.5%) as a light yellow solid: LC/MS m/e calcd for $C_{31}H_{32}FN_3O_3S$ [M+H]$^+$ 546.69, observed 546.1.

A solution of 4-[1-(1-benzenesulfonyl-5-fluoro-1H-pyrrolo[2,3-b]pyridin-2-yl)-2-cyclopentyl-vinyl]-N-tert-butyl-benzamide (1.0 g, 1.83 mmol) in tetrahydrofuran (0.5 mL) and a tetrabutylammonium fluoride solution in tetrahydrofuran (1 M, 10 mL, 10 mmol) was stirred at room temperature for 12 h. The mixture was diluted with ethyl acetate (150 mL), washed with a saturated aqueous ammonium chloride solution and brine, dried over anhydrous sodiumsulfate and concentrated in vacuo to afford N-tert-butyl-4-[2-cyclopentyl-1-(5-fluoro-1H-pyrrolo[2,3-b]pyridin-2-yl)-vinyl]-benzamide (380 mg, 51.1%) as a white solid: LC/MS m/e calcd for $C_{25}H_{28}FN_3O$ [M+H]$^+$ 406.52, observed 406.0.

A mixture of N-tert-butyl-4-[2-cyclopentyl-1-(5-fluoro-1H-pyrrolo[2,3-b]pyridin-2-yl)-vinyl]-benzamide (380 mg, 0.938 mmol) and 10% palladium on activated carbon (100 mg) in methanol (250 mL) was heated at 50° C. under hydrogen (50 psi) for 6 h. The mixture was cooled to room temperature. The catalyst was removed by filtration and washed with ethyl acetate. The filtrate was concentrated in vacuo to afford N-tert-butyl-4-[2-cyclopentyl-1-(5-fluoro-1H-pyrrolo[2,3-b]pyridin-2-yl)-ethyl]-benzamide (350 mg, 91.9%) as a white solid: LC/MS m/e calcd for $C_{25}H_{30}FN_3O$ [M+H]$^+$ 408.54, observed 408.1.

To a stirred solution of N-tert-butyl-4-[2-cyclopentyl-1-(5-fluoro-1H-pyrrolo[2,3-b]pyridin-2-yl)-ethyl]-benzamide (250 mg, 0.61 mmol) in chloroform (6 mL) at room temperature was added phosphorus oxychloride (0.32 mL, 3.15 mmol). The mixture was heated at 80° C. and stirred for 3 h. The resulting mixture was concentrated in vacuo and the residue was extracted with ethyl acetate, washed with a saturated aqueous sodium bicarbonate solution (2×50 mL), brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 4-[2-cyclopentyl-1-(5-fluoro-1H-pyrrolo[2,3-b]pyridin-2-yl)-ethyl]-benzonitrile (120 mg, 58.8%) as a white solid: LC/MS m/e calcd for $C_{21}H_{20}FN_3$ [M+H]$^+$ 334.41, observed 334.1; $^1$H NMR (400 MHz, CD$_3$OD) δ ppm 8.01 (s, 1H), 7.63-7.70 (m, 3H), 7.53 (d, J=8.3 Hz, 2H), 6.39 (s, 1H), 4.28 (t, J=7.8 Hz, 1H), 2.23-2.31 (m, 1H), 2.03-2.13 (m, 1H), 1.61-1.87 (m, 5H), 1.51 (dd, J=7.3, 4.0 Hz, 2H), 1.17-1.35 (m, 2H).

Example 51

4-[2-Cyclopentyl-1(R)-(5-fluoro-1H-pyrrolo[2,3-b]pyridin-2-yl)-ethyl]-benzonitrile

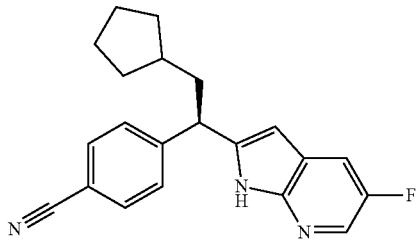

The 1:1 mixture of enantiomers of 4-[2-cyclopentyl-1-(5-fluoro-1H-pyrrolo[2,3-b]pyridin-2-yl)-ethyl]-benzonitrile (prepared as in Example 50, 100 mg) were separated by Agilent high performance liquid chromatography (chiral column: Daicel IA-H, 250 mm×20 mm i. d., 5 µm-particle size, temperature: 25° C., flow rate of 15 mL/min, 60% ethanol/hexanes as mobile phase and UV detection: 214 and 254 nm) to afford two pure enantiomers. The first peak, 4-[2-cyclopentyl-1(R)-(5-fluoro-1H-pyrrolo[2,3-b]pyridin-2-yl)-ethyl]-benzonitrile (30 mg) was isolated as a white solid: $^1$H NMR (400 MHz, CD$_3$OD) δ ppm 8.01 (s, 1H), 7.63-7.70 (m, 3H), 7.53 (d, J=8.3 Hz, 2H), 6.39 (s, 1H), 4.28 (t, J=8.0 Hz, 1H), 2.23-2.31 (m, 1H), 2.05-2.13 (m, 1H), 1.61-1.86 (m, 5H), 1.46-1.61 (m, 2H), 1.16-1.32 (m, 2H).

Example 52

2-[2-Cyclopentyl-1-(4-methanesulfonyl-phenyl)-ethyl]-1H-pyrrolo[2,3-b]pyridin-5-carbonitrile

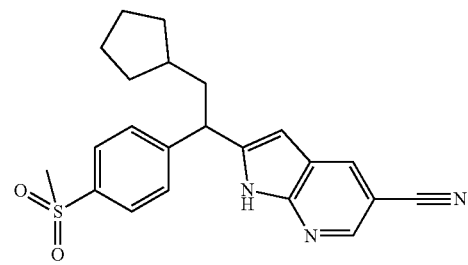

To a solution of 2-[2-cyclopentyl-1-(4-methanesulfonyl-phenyl)-ethyl]-1H-pyrrolo[2,3-b]pyridin-5-carboxylic acid (prepared as in Example 3, 240 mg, 0.58 mmol) and tert-butylamine (122 μL, 1.16 mmol) in dichloromethane (4 mL), N,N-dimethylformamide (500 μL) and N-methylmorpholine (160 μL, 1.55 mmol) was added 1-hydroxybenzotriazole hydrate (132 mg, 0.97 mmol) followed by N-(3-dimethylaminopropyl)-N'-ethylcarbodiimide hydrochloride (186 mg, 0.97 mmol) in one portion at room temperature. The resulting mixture was stirred for 14 h. The mixture was diluted with ethyl acetate (100 mL), washed with a 1N aqueous sodium bicarbonate solution, 1 N aqueous hydrochloric acid solution, brine, dried over anhydrous sodium sulfate and concentrated in vacuo to afford 2-[2-cyclopentyl-1-(4-methanesulfonyl-phenyl)-ethyl]-1H-pyrrolo[2,3-b]pyridin-5-carboxylic acid tert-butylamide (280 mg, quant.) as a light yellow solid which was used without further purification: LC/MS m/e calcd for $C_{26}H_{33}N_3O_3S$ $[M+H]^+$ 468.64, observed 467.8.

To a stirred solution of 2-[2-cyclopentyl-1-(4-methanesulfonyl-phenyl)-ethyl]-1H-pyrrolo[2,3-b]pyridin-5-carboxylic acid tert-butylamide (240 mg, 0.51 mmol) in chloroform (5 mL) was added phosphorus oxychloride (0.72 mL, 7.71 mmol) at room temperature. The mixture was heated at 80° C. and stirred for 3 h. The resulting mixture was concentrated in vacuo and the residue was extracted with ethyl acetate, washed with a saturated aqueous sodium bicarbonate solution (2×50 mL), brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(4-methanesulfonyl-phenyl)-ethyl]-1H-pyrrolo[2,3-b]pyridin-5-carbonitrile (35 mg, 14.9%) as a white solid: LC/MS m/e calcd for $C_{22}H_{23}N_3O_2S$ $[M+H]^+$ 394.51, observed 393.8; $^1$H NMR (400 MHz, CD$_3$OD) δ ppm 8.42 (s, 1H), 8.26 (d, J=1.5 Hz, 1H), 7.90 (d, J=8.1 Hz, 1H), 7.60 (d, J=8.3 Hz, 1H), 6.54 (s, 1H), 4.34 (t, J=8.0 Hz, 1H), 3.32-3.32 (m, 1H), 3.31 (s, 8H), 3.09 (s, 2H), 2.24-2.32 (m, 1H), 2.10-2.18 (m, 1H), 1.60-1.87 (m, 3H), 1.44-1.55 (m, 1H), 1.17-1.32 (m, 2H).

Example 53

2-[2-Cyclopentyl-1(R)-(4-methanesulfonyl-phenyl)-ethyl]-1H-pyrrolo[2,3-b]pyridin-5-carbonitrile

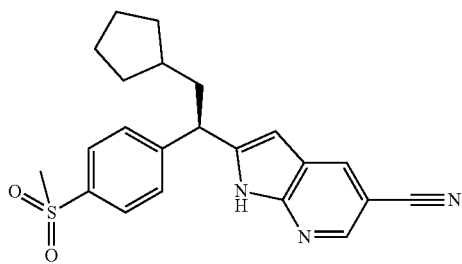

The 1:1 mixture of enantiomers of 2-[2-cyclopentyl-1-(4-methanesulfonyl-phenyl)-ethyl]-1H-pyrrolo[2,3-b]pyridin-5-carbonitrile (prepared as in Example 52, 20 mg) were separated by Agilent high performance liquid chromatography (chiral column: Daicel IA-H, 250 mm×20 mm i. d., 5 μm-particle size, temperature: 25° C., flow rate of 15 mL/min, 50% isopropyl alcohol/hexanes as mobile phase and UV detection: 214 and 254 nm) to afford two pure enantiomers. The second peak, 2-[2-cyclopentyl-1(R)-(4-methanesulfonyl-phenyl)-ethyl]-1H-pyrrolo[2,3-b]pyridin-5-carbonitrile (4 mg) was isolated as a white solid: $^1$H NMR (400 MHz, CD$_3$OD) δ ppm 8.40 (d, J=1.8 Hz, 1H), 8.24 (d, J=2.0 Hz, 1H), 7.86-7.91 (m, J=8.3 Hz, 2H), 7.50-7.61 (m, 2H), 6.52 (s, 1H), 4.32 (t, J=8.0 Hz, 1H), 3.05-3.12 (m, 3H), 2.23-2.31 (m, 1H), 2.08-2.16 (m, 1H), 1.58-1.85 (m, 5H), 1.42-1.54 (m, 2H), 1.13-1.30 (m, 2H).

Example 54

2-[2-Cyclopentyl-1-(4-methanesulfonyl-phenyl)-ethyl]-1H-pyrrolo[2,3-b]pyridin-5-carboxylic acid methyl ester

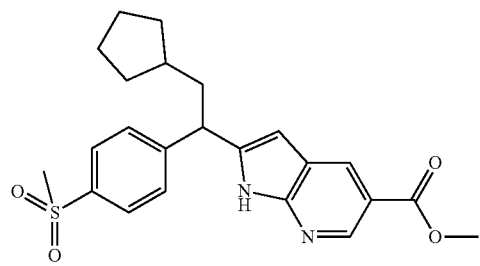

A mixture of 1-benzenesulfonyl-2-[2-cyclopentyl-1-(4-methanesulfonyl-phenyl)-vinyl]-1H-pyrrolo[2,3-b]pyridin-5-carboxylic acid methyl ester (prepared as in Example 3, 4 g, 7.1 mmol) in tetrahydrofuran (5 mL) and a tetrabutylammonium fluoride solution in tetrahydrofuran (1 M, 15 mL, 15 mmol) was stirred at room temperature for 12 h. The mixture was diluted with ethyl acetate (150 mL), washed with a saturated aqueous ammonium chloride solution and brine, dried over anhydrous sodium sulfate and then concentrated in vacuo to afford 2-[2-cyclopentyl-1-(4-methanesulfonyl-phenyl)-vinyl]-1H-pyrrolo[2,3-b]pyridin-5-carboxylic acid methyl ester (2.5 g, 83.3%) as a white solid: LC/MS m/e calcd for $C_{23}H_{24}N_2O_4S$ $[M+H]^+$ 425.52, observed 424.9.

A mixture of 2-[2-cyclopentyl-1-(4-methanesulfonyl-phenyl)-vinyl]-1H-pyrrolo[2,3-b]pyridin-5-carboxylic acid methyl ester (2.5 g, 5.89 mmol) and 10% palladium on activated carbon (900 mg) in methanol (600 mL) was heated at 50° C. under 50 bar of hydrogen in a steel bomb for 5 h. The mixture was cooled to 25° C., the solids filtered off, washed with ethyl acetate and concentrated in vacuo to afford 2-[2-cyclopentyl-1-(4-methanesulfonyl-phenyl)-ethyl]-1H-pyrrolo[2,3-b]pyridin-5-carboxylic acid methyl ester (1.7 g, 68%) as a white solid which was used without further purification: LC/MS m/e calcd for $C_{23}H_{26}N_2O_4S$ $[M+H]^+$ 427.54, observed 426.8; $^1$H NMR (400 MHz, CDCl$_3$) δ ppm 10.81 (br. s., 1H), 8.79 (br. s., 1H), 8.56 (s, 1H), 7.88-7.93 (m, J=8.3 Hz, 2H), 7.48-7.53 (m, J=8.1 Hz, 2H), 6.48 (s, 1H), 5.31 (s, 1H), 4.30 (t, J=7.7 Hz, 1H), 3.99 (s, 3H), 3.03 (s, 3H), 2.12-2.33 (m, 2H), 1.59-1.86 (m, 4H), 1.45-1.56 (m, 2H), 1.15-1.29 (m, 2H).

Example 55

2-[2-Cyclopentyl-1(R)-(4-methanesulfonyl-phenyl)-ethyl]-1H-pyrrolo[2,3-b]pyridin-5-carboxylic acid methyl ester

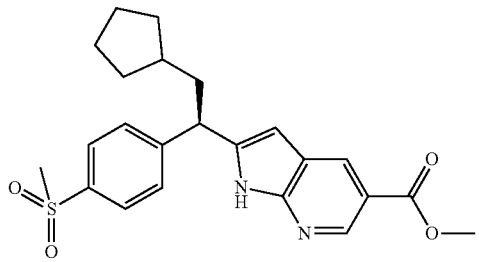

The 1:1 mixture of enantiomers of 2-[2-cyclopentyl-1-(4-methanesulfonyl-phenyl)-ethyl]-1H-pyrrolo[2,3-b]pyridin-5-carboxylic acid methyl ester (prepared as in Example 54, 1.7 g, 4 mmol) were separated by Berger SFC-Minigram High performance Liquid chromatography (chiral column: Daicel OJ-H, 250 mm×10 mm i. d., 5 μm-particle size, temperature: 25° C., flow rate of 10 mL/min, 30% methanol as mobile phase and UV detection: 214 and 254 nm) to afford two pure enantiomers. The first peak, 2-[2-cyclopentyl-1(R)-(4-methanesulfonyl-phenyl)-ethyl]-1H-pyrrolo[2,3-b]pyridin-5-carboxylic acid methyl ester (640 mg) was isolated as a white solid: LC/MS m/e calcd for $C_{23}H_{26}N_2O_4S$ [M+H]$^+$ 427.54, observed 426.8; $^1$H NMR (400 MHz, CD$_3$OD) δ ppm 8.82 (d, J=1.8 Hz, 1H), 8.57 (d, J=2.0 Hz, 1H), 7.94-7.98 (m, J=8.3 Hz, 2H), 7.64-7.68 (m, J=8.3 Hz, 2H), 6.59 (s, 1H), 4.39 (t, J=7.8 Hz, 1H), 3.99 (s, 3H), 3.15 (s, 3H), 2.31-2.39 (m, 1H), 2.15-2.23 (m, 1H), 1.66-1.93 (m, 5H), 1.50-1.62 (m, 2H), 1.23-1.36 (m, 2H).

Example 56

2-[2-Cyclopentyl-1(R)-(4-methanesulfonyl-phenyl)-ethyl]-1H-pyrrolo[2,3-b]pyridin-5-carboxylic acid

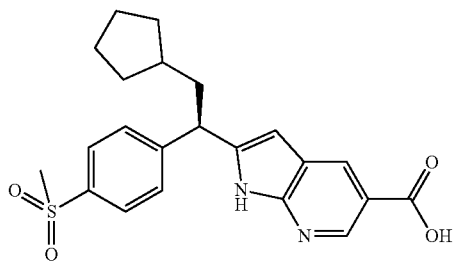

A mixture of 2-[2-cyclopentyl-1(R)-(4-methanesulfonyl-phenyl)-ethyl]-1H-pyrrolo[2,3-b]pyridin-5-carboxylic acid methyl ester (prepared as in Example 55, 610 mg, 1.43 mmol) in tetrahydrofuran (8 mL) and 10% aqueous sodium hydroxide solution (3 mL) was heated at 70° C. for 10 h. The mixture was neutralized with a 3N aqueous hydrochloric acid solution, diluted with ethyl acetate (150 mL), washed with brine, dried over anhydrous sodium sulfate and concentrated in vacuo to afford 2-[2-cyclopentyl-1(R)-(4-methanesulfonyl-phenyl)-ethyl]-1H-pyrrolo[2,3-b]pyridin-5-carboxylic acid (510 mg, 86.6%, 93% ee) as a light yellow solid which was further separated by Agilent high performance liquid chromatography (chiral column: Daicel OJ-H, 250 mm×20 mm i. d., 5 μm-particle size, temperature: 25° C., flow rate of 15 mL/min, 30% ethanol/hexanes as mobile phase and UV detection: 214 and 254 nm) to afford two pure enantiomers. The first peak, 2-[2-cyclopentyl-1(R)-(4-methanesulfonyl-phenyl)-ethyl]-1H-pyrrolo[2,3-b]pyridin-5-carboxylic acid (220 mg) was isolated as a light yellow solid: LC/MS m/e calcd for $C_{22}H_{24}N_2O_4S$ [M+H]$^+$ 413.51, observed 412.9; $^1$H NMR (400 MHz, CD$_3$OD) δ ppm 8.73 (br. s., 1H), 8.47 (d, J=1.5 Hz, 1H), 8.03 (br. s., 1H), 7.83-7.87 (m, J=8.3 Hz, 2H), 7.53-7.58 (m, J=8.3 Hz, 2H), 6.48 (s, 1H), 4.28 (t, J=7.8 Hz, 1H), 3.04 (s, 3H), 2.20-2.28 (m, 1H), 2.04-2.12 (m, 1H), 1.55-1.82 (m, 5H), 1.38-1.51 (m, 2H), 1.05-1.26 (m, 2H).

Example 57

2-{2-Cyclopentyl-1-[3-fluoro-4-(1-hydroxy-1-methyl-ethyl)-phenyl]-ethyl}-1H-pyrrolo[2,3-b]pyridin-5-carboxylic acid

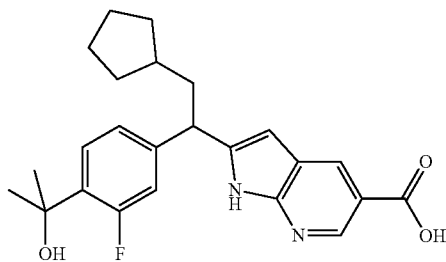

To a stirred solution of 4-bromo-2-fluoro-benzoic acid methyl ester (20 g, 85.84 mmol) in dry tetrahydrofuran (55 mL) at 0° C. was added a methylmagnesium chloride solution in tetrahydrofuran (3 M, 86 mL, 258 mmol). The mixture was warmed to room temperature and stirred for 2 h. The reaction was quenched with a saturated aqueous ammonium chloride solution, extracted with ethyl acetate, washed with brine, dried over anhydrous sodium sulfate. The solvent was evaporated in vacuo to afford 2-(4-bromo-2-fluoro-phenyl)-propan-2-ol (18.5 g, 92.5%) as a light yellow oil which was used in the next step without further purification.

To a stirred solution of 2-(4-bromo-2-fluoro-phenyl)-propan-2-ol (18.5 g, 79.4 mmol) and 3,4-dihydro-2H-pyran (10.9 mL, 119.1 mmol) in dichloromethane (165 mL) was added pyridinium-p-toluene sulfonate (2 g, 7.91 mmol) at room temperature. The resulting mixture was stirred at room temperature for 12 h, extracted with ethyl acetate, washed with brine, dried over anhydrous sodium sulfate. The solvent was evaporated in vacuo and the residue was purified by flash column chromatography (QingDao silica gel, 200-300 mesh, 25% ethyl acetate/hexanes) to afford 2-[1-(4-bromo-2-fluoro-phenyl)-1-methyl-ethoxy]-tetrahydro-pyran (9.7 g, 38.6%) as a light yellow oil.

To a stirred solution of 2-[1-(4-bromo-2-fluoro-phenyl)-1-methyl-ethoxy]-tetrahydro-pyran (9.7 g, 30.6 mmol), potassium acetate (9 g, 91.8 mmol) and bis(pinacolato)diboron (9.7 g, 38.2 mmol) in dimethylsulfoxide (65 mL) was added 1,1-bis(diphenylphosphino)ferrocenedichloropalladium(II) (2.5 g, 3.06 mmol) at room temperature. The mixture was heated at 80° C. and stirred for 3 h and then cooled to room temperature and then 1-benzenesulfonyl-2-[2-cyclopentyl-1-(toluene-4-sulfonyloxy)-vinyl]-1H-pyrrolo[2,3-b]pyridin-5- carboxylic acid methyl ester (prepared as in Example 3, 9 g, 15.52 mmol) and an aqueous sodium carbonate solution (2 M, 17.85 mL) were added. The mixture was heated at 100° C. and stirred for 3 h. The resulting mixture was cooled to room temperature, extracted with ethyl acetate, washed with brine, dried over anhydrous sodium sulfate. The solvent was evaporated in vacuo and the residue was purified by flash column chromatography (QingDao silica gel, 200-300 mesh, 20% ethyl acetate/hexanes) to afford 1-benzenesulfonyl-2-(2-cyclopentyl-1-{3-fluoro-4-[1-methyl-1-(tetrahydro-pyran-2-yloxy)-ethyl]-phenyl}-vinyl)-1H-pyrrolo[2,3-b]pyridin-5-carboxylic acid methyl ester (6 g, 60%) as a light yellow oil: LC/MS m/e calcd for $C_{36}H_{39}FN_2O_6S$ [M+H]$^+$ 647.78, observed 647.0.

A mixture of 1-benzenesulfonyl-2-(2-cyclopentyl-1-{3-fluoro-4-[1-methyl-1-(tetrahydro-pyran-2-yloxy)-ethyl]-phenyl}-vinyl)-1H-pyrrolo[2,3-b]pyridin-5-carboxylic acid methyl ester (6 g, 9.1 mmol) in tetrahydrofuran (5 mL) and a tetrabutylammonium fluoride solution in tetrahydrofuran (1 M, 15 mL, 15 mmol) was stirred at room temperature for 12 h. The mixture was diluted with ethyl acetate (150 mL), washed with a saturated aqueous ammonium chloride solution and brine, dried over anhydrous sodium sulfate and concentrated in vacuo to afford 2-(2-cyclopentyl-1-{3-fluoro-4-[1-methyl-1-(tetrahydro-pyran-2-yloxy)-ethyl]-phenyl}-vinyl)-1H-pyrrolo[2,3-b]pyridin-5-carboxylic acid methyl ester (3 g, 63.8%) as a white solid: LC/MS m/e calcd for $C_{30}H_{35}FN_2O_4$ [M+H]$^+$ 507.62, observed 507.0.

A mixture of 2-(2-cyclopentyl-1-{3-fluoro-4-[1-methyl-1-(tetrahydro-pyran-2-yloxy)-ethyl]-phenyl}-vinyl)-1H-pyrrolo[2,3-b]pyridin-5-carboxylic acid methyl ester (3 g, 5.93 mmol) and 10% palladium on activated carbon (900 mg) in methanol (600 mL) was heated at 50° C. under hydrogen (50 bar) for 5 h. The resulting mixture was cooled to 25° C., the catalyst was removed by filtration, washed with ethyl acetate and concentrated in vacuo to afford 2-(2-cyclopentyl-1-{3-fluoro-4-[1-methyl-1-(tetrahydro-pyran-2-yloxy)-ethyl]-phenyl}-ethyl)-1H-pyrrolo[2,3-b]pyridin-5-carboxylic acid methyl ester (1.8 g, 60%) as a white solid which was used in the next step without further purification: LC/MS m/e calcd for $C_{30}H_{37}FN_2O_4$ [M+H]$^+$ 509.64, observed 508.9.

A mixture of 2-(2-cyclopentyl-1-{3-fluoro-4-[1-methyl-1-(tetrahydro-pyran-2-yloxy)-ethyl]-phenyl}-ethyl)-1H-pyrrolo[2,3-b]pyridin-5-carboxylic acid methyl ester (1.8 g, 3.54 mmol) in tetrahydrofuran (8 mL) and a 10% aqueous sodium hydroxide solution (13 mL) was heated at 70° C. for 10 h. The mixture was neutralized with a 3N aqueous hydrochloric acid solution, diluted with ethyl acetate (150 mL), washed with brine, dried over anhydrous sodium sulfate and concentrated in vacuo to afford 2-(2-cyclopentyl-1-{3-fluoro-4-[1-methyl-1-(tetrahydro-pyran-2-yloxy)-ethyl]-phenyl}-ethyl)-1H-pyrrolo[2,3-b]pyridin-5-carboxylic acid (1.5 g, 85.8%) as a light yellow solid: LC/MS m/e calcd for $C_{29}H_{35}FN_2O_4$ [M+H]$^+$ 495.61, observed 494.9.

To a stirred solution of 2-(2-cyclopentyl-1-{3-fluoro-4-[1-methyl-1-(tetrahydro-pyran-2-yloxy)-ethyl]-phenyl}-ethyl)-1H-pyrrolo[2,3-b]pyridine-5-carboxylic acid (1.5 g, 3.04 mmol) in 95% ethanol (50 mL) was added cupric chloride dihydrate (52 mg, 0.3 mmol) at room temperature. The mixture was refluxed for 3 h and then cooled to room temperature. The resulting mixture was concentrated in vacuo. The residue was dissolved in ethyl acetate, washed with brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-cyclopentyl-1-[3-fluoro-4-(1-hydroxy-1-methyl-ethyl)-phenyl]-ethyl}-1H-pyrrolo[2,3-b]pyridin-5-carboxylic acid (350 mg, 28.1%) as a light yellow solid: LC/MS m/e calcd for $C_{24}H_{27}FN_2O_3$ [M+H]$^+$ 411.49, observed 410.9; $^1$H NMR (400 MHz, $CD_3OD$) δ ppm 8.79 (br. s., 1H), 8.56 (br. s., 1H), 7.53-7.60 (m, 1H), 7.13 (br. s., 1H), 7.02 (d, J=12.1 Hz, 1H), 6.51 (br. s., 1H), 4.19 (br. s., 1H), 2.22 (br. s., 1H), 2.12 (br. s., 1H), 1.61-1.88 (m, 5H), 1.56 (br. s., 6H), 1.51 (br. s., 2H), 1.23 (br. s., 2H).

Example 58

2-{2-Cyclopentyl-1(R)-[3-fluoro-4-(1-hydroxy-1-methyl-ethyl)-phenyl]-ethyl}-1H-pyrrolo[2,3-b]pyridin-5-carboxylic acid

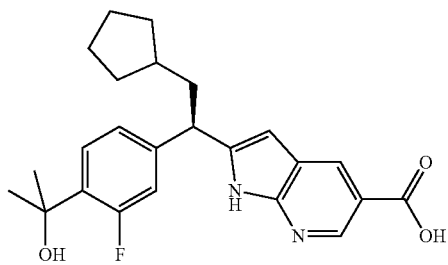

The 1:1 mixture of enantiomers of 2-{2-cyclopentyl-1-[3-fluoro-4-(1-hydroxy-1-methyl-ethyl)-phenyl]-ethyl}-1H-pyrrolo[2,3-b]pyridin-5-carboxylic acid (prepared as in Example 57, 320 mg, 0.78 mmol) were separated by Agilent high performance liquid chromatography (chiral column: Daicel IA-H, 250 mm×20 mm i. d., 5 μm-particle size, temperature: 25° C., flow rate of 16 mL/min, 60% ethanol/hexanes as mobile phase and UV detection: 214 and 254 nm) to afford two pure enantiomers. The second peak, 2-{2-cyclopentyl-1(R)-[3-fluoro-4-(1-hydroxy-1-methyl-ethyl)-phenyl]-ethyl}-1H-pyrrolo[2,3-b]pyridin-5-carboxylic acid (5 mg) was isolated as a white solid; $^1$H NMR (400 MHz, $CD_3OD$) δ ppm 8.82 (br. s., 1H), 8.58 (s, 1H), 7.59 (t, J=8.3 Hz, 1H), 7.12-7.19 (m, 1H), 7.05 (d, J=13.1 Hz, 1H), 6.53 (s, 1H), 4.22 (t, J=7.8 Hz, 1H), 2.25 (dt, J=13.7, 7.2 Hz, 1H), 2.07-2.18 (m, 1H), 1.64-1.87 (m, 5H), 1.51-1.62 (m, 8H), 1.17-1.34 (m, 2H).

Example 59

2-[2-Cyclopentyl-1-(6-methanesulfonyl-pyridin-3-yl)-ethyl]-1H-pyrrolo[2,3-b]pyridin-5-carboxylic acid(2-hydroxy-ethyl)-amide

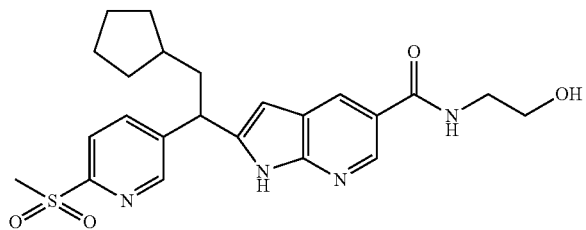

To a mixture of 1-benzenesulfonyl-2-[2-cyclopentyl-1-(toluene-4-sulfonyloxy)-vinyl]-1H-pyrrolo[2,3-b]pyridin-5- carboxylic acid methyl ester (prepared as in Example 3, 0.90 g, 1.55 mmol), 2-(methylsulfanyl)pyridine-5-boronic acid hydrate (0.52 g, 3.1 mmol) and dichlorobis(triphenylphosphine)palladium (II) (108 mg, 0.15 mmol) in dioxane (6 mL) was added an aqueous sodium carbonate solution (2 M, 3.1 mL). The resulting mixture was subjected to microwave irradiation for 60 min at 100° C. The mixture was diluted with ethyl acetate (150 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 1-benzenesulfonyl-2-[2-cyclopentyl-1-(6-methylsulfanyl-pyridin-3-yl)-vinyl]-1H-pyrrolo[2,3-b]pyridin-5-carboxylic acid methyl ester (300 mg, 36%) as a white solid: LC/MS m/e calcd for $C_{28}H_{27}N_3O_4S_2$ [M+H]$^+$ 534.67, observed 534.1.

To a mixture of sodium metaperiodate (360 mg, 1.69 mmol) in water (10 ml) was added a solution of 1-benzenesulfonyl-2-[2-cyclopentyl-1-(6-methylsulfanyl-pyridin-3-yl)-vinyl]-1H-pyrrolo[2,3-b]pyridin-5-carboxylic acid methyl ester (300 mg, 0.56 mmol) in methanol (40 ml). The reaction mixture was stirred at 25° C. for 60 h. The suspension was filtered. The filtrate was concentrated and extracted with ethyl acetate (2×30 mL). The combined organic extracts were washed with water (2×20 mL), dried over anhydrous sodium sulfate and then concentrated in vacuo to afford 1-benzenesulfonyl-2-[2-cyclopentyl-1-(6-methanesulfinyl-pyridin-3-yl)-vinyl]-1H-pyrrolo[2,3-b]pyridin-5-carboxylic acid methyl ester (301 mg, 97%) as a solid which was used in the next step without further purification: LC/MS m/e calcd for $C_{28}H_{27}N_3O_5S_2$ [M+H]$^+$ 550.67, observed 549.9.

To a mixture of 1-benzenesulfonyl-2-[2-cyclopentyl-1-(6-methanesulfinyl-pyridin-3-yl)-vinyl]-1H-pyrrolo[2,3-b]pyridin-5-carboxylic acid methyl ester (301 mg, 0.55 mmol) in methanol (30 ml) was added a solution of potassium permanganate (88 mg, 0.55 mmol) in water (30 ml). The reaction mixture was stirred at 25° C. for 1 h. The suspension was filtered through a short silica gel pad and then washed with ethyl acetate (3×30 mL). The filtrate was concentrated and extracted with ethyl acetate (2×50 mL). The combined organic extracts were washed with water (2×20 mL), dried over anhydrous sodium sulfate and then concentrated in vacuo to afford 1-benzenesulfonyl-2-[2-cyclopentyl-1-(6-methanesulfonyl-pyridin-3-yl)-vinyl]-1H-pyrrolo[2,3-b]pyridin-5-carboxylic acid methyl ester (230 mg, 72%): LC/MS m/e calcd for $C_{28}H_{27}N_3O_6S_2$ [M+H]$^+$ 566.67, observed 565.9.

A mixture of 1-benzenesulfonyl-2-[2-cyclopentyl-1-(6-methanesulfonyl-pyridin-3-yl)-vinyl]-1H-pyrrolo[2,3-b]pyridin-5-carboxylic acid methyl ester (230 mg, 0.41 mmol) and a tetrabutylammonium fluoride solution in tetrahydrofuran (1 M, 3.2 mL) was stirred at 25° C. for 16 h. The mixture was diluted with ethyl acetate (100 mL), washed with a saturated aqueous ammonium chloride solution (4×100 mL), brine, dried over anhydrous sodium sulfate and then concentrated in vacuo to afford 2-[2-cyclopentyl-1-(6-methanesulfonyl-pyridin-3-yl)-vinyl]-1H-pyrrolo[2,3-b]pyridin-5-carboxylic acid methyl ester (150 mg, 86%) which was used in the next step without further purification: LC/MS m/e calcd for $C_{22}H_{23}N_3O_4S$ [M+H]$^+$ 426.51, observed 426.2.

A mixture of 2-[2-cyclopentyl-1-(6-methanesulfonyl-pyridin-3-yl)-vinyl]-1H-pyrrolo[2,3-b]pyridin-5-carboxylic acid methyl ester (150 mg, 0.35 mmol) and 10% palladium on activated carbon (45 mg) in methanol (300 mL) was heated at 50° C. under hydrogen (50 bar) for 5 h. The mixture was cooled to room temperature. The catalyst was removed by filtration and washed with ethyl acetate. The filtrate was concentrated in vacuo to afford 2-[2-cyclopentyl-1-(6-methanesulfonyl-pyridin-3-yl)-ethyl]-1H-pyrrolo[2,3-b]pyridin-5-carboxylic acid methyl ester (110 mg, 73%) which was used in the next step without further purification: LC/MS m/e calcd for $C_{22}H_{25}N_3O_4S$ [M+H]$^+$ 428.53, observed 427.9.

A mixture of 2-[2-cyclopentyl-1-(6-methanesulfonyl-pyridin-3-yl)-ethyl]-1H-pyrrolo[2,3-b]pyridin-5-carboxylic acid methyl ester (110 mg, 0.25 mmol) in ethanol (4 mL) and tetrahydrofuran (4 mL), was treated with an aqueous sodium hydroxide solution (10%, 1.5 mL) and stirred at 50° C. for 1 h. The mixture was acidified to pH 4-5 with a 2N aqueous hydrochloric acid solution, diluted with dichloromethane (150 mL), washed with water, dried over anhydrous sodium sulfate and then concentrated in vacuo to afford 2-[2-cyclopentyl-1-(6-methanesulfonyl-pyridin-3-yl)-ethyl]-1H-pyrrolo[2,3-b]pyridin-5-carboxylic acid (100 mg, 94%) as a white solid which was used in the next step without further purification: LC/MS m/e calcd for $C_{21}H_{23}N_3O_4S$ [M+H]$^+$ 414.50, observed 414.0.

To a solution of 2-[2-cyclopentyl-1-(6-methanesulfonyl-pyridin-3-yl)-ethyl]-1H-pyrrolo[2,3-b]pyridin-5-carboxylic acid (80 mg, 0.19 mmol) and 2-amino-ethanol (14 uL, 0.23 mmol) in dichloromethane (1 mL), N,N-dimethylformamide (1 mL) and N-methylmorpholine (60 uL, 0.58 mmol) was added 1-hydroxybenzotriazole hydrate (54 mg, 0.39 mmol), followed by N-(3-dimethylaminopropyl)-N'-ethylcarbodiimide hydrochloride (75 mg, 0.39 mmol) in one portion. The mixture was then stirred at 25° C. for 14 h. The mixture was diluted with ethyl acetate (100 mL), washed with a 1 N sodium bicarbonate solution, 1 N aqueous hydrochloric acid solution, brine, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(6-methanesulfonyl-pyridin-3-yl)-ethyl]-1H-pyrrolo[2,3-b]pyridin-5-carboxylic acid(2-hydroxy-ethyl)-amide (30 mg, 34%) as a white solid: LC/MS m/e calcd for $C_{23}H_{28}N_4O_4S$ [M+H]$^+$ 456.57, observed 457.0; $^1$H NMR (400 MHz, CDCl$_3$) δ ppm 1.17 (m, 2H), 1.47 (m, 2H), 1.55-1.84 (m, 5H, H), 2.08 (m, 1H), 2.24 (m, 1H), 3.20 (s, 3H), 3.60 (m, 2H), 3.80 (m, 2H), 4.26 (m, 1H), 6.37 (s, 1H), 7.61 (br, 1 H), 7.85 (br, 1H), 7.97 (m, 1H), 8.29 (m, 1H), 8.59 (br. s., 1H), 8.63 (s, 1H), 11.01 (br, 0.2H).

Example 60

2-[1-(4-Methanesulfonyl-phenyl)-2-(tetrahydro-pyran-2-yl)-ethyl-]-1H-pyrrolo[2,3-b]pyridine diastereomer 1

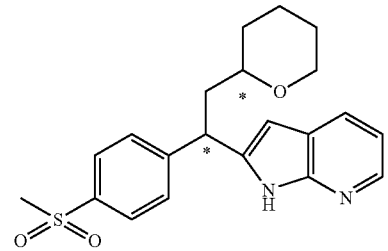

A solution of 2-hydroxytetrahydropyran (59.2 g, 0.58 mol) and triphenyl-λ5-phosphanylidene)-acetic acid ethyl ester (201.3 g, 0.58 mol) in tetrahydrofuran (1.2 L) was heated at reflux for 14 h. The mixture was cooled to room temperature to afford 7-hydroxy-hept-2-enoic acid ethyl ester in tetrahydrofuran and was then used directly in the next step.

To a solution of 7-hydroxy-hept-2-enoic acid ethyl ester (99.9 g, 0.58 mol) in tetrahydrofuran prepared in the previous step, cooled with ice-water bath, was added sodium hydride (4.80 g, 0.12 mol, 60%) in two portions. The mixture was stirred at 0° C. for 2 h and then at room temperature for 2 h. The mixture was neutralized with a 1 M aqueous hydrochloric acid solution (pH ~5.0-6.0). Water (1 L) was then added and the mixture was extracted with ethyl acetate (3×1 L). The combined organic layers were dried over anhydrous sodium sulfate and concentrated in vacuo. The residue was treated with hexanes/ethyl acetate (3×800 mL, hexanes/ethyl acetate=10/1, v/v). The mixture was filtered and dried over anhydrous sodium sulfate. The filtrate was concentrated and the crude product was purified by flash column chromatography (QingDao silica gel, 200-300 mesh, 10% ethyl acetate/hexanes) to afford (tetrahydro-pyran-2-yl)-acetic acid ethyl ester (77.1 g, 77% yield).

To a solution of (tetrahydro-pyran-2-yl)-acetic acid ethyl ester (77.1 g, 0.45 mol) in tetrahydrofuran (1.5 L) at 0° C. was added lithium aluminium hydride (22.1 g, 0.58 mol) in several portions. The mixture was stirred at 0° C. for 2 h and quenched with 1 N sodium hydroxide solution. The mixture was filtered and the filter cake was washed with dichloromethane (4×300 mL). The combined organic layers were concentrated in vacuo. The crude product was purified by distillation under reduced pressure to afford 2-(tetrahydro-pyran-2-yl)-ethanol (53.5 g, 92% yield) as a colorless oil.

To a solution of 2-(tetrahydro-pyran-2-yl)-ethanol (53.5 g, 0.41 mol) in dichloromethane (1 L) was added pyridinium chlorochromate (176.8 g, 0.82 mol) in small portions at room temperature. The dark suspension was stirred for 3 h. The mixture was filtered through a short pad of silica gel. The filtrate was concentrated in vacuo and the residue was diluted with n-hexane (400 mL). The mixture was filtered through a short pad of silica gel and the filtrate was concentrated in vacuo to afford (tetrahydro-pyran-2-yl)-acetaldehyde (38 g) as a colorless oil.

To a suspension of 1-benzenesulfonyl-1H-pyrrolo[2,3-b]pyridine (5.0 g, 19.4 mmol) in dry tetrahydrofuran (125 mL) at −78° C. was added freshly prepared lithium diisopropylamide [prepared by adding 1.6 M n-butyllithium in n-hexane (18 mL, 29 mmol) to a 0° C. solution of diisopropylamine (4.4 mL, 31 mmol) in dry tetrahydrofuran (17 mL)] dropwise. The mixture was stirred at −78° C. for 5 min and then treated with (tetrahydro-pyran-2-yl)-acetaldehyde (4.6 g, 26 mmol) dropwise. The resulting mixture was stirred at −78° C. for 1 h and quenched with brine. The mixture was extracted with ethyl acetate (2×150 mL), washed with brine, dried over anhydrous sodium sulfate and concentrated in vacuo. Purification by flash column chromatography (QingDao silica gel, 200-300 mesh, 25% ethyl acetate/hexanes) afforded 1-(1-benzenesulfonyl-1H-pyrrolo[2,3-b]pyridin-2-yl)-2-(tetrahydro-pyran-2-yl)-ethanol (4.5 g, 60%) as a colorless oil: LC/MS m/e calcd for $C_{20}H_{22}N_2O_4S$ $[M+H]^+$ 387.47, observed 387.2.

To a solution of 1-(1-benzenesulfonyl-1H-pyrrolo[2,3-b]pyridin-2-yl)-2-(tetrahydro-pyran-2-yl)-ethanol (2.5 g, 6.5 mmol) in dichloromethane (100 mL) at 25° C. was added Dess-Martin periodinane (9.6 g, 23 mmol). The reaction mixture was stirred at 25° C. for 1 h and then quenched with a saturated aqueous sodium bicarbonate solution (100 mL). The mixture was extracted with dichloromethane (50 mL), washed with a saturated aqueous sodium bicarbonate solution (3×100 mL), brine, dried over anhydrous sodium sulfate and then concentrated in vacuo to afford 1-(1-benzenesulfonyl-1H-pyrrolo[2,3-b]pyridin-2-yl)-2-(tetrahydro-pyran-2-yl)-ethanone (2.1 g, 84%) as a light yellow solid: LC/MS m/e calcd for $C_{20}H_{20}N_2O_4S$ $[M+H]^+$ 385.46, observed 385.1.

The 1:1 mixture of enantiomers of 1-(1-benzenesulfonyl-1H-pyrrolo[2,3-b]pyridin-2-yl)-2-(tetrahydro-pyran-2-yl)-ethanone (2 g) were separated by Agilent high performance liquid chromatography (chiral column: Daicel IA-H, 250 mm×20 mm i. d., 5 μm-particle size, temperature: 25° C., flow rate of 15 mL/min, 45% isopropyl alcohol/hexanes as mobile phase and UV detection: 214 and 254 nm) to afford the two pure enantiomers of 1-(1-benzenesulfonyl-1H-pyrrolo[2,3-b]pyridin-2-yl)-2-(tetrahydro-pyran-2-yl)-ethanone. The second peak, enantiomer 2 (450 mg) was isolated as a white solid.

To a solution of 1-(1-benzenesulfonyl-1H-pyrrolo[2,3-b]pyridin-2-yl)-2-(tetrahydro-pyran-2-yl)-ethanone (enantiomer 2, 0.45 g, 1.17 mmol) in dry tetrahydrofuran (10 mL) at −78° C. was added lithium bis(trimethylsilyl)amide (1.0M in tetrahydrofuran, 1.8 mL, 1.76 mmol) dropwise. After stirring at −78° C. for 1 h, a solution of p-toluenesulfonic anhydride (0.57 g, 1.76 mmol) in tetrahydrofuran (5 mL) was added dropwise. The resulting solution was kept at −78° C. for 1.5 h. The reaction was quenched with water, extracted with ethyl acetate (300 mL), washed with brine, dried over anhydrous sodium sulfate and then concentrated in vacuo to afford toluene-4-sulfonic acid 1-(1-benzenesulfonyl-1H-pyrrolo[2,3-b]pyridin-2-yl)-2-(tetrahydro-pyran-2-yl)-vinyl ester (0.52 g, 82%) as a white solid: LC/MS m/e calcd for $C_{27}H_{26}N_2O_6S_2$ $[M+H]^+$ 539.65, observed: 539.1.

To a mixture of toluene-4-sulfonic acid 1-(1-benzenesulfonyl-1H-pyrrolo[2,3-b]pyridin-2-yl)-2-(tetrahydro-pyran-yl)-vinyl ester (0.52 g, 0.97 mmol), 4-(methanesulfonyl)phenylboronic acid (0.48 g, 2.4 mmol) and dichlorobis (triphenylphosphine)palladium (II) (68 mg, 0.1 mmol) in dioxane (6 mL) was added an aqueous sodium carbonate solution (2 M, 1.2 mL). The resulting mixture was subjected to microwave irradiation for 4 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 30% ethyl acetate/hexanes) afforded 1-benzenesulfonyl-2-[1-(4-methanesulfonyl-phenyl)-2-(tetrahydro-pyran-2-yl)-vinyl]-1H-pyrrolo[2,3-b]pyridine (0.36 g, 57%) as a white solid: LC/MS m/e calcd for $C_{27}H_{26}N_2O_5S_2$ $[M+H]^+$ 523.65, observed 523.1.

A mixture of 1-benzenesulfonyl-2-[1-(4-methanesulfonyl-phenyl)-2-(tetrahydro-pyran-2-yl)-vinyl]-1H-pyrrolo[2,3-b]pyridine (0.36 g, 6.9 mmol) in ethanol (3 mL), tetrahydrofuran (3 mL) and an aqueous sodium hydroxide solution (10%, 1 mL) was heated at 50° C. for 2 h. The mixture was diluted with dichloromethane (50 mL), washed with water, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[1-(4-methanesulfonyl-phenyl)-2-(tetrahydro-pyran-2-yl)-vinyl]-1H-pyrrolo[2,3-b]pyridine (220 mg, 84%): LC/MS m/e calcd for $C_{21}H_{22}N_2O_3S$ $[M+H]^+$ 383.49, observed 383.1.

A mixture of 2-[1-(4-methanesulfonyl-phenyl)-2-(tetrahydro-pyran-2(S)-yl)-vinyl]-1H-pyrrolo[2,3-b]pyridine (220 mg, 5.7 mmol) and 10% palladium on activated carbon (66 mg) in methanol (200 mL) was heated at 50° C. under hydrogen (50 psi) and kept for 16 h. The mixture was cooled to 25°

C., the catalyst was removed by filtration and then washed with ethyl acetate and the filtrate concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[1-(4-methanesulfonyl-phenyl)-2-(tetrahydro-pyran-2-yl)-ethyl]-1H-pyrrolo[2,3-b]pyridine (60 mg, 27%) as a mixture of two diastereoisomers: LC/MS m/e calcd for $C_{21}H_{24}N_2O_3S$ $[M+H]^+$ 385.50, observed 385.2; $^1H$ NMR (400 MHz, $CDCl_3$) δ ppm 1.34-1.67 (m, 5H), 1.82 (m, 1H), 2.15 (m, 1H), 2.36 (m, 1H), 3.05, 3.09 (2×s, 3H), 3.21-3.40 (m, 2H), 4.13, 4.18 (2×m, 1H), 4.61, 4.67 (2×dd, 1H), 6.33, 6.42 (2×s, 1H), 7.18, 7.26 (2×m, 1H), 7.52, 7.59 (d, J=8.5 Hz, 2H), 7.89, 7.94 (2×m, 3H), 8.16 (m, 1H), 11.47 (br, 1H).

The mixture of diastereomers of 2-[1-(4-methanesulfonyl-phenyl)-2-(tetrahydro-pyran-2(S)-yl)-ethyl]-1H-pyrrolo[2,3-b]pyridine (60 mg) was separated by Agilent high performance liquid chromatography (chiral column: Daicel OJ-H, 250 mm×20 mm i. d., 5 μm-particle size, temperature: 25° C., flow rate of 15 mL/min, 60% ethanol/hexanes as mobile phase and UV detection: 214 and 254 nm) to afford two pure diastereomers of 2-[1(R)-(4-methanesulfonyl-phenyl)-2-(tetrahydro-pyran-2(S)-yl)-ethyl]-1H-pyrrolo[2,3-b]pyridine. The first peak, diastereomer 1 was isolated as a white solid (32 mg): $^1H$ NMR (400 MHz, $CDCl_3$) δ ppm 11.51 (br. s, 1H), 8.16 (d, J=4.5 Hz, 1H), 7.82-7.91 (m, 3H), 7.52 (d, J=8.1 Hz, 2H), 7.05 (dd, J=7.7, 4.9 Hz, 1H), 6.23 (s, 1H), 4.64 (dd, J=10.4, 4.5 Hz, 1H), 3.99-4.10 (m, 1H), 3.26-3.36 (m, 1H), 2.92-3.09 (m, 4H), 2.43 (ddd, J=14.0, 10.0, 4.5 Hz, 1H), 2.07-2.15 (m, 1H), 1.75-1.84 (m, 1H), 1.48-1.64 (m, 3H), 1.31-1.45 (m, 2H), 1.23 (dd, J=15.2, 6.8 Hz, 1H).

Example 61

2-[2-Cyclopentyl-1-(6-methoxy-pyridin-3-yl))-ethyl]-1H-pyrrolo[2,3-b]pyridine

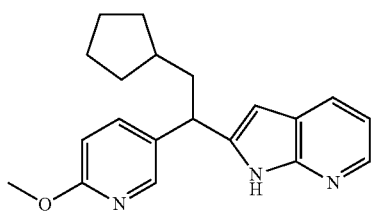

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.15 g, 0.28 mmol), 2-methoxy-5-pyridineboronic acid (110 mg, 0.72 mmol) and dichlorobis(triphenylphosphine)palladium (II) (21 mg, 0.03 mmol) in dioxane (3 mL) was added an aqueous sodium carbonate solution (2 M, 0.36 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 30% ethyl acetate/hexanes) afforded 1-benzenesulfonyl-2-[2-cyclopentyl-1-(6-methoxy-pyridin-3-yl)-vinyl]-1H-pyrrolo[2,3-b]pyridine (110 mg, 83%) as a white solid: LC/MS m/e calcd for $C_{26}H_{25}N_3O_3S$ $[M+H]^+$ 460.57, observed 460.0.

A mixture of 1-benzenesulfonyl-2-[2-cyclopentyl-1-(6-methoxy-pyridin-3-yl)-vinyl]-1H-pyrrolo[2,3-b]pyridine (110 mg, 0.24 mmol), ethanol (6 mL), tetrahydrofuran (3 mL) and an aqueous sodium hydroxide solution (10%, 1 mL) was heated at 40° C. for 4 h. The mixture was diluted with ethyl acetate (100 mL), washed with water, dried over anhydrous sodium sulfate and then concentrated in vacuo to afford 2-[2-cyclopentyl-1-(6-methoxy-pyridin-3-yl))-vinyl]-1H-pyrrolo[2,3-b]pyridine (72 mg, 94%) as a white solid: LC/MS m/e calcd for $C_{20}H_{21}N_3O$ $[M+H]^+$ 320.41, observed 320.0.

A mixture of to 2-[2-cyclopentyl-1-(6-methoxy-pyridin-3-yl))-vinyl]-1H-pyrrolo[2,3-b]pyridine (72 mg, 0.22 mmol) and 10% palladium on activated carbon (24 mg) in methanol (150 mL) was heated at 50° C. under hydrogen (50 psi) for 5 h. The mixture was cooled to room temperature, the catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(6-methoxy-pyridin-3-yl))-ethyl]-1H-pyrrolo[2,3-b]pyridine (21 mg, 29%): LC/MS m/e calcd for $C_{20}H_{23}N_3O$ $[M+H]^+$ 322.43, observed 322.2; $^1H$ NMR (400 MHz, $CDCl_3$) δ ppm 1.17 (m, 2H), 1.48 (m, 2H), 1.62 (m, 2H), 1.68-1.87 (m, 3H), 2.09 (m, 1H), 2.21 (m, 1H), 3.91 (s, 3H), 4.15 (dd, J=6.9, 8.7 Hz, 1H), 6.33 (s, 1H), 6.68 (d, J=8.6 Hz, 1H), 7.08 (dd, J=4.9, 7.7 Hz, 1H), 7.48 (dd, J=2.5 Hz, J=8.6 Hz, 1H), 7.91 (d, J=7.7 Hz, 1H), 8.14 (d, J=2.5 Hz, 1H), 8.15 (d, J=4.9 Hz, 1H), 11.16 (br, 1H).

Example 62

2-[2-Cyclopentyl-1-(2,3-dihydro-benzo[1,4]-dioxin-6-yl)-ethyl]-1H-pyrrolo[2,3-b]pyridine

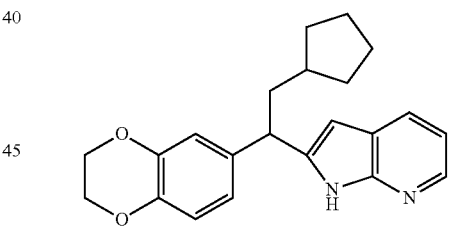

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.15 g, 0.28 mmol), 1,4-benzodioxane-6-boronic acid (0.13 g, 0.72 mmol) and dichlorobis(triphenylphosphine)palladium (II) (21 mg, 0.03 mmol) in dioxane (3 mL) was added an aqueous sodium carbonate solution (2 M, 0.36 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-2-[2-cyclopentyl-1-(2,3-dihydro-benzo[1,4]dioxin-6-yl)-vinyl]-1H-pyrrolo[2,3-b]pyridine (130 mg, 96%) as a white solid: LC/MS m/e calcd for $C_{28}H_{26}N_2O_4S$ $[M+H]^+$ 487.59, observed 487.2.

A mixture of 1-benzenesulfonyl-2-[2-cyclopentyl-1-(2,3-dihydro-benzo[1,4]dioxin-6-yl)-vinyl]-1H-pyrrolo[2,3-b]pyridine (130 mg, 0.27 mmol) in ethanol (6 mL) and tetrahydrofuran (3 mL) and an aqueous sodium hydroxide solution (10%, 1 mL) was stirred at 40° C. for 48 h. The mixture was diluted with ethyl acetate (100 mL), washed with water, dried over anhydrous sodium sulfate and then concentrated in vacuo to afford 2-[2-cyclopentyl-1-(2,3-dihydro-benzo[1,4]dioxin-6-yl)-vinyl]-1H-pyrrolo[2,3-b]pyridine (80 mg, 87%) as a white solid: LC/MS m/e calcd for $C_{22}H_{22}N_2O_2$ [M+H]$^+$ 347.43, observed 347.1.

A mixture of 2-[2-cyclopentyl-1-(2,3-dihydro-benzo[1,4]dioxin-6-yl)-vinyl]-1H-pyrrolo[2,3-b]pyridine (70 mg, 0.2 mmol) and 10% palladium on activated carbon (21 mg) in methanol (250 mL) was heated at 50° C. under hydrogen (50 psi) for 5 h. The mixture was cooled to room temperature, the catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(2,3-dihydro-benzo[1,4]dioxin-6-yl)-ethyl]-1H-pyrrolo[2,3-b]pyridine (40 mg, 57%): LC/MS m/e calcd for $C_{22}H_{24}N_2O_2$ [M+H]$^+$ 349.45, observed 349.3; $^1$H NMR (400 MHz, CDCl$_3$) δ ppm 1.17 (m, 2H), 1.47 (m, 2H), 1.61 (m, 2H), 1.77 (m, 3H), 2.08 (m, 1H), 2.16 (m, 1H), 4.07 (m, 1H), 4.22 (s, 4H, 2×OCH$_2$), 6.33 (s, 1H), 6.79 (m, 3H), 7.05 (dd, J=4.6, 7.8 Hz, 1H), 7.87 (d, J=7.8 Hz, 1H), 8.15 (d, J=4.6 Hz, 1H), 10.66 (br, 1H).

Example 63

2-[2-Cyclopentyl-1-(6-methyl-pyridin-3-yl))-ethyl]-1H-pyrrolo[2,3-b]pyridine

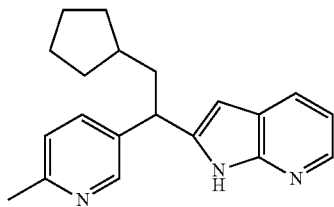

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.15 g, 0.28 mmol), 2-methylpyridine-5-boronic acid hydrate (98 mg, 0.72 mmol) and dichlorobis(triphenylphosphine)palladium (II) (21 mg, 0.03 mmol) in dioxane (3 mL) was added an aqueous sodium carbonate solution (2 M, 0.36 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-2-[2-cyclopentyl-1-(6-methyl-pyridin-3-yl)-vinyl-1H-pyrrolo[2,3-b]pyridine (100 mg, 78%) as a white solid: LC/MS m/e calcd for $C_{26}H_{25}N_3O_2S$ [M+H]$^+$ 444.57, observed 444.0.

A mixture of 1-benzenesulfonyl-2-[2-cyclopentyl-1-(6-methyl-pyridin-3-yl)-vinyl-1H-pyrrolo[2,3-b]pyridine (100 mg, 0.22 mmol) in ethanol (6 mL), tetrahydrofuran (3 mL) and an aqueous sodium hydroxide solution (10%, 1 mL) was heated at reflux for 4 h. The mixture was diluted with ethyl acetate (100 mL), washed with water, dried over anhydrous sodium sulfate and then concentrated in vacuo to afford 2-[2-cyclopentyl-1-(6-methyl-pyridin-3-yl))-vinyl]-1H-pyrrolo[2,3-b]pyridine (60 mg, 68%) as a white solid: LC/MS m/e calcd for $C_{23}H_{26}N_2O$ [M+H]$^+$ 304.41, observed 304.0.

A mixture of 2-[2-cyclopentyl-1-(6-methyl-pyridin-3-yl))-vinyl]-1H-pyrrolo[2,3-b]pyridine (50 mg, 0.16 mmol) and 10% palladium on activated carbon (15 mg) in methanol (250 mL) was heated at 50° C. under hydrogen (50 psi) for 5 h. The mixture was cooled to room temperature. The catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(6-methyl-pyridin-3-yl))-ethyl]-1H-pyrrolo[2,3-b]pyridine (6 mg, 12%): LC/MS m/e calcd for $C_{20}H_{23}N_3$[M+H]$^+$ 306.43, observed 306.2; $^1$H NMR (400 MHz, CDCl$_3$) δ ppm 1.18 (m, 2H), 1.48 (m, 2H), 1.56-1.87 (m, 5H, H), 2.11 (m, 1H), 2.27 (m, 1H), 2.66 (s, 3H), 4.30 (t, J=8.1 Hz, 1H), 6.40 (s, 1H), 7.13 (dd, J=4.9, 7.8 Hz, 1H), 7.26 (d, J=8.2 Hz, 1H), 7.78 (dd, J=2.0 Hz, J=8.2 Hz, 1H), 7.96 (dd, J=1.3 Hz, J=7.8 Hz, 1H), 8.18 (d, J=4.9 Hz, 1H), 8.56 (d, J=2.0 Hz, 1H), 10.99 (br, 1H).

Example 64

1-{4-[2-Cyclopentyl-1-(1H-pyrrolo[2,3-b]pyridin-2-yl)-ethyl]-phenyl}-ethanol

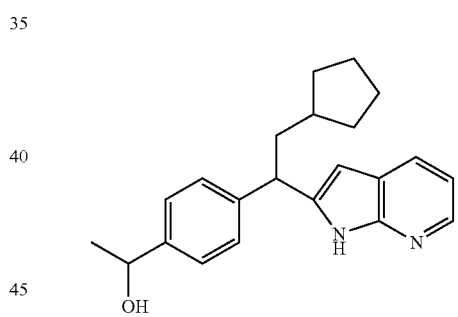

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.5 g, 0.96 mmol), 4-acetylphenylboronic acid (394 mg, 2.4 mmol) and dichlorobis(triphenylphosphine)palladium (II) (67 mg, 0.1 mmol) in dioxane (8 mL) was added an aqueous sodium carbonate solution (2 M, 1.2 mL). The resulting mixture was subjected to microwave irradiation for 2 h at 100° C. The mixture was diluted with ethyl acetate (200 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 30% ethyl acetate/hexanes) afforded 1-{4-[1-(1-benzenesulfonyl-1H-pyrrolo[2,3-b]pyridin-2-yl)-2-cyclopentyl-vinyl]-phenyl}-ethanone (400 mg, 89%) as a white solid: LC/MS m/e calcd for $C_{28}H_{26}N_2O_3S$ [M+H]$^+$ 471.60, observed 471.0.

A mixture of 1-{4-[1-(1-benzenesulfonyl-1H-pyrrolo[2,3-b]pyridin-2-yl)-2-cyclopentyl-vinyl]-phenyl}-ethanone (400 mg, 0.85 mmol) in ethanol (6 mL), tetrahydrofuran (4 mL) and an aqueous sodium hydroxide solution (10%, 1.5 mL) was heated at reflux for 48 h. The mixture was diluted with ethyl acetate (200 mL), washed with water, dried over anhydrous sodium sulfate and then concentrated in vacuo to afford 1-{4-[2-cyclopentyl-1-(1H-pyrrolo[2,3-b]pyridin-2-yl)-vinyl]-phenyl}-ethanone (250 mg, 89%) as a white solid: LC/MS m/e calcd for $C_{22}H_{22}N_2O$ [M+H]$^+$ 331.43, observed 331.0.

A mixture of 1-{4-[2-cyclopentyl-1-(1H-pyrrolo[2,3-b]pyridin-2-yl)-vinyl]-phenyl}-ethanone (240 mg, 0.72 mmol) and 10% palladium on activated carbon (100 mg) in methanol (200 mL) was heated at 50° C. under hydrogen (50 psi) for 16 h. The mixture was cooled to room temperature, the catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 1-{4-[2-cyclopentyl-1-(1H-pyrrolo[2,3-b]pyridin-2-yl)-ethyl]-phenyl}-ethanol (35 mg, 14%): LC/MS m/e calcd for $C_{22}H_{26}N_2O$ [M+H]$^+$ 335.47, observed 335.2; $^1$H NMR (400 MHz, CD$_3$OD) δ ppm 1.17 (m, 2H), 1.39 (d, J=6.5 Hz, 3H), 1.43 (m, 2H), 1.52-1.85 (m, 5H, H), 2.05 (m, 1H), 2.16 (m, 1H), 4.13 (t, J=7.8 Hz, 1H), 4.77 (q, J=6.5 Hz, 1H), 6.30 (s, 1H), 7.01 (br, 1H), 7.27 (m, 4H), 7.86 (d, J=7.1 Hz, 1H), 8.05 (br, 1H).

Example 65

{4-[2-Cyclopentyl-1-(1H-pyrrolo[2,3-b]pyridin-2-yl)-ethyl]-phenyl}-dimethyl-amine

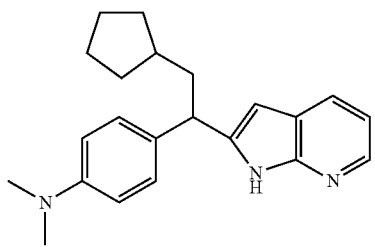

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.15 g, 0.28 mmol), 4-(dimethylamino)-phenyl boronic acid (0.12 g, 0.72 mmol) and dichlorobis(triphenylphosphine)palladium (II) (21 mg, 0.03 mmol) in dioxane (3 mL) was added an aqueous sodium carbonate solution (2 M, 0.36 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded {4-[1-(1-benzenesulfonyl-1H-pyrrolo[2,3-b]pyridin-2-yl)-2-cyclopentyl-vinyl]-phenyl}-dimethyl-amine (80 mg, 59%) as a white solid: LC/MS m/e calcd for $C_{28}H_{29}N_3O_2S$ [M+H]$^+$ 472.63, observed 472.2.

A mixture of {4-[1-(1-benzenesulfonyl-1H-pyrrolo[2,3-b]pyridin-2-yl)-2-cyclopentyl-vinyl]-phenyl}-dimethyl-amine (80 mg, 0.17 mmol) in ethanol (3 mL), tetrahydrofuran (3 mL) and an aqueous sodium hydroxide solution (10%, 2 mL) was heated at reflux for 36 h. The mixture was diluted with ethyl acetate (100 mL), washed with water, dried over anhydrous sodium sulfate and then concentrated in vacuo to afford {4-[2-cyclopentyl-1-(1H-pyrrolo[2,3-b]pyridin-2-yl)-vinyl]-phenyl}-dimethyl-amine (50 mg, 89%) as a white solid: LC/MS m/e calcd for $C_{22}H_{25}N_3$ [M+H]$^+$ 332.46, observed 332.1.

A mixture of {4-[2-cyclopentyl-1-(1H-pyrrolo[2,3-b]pyridin-2-yl)-vinyl]-phenyl}-dimethyl-amine (45 mg, 0.13 mmol) and 10% palladium on activated carbon (15 mg) in methanol (200 mL) was heated at 50° C. under hydrogen (50 psi) for 5 h. The mixture was cooled to room temperature, the catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded {4-[2-cyclopentyl-1-(1H-pyrrolo[2,3-b]pyridin-2-yl)-ethyl]-phenyl}-dimethyl-amine (23 mg, 51%): LC/MS m/e calcd for $C_{22}H_{27}N_3$ [M+H]$^+$ 334.48, observed 334.2; $^1$H NMR (400 MHz, CDCl$_3$) δ ppm 8.13 (br. s., 1H), 7.91 (br. s., 1H), 7.11-7.20 (m, 2H), 7.01-7.11 (m, 1H), 6.68-6.77 (m, 2H), 6.33-6.38 (m, 1H), 4.03-4.13 (m, 1H), 2.91-2.97 (m, 6H), 2.07-2.20 (m, 2H), 1.70-1.87 (m, 3H), 1.62 (br. s., 2H), 1.48 (br. s., 2H), 1.13-1.28 (m, 2H).

Example 66

2-[2-Cyclopentyl-1-(3,5-dimethyl-phenyl)-ethyl]-1H-pyrrolo[2,3-b]pyridine

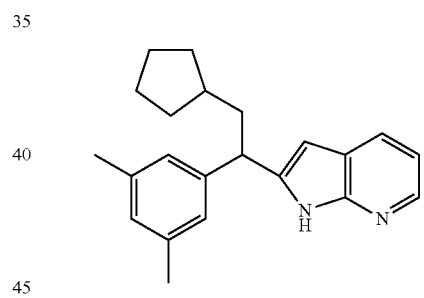

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.15 g, 0.28 mmol), 3,5-dimethylbenzene boronic acid (0.11 g, 0.72 mmol) and dichlorobis(triphenylphosphine)palladium (II) (21 mg, 0.03 mmol) in dioxane (3 mL) was added an aqueous sodium carbonate solution (2 M, 0.36 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 1-benzenesulfonyl-2-[2-cyclopentyl-1-(3,5-dimethyl-phenyl)-vinyl]-1H-pyrrolo[2,3-b]pyridine (130 mg, 99%) as a white solid: LC/MS m/e calcd for $C_{28}H_{28}N_2O_2S$ [M+H]$^+$ 457.61, observed 457.2.

A mixture of 1-benzenesulfonyl-2-[2-cyclopentyl-1-(3,5-dimethyl-phenyl)-vinyl]-1H-pyrrolo[2,3-b]pyridine (130 mg, 0.28 mmol) in ethanol (3 mL), tetrahydrofuran (3 mL), and aqueous sodium hydroxide solution (10%, 1 mL) was heated at reflux for 24 h. The mixture was diluted with ethyl acetate (100 mL), washed with water, dried over anhydrous sodium sulfate and then concentrated in vacuo to afford 2-[2-cyclopentyl-1-(3,5-dimethyl-phenyl)-vinyl]-1H-pyrrolo[2,3-b]pyridine (90 mg, 99%) as a white solid: LC/MS m/e calcd for $C_{22}H_{24}N_2$ [M+H]$^+$ 317.45, observed 317.2.

A mixture of 2-[2-cyclopentyl-1-(3,5-dimethyl-phenyl)-vinyl]-1H-pyrrolo[2,3-b]pyridine (90 mg, 0.28 mmol) and 10% palladium on activated carbon (30 mg) in methanol (200 mL) was heated at 50° C. under hydrogen (50 psi) for 6 h. The mixture was cooled to room temperature, the catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(3,5-dimethyl-phenyl)-ethyl]-1H-pyrrolo[2,3-b]pyridine (23 mg, 25%): LC/MS m/e calcd for $C_{22}H_{26}N$ [M+H]$^+$ 319.47, observed 319.2; $^1$H NMR (400 MHz, CDCl$_3$) δ ppm 8.12 (br. s., 1H), 8.05 (d, J=7.8 Hz, 1H), 7.00-7.20 (m, 4H), 6.42 (s, 1H), 5.31 (s, 1H), 4.09 (t, J=7.8 Hz, 1H), 2.08-2.26 (m, 8H), 1.57-1.85 (m, 5H), 1.42-1.53 (m, 2H), 1.14-1.24 (m, 2H).

Example 67

2-[1(R)-(4-Methanesulfonyl-phenyl)-2-(tetrahydro-pyran-4-yl)-ethyl]-1H-pyrrolo[2,3-b]pyridine

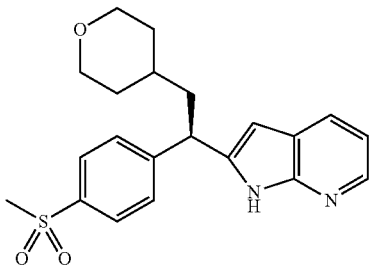

To a solution of tetrahydro-pyran-4-one (25 g, 0.25 mol) in acetonitrile (250 mL) was added (carbethoxymethylene)triphenylphosphorane (96 g, 0.28 mol) at room temperature. The resulting mixture was heated at 70° C. for 16 h. The reaction mixture concentrated in vacuo. Purification by flash column chromatography (silica gel from QingDao, 200-300 mesh, glass column from Shanghai SD company, 30% ethyl acetate/hexanes) afforded (tetrahydro-pyran-4-ylidene)-acetic acid ethyl ester (27 g, 63%) as a yellow oil.

A mixture of (tetrahydro-pyran-4-ylidene)-acetic acid ethyl ester (27 g, 159 mmol) and 10% palladium on activated carbon (3 g) in methanol (300 mL) was stirred at 25° C. under 30 psi of hydrogen for 20 h. The catalyst was filtered off, washed with ethyl acetate and concentrated in vacuo to afford (tetrahydro-pyran-4-yl)-acetic acid ethyl ester (25 g, 91%) as a colorless oil which was used in the next step without purification.

To a suspension of lithium aluminium hydride (11 g, 0.29 mol) in dry tetrahydrofuran (350 mL) at 0° C. was added a solution of (tetrahydro-pyran-4-yl)-acetic acid ethyl ester (25 g, 0.145 mol) in dry tetrahydrofuran (100 mL) dropwise. The resulting mixture was then refluxed for 16 h. After cooling to 0° C., the reaction mixture was quenched carefully by slow addition of a saturated sodium carbonate solution (50 mL). The mixture was decanted and the precipitate was washed with tetrahydrofuran (2×200 mL). The combined tetrahydrofuran layers were dried over anhydrous sodium sulfate and then concentrated in vacuo to afford 2-(tetrahydro-pyran-4-yl)-ethanol (13 g, 69%) as a yellow oil which was used in the next step without purification.

To a solution of 2-(tetrahydro-pyran-4-yl)-ethanol (13 g, 0.1 mol) in dichloromethane (150 mL) was added pyridinium chlorochromate (43 g, 0.2 mol) portion-wise at room temperature. The dark suspension was stirred at room temperature for 5 h. The reaction mixture was filtered through a short pad of silica gel. The filtrate was concentrated in vacuo to afford (tetrahydro-pyran-4-yl)-acetaldehyde (6.5 g, 50%) as a yellow oil which was used in the next step without purification.

To a suspension of 1-benzenesulfonyl-1H-pyrrolo[2,3-b]pyridine (5.0 g, 19.4 mmol) in dry tetrahydrofuran (125 mL) at −78° C. was added freshly prepared lithium diisopropylamide [prepared by adding 1.6 M n-butyllithium in n-hexane (18 mL, 29 mmol) to a 0° C. solution of diisopropylamine (4.4 mL, 31 mmol) in dry tetrahydrofuran (17 mL)] dropwise. The mixture was stirred at −78° C. for 5 min and then treated with (tetrahydro-pyran-4-yl)-acetaldehyde (3.7 g, 29 mmol) dropwise. The resulting mixture was stirred at −78° C. for 1 h and quenched with brine. The mixture was extracted with ethyl acetate (2×150 mL), washed with brine, dried over anhydrous sodium sulfate and concentrated in vacuo. Purification by flash column chromatography (QingDao silica gel, 200-300 mesh, 50% ethyl acetate/hexanes) afforded 1-(1-benzenesulfonyl-1H-pyrrolo[2,3-b]pyridin-2-yl)-2-(tetrahydro-pyran-4-yl)-ethanol as a colorless oil (4.3 g, 57%): LC/MS m/e calcd for $C_{20}H_{22}N_2O_4S$ [M+H]$^+$ 387.47, observed 387.1.

To a solution of 1-(1-benzenesulfonyl-1H-pyrrolo[2,3-b]pyridin-2-yl)-2-(tetrahydro-pyran-4-yl)-ethanol (2.1 g, 11 mmol) in dichloromethane (75 mL) was added Dess-Martin periodinane (8.3 g, 39 mmol) at 25° C. The reaction mixture was stirred at 25° C. for 2 h and then quenched with a saturated aqueous sodium bicarbonate solution (100 mL). The mixture was extracted with dichloromethane (50 mL), washed with a saturated aqueous sodium bicarbonate solution (3×100 mL), brine, dried over anhydrous sodium sulfate and then concentrated in vacuo to afford 1-(1-benzenesulfonyl-1H-pyrrolo[2,3-b]pyridin-2-yl)-2-(tetrahydro-pyran-2-yl)-ethanone (2.0 g, 93%) as a light yellow solid which was used in the next step without further purification: LC/MS m/e calcd for $C_{20}H_{20}N_2O_4S$ [M+H]$^+$ 385.46, observed 385.1.

To a solution of 1-(1-benzenesulfonyl-1H-pyrrolo[2,3-b]pyridin-2-yl)-2-(tetrahydro-pyran-4-yl)-ethanone (0.6 g, 1.56 mmol) in dry tetrahydrofuran (40 mL) at −78° C. was added lithium bis(trimethylsilyl)amide (1.0 M in tetrahydrofuran, 2.34 mL, 2.34 mmol) dropwise. After stirring at −78° C. for 1 h, a solution of p-toluenesulfonic anhydride (0.76 g, 2.34 mmol) in tetrahydrofuran (20 mL) was added dropwise. The resulting solution was kept at −78° C. for another 1 h. The reaction was quenched with water, extracted with ethyl acetate (300 mL), washed with brine, dried over anhydrous sodium sulfate and then concentrated in vacuo. Purification by flash column chromatography (QingDao silica gel, 200-300 mesh, 50% ethyl acetate/hexanes) afforded toluene-4-sulfonic acid 1-(1-benzenesulfonyl-1H-pyrrolo[2,3-b]pyridin-2-yl)-2-(tetrahydro-pyran-4-yl)-vinyl ester (0.45 g, 53%) as a white solid: LC/MS m/e calcd for $C_{27}H_{26}N_2O_6S_2$ [M+H]$^+$ 539.65, observed: 539.3.

To a mixture of toluene-4-sulfonic acid 1-(1-benzenesulfonyl-1H-pyrrolo[2,3-b]pyridin-2-yl)-2-(tetrahydro-pyran-4-yl)-vinyl ester (0.45 g, 0.84 mmol), 4-(methanesulfonyl)phenylboronic acid (0.50 g, 2.5 mmol) and dichlorobis(triphenylphosphine)palladium (II) (59 mg, 0.08 mmol) in dioxane (8 mL) was added an aqueous sodium carbonate solution (2 M, 1.25 mL). The resulting mixture was subjected to microwave irradiation for 2 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-2-[1-(4-methanesulfonyl-phenyl)-2-(tetrahydro-pyran-4-yl)-vinyl]-1H-pyrrolo[2,3-b]pyridine (0.36 g, 57%) as a white solid: LC/MS m/e calcd for $C_{27}H_{26}N_2O_5S_2$ [M+H]$^+$ 523.65, observed 523.3.

A mixture of 1-benzenesulfonyl-2-[1-(4-methanesulfonyl-phenyl)-2-(tetrahydro-pyran-4-yl)-vinyl]-1H-pyrrolo[2,3-b]pyridine (0.45 g, 8.6 mmol) in ethanol (8 mL), tetrahydrofuran (8 mL) and an aqueous sodium hydroxide solution (10%, 3 mL) was heated at 50° C. for 2 h. The mixture was diluted with dichloromethane (50 mL), washed with water, dried over anhydrous sodium sulfate and then concentrated in vacuo to afford 2-[1-(4-methanesulfonyl-phenyl)-2-(tetrahydro-pyran-4-yl)-vinyl]-1H-pyrrolo[2,3-b]pyridine (260 mg, 78%) which was used in the next step without further purification: LC/MS m/e calcd for $C_{21}H_{22}N_2O_3S$ [M+H]$^+$ 383.49, observed 383.4.

A mixture of 2-[1-(4-methanesulfonyl-phenyl)-2-(tetrahydro-pyran-4-yl)-vinyl]-1H-pyrrolo[2,3-b]pyridine (260 mg, 6.8 mmol) and 10% palladium on activated carbon (66 mg) in methanol (200 mL) was heated at 50° C. under hydrogen (50 psi) and kept for 16 h. The mixture was cooled to 25° C., the catalyst filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[1-(4-methanesulfonyl-phenyl)-2-(tetrahydro-pyran-4-yl)-ethyl]-1H-pyrrolo[2,3-b]pyridine (60 mg, 27%) as a white solid: LC/MS m/e calcd for $C_{21}H_{24}N_2O_3S$ [M+H]$^+$ 385.50, observed 385.1.

The 1:1 mixture of enantiomers of 2-[1-(4-methanesulfonyl-phenyl)-2-(tetrahydro-pyran-4-yl)-ethyl]-1H-pyrrolo[2,3-b]pyridine (150 mg) was separated by Agilent high performance liquid chromatography (chiral column: Daicel OJ-H, 250 mm×20 mm i. d., 5 µm-particle size, temperature: 25° C., flow rate of 17 mL/min, 60% ethanol/hexanes as mobile phase and UV detection: 214 and 254 nm) to afford two pure enantiomers. The first peak was 2-[1(R)-(4-methanesulfonyl-phenyl)-2-(tetrahydro-pyran-4-yl)-ethyl]-1H-pyrrolo[2,3-b]pyridine (50 mg) which was isolated as a white solid: $^1$H NMR (400 MHz, CD$_3$OD) δ ppm 8.08 (d, J=4.3 Hz, 1H), 7.89 (d, J=8.3 Hz, 3H), 7.60 (d, J=8.3 Hz, 2H), 7.04 (dd, J=7.7, 4.9 Hz, 1H), 6.40 (s, 1H), 4.44 (t, J=8.0 Hz, 1H), 3.88 (d, J=11.4 Hz, 2H), 3.23-3.29 (m, 1H), 3.08 (s, 3H), 2.23 (dt, J=14.1, 7.3 Hz, 1H), 2.01 (dt, J=13.8, 7.1 Hz, 1H), 1.71 (t, J=14.9 Hz, 2H), 1.43-1.54 (m, 1H), 1.28-1.42 (m, 2H).

Example 68

2-[2-(Tetrahydro-pyran-4-yl)-1-(4-trifluoromethyl-phenyl)-ethyl]-1H-pyrrolo[2,3-b]pyridine

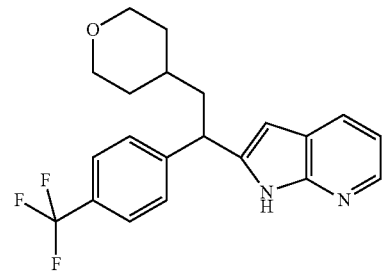

To a mixture of toluene-4-sulfonic acid 1-(1-benzenesulfonyl-1H-pyrrolo[2,3-b]pyridin-2-yl)-2-(tetrahydro-pyran-4-yl)-vinyl ester (prepared as in Example 67, 0.5 g, 0.93 mmol), 4-(trifluoromethyl)phenylboronic acid (0.56 g, 2.8 mmol) and dichlorobis(triphenylphosphine)palladium (II) (63 mg, 0.09 mmol) in dioxane (8 mL) was added an aqueous sodium carbonate solution (2 M, 1.4 mL). The resulting mixture was subjected to microwave irradiation for 4 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-2-[1-(4-methanesulfonyl-phenyl)-2-(tetrahydro-pyran-4-yl)-vinyl]-1H-pyrrolo[2,3-b]pyridine (0.23 g, 47%) as a white solid.

A mixture of 1-benzenesulfonyl-2-[1-(4-methanesulfonyl-phenyl)-2-(tetrahydro-pyran-4-yl)-vinyl]-1H-pyrrolo[2,3-b]pyridine (0.25 g, 0.49 mmol) in ethanol (5 mL), tetrahydrofuran (5 mL) and an aqueous sodium hydroxide solution (10%, 2 mL) was heated at 50° C. for 16 h. The mixture diluted with dichloromethane (50 mL), washed with water, dried over anhydrous sodium sulfate and then concentrated in vacuo to afford 2-[2-(tetrahydro-pyran-4-yl)-1-(4-trifluoromethyl-phenyl)-vinyl]-1H-pyrrolo[2,3-b]pyridine (170 mg, 94%) which was used in the next step without further purification: LC/MS m/e calcd for $C_{21}H_{19}F_3N_2O$ [M+H]$^+$ 373.39, observed 373.2.

A mixture of 2-[2-(tetrahydro-pyran-4-yl)-1-(4-trifluoromethyl-phenyl)-vinyl]-1H-pyrrolo[2,3-b]pyridine (170 mg, 4.5 mmol) and 10% palladium on activated carbon (51 mg) in methanol (200 mL) was heated at 50° C. under hydrogen (50 psi) and kept for 6 h. The mixture was cooled to 25° C., the solids filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-(tetrahydro-pyran-4-yl)-1-(4-trifluoromethyl-phenyl)-ethyl]-1H-pyrrolo[2,3-b]pyridine (60 mg, 35%) as a white solid: LC/MS m/e calcd for $C_{21}H_{21}F_3N_2O$ [M+H]$^+$ 375.41, observed 375.4; $^1$H NMR (400 MHz, CDCl$_3$) δ ppm 8.12 (d, J=4.5 Hz, 1H), 7.92 (d, J=7.6 Hz, 1H), 7.49-7.58 (m, J=8.1 Hz, 2H), 7.39-7.47 (m, J=8.1 Hz, 2H), 7.09 (dd, J=7.6, 5.1 Hz, 1H), 6.36 (s, 1H), 4.39 (t, J=7.8 Hz, 1H), 3.92 (d, J=11.1 Hz, 2H), 3.27 (t, J=11.6 Hz, 2H), 2.26 (dt, J=14.1, 7.2 Hz, 1H), 2.03 (dt, J=14.0, 7.0 Hz, 1H), 1.66 (d, J=12.4 Hz, 2H), 1.33-1.56 (m, 3H).

Example 69

2-[2-Cyclopentyl-1-[4-(propane-2-sulfonyl-phenyl)-ethyl]-1H-pyrrolo[2,3-b]pyridine

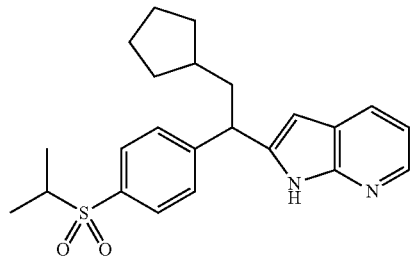

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.15 g, 0.28 mmol), 4-(propane-2-sulfonyl)phenyl boronic acid (0.12 g, 0.72 mmol) and dichlorobis(triphenylphosphine)palladium (II) (21 mg, 0.03 mmol) in dioxane (3 mL) was added an aqueous sodium carbonate solution (2 M, 0.36 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 1-benzenesulfonyl-2-{2-cyclopentyl-1-[4-(propane-2-sulfonyl)-phenyl]-vinyl}-1H-pyrrolo[2,3-b]pyridine (130 mg, 84%) as a white solid: LC/MS m/e calcd for $C_{29}H_{30}N_2O_4S_2$ [M+H]$^+$ 535.70, observed 535.4.

A mixture of 1-benzenesulfonyl-2-{2-cyclopentyl-1-[4-(propane-2-sulfonyl)-phenyl]-vinyl}-1H-pyrrolo[2,3-b]pyridine (130 mg, 0.24 mmol) in ethanol (5 mL), tetrahydrofuran (5 mL) and an aqueous sodium hydroxide solution (10%, 1.5 mL) was heated at 50° C. for 7 h. The mixture was diluted with ethyl acetate (100 mL), washed with water, dried over anhydrous sodium sulfate and then concentrated in vacuo to afford 2-[2-cyclopentyl-1-[4-(propane-2-sulfonyl-phenyl)-vinyl]-1H-pyrrolo[2,3-b]pyridine (90 mg, 93%) as a white solid: LC/MS m/e calcd for $C_{23}H_{26}NO_2S$ [M+H]$^+$ 395.54, observed 395.4.

A mixture of 2-[2-cyclopentyl-1-[4-(propane-2-sulfonyl-phenyl)-vinyl]-1H-pyrrolo[2,3-b]pyridine (90 mg, 0.23 mmol) and 10% palladium on activated carbon (30 mg) in methanol (250 mL) was heated at 50° C. under hydrogen (50 psi) for 5 h. The mixture was cooled to room temperature, the catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-[4-(propane-2-sulfonyl-phenyl)-ethyl]-1H-pyrrolo[2,3-b]pyridine (29 mg, 32%): LC/MS m/e calcd for $C_{23}H_{28}N_2O_2S$ [M+H]$^+$ 397.56, observed 397.4; $^1$H NMR (400 MHz, CD$_3$OD) δ ppm 8.10 (d, J=4.0 Hz, 1H), 7.92 (d, J=7.1 Hz, 1H), 7.80-7.86 (m, J=8.3 Hz, 2H), 7.59-7.65 (m, J=8.3 Hz, 2H), 7.01-7.08 (m, 1H), 6.42 (s, 1H), 4.34 (t, J=7.8 Hz, 1H), 3.25-3.31 (m, 1H), 2.31 (dt, J=13.7, 7.2 Hz, 1H), 2.05-2.18 (m, 1H), 1.62-1.88 (m, 5H), 1.46-1.62 (m, 2H), 1.18-1.31 (m, 8H).

Example 70

(E)-2-[1-(4-Methanesulfonyl-phenyl)-2-(tetrahydro-furan-2-yl)-vinyl]-1H-pyrrolo[2,3-b]pyridine

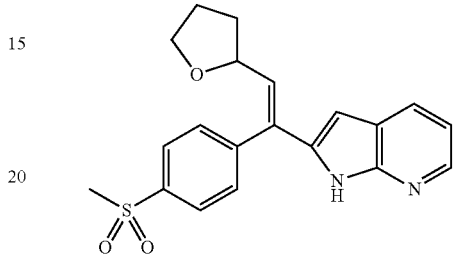

To a suspension of 1-benzenesulfonyl-1H-pyrrolo[2,3-b]pyridine (6.16 g, 24 mmol) in dry tetrahydrofuran (150 mL) at −78° C. was added freshly prepared lithium diisopropylamide [prepared by adding 1.6 M n-butyllithium in n-hexane (22.5 mL, 36 mmol) to a 0° C. solution of diisopropylamine (5.4 mL, 38 mmol) in dry tetrahydrofuran (20 mL)] dropwise. The mixture was stirred at −78° C. for 15 min and then treated with (tetrahydro-furan-2-yl)-acetaldehyde (4.9 g, 43 mmol) dropwise. The resulting mixture was stirred at −78° C. for 1 h and quenched with brine. The mixture was extracted with ethyl acetate (2×150 mL), washed with brine, dried over anhydrous sodium sulfate and concentrated in vacuo. Purification by flash column chromatography (QingDao silica gel, 200-300 mesh, 30% ethyl acetate/hexanes) afforded 1-(1-benzenesulfonyl-1H-pyrrolo[2,3-b]pyridin-2-yl)-2-(tetrahydro-furan-2-yl)-ethanol as a colorless oil (0.9 g, 31%): LC/MS m/e calcd for $C_{19}H_{20}N_2O_4S$ [M+H]$^+$ 373.45, observed 373.3.

To a solution of 1-(1-benzenesulfonyl-1H-pyrrolo[2,3-b]pyridin-2-yl)-2-(tetrahydro-furan-2-yl)-ethanol (0.9 g, 2.4 mmol) in dichloromethane (100 mL) was added Dess-Martin periodinane (2.56 g, 6 mmol) at 25° C. The reaction mixture was stirred at 25° C. for 1 h and then quenched with a saturated aqueous sodium bicarbonate solution (100 mL). The mixture was extracted with dichloromethane (50 mL), washed with a saturated aqueous sodium bicarbonate solution (3×100 mL), brine, dried over anhydrous sodium sulfate and then concentrated in vacuo to afford 1-(1-benzenesulfonyl-1H-pyrrolo[2,3-b]pyridin-2-yl)-2-(tetrahydro-furan-2-yl)-ethanone (0.5 g, 56%) as a light yellow solid: LC/MS m/e calcd for $C_{19}H_{18}N_2O_4S$ [M+H]$^+$ 371.43, observed 371.2.

To a solution of 1-(1-benzenesulfonyl-1H-pyrrolo[2,3-b]pyridin-2-yl)-2-(tetrahydro-furan-2-yl)-ethanone (0.5 g, 1.35 mmol) in dry tetrahydrofuran (5 mL) was added lithium bis(trimethylsilyl)amide (1.0 M in tetrahydrofuran, 2 mL, 2 mmol) dropwise at −78° C. After stirring at −78° C. for 1 h, a solution of p-toluenesulfonic anhydride (0.66 g, 2 mmol) in tetrahydrofuran (5 mL) was added dropwise. The resulting solution was kept at −78° C. for an additional 1.5 h. The reaction was quenched with water, extracted with ethyl acetate (100 mL), washed with brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded toluene-4-sulfonic acid 1-(1-benzenesulfonyl-1H-pyrrolo[2,3-b]pyridin-2-yl)-2-(tetrahydro-furan-2-yl)-vinyl ester (0.6 g, 84%) as a white solid: LC/MS m/e calcd for $C_{26}H_{24}N_2O_6S_2$ [M+H]$^+$ 525.62, observed: 525.3.

To a mixture of toluene-4-sulfonic acid 1-(1-benzenesulfonyl-1H-pyrrolo[2,3-b]pyridin-2-yl)-2-(tetrahydro-furan-2-yl)-vinyl ester (0.6 g, 1.14 mmol), 4-(methanesulfonyl)phenylboronic acid (0.57 g, 2.86 mmol) and dichlorobis(triphenylphosphine)palladium (II) (81 mg, 0.11 mmol) in dioxane (8 mL) was added an aqueous sodium carbonate solution (2 M, 1.4 mL). The resulting mixture was subjected to microwave irradiation for 8 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 30% ethyl acetate/hexanes) afforded 1-benzenesulfonyl-2-[1-(4-methanesulfonyl-phenyl)-2-(tetrahydro-furan-2-yl)-vinyl]-1H-pyrrolo[2,3-b]pyridine (0.24 g, 41%) as a white solid: LC/MS m/e calcd for $C_{26}H_{24}N_2O_5S_2$ [M+H]$^+$ 509.62, observed 509.3.

A mixture of 1-benzenesulfonyl-2-[1-(4-methanesulfonyl-phenyl)-2-(tetrahydro-furan-2-yl)-vinyl]-1H-pyrrolo[2,3-b]pyridine (0.24 g, 0.47 mmol) in ethanol (2 mL), tetrahydrofuran (2 mL) and an aqueous sodium hydroxide solution (10%, 1 mL) was heated at 50° C. for 2 h. The mixture diluted with dichloromethane (50 mL), washed with water, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded (Z)-2-[1-(4-methanesulfonyl-phenyl)-2-(tetrahydro-furan-2-yl)-vinyl]-1H-pyrrolo[2,3-b]pyridine (130 mg, 75%): LC/MS m/e calcd for $C_{20}H_{20}N_2O_3S$ [M+H]$^+$ 369.46, observed 369.3; and (E)-2-[1-(4-methanesulfonyl-phenyl)-2-(tetrahydro-furan-2-yl)-vinyl]-1H-pyrrolo[2,3-b]pyridine (5 mg, 2%): LC/MS m/e calcd for $C_{20}H_{20}N_2O_3S$ [M+H]$^+$ 369.46, observed 369.3; $^1$H NMR (400 MHz, CD$_3$OD) δ ppm 8.28 (d, J=5.1 Hz, 1H), 8.20 (d, J=7.8 Hz, 1H), 8.07-8.11 (m, J=8.3 Hz, 2H), 7.61-7.66 (m, J=8.1 Hz, 2H), 7.29-7.34 (m, 1H), 6.59 (d, J=9.1 Hz, 1H), 6.15 (s, 1H), 4.24 (q, J=7.4 Hz, 1H), 3.98 (q, J=7.0 Hz, 1H), 3.75-3.81 (m, 1H), 3.23 (s, 3H), 2.05-2.15 (m, 2H), 1.80-1.99 (m, 2H).

Example 71

2-[1-(4-Methanesulfonyl-phenyl)-2-(tetrahydro-furan-2-yl)-ethyl]-1H-pyrrolo[2,3-b]pyridine

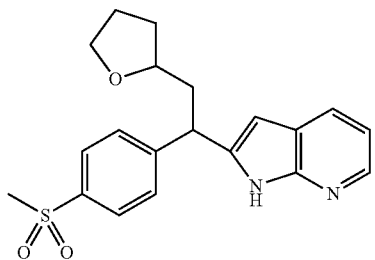

A mixture of (Z)-2-[1-(4-methanesulfonyl-phenyl)-2-(tetrahydro-furan-2-yl)-vinyl]-1H-pyrrolo[2,3-b]pyridine (prepared as in Example 70, 60 mg, 0.16 mmol) and 10% palladium on activated carbon (18 mg) in methanol (250 mL) was heated at 50° C. under hydrogen (50 psi) for 16 h. The mixture was cooled to 25° C., the catalyst filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[1-(4-methanesulfonyl-phenyl)-2-(tetrahydro-furan-2-yl)-ethyl]-1H-pyrrolo[2,3-b]pyridine (15 mg, 24%) as a mixture of stereoisomers: LC/MS m/e calcd for $C_{20}H_{22}N_2O_3S$ [M+H]$^+$ 371.47, observed 371.3; $^1$H NMR (400 MHz, CD$_3$OD) δ ppm 8.12 (d, J=3.8 Hz, 1H), 7.90-8.00 (m, 3H), 7.62-7.67 (m, 2H), 7.06-7.11 (m, 1H), 6.43-6.48 (m, 1H), 4.50-4.61 (m, 2H), 3.83-3.97 (m, 1H), 3.65-3.78 (m, 2H), 3.11-3.19 (m, 3H), 2.43-2.55 (m, 1H), 2.21-2.36 (m, 1H), 1.85-2.11 (m, 3H), 1.57-1.67 (m, 1H).

Example 72

2-Cyclobutyl-1-(4-methanesulfonyl-3-trifluoromethyl-phenyl)-1-(5-methoxy-1H-pyrrolo[2,3-b]pyridin-2-yl)-ethanol

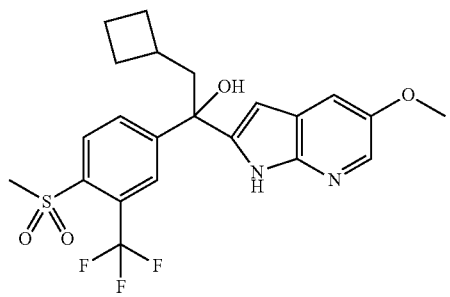

To a −78° C. suspension of 1-benzenesulfonyl-5-methoxy-1H-pyrrolo[2,3-b]pyridine (3.17 g, 11 mmol) in dry tetrahydrofuran (50 mL) was added n-butyllithium in n-hexane (1.6 M, 6.9 mL, 11 mmol) dropwise. The mixture was stirred at −78° C. for 30 min before adding 4-methylsulfanyl-3-trifluoromethyl-benzaldehyde (2.65 g, 12 mmol) dropwise. The resulting mixture was stirred at −78° C. for 1 h and quenched by adding brine (20 mL). The mixture was extracted with ethyl acetate (300 mL), washed with brine, dried over anhydrous sodium sulfate and concentrated in vacuo. Purification by flash silica gel chromatography (silica gel from QingDao, 200-300 mesh, glass column from Shanghai SD company) (20% ethyl acetate/hexanes) afforded (1-benzenesulfonyl-5-methoxy-1H-pyrrolo[2,3-b]pyridin-2-yl)-(4-methylsulfanyl-3-trifluoromethyl-phenyl)-methanol as colorless oil (5.08 g, 91%): LC/MS m/e calcd for $C_{23}H_{20}F_3N_2O_4S_2$ [M+H]$^+$ 509.07, observed 509.0.

To a 250 mL round bottomed flask charged with ((1-benzenesulfonyl-5-methoxy-1H-pyrrolo[2,3-b]pyridin-2-yl)-(4-methylsulfanyl-3-trifluoromethyl-phenyl)-methanol (5.08 g, 10 mmol) and dichloromethane (50 mL) was added Dess-Martin periodinane (10.65 g, 25 mmol) at 25° C. The reaction mixture was stirred at 25° C. for 2 h before quenching with saturated aqueous sodium bicarbonate solution (100 mL). The mixture was extracted with ethyl acetate (250 mL), washed with saturated aqueous sodium bicarbonate solution (3×50 mL), brine, dried over anhydrous sodium sulfate and then concentrated in vacuo to give (1-benzenesulfonyl-5- methoxy-1H-pyrrolo[2,3-b]pyridin-2-yl)-(4-methylsulfa-nyl-3-trifluoromethyl-phenyl)-methanone as a light yellow solid (4.3 g, 85%) which was used for the next step without further purification: LC/MS m/e calcd for $C_{23}H_{18}F_3N_2O_4S_2$ $[M+H]^+$ 507.06, observed 507.0.

To a solution of (1-benzenesulfonyl-5-methoxy-1H-pyrrolo[2,3-b]pyridin-2-yl)-4-methylsulfanyl-3-trifluoromethyl-phenyl)-methanone (0.76 g, 1.5 mmol) in dry tetrahydrofuran (2 mL) at 0° C. was added cyclobutanemethyl magnesium bromide solution in tetrahydrofuran (prepared as in Example 115, 4.5 mmol) dropwise. After stirring at 0° C. for 1 h, the mixture was quenched with a saturated aqueous ammonium chloride solution (20 mL), extracted with ethyl acetate (2×50 mL), washed with brine, dried over anhydrous sodium sulfate and concentrated in vacuo. Purification by flash silica gel chromatography (silica gel from QingDao, 200-300 mesh, glass column from Shanghai SD company, 50% ethyl acetate/hexanes) afforded 2-cyclobutyl-1-(5-methoxy-1H-pyrrolo[2,3-b]pyridin-2-yl)-1-(4-methylsulfa-nyl-3-trifluoromethyl-phenyl)-ethanol (0.2 g, 24%) as a white solid: LC/MS m/e calcd for $C_{22}H_{23}F_3N_2O_2S$ $[M+H]^+$ 437.50, observed 437.4.

To a mixture of sodium metaperiodate (0.3 g, 1.4 mmol) in water (10 mL) was added a solution of 2-cyclobutyl-1-(5-methoxy-1H-pyrrolo[2,3-b]pyridin-2-yl)-1-(4-methylsulfa-nyl-3-trifluoromethyl-phenyl)-ethanol (0.2 g, 0.46 mmol) in methanol (30 mL). The reaction mixture was stirred at 25° C. for 16 h and the suspension was then filtered. The filtrate was then treated with potassium permanganate (0.07 g, 0.46 mmol) and the reaction mixture was stirred at 25° C. for 10 h. The suspension was filtered through a short silica gel pad and washed with ethyl acetate (3×50 mL). The filtrate was concentrated and extracted with ethyl acetate (2×25 mL). The combined organic extracts were washed with water (2×25 mL), dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-cyclobutyl-1-(4-methanesulfonyl-3-trifluoromethyl-phenyl)-1-(5-methoxy-1H-pyrrolo[2,3-b]pyridin-2-yl)-ethanol as a solid (35 mg, 16%): LC/MS m/e calcd for $C_{22}H_{23}F_3N_2O_4S_2$ $[M+H]^+$ 469.50, observed 469.0; $^1H$ NMR (400 MHz, $CD_3OD$) δ ppm 8.11-8.22 (m, 2H), 7.93 (d, J=8.3 Hz, 1H), 7.83-7.88 (m, 1H), 7.52 (d, J=2.3 Hz, 1H), 6.47 (s, 1H), 4.59 (s, 1H), 3.84 (s, 3H), 3.16 (s, 3H), 2.41-2.53 (m, 3H), 1.92 (d, J=5.1 Hz, 1H), 1.62-1.81 (m, 3H), 1.53 (d, J=5.1 Hz, 1H), 1.41 (q, J=9.1 Hz, 1H).

Example 73

2-[(E)-1-(4-Methanesulfonyl-phenyl)-3,3-dimethyl-but-1-enyl]-1H-pyrrolo[2,3-b]pyridine

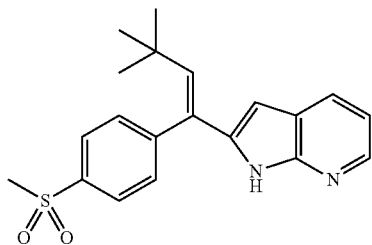

To a suspension of 1-benzenesulfonyl-1H-pyrrolo[2,3-b]pyridine (3.5 g, 13 mmol) in dry tetrahydrofuran (150 mL) at −78° C. was added freshly prepared lithium diisopropylamide [prepared by adding 1.6 M n-butyllithium in n-hexane (12.5 mL, 20 mmol) to a 0° C. solution of diisopropylamine (3.06 mL, 21 mmol) in dry tetrahydrofuran (10 mL)] dropwise. The mixture was stirred at −78° C. for 15 min and then treated with 3,3-dimethyl-butyraldehyde (3.1 mL, 24 mmol) dropwise. The resulting mixture was stirred at −78° C. for 1 h and quenched with brine. The mixture was extracted with ethyl acetate (2×150 mL), washed with brine, dried over anhydrous sodium sulfate and concentrated in vacuo. Purification by flash column chromatography (QingDao silica gel, 200-300 mesh, 25% ethyl acetate/hexanes) afforded 1-(1-benzene-sulfonyl-1H-pyrrolo[2,3-b]pyridin-2-yl)-3,3-dimethyl-bu-tan-1-ol as a colorless oil (3.1 g, 63%): LC/MS m/e calcd for $C_{19}H_{22}N_2O_3S$ $[M+H]^+$ 359.46, observed 359.2.

To a solution of 1-(1-benzenesulfonyl-1H-pyrrolo[2,3-b]pyridin-2-yl)-3,3-dimethyl-butan-1-ol (3.1 g, 8.7 mmol) in dichloromethane (150 mL) was added Dess-Martin periodi-nane (9.3 g, 22 mmol) at 25° C. The reaction mixture was stirred at 25° C. for 2 h and then quenched with a saturated aqueous sodium bicarbonate solution (100 mL). The mixture was extracted with dichloromethane (50 mL), washed with a saturated aqueous sodium bicarbonate solution (3×100 mL), brine, dried over anhydrous sodium sulfate and then concentrated in vacuo to afford 1-(1-benzenesulfonyl-1H-pyrrolo[2,3-b]pyridin-2-yl)-3,3-dimethyl-butan-1-one (2.5 g, 83%) as a light yellow solid which was used in the next step without further purification: LC/MS m/e calcd for $C_{19}H_{20}N_2O_3S$ $[M+H]^+$ 357.45, observed 357.3.

To a solution of 1-(1-benzenesulfonyl-1H-pyrrolo[2,3-b]pyridin-2-yl)-3,3-dimethyl-butan-1-one (0.6 g, 1.68 mmol) in dry tetrahydrofuran (2 mL) at 0° C. was added 4-thioani-solemagnesium bromide solution in tetrahydrofuran (0.5 M, 13.5 mL, 6.7 mmol) dropwise. After stirring at 0° C. for 1 h, it was quenched with a saturated aqueous ammonium chloride solution (50 mL). The mixture was extracted with ethyl acetate (2×100 mL), washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-(1-benzenesulfonyl-1H-pyrrolo[2,3-b]pyridin-2-yl)-3,3-dimethyl-1-(4-methyl-sulfanyl-phenyl)-butan-1-ol (0.2 g, 25%) as a white solid: LC/MS m/e calcd for $C_{26}H_{28}N_2O_3S_2$ $[M+H]^+$ 481.65, observed 481.3.

To a mixture of sodium (meta)periodate (0.267 g, 1.25 mmol) in water (10 mL) was added a solution of 1-(1-benze-nesulfonyl-1H-pyrrolo[2,3-b]pyridin-2-yl)-3,3-dimethyl-1-(4-methylsulfanyl-phenyl)-butan-1-ol (0.2 g, 0.42 mmol) in methanol (25 mL) and ethyl acetate (10 mL). The reaction mixture was stirred at 25° C. for 16 h and the suspension was filtered. The filtrate was treated with potassium permanganate (0.07 g, 0.42 mmol). The reaction mixture was stirred at 25° C. for 2 h. The suspension was filtered through a short silica gel pad and washed with ethyl acetate (3×50 mL). The filtrate was concentrated and extracted with ethyl acetate (2×50 mL). The combined organic extracts were washed with water (2×25 mL), dried over anhydrous sodium sulfate and then concentrated in vacuo to afford 1-(1-benzenesulfonyl-1H-pyrrolo[2,3-b]pyridin-2-yl)-1-(4-methanesulfonyl-phenyl)-3,3-dimethyl-butan-1-ol as a solid (0.19 g, 89%): LC/MS m/e calcd for $C_{27}H_{28}N_2O_5S_2$ $[M+H]^+$ 513.65, observed 513.4.

A mixture of 1-(1-benzenesulfonyl-1H-pyrrolo[2,3-b]py-ridin-2-yl)-1-(4-methanesulfonyl-phenyl)-3,3-dimethyl-bu-tan-1-ol (190 mg, 0.37 mmol) and tetrabutylammonium fluoride solution in tetrahydrofuran (1 M, 3 mL) was stirred at 25° C. for 16 h. The reaction was quenched with a saturated aqueous ammonium chloride solution (20 mL). The mixture was extracted with ethyl acetate (2×50 mL), washed with a saturated aqueous ammonium chloride solution (3×25 mL), brine, dried over anhydrous sodium sulfate and concentrated in vacuo to afford 2-[(E)-1-(4-methanesulfonyl-phenyl)-3,3-dimethyl-but-1-enyl]-1H-pyrrolo[2,3-b]pyridine (50 mg, 96%): LC/MS m/e calcd for $C_{20}H_{22}N_2O_2S$ [M+H]$^+$ 355.47, observed 355.3; $^1$H NMR (400 MHz, $CD_3OD$) δ ppm 8.23 (d, J=7.6 Hz, 2H), 8.00-8.06 (m, J=8.1 Hz, 2H), 7.54-7.61 (m, J=8.1 Hz, 2H), 7.31-7.37 (m, 1H), 6.67 (s, 1H), 5.86 (s, 1H), 3.16-3.27 (s, 3H), 0.95-1.03 (s, 9H).

Example 74

2-[1-(4-Methanesulfonyl-phenyl)-3,3-dimethyl-butyl]-1H-pyrrolo[2,3-b]pyridine

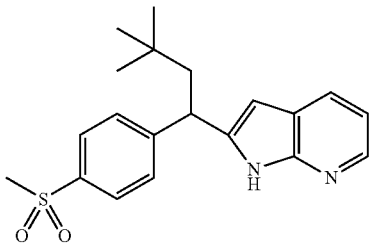

A mixture of 2-[(E)-1-(4-methanesulfonyl-phenyl)-3,3-dimethyl-but-1-enyl]-1H-pyrrolo[2,3-b]pyridine (prepared as in Example 73, 40 mg, 0.11 mmol) and 10% palladium on activated carbon (12 mg) in methanol (250 mL) was heated at 50° C. under hydrogen (50 psi) for 16 h. The mixture was cooled to 25° C., the catalyst filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[1-(4-methanesulfonyl-phenyl)-3,3-dimethyl-butyl]-1H-pyrrolo[2,3-b]pyridine (10 mg, 25%) as a white solid: LC/MS m/e calcd for $C_{20}H_{24}N_2O_2S$ [M+H]$^+$ 357.49, observed 357.4; $^1$H NMR (400 MHz, $CD_3OD$) δ ppm 8.09 (br. s., 1H), 7.84-7.93 (m, 3H), 7.65 (d, J=8.3 Hz, 2H), 7.05 (dd, J=7.7, 4.9 Hz, 1H), 6.43 (s, 1H), 4.41-4.47 (m, 1H), 3.04-3.15 (m, 3H), 2.40 (dd, J=14.0, 7.7 Hz, 1H), 1.99-2.06 (m, 1H), 0.91 (s, 9H).

Example 75

N-{4-[2-Cyclopentyl-1-(1H-pyrrolo[2,3-b]pyridin-2-yl)-ethyl]-phenyl}-methanesulfonamide

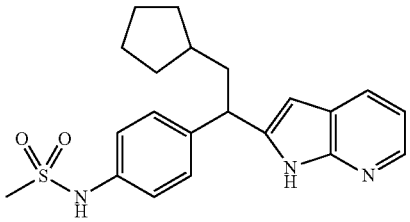

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 0.15 g, 0.28 mmol), 4-(methanesulfonylamino)phenyl boronic acid pinacol ester (0.21 g, 0.72 mmol) and dichlorobis(triphenylphosphine)palladium (II) (21 mg, 0.03 mmol) in dioxane (3 mL) was added an aqueous sodium carbonate solution (2 M, 0.36 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 30% ethyl acetate/hexanes) afforded N-{4-[1-(1-benzenesulfonyl-1H-pyrrolo[2,3-b]pyridin-2-yl)-2-cyclopentyl-vinyl]-phenyl}-methanesulfonamide (130 mg, 96%) as a white solid: LC/MS m/e calcd for $C_{27}H_{27}N_3O_4S_2$ [M+H]$^+$ 522.66, observed 522.3.

A mixture of N-{4-[1-(1-benzenesulfonyl-1H-pyrrolo[2, 3-b]pyridin-2-yl)-2-cyclopentyl-vinyl]-phenyl}-methanesulfonamide (150 mg, 0.28 mmol) and tetrabutylammonium fluoride solution in tetrahydrofuran (1 M, 3 ml) was stirred at 45° C. for 96 h. The reaction was quenched with a saturated aqueous ammonium chloride solution (20 mL). The mixture was extracted with ethyl acetate (2×50 mL), washed with a saturated aqueous ammonium chloride solution (3×50 mL), brine, dried over anhydrous sodium sulfate and concentrated in vacuo to afford N-{4-[2-cyclopentyl-1-(1H-pyrrolo[2,3-b]pyridin-2-yl)-vinyl]-phenyl}-methanesulfonamide (83 mg, 75%) as a white solid: LC/MS m/e calcd for $C_{21}H_{23}N_3O_2S$ [M+H]$^+$ 382.50, observed 382.0.

A mixture of N-{4-[2-cyclopentyl-1-(1H-pyrrolo[2,3-b]pyridin-2-yl)-vinyl]-phenyl}-methanesulfonamide (83 mg, 0.22 mmol) and 10% palladium on activated carbon (30 mg) in methanol (250 mL) was heated at 50° C. under hydrogen (50 psi) for 5 h. The mixture was cooled to room temperature, the catalyst was removed by filtration and washed with ethyl acetate. The filtrate was concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded N-{4-[2-cyclopentyl-1-(1H-pyrrolo[2,3-b]pyridin-2-yl)-ethyl]-phenyl}-methanesulfonamide (45 mg, 54%): LC/MS m/e calcd for $C_{21}H_{25}N_3O_2S$ [M+H]$^+$ 384.52, observed 384.0; $^1$H NMR (400 MHz, $CD_3OD$) δ ppm 8.04 (d, J=4.0 Hz, 1H), 7.85 (d, J=7.6 Hz, 1H), 7.25-7.31 (m, J=8.3 Hz, 2H), 7.14-7.21 (m, J=8.3 Hz, 2H), 7.00 (dd, J=7.7, 4.9 Hz, 1H), 6.30 (s, 1H), 4.60 (br. s., 1H), 4.13 (t, J=7.8 Hz, 1H), 2.89 (s, 3H), 2.19 (dt, J=13.7, 7.2 Hz, 1H), 2.00-2.08 (m, 1H), 1.57-1.84 (m, 5H), 1.42-1.53 (m, 2H), 1.12-1.26 (m, 2H).

Example 76

2-Cyclobutyl-1-(4-methanesulfonyl-3-trifluoromethyl-phenyl)-1-(1H-pyrrolo[2,3-b]pyridin-2-yl)-ethanol

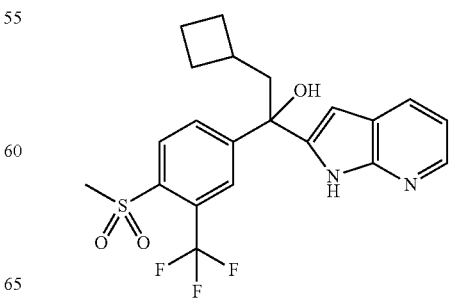

To a −78° C. suspension of 1-benzenesulfonyl-1H-pyrrolo[2,3-b]pyridine (2.84 g, 11 mmol) in dry tetrahydrofuran (50 mL) was added n-butyllithium in n-hexane (1.6 M, 6.9 mL, 11 mmol) dropwise. The mixture was stirred at −78° C. for 30 min before adding 4-methylsulfanyl-3-trifluoromethyl-benzaldehyde (2.65 g, 12 mmol) dropwise. The resulting mixture was stirred at −78° C. for 1 h and quenched by adding brine (20 mL). The mixture was extracted with ethyl acetate (300 mL), washed with brine, dried over anhydrous sodium sulfate and concentrated in vacuo. Purification by flash silica gel chromatography (silica gel from QingDao, 200-300 mesh, glass column from Shanghai SD company) (20% ethyl acetate/hexanes) afforded (1-benzenesulfonyl-1H-pyrrolo[2,3-b]pyridin-2-yl)-(4-methylsulfanyl-3-trifluoromethyl-phenyl)-methanol as colorless oil (4.78 g, 91%): LC/MS m/e calcd for $C_{23}H_{20}F_3N_2O_4S_2$ $[M+H]^+$ 479.06, observed 479.0;

To a 250 mL round bottomed flask charged with (1-benzenesulfonyl-1H-pyrrolo[2,3-b]pyridin-2-yl)-(4-methylsulfanyl-3-trifluoromethyl-phenyl)-methanol (4.78 g, 10 mmol) and dichloromethane (50 mL) was added Dess-Martin periodinane (10.65 g, 25 mmol) at 25° C. The reaction mixture was stirred at 25° C. for 2 h before quenching with saturated aqueous sodium bicarbonate solution (100 mL). The mixture was extracted with ethyl acetate (250 mL), washed with saturated aqueous sodium bicarbonate solution (3×50 mL), brine, dried over anhydrous sodium sulfate and then concentrated in vacuo to give (1-benzenesulfonyl-1H-pyrrolo[2,3-b]pyridin-2-yl)-(4-methylsulfanyl-3-trifluoromethyl-phenyl)-methanone as a light yellow solid (3.8 g, 80%) which was used for the next step without further purification: LC/MS m/e calcd for $C_{22}H_{16}F_3N_2O_3S_2$ $[M+H]^+$ 477.05, observed 477.0.

To a solution of (1-benzenesulfonyl-1H-pyrrolo[2,3-b]pyridin-2-yl)-4-methylsulfanyl-3-trifluoromethyl-phenyl)-methanone (0.71 g, 1.5 mmol) in dry tetrahydrofuran (2 mL) at 0° C. was added cyclobutanemethyl magnesium bromide solution in tetrahydrofuran (prepared as in Example 115, 4.5 mmol) dropwise. After stirring at 0° C. for 1 h, it was quenched with a saturated aqueous ammonium chloride solution (20 mL). The mixture was extracted with ethyl acetate (2×50 mL), washed with brine, dried over anhydrous sodium sulfate and concentrated in vacuo. Purification by flash silica gel chromatography (silica gel from QingDao, 200-300 mesh, glass column from Shanghai SD company, 50% ethyl acetate/hexanes) afforded 2-cyclobutyl-1-(4-methylsulfanyl-3-trifluoromethyl-phenyl)-1-(1H-pyrrolo[2,3-b]pyridin-2-yl)-ethanol (0.28 g, 45%) as a white solid: LC/MS m/e calcd for $C_{21}H_{21}F_3N_2OS$ $[M+H]^+$ 407.47, observed 407.4.

To a mixture of sodium metaperiodate (0.45 g, 2.1 mmol) in water (20 mL) was added a solution 2-cyclobutyl-1-(4-methylsulfanyl-3-trifluoromethyl-phenyl)-1-(1H-pyrrolo[2,3-b]pyridin-2-yl)-ethanol (0.28 g, 0.7 mmol) in methanol (70 mL). The reaction mixture was stirred at 25° C. for 16 h. The suspension was filtered and the filtrate was treated with potassium permanganate (0.09 g, 0.56 mmol) and the reaction mixture was stirred at 25° C. for 10 h. The suspension was filtered through a short silica gel pad and washed with ethyl acetate (3×50 mL). The filtrate was concentrated and extracted with ethyl acetate (2×25 mL). The combined organic extracts were washed with water (2×25 mL), dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-cyclobutyl-1-(4-methanesulfonyl-3-trifluoromethyl-phenyl)-1-(1H-pyrrolo[2,3-b]pyridin-2-yl)-ethanol as a solid (61 mg, 21%): LC/MS m/e calcd for $C_{22}H_{23}F_3N_2O_4S_2$ $[M+H]^+$ 439.47, observed 439.4; $^1$H NMR (400 MHz, CD$_3$OD) δ ppm 8.22-8.28 (m, 2H), 8.17 (d, J=4.5 Hz, 1H), 7.97-8.02 (m, 2H), 7.11 (dd, J=7.7, 4.9 Hz, 1H), 6.60 (s, 1H), 3.23 (s, 3H), 2.49-2.61 (m, 3H), 1.99 (d, J=5.1 Hz, 1H), 1.70-1.87 (m, 3H), 1.56-1.65 (m, 1H), 1.48 (q, J=9.1 Hz, 1H).

Example 77

2-[2-Cyclobutyl-1-(4-methanesulfonyl-3-trifluoromethyl-phenyl)-ethyl]-1H-pyrrolo[2,3-b]pyridine

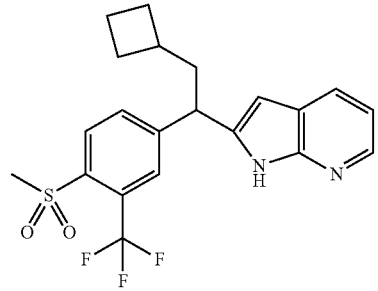

A mixture of 2-cyclobutyl-1-(4-methanesulfonyl-3-trifluoromethyl-phenyl)-1-(1H-pyrrolo[2,3-b]pyridin-2-yl)-ethanol (prepared as in Example 76, 50 mg, 0.11 mmol) in trifluoroacetic acid (12.5 mL) and triethylsilane (0.09 mL, 0.57 mmol) was heated at 65° C. for 27 h. The mixture was diluted with dichloromethane (50 mL), washed with water, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded: 2-[2-cyclobutyl-1-(4-methanesulfonyl-3-trifluoromethyl-phenyl)-ethyl]-1H-pyrrolo[2,3-b]pyridine (21 mg, 43%) as a white solid: LC/MS m/e calcd for $C_{21}H_{21}F_3N_2O_2S$ $[M+H]^+$ 423.47, observed 423.0; $^1$H NMR (400 MHz, CD$_3$OD) δ ppm 8.21 (d, J=8.3 Hz, 1H), 8.08 (d, J=4.5 Hz, 1H), 7.85-7.92 (m, 2H), 7.80 (d, J=8.1 Hz, 1H), 7.03 (dd, J=7.6, 4.8 Hz, 1H), 6.41 (s, 1H), 4.27 (t, J=7.5 Hz, 1H), 3.16 (s, 3H), 2.32-2.42 (m, 1H), 2.11-2.29 (m, 2H), 1.96-2.05 (m, 1H), 1.92 (dd, J=6.3, 3.5 Hz, 1H), 1.59-1.85 (m, 4H).

Example 78

3-[2-(4-Methanesulfonyl-phenyl)-2-(1H-pyrrolo[2,3-b]pyridin-2-yl)-ethyl]-cyclopentanone diastereomer 2

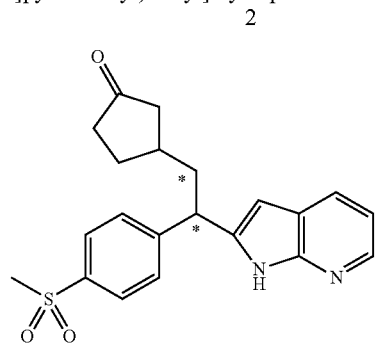

To excess ethane thiol at 0° C. was added malonyl dichloride (12.5 g, 88.6 mmol). The resulting solution was stirred at 35° C. for 1 h. Dithiomalonic acid di-S-ethyl ester (14.0 g, 82%) was obtained by distillation under reduced pressure as a colorless liquid.

A solution of dithiomalonic acid di-S-ethyl ester (42.3 g, 0.22 mol) and 1,4-diazabicyclo[2,2,2]octane (24.7 g, 0.22 mol), cyclopent-2-enone (17.6 g, 0.21 mol) in 1,2-dimethoxyethane (300 mL) was stirred at room temperature under nitrogen for 48 h. The mixture was concentrated in vacuo to give a residue which was purified by flash column chromatography (QingDao silica gel, 200-300 mesh, 5% ethyl acetate/pentane) afforded 2-(3-oxo-cyclopentyl)-dithiomalonic acid di-S-ethyl ester as a white solid (50.0 g, 82%).

A mixture of 2-(3-oxo-cyclopentyl)-dithiomalonic acid di-S-ethyl ester (43.6 g, 0.159 mol), ethane-1,2-diol (49.3 g, 0.796 mol), p-toluenesulfonic acid (5.5 g, 0.032 mol) and benzene (500 mL) were heated to reflux and water was removed with a Dean-Stark trap. After 16 h, the mixture was quenched with water and saturated aqueous sodium bicarbonate, extracted with ethyl acetate, dried and concentrated to afford crude product. Purification by flash column chromatography (QingDao silica gel, 200-300 mesh, 5% ethyl acetate/hexanes) afforded 2-(1,4-dioxa-spiro[4.4]non-7-yl)-dithiomalonic acid di-S-ethyl ester as a white solid (47.0 g, 92%).

To a solution Raney-Ni (250 mL) in benzene (100 mL) was added a solution of 2-(1,4-dioxa-spiro[4.4]non-7-yl)-dithiomalonic acid di-S-ethyl ester (28.7 g, 90 mmol) in benzene (600 mL). The mixture was stirred for 16 h at room temperature under nitrogen. The mixture was filtered to remove Raney-Ni and the filtrate was concentrated in vacuo. Purification by flash column chromatography (QingDao silica gel, 200-300 mesh, 5% ethyl acetate/pentane) afforded 2-(1,4-dioxa-spiro[4.4]non-7-yl)-ethanol (7 g, 45%).

To a solution of 2-(1,4-dioxa-spiro[4.4]non-7-yl)-ethanol (7 g, 40.6 mmol) in dichloromethane (400 mL) was added Dess-Martin periodinane (43 g, 101.6 mmol) at 25° C. The reaction mixture was stirred at 25° C. for 2 h and then quenched with a saturated aqueous sodium bicarbonate solution (100 mL). The mixture was extracted with dichloromethane (2×100 mL), washed with a saturated aqueous sodium bicarbonate solution (3×200 mL), brine, dried over anhydrous sodium sulfate and then concentrated in vacuo. The residue was diluted with n-hexane (400 mL) and filtered. The filtrate was concentrated in vacuo to afford (1,4-dioxa-spiro[4.4]non-7-yl)-acetaldehyde (5.5 g, 79%) as a light yellow solid: LC/MS m/e calcd for $C_9H_{14}O_3$ [M+H]$^+$ 171.21.

To a suspension of 1-benzenesulfonyl-1H-pyrrolo[2,3-b]pyridine (4.2 g, 16 mmol) in dry tetrahydrofuran (100 mL) at −78° C. was added a solution of n-butyllithium in n-hexane (1.6 M, 15 mL, 24 mmol) dropwise. The mixture was stirred at −78° C. for 15 min and then treated with (1,4-dioxa-spiro[4.4]non-7-yl)-acetaldehyde (5 g, 29 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (QingDao silica gel, 200-300 mesh, 30% ethyl acetate/hexanes) afforded 1-(1-benzenesulfonyl-1H-pyrrolo[2,3-b]pyridin-2-yl)-2-(1,4-dioxa-spiro[4.4]non-7-yl)-ethanol as a colorless oil (5.5 g, 74%): LC/MS m/e calcd for $C_{22}H_{24}N_2O_5S$ [M+H]$^+$ 429.51, observed 429.3.

To a solution of 1-(1-benzenesulfonyl-1H-pyrrolo[2,3-b]pyridin-2-yl)-2-(1,4-dioxa-spiro[4.4]non-7-yl)-ethanol (2.5 g, 5.84 mmol) in dichloromethane (150 mL) was added Dess-Martin periodinane (6.2 g, 14.6 mmol) at 25° C. The reaction mixture was stirred at 25° C. for 2 h and then quenched with a saturated aqueous sodium bicarbonate solution (100 mL). The mixture was extracted with dichloromethane (50 mL), washed with a saturated aqueous sodium bicarbonate solution (3×100 mL), brine, dried over anhydrous sodium sulfate and then concentrated in vacuo. Purification by flash column chromatography (QingDao silica gel, 200-300 mesh, 50% ethyl acetate/hexanes) afforded 1-(1-benzenesulfonyl-1H-pyrrolo[2,3-b]pyridin-2-yl)-2-(1,4-dioxa-spiro[4.4]non-7-yl)-ethanone (2.45 g, 98%) as a light yellow solid: LC/MS m/e calcd for $C_{22}H_{22}N_2O_5S$ [M+H]$^+$ 427.50, observed 427.5.

To a solution of 1-(1-benzenesulfonyl-1H-pyrrolo[2,3-b]pyridin-2-yl)-2-(1,4-dioxa-spiro[4.4]non-7-yl)-ethanone (2.4 g, 5.63 mmol) in dry tetrahydrofuran (160 mL) at −78° C. was added a lithium bis(trimethylsilyl)amide solution in tetrahydrofuran (1.0 M, 8.45 mL, 8.45 mmol) dropwise. After stirring at −78° C. for 1 h, a solution of p-toluenesulfonic anhydride (2.76 g, 8.45 mmol) in tetrahydrofuran (80 mL) was added dropwise. The resulting solution was kept at −78° C. for an additional 1 h. The reaction was quenched with water, extracted with ethyl acetate (100 mL), washed with brine, dried over anhydrous sodium sulfate and then concentrated in vacuo. Purification by flash column chromatography (QingDao silica gel, 200-300 mesh, 50% ethyl acetate/hexanes) afforded toluene-4-sulfonic acid 1-(1-benzenesulfonyl-1H-pyrrolo[2,3-b]pyridin-2-yl)-2-(1,4-dioxa-spiro[4.4]non-7-yl)-vinyl ester (1.7 g, 52%) as a white solid: LC/MS m/e calcd for $C_{29}H_{28}N_2O_7S_2$ [M+H]$^+$ 581.68, observed 581.6.

To a mixture of toluene-4-sulfonic acid 1-(1-benzenesulfonyl-1H-pyrrolo[2,3-b]pyridin-2-yl)-2-(1,4-dioxa-spiro[4.4]non-7-yl)-vinyl ester (1 g, 1.72 mmol), 4-(methanesulfonyl)phenylboronic acid (862 mg, 4.31 mmol) and dichlorobis(triphenylphosphine)palladium (II) (121 mg, 0.17 mmol) in dioxane (10 mL) was added an aqueous sodium carbonate solution (2 M, 2.15 mL). The resulting mixture was subjected to microwave irradiation for 4 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 30% ethyl acetate/hexanes) afforded (Z)-1-benzenesulfonyl-2-[2-(1,4-dioxa-spiro[4.4]non-7-yl)-1-(4-methanesulfonyl-phenyl)-vinyl]-1H-pyrrolo[2,3-b]pyridine (800 mg, 82%) as a white solid: LC/MS m/e calcd for $C_{29}H_{28}N_2O_6S_2$ [M+H]$^+$ 565.68, observed 565.5.

A mixture of (Z)-1-benzenesulfonyl-2-[2-(1,4-dioxa-spiro[4.4]non-7-yl)-1-(4-methanesulfonyl-phenyl)-vinyl]-1H-pyrrolo[2,3-b]pyridine (800 mg, 1.42 mmol) in ethanol (24 mL), tetrahydrofuran (16 mL) and an aqueous sodium hydroxide solution (10%, 4 mL) was heated at 45° C. for 3 h. The mixture was diluted with dichloromethane (50 mL), washed with water, dried over anhydrous sodium sulfate and then concentrated in vacuo to afford (Z)-2-[2-(1,4-dioxa-spiro[4.4]non-7-yl)-1-(4-methanesulfonyl-phenyl)-vinyl]-1H-pyrrolo[2,3-b]pyridine (570 mg, 95%): LC/MS m/e calcd for $C_{23}H_{24}FN_2O_4S$ [M+H]$^+$ 425.52, observed 425.0.

The 1:1 mixture of enantiomers of (Z)-2-[2-(1,4-dioxa-spiro[4.4]non-7-yl)-1-(4-methanesulfonyl-phenyl)-vinyl]-1H-pyrrolo[2,3-b]pyridine (570 mg) was separated by Agilent high performance liquid chromatography (chiral column: Daicel OJ-H, 250 mm×20 mm i. d., 5 μm-particle size, temperature: 25° C., flow rate of 17 mL/min, 30% ethanol/hexanes as mobile phase and UV detection: 214 and 254 nm) to afford two pure enantiomers of (Z)-2-[2-(1,4-dioxa-spiro[4.4]non-7-yl)-1-(4-methanesulfonyl-phenyl)-vinyl]-1H-pyrrolo[2,3-b]pyridine. The first peak, enantiomer 1 (138 mg) as a white solid. The second peak, enantiomer 2 (140 mg) was isolated as a white solid.

A mixture of (Z)-2-[2-(1,4-dioxa-spiro[4.4]non-7-yl)-1-(4-methanesulfonyl-phenyl)-vinyl]-1H-pyrrolo[2,3-b]pyridine (enantiomer 2, 150 mg, 0.35 mmol) and 10% palladium on activated carbon (45 mg) in methanol (250 mL) was heated at 50° C. under hydrogen (50 psi) for 5 h. The mixture was cooled to 25° C., the catalyst filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-(1,4-dioxa-spiro[4.4]non-7-yl)-1-(4-methanesulfonyl-phenyl)-ethyl]-1H-pyrrolo[2,3-b]pyridine (85 mg, 56%): LC/MS m/e calcd for $C_{23}H_{26}N_2O_4S$ [M+H]$^+$ 427.54, observed 427.1.

A mixture of 2-[2-(1,4-dioxa-spiro[4.4]non-7-yl)-1-(4-methanesulfonyl-phenyl)-ethyl]-1H-pyrrolo[2,3-b]pyridine (80 mg, 0.18 mmol) in tetrahydrofuran (12 mL) and aqueous hydrochloric acid solution (2 N, 6 mL) was stirred at 25° C. for 5 h. The mixture was diluted with ethyl acetate (50 mL), washed with a saturated aqueous sodium bicarbonate solution (2×20 mL), brine, dried over anhydrous sodium sulfate and then concentrated in vacuo. Purification by flash silica gel chromatography (silica gel from QingDao, 200-300 mesh, glass column from Shanghai SD company, 50% dichloromethane/ethyl acetate) afforded 3-[2-(4-methanesulfonyl-phenyl)-2-(1H-pyrrolo[2,3-b]pyridin-2-yl)-ethyl]-cyclopentanone (diastereomer 2, 13 mg, 18%) as a white solid: LC/MS m/e calcd for $C_{21}H_{22}N_2O_3S$ [M+H]$^+$ 383.49, observed 383.0; $^1$H NMR (400 MHz, CD$_3$OD) δ ppm 8.09 (d, J=4.5 Hz, 1H), 7.87-7.94 (m, 3H), 7.60-7.66 (m, 2H), 7.03-7.10 (m, 1H), 6.44 (d, J=3.0 Hz, 1H), 4.35-4.41 (m, 1H), 3.06-3.11 (m, 3H), 2.38-2.49 (m, 1H), 2.07-2.31 (m, 5H), 1.87-1.99 (m, 1H), 1.59-1.71 (m, 1H).

Example 79

3-[2-(4-Methanesulfonyl-phenyl)-2-(1H-pyrrolo[2,3-b]pyridin-2-yl)-ethyl]-cyclopentanone diastereomer 1

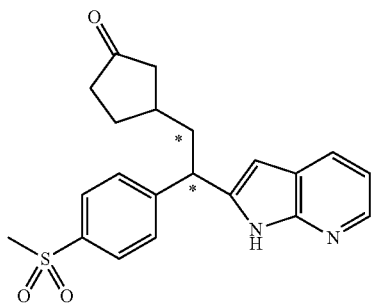

A mixture of (Z)-2-[2-(1,4-dioxa-spiro[4.4]non-7-yl)-1-(4-methanesulfonyl-phenyl)-vinyl]-1H-pyrrolo[2,3-b]pyridine (enantiomer 1, prepared as in Example 78, 140 mg, 0.33 mmol) and 10% palladium on activated carbon (50 mg) in methanol (125 mL) was heated at 50° C. under hydrogen (50 psi) for 96 h. The mixture was cooled to 25° C., the catalyst was filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.05% trifluoroacetic acid in water) afforded 3-[2-(4-methanesulfonyl-phenyl)-2-(1H-pyrrolo[2,3-b]pyridin-2-yl)-ethyl]-cyclopentanone (diastereomer 1, 8 mg, 6%): LC/MS m/e calcd for $C_{21}H_{22}N_2O_3S$ [M+H]$^+$ 383.49, observed 383.0; $^1$H NMR (400 MHz, CD$_3$OD) δ 8.09 (d, J=4.5 Hz, 1H), 7.90 (d, J=7.8 Hz, 2H), 7.63 (d, J=7.8 Hz, 2H), 7.05 (dd, J=7.7, 4.9 Hz, 1H), 6.43 (d, J=3.0 Hz, 1H), 4.75-4.84 (m, 1H), 4.59 (br. s., 1H), 4.38 (t, J=7.8 Hz, 1H), 3.08 (s, 2H), 2.37-2.49 (m, 1H), 2.05-2.30 (m, 4H), 1.88-1.99 (m, 1H), 1.58-1.71 (m, 1H), 1.22-1.38 (m, 1H), 0.90 (t, J=6.6 Hz, 1H).

Example 80

1-{4-[2-Cyclopentyl-1-(1H-pyrrolo[2,3-b]pyridin-2-yl)-ethyl]-phenyl}-ethanone

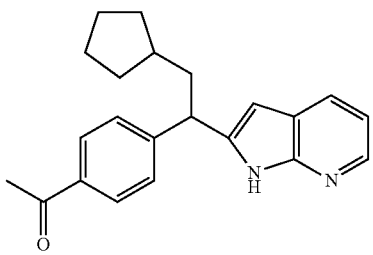

A mixture 1-{4-[2-cyclopentyl-1-(1H-pyrrolo[2,3-b]pyridin-2-yl)-vinyl]-phenyl}-ethanone (prepared as in Example 64, 280 mg, 0.84 mmol) and 10% palladium on activated carbon (56 mg) in methanol (200 mL) was heated at 50° C. under hydrogen (50 psi) for 5 h. The mixture was cooled to 25° C., the solids filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{4-[2-cyclopentyl-1-(1H-pyrrolo[2,3-b]pyridin-2-yl)-ethyl]-phenyl}-ethanone (100 mg, 35%): LC/MS m/e calcd for $C_{22}H_{24}N_2O$ [M+H]$^+$ 333.45, observed 333.1; $^1$H NMR (400 MHz, CD$_3$OD) δ ppm 8.06 (d, J=4.5 Hz, 1H), 7.85-7.95 (m, 3H), 7.45 (d, J=7.6 Hz, 2H), 6.99-7.05 (m, 1H), 6.35 (s, 1H), 4.25 (t, J=7.8 Hz, 1H), 2.56 (s, 3H), 2.24 (dt, J=13.6, 7.0 Hz, 1H), 2.09 (dt, J=13.6, 7.0 Hz, 1H), 1.57-1.85 (m, 5H), 1.41-1.54 (m, 2H), 1.13-1.27 (m, 2H).

Example 81

2-{4-[2-Cyclopentyl-1-(1H-pyrrolo[2,3-b]pyridin-2-yl)-ethyl]-phenyl}-propan-2-ol

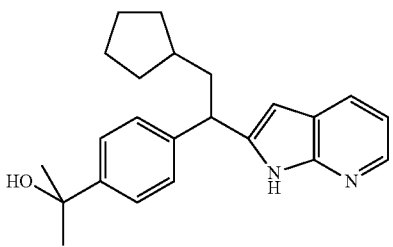

To a solution of 1-{4-[1-(1-benzenesulfonyl-1H-pyrrolo[2,3-b]pyridin-2-yl)-2-cyclopentyl-vinyl]-phenyl}-ethanone (prepared as in Example 80, 450 mg, 0.95 mmol) in dry tetrahydrofuran (20 mL) at 0° C. was added methylmagnesium chloride solution in tetrahydrofuran (3.0 M, 0.7 mL, 2.1 mmol) dropwise. After stirring at 0° C. for 1 h, the reaction was quenched with a saturated aqueous ammonium chloride solution (20 mL). The mixture was extracted with ethyl acetate (2×50 mL), washed with brine, dried over anhydrous sodium sulfate and concentrated in vacuo. Purification by flash silica gel chromatography (silica gel from QingDao, 200-300 mesh, glass column from Shanghai SD company, 50% ethyl acetate/hexanes) afforded 2-{4-[1-(1-benzenesulfonyl-1H-pyrrolo[2,3-b]pyridin-2-yl)-2-cyclopentyl-vinyl]-phenyl}-propan-2-ol (440 mg, 94%) as a white solid: LC/MS m/e calcd for $C_{29}H_{30}N_2O_3S$ [M+H]$^+$ 487.64, observed 487.2.

A mixture of 2-{4-[1-(1-benzenesulfonyl-1H-pyrrolo[2,3-b]pyridin-2-yl)-2-cyclopentyl-vinyl]-phenyl}-propan-2-ol (440 mg, 0.90 mmol) in ethanol (8 mL), tetrahydrofuran (10 mL) and an aqueous sodium hydroxide solution (10%, 3 mL) was heated at 50° C. for 16 h. The mixture was diluted with dichloromethane (50 mL), washed with water, dried over anhydrous sodium sulfate and then concentrated in vacuo to afford 2-{4-[2-cyclopentyl-1-(1H-pyrrolo[2,3-b]pyridin-2-yl)-vinyl]-phenyl}-propan-2-ol (290 mg, 92%) which was used in the next step without further purification: LC/MS m/e calcd for $C_{23}H_{26}N_2O$ [M+H]$^+$ 347.48, observed 347.2.

A mixture of 2-{4-[2-cyclopentyl-1-(1H-pyrrolo[2,3-b]pyridin-2-yl)-vinyl]-phenyl}-propan-2-ol (290 mg, 0.84 mmol) and 10% palladium on activated carbon (120 mg) in methanol (250 mL) was heated at 50° C. under hydrogen (50 psi) for 16 h. The mixture was cooled to 25° C., the solids filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{4-[2-cyclopentyl-1-(1H-pyrrolo[2,3-b]pyridin-2-yl)-ethyl]-phenyl}-propan-2-ol (170 mg, 58%): LC/MS m/e calcd for $C_{23}H_{28}N_2O$ [M+H]$^+$ 349.49, observed 349.4; $^1$H NMR (400 MHz, CD$_3$OD) δ ppm 8.03 (d, J=4.5 Hz, 1H), 7.84 (d, J=7.6 Hz, 1H), 7.38-7.43 (m, J=8.3 Hz, 2H), 7.23-7.28 (m, J=8.1 Hz, 2H), 7.00 (dd, J=7.7, 4.9 Hz, 1H), 6.29 (s, 1H), 4.13 (t, J=7.8 Hz, 1H), 2.02-2.21 (m, 2H), 1.56-1.84 (m, 5H), 1.39-1.51 (m, 8H), 1.12-1.27 (m, 2H).

Example 82

2-{4-[2-Cyclopentyl-1(R)-(1H-pyrrolo[2,3-b]pyridin-2-yl)-ethyl]-phenyl}-propan-2-ol

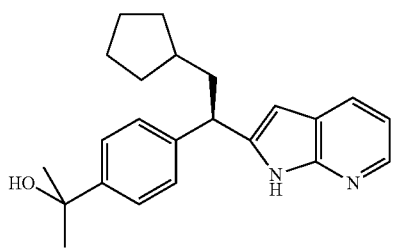

The 1:1 mixture of enantiomers of 2-{4-[2-cyclopentyl-1-(1H-pyrrolo[2,3-b]pyridin-2-yl)-ethyl]-phenyl}-propan-2-ol (prepared as in Example 81, 95 mg) was separated by Agilent high performance liquid chromatography (chiral column: Daicel IA-H, 250 mm×20 mm i. d., 5 μm-particle size, temperature: 25° C., flow rate of 15 mL/min, 20% ethanol/hexanes as mobile phase and UV detection: 214 and 254 nm) to afford two pure enantiomers. The second peak, 2-{4-[2-cyclopentyl-1(R)-(1H-pyrrolo[2,3-b]pyridin-2-yl)-ethyl]-phenyl}-propan-2-ol (39.6 mg) was isolated as a white solid: $^1$H NMR (400 MHz, CD$_3$OD) δ ppm 8.01 (d, J=4.3 Hz, 1H), 7.82 (d, J=7.8 Hz, 1H), 7.35-7.43 (m, J=8.3 Hz, 2H), 7.19-7.28 (m, J=8.1 Hz, 2H), 6.97 (dd, J=7.7, 4.9 Hz, 1H), 6.27 (s, 1H), 4.06-4.15 (m, 1H), 1.98-2.20 (m, 2H), 1.54-1.83 (m, 5H), 1.39-1.50 (m, 8H), 1.07-1.27 (m, 1H).

Example 83

3-{4-[2-Cyclopentyl-1-(1H-pyrrolo[2,3-b]pyridin-2-yl)-ethyl]-phenyl}-pentan-3-ol

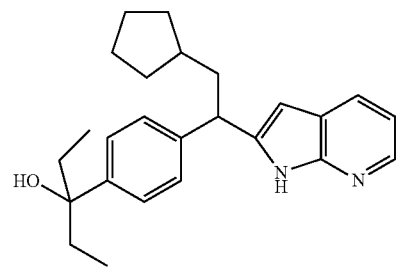

To a mixture of toluene-4-sulfonic acid-1-(1-benzenesulfonyl-1H-pyrrolo[2,3-b]pyridin-2-yl)-2-cyclopentyl-vinyl ester (prepared as in Example 43, 1.0 g, 1.92 mmol), 4-methoxycarbonylphenylboronic acid (0.86 g, 4.8 mmol) and dichlorobis(triphenylphosphine)palladium (II) (134 mg, 0.02 mmol) in dioxane (16 mL) was added an aqueous sodium carbonate solution (2 M, 2.4 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 4-[1-(1-benzenesulfonyl-1H-pyrrolo[2,3-b]pyridin-2-yl)-2-cyclopentyl-vinyl]-benzoic acid methyl ester (0.67 g, 72%) as a white solid: LC/MS m/e calcd for $C_{28}H_{26}N_2O_4S$ [M+H]$^+$ 487.59, observed 487.0.

To a solution of 4-[1-(1-benzenesulfonyl-1H-pyrrolo[2,3-b]pyridin-2-yl)-2-cyclopentyl-vinyl]-benzoic acid methyl ester (330 mg, 0.68 mmol) in dry tetrahydrofuran (20 mL) at 0° C. was added an ethylmagnesium bromide solution in tetrahydrofuran (3.0 M, 1.14 mL, 3.4 mmol) dropwise. After stirring at 0° C. for 1 h, the reaction was quenched with a saturated aqueous ammonium chloride solution (20 mL). The mixture was extracted with ethyl acetate (2×50 mL), washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 3-{4-[1-(1-benzenesulfonyl-1H-pyrrolo[2,3-b]pyridin-2-yl)-2-cyclopentyl-vinyl]-phenyl}-pentan-3-ol (220 mg, 63%) as a white solid: LC/MS m/e calcd for $C_{31}H_{34}N_2O_3S$ [M+H]$^+$ 515.69, observed 515.2.

A mixture of 3-{4-[1-(1-benzenesulfonyl-1H-pyrrolo[2,3-b]pyridin-2-yl)-2-cyclopentyl-vinyl]-phenyl}-pentan-3-ol (220 mg, 0.43 mmol) in ethanol (6 mL), tetrahydrofuran (8 mL) and an aqueous sodium hydroxide solution (10%, 1.5 mL) was heated at 50° C. for 48 h. The mixture diluted with dichloromethane (50 mL), washed with water, dried over anhydrous sodium sulfate and then concentrated in vacuo to afford 3-{4-[2-cyclopentyl-1-(1H-pyrrolo[2,3-b]pyridin-2-yl)-vinyl]-phenyl}-pentan-3-ol (120 mg, 75%) which was used in the next step without further purification: LC/MS m/e calcd for $C_{25}H_{30}N_2O$ [M+H]$^+$ 375.53, observed 375.3.

A mixture of 3-{4-[2-cyclopentyl-1-(1H-pyrrolo[2,3-b]pyridin-2-yl)-vinyl]-phenyl}-pentan-3-ol (120 mg, 0.32 mmol) and 10% palladium on activated carbon (36 mg) in methanol (250 mL) was heated at 50° C. under hydrogen (50 psi) for 16 h. The mixture was cooled to 25° C., the solids filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 3-{4-[2-cyclopentyl-1-(1H-pyrrolo[2,3-b]pyridin-2-yl)-ethyl]-phenyl}-pentan-3-ol (68 mg, 60%): LC/MS m/e calcd for $C_{25}H_{32}N_2O$ [M+H]$^+$ 377.55, observed 377.3; $^1$H NMR (400 MHz, CD$_3$OD) δ ppm 8.04 (d, J=3.8 Hz, 1H), 7.87 (dd, J=7.7, 1.1 Hz, 1H), 7.25-7.34 (m, 4H), 7.02 (dd, J=7.7, 4.9 Hz, 1H), 6.31 (s, 1H), 4.15 (t, J=7.8 Hz, 1H), 2.21 (dt, J=13.7, 7.2 Hz, 1H), 2.03-2.11 (m, 1H), 1.58-1.85 (m, 9H), 1.42-1.54 (m, 2H), 1.14-1.28 (m, 2H), 0.72 (td, J=7.4, 2.1 Hz, 6H).

Example 84

3-{4-[2-Cyclopentyl-1(R)-(1H-pyrrolo[2,3-b]pyridin-2-yl)-ethyl]-phenyl}-pentan-3-ol

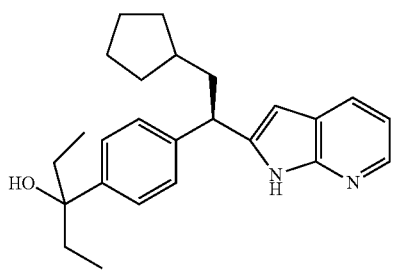

The 1:1 mixture of enantiomers of 3-{4-[2-cyclopentyl-1-(1H-pyrrolo[2,3-b]pyridin-2-yl)-ethyl]-phenyl}-pentan-3-ol (prepared as in Example 83, 68 mg) was separated by Agilent high performance liquid chromatography (chiral column: Daicel IA-H, 250 mm×20 mm i. d., 5 μm-particle size, temperature: 25° C., flow rate of 15 mL/min, 35% isopropyl alcohol/hexanes as mobile phase and UV detection: 214 and 254 nm) to afford two pure enantiomers. The second peak, 3-{4-[2-cyclopentyl-1(R)-(1H-pyrrolo[2,3-b]pyridin-2-yl)-ethyl]-phenyl}-pentan-3-ol (27 mg) which was isolated as a white solid: $^1$H NMR (400 MHz, CD$_3$OD) δ ppm 8.03 (dd, J=4.8, 1.3 Hz, 1H), 7.84 (dd, J=7.8, 1.3 Hz, 1H), 7.23-7.32 (m, 4H), 6.99 (dd, J=7.8, 4.8 Hz, 1H), 6.29 (s, 1H), 4.13 (t, J=7.8 Hz, 1H), 2.19 (dt, J=13.7, 7.2 Hz, 1H), 2.00-2.09 (m, 1H), 1.55-1.83 (m, 9H), 1.39-1.51 (m, 2H), 1.08-1.28 (m, 2H), 0.71 (td, J=7.3, 2.3 Hz, 6H).

Example 85

2-{4-[2-Cyclopentyl-1-(1H-pyrrolo[2,3-b]pyridin-2-yl)-ethyl]-phenyl}-3-methyl-butan-2-ol

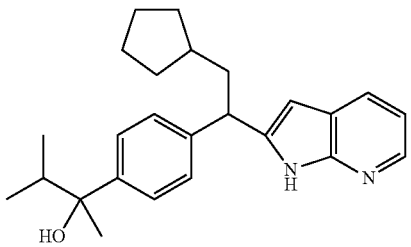

To a solution of 1-{4-[1-(1-benzenesulfonyl-1H-pyrrolo[2,3-b]pyridin-2-yl)-2-cyclopentyl-vinyl]-phenyl}-ethanone (prepared as in Example 64, 450 mg, 0.95 mmol) in dry tetrahydrofuran (20 mL) at 0° C. was added isopropylmagnesium chloride solution in tetrahydrofuran (2 M, 1.05 mL, 2.1 mmol) dropwise. After stirring at 0° C. for 3 h, the reaction was quenched with a saturated aqueous ammonium chloride solution (20 mL). The mixture was extracted with ethyl acetate (2×50 mL), washed with brine, dried over anhydrous sodium sulfate and concentrated in vacuo. Purification by flash silica gel chromatography (silica gel from QingDao, 200-300 mesh, glass column from Shanghai SD company, 50% ethyl acetate/hexanes) afforded 2-{4-[1-(1-benzenesulfonyl-1H-pyrrolo[2,3-b]pyridin-2-yl)-2-cyclopentyl-vinyl]-phenyl}-3-methyl-butan-2-ol (90 mg, 20%) as a white solid: LC/MS m/e calcd for $C_{31}H_{34}N_2O_3S$ [M+H]$^+$ 515.69, observed 515.2.

A mixture of 2-{4-[1-(1-benzenesulfonyl-1H-pyrrolo[2,3-b]pyridin-2-yl)-2-cyclopentyl-vinyl]-phenyl}-3-methyl-butan-2-ol (90 mg, 0.17 mmol) in ethanol (4 mL), tetrahydrofuran (6 mL) and an aqueous sodium hydroxide solution (10%, 2 mL) was heated at 50° C. for 36 h. The mixture was diluted with dichloromethane (50 mL), washed with water, dried over anhydrous sodium sulfate and then concentrated in vacuo to afford 2-{4-[2-cyclopentyl-1-(1H-pyrrolo[2,3-b]pyridin-2-yl)-vinyl]-phenyl}-3-methyl-butan-2-ol (50 mg, 76%) which was used in the next step without further purification: LC/MS m/e calcd for $C_{25}H_{30}N_2O$ [M+H]$^+$ 375.53, observed 375.1.

A mixture of 2-{4-[2-cyclopentyl-1-(1H-pyrrolo[2,3-b]pyridin-2-yl)-vinyl]-phenyl}-3-methyl-butan-2-ol (50 mg, 0.13 mmol) and 10% palladium on activated carbon (15 mg) in methanol (250 mL) was heated at 50° C. under hydrogen (50 psi) for 16 h. The mixture was cooled to 25° C., the solids filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{4-[2-cyclopentyl-1-(1H-pyrrolo[2,3-b]pyridin-2-yl)-ethyl]-phenyl}-3-methyl-butan-2-ol (30 mg, 60%): LC/MS m/e calcd for $C_{25}H_{32}N_2O$ [M+H]$^+$ 377.55, observed 377.2; $^1$H NMR (400 MHz, CD$_3$OD) δ ppm 0.80 (d, J=6.82 Hz, 4H) 0.86 (d, J=6.82 Hz, 4H) 1.20-1.31 (m, 1H) 1.46-1.53 (m, 5H) 1.59-1.77 (m, 3H) 1.97 (t, J=6.82 Hz, 1H) 2.05-2.13 (m, 1H) 2.19-2.26 (m, 1H) 4.17 (t, J=7.96 Hz, 1H) 6.33 (s, 1H) 7.04 (dd, J=7.71, 4.93 Hz, 1H) 7.28 (m, J=8.34 Hz, 2H) 7.38 (m, J=8.08 Hz, 2H) 7.89 (dd, J=7.83, 1.26 Hz, 1H) 8.06 (d, J=3.79 Hz, 1H).

Example 86

2-Cyclopentyl-1-(4-methanesulfonyl-phenyl)-1-(1H-pyrrolo[2,3-b]pyridin-2-yl)-ethanol

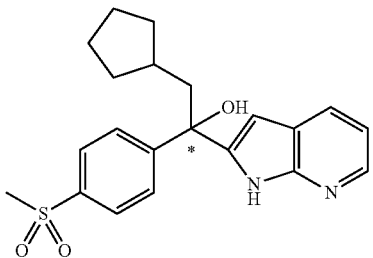

To a solution of 1-(1-benzenesulfonyl-1H-pyrrolo[2,3-b]pyridin-2-yl)-2-cyclopentyl-ethanone (prepared as in Example 43, 2.0 g, 5.43 mmol) in dry tetrahydrofuran (5 mL) at 0° C. was added 4-thioanisolemagnesium bromide solution in tetrahydrofuran (0.5 M, 32.6 mL, 16.3 mmol) dropwise. After stirring at 0° C. for 1 h, the reaction was quenched with a saturated aqueous ammonium chloride solution (50 mL). The mixture was extracted with ethyl acetate (2×100 mL), washed with brine, dried over anhydrous sodium sulfate and concentrated in vacuo. Purification by flash silica gel chromatography (silica gel from QingDao, 200-300 mesh, glass column from Shanghai SD company, 25% ethyl acetate/hexanes) afforded 1-(1-benzenesulfonyl-1H-pyrrolo[2,3-b]pyridin-2-yl)-2-cyclopentyl-1-(4-methylsulfanyl-phenyl)-ethanol (1.9 g, 24%) as a white solid: LC/MS m/e calcd for $C_{27}H_{28}N_2O_3S_2$ [M+H]$^+$ 493.66, observed 493.1.

To a mixture of sodium metaperiodate (2.5 g, 11.6 mmol) in water (80 mL) was added a solution of 1-(1-benzenesulfonyl-1H-pyrrolo[2,3-b]pyridin-2-yl)-2-cyclopentyl-1-(4-methylsulfanyl-phenyl)-ethanol (1.9 g, 3.86 mmol) in methanol (250 mL) and ethyl acetate (100 mL). The reaction mixture was stirred at 25° C. for 16 h. The suspension was filtered and the filtrate was treated with potassium permanganate (0.49 g, 3.09 mmol) and stirred at 25° C. for 2 h. The suspension was filtered through a short silica gel pad and washed with ethyl acetate (3×100 mL). The filtrate was concentrated and extracted with ethyl acetate (2×100 mL). The combined organic extracts were washed with water (2×50 mL), dried over anhydrous sodium sulfate and then concentrated in vacuo to afford 1-(1-benzenesulfonyl-1H-pyrrolo[2,3-b]pyridin-2-yl)-2-cyclopentyl-1-(4-methanesulfonyl-phenyl)-ethanol as a solid (1.4 g, 69%): LC/MS m/e calcd for $C_{27}H_{28}N_2O_5S_2$ [M+H]$^+$ 525.66, observed 525.1.

A mixture of 1-(1-benzenesulfonyl-1H-pyrrolo[2,3-b]pyridin-2-yl)-2-cyclopentyl-1-(4-methanesulfonyl-phenyl)-ethanol (1 g, 1.9 mmol) in ethanol (20 mL), tetrahydrofuran (30 mL) and an aqueous sodium hydroxide solution (10%, 4 mL) was heated at 40° C. for 4 h. The mixture diluted with dichloromethane (100 mL), washed with water, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded a mixture of 2-cyclopentyl-1-(4-methanesulfonyl-phenyl)-1-(1H-pyrrolo[2,3-b]pyridin-2-yl)-ethanol and 2-[2-cyclopentyl-1-ethoxy-1-(4-methanesulfonyl-phenyl)-ethyl]-1H-pyrrolo[2,3-b]pyridine (120 mg, 16%) as a white solid. This mixture was further separated by Agilent high performance liquid chromatography (chiral column: Daicel IA-H, 250 mm×20 mm i. d., 5 μm-particle size, temperature: 25° C., flow rate of 15 mL/min, 60% ethanol/hexanes as mobile phase and UV detection: 214 and 254 nm) to afford three compounds. The first peak, 2-cyclopentyl-(4-methanesulfonyl-phenyl)-1-(1H-pyrrolo[2,3-b]pyridin-2-yl)-ethanol (enantiomer 1, 50 mg) was isolated as a white solid: $^1$H NMR (400 MHz, CD$_3$OD) δ ppm 7.59-8.42 (m, 7H), 7.14 (dd, J=7.8, 4.8 Hz, 1H), 6.60 (s, 1H), 3.09-3.26 (m, 4H), 2.46-2.69 (m, 2H), 1.79-2.07 (m, 2H), 1.40-1.74 (m, 5H), 1.23-1.39 (m, 1H), 1.01-1.19 (m, 1H).

Example 87

2-[2-Cyclopentyl-1-ethoxy-1-(4-methanesulfonyl-phenyl)-ethyl]-1H-pyrrolo[2,3-b]pyridine

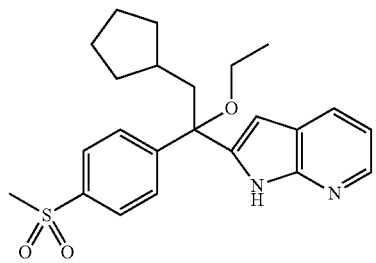

A mixture of 1-(1-benzenesulfonyl-1H-pyrrolo[2,3-b]pyridin-2-yl)-2-cyclopentyl-1-(4-methanesulfonyl-phenyl)-ethanol (prepared as in Example 86, 1 g, 1.9 mmol) in ethanol (20 mL), tetrahydrofuran (30 mL) and an aqueous sodium hydroxide solution (10%, 4 mL) was heated at 40° C. for 4 h. The mixture diluted with dichloromethane (100 mL), washed with water, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded a mixture of 2-cyclopentyl-1-(4-methanesulfonyl-phenyl)-1-(1H-pyrrolo[2,3-b]pyridin-2-yl)-ethanol and 2-[2-cyclopentyl-1-ethoxy-1-(4-methanesulfonyl-phenyl)-ethyl]-1H-pyrrolo[2,3-b]pyridine (120 mg, 16%) as a white solid. This mixture was further separated by Agilent high performance liquid chromatography (chiral column: Daicel IA-H, 250 mm×20 mm i. d., 5 μm-particle size, temperature: 25° C., flow rate of 15 mL/min, 60% ethanol/hexanes as mobile phase and UV detection: 214 and 254 nm) to afford three compounds. The third peak, 2-[2-cyclopentyl-1-ethoxy-1-(4-methanesulfonyl-phenyl)-ethyl]-1H-pyrrolo[2,3-b]pyridine (70 mg, 9%) was isolated as a white solid: LC/MS m/e calcd for $C_{23}H_{28}N_2O_3S$ [M+H]$^+$ 413.56, observed 413.1; $^1$H NMR (400 MHz, CDCl$_3$) δ ppm 7.99 (d, J=7.6 Hz, 1H), 7.82-7.88 (m, J=7.8 Hz, 2H), 7.64-7.70 (m, J=7.8 Hz, 2H), 7.13 (br. s., 1H), 6.56-6.63 (m, 1H), 3.47 (t, J=7.3 Hz, 1H), 3.12-3.21 (m, 1H), 3.03 (s, 3H), 2.63 (dd, J=14.4, 5.6 Hz, 1H), 2.37 (dd, J=14.4, 6.1 Hz, 1H), 2.25 (br.

s., 2H), 1.73-1.83 (m, 1H), 1.62-1.70 (m, 1H), 1.32-1.60 (m, 4H), 1.09-1.28 (m, 5H), 0.72-0.83 (m, 1H).

Example 88

2-{4-[2-Cyclopentyl-1-(5-fluoro-1H-pyrrolo[2,3-b]pyridin-2-yl)-ethyl]-benzenesulfonyl}-ethanol

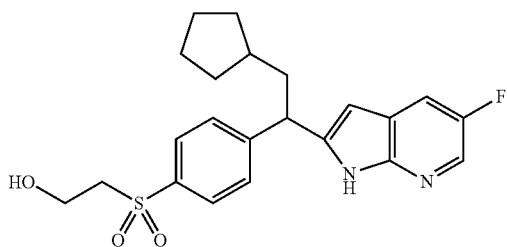

To a solution of 4-mercaptophenylboronic acid (3.08 g, 20 mmol) in anhydrous N,N-dimethylormamide (50 mL) was added solid potassium carbonate (9.7 g, 70 mmol). The mixture was stirred at 25° C. for 10 min and then treated with 1-bromo-2-methoxy-ethane (6.6 mL, 70 mmol) dropwise. The resulting mixture was stirred at 25° C. for 7 h and quenched with water. The mixture was extracted with ethyl acetate (2×150 mL), washed with water (3×100 mL), dried over anhydrous sodium sulfate and concentrated in vacuo to afford 4-(2-methoxy-ethylsulfanyl)-phenylboronic acid (4 g, 94%) which was used in the next step without further purification.

To a mixture of sodium metaperiodate (12.1 g, 56.6 mmol) in water (100 ml) was added a solution of 4-(2-methoxy-ethylsulfanyl)-phenylboronic acid (4 g, 18.8 mmol) in methanol (250 ml). The reaction mixture was stirred at 25° C. for 16 h. The suspension was filtered and the filtrate treated with potassium permanganate (1.78 g, 11.3 mmol) and stirred at 25° C. for 2 h. The suspension was filtered through a short silica gel pad and washed with ethyl acetate (3×100 mL). The filtrate was concentrated and extracted with ethyl acetate (2×100 mL). The combined organic extracts were washed with water (2×50 mL), dried over anhydrous sodium sulfate and then concentrated in vacuo to afford 4-(2-methoxy-ethanesulfonyl)-phenylboronic acid as a yellow oil (4.3 g, 93%): LC/MS m/e calcd for $C_9H_{13}BO_5S$ [M+H]$^+$ 245.08, observed 245.1.

To a suspension of 1-benzenesulfonyl-5-fluoro-1H-pyrrolo[2,3-b]pyridine (2.0 g, 7.25 mmol) in dry tetrahydrofuran (150 mL) at −78° C. was added a solution of n-butyllithium in n-hexane (1.6 M, 6.8 mL, 10.9 mmol) dropwise. The mixture was stirred at −78° C. for 30 min and then treated with cyclopentanecarbaldehyde (1.5 g, 13.04 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (QingDao silica gel, 200-300 mesh, 15% ethyl acetate/hexanes) afforded 1-(1-benzenesulfonyl-5-fluoro-1H-pyrrolo[2,3-b]pyridin-2-yl)-2-cyclopentyl-ethanol as a colorless oil (2.1 g, 74%): LC/MS m/e calcd for $C_{20}H_{21}FN_2O_3S$ [M+H]$^+$ 389.46, observed 389.0.

To a solution of 1-(1-benzenesulfonyl-5-fluoro-1H-pyrrolo[2,3-b]pyridin-2-yl)-2-cyclopentyl-ethanol (2.1 g, 5.4 mmol) in dichloromethane (200 mL) was added Dess-Martin periodinane (5.7 g, 13.5 mmol) at 25° C. The reaction mixture was stirred at 25° C. for 1 h and then quenched with a saturated aqueous sodium bicarbonate solution (100 mL). The mixture was extracted with dichloromethane (50 mL), washed with a saturated aqueous sodium bicarbonate solution (3×100 mL), brine, dried over anhydrous sodium sulfate and then concentrated in vacuo. Purification by flash column chromatography (QingDao silica gel, 200-300 mesh, 30% ethyl acetate/hexanes) afforded 1-(1-benzenesulfonyl-5-fluoro-1H-pyrrolo[2,3-b]pyridin-2-yl)-2-cyclopentyl-ethanone (1.6 g, 76%) as a light yellow solid: LC/MS m/e calcd for $C_{20}H_{19}FN_2O_3S$ [M+H]$^+$ 387.45, observed 387.0.

To a solution of 1-(1-benzenesulfonyl-5-fluoro-1H-pyrrolo[2,3-b]pyridin-2-yl)-2-cyclopentyl-ethanone (1.6 g, 4.1 mmol) in dry tetrahydrofuran (100 mL) at −78° C. was added lithium bis(trimethylsilyl)amide (1.0 M in tetrahydrofuran, 6.2 mL, 6.2 mmol) dropwise. After stirring at −78° C. for 1 h, a solution of p-toluenesulfonic anhydride (2.0 g, 6.2 mmol) in tetrahydrofuran (10 mL) was added dropwise. The resulting solution was kept at −78° C. for an additional 1 h. The reaction was quenched with water, extracted with ethyl acetate (100 mL), washed with brine, dried over anhydrous sodium sulfate and then concentrated in vacuo. Purification by flash column chromatography (QingDao silica gel, 200-300 mesh, 25% dichloromethane/ethyl acetate) afforded toluene-4-sulfonic acid 1-(1-benzenesulfonyl-5-fluoro-1H-pyrrolo[2,3-b]pyridin-2-yl)-2-cyclopentyl-vinyl ester (1.9 g, 84%) as a white solid: LC/MS m/e calcd for $C_{27}H_{25}FN_2O_5S_2$ [M+H]$^+$ 541.64, observed 541.0.

To a mixture of toluene-4-sulfonic acid 1-(1-benzenesulfonyl-5-fluoro-1H-pyrrolo[2,3-b]pyridin-2-yl)-2-cyclopentyl-vinyl ester (600 mg, 1.1 mmol), 4-(2-methoxy-ethanesulfonyl)-phenylboronic acid (678 mg, 2.8 mmol) and dichlorobis(triphenylphosphine)palladium (II) (77 mg, 0.1 mmol) in dioxane (6 mL) was added an aqueous sodium carbonate solution (2 M, 1.4 mL). The resulting mixture was subjected to microwave irradiation for 2 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 1-benzenesulfonyl-2-{2-cyclopentyl-1-[4-(2-methoxy-ethanesulfonyl)-phenyl]-vinyl}-5-fluoro-1H-pyrrolo[2,3-b]pyridine (400 mg, 63%) as a white solid: LC/MS m/e calcd for $C_{29}H_{29}FN_2O_5S_2$ [M+H]$^+$ 569.69, observed 569.1.

A mixture of 1-benzenesulfonyl-2-{2-cyclopentyl-1-[4-(2-methoxy-ethanesulfonyl)-phenyl]-vinyl}-5-fluoro-1H-pyrrolo[2,3-b]pyridine (400 mg, 0.7 mmol) in ethanol (4 mL), tetrahydrofuran (8 mL) and an aqueous sodium hydroxide solution (10%, 2 mL) was heated at 50° C. for 5 h. The mixture was diluted with dichloromethane (50 mL), washed with water, dried over anhydrous sodium sulfate and then concentrated in vacuo to afford 2-{2-cyclopentyl-1-[4-(2-ethoxy-ethanesulfonyl)-phenyl]-vinyl}-5-fluoro-1H-pyrrolo[2,3-b]pyridine (300 mg, 96%) which was used in the next step without further purification: LC/MS m/e calcd for $C_{24}H_{27}FN_2O_3S$ [M+H]$^+$ 443.56, observed 443.3.

A mixture of 2-{2-cyclopentyl-1-[4-(2-ethoxy-ethanesulfonyl)-phenyl]-vinyl}-5-fluoro-1H-pyrrolo[2,3-b]pyridine (300 mg, 0.68 mmol) and 10% palladium on activated carbon (90 mg) in methanol (250 mL) was heated at 50° C. under hydrogen (50 psi) for 5 h. The mixture was cooled to 25° C., the solids filtered off, washed with ethyl acetate and concentrated in vacuo. Purification by flash silica gel chromatography (silica gel from QingDao, 200-300 mesh, glass column from Shanghai SD company, 50% dichloromethane/ ethyl acetate) afforded 2-{2-cyclopentyl-1-[4-(2-ethoxy-ethanesulfonyl)-phenyl]-ethyl}-5-fluoro-1H-pyrrolo[2,3-b]pyridine (280 mg, 93%): LC/MS m/e calcd for $C_{24}H_{29}FN_2O_3S$ [M+H]$^+$ 445.57, observed 445.1.

To a solution of 2-{2-cyclopentyl-1-[4-(2-ethoxy-ethanesulfonyl)-phenyl]-ethyl}-5-fluoro-1H-pyrrolo[2,3-b]pyridine (210 mg, 0.47 mmol) in dichloromethane (10 mL) at 0° C. was added a solution of boron tribromide (0.22 ml, 2.36 mmol) in dichloromethane (10 ml). The mixture was stirred at 0° C. for 1 h. The reaction was quenched with a saturated aqueous sodium bicarbonate solution (20 mL). The mixture was extracted with dichloromethane (2×50 mL), washed with a saturated aqueous sodium bicarbonate solution (3×20 mL) and brine (3×20 mL), dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded (2-{4-[2-cyclopentyl-1-(5-fluoro-1H-pyrrolo[2,3-b]pyridin-2-yl)-ethyl]-benzenesulfonyl}-ethanol (40 mg, 20%) as a white solid: LC/MS m/e calcd for $C_{22}H_{25}FN_2O_3S$ [M+H]$^+$ 417.52, observed 417.0; $^1$H NMR (400 MHz, CD$_3$OD) δ ppm 7.98 (t, J=2.3 Hz, 1H), 7.83-7.88 (m, J=8.3 Hz, 2H), 7.56-7.65 (m, 3H), 6.38 (s, 1H), 4.89-4.99 (m, 1H), 4.68-4.84 (m, 1H), 4.59 (br. s., 1H), 4.29 (t, J=8.0 Hz, 1H), 3.82 (t, J=6.2 Hz, 2H), 3.37 (t, J=6.2 Hz, 2H), 2.22-2.30 (m, 1H), 2.05-2.13 (m, 1H), 1.58-1.85 (m, 4H), 1.42-1.54 (m, 2H), 1.13-1.34 (m, 3H).

Example 89

(2-{4-[1-(5-Fluoro-1H-pyrrolo[2,3-b]pyridin-2-yl)-2-(tetrahydro-pyran-4-yl)-ethyl]-benzenesulfonyl}-ethanol

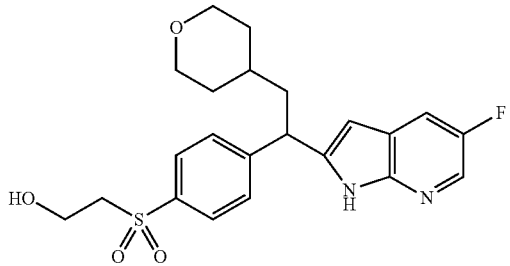

To a mixture of toluene-4-sulfonic acid 1-(1-benzenesulfonyl-5-fluoro-1H-pyrrolo[2,3-b]pyridin-2-yl)-2-(tetrahydro-pyran-4-yl)-vinyl ester (prepared as in Example 122, 550 mg, 0.99 mmol), 4-(2-methoxy-ethanesulfonyl)-phenylboronic acid (603 mg, 2.47 mmol) and dichlorobis(triphenylphosphine)palladium (II) (70 mg, 0.01 mmol) in dioxane (6 mL) was added an aqueous sodium carbonate solution (2 M, 1.24 mL). The resulting mixture was subjected to microwave irradiation for 2 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-5-fluoro-2-[1-[4-(2-methoxy-ethanesulfonyl)-phenyl]-2-(tetrahydro-pyran-4-yl)-vinyl]-1H-pyrrolo[2,3-b]pyridine (320 mg, 55%) as a white solid: LC/MS m/e calcd for $C_{29}H_{29}FN_2O_6S_2$ [M+H]$^+$ 585.69, observed 585.1.

A mixture of 1-benzenesulfonyl-5-fluoro-2-[1-[4-(2-methoxy-ethanesulfonyl)-phenyl]-2-(tetrahydro-pyran-4-yl)-vinyl]-1H-pyrrolo[2,3-b]pyridine (320 mg, 0.55 mmol) in ethanol (4 mL), tetrahydrofuran (8 mL) and an aqueous sodium hydroxide solution (10%, 2 mL) was heated at 50° C. for 5 h. The mixture diluted with dichloromethane (50 mL), washed with water, dried over anhydrous sodium sulfate and then concentrated in vacuo to afford 2-[1-[4-(2-ethoxy-ethanesulfonyl)-phenyl]-2-(tetrahydro-pyran-4-yl)-vinyl]-5-fluoro-1H-pyrrolo[2,3-b]pyridine (250 mg, 99%) which was used in the next step without further purification: LC/MS m/e calcd for $C_{24}H_{27}FN_2O_4S$ [M+H]$^+$ 459.56, observed 459.3.

A mixture of 2-[1-[4-(2-ethoxy-ethanesulfonyl)-phenyl]-2-(tetrahydro-pyran-4-yl)-vinyl]-5-fluoro-1H-pyrrolo[2,3-b]pyridine (250 mg, 0.54 mmol) and 10% palladium on activated carbon (74 mg) in methanol (250 mL) was heated at 50° C. under hydrogen (50 psi) for 5 h. The mixture was cooled to 25° C., the solids filtered off, washed with ethyl acetate and concentrated in vacuo. Purification by flash silica gel chromatography (silica gel from QingDao, 200-300 mesh, glass column from Shanghai SD company, 50% dichloromethane/ethyl acetate) afforded 2-[1-[4-(2-ethoxy-ethanesulfonyl)-phenyl]-2-(tetrahydro-pyran-4-yl)-ethyl]-5-fluoro-1H-pyrrolo[2,3-b]pyridine (145 mg, 57%): LC/MS m/e calcd for $C_{24}H_{29}FN_2O_4S$ [M+H]$^+$ 461.57, observed 461.1.

To a solution of 2-[1-[4-(2-ethoxy-ethanesulfonyl)-phenyl]-2-(tetrahydro-pyran-4-yl)-ethyl]-5-fluoro-1H-pyrrolo[2,3-b]pyridine (95 mg, 0.2 mmol) in dichloromethane (10 mL) at 0° C. was added a solution of boron tribromide (0.1 ml, 1 mmol) in dichloromethane (10 ml). The mixture was stirred at 0° C. for 1 h. The reaction was quenched with a saturated aqueous sodium bicarbonate solution (20 mL). The mixture was extracted with dichloromethane (2×50 mL), washed with a saturated aqueous sodium bicarbonate solution (3×20 mL) and brine (3×20 mL), dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded (2-{4-[1-(5-fluoro-1H-pyrrolo[2,3-b]pyridin-2-yl)-2-(tetrahydro-pyran-4-yl)-ethyl]-benzenesulfonyl}-ethanol (27 mg, 30%) as a white solid: LC/MS m/e calcd for $C_{22}H_{25}FN_2O_4S$ [M+H]$^+$ 433.52, observed 433.0; $^1$H NMR (400 MHz, CD$_3$OD) δ ppm 8.00 (t, J=2.1 Hz, 1H), 7.88 (d, J=8.3 Hz, 2H), 7.58-7.66 (m, 3H), 6.41 (s, 1H), 4.43 (t, J=8.0 Hz, 1H), 3.81-3.91 (m, 4H), 3.38 (t, J=6.2 Hz, 2H), 3.24-3.29 (m, 2H), 2.18-2.26 (m, 1H), 2.01 (dt, J=14.0, 7.1 Hz, 1H), 1.70 (t, J=14.1 Hz, 2H), 1.28-1.51 (m, 3H).

Example 90

2-{2-Cyclopentyl-1-[4-(2-ethoxy-ethanesulfonyl)-phenyl]-ethyl}-1H-pyrrolo[2,3-b]pyridine

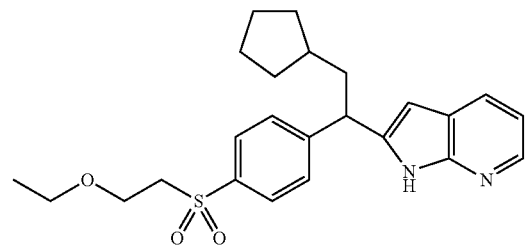

To a mixture of toluene-4-sulfonic acid 1-(1-benzenesulfonyl-1H-pyrrolo[2,3-b]pyridin-2-yl)-2-cyclopentyl-vinyl ester (prepared as in Example 43, 2.14 g, 4 mmol), 4-(2-methoxy-ethanesulfonyl)-phenylboronic acid (prepared as in Example 88, 2.5 g, 10 mmol) and dichlorobis(triphenylphosphine)palladium (II) (280 mg, 0.4 mmol) in dioxane (20 mL) was added an aqueous sodium carbonate solution (2 M, 10 mL). The resulting mixture was subjected to microwave irradiation for 2 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 1-benzenesulfonyl-2-{2-cyclopentyl-1-[4-(2-methoxy-ethanesulfonyl)-phenyl]-vinyl}-1H-pyrrolo[2,3-b]pyridine (1.3 g, 57%) as a white solid: LC/MS m/e calcd for $C_{29}H_{30}N_2O_5S_2$ [M+H]$^+$ 551.70, observed 551.4.

A mixture of 1-benzenesulfonyl-2-{2-cyclopentyl-1-[4-(2-methoxy-ethanesulfonyl)-phenyl]-vinyl}-1H-pyrrolo[2,3-b]pyridine (1.3 g, 2.36 mmol) in ethanol (10 mL), tetrahydrofuran (20 mL) and an aqueous sodium hydroxide solution (10%, 6 mL) was heated at 50° C. for 5 h. The mixture was diluted with dichloromethane (150 mL), washed with water, dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-cyclopentyl-1-[4-(2-ethoxy-ethanesulfonyl)-phenyl]-vinyl}-1H-pyrrolo[2,3-b]pyridine (900 mg, 90%): LC/MS m/e calcd for $C_{24}H_{28}N_2O_3S$ [M+H]$^+$ 425.57, observed 425.4.

A mixture of 2-{2-cyclopentyl-1-[4-(2-ethoxy-ethanesulfonyl)-phenyl]-vinyl}-1H-pyrrolo[2,3-b]pyridine (900 mg, 2.12 mmol) and 10% palladium on activated carbon (270 mg) in methanol (300 mL) was heated at 50° C. under hydrogen (50 psi) for 16 h. The mixture was cooled to 25° C., the solids filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-cyclopentyl-1-[4-(2-ethoxy-ethanesulfonyl)-phenyl]-ethyl}-1H-pyrrolo[2,3-b]pyridine (680 mg, 75%): LC/MS m/e calcd for $C_{24}H_{30}N_2O_3S$ [M+H]$^+$ 427.58, observed 427.4; $^1$H NMR (400 MHz, CD$_3$OD) δ ppm 8.08-8.15 (m, 1H), 7.86-7.94 (m, 3H), 7.62 (d, J=8.3 Hz, 2H), 7.07 (dd, J=7.7, 4.9 Hz, 1H), 6.41 (s, 1H), 4.34 (t, J=7.8 Hz, 1H), 3.75 (t, J=5.8 Hz, 2H), 3.48 (t, J=5.7 Hz, 2H), 3.28 (q, J=7.0 Hz, 2H), 2.26-2.35 (m, 1H), 2.07-2.20 (m, 1H), 1.62-1.89 (m, 5H), 1.46-1.57 (m, 2H), 1.19-1.33 (m, 2H), 0.86 (t, J=6.9 Hz, 3H).

Example 91

(2-{4-[2-Cyclopentyl-1-(1H-pyrrolo[2,3-b]pyridin-2-yl)-ethyl]-benzenesulfonyl}-ethanol

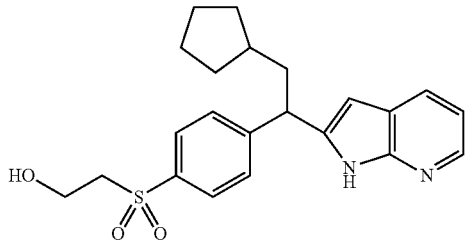

To a solution of 2-{2-cyclopentyl-1-[4-(2-ethoxy-ethanesulfonyl)-phenyl]-ethyl}-1H-pyrrolo[2,3-b]pyridine (prepared as in Example 90, 680 mg, 1.6 mmol) in dichloromethane (20 mL) at 0° C. was added a solution of boron tribromide (0.76 ml, 8.0 mmol) in dichloromethane (10 ml). The mixture was stirred at 0° C. for 1 h. The reaction was quenched with a saturated aqueous sodium bicarbonate solution (20 mL). The mixture was extracted with dichloromethane (2×50 mL), washed with a saturated aqueous sodium bicarbonate solution (3×20 mL) and brine (3×20 mL), dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded (2-{4-[2-cyclopentyl-1-(1H-pyrrolo[2,3-b]pyridin-2-yl)-ethyl]-benzenesulfonyl}-ethanol (600 mg, 94%): LC/MS m/e calcd for $C_{22}H_{26}N_2O_3S$ [M+H]$^+$ 399.53, observed 399.1; $^1$H NMR (400 MHz, CD$_3$OD) δ ppm 8.09 (d, J=4.0 Hz, 1H), 7.85-7.93 (m, 2H), 7.61 (d, J=8.1 Hz, 2H), 7.06 (dd, J=7.7, 4.9 Hz, 1H), 6.41 (s, 1H), 4.33 (t, J=7.8 Hz, 1H), 3.85 (t, J=6.2 Hz, 2H), 3.35-3.46 (m, 2H), 2.26-2.34 (m, 1H), 2.04-2.21 (m, 1H), 1.60-1.88 (m, 4H), 1.44-1.57 (m, 2H), 1.18-1.35 (m, 3H).

Example 92

(2-{4-[2-Cyclopentyl-1-(1H-pyrrolo[2,3-b]pyridin-2-yl)-ethyl]-benzenesulfonyl}-ethyl)-dimethyl-amine

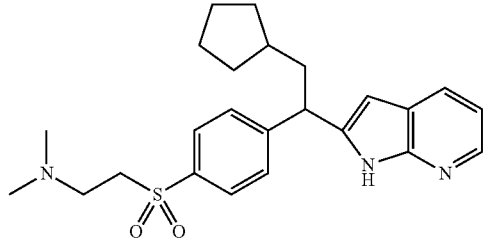

To a solution of (2-{4-[2-cyclopentyl-1-(1H-pyrrolo[2,3-b]pyridin-2-yl)-ethyl]-benzenesulfonyl}-ethanol (prepared as in Example 91, 600 mg, 1.5 mmol) and triethylamine (0.42 ml, 3.0 mmol) in dichloromethane (15 mL) at 0° C. was added a solution of methanesulfonyl chloride (0.18 ml, 2.2 mmol) in dichloromethane. The mixture was stirred at 0° C. for 30 min. The reaction was quenched with a water (20 mL). The mixture was extracted with dichloromethane (2×50 mL), washed with brine (3×20 mL), dried over anhydrous sodium sulfate and concentrated in vacuo. Purification by flash silica gel chromatography (silica gel from QingDao, 200-300 mesh, glass column from Shanghai SD company, 50% ethyl acetate/dichloromethane) afforded 2-[2-cyclopentyl-1-(4-ethenesulfonyl-phenyl)-ethyl]-1H-pyrrolo[2,3-b]pyridine (380 mg, 66%) as a solid: LC/MS m/e calcd for $C_{22}H_{24}N_2O_2S$ [M+H]$^+$ 381.51, observed 381.0.

A mixture of 2-[2-cyclopentyl-1-(4-ethenesulfonyl-phenyl)-ethyl]-1H-pyrrolo[2,3-b]pyridine (150 mg, 0.39 mmol) and dimethylamine solution in methanol (2 M, 3 ml, 6 mmol) was stirred at 25° C. for 20 min. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded (2-{4-[2-cyclopentyl-1-(1H-pyrrolo[2,3-b]pyridin-2-yl)-ethyl]-benzenesulfonyl}-ethyl)-dimethyl-amine (20 mg, 12%) as a white solid: LC/MS m/e calcd for $C_{24}H_{31}N_3O_2S$ [M+H]$^+$ 426.60, observed 426.1; $^1$H NMR (400 MHz, CD$_3$OD) δ ppm 8.08 (d, J=4.5 Hz, 1H), 7.83-7.91 (m, 2H), 7.61 (d, J=8.1 Hz, 1H), 7.04 (dd, J=7.6, 5.1

Hz, 1H), 6.39 (s, 1H), 5.49 (s, 7H), 4.32 (t, J=7.8 Hz, 1H), 3.33-3.39 (m, 2H), 2.64-2.71 (m, 1H), 2.21-2.33 (m, 1H), 2.07-2.19 (m, 5H), 1.59-1.86 (m, 4H), 1.43-1.59 (m, 2H), 1.15-1.34 (m, 2H).

Example 93

2-{2-Cyclopentyl-1-[4-(2-morpholin-4-yl-ethane-sulfonyl)-phenyl]-ethyl}-1H-pyrrolo[2,3-b]pyridine

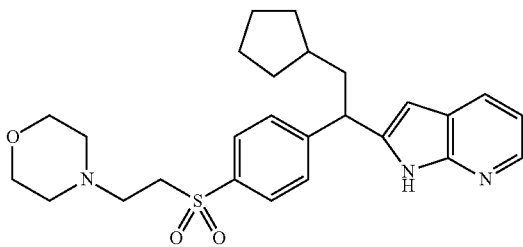

A mixture of 2-[2-cyclopentyl-1-(4-ethenesulfonyl-phenyl)-ethyl]-1H-pyrrolo[2,3-b]pyridine (prepared as in Example 92, 50 mg, 0.13 mmol) and morpholine (1.5 ml) was stirred at 25° C. for 20 min. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-cyclopentyl-1-[4-(2-morpholin-4-yl-ethanesulfonyl)-phenyl]-ethyl}-1H-pyrrolo[2,3-b]pyridine (4 mg, 6%) as a white solid: LC/MS m/e calcd for $C_{26}H_{33}N_3O_3S$ [M+H]$^+$ 468.64, observed 468.1; $^1$H NMR (400 MHz, CD$_3$OD) δ ppm 8.09 (d, J=4.3 Hz, 1H), 7.87-7.93 (m, 3H), 7.63 (d, J=8.3 Hz, 2H), 7.06 (dd, J=7.8, 5.1 Hz, 1H), 6.42 (s, 1H), 4.34 (t, J=8.0 Hz, 1H), 3.40-3.50 (m, 6H), 3.27-3.30 (m, 1H), 2.81 (t, J=6.4 Hz, 2H), 2.42 (br. s., 4H), 2.30 (dt, J=13.9, 7.2 Hz, 1H), 2.11-2.19 (m, 1H), 1.62-1.89 (m, 5H), 1.46-1.57 (m, 2H), 1.19-1.31 (m, 2H).

Example 94

2-{4-[2-Cyclopentyl-1-(1H-pyrrolo[2,3-b]pyridin-2-yl)-ethyl]-3-fluoro-phenyl}-propan-2-ol

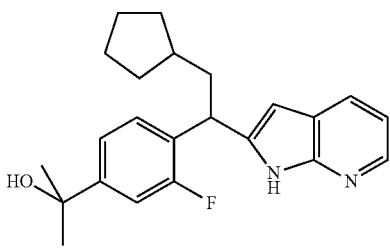

A mixture of 4-bromo-3-fluoro-benzoic acid methyl ester (10 g, 43 mmol), bis(pinacolato)diboron (13.7 g, 54 mmol) and potassium acetate (12.7 g, 129 mmol) in dimethylsulfoxide (100 ml) was purged with argon, followed by addition of [1,1'-bis(diphenylphosphino)ferrocene]dichloropalladium (II) (3.5 g, 4.3 mmol). The mixture was heated at 80° C. for 3 h. After this time the mixture was cooled to 25° C., washed with water, extracted with ethyl acetate and concentrated. The resulting black oil was redissolved in ethyl acetate:hexanes 1:2 and filtered through a short pad of silica gel (silica gel from QingDao, 200-300 mesh, glass column from Shanghai SD company). The filterate was concentrated in vacuo to afford 3-fluoro-4-(4,4,5,5-tetramethyl-[1,3,2]dioxaborolan-2-yl)-benzoic acid methyl ester (12 g, 99%) as a solid which was used in the next step without further purification.

To a mixture of toluene-4-sulfonic acid 1-(1-benzenesulfonyl-1H-pyrrolo[2,3-b]pyridin-2-yl)-2-cyclopentyl-vinyl ester (prepared as in Example 43, 0.55 g, 1 mmol), 3-fluoro-4-(4,4,5,5-tetramethyl-[1,3,2]dioxaborolan-2-yl)-benzoic acid methyl ester (1.0 g, 3 mmol) and dichlorobis(triphenylphosphine)palladium (II) (70 mg, 0.1 mmol) in dioxane (6 mL) was added an aqueous sodium carbonate solution (2 M, 1.5 mL). The mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 4-[1-(1-benzenesulfonyl-1H-pyrrolo[2,3-b]pyridin-2-yl)-2-cyclopentyl-vinyl]-3-fluoro-benzoic acid methyl ester (260 mg, 49%) as a white solid: LC/MS m/e calcd for $C_{28}H_{25}FN_2O_4S$ [M+H]$^+$ 505.58, observed 505.0.

A mixture of 4-[1-(1-benzenesulfonyl-1H-pyrrolo[2,3-b]pyridin-2-yl)-2-cyclopentyl-vinyl]-3-fluoro-benzoic acid methyl ester (260 mg, 0.51 mmol) and tetrabutylammonium fluoride solution in tetrahydrofuran (1 M, 3 ml) was stirred at 25° C. for 16 h. The reaction was quenched with a saturated aqueous ammonium chloride solution (20 mL). The mixture was extracted with ethyl acetate (2×100 mL), washed with a saturated aqueous ammonium chloride solution (3×50 mL), brine, dried over anhydrous sodium sulfate and concentrated in vacuo to afford 4-[2-cyclopentyl-1-(1H-pyrrolo[2,3-b]pyridin-2-yl)-vinyl]-3-fluoro-benzoic acid methyl ester (160 mg, 85%) as a solid which was used in the next step without further purification; LC/MS m/e calcd for $C_{22}H_{21}FN_2O_2$ [M+H]$^+$ 365.42, observed 365.1.

A mixture of 4-[2-cyclopentyl-1-(1H-pyrrolo[2,3-b]pyridin-2-yl)-vinyl]-3-fluoro-benzoic acid methyl ester (160 mg, 0.44 mmol) and 10% palladium on activated carbon (75 mg) in methanol (250 mL) was heated at 50° C. under hydrogen (50 psi) for 16 h. The mixture was cooled to 25° C., the solids filtered off, washed with ethyl acetate and concentrated in vacuo to afford 4-[2-cyclopentyl-1-(1H-pyrrolo[2,3-b]pyridin-2-yl)-ethyl]-3-fluoro-benzoic acid methyl ester (140 mg, 87%) as a solid which was used in the next step without further purification: LC/MS m/e calcd for $C_{22}H_{23}FN_2O_2$ [M+H]$^+$ 367.4, observed 367.1.

To a solution of 4-[2-cyclopentyl-1-(1H-pyrrolo[2,3-b]pyridin-2-yl)-ethyl]-3-fluoro-benzoic acid methyl ester (140 mg, 0.38 mmol) in dry tetrahydrofuran (5 mL) at 0° C. was added methylmagnesium chloride solution in tetrahydrofuran (3 M, 0.64 mL, 1.91 mmol) dropwise. After stirring at 0° C. for 3 h, the reaction was quenched with a saturated aqueous ammonium chloride solution (20 mL), extracted with ethyl acetate (2×50 mL), washed with brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{4-[2-cyclopentyl-1-(1H-pyrrolo[2,3-b]pyridin-2-yl)-ethyl]-3-fluoro-phenyl}-propan-2-ol (49 mg, 35%) as a white solid: LC/MS m/e calcd for $C_{23}H_{27}FN_2O_2$ [M+H]$^+$ 367.48, observed 366.9; $^1$H NMR (400 MHz, CD$_3$OD) δ ppm 7.89-8.08 (m, 1H), 7.79 (d, J=7.8

Hz, 1H), 7.63 (br. s., 1H), 7.11-7.26 (m, 2H), 6.94 (dd, J=7.6, 4.8 Hz, 1H), 4.04 (q, J=7.2 Hz, 1H), 2.08-2.22 (m, 1H), 1.88-2.05 (m, 1H), 1.64-1.86 (m, 3H), 1.33-1.60 (m, 7H), 1.00-1.25 (m, 5H), 0.75-0.96 (m, 1H).

Example 95

2-{4-[2-Cyclopentyl-1-(1H-pyrrolo[2,3-b]pyridin-2-yl)-ethyl]-2-fluoro-phenyl}-propan-2-ol

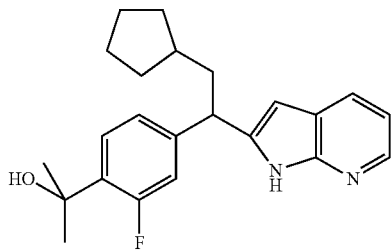

A mixture of 4-bromo-2-fluoro-benzoic acid methyl ester (10 g, 43 mmol), bis(pinacolato)diboron (13.7 g, 54 mmol) and potassium acetate (12.7 g, 129 mmol) in dimethylsulfoxide (100 ml) was purged with argon, followed by addition of [1,1'-bis(diphenylphosphino)ferrocene]dichloropalladium (II) (3.5 g, 4.3 mmol) and the solution was purged again with argon. The mixture was heated at 80° C. for 3 h. After this time the mixture was cooled to 25° C., diluted with water, extracted with ethyl acetate and concentrated. The resulting black oil was dissolved in ethyl acetate:hexane 1:2 and filtered through a short pad of silica gel (silica gel from QingDao, 200-300 mesh, glass column from Shanghai SD company). The filterate was concentrated in vacuo to afford 2-fluoro-4-(4,4,5,5-tetramethyl-[1,3,2]dioxaborolan-2-yl)-benzoic acid methyl ester (11.5 g, 95%) as a white solid which was used in the next step without further purification.

To a mixture of toluene-4-sulfonic acid 1-(1-benzenesulfonyl-1H-pyrrolo[2,3-b]pyridin-2-yl)-2-cyclopentyl-vinyl ester (prepared as in Example 43, 0.55 g, 1 mmol), 2-fluoro-4-(4,4,5,5-tetramethyl-[1,3,2]dioxaborolan-2-yl)-benzoic acid methyl ester (1.0 g, 3 mmol) and dichlorobis(triphenylphosphine)palladium (II) (70 mg, 0.1 mmol) in dioxane (6 mL) was added an aqueous sodium carbonate solution (2 M, 1.5 mL). The mixture was subjected to microwave irradiation for 2 h at 100° C. The resulting mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 4-[1-(1-benzenesulfonyl-1H-pyrrolo[2,3-b]pyridin-2-yl)-2-cyclopentyl-vinyl]-2-fluoro-benzoic acid methyl ester (360 mg, 68%) as a white solid: LC/MS m/e calcd for $C_{28}H_{25}FN_2O_4S$ [M+H]$^+$ 505.58, observed 505.0.

A mixture of 4-[1-(1-benzenesulfonyl-1H-pyrrolo[2,3-b]pyridin-2-yl)-2-cyclopentyl-vinyl]-2-fluoro-benzoic acid methyl ester (360 mg, 0.71 mmol) and tetrabutylammonium fluoride solution in tetrahydrofuran (1 M, 3 ml) was stirred at 25° C. for 16 h. The reaction was quenched with a saturated aqueous ammonium chloride solution (20 mL). The mixture was extracted with ethyl acetate (2×100 mL), washed with a saturated aqueous ammonium chloride solution (3×50 mL), brine, dried over anhydrous sodium sulfate and concentrated in vacuo to afford 4-[2-cyclopentyl-1-(1H-pyrrolo[2,3-b]pyridin-2-yl)-vinyl]-2-fluoro-benzoic acid methyl ester (250 mg, 96%) as a white solid which was used in the next step without further purification.

A mixture of 4-[2-cyclopentyl-1-(1H-pyrrolo[2,3-b]pyridin-2-yl)-vinyl]-2-fluoro-benzoic acid methyl ester (250 mg, 0.69 mmol) and 10% palladium on activated carbon (75 mg) in methanol (250 mL) was heated at 50° C. under hydrogen (50 psi) for 16 h. The mixture was cooled to 25° C., the solids filtered off, washed with ethyl acetate and concentrated in vacuo to afford 4-[2-cyclopentyl-1-(1H-pyrrolo[2,3-b]pyridin-2-yl)-ethyl]-2-fluoro-benzoic acid methyl ester (240 mg, 95%) as a white solid which was used in the next step without further purification: LC/MS m/e calcd for $C_{22}H_{23}FN_2O_2$ [M+H]$^+$ 367.4, observed 367.0.

To a solution of 4-[2-cyclopentyl-1-(1H-pyrrolo[2,3-b]pyridin-2-yl)-ethyl]-2-fluoro-benzoic acid methyl ester (240 mg, 0.66 mmol) in dry tetrahydrofuran (5 mL) at 0° C. was added methylmagnesium chloride solution (3 M in tetrahydrofuran, 2.2 mL, 6.6 mmol) dropwise. After stirring at 0° C. for 3 h, the reaction was quenched with a saturated aqueous ammonium chloride solution (20 mL). The mixture was extracted with ethyl acetate (2×50 mL), washed with brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{4-[2-cyclopentyl-1-(1H-pyrrolo[2,3-b]pyridin-2-yl)-ethyl]-2-fluoro-phenyl}-propan-2-ol (65 mg, 27%) as a white solid: LC/MS m/e calcd for $C_{23}H_{27}FN_2O_2$ [M+H]$^+$ 367.48, observed 367.0; $^1$H NMR (400 MHz, CD$_3$OD) δ ppm 8.08 (d, J=4.5 Hz, 1H), 7.89 (d, J=7.8 Hz, 1H), 7.55 (t, J=8.3 Hz, 1H), 7.12 (d, J=8.1 Hz, 1H), 6.98-7.06 (m, 2H), 6.34 (s, 1H), 4.17 (t, J=7.8 Hz, 1H), 2.21 (dt, J=13.7, 7.2 Hz, 1H), 2.03-2.12 (m, 1H), 1.55-1.84 (m, 11H), 1.47-1.53 (m, 2H), 1.16-1.31 (m, 2H).

Example 96

2-{4-[2-Cyclopentyl-1(R)-(1H-pyrrolo[2,3-b]pyridin-2-yl)-ethyl]-2-fluoro-phenyl}-propan-2-ol

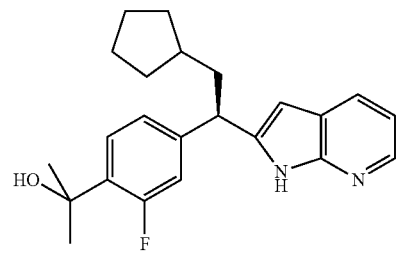

The 1:1 mixture of enantiomers of 2-{4-[2-cyclopentyl-1-(1H-pyrrolo[2,3-b]pyridin-2-yl)-ethyl]-2-fluoro-phenyl}-propan-2-ol (prepared as in Example 95, 700 mg) was separated by Agilent high performance liquid chromatography (chiral column: Daicel IA-H, 250 mm×20 mm i. d., 5 μm-particle size, temperature: 25° C., flow rate of 15 mL/min, 30% ethanol/hexanes as mobile phase and UV detection: 214 and 254 nm) to afford two pure enantiomers. The second peak, 2-{4-[2-cyclopentyl-1(R)-(1H-pyrrolo[2,3-b]pyridin-2-yl)-ethyl]-2-fluoro-phenyl}-propan-2-ol (160 mg) was isolated as a white solid: $^1$H NMR (400 MHz, CD$_3$OD) δ ppm 8.02-8.05 (m, 1H), 7.86 (dd, J=7.8, 1.3 Hz, 1H), 7.50 (t, J=8.5 Hz, 1H), 7.08 (dd, J=8.1, 1.5 Hz, 1H), 6.95-7.03 (m, 2H), 6.31 (s, 1H), 4.14 (t, J=8.0 Hz, 1H), 2.14-2.22 (m, 1H), 2.01-2.08 (m, 1H), 1.57-1.84 (m, 5H), 1.44-1.54 (m, 8H), 1.12-1.27 (m, 2H).

Example 97

2-{2-Fluoro-4-[1-(5-fluoro-1H-pyrrolo[2,3-b]pyridin-2-yl)-2-(tetrahydro-pyran-4-yl)-ethyl]-phenyl}-propan-2-ol

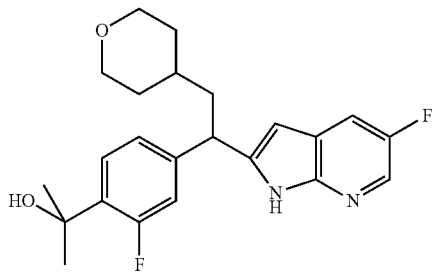

To a mixture of toluene-4-sulfonic acid 1-(1-benzenesulfonyl-5-fluoro-1H-pyrrolo[2,3-b]pyridin-2-yl)-2-(tetrahydro-pyran-4-yl)-vinyl ester (prepared as in Example 122, 0.57 g, 1 mmol), 2-fluoro-4-(4,4,5,5-tetramethyl-[1,3,2]dioxaborolan-2-yl)-benzoic acid methyl ester (prepared as in Example 95, 1.2 g, 4.2 mmol) and dichlorobis(triphenylphosphine)palladium (II) (70 mg, 0.1 mmol) in dioxane (8 mL) was added an aqueous sodium carbonate solution (2 M, 1.25 mL). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 4[1-(1-benzenesulfonyl-5-fluoro-1H-pyrrolo[2,3-b]pyridin-2-yl)-2-(tetrahydro-pyran-4-yl)-vinyl]-2-fluoro-benzoic acid methyl ester (400 mg, 72%) as a white solid: LC/MS m/e calcd for $C_{28}H_{24}F_2N_2O_5S$ [M+H]$^+$ 539.57, observed 539.0.

A mixture of 4[1-(1-benzenesulfonyl-5-fluoro-1H-pyrrolo[2,3-b]pyridin-2-yl)-2-(tetrahydro-pyran-4-yl)-vinyl]-2-fluoro-benzoic acid methyl ester (400 mg, 0.74 mmol) and tetrabutylammonium fluoride solution in tetrahydrofuran (1 M, 4 ml) was stirred at 25° C. for 16 h. The reaction was quenched with a saturated aqueous ammonium chloride solution (20 mL). The mixture was extracted with ethyl acetate (2×100 mL), washed with a saturated aqueous ammonium chloride solution (3×50 mL), brine, dried over anhydrous sodium sulfate and concentrated in vacuo to afford 2-fluoro-4-[1-(5-fluoro-1H-pyrrolo[2,3-b]pyridin-2-yl)-2-(tetrahydro-pyran-4-yl)-vinyl]-benzoic acid methyl ester (250 mg, 84%) as a solid which was used in the next step without further purification: LC/MS m/e calcd for $C_{22}H_{20}F_2N_2O_3$ [M+H] 399.41, observed 399.0.

A mixture of 2-fluoro-4-[1-(5-fluoro-1H-pyrrolo[2,3-b]pyridin-2-yl)-2-(tetrahydro-pyran-4-yl)-vinyl]-benzoic acid methyl ester (250 mg, 0.63 mmol) and 10% palladium on activated carbon (75 mg) in methanol (250 mL) was heated at 50° C. under hydrogen (50 psi) for 16 h. The mixture was cooled to 25° C., the solids filtered off, washed with ethyl acetate and concentrated in vacuo to afford 2-fluoro-4-[1-(5-fluoro-1H-pyrrolo[2,3-b]pyridin-2-yl)-2-(tetrahydro-pyran-4-yl)-ethyl]-benzoic acid methyl ester (230 mg, 91%) which was used in the next step without further purification: LC/MS m/e calcd for $C_{22}H_{22}F_2N_2O_3$ [M+H]$^+$ 401.43, observed 400.9.

To a solution of 2-fluoro-4-[1-(5-fluoro-1H-pyrrolo[2,3-b]pyridin-2-yl)-2-(tetrahydro-pyran-4-yl)-ethyl]-benzoic acid methyl ester (230 mg, 0.57 mmol) in dry tetrahydrofuran (5 mL) at 0° C. was added a methylmagnesium chloride solution in tetrahydrofuran (3 M, 2.0 mL, 5.7 mmol) dropwise. After stirring at 0° C. for 3 h, the reaction was quenched with a saturated aqueous ammonium chloride solution (20 mL). The mixture was extracted with ethyl acetate (2×50 mL), washed with brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-fluoro-4-[1-(5-fluoro-1H-pyrrolo[2,3-b]pyridin-2-yl)-2-(tetrahydro-pyran-4-yl)-ethyl]-phenyl}-propan-2-ol (55 mg, 24%) as a white solid: LC/MS m/e calcd for $C_{23}H_{26}F_2N_2O_2$ [M+H]$^+$ 401.47, observed 401.0; $^1$H NMR (400 MHz, CD$_3$OD) δ ppm 8.01 (t, J=2.1 Hz, 1H), 7.65 (dd, J=9.1, 2.5 Hz, 1H), 7.44-7.59 (m, 1H), 7.12-7.16 (m, 1H), 7.01-7.07 (m, 1H), 6.36 (s, 1H), 4.30 (t, J=8.0 Hz, 1H), 3.87-3.97 (m, 2H), 3.27-3.32 (m, 2H), 2.13-2.21 (m, 1H), 1.93-2.07 (m, 2H), 1.72 (t, J=16.3 Hz, 2H), 1.46-1.59 (m, 7H), 1.31-1.42 (m, 2H).

Example 98

2-{2-Fluoro-4-[1(R)-(5-fluoro-1H-pyrrolo[2,3-b]pyridin-2-yl)-2-(tetrahydro-pyran-4-yl)-ethyl]phenyl}-propan-2-ol

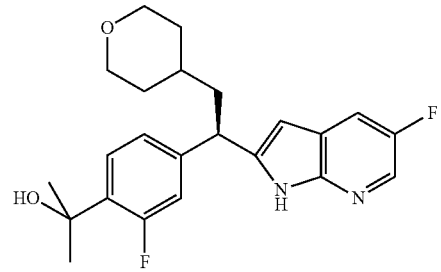

The 1:1 mixture of enantiomers of 2-{2-fluoro-4-[1-(5-fluoro-1H-pyrrolo[2,3-b]pyridin-2-yl)-2-(tetrahydro-pyran-4-yl)-ethyl]-phenyl}-propan-2-ol (prepared as in Example 97, 46 mg) was separated by Agilent high performance liquid chromatography (chiral column: Daicel IA-H, 250 mm×20 mm i. d., 5 μm-particle size, temperature: 25° C., flow rate of 15 mL/min, 50% isopropyl alcohol/hexanes as mobile phase and UV detection: 214 and 254 nm) to afford two pure enantiomers. The second peak, 2-{2-fluoro-4-[1(R)-(5-fluoro-1H-pyrrolo[2,3-b]pyridin-2-yl)-2-(tetrahydro-pyran-4-yl)-ethyl]-phenyl}-propan-2-ol (19 mg) was isolated as a white solid: $^1$H NMR (400 MHz, CD$_3$OD) δ ppm 7.97-8.02 (m, 1H), 7.53-7.65 (m, 2H), 7.13 (d, J=8.1 Hz, 1H), 7.03 (d, J=13.1 Hz, 1H), 6.34 (s, 1H), 4.28 (t, J=8.0 Hz, 1H), 3.85-3.97 (m, 2H), 3.30-3.34 (m, 2H), 2.15 (dt, J=14.0, 7.3 Hz, 1H), 1.90-2.04 (m, 1H), 1.61-1.76 (m, 2H), 1.44-1.60 (m, 7H), 1.34 (qd, J=12.0, 4.5 Hz, 2H).

Example 99

5-Fluoro-2-[1-(4-methanesulfonyl-phenyl)-3-methyl-butyl]-1H-pyrrolo[2,3-b]pyridine

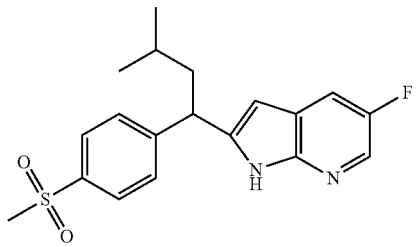

To a suspension of 1-benzenesulfonyl-5-fluoro-1H-pyrrolo[2,3-b]pyridine (10 g, 36.2 mmol) in dry tetrahydrofuran (400 mL) at −78° C. was added a n-butyllithium solution in n-hexane (2.5 M, 21.7 mL, 54.3 mmol) dropwise. The mixture was stirred at −78° C. for 30 min and then treated with 3-methyl-butyraldehyde (7 mL, 65.2 mmol) dropwise. The resulting mixture was stirred at −78° C. for 1 h and quenched with brine. The mixture was extracted with ethyl acetate (2×200 mL), washed with brine, dried over anhydrous sodium sulfate and concentrated in vacuo. Purification by flash column chromatography (QingDao silica gel, 200-300 mesh, 20% ethyl acetate/hexanes) afforded 1-(1-benzenesulfonyl-5-fluoro-1H-pyrrolo[2,3-b]pyridin-2-yl)-3-methyl-butan-1-ol as a colorless oil (9.4 g, 71%): LC/MS m/e calcd for $C_{20}H_{22}N_2O_4S$ [M+H]$^+$ 363.43, observed 362.8.

To a solution of 1-(1-benzenesulfonyl-5-fluoro-1H-pyrrolo[2,3-b]pyridin-2-yl)-3-methyl-butan-1-ol (9.4 g, 26 mmol) in dichloromethane (400 mL) was added Dess-Martin periodinane (16.6 g, 39 mmol) at 25° C. The reaction mixture was stirred at 25° C. for 1 h and then quenched with a saturated aqueous sodium bicarbonate solution (200 mL). The mixture was extracted with dichloromethane (100 mL), washed with a saturated aqueous sodium bicarbonate solution (3×100 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 1-(1-benzenesulfonyl-5-fluoro-1H-pyrrolo[2,3-b]pyridin-2-yl)-3-methyl-butan-1-one (8.3 g, 84%) as a light yellow solid: LC/MS m/e calcd for $C_{18}H_{17}FN_2O_3S$ [M+H]$^+$ 361.41, observed 360.8.

To a solution of 1-(1-benzenesulfonyl-5-fluoro-1H-pyrrolo[2,3-b]pyridin-2-yl)-3-methyl-butan-1-one (8.3 g, 23 mmol) in dry tetrahydrofuran (200 mL) at −78° C. was added lithium bis(trimethylsilyl)amide in tetrahydrofuran (1 M, 34.6 mL, 34.6 mmol) dropwise. After stirring at −78° C. for 1 h, a solution of p-toluenesulfonic anhydride (0.57 g, 1.76 mmol) in tetrahydrofuran (5 mL) was added dropwise. The resulting solution was kept at −78° C. for another 1 h. The reaction was quenched with water, extracted with ethyl acetate (300 mL), washed with brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded toluene-4-sulfonic acid 1-(1-benzenesulfonyl-5-fluoro-1H-pyrrolo[2,3-b]pyridin-2-yl)-3-methyl-but-1-enyl ester (8 g, 67%) as a white solid: LC/MS m/e calcd for $C_{25}H_{23}FN_2O_5S_2$ [M+H]$^+$ 515.60, observed; 515.0.

To a mixture of toluene-4-sulfonic acid 1-(1-benzenesulfonyl-5-fluoro-1H-pyrrolo[2,3-b]pyridin-2-yl)-3-methyl-but-1-enyl ester (1 g, 2 mmol), 4-(methanesulfonyl)phenylboronic acid (1 g, 5 mmol) and dichlorobis(triphenylphosphine) palladium (II) (140 mg, 0.2 mmol) in dioxane (8 mL) was added an aqueous sodium carbonate solution (2 M, 2.5 mL). The resulting mixture was subjected to microwave irradiation for 2 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-5-fluoro-2-[1-(4-methanesulfonyl-phenyl)-3-methyl-but-1-enyl]-1H-pyrrolo[2,3-b]pyridine (0.9 g, 92%) as a white solid: LC/MS m/e calcd for $C_{25}H_{23}FN_2O_4S_2$ [M+H]$^+$ 499.60, observed 498.8.

A mixture of 1-benzenesulfonyl-5-fluoro-2-[1-(4-methanesulfonyl-phenyl)-3-methyl-but-1-enyl]-1H-pyrrolo[2,3-b]pyridine (900 mg, 1.8 mmol) and tetrabutylammonium fluoride solution in tetrahydrofuran (1 M, 4 ml) was stirred at 25° C. for 20 h. The reaction was quenched with a saturated aqueous ammonium chloride solution (30 mL). The mixture was extracted with ethyl acetate (2×50 mL), washed with a saturated aqueous ammonium chloride solution (3×25 mL), brine, dried over anhydrous sodium sulfate and concentrated in vacuo to afford 5-fluoro-2-[1-(4-methanesulfonyl-phenyl)-3-methyl-but-1-enyl]-1H-pyrrolo[2,3-b]pyridine (600 mg, 92%): LC/MS m/e calcd for $C_{19}H_{19}FN_2O_2S$ [M+H]$^+$ 359.44, observed 358.8.

A mixture of 5-fluoro-2-[1-(4-methanesulfonyl-phenyl)-3-methyl-but-1-enyl]-1H-pyrrolo[2,3-b]pyridine (600 mg, 1.67 mmol) and 10% palladium on activated carbon (180 mg) in methanol (300 mL) was heated at 50° C. under hydrogen (50 psi) for 6 h. The mixture was cooled to 25° C., the solids filtered off, washed with ethyl acetate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 5-fluoro-2-[1-(4-methanesulfonyl-phenyl)-3-methyl-butyl]-1H-pyrrolo[2,3-b]pyridine (380 mg, 63%) as a white solid: LC/MS m/e calcd for $C_{19}H_{21}FN_2O_2S$ [M+H]$^+$ 361.45, observed 361.0; $^1$H NMR (400 MHz, CDCl$_3$) δ ppm 11.77 (br. s., 1H), 8.16 (br. s., 1H), 7.97-8.01 (m, 1H), 7.90 (d, J=8.1 Hz, 2H), 7.52-7.60 (m, 2H), 6.52 (s, 1H), 4.45 (t, J=7.8 Hz, 1H), 3.03-3.07 (m, 3H), 1.98-2.16 (m, 2H), 1.50 (dt, J=13.5, 6.6 Hz, 1H), 0.95-1.02 (m, 6H).

Example 100

5-Fluoro-2-[1(R)-(4-methanesulfonyl-phenyl)-3-methyl-butyl]-1H-pyrrolo[2,3-b]pyridine

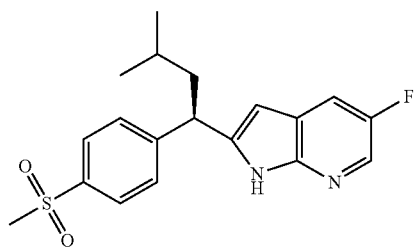

The 1:1 mixture of enantiomers of 5-fluoro-2-[1-(4-methanesulfonyl-phenyl)-3-methyl-butyl]-1H-pyrrolo[2,3-b]pyridine (prepared as in Example 99, 380 mg) was separated by Agilent high performance liquid chromatography (chiral column: Daicel IA-H, 250 mm×20 mm i. d., 5 μm-particle size, temperature: 25° C., flow rate of 15 mL/min, 60% ethanol/hexanes as mobile phase and UV detection: 214 and 254 nm) to afford two pure enantiomers. The second peak, 5-fluoro-2-[1(R)-(4-methanesulfonyl-phenyl)-3-methyl-butyl]-1H-pyrrolo[2,3-b]pyridine (140 mg) was isolated as a white solid: $^1$H NMR (400 MHz, CD$_3$OD) δ ppm 8.07 (br. s., 1H), 7.95 (d, J=8.3 Hz, 2H), 7.61-7.71 (m, 3H), 6.43 (s, 1H), 4.43 (t, J=8.0 Hz, 1H), 3.14 (s, 3H), 2.14-2.23 (m, 1H), 2.00 (dt, J=13.9, 7.2 Hz, 1H), 1.55 (dt, J=13.3, 6.6 Hz, 1H), 1.17-1.29 (m, 1H), 1.02 (t, J=7.2 Hz, 6H).

Example 101

(2-{4-[1-(5-Fluoro-(1H-pyrrolo[2,3-b]pyridin-2-yl)-3-methyl-butyl]-benzenesulfonyl}-ethanol

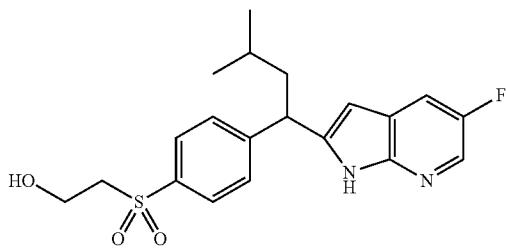

To a mixture of toluene-4-sulfonic acid 1-(1-benzenesulfonyl-5-fluoro-1H-pyrrolo[2,3-b]pyridin-2-yl)-3-methyl-but-1-enyl ester (prepared as in Example 99, 1 g, 2 mmol), 4-(2-methoxy-ethanesulfonyl)-phenylboronic acid (1.2 g, 5 mmol) and dichlorobis(triphenylphosphine)palladium (II) (140 mg, 0.2 mmol) in dioxane (8 mL) was added an aqueous sodium carbonate solution (2 M, 2.5 mL). The resulting mixture was subjected to microwave irradiation for 2 h at 100° C. The mixture was diluted with ethyl acetate (100 mL), washed with a saturated aqueous sodium bicarbonate solution (2×50 mL), brine, dried over anhydrous sodium sulfate and then concentrated in vacuo. Purification by flash silica gel chromatography (silica gel from QingDao, 200-300 mesh, glass column from Shanghai SD company, 50% ethyl acetate/hexanes) afforded 1-benzenesulfonyl-5-fluoro-2-{1-[4-(2-methoxy-ethanesulfonyl)-phenyl]-3-methyl-but-1-enyl}-1H-pyrrolo[2,3-b]pyridine (0.6 g, 57%) as a white solid: LC/MS m/e calcd for C$_{27}$H$_{27}$FN$_2$O$_5$S$_2$ [M+H]$^+$ 543.65, observed 543.0.

A mixture of 1-benzenesulfonyl-5-fluoro-2-{1-[4-(2-methoxy-ethanesulfonyl)-phenyl]-3-methyl-but-1-enyl}-1H-pyrrolo[2,3-b]pyridine (0.6 g, 1.1 mmol) in ethanol (8 mL), tetrahydrofuran (15 mL) and an aqueous sodium hydroxide solution (10%, 10 mL) was heated at 45° C. for 16 h. The mixture was diluted with dichloromethane (150 mL), washed with water, dried over anhydrous sodium sulfate and then concentrated in vacuo. Purification by flash silica gel chromatography (silica gel from QingDao, 200-300 mesh, glass column from Shanghai SD company, 30% ethyl acetate/hexanes) afforded 2-{1-[4-(2-ethoxy-ethanesulfonyl)-phenyl]-3-methyl-but-1-enyl}-5-fluoro-1H-pyrrolo[2,3-b]pyridine (160 mg, 34%): LC/MS m/e calcd for C$_{22}$H$_{25}$FN$_2$O$_3$S [M+H]$^+$ 417.52, observed 416.8.

A mixture of 2-{1-[4-(2-ethoxy-ethanesulfonyl)-phenyl]-3-methyl-but-1-enyl}-5-fluoro-1H-pyrrolo[2,3-b]pyridine (160 mg, 0.38 mmol) and 10% palladium on activated carbon (70 mg) in methanol (250 mL) was heated at 50° C. under hydrogen (50 psi) for 16 h. The mixture was cooled to 25° C., the solids filtered off, washed with ethyl acetate and concentrated in vacuo to afford 2-{1-[4-(2-ethoxy-ethanesulfonyl)-phenyl]-3-methyl-butyl}-5-fluoro}-1H-pyrrolo[2,3-b]pyridine (150 mg, 93%) which was used in the next step without further purification: LC/MS m/e calcd for C$_{22}$H$_{27}$FN$_2$O$_3$S [M+H]$^+$ 419.53, observed 419.0.

To a solution of 2-{1-[4-(2-ethoxy-ethanesulfonyl)-phenyl]-3-methyl-butyl}-5-fluoro}-1H-pyrrolo[2,3-b]pyridine (150 mg, 0.36 mmol) in dichloromethane (30 mL) at 0° C. was added a solution of boron tribromide (0.17 ml, 1.8 mmol) in dichloromethane (20 ml). The mixture was stirred at 0° C. for 1 h. The reaction was quenched with a saturated aqueous sodium bicarbonate solution (20 mL). The mixture was extracted with dichloromethane (2×50 mL), washed with a saturated aqueous sodium bicarbonate solution (3×20 mL) and brine (3×20 mL), dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded (2-{4-[1-(5-fluoro-(1H-pyrrolo[2,3-b]pyridin-2-yl)-3-methyl-butyl]-benzenesulfonyl}-ethanol (70 mg, 50%): LC/MS m/e calcd for C$_{22}$H$_{26}$N$_2$O$_3$S [M+H]$^+$ 391.48, observed 390.8; $^1$H NMR (400 MHz, CD$_3$OD) δ ppm 8.08 (s, 1H), 7.96 (d, J=8.3 Hz, 2H), 7.66-7.74 (m, 3H), 6.48 (s, 1H), 4.46 (t, J=8.0 Hz, 1H), 3.93 (t, J=6.3 Hz, 2H), 3.47 (t, J=6.3 Hz, 2H), 2.19-2.27 (m, 1H), 2.01-2.13 (m, 2H), 1.60 (dt, J=13.3, 6.6 Hz, 1H), 1.07 (t, J=7.2 Hz, 6H).

Example 102

(2-{4-[1(R)-(5-Fluoro-(1H-pyrrolo[2,3-b]pyridin-2-yl)-3-methyl-butyl]-benzenesulfonyl}-ethanol

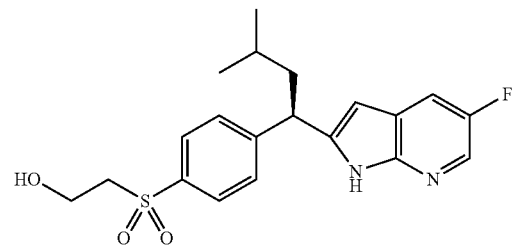

The 1:1 mixture of enantiomers of (2-{4-[1-(5-fluoro-(1H-pyrrolo[2,3-b]pyridin-2-yl)-3-methyl-butyl]-benzenesulfonyl}-ethanol (prepared as in Example 101, 64 mg) was separated by Agilent high performance liquid chromatography (chiral column: Daicel IA-H, 250 mm×20 mm i. d., 5 μm-particle size, temperature: 25° C., flow rate of 15 mL/min, 40% isopropyl alcohol/hexanes as mobile phase and UV detection: 214 and 254 nm) to afford two pure enantiomers. The second peak, (2-{4-[1(R)-(5-fluoro-(1H-pyrrolo[2,3-b]pyridin-2-yl)-3-methyl-butyl]-benzenesulfonyl}-ethanol (23 mg) was isolated as a white solid: $^1$H NMR (400 MHz, CD$_3$OD) δ ppm 8.00 (s, 1H), 7.87 (s, 2H), 7.45-7.71 (m, 3H), 6.39 (s, 1H), 4.22-4.48 (m, 1H), 3.85 (t, J=6.2 Hz, 2H), 3.39

(t, J=6.3 Hz, 2H), 2.06-2.23 (m, 1H), 1.86-2.04 (m, 1H), 1.50 (dt, J=13.4, 6.7 Hz, 1H), 1.17 (d, J=6.3 Hz, 1H), 0.98 (t, J=7.3 Hz, 6H).

Example 103

2-{4-[2-Cyclopentyl-1-(5-fluoro-1H-pyrrolo[2,3-b]pyridin-2-yl)-ethyl]-2-fluoro-phenyl}-propan-2-ol

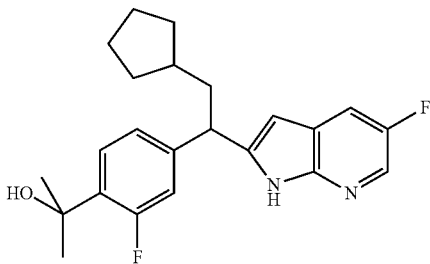

To a mixture of toluene-4-sulfonic acid 1-(1-benzenesulfonyl-5-fluoro-1H-pyrrolo[2,3-b]pyridin-2-yl)-2-cyclopentyl-vinyl ester (prepared as in Example 88, 3 g, 5.75 mmol), 2-fluoro-4-(4,4,5,5-tetramethyl-[1,3,2]dioxaborolan-2-yl)-benzoic acid methyl ester (prepared as in Example 95, 3.9 g, 13.9 mmol) and dichlorobis(triphenylphosphine)palladium (II) (390 mg, 0.6 mmol) in dioxane (24 mL) was added an aqueous sodium carbonate solution (2 M, 6.93 mL). The resulting mixture was subjected to microwave irradiation for 2 h at 100° C. The mixture was diluted with ethyl acetate (200 mL), washed with a saturated aqueous sodium bicarbonate solution (3×50 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 4-[1-(1-benzenesulfonyl-5-fluoro-1H-pyrrolo[2,3-b]pyridin-2-yl)-2-cyclopentyl-vinyl]-2-fluoro-benzoic acid methyl ester (2.50 g, 86%) as a white solid: LC/MS m/e calcd for $C_{28}H_{24}F_2N_2O_4S$ [M+H]$^+$ 523.58, observed 522.7.

A mixture of 4-[1-(1-benzenesulfonyl-5-fluoro-1H-pyrrolo[2,3-b]pyridin-2-yl)-2-cyclopentyl-vinyl]-2-fluoro-benzoic acid methyl ester (2.50 g, 4.79 mmol) and tetrabutylammonium fluoride solution in tetrahydrofuran (1 M, 8 mL) was stirred at 25° C. for 16 h. The reaction was quenched with a saturated aqueous ammonium chloride solution (20 mL). The mixture was extracted with ethyl acetate (2×100 mL), washed with a saturated aqueous ammonium chloride solution (3×50 mL), brine, dried over anhydrous sodium sulfate and concentrated in vacuo to afford 4-[2-cyclopentyl-1-(5-fluoro-1H-pyrrolo[2,3-b]pyridin-2-yl)-vinyl]-2-fluoro-benzoic acid methyl ester (1.50 g, 81%) which was used in the next step without further purification: LC/MS m/e calcd for $C_{22}H_{20}F_2N_2O_2$ [M+H]$^+$ 383.41, observed 382.9.

A mixture of 4-[2-cyclopentyl-1-(5-fluoro-1H-pyrrolo[2,3-b]pyridin-2-yl)-vinyl]-2-fluoro-benzoic acid methyl ester (1.50 g, 3.93 mmol) and 10% palladium on activated carbon (300 mg) in methanol (300 mL) was heated at 50° C. under hydrogen (50 psi) for 5 h. The mixture was cooled to 25° C., the solids filtered off, washed with ethyl acetate and concentrated in vacuo. Purification by flash silica gel chromatography (silica gel from QingDao, 200-300 mesh, glass column from Shanghai SD company, 20% ethyl acetate/hexanes) afforded 4-[2-cyclopentyl-1-(5-fluoro-1H-pyrrolo[2,3-b]pyridin-2-yl)-ethyl]-2-fluoro-benzoic acid methyl ester (1.40 g, 92%): LC/MS m/e calcd for $C_{22}H_{22}F_2N_2O_2$ [M+H]$^+$ 385.43, observed 384.9.

To a solution of 4-[2-cyclopentyl-1-(5-fluoro-1H-pyrrolo[2,3-b]pyridin-2-yl)-ethyl]-2-fluoro-benzoic acid methyl ester (1.40 g, 3.64 mmol) in dry tetrahydrofuran (15 mL) at 0° C. was added methylmagnesium chloride solution in tetrahydrofuran (3 M, 12.1 mL, 36.4 mmol) dropwise. After stirring at 0° C. for 3 h, the reaction was quenched with a saturated aqueous ammonium chloride solution (20 mL). The mixture was extracted with ethyl acetate (2×100 mL), washed with brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{4-[2-cyclopentyl-1-(5-fluoro-1H-pyrrolo[2,3-b]pyridin-2-yl)-ethyl]-2-fluoro-phenyl}-propan-2-ol (700 mg, 50%) as a white solid: LC/MS m/e calcd for $C_{23}H_{26}F_2N_2O$ [M+H]$^+$ 385.47, observed 385.0; $^1$H NMR (400 MHz, CD$_3$OD) δ ppm 7.99 (s, 1H), 7.52-7.65 (m, 2H), 7.12 (d, J=6.8 Hz, 1H), 7.01 (d, J=13.1 Hz, 1H), 6.35 (s, 1H), 4.17 (t, J=8.0 Hz, 1H), 2.17-2.25 (m, 1H), 2.04-2.12 (m, 1H), 1.61-1.86 (m, 6H), 1.47-1.60 (m, 9H), 1.18-1.29 (m, 2H).

Example 104

2-{4-[2-Cyclopentyl-1(R)-(5-fluoro-1H-pyrrolo[2,3-b]pyridin-2-yl)-ethyl]-2-fluoro-phenyl}-propan-2-ol

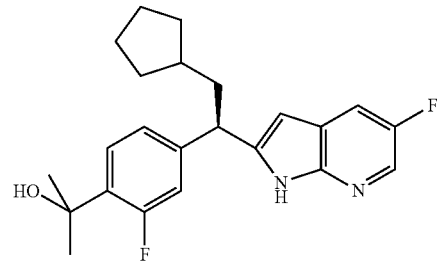

The 1:1 mixture of enantiomers of 2-{4-[2-cyclopentyl-1-(5-fluoro-1H-pyrrolo[2,3-b]pyridin-2-yl)-ethyl]-2-fluoro-phenyl}-propan-2-ol (prepared as in Example 103, 370 mg) was separated by Agilent high performance liquid chromatography (chiral column: Daicel IA-H, 250 mm×20 mm i. d., 5 μm-particle size, temperature: 25° C., flow rate of 15 mL/min, 30% ethanol/hexanes as mobile phase and UV detection: 214 and 254 nm) to afford two pure enantiomers. The second peak, 2-{4-[2-cyclopentyl-1(R)-(5-fluoro-1H-pyrrolo[2,3-b]pyridin-2-yl)-ethyl]-2-fluoro-phenyl}-propan-2-ol (135 mg) was isolated as a white solid: $^1$H NMR (400 MHz, CD$_3$OD) δ ppm 7.99 (br. s., 1H), 7.64 (dd, J=9.2, 2.7 Hz, 1H), 7.55 (t, J=8.5 Hz, 1H), 7.12 (d, J=8.1 Hz, 1H), 7.01 (d, J=13.1 Hz, 1H), 6.35 (s, 1H), 4.17 (t, J=8.0 Hz, 1H), 2.17-2.25 (m, 1H), 2.00-2.12 (m, 1H), 1.63-1.73 (m, 2H), 1.48-1.58 (m, 10H), 1.23 (d, J=8.1 Hz, 2H).

Example 105

2-{2-Fluoro-4-[1-(5-fluoro-1H-pyrrolo[2,3-b]pyridin-2-yl)-3-methyl-butyl]-phenyl}-propan-2-ol

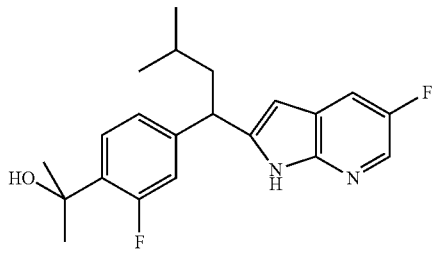

To a mixture of toluene-4-sulfonic acid 1-(1-benzenesulfonyl-5-fluoro-1H-pyrrolo[2,3-b]pyridin-2-yl)-3-methyl-but-1-enyl ester (prepared as in Example 99, 3.09 g, 6 mmol), 2-fluoro-4-(4,4,5,5-tetramethyl-[1,3,2]dioxaborolan-2-yl)-benzoic acid methyl ester (prepared as in Example 95, 5.88 g, 21 mmol) and dichlorobis(triphenylphosphine)palladium (II) (420 mg, 0.6 mmol) in dioxane (24 mL) was added an aqueous sodium carbonate solution (2 M, 7.5 mL). The resulting mixture was subjected to microwave irradiation for 4 h at 100° C. The mixture was diluted with ethyl acetate (200 mL), washed with a saturated aqueous sodium bicarbonate solution (3×50 mL), brine, dried over anhydrous sodium sulfate and then concentrated in vacuo. Purification by flash silica gel chromatography (silica gel from QingDao, 200-300 mesh, glass column from Shanghai SD company, 25% ethyl acetate/hexanes) afforded 4-[1-(1-benzenesulfonyl-5-fluoro-1H-pyrrolo[2,3-b]pyridin-2-yl)-3-methyl-but-1-enyl]-2-fluoro-benzoic acid methyl ester (2.50 g, 83%) as a white solid: LC/MS m/e calcd for $C_{26}H_{22}F_2N_2O_4S$ [M+H]$^+$ 497.54, observed 496.7.

A mixture of 4-[1-(1-benzenesulfonyl-5-fluoro-1H-pyrrolo[2,3-b]pyridin-2-yl)-3-methyl-but-1-enyl]-2-fluoro-benzoic acid methyl ester (2.50 g, 5 mmol) and tetrabutylammonium fluoride solution in tetrahydrofuran (1 M, 50 mL) was stirred at 25° C. for 40 h. The reaction was quenched with a saturated aqueous ammonium chloride solution (50 mL). The mixture was extracted with ethyl acetate (2×150 mL), washed with a saturated aqueous ammonium chloride solution (3×100 mL), brine, dried over anhydrous sodium sulfate and concentrated in vacuo to afford 2-fluoro-4-[1-(5-fluoro-1H-pyrrolo[2,3-b]pyridin-2-yl)-3-methyl-but-1-enyl]-benzoic acid methyl ester (660 mg, 36%) which was used in the next step without further purification: LC/MS m/e calcd for $C_{20}H_{18}F_2N_2O_2$ [M+H]$^+$ 357.38, observed 356.9.

A mixture of 2-fluoro-4-[1-(5-fluoro-1H-pyrrolo[2,3-b]pyridin-2-yl)-3-methyl-but-1-enyl]-benzoic acid methyl ester (660 mg, 1.85 mmol) and 10% palladium on activated carbon (198 mg) in methanol (250 mL) was heated at 50° C. under hydrogen (50 psi) for 16 h. The mixture was cooled to 25° C., the solids filtered off, washed with ethyl acetate and concentrated in vacuo. Purification by flash silica gel chromatography (silica gel from QingDao, 200-300 mesh, glass column from Shanghai SD company, 20% ethyl acetate/hexanes) afforded 2-fluoro-4-[1-(5-fluoro-1H-pyrrolo[2,3-b]pyridin-2-yl)-3-methyl-butyl]-benzoic acid methyl ester (658 mg, 97%): LC/MS m/e calcd for $C_{20}H_{20}F_2N_2O_2$ [M+H]$^+$ 385.43, observed 384.9.

To a solution of 2-fluoro-4-[1-(5-fluoro-1H-pyrrolo[2,3-b]pyridin-2-yl)-3-methyl-butyl]-benzoic acid methyl ester (650 mg, 1.8 mmol) in dry tetrahydrofuran (20 mL) at 0° C. was added methylmagnesium chloride solution in tetrahydrofuran (3 M, 6 mL, 18 mmol) dropwise. After stirring at 0° C. for 2 h, and quenched with a saturated aqueous ammonium chloride solution (20 mL). The mixture was extracted with ethyl acetate (2×100 mL), washed with brine, dried over anhydrous sodium sulfate and concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{2-fluoro-4-[1-(5-fluoro-1H-pyrrolo[2,3-b]pyridin-2-yl)-3-methyl-butyl]-phenyl}-propan-2-ol (380 mg, 58%) as a white solid: LC/MS m/e calcd for $C_{21}H_{24}F_2N_2O$ [M+H]$^+$ 359.44, observed 359.0; $^1$H NMR (400 MHz, CD$_3$OD) δ ppm 7.99 (t, J=2.1 Hz, 1H), 7.64 (dd, J=9.2, 2.7 Hz, 1H), 7.55 (t, J=8.3 Hz, 1H), 7.11-7.14 (m, 1H), 7.02 (d, J=13.1 Hz, 1H), 6.35 (s, 1H), 4.23 (t, J=8.0 Hz, 1H), 2.04-2.11 (m, 2H), 1.90-1.98 (m, 1H), 1.47-1.58 (m, 7H), 0.98 (t, J=6.9 Hz, 6H).

Example 106

2-{2-Fluoro-4-[1(R)-(5-fluoro-1H-pyrrolo[2,3-b]pyridin-2-yl)-3-methyl-butyl]-phenyl}-propan-2-ol

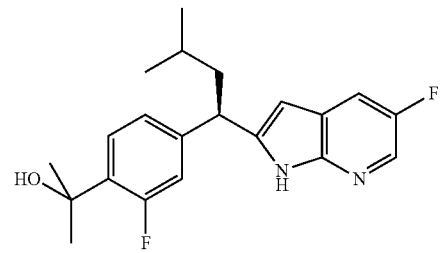

The 1:1 mixture of enantiomers of 2-{2-fluoro-4-[1-(5-fluoro-1H-pyrrolo[2,3-b]pyridin-2-yl)-3-methyl-butyl]-phenyl}-propan-2-ol (prepared as in Example 105, 380 mg) was separated by Agilent high performance liquid chromatography (chiral column: Daicel IA-H, 250 mm×20 mm i. d., 5 μm-particle size, temperature: 25° C., flow rate of 15 mL/min, 40% ethanol/hexanes as mobile phase and UV detection: 214 and 254 nm) to afford two pure enantiomers. The second peak, 2-{2-fluoro-4-[1(R)-(5-fluoro-1H-pyrrolo[2,3-b]pyridin-2-yl)-3-methyl-butyl]-phenyl}-propan-2-ol (140 mg) was isolated as a white solid: $^1$H NMR (400 MHz, CD$_3$OD) δ ppm 7.97 (t, J=2.3 Hz, 1H), 7.61 (dd, J=9.2, 2.7 Hz, 1H), 7.52 (t, J=8.5 Hz, 1H), 7.10 (dd, J=8.1, 1.5 Hz, 1H), 6.99 (dd, J=13.3, 1.4 Hz, 1H), 6.32 (s, 1H), 4.21 (t, J=8.0 Hz, 1H), 2.01-2.09 (m, 1H), 1.87-1.95 (m, 1H), 1.44-1.55 (m, 7H), 0.96 (t, J=6.9 Hz, 6H).

Example 107

N-{2-[2-Cyclopentyl-1-(4-methanesulfonyl-phenyl)-ethyl]-1H-pyrrolo[2,3-b]pyridin-5-yl}-2-dimethylamino-acetamide

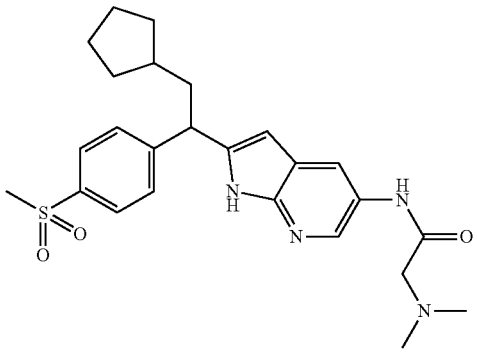

A mixture of 2-amino-5-nitropyridine (86.3 g, 0.625 mol) and potassium iodate (53.5 g, 0.25 mol) in 2 M sulfuric acid was heated at 100° C. and a solution of potassium iodide (100 g, 0.603 mol) in water (250 mL) was added dropwise over 1 h. The resulting brown mixture was refluxed for 12 h. After being cooled to room temperature, the mixture was adjusted to pH 7 by careful addition of solid sodium bicarbonate. The mixture was extracted with dichloromethane, washed with a saturated sodium thiosulfate solution, dried over anhydrous sodium sulfate, and the solvent removed in vacuo to afford 2-amino-3-iodo-5-nitropyridine (89.3 g, 60%) as a yellow solid: LC/MS m/e calcd for $C_5H_4IN_3O_2$ [M+H]$^+$ 266.01, observed 266.

2-Amino-3-iodo-5-nitropyridine (10.0 g, 37.75 mmol) was dissolved in a mixture of triethylamine (250 mL), tetrahydrofuran (40 mL), N,N-dimethylacetamide (80 mL) and the solution was degassed and purged with nitrogen. Trimethylsilylacetylene (8.0 mL, 56.5 mmol), copper(I) iodide (0.145 g, 0.75 mmol) and bis(triphenylphosphino) palladium (II) chloride (0.53 g, 0.75 mmol) were added. The mixture was degassed and purged with nitrogen one more time, then stirred at ambient temperature for 16 h. The precipitate was removed by filtration, and the filtrate was concentrated in vacuo. The residue was purified by flash column chromatography (silica gel from QingDao, 200-300 mesh, 15%-35% ethyl acetate/hexanes) to afford 5-nitro-3-trimethylsilanylethynyl-pyridin-2-ylamine (6.2 g, 70%) as a yellow solid: LC/MS m/e calcd for $C_{10}H_{13}N_3O_2Si$ [M+H]$^+$ 236.32, observed 236.0.

5-Nitro-3-trimethylsilanylethynyl-pyridin-2-ylamine (0.7 g, 2.98 mmol) and copper(I) iodide (114 mg, 0.60 mmol) were dissolved in N,N-dimethylacetamide (14 mL). The mixture was irradiated in a microwave reactor at 190° C. for 30 min. The mixture was evaporated to remove N,N-dimethylacetamide in vacuo. The residue was dissolved in hot tetrahydrofuran (50° C., 250 mL) and filtered through a short pad of silica gel (from QingDao, 200-300 mesh). The filtrate was concentrated to afford 5-nitro-1H-pyrrolo[2,3-b]pyridine (0.4 g, 83%) as a yellow solid: LC/MS m/e calcd for $C_7H_5N_3O_2$ [M+H]$^+$ 164.14, observed 164.0.

To a mixture of 5-nitro-1H-pyrrolo[2,3-b]pyridine (2.0 g, 12.3 mmol), triethylamine (2.48 g, 24.6 mmol), 4-dimethylaminopyridine (0.15 g, 1.23 mmol) in dichloromethane/N,N-dimethylformamide (1:1, 60 mL) was added benzenesulfonyl chloride (3.25 g, 18.4 mmol) at 0° C. After stirring for 48 h at room temperature, the reaction was quenched with water (50 mL) and extracted with dichloromethane (2×120 mL). The organic layer was washed with a saturated sodium bicarbonate (2×30 mL), water (2×30 mL), brine (50 mL), dried over anhydrous sodium sulfate and concentrated in vacuo. The residue was purified by flash column chromatography (silica gel from QingDao, 200-300 mesh, 33% dichloromethane/hexanes) to afford 1-benzenesulfonyl-5-nitro-1H-pyrrolo[2,3-b]pyridine (2.8 g, 76%) as a yellow solid: LC/MS m/e calcd for $C_{13}H_9N_3O_4S$ [M+H]$^+$ 304.30, observed 303.9.

To a solution of 1-benzenesulfonyl-5-nitro-1H-pyrrolo[2,3-b]pyridine (2.8 g, 9.24 mmol) in tetrahydrofuran (50 mL) was added 10% palladium on activated carbon (0.98 g). The resulting mixture was stirred under hydrogen (50 psi) for 48 h at room temperature. The catalyst was removed by filtration and the filtrate was concentrated to afford 1-benzenesulfonyl-1H-pyrrolo[2,3-b]pyridin-5-ylamine (2.52 g, 100%) as a yellow oil which was used in the next step without purification: LC/MS m/e calcd for $C_{13}H_{11}N_3O_2S$ [M+H]$^+$ 274.32, observed 274.1.

To a solution of 1-benzenesulfonyl-1H-pyrrolo[2,3-b]pyridin-5-ylamine (2.6 g, 9.5 mmol) and triethylamine (2.6 mL, 19 mmol) in tetrahydrofuran (20 mL) was added di-tert-butyl dicarbonate (3.1 g, 14.25 mmol) slowly. The resulting mixture was stirred for 12 h at room temperature. The solvents were removed and the residue was purified by flash column chromatography (silica gel from QingDao, 200-300 mesh, ethyl acetate/hexanes/dichloromethane=1:2:1) to afford (1-benzenesulfonyl-1H-pyrrolo[2,3-b]pyridin-5-yl)-carbamic acid tert-butyl ester (2.58 g, 73%): LC/MS m/e calcd for $C_{18}H_{19}N_3O_4S$ [M+H]$^+$ 374.43, observed 374.1.

To a suspension of (1-benzenesulfonyl-1H-pyrrolo[2,3-b]pyridin-5-yl)-carbamic acid tert-butyl ester (3.48 g, 9.33 mmol) in dry tetrahydrofuran (100 mL) at −78° C. was added freshly prepared lithium diisopropylamide [prepared by adding 1.6 M n-butyllithium in n-hexane (17.5 mL, 28 mmol) to a 0° C. solution of diisopropylamine (2.83 g, 28 mmol) in dry tetrahydrofuran (40 mL)] dropwise. The mixture was stirred at −78° C. for 5 min and then treated with cyclopentanecarbaldehyde (1.57 g, 14 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (QingDao silica gel, 200-300 mesh, 25% ethyl acetate/hexanes) afforded [1-benzenesulfonyl-2-(2-cyclopentyl-1-hydroxy-ethyl)-1H-pyrrolo[2,3-b]pyridin-5-yl]-carbamic acid tert-butyl ester as a white solid (0.57 g, 44%): LC/MS m/e calcd for $C_{25}H_{31}N_3O_5S$ [M+H]$^+$ 486.61, observed 486.0.

To a solution of [1-benzenesulfonyl-2-(2-cyclopentyl-1-hydroxy-ethyl)-1H-pyrrolo[2,3-b]pyridin-5-yl]-carbamic acid tert-butyl ester (0.57 g, 1.18 mmol) in dichloromethane (10 mL) was added a solution of Dess-Martin periodinane in dichloromethane (0.3 M, 7.87 mL, 2.36 mmol) at 25° C. The mixture was stirred at 25° C. for 1 h and then quenched with a saturated aqueous sodium bicarbonate solution (20 mL). The mixture was extracted with ethyl acetate (100 mL), washed with a saturated aqueous sodium bicarbonate solution (3×20 mL), brine, dried over anhydrous sodium sulfate and then concentrated in vacuo. The residue was purified by flash column chromatography (silica gel from QingDao, 200-300 mesh, 25% ethyl acetate/hexanes) afforded [1-benzenesulfonyl-2-(2-cyclopentyl-acetyl)-1H-pyrrolo[2,3-b]pyridin-5-yl]-carbamic acid tert-butyl ester (0.375 g, 66%) as a light yellow solid: LC/MS m/e calcd for $C_{25}H_{29}N_3O_5S$ [M+H]$^+$ 484.59, observed 484.2.

To a solution of [1-benzenesulfonyl-2-(2-cyclopentyl-acetyl)-1H-pyrrolo[2,3-b]pyridin-5-yl]-carbamic acid tert-butyl ester (0.375 g, 0.78 mmol) in tetrahydrofuran (15 mL) at −78° C. was added lithium bis(trimethylsilyl)amide in tetrahydrofuran (1 M, 1.94 mL, 1.94 mmol) dropwise. After stirring at −78° C. for 0.5 h, a solution of p-toluenesulfonic anhydride (458 mg, 1.40 mmol) in tetrahydrofuran (6 mL) was added dropwise. The resulting solution was kept at −78° C. for an additional 1 h. The reaction was quenched with water, extracted with ethyl acetate (100 mL), washed with brine, dried over anhydrous sodium sulfate and then concentrated in vacuo. Purification by flash column chromatography (silica gel from QingDao, 200-300 mesh, 30% ethyl acetate/hexanes) afforded toluene-4-sulfonic acid 1-(1-benzenesulfonyl-5-tert-butoxycarbonylamino-1H-pyrrolo[2,3-b]pyridin-2-yl)-2-cyclopentyl-vinyl ester (0.32 g, 65%) as a light yellow solid: LC/MS m/e calcd for $C_{32}H_{35}N_3O_7S_2$ [M+H]$^+$ 638.78, observed 638.2.

To a mixture of toluene-4-sulfonic acid 1-(1-benzenesulfonyl-5-tert-butoxycarbonylamino-1H-pyrrolo[2,3-b]pyridin-2-yl)-2-cyclopentyl-vinyl ester (0.5 g, 0.78 mmol), 4-methylsulfonyl phenylboronic acid (468 mg, 2.34 mmol), dichlorobis(triphenylphosphine)palladium (II) (55 mg, 0.08 mmol) in dioxane (5 mL) was added an aqueous sodium carbonate solution (2 M, 1.17 mL, 2.34 mmol). The resulting mixture was subjected to microwave irradiation for 3 h at 100° C. The mixture was diluted with ethyl acetate (80 mL), washed with a saturated aqueous sodium bicarbonate solution (2×20 mL), brine, dried over anhydrous sodium sulfate and then concentrated in vacuo. Purification by flash column chromatography (QingDao silica gel, 200-300 mesh, 33% ethyl acetate/hexanes) afforded {1-benzenesulfonyl-2-[2-cyclopentyl-1-(4-methanesulfonyl-phenyl)-vinyl]-1H-pyrrolo[2,3-b]pyridin-5-yl}-carbamic acid tert-butyl ester (326 mg, 67%) as a light yellow solid: LC/MS m/e calcd for $C_{32}H_{35}N_3O_6S_2$ [M+H]$^+$ 622.78, observed 622.1.

A mixture of {1-benzenesulfonyl-2-[2-cyclopentyl-1-(4-methanesulfonyl-phenyl)-vinyl]-1H-pyrrolo[2,3-b]pyridin-5-yl}-carbamic acid tert-butyl ester (0.75 g, 1.21 mmol) and tetrabutylammonium fluoride in tetrahydrofuran (1 M, 24 mL, 24 mmol) was stirred for 3 h at 60° C. After cooling, the mixture was poured into brine (15 mL), extracted with ethyl acetate (2×100 mL), washed with a saturated aqueous ammonium chloride solution (3×50 mL), dried over anhydrous sodium sulfate and then concentrated in vacuo to give {2-[2-cyclopentyl-1-(4-methanesulfonyl-phenyl)-vinyl]-1H-pyrrolo[2,3-b]pyridin-5-yl}-carbamic acid tert-butyl ester (0.58 g, 100%) which was used in the next step without purification: LC/MS m/e calcd for $C_{26}H_{31}N_3O_4S$ [M+H]$^+$ 482.62, observed 482.2

A mixture of {2-[2-cyclopentyl-1-(4-methanesulfonyl-phenyl)-vinyl]-1H-pyrrolo[2,3-b]pyridin-5-yl}-carbamic acid tert-butyl ester (582 mg, 1.21 mmol) and 10% palladium on activated carbon (0.6 g) in methanol (200 mL) was heated at 50° C. under hydrogen (5 atm) for 5 h. After cooling, the catalyst was removed by filtration and washed with ethyl acetate. The filtrate was concentrated in vacuo to give {2-[2-cyclopentyl-1-(4-methanesulfonyl-phenyl)-ethyl]-1H-pyrrolo[2,3-b]pyridin-5-yl}-carbamic acid tert-butyl ester (584 mg) which was used in the next step without purification: LC/MS m/e calcd for $C_{26}H_{33}N_3O_4S$ [M+H]$^+$ 484.63, observed 484.2.

To a solution of {2-[2-cyclopentyl-1-(4-methanesulfonyl-phenyl)-ethyl]-1H-pyrrolo[2,3-b]pyridin-5-yl}-carbamic acid tert-butyl ester (584 mg, 1.21 mmol) in dichloromethane (20 mL) was bubbled in dry hydrogen chloride gas for 30 min. The resulting mixture was stirred for 3 h at room temperature.

The solvent was removed to afford 2-[2-cyclopentyl-1-(4-methanesulfonyl-phenyl)-ethyl]-1H-pyrrolo[2,3-b]pyridin-5-ylamine hydrochloride salt (508 mg, 100%) which was used in the next step without purification: LC/MS m/e calcd for $C_{21}H_{25}N_3O_2S$ [M+H]$^+$ 384.52, observed 384.2.

A mixture of 2-[2-cyclopentyl-1-(4-methanesulfonyl-phenyl)-ethyl]-1H-pyrrolo[2,3-b]pyridin-5-ylamine hydrochloride (0.25 g, 0.6 mmol), N,N-dimethyl glycine hydrochloride (0.13 g, 0.9 mmol), 1-ethyl-3-(3-dimethylaminopropyl)carbodiimide hydrochloride (0.23 g, 1.2 mmol), 1-hydroxybenzotriazole (0.16 g, 1.2 mmol), 4-dimethylaminopyridine (7.3 mg, 0.06 mmol), triethylamine (0.3 g, 3.0 mmol) and N,N-dimethylformamide (2 mL) in dichloromethane (5 mL) was stirred for 12 h at room temperature. The reaction was quenched with water (5 mL), extracted with ethyl acetate (2×10 mL), dried over anhydrous sodium sulfate and concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford N-{2-[2-cyclopentyl-1-(4-methanesulfonyl-phenyl)-ethyl]-1H-pyrrolo[2,3-b]pyridin-5-yl}-2-dimethylamino-acetamide (45 mg, 16%): LC/MS m/e calcd for $C_{25}H_{32}N_4O_3S$ [M+H]$^+$ 469.62, observed 469.1; $^1$H NMR (400 MHz, CDCl$_3$) δ ppm 1.17 (m, 2H), 1.45 (m, 2H), 1.53-1.83 (m, 5H, H), 2.10 (m, 1H), 2.24 (m, 1H), 2.44 (s, 6H), 3.01 (s, 3H), 3.17 (s, 2H), 4.26 (t, J=7.8 Hz, 1H), 6.33 (s, 1H), 7.50 (d, J=8.3 Hz, 2H), 7.84 (d, J=8.3 Hz, 2H), 8.17 (d, J=2.1 Hz, 1H), 8.28 (d, J=2.1 Hz, 1H), 9.19 (s, 1H), 10.96 (s, 1H).

Example 108

2-[2-Cyclopentyl-1-(6-ethoxy-pyridin-3-yl)-ethyl]-1H-pyrrolo[2,3-b]pyridine

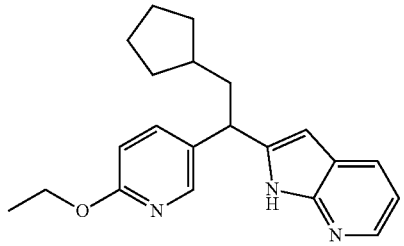

To a mixture of toluene-4-sulfonic acid 1-(1-benzenesulfonyl-1H-pyrrolo[2,3-b]pyridin-2-yl)-2-cyclopentyl-vinyl ester (prepared as in Example 43, 0.5 g, 0.96 mmol), 6-methylsulfanyl-pyridine-3-boronic acid (370 mg, 2.2 mmol) and dichlorobis(triphenylphosphine)palladium (II) (67.4 mg, 0.096 mmol) in dioxane (6 mL) was added an aqueous sodium carbonate solution (2 M, 0.96 mL, 1.92 mmol). The resulting mixture was subjected to microwave irradiation for 3 h at 100° C. The mixture was diluted with ethyl acetate (80 mL), washed with a saturated aqueous sodium bicarbonate solution (2×20 mL), brine, dried over anhydrous sodium sulfate and then concentrated in vacuo. Purification by flash column chromatography (QingDao silica gel, 200-300 mesh, 25% ethyl acetate/hexanes) afforded 1-benzenesulfonyl-2-[2-cyclopentyl-1-(6-methylsulfanyl-pyridin-3-yl)-vinyl]-1H-pyrrolo[2,3-b]pyridine (400 mg, 88%) as a light yellow solid: LC/MS m/e calcd for $C_{26}H_{25}N_3O_2S_2$ [M+H]$^+$ 476.64, observed 476.0.

A solution of 1-benzenesulfonyl-2-[2-cyclopentyl-1-(6-methylsulfanyl-pyridin-3-yl)-vinyl]-1H-pyrrolo[2,3-b]pyridine (400 mg, 0.84 mmol) in methanol (12 mL) was added a sodium metaperiodate (540 mg, 2.53 mmol) solution in water (4 mL). The resulting mixture was stirred for 12 h at room temperature, extracted with ethyl acetate (3×20 mL), dried over anhydrous sodium sulfate, concentrated in vacuo to afford 1-benzenesulfonyl-2-[2-cyclopentyl-1-(6-methanesulfinyl-pyridin-3-yl)-vinyl]-1H-pyrrolo[2,3-b]pyridine (412 mg, 100%) which was used in the next step without purification: LC/MS m/e calcd for $C_{26}H_{25}N_3O_3S_2$ [M+H]$^+$ 492.64, observed 492.2.

To a solution of 1-benzenesulfonyl-2-[2-cyclopentyl-1-(6-methanesulfinyl-pyridin-3-yl)-vinyl]-1H-pyrrolo[2,3-b]pyridine (412 mg, 0.84 mmol) in methanol (46 mL) at 0° C. was added a solution of potassium permanganate (133 mg, 0.84 mmol) in water (23 mL) dropwise. After stirring for 2 h at 0° C., the mixture was extracted with ethyl acetate, washed with brine, dried over anhydrous sodium sulfate, filtered through a short silical gel pad (QingDao silica gel, 200-300 mesh), and concentrated in vacuo to afford 1-benzenesulfonyl-2-[2-cyclopentyl-1-(6-methanesulfonyl-pyridin-3-yl)-vinyl]-1H-pyrrolo[2,3-b]pyridine (370 mg, 87%): LC/MS m/e calcd for $C_{26}H_{25}N_3O_4S_2$ [M+H]$^+$ 508.63, observed 508.2.

To a mixture of 1-benzenesulfonyl-2-[2-cyclopentyl-1-(6-methanesulfonyl-pyridin-3-yl)-vinyl]-1H-pyrrolo[2,3-b]pyridine (370 mg, 0.73 mmol), and ammonia (2 mL) in ethanol (20 mL) and tetrahydrofuran (10 mL) was added a solution of sodium hydroxide in water (10%, 3 mL). After refluxing for 5 h, the mixture was cooled to room temperature, extracted with ethyl acetate, dried over anhydrous sodium sulfate, and concentrated in vacuo to afford a mixture of 2-[2-cyclopentyl-1-(6-ethoxy-pyridin-3-yl)-vinyl]-1H-pyrrolo[2,3-b]pyridine (60 mg, 23%): LC/MS m/e calcd for $C_{21}H_{23}N_3O$ [M+H]$^+$ 334.44, observed 334.1; 242-cyclopentyl-1-(6-methanesulfonyl-pyridin-3-yl)-vinyl]-1H-pyrrolo[2,3-b]pyridine (100 mg, 37%): LC/MS m/e calcd for $C_{20}H_{21}N_3O_2S$ [M+H]$^+$ 368.47, observed 368.1; and 5-[2-cyclopentyl-1-(1H-pyrrolo[2,3-b]pyridin-2-yl)-vinyl]-1H-pyridin-2-one (100 mg, 37%): LC/MS m/e calcd for $C_{19}H_{19}N_3O$ [M+H]$^+$ 306.38, observed 306.0.

A mixture containing 2-[2-cyclopentyl-1-(6-ethoxy-pyridin-3-yl)-vinyl]-1H-pyrrolo[2,3-b]pyridine (60 mg, 0.18 mmol) and 10% palladium on activated carbon (60 mg) in methanol (20 mL) was heated at 50° C. under hydrogen (5 atm) for 5 h. After cooling to room temperature, the catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(6-ethoxy-pyridin-3-yl)-ethyl]-1H-pyrrolo[2,3-b]pyridine (33 mg, 54%): LC/MS m/e calcd for $C_{21}H_{25}N_3O$ [M+H]$^+$ 336.45, observed 336; $^1$H NMR (400 MHz, CDCl$_3$) δ ppm 1.18 (m, 2H), 1.37 (t, J=7.1 Hz, 3H), 1.47 (m, 2H), 1.62 (m, 2H), 1.68-1.87 (m, 3H), 2.09 (m, 1H), 2.23 (m, 1H), 4.15 (t, J=7.8 Hz, 1H), 4.32 (q, J=7.1 Hz, 2H), 6.32 (s, 1H), 6.65 (d, J=8.6 Hz, 1H), 7.06 (dd, J=5.0, 7.8 Hz, 1H), 7.49 (dd, J=2.1 Hz, J=8.6 Hz, 1H), 7.88 (d, J=7.8 Hz, 1H), 8.13 (m, 2H), 11.47 (s, 1H).

Example 109

2-[2-Cyclopentyl-1-(6-methanesulfonyl-pyridin-3-yl)-ethyl]-1H-pyrrolo[2,3-b]pyridine

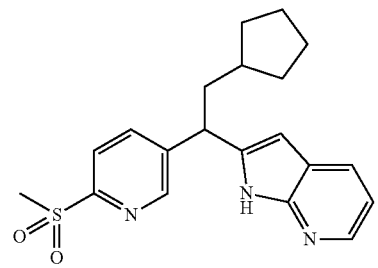

A mixture containing 2-[2-cyclopentyl-1-(6-methanesulfonyl-pyridin-3-yl)-vinyl]-1H-pyrrolo[2,3-b]pyridine (prepared as in Example 108, 100 mg, 0.27 mmol) and 10% palladium on activated carbon (80 mg) in methanol (20 mL) was heated at 50° C. under hydrogen (5 atm) for 5 h. After cooling, the catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(6-methanesulfonyl-pyridin-3-yl)-ethyl]-1H-pyrrolo[2,3-b]pyridine (40 mg, 40%): LC/MS m/e calcd for $C_{20}H_{23}N_3O_2S$ [M+H]$^+$ 370.49, observed 370; $^1$H NMR (400 MHz, CDCl$_3$) δ ppm 1.20 (m, 2H), 1.49 (m, 2H), 1.56-1.87 (m, 5H, H), 2.15 (m, 1H), 2.34 (m, 1H), 3.19 (s, 3H), 4.38 (t, J=8.0 Hz, 1H), 6.41 (s, 1H), 7.14 (m, 1H), 7.90 (dd, J=1.9 Hz, J=8.1 Hz, 1H), 7.98 (m, 2H), 8.16 (d, J=4.8 Hz, 1H), 8.72 (d, J=1.9 Hz, 1H), 11.75 (br, 1H).

Example 110

2-(2-Cyclopentyl-1-pyridin-3-yl-ethyl)-1H-pyrrolo[2,3-b]pyridine

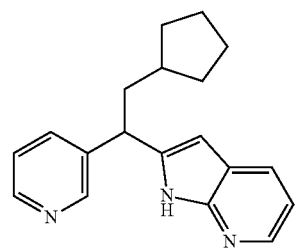

A mixture containing 5-[2-cyclopentyl-1-(1H-pyrrolo[2,3-b]pyridin-2-yl)-vinyl]-1H-pyridin-2-one (prepared as in Example 108, 100 mg, 0.33 mmol) and 10% palladium on activated carbon (80 mg) in methanol (20 mL) was heated at 50° C. under hydrogen (5 atm) for 5 h. After cooling to room temperature, the catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-(2-cyclopentyl-1-pyridin-3-yl-ethyl)-1H-pyrrolo[2,3-b]pyridine (20 mg, 10%): LC/MS m/e calcd for $C_{19}H_{21}N_3$ [M+H]$^+$ 292.40, observed 292; $^1$H NMR (400 MHz, CDCl$_3$) δ ppm 1.24 (m, 2H), 1.49 (m, 2H), 1.58-1.90 (m, 5H, H), 2.16 (m, 1H), 2.30 (m, 1H), 4.43 (t, J=7.8 Hz, 1H), 6.54 (s, 1H), 7.32 (dd, J=6.1, 7.6 Hz, 1H), 7.48 (m, 1H), 7.97 (d, J=7.8 Hz, 1H), 8.23 (m, 2H), 8.58 (d, J=4.4 Hz, 1H), 8.73 (s, 1H), 12.00 (br, 1H).

Example 111

5-Chloro-2-[2-cyclopentyl-1-(4-methanesulfonyl-phenyl)-ethyl]-1H-pyrrolo[2,3-b]pyridine

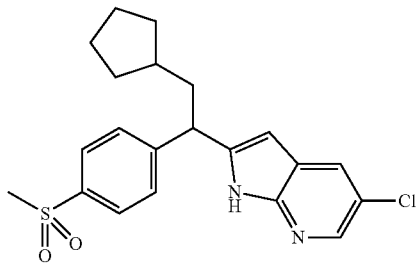

To a solution of 2-[2-cyclopentyl-1-(4-methanesulfonyl-phenyl)-ethyl]-1H-pyrrolo[2,3-b]pyridin-5-ylamine hydrochloride (prepared as in Example 107, 327 mg, 0.78 mmol) in concentrated hydrochloric acid (5 mL) at 0° C. was added a solution of sodium nitrite (270 mg, 3.9 mmol) in water (3 mL) dropwise. After stirring for 10 min at 0° C., a solution of copper (I) chloride (232 mg, 2.34 mmol) in concentrated hydrochloric acid (3 mL) was added. After stirring for another 10 min at 60° C., the mixture was adjusted to pH 8 with a 20% aqueous sodium hydroxide solution, extracted with dichloromethane, dried over anhydrous sodium sulfate and concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 5-chloro-2-[2-cyclopentyl-1-(4-methanesulfonyl-phenyl)-ethyl]-1H-pyrrolo[2,3-b]pyridine (94 mg, 30%): LC/MS m/e calcd for $C_{21}H_{23}ClN_2O_2S$ [M+H]$^+$ 403.95, observed 403.3; $^1$H NMR (400 MHz, CD$_3$OD) δ ppm 1.22 (m, 2H), 1.49 (m, 2H), 1.60-1.88 (m, 5H, H), 2.11 (m, 1H), 2.26 (m, 1H), 3.08 (s, 3H), 4.30 (t, J=7.9 Hz, 1H), 6.37 (s, 1H), 7.59 (d, J=8.4 Hz, 2H), 7.88 (s, 1H), 7.89 (d, J=8.4 Hz, 2H), 8.05 (br, 1H).

Example 112

2-[2-Cyclopentyl-1-(5-methanesulfonyl-pyridin-2-yl)-ethyl]-1H-pyrrolo[2,3-b]pyridine

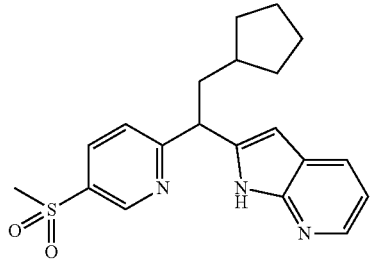

To a solution of 5-bromo-2-iodopyridine (4.27 g, 15.0 mmol) in anhydrous tetrahydrofuran (60 mL) at 0° C. was added a solution of isopropylmagnesium chloride in tetrahydrofuran (2 M, 7.5 mL, 15.04 mmol) dropwise. After stirring for 30 min at 0° C., a solution of 1-(1-benzenesulfonyl-1H-pyrrolo[2,3-b]pyridin-2-yl)-2-cyclopentyl-ethanone (prepared as in Example 43, 1.38 g, 3.76 mmol) in dry tetrahydrofuran (10 mL) was added dropwise. The resulting mixture was stirred for 14 h at room temperature, quenched with a saturated sodium chloride, extracted with ethyl acetate, dried over anhydrous sodium sulfate, and concentrated in vacuo. Purification by flash column chromatography (QingDao silica gel, 200-300 mesh, 20% ethyl acetate/hexanes) afforded 1-(1-benzenesulfonyl-1H-pyrrolo[2,3-b]pyridin-2-yl)-1-(5-bromo-pyridin-2-yl)-2-cyclopentyl-ethanol (870 mg, 15%) as a light yellow solid: LC/MS m/e calcd for $C_{25}H_{24}BrN_3O_3S$ [M+H]$^+$ 527.46, observed 527.

To a mixture of 1-(1-benzenesulfonyl-1H-pyrrolo[2,3-b]pyridin-2-yl)-1-(5-bromo-pyridin-2-yl)-2-cyclopentyl-ethanol (0.28 g, 0.53 mmol), sodium methanesulfinate (82 mg, 0.8 mmol), and copper (I) iodide (10 mg, 0.05 mmol) in dimethylsulfoxide (5 mL) was added sodium hydroxide (4 mg, 0.106 mmol). The resulting mixture was heated at 95° C. After stirring for 12 h, the mixture was poured into water (10 mL), extracted with ethyl acetate, washed with water, dried over anhydrous sodium sulfate, concentrated in vacuo. Purification by flash column chromatography (QingDao silica gel, 200-300 mesh, 20% ethyl acetate/hexanes) afforded 1-(1-benzenesulfonyl-1H-pyrrolo[2,3-b]pyridin-2-yl)-2-cyclopentyl-1-(5-methanesulfonyl-pyridin-2-yl)-ethanol (0.12 g, 43%): LC/MS m/e calcd for $C_{26}H_{27}N_3O_5S_2$ [M+H]$^+$ 526.65, observed 526.3.

A mixture of 1-(1-benzenesulfonyl-1H-pyrrolo[2,3-b]pyridin-2-yl)-2-cyclopentyl-1-(5-methanesulfonyl-pyridin-2-yl)-ethanol (0.12 g, 0.23 mmol) and tetrabutylammonium fluoride in tetrahydrofuran (1 M, 4.6 mL, 4.6 mmol) was stirred for 3 h at room temperature. After cooling to room temperature, the mixture was poured into brine (15 mL), extracted with ethyl acetate (2×100 mL), washed with a saturated aqueous ammonium chloride solution (3×50 mL), dried over anhydrous sodium sulfate and then concentrated in vacuo to afford 2-[2-cyclopentyl-1-(5-methanesulfonyl-pyridin-2-yl)-vinyl]-1H-pyrrolo[2,3-b]pyridine (84 mg, 100%) which was used in the next step without purification: LC/MS m/e calcd for $C_{20}H_{21}N_3O_2S$ [M+H]$^+$ 368.47, observed 368.1.

A mixture of 2-[2-cyclopentyl-1-(5-methanesulfonyl-pyridin-2-yl)-vinyl]-1H-pyrrolo[2,3-b]pyridine (84 mg, 0.23 mmol) and 10% palladium on activated carbon (50 mg) in methanol (150 mL) was heated at 50° C. under hydrogen (5 atm) for 5 h. After cooling to room temperature, the catalyst was removed by filtration and washed with ethyl acetate. The filtrate was concentrated in vacuo and purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(5-methanesulfonyl-pyridin-2-yl)-ethyl]-1H-pyrrolo[2,3-b]pyridine (18 mg, 21%): LC/MS m/e calcd for $C_{20}H_{23}N_3O_2S$ [M+H]$^+$ 370.49, observed 370.0; $^1$H NMR (400 MHz, CDCl$_3$) δ ppm 1.17 (m, 2H), 1.47 (m, 2H), 1.61 (m, 3H), 1.77 (m, 2H), 2.25 (m, 2H), 3.08 (s, 3H), 4.44 (t, J=7.7 Hz, 1H), 6.44 (s, 1H), 7.11 (dd, J=4.9, 7.8 Hz, 1H), 7.49 (d, J=8.2 Hz, 1H), 7.95 (d, J=7.8 Hz, 1H), 8.13 (dd, J=2.3 Hz, J=8.2 Hz, 1H), 8.27 (d, J=4.9 Hz, 1H), 9.14 (d, J=2.0 Hz, 1H), 10.97 (br, 1H).

Example 113

2-[2-Cyclopentyl-1-(4-methanesulfonyl-phenyl)-ethyl]-6-methoxy-1H-pyrrolo[2,3-b]pyridine

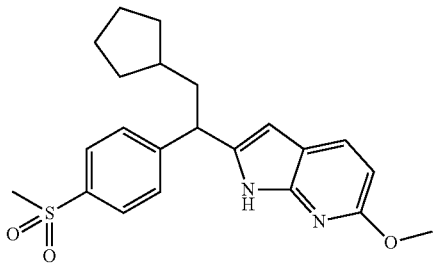

To a solution of 7-azaindole (84.8 g, 0.72 mol) in ethyl acetate (700 mL) at 0° C. was added a solution of m-chloroperoxybenzoic acid (19.6 g, 1.14 mol) in ethyl acetate (600 mL) over 1.5 h. The resulting solution was stirred at room temperature for 4 h. After cooling to 0° C., the resulting slurry was filtered and the solid was washed with ethyl acetate (3×30 mL), and the filtrate concentrated in vacuo. The residue was treated at 0° C. with an aqueous 30% potassium carbonate solution to pH 9.5~10.5. This mixture was stirred for 2 h at 0° C., filtered to collect the precipitate and the precipitate washed with water (2×20 mL) and dried in vacuo to afford 7-azaindole N-oxide (77 g, 80%); LC/MS m/e calcd for $C_7H_6N_2O$ [M+H]$^+$ 135.15, observed 134.9.

A mixture of 7-azaindole N-oxide (4.2 g, 31.3 mmol) in acetic anhydride (23 mL) was heated to reflux for 12 h. The mixture was cooled, concentrated to half its volume, diluted with dichloromethane (100 mL), washed with water (2×20 mL), dried over anhydrous sodium sulfate and concentrated in vacuo. The residue was purified by column chromatography (silica gel from QingDao, 200-300 mesh, 15% ethyl acetate/hexanes) afforded acetic acid 1-acetyl-1H-pyrrolo[2,3-b]pyridin-6-yl ester (4.0 g, 59%): LC/MS m/e calcd for $C_{11}H_{10}N_2O_3$ [M+H]$^+$ 219.21, observed 219.1.

A mixture of acetic acid 1-acetyl-1H-pyrrolo[2,3-b]pyridin-6-yl ester (4.0 g, 18.3 mmol) and potassium carbonate (10.45 g, 75.7 mmol) in methanol/water (50%, 260 mL) was stirred at room temperature for 12 h. The reaction mixture was concentrated to half its volume and extracted with chloroform. The organic layer was dried over anhydrous sodium sulfate and evaporated. The residue was purified by flash column chromatography (silica gel from QingDao, 200-300 mesh, 10% methanol/dichloromethane) afforded 1H-pyrrolo[2,3-b]pyridin-6-ol (1.52 g, 62%): LC/MS m/e calcd for $C_7H_6N_2O$ [M+H]$^+$ 135.14, observed 135.0.

A mixture of 1H-pyrrolo[2,3-b]pyridin-6-ol (1.52 g, 11.4 mmol) and potassium carbonate (7.86 g, 57 mmol) in acetone (100 mL) was stirred under nitrogen at room temperature for 1 h. Iodomethane (2.6 g, 18.2 mmol) was added and the resulting mixture stirred at 56° C. for 12 h. The mixture was filtered, and the filtrate was concentrated to half its volume, diluted with water, and extracted with dichloromethane. The combined organic layers were dried over anhydrous sodium sulfate and evaporated. The residue was purified by flash column chromatography (silica gel from QingDao, 200-300 mesh, 20% ethyl acetate/hexanes) to afford 6-methoxy-1H-pyrrolo[2,3-b]pyridine (0.5 g, 30%): LC/MS m/e calcd for $C_8H_8N_2O$ [M+H]$^+$ 149.17, observed 149.1.

To a mixture of 6-methoxy-1H-pyrrolo[2,3-b]pyridine (1.2 g, 8.1 mmol), sodium hydroxide (0.97 g, 24.3 mmol) and tetrabutylammonium bromide (78.4 mg, 0.24 mmol) in dichloromethane (50 mL) at 0° C. was added benzenesulfonyl chloride (2.14 g, 12.15 mmol) dropwise. The resulting mixture was stirred for 12 h at room temperature. The mixture was washed with water (2×10 mL), dried over anhydrous sodium sulfate and concentrated in vacuo to give a residue which was purified by flash column chromatography (silica gel from QingDao, 200-300 mesh, 100% dichloromethane) to afford 1-benzenesulfonyl-6-methoxy-1H-pyrrolo[2,3-b]pyridine (2.0 g, 85%): LC/MS m/e calcd for $C_{14}H_{12}N_2O_3S$ [M+H]$^+$ 290.33, observed 289.0.

To a suspension of 1-benzenesulfonyl-6-methoxy-1H-pyrrolo[2,3-b]pyridine (2.0 g, 6.74 mmol) in dry tetrahydrofuran (60 mL) at −78° C. was added freshly prepared lithium diisopropylamide [prepared by adding 1.6 M n-butyllithium in n-hexane (6.6 mL, 10.42 mmol) to a 0° C. solution of diisopropylamine (1.12 g, 11.1 mmol) in dry tetrahydrofuran (20 mL)] dropwise. The mixture was stirred at −78° C. for 20 min and then treated with cyclopentanecarbaldehyde (1.56 g, 13.8 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (silica gel from QingDao, 200-300 mesh, 25% ethyl acetate/hexanes) afforded 1-benzenesulfonyl-6-methoxy-1H-pyrrolo[2,3-b]pyridin-2-yl]-2-cyclopentyl-ethanol as a white solid (2.54 g, 91%): LC/MS m/e calcd for $C_{21}H_{24}N_2O_4S$ [M+H]$^+$ 401.50, observed 401.2.

To a solution of 1-(-benzenesulfonyl-6-methoxy-1H-pyrrolo[2,3-b]pyridin-2-yl]-2-cyclopentyl-ethanol (1.39 g, 3.47 mmol) in dichloromethane (15 mL) was added Dess-Martin periodinane (5.15 g, 12.15 mmol) at 25° C. The reaction mixture was stirred at 25° C. for 1 h and then quenched with a saturated aqueous sodium bicarbonate solution (60 mL). The mixture was extracted with ethyl acetate (250 mL), washed with a saturated aqueous sodium bicarbonate solution (3×50 mL), brine, dried over anhydrous sodium sulfate and then concentrated in vacuo. The residue was purified by flash column chromatography (silica gel from QingDao, 200-300 mesh, 18% ethyl acetate/hexanes) afforded 1-(-benzenesulfonyl-6-methoxy-1H-pyrrolo[2,3-b]pyridin-2-yl]-2-cyclopentyl-ethanone (0.59 g, 42%) as a light yellow solid: LC/MS m/e calcd for $C_{21}H_{22}N_2O_4S$ [M+H]$^+$ 399.48, observed 399.1.

To a solution of 1-(-benzenesulfonyl-6-methoxy-1H-pyrrolo[2,3-b]pyridin-2-yl]-2-cyclopentyl-ethanone (0.59 g, 1.48 mmol) in anhydrous tetrahydrofuran (30 mL) at −78° C. under nitrogen atmosphere was added a solution of lithium bis(trimethylsilyl)amide in tetrahydrofuran (1.0 M, 2.2 mL, 2.2 mmol) dropwise. After stirring at −78° C. for 1 h, a solution of p-toluenesulfonic anhydride (870 mg, 2.66 mmol) in tetrahydrofuran (5 mL) was added dropwise. The resulting mixture was stirred for an additional 1.5 h at −78° C. The reaction was quenched with water, extracted with ethyl acetate (100 mL), washed with brine, dried over anhydrous sodium sulfate and then concentrated in vacuo. Purification by flash column chromatography (silica gel from QingDao, 200-300 mesh, 25% ethyl acetate/hexanes) afforded toluene-4-sulfonic acid 1-(1-benzenesulfonyl-6-methoxy-1H-pyrrolo[2,3-b]pyridin-2-yl)-2-cyclopentyl-vinyl ester (0.60 g, 74.1%) as a light yellow solid: LC/MS m/e calcd for $C_{28}H_{28}N_2O_6S_2$ [M+H]$^+$ 553.67, observed 553.0.

To a mixture of toluene-4-sulfonic acid-1-benzenesulfonyl-6-methoxy-1H-pyrrolo[2,3-b]pyridin-2-yl)-2-cyclopentyl-vinyl ester (0.6 g, 1.1 mmol), 4-methylsulfonyl phenylboronic acid (650 mg, 3.3 mmol) and dichlorobis(triphenylphosphine)palladium (II) (77.2 mg, 0.11 mmol) in dioxane (5 mL) was added an aqueous sodium carbonate solution (2 M, 1.65 mL, 3.3 mmol). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash column chromatography (silica gel from QingDao, 200-300 mesh, 33% ethyl acetate/hexanes) afforded 1-benzenesulfonyl-2-[2-cyclopentyl-1-(4-methanesulfonyl-phenyl)-vinyl]-6-methoxy-1H-pyrrolo[2,3-b]pyridine (300 mg, 52%) as a light yellow solid: LC/MS m/e calcd for $C_{28}H_{28}N_2O_5S_2$ $[M+H]^+$ 537.67, observed 537.1.

A mixture of 1-benzenesulfonyl-2-[2-cyclopentyl-1-(4-methanesulfonyl-phenyl)-vinyl]-6-methoxy-1H-pyrrolo[2,3-b]pyridine (300 mg, 0.56 mmol) and tetrabutylammonium fluoride in tetrahydrofuran (1.0 M, 20 mL, 20 mmol) was stirred for 12 h at room temperature. The mixture was poured into brine (15 mL), extracted with ethyl acetate (2×100 mL), washed with a saturated aqueous ammonium chloride solution (3×50 mL), dried over anhydrous sodium sulfate and then concentrated in vacuo to give 2-[2-cyclopentyl-1-(4-methanesulfonyl-phenyl)-vinyl]-6-methoxy-1H-pyrrolo[2,3-b]pyridine (0.22 g, 100%) as a solid which was used in the next step without purification: LC/MS m/e calcd for $C_{22}H_{24}N_2O_3S$ $[M+H]^+$ 397.51, observed 397.2.

A mixture of 2-[2-cyclopentyl-1-(4-methanesulfonyl-phenyl)-vinyl]-6-methoxy-1H-pyrrolo[2,3-b]pyridine (0.22 g, 0.56 mmol) and 10% palladium on activated carbon (0.2 g) in methanol (150 mL) was heated at 50° C. under hydrogen (50 psi) for 12 h. After cooling to room temperature, the catalyst was removed by filtration and washed with ethyl acetate. The filtrate was concentrated in vacuo to give a residue which was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-6-methoxy-1H-pyrrolo[2,3-b]pyridine (18 mg, 8.2%) as a white solid: LC/MS m/e calcd for $C_{22}H_{26}N_2O_3S$ $[M+H]^+$ 399.53, observed 399.3; $^1H$ NMR (400 MHz, CDCl$_3$) δ ppm 1.16 (m, 2H), 1.48 (m, 2H), 1.56-1.85 (m, 5H, H), 2.04 (m, 1H), 2.17 (m, 1H), 3.05 (s, 3H), 3.90 (s, 3H), 4.14 (t, J=7.7 Hz, 1H), 6.29 (s, 1H), 6.55 (d, J=8.5 Hz, 1H), 7.42 (d, J=8.1 Hz, 2H), 7.73 (d, J=8.5 Hz, 1H), 7.86 (d, J=8.1 Hz, 2H), 8.31 (s, 1H).

Example 114

5-Chloro-2-[1-(4-methanesulfonyl-phenyl)-2-(tetrahydro-pyran-4-yl)-ethyl]-1H-pyrrolo[2,3-b]pyridine

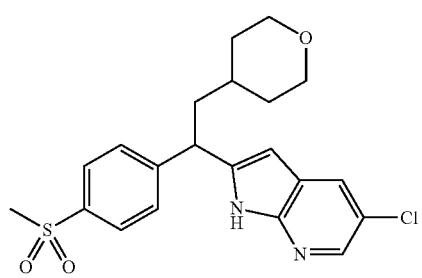

To a suspension of (1-benzenesulfonyl-1H-pyrrolo[2,3-b]pyridin-5-yl)-carbamic acid tert-butyl ester (prepared as in Example 107, 3.4 g, 9.1 mmol) in dry tetrahydrofuran (120 mL) at −78° C. was added freshly prepared lithium diisopropylamide [prepared by adding 1.6 M n-butyllithium in n-hexane (17.1 mL, 27.3 mmol) to a 0° C. solution of diisopropylamine (2.76 g, 27.3 mmol) in dry tetrahydrofuran (20 mL)] dropwise. The mixture was stirred at −78° C. for 5 min and then treated with (tetrahydro-pyran-4-yl)-acetaldehyde (2.91 g, 22.75 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (QingDao silica gel, 200-300 mesh, 75% ethyl acetate/hexanes) afforded {1-benzenesulfonyl-2-[1-hydroxy-2-(tetrahydro-pyran-4-yl)-ethyl]-1H-pyrrolo[2,3-b]pyridin-5-yl}-carbamic acid tert-butyl ester (1.5 g, 33%) as a white solid: LC/MS m/e calcd for $C_{25}H_{31}N_3O_6S$ $[M+H]^+$ 502.61, observed 502.2.

To a solution of {1-benzenesulfonyl-2-[1-hydroxy-2-(tetrahydro-pyran-4-yl)-ethyl]-1H-pyrrolo[2,3-b]pyridin-5-yl}-carbamic acid tert-butyl ester (1.5 g, 3.0 mmol) in dichloromethane (15 mL) was added Dess-Martin periodinane (4.44 g, 10.4 mmol) at 25° C. The reaction mixture was stirred at 25° C. for 1 h and then quenched with a saturated aqueous sodium bicarbonate solution (20 mL). The mixture was extracted with ethyl acetate (100 mL), washed with a saturated aqueous sodium bicarbonate solution (3×20 mL), brine, dried over anhydrous sodium sulfate and then concentrated in vacuo. The residue was purified by flash column chromatography (silica gel from QingDao, 200-300 mesh, 50% ethyl acetate/hexanes) afforded [1-benzenesulfonyl-2-(2-tetrahydro-pyran-4-yl-acetyl)-1H-pyrrolo[2,3-b]pyridin-5-yl]-carbamic acid tert-butyl ester (1.0 g, 67%) as a light yellow solid: LC/MS m/e calcd for $C_{25}H_{29}N_3O_6S$ $[M+H]^+$ 500.59, observed 500.2.

To a solution of [1-benzenesulfonyl-2-(2-tetrahydro-pyran-4-yl-acetyl)-1H-pyrrolo[2,3-b]pyridin-5-yl]-carbamic acid tert-butyl ester (1.0 g, 2.0 mmol) in tetrahydrofuran (40 mL) at −78° C. was added lithium bis(trimethylsilyl)amide in tetrahydrofuran (1 M, 5.0 mL, 5.0 mmol) dropwise. After stirring at −78° C. for 0.5 h, a solution of p-toluenesulfonic anhydride (980 mg, 3.0 mmol) in tetrahydrofuran (10 mL) was added dropwise. The resulting solution was stirred at −78° C. for an additional 1 h. The reaction was quenched with water, extracted with ethyl acetate (100 mL), washed with brine, dried over anhydrous sodium sulfate and then concentrated in vacuo. Purification by flash column chromatography (silica gel from QingDao, 200-300 mesh, 50% ethyl acetate/hexanes) afforded toluene-4-sulfonic acid 1-(1-benzenesulfonyl-5-tert-butoxycarbonylamino-1H-pyrrolo[2,3-b]pyridin-2-yl)-2-(tetrahydro-pyran-4-yl)-vinyl ester (0.8 g, 61%) as a light yellow solid: LC/MS m/e calcd for $C_{32}H_{35}N_3O_8S_2$ $[M+H]^+$ 654.78, observed 654.4.

To a mixture of 1-(1-benzenesulfonyl-5-tert-butoxycarbonylamino-1H-pyrrolo[2,3-b]pyridin-2-yl)-2-(tetrahydro-pyran-4-yl)-vinyl ester (0.7 g, 1.07 mmol), 4-methylsulfonyl phenylboronic acid (640 mg, 3.22 mmol), and dichlorobis(triphenylphosphine)palladium (II) (75 mg, 0.11 mmol) in dioxane (5 mL) was added an aqueous sodium carbonate solution (2 M, 1.61 mL, 3.22 mmol). The resulting mixture was subjected to microwave irradiation for 3 h at 100° C. The mixture was diluted with ethyl acetate (100 mL), washed with a saturated aqueous sodium bicarbonate solution (2×20 mL), brine, dried over anhydrous sodium sulfate and then concentrated in vacuo. Purification by flash column chromatography (QingDao silica gel, 200-300 mesh, 75% ethyl acetate/hexanes) afforded {1-benzenesulfonyl-2-[1-(4-methanesulfonyl-phenyl)-2-(tetrahydro-pyran-4-yl)-vinyl]-1H-pyrrolo[2, 3-b]pyridin-5-yl}-carbamic acid tert-butyl ester (670 mg, 98%) as a light yellow solid: LC/MS m/e calcd for $C_{32}H_{35}N_3O_7S_2$ [M+H]$^+$ 638.78, observed 638.2.

A mixture of {1-benzenesulfonyl-2-[1-(4-methanesulfonyl-phenyl)-2-(tetrahydro-pyran-4-yl)-vinyl]-1H-pyrrolo[2,3-b]pyridin-5-yl}-carbamic acid tert-butyl ester (670 mg, 1.05 mmol) and tetrabutylammonium fluoride in tetrahydrofuran (1 M, 21 mL, 21 mmol) was stirred for 3 h at 60° C. After cooling to room temperature, the mixture was poured into brine (20 mL), extracted with ethyl acetate (2×100 mL), washed with a saturated aqueous ammonium chloride solution (3×50 mL), dried over anhydrous sodium sulfate and then concentrated in vacuo to give {2-[1-(4-methanesulfonyl-phenyl)-2-(tetrahydro-pyran-4-yl)-vinyl]-1H-pyrrolo[2,3-b]pyridin-5-yl}-carbamic acid tert-butyl ester (0.52 g, 100%) which was used in the next step without purification: LC/MS m/e calcd for $C_{26}H_{31}N_3O_5S$ [M+H]$^+$ 498.62, observed 498.2.

A mixture of {2-[1-(4-methanesulfonyl-phenyl)-2-(tetrahydro-pyran-4-yl)-vinyl]-1H-pyrrolo[2,3-b]pyridin-5-yl}-carbamic acid tert-butyl ester (520 mg, 1.05 mmol) and 10% palladium on activated carbon (0.2 g) in methanol (150 mL) was heated at 50° C. under hydrogen (5 atm) for 12 h. After cooling to room temperature, the catalyst was removed by filtration and washed with ethyl acetate. The filtrate was concentrated in vacuo to give {2-[1-(4-methanesulfonyl-phenyl)-2-(tetrahydro-pyran-4-yl)-ethyl]-1H-pyrrolo[2,3-b]pyridin-5-yl}-carbamic acid tert-butyl ester (520 mg, 100%) which was used in the next step without purification: LC/MS m/e calcd for $C_{26}H_{33}N_3O_5S$ [M+H]$^+$ 500.63, observed 500.2.

A solution of {2-[1-(4-methanesulfonyl-phenyl)-2-(tetrahydro-pyran-4-yl)-ethyl]-1H-pyrrolo[2,3-b]pyridin-5-yl}-carbamic acid tert-butyl ester (520 mg, 1.05 mmol) in dichloromethane (10 mL) was treated with dry hydrogen chloride gas for 30 min. The resulting mixture was stirred for 3 h at room temperature. The solvent was removed to afford 2-[1-(4-methanesulfonyl-phenyl)-2-(tetrahydro-pyran-4-yl)-ethyl]-1H-pyrrolo[2,3-b]pyridin-5-ylamine hydrochloride salt (454 mg, 100%): LC/MS m/e calcd for $C_{21}H_{25}N_3O_3S$ [M+H]$^+$ 400.52, observed 400.0.

To a solution of 2-[1-(4-methanesulfonyl-phenyl)-2-(tetrahydro-pyran-4-yl)-ethyl]-1H-pyrrolo[2,3-b]pyridin-5-ylamine hydrochloride (454 mg, 1.05 mmol) in concentrated hydrochloric acid (6 mL) at 0° C. was added a solution of sodium nitrite (360 mg, 5.25 mmol) in water (3 mL) dropwise. After stirring for 10 min at 0° C., a solution of copper (I) chloride (310 mg, 3.15 mmol) in concentrated hydrochloric acid (3 mL) was added. After stirring for another 10 min at 60° C., the mixture was treated with 20% sodium hydroxide solution (pH 8), extracted with dichloromethane, dried over anhydrous sodium sulfate and concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 5-chloro-2-[1-(4-methanesulfonyl-phenyl)-2-(tetrahydro-pyran-4-yl)-ethyl]-1H-pyrrolo[2,3-b]pyridine (50 mg, 11%): LC/MS m/e calcd for $C_{21}H_{23}ClN_2O_3S$ [M+H]$^+$ 419.95, observed 419.3; $^1$H NMR (400 MHz, CD$_3$OD) δ ppm 8.06 (s, 1H), 7.87-7.92 (m, 3H), 7.60 (d, J=8.1 Hz, 2H), 6.39 (s, 1H), 4.43 (t, J=8.0 Hz, 1H), 3.85-3.92 (m, 2H), 3.21-3.29 (m, 2H), 3.09 (s, 3H), 2.18-2.26 (m, 1H), 1.98-2.06 (m, 1H), 1.62-1.75 (m, 2H), 1.30-1.51 (m, 3H).

Example 115

2-Cyclobutyl-1-(4-methanesulfonyl-phenyl)-1-(1H-pyrrolo[2,3-]pyridin-2-yl)-ethanol

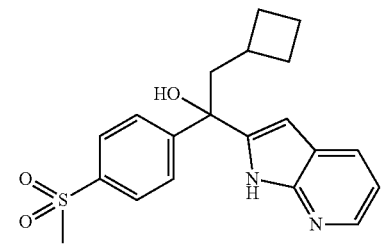

To a suspension of 1-benzenesulfonyl-1H-pyrrolo[2,3-b]pyridine (6.0 g, 23.3 mmol) in dry tetrahydrofuran (300 mL) at −78° C. was added n-butyllithium in n-hexane (1.6 M, 10 mL, 16 mmol). The mixture was stirred at −78° C. for 5 min and then treated with 4-methylsulfanylbenzaldehyde (2.4 g, 15.8 mmol) dropwise. The resulting mixture was stirred at −78° C. for 1 h and quenched with brine. The mixture was extracted with ethyl acetate (2×500 mL), washed with brine, dried over anhydrous sodium sulfate and concentrated in vacuo. The residue was washed with dichloromethane (2×5 mL) and dried in vacuo to afford (1-benzenesulfonyl-1H-pyrrolo[2,3-b]pyridin-2-yl)-(4-methylsulfanyl-phenyl)-methanol (7.0 g, 73%) as a white solid: LC/MS m/e calcd for $C_{21}H_{18}N_2O_3S_2$ [M+H]$^+$ 411.52, observed 411.3.

To a solution of (1-benzenesulfonyl-1H-pyrrolo[2,3-b]pyridin-2-yl)-(4-methylsulfanyl-phenyl)-methanol (7.0 g, 17.1 mmol) in dichloromethane (600 ml) was added Dess-Martin periodinane (21.8 g, 51.3 mmol) at 25° C. The reaction mixture was stirred at 25° C. for 1 h and then quenched with a saturated aqueous sodium bicarbonate solution (100 mL). The mixture was extracted with ethyl acetate (500 mL), washed with a saturated aqueous sodium bicarbonate solution (3×80 mL), brine, dried over anhydrous sodium sulfate and then concentrated in vacuo. Purification by flash column chromatography (silica gel from QingDao, 200-300 mesh, 30% ethyl acetate/hexanes) afforded (1-benzenesulfonyl-1H-pyrrolo[2,3-b]pyridin-2-yl)-(4-methylsulfanyl-phenyl)-methanone (6.73 g, 97%) as a white solid: LC/MS m/e calcd for $C_{21}H_{16}N_2O_3S_2$ [M+H]$^+$ 409.50, observed 409.2.

To a solution of (1-benzenesulfonyl-1H-pyrrolo[2,3-b]pyridin-2-yl)-(4-methylsulfanyl-phenyl)-methanone (0.6 g, 1.47 mmol) in anhydrous tetrahydrofuran (5 mL) at 0° C. was added a solution of freshly prepared Grignard reagent [To a suspension of magnesium turnings (0.14 g, 5.88 mmol) in anhydrous tetrahydrofuran (5 mL) was added (bromomethyl)cyclobutane (0.44 g, 2.94 mmol) at room temperature. After initiation by iodine, the resulting solution was refluxed for 30 min, and then cooled to room temperature] dropwise. After stirring for 3 h at 0° C., the mixture was poured into brine (10 mL), extracted with ethyl acetate (3×20 mL), dried over anhydrous sodium sulfate and then concentrated in vacuo. The residue was purified by flash column chromatography (silica gel from QingDao, 200-300 mesh, 25% ethyl acetate/hexanes) afforded 2-cyclobutyl-1-(4-methylsulfanyl-phenyl)-1-(1H-pyrrolo[2,3-b]pyridin-2-yl)-ethanol (90 mg, 18%) as a white solid: LC/MS m/e calcd for $C_{20}H_{22}N_2OS$ [M+H]$^+$ 339.48, observed 339.0.

A solution of 2-cyclobutyl-1-(4-methylsulfanyl-phenyl)-1-(1H-pyrrolo[2,3-b]pyridin-2-yl)-ethanol (90 mg, 0.266 mmol) in methanol (6 mL) was added a sodium metaperiodate (171 mg, 0.798 mmol) solution in water (3 mL). The resulting mixture was stirred for 12 h at room temperature, extracted with ethyl acetate (3×20 mL), dried over anhydrous sodium sulfate, concentrated in vacuo to afford 2-cyclobutyl-1-(4-methanesulfinyl-phenyl)-1-(1H-pyrrolo[2,3-b]pyridin-2-yl)-ethanol (94.2 mg, 100%) which was used in the next step without purification: LC/MS m/e calcd for $C_{20}H_{22}N_2O_2S$ [M+H]$^+$ 355.47, observed 355.4.

To a solution of 2-cyclobutyl-1-(4-methanesulfinyl-phenyl)-1-(1H-pyrrolo[2,3-b]pyridin-2-yl)-ethanol (94.2 mg, 0.266 mmol) in methanol (10 mL) at 0° C. was added a solution of potassium permanganate (42.0 mg, 0.266 mmol) in water (5 mL) dropwise. The mixture was stirred for 2 h at 0° C., extracted with ethyl acetate, washed with brine, dried over anhydrous sodium sulfate, filtered through a short silica gel pad (QingDao silica gel, 200-300 mesh), and concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-cyclobutyl-1-(4-methanesulfonyl-phenyl)-1-(1H-pyrrolo[2,3-b]pyridin-2-yl)-ethanol (32.2 mg, 33%): LC/MS m/e calcd for $C_{20}H_{22}N_2O_3S$ [M+H]$^+$ 371.47, observed 371.2; $^1$H NMR (400 MHz, CD$_3$OD) δ ppm 1.49 (m, 1H), 1.57-1.83 (m, 4H), 1.95 (m, 1H), 2.52 (m, 3H), 3.10 (s, 3H), 6.53 (s, 1H), 7.07 (dd, J=4.9, 7.8 Hz, 1H), 7.79 (d, J=8.7 Hz, 2H), 7.90 (d, J=8.7 Hz, 2H), 7.95 (dd, J=1.5 Hz, J=7.8 Hz, 1H), 7.95 (dd, J=1.5 Hz, J=4.9 Hz, 1H).

Example 116

2-[(E)-2-cyclopentyl-1-(4-methanesulfonyl-phenyl)-vinyl]-5-fluoro-1H-pyrrolo[2,3-b]pyridine

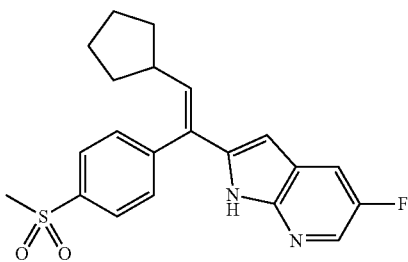

To a solution of 1-benzenesulfonyl-1H-pyrrolo[2,3-b]pyridin-5-ylamine (3.0 g, 11 mmol) in 40% fluoroboric acid (45 mL) at 0° C. was added a solution of sodium nitrite (0.91 g, 13.2 mmol) in water (2 mL) dropwise. After stirring for 20 min at 0° C., the mixture was filtered to collect the precipitate. The precipitate was washed with ethanol (20 mL) and ether (20 mL), dried in vacuo to afford the diazonium fluoroborate which was carefully decomposed at 130° C.~150° C. for 10 min. After cooling to room temperature, the residue was dissolved in dichloromethane (100 mL), washed with a saturated sodium carbonate solution (2×30 mL), dried over anhydrous sodium sulfate and then concentrated in vacuo. The residue was purified by flash column chromatography (silica gel from QingDao, 200-300 mesh, 50% dichloromethane/hexanes) to afford 1-benzenesulfonyl-5-fluoro-1H-pyrrolo[2,3-b]pyridine (1.1 g, 36%): LC/MS m/e calcd for $C_{13}H_9N_2O_2S$ [M+H]$^+$ 277.29, observed 277.1.

To a suspension of 1-benzenesulfonyl-5-fluoro-1H-pyrrolo[2,3-b]pyridine (1.1 g, 3.99 mmol) in dry tetrahydrofuran (30 mL) at −78° C. at was added n-butyllithium in n-hexane (1.6 M, 2.74 mL, 4.38 mmol) dropwise. The mixture was stirred at −78° C. for 5 min and then treated with cyclopentanecarbaldehyde (0.67 g, 5.99 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (QingDao silica gel, 200-300 mesh, 50% dichloromethane/hexanes) afforded 1-(1-benzenesulfonyl-5-fluoro-1H-pyrrolo[2,3-b]pyridin-2-yl)-2-cyclopentyl-ethanol (1.55 g, 100%): LC/MS m/e calcd for $C_{20}H_{21}FN_2O_3S$ [M+H]$^+$ 389.46, observed 389.2.

To a solution of 1-(1-benzenesulfonyl-5-fluoro-1H-pyrrolo[2,3-b]pyridin-2-yl)-2-cyclopentyl-ethanol (1.55 g, 3.99 mmol) in dichloromethane (100 ml) was added Dess-Martin periodinane (5.08 g, 11.97 mmol) at 25° C. The reaction mixture was stirred at 25° C. for 1 h and then quenched with a saturated aqueous sodium bicarbonate solution (60 mL). The mixture was extracted with ethyl acetate (150 mL), washed with a saturated aqueous sodium bicarbonate solution (3×30 mL), brine, dried over anhydrous sodium sulfate and then concentrated in vacuo. The residue was purified by flash column chromatography (silica gel from QingDao, 200-300 mesh, 50% dichloromethane/hexanes) to afford 1-(1-benzenesulfonyl-5-fluoro-1H-pyrrolo[2,3-b]pyridin-2-yl)-2-cyclopentyl-ethanone (1.0 g, 65%) as a light yellow solid: LC/MS m/e calcd for $C_{20}H_{19}FN_2O_3S$ [M+H]$^+$ 387.45, observed 387.1.

To a solution of 1-(1-benzenesulfonyl-5-fluoro-1H-pyrrolo[2,3-b]pyridin-2-yl)-2-cyclopentyl-ethanone (1.0 g, 2.6 mmol) in anhydrous tetrahydrofuran (30 mL) at −78° C. under nitrogen atmosphere was added a solution of lithium bis(trimethylsilyl)amide in tetrahydrofuran (1 M, 3.9 mL, 3.9 mmol) dropwise. After stirring at −78° C. for 1 h, a solution of p-toluenesulfonic anhydride (1.3 g, 3.9 mmol) in tetrahydrofuran (5 mL) was added dropwise. The resulting mixture was stirred at −78° C. for an additional 1.5 h. The reaction was quenched with water, extracted with ethyl acetate (100 mL), washed with brine, dried over anhydrous sodium sulfate and then concentrated in vacuo. Purification by flash column chromatography (silica gel from QingDao, 200-300 mesh, 25% ethyl acetate/hexanes) afforded toluene-4-sulfonic acid 1-(1-benzenesulfonyl-5-fluoro-1H-pyrrolo[2,3-b]pyridin-2-yl)-2-cyclopentyl-vinyl ester (1.0 g, 71%) as a light yellow solid: LC/MS m/e calcd for $C_{27}H_{25}FN_2O_5S_2$ [M+H]$^+$ 541.64, observed 541.1.

To a mixture of toluene-4-sulfonic acid 1-(1-benzenesulfonyl-5-fluoro-1H-pyrrolo[2,3-b]pyridin-2-yl)-2-cyclopentyl-vinyl ester (500 mg, 0.93 mmol), 4-methylsulfonyl phenylboronic acid (560 mg, 2.78 mmol), and dichlorobis(triphenylphosphine)palladium (II) (65.3 mg, 0.09 mmol) in dioxane (4 mL) was added an aqueous sodium carbonate solution (2 M, 1.40 mL, 2.8 mmol). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. The residue was purified by flash column chromatography (silica gel from QingDao, 200-300 mesh, 25% ethyl acetate/hexanes) to afford 1-benzenesulfonyl-2-[2-cyclopentyl-1-(4-methanesulfonyl-phenyl)-vinyl]-5-fluoro-1H-pyrrolo[2,3-b]pyridine (200 mg, 41%) as a light yellow solid: LC/MS m/e calcd for $C_{27}H_{25}FN_2O_4S_2$ [M+H]$^+$ 525.64, observed 525.1.

A mixture of 1-benzenesulfonyl-2-[2-cyclopentyl-1-(4-methanesulfonyl-phenyl)-vinyl]-5-fluoro-1H-pyrrolo[2,3-b]pyridine (200 mg, 0.38 mmol) and tetrabutylammonium fluoride in tetrahydrofuran (1 M, 7.6 mL, 7.6 mmol) was stirred for 12 h at room temperature. The mixture was poured into brine (15 mL), extracted with ethyl acetate (2×50 mL), washed with a saturated aqueous ammonium chloride solution (3×20 mL), dried over anhydrous sodium sulfate and then concentrated in vacuo to give 2-[(E)-2-cyclopentyl-1-(4-methanesulfonyl-phenyl)-vinyl]-5-fluoro-1H-pyrrolo[2,3-b]pyridine (147 mg, 100%) as a solid which was used in the next step without purification: LC/MS m/e calcd for $C_{21}H_{21}FN_2O_2S$ [M+H]$^+$ 385.48, observed 385.2; $^1$H NMR (400 MHz, MeOD) δ ppm 8.04 (d, J=8.3 Hz, 3H), 7.51-7.56 (m, 3H), 6.45 (d, J=10.1 Hz, 1H), 5.77 (s, 1H), 3.32 (br. s., 1H), 3.16-3.20 (m, 3H), 2.37-2.44 (m, 1H), 1.72-1.82 (m, 4H), 1.45-1.57 (m, 4H).

Example 117

2-[2-Cyclopentyl-1-(4-methanesulfonyl-phenyl)-ethyl]-5-fluoro-1H-pyrrolo[2,3-b]pyridine

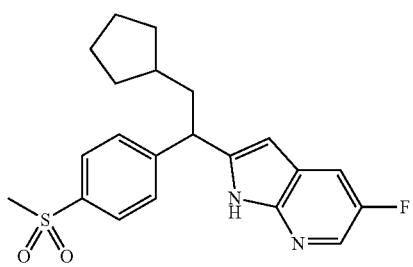

A mixture of 2-[2-cyclopentyl-1-(4-methanesulfonyl-phenyl)-vinyl]-5-fluoro-1H-pyrrolo[2,3-b]pyridine (prepared as in Example 116, 147 mg, 0.38 mmol) and 10% palladium on activated carbon (0.2 g) in methanol (50 mL) was heated at 50° C. under hydrogen (50 psi) for 5 h. After cooling to room temperature, the catalyst was removed by filtration and washed with ethyl acetate. The filtrate was concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-5-fluoro-1H-pyrrolo[2,3-b]pyridine as a white solid (60 mg, 41%): LC/MS m/e calcd for $C_{21}H_{23}FN_2O_2S$ [M+H]$^+$ 387.49, observed 387.2; $^1$H NMR (400 MHz, CD$_3$OD) δ ppm 8.00 (t, J=2.3 Hz, 1H), 7.90 (d, J=8.3 Hz, 2H), 7.58-7.66 (m, 3H), 6.40 (s, 1H), 4.31 (t, J=8.0 Hz, 1H), 3.09 (s, 3H), 2.24-2.32 (m, 1H), 2.08-2.16 (m, 1H), 1.60-1.87 (m, 5H), 1.45-1.56 (m, 2H), 1.18-1.30 (m, 2H).

Example 118

2-[2-Cyclopentyl-1(R)-(4-methanesulfonyl-phenyl)-ethyl]-5-fluoro-1H-pyrrolo[2,3-b]pyridine

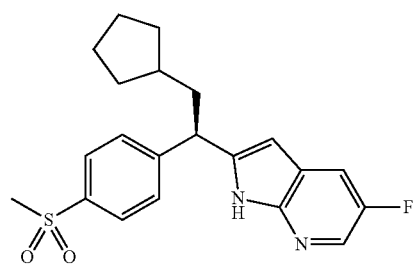

The 1:1 mixture of enantiomers of 2-[2-cyclopentyl-1-(4-methanesulfonyl-phenyl)-ethyl]-5-fluoro-1H-pyrrolo[2,3-b]pyridine (prepared as in Example 117) were separated by Agilent high performance liquid chromatography (chiral column: Daicel IA-H, 250 mm×20 mm i. d., 5 μm-particle size, temperature: 25° C., flow rate of 15 mL/min, 50% alcohol/hexanes as mobile phase and UV detection: 214 and 254 nm) to afford two pure enantiomers. The second peak, 2-[2-cyclopentyl-1(R)-(4-methanesulfonyl-phenyl)-ethyl]-5-fluoro-1H-pyrrolo[2,3-b]pyridine was isolated as white solid: LC/MS m/e calcd for $C_{21}H_{23}FN_2O_2S$ [M+H]$^+$ 387.49, observed 387.2; $^1$H NMR (400 MHz, CD$_3$OD) δ ppm 1.21 (m, 2H), 1.48 (m, 2H), 1.56-1.87 (m, 5H, H), 2.10 (m, 1H), 2.25 (m, 1H), 3.08 (s, 3H), 4.30 (t, J=7.9 Hz, 1H), 6.38 (s, 1H), 7.59 (d, J=8.4 Hz, 2H), 7.63 (dd, J=2.7 Hz, $^3J_{HF}$=9.3 Hz, 1H), 7.88 (d, J=8.4 Hz, 2H), 7.99 (dd, $^3J_{HF}$=2.1 Hz, J=2.7 Hz, 1H).

Example 119

2-{4-[2-Cyclopentyl-1-(5-fluoro-1H-pyrrolo[2,3-b]pyridin-2-yl)-ethyl]-phenyl}-propan-2-ol

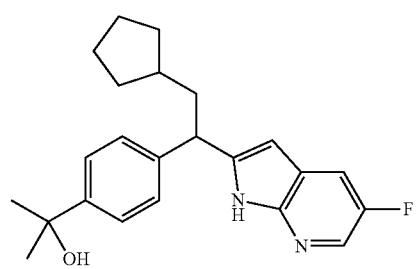

To a mixture of toluene-4-sulfonic acid 1-(1-benzenesulfonyl-5-fluoro-1H-pyrrolo[2,3-b]pyridin-2-yl)-2-cyclopentyl-vinyl ester (prepared as in Example 116, 500 g, 0.93 mmol), 4-ethanone phenylboronic acid (456 mg, 2.78 mmol), and dichlorobis(triphenylphosphine)palladium (II) (65.3 mg, 0.09 mmol) in dioxane (4 mL) was added an aqueous sodium carbonate solution (2 M, 1.40 mL, 2.8 mmol). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. The residue was purified by flash column chromatography (silica gel from QingDao, 200-300 mesh, 25% ethyl acetate/hexanes) to afford 1-{4-[1-(1-benzenesulfonyl-5-fluoro-1H-pyrrolo[2,3-b]pyridin-2-yl)-2-cyclopentyl-vinyl]-phenyl}-ethanone (210 mg, 47%) as a light yellow solid: LC/MS m/e calcd for $C_{28}H_{25}FN_2O_3S$ $[M+H]^+$ 489.59, observed 489.0.

To a solution of 1-{4-[1-(1-benzenesulfonyl-5-fluoro-1H-pyrrolo[2,3-b]pyridin-2-yl)-2-cyclopentyl-vinyl]-phenyl}-ethanone (210 mg, 0.43 mmol) in anhydrous tetrahydrofuran (5 mL) at 0° C. was added methylmagnesium chloride in tetrahydrofuran (3 M, 0.43 ml, 1.29 mmol) dropwise. After stirring for 2 h at 0° C., the reaction mixture was poured into brine (15 mL), extracted with ethyl acetate (2×50 mL), dried over anhydrous sodium sulfate and then concentrated in vacuo. Purification by flash column chromatography (silica gel from QingDao, 200-300 mesh, 33% ethyl acetate/hexanes) afforded 2-{4-[1-(1-benzenesulfonyl-5-fluoro-1H-pyrrolo[2,3-b]pyridin-2-yl)-2-cyclopentyl-vinyl]-phenyl}-propan-2-ol (220 mg, 100%): LC/MS m/e calcd for $C_{29}H_{29}FN_2O_3S$ $[M+H]^+$ 505.63, observed 505.2.

To a solution of 2-{4-[1-(1-benzenesulfonyl-5-fluoro-1H-pyrrolo[2,3-b]pyridin-2-yl)-2-cyclopentyl-vinyl]-phenyl}-propan-2-ol (220 mg, 0.43 mmol) in ethanol (20 mL) and tetrahydrofuran (10 mL) was added an aqueous sodium hydroxide solution (10%, 3.0 mL) and an aqueous saturated ammonia solution (1.5 mL). The mixture was refluxed for 12 h, cooled to room temperature, extracted with ethyl acetate, dried over anhydrous sodium sulfate and then concentrated in vacuo to afford 2-{4-[2-cyclopentyl-1-(5-fluoro-1H-pyrrolo[2,3-b]pyridin-2-yl)-vinyl]-phenyl}-propan-2-ol (150 mg, 94%) which was used in the next step without purification: LC/MS m/e calcd for $C_{23}H_{25}FN_2O$ $[M+H]^+$ 365.47, observed 365.3.

A mixture of 2-{4-[2-cyclopentyl-1-(5-fluoro-1H-pyrrolo[2,3-b]pyridin-2-yl)-vinyl]-phenyl}-propan-2-ol (150 mg, 0.41 mmol) and 10% palladium on activated carbon (0.2 g) in methanol (50 mL) was heated at 50° C. under hydrogen (50 psi) for 5 h. After cooling to room temperature, the catalyst was removed by filtration and washed with ethyl acetate. The filtrate was concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-{4-[2-cyclopentyl-1-(5-fluoro-1H-pyrrolo[2,3-b]pyridin-2-yl)-ethyl]-phenyl}-propan-2-ol (60 mg, 40%) as a white solid: LC/MS m/e calcd for $C_{23}H_{27}FN_2O$ $[M+H]^+$ 367.48, observed 367.3; $^1$H NMR (400 MHz, MeOD) $^1$H NMR (400 MHz, MeOD) δ ppm 7.96 (t, J=2.5 Hz, 1H), 7.61 (dd, J=9.2, 2.5 Hz, 1H), 7.43 (d, J=8.3 Hz, 2H), 7.28 (d, J=8.3 Hz, 2H), 6.31 (s, 1H), 4.14 (t, J=7.7 Hz, 1H), 2.05-2.25 (m, 2H), 1.57-1.89 (m, 5H), 1.51 (s, 6H), 1.43-1.50 (m, 2H), 1.21 (d, J=8.6 Hz, 2H).

Example 120

2-{4-[2-Cyclopentyl-1(R)-(5-fluoro-1H-pyrrolo[2,3-b]pyridin-2-yl)-ethyl]-phenyl}-propan-2-ol

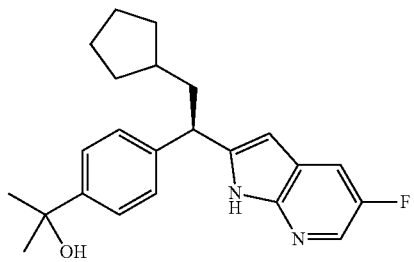

The 1:1 mixture of enantiomers of 2-{4-[2-cyclopentyl-1-(5-fluoro-1H-pyrrolo[2,3-b]pyridin-2-yl)-ethyl]-phenyl}-propan-2-ol (prepared as in Example 119) were separated by Agilent high performance liquid chromatography (chiral column: Daicel IA-H, 250 mm×20 mm i. d., 5 μm-particle size, temperature: 25° C., flow rate of 15 mL/min, 50% ethanol/hexanes as mobile phase and UV detection: 214 and 254 nm) to afford two pure enantiomers. The second peak, 2-{4-[2-cyclopentyl-1(R)-(5-fluoro-1H-pyrrolo[2,3-b]pyridin-2-yl)-ethyl]-phenyl}-propan-2-ol was isolated as a white solid: LC/MS m/e calcd for $C_{23}H_{27}FN_2O$ $[M+H]^+$ 367.48, observed 367.3; $^1$H NMR (400 MHz, CD$_3$OD) δ ppm 1.19 (m, 2H), 1.47 (m, 2H), 1.50 (s, 6H), 1.57-1.87 (m, 5H, H), 2.06 (m, 1H), 2.17 (m, 1H), 4.13 (t, J=7.8 Hz, 1H), 6.30 (s, 1H), 7.26 (d, J=8.3 Hz, 2H), 7.42 (d, J=8.3 Hz, 2H), 7.60 (dd, J=2.5 Hz, $^3J_{HF}$=9.2 Hz, 1H), 7.95 (m, 1H).

Example 121

2-[2-Cyclopentyl-1-(4-isopropyl-phenyl)-ethyl]-5-fluoro-1H-pyrrolo[2,3-b]pyridine

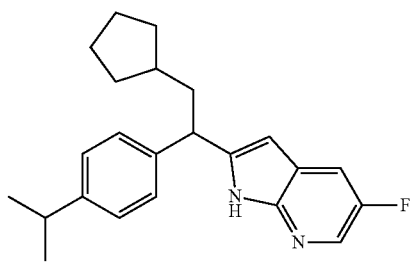

A mixture of 2-{4-[2-cyclopentyl-1-(5-fluoro-1H-pyrrolo[2,3-b]pyridin-2-yl)-vinyl]-phenyl}-propan-2-ol (prepared as in Example 119, 150 mg, 0.41 mmol) and 10% palladium on activated carbon (0.2 g) in methanol (50 mL) was heated at 50° C. under hydrogen (50 psi) for 5 h. After cooling to room temperature, the catalyst was removed by filtration and washed with ethyl acetate. The filtrate was concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-isopropyl-phenyl)-ethyl]-5-fluoro-1H-pyrrolo[2,3-b]pyridine as a white solid (5.7 mg, 4%): LC/MS m/e calcd for $C_{23}H_{27}FN_2$ [M+H]$^+$ 351.48, observed 351.26; $^1$H NMR (400 MHz, CD$_3$OD) δ ppm 1.19 (m, 2H), 1.22 (d, J=6.8 Hz, 6H), 1.48 (m, 2H), 1.57-1.87 (m, 5H, H), 2.06 (m, 1H), 2.17 (m, 1H), 2.86 (m, 1H), 4.11 (t, J=7.8 Hz, 1H), 6.29 (s, 1H), 7.16 (d, J=8.3 Hz, 2H), 7.22 (d, J=8.3 Hz, 2H), 7.60 (dd, J=2.5 Hz, $^3J_{HF}$=9.2 Hz, 1H), 7.95 (brm, 1H).

Example 122

5-Fluoro-2-[(E)-1-(4-methanesulfonyl-phenyl)-2-(tetrahydro-pyran-4-yl)-vinyl]-1H-pyrrolo[2,3-b]pyridine

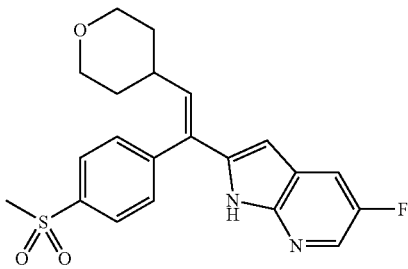

To a suspension of 1-benzenesulfonyl-5-fluoro-1H-pyrrolo[2,3-b]pyridine (1.0 g, 3.62 mmol) in dry tetrahydrofuran (30 mL) at −78° C. was added a solution of n-butyllithium in n-hexane (1.6M, 2.72 mL, 4.35 mmol). The mixture was stirred at −78° C. for 5 min and then treated with (tetrahydropyran-4-yl)-acetaldehyde (0.7 g, 5.43 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (QingDao silica gel, 200-300 mesh, 25% ethyl acetate/hexanes) afforded 1-(1-benzenesulfonyl-5-fluoro-1H-pyrrolo[2,3-b]pyridin-2-yl)-2-(tetrahydro-pyran-4-yl)-ethanol (1.23 g, 84%): LC/MS m/e calcd for $C_{20}H_{21}FN_2O_4S$ [M+H]$^+$ 405.46, observed 405.2.

To a solution of 1-(1-benzenesulfonyl-5-fluoro-1H-pyrrolo[2,3-b]pyridin-2-yl)-2-(tetrahydro-pyran-4-yl)-ethanol (1.23 g, 3.04 mmol) in dichloromethane (100 ml) was added Dess-Martin periodinane (3.87 g, 9.12 mmol) at 25° C. The reaction mixture was stirred at 25° C. for 1 h and then quenched with a saturated aqueous sodium bicarbonate solution (60 mL). The mixture was extracted with ethyl acetate (150 mL), washed with a saturated aqueous sodium bicarbonate solution (3×30 mL), brine, dried over anhydrous sodium sulfate and then concentrated in vacuo. The residue was purified by flash column chromatography (silica gel from QingDao, 200-300 mesh, 33% ethyl acetate/hexanes) to afford 1-(1-benzenesulfonyl-5-fluoro-1H-pyrrolo[2,3-b]pyridin-2-yl)-2-(tetrahydro-pyran-4-yl)-ethanone (1.1 g, 90%) as a light yellow solid: LC/MS m/e calcd for $C_{20}H_{19}FN_2O_4S$ [M+H]$^+$ 403.45, observed 403.2.

To a solution of 1-(1-benzenesulfonyl-5-fluoro-1H-pyrrolo[2,3-b]pyridin-2-yl)-2-(tetrahydro-pyran-4-yl)-ethanone (1.1 g, 2.74 mmol) in anhydrous tetrahydrofuran (50 mL) at −78° C. under nitrogen atmosphere was added a solution of lithium bis(trimethylsilyl)amide in tetrahydrofuran (1 M, 4.1 mL, 4.1 mmol) dropwise. After stirring at −78° C. for 1 h, a solution of p-toluenesulfonic anhydride (1.34 g, 4.1 mmol) in tetrahydrofuran (5 mL) was added dropwise. The resulting mixture was stirred at −78° C. for an additional 1.5 h. The reaction was quenched with water, extracted with ethyl acetate (100 mL), washed with brine, dried over anhydrous sodium sulfate and then concentrated in vacuo. Purification by flash column chromatography (silica gel from QingDao, 200-300 mesh, 40% ethyl acetate/hexanes) afforded toluene-4-sulfonic acid 1-(1-benzenesulfonyl-5-fluoro-1H-pyrrolo[2,3-b]pyridin-2-yl)-2-(tetrahydro-pyran-4-yl)-vinyl ester (1.52 g, 100%) as a light yellow solid: LC/MS m/e calcd for $C_{27}H_{25}FN_2O_6S_2$ [M+H]$^+$ 557.64, observed 557.1.

To a mixture of toluene-4-sulfonic acid 1-(1-benzenesulfonyl-5-fluoro-1H-pyrrolo[2,3-b]pyridin-2-yl)-2-(tetrahydro-pyran-4-yl)-vinyl ester (500 mg, 0.9 mmol), 4-methylsulfonyl phenylboronic acid (540 mg, 2.7 mmol) and dichlorobis(triphenylphosphine)palladium (II) (63 mg, 0.09 mmol) in dioxane (4 mL) was added an aqueous sodium carbonate solution (2 M, 1.40 mL, 2.8 mmol). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash column chromatography (silica gel from QingDao, 200-300 mesh, 40% ethyl acetate/hexanes) afforded 1-benzenesulfonyl-5-fluoro-2-[1-(4-methanesulfonyl-phenyl)-2-(tetrahydro-pyran-4-yl)-vinyl]-1H-pyrrolo[2,3-b]pyridine (405 mg, 83%) as a light yellow solid: LC/MS m/e calcd for $C_{27}H_{25}FN_2O_5S_2$ [M+H]$^+$ 541.64, observed 541.2.

A mixture of 1-benzenesulfonyl-5-fluoro-2-[1-(4-methanesulfonyl-phenyl)-2-(tetrahydro-pyran-4-yl)-vinyl]-1H-pyrrolo[2,3-b]pyridine (405 mg, 0.75 mmol) and tetrabutylammonium fluoride in tetrahydrofuran (1 M, 15 mL, 15 mmol) was stirred for 12 h at room temperature. The mixture was poured into brine (15 mL), extracted with ethyl acetate (2×50 mL), washed with a saturated aqueous ammonium chloride solution (3×20 mL), dried over anhydrous sodium sulfate and then concentrated in vacuo to afford 5-fluoro-2-[(E)-1-(4-methanesulfonyl-phenyl)-2-(tetrahydro-pyran-4-yl)-vinyl]-1H-pyrrolo[2,3-b]pyridine (300 mg, 100%) as a solid: LC/MS m/e calcd for $C_{21}H_{21}FN_2O_3S$ [M+H]$^+$ 401.48, observed 401.2; $^1$H NMR (400 MHz, CDCl$_3$) δ ppm 10.24 (br. s., 1H), 7.98 (br. s., 1H), 7.76-7.95 (m, 3H), 7.40-7.56 (m, 2H), 6.54 (s, 1H), 6.17 (d, J=10.1 Hz, 1H), 3.93-4.03 (m, 2H), 3.33-3.48 (m, 2H), 2.95-3.09 (m, 3H), 2.79-2.90 (m, 1H), 1.64-1.83 (m, 4H).

Example 123

5-Fluoro-2-[1-(4-methanesulfonyl-phenyl)-2-(tetrahydro-pyran-4-yl)-ethyl]-1H-pyrrolo[2,3-b]pyridine

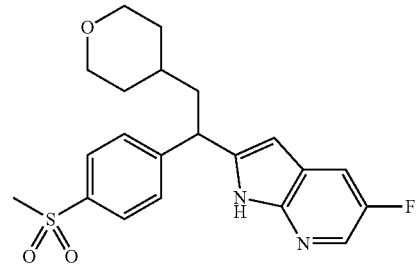

A mixture of 5-fluoro-2-[(E)-1-(4-methanesulfonyl-phenyl)-2-(tetrahydro-pyran-4-yl)-vinyl]-1H-pyrrolo[2,3-b]pyridine (prepared as in Example 122, 300 mg, 0.75 mmol) and 10% palladium on activated carbon (0.2 g) in methanol (50 mL) was heated at 45° C. under hydrogen (50 psi) for 5 h. After cooling to room temperature, the catalyst was removed by filtration and washed with ethyl acetate. The filtrate was concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 5-fluoro-2-[1-(4-methanesulfonyl-phenyl)-2-(tetrahydro-pyran-4-yl)-ethyl]-1H-pyrrolo[2,3-b]pyridine as a white solid (180 mg, 60%): LC/MS m/e calcd for $C_{21}H_{23}FN_2O_3S$ [M+H]$^+$ 403.49, observed 403.2; $^1$H NMR (400 MHz, $CD_3OD$) δ ppm 8.01 (t, J=2.1 Hz, 1H), 7.91 (d, J=8.3 Hz, 2H), 7.60-7.67 (m, 3H), 6.41 (s, 1H), 4.44 (t, J=8.1 Hz, 1H), 3.90 (d, J=11.4 Hz, 2H), 3.25-3.30 (m, 2H), 3.08-3.14 (m, 3H), 2.24 (dt, J=14.1, 7.3 Hz, 1H), 1.99-2.07 (m, 1H), 1.72 (t, J=14.1 Hz, 2H), 1.32-1.52 (m, 3H).

Example 124

5-Fluoro-2-[1(R)-(4-methanesulfonyl-phenyl)-2-(tetrahydro-pyran-4-yl)-ethyl]-1H-pyrrolo[2,3-b]pyridine

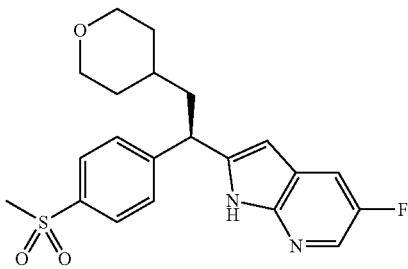

The 1:1 mixture of enantiomers of 5-fluoro-2-[1-(4-methanesulfonyl-phenyl)-2-(tetrahydro-pyran-4-yl)-ethyl]-1H-pyrrolo[2,3-b]pyridine (prepared as in Example 123) were separated by Agilent high performance liquid chromatography (chiral column: Daicel IA-H, 250 mm×20 mm i. d., 5 μm-particle size, temperature: 25° C., flow rate of 15 mL/min, 60% alcohol/hexanes as mobile phase and UV detection: 214 and 254 nm) to afford two pure enantiomers. The second peak, 5-fluoro-2-[1(R)-(4-methanesulfonyl-phenyl)-2-(tetrahydro-pyran-4-yl)-ethyl]-1H-pyrrolo[2,3-b]pyridine was isolated as white solid: LC/MS m/e calcd for $C_{21}H_{23}FN_2O_3S$ [M+H]$^+$ 403.49, observed 403.2; $^1$H NMR (400 MHz, $CD_3OD$) δ ppm 7.82-8.07 (m, 3H), 7.49-7.74 (m, 2H), 6.39 (s, 1H), 4.32-4.52 (m, 1H), 3.88 (d, J=11.6 Hz, 2H), 3.23-3.28 (m, 1H), 3.12 (br. s., 3H), 2.13-2.36 (m, 1H), 2.01 (dt, J=13.8, 7.1 Hz, 1H), 1.70 (t, J=14.4 Hz, 2H), 1.18-1.53 (m, 3H).

Example 125

2-[2-Cyclopentyl-1-(4-methanesulfonyl-phenyl)-ethyl]-5-ethanesulfonyl-1H-pyrrolo[2,3-b]pyridine

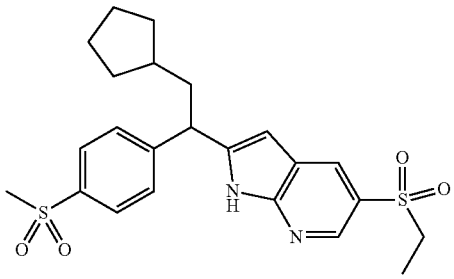

To a solution 5-bromo-1-(tert-butyl-dimethyl-silanyl)-2,3-dihydro-1H-pyrrolo[2,3-b]pyridine (prepared as in Example 7, 3.3 g, 10.5 mmol) in anhydrous tetrahydrofuran (50 mL) at −78° C. was added a solution of n-butyllithium in n-hexane (1.6M, 10 mL, 16 mmol) dropwise. After stirring for 20 min at −78° C., ethyl disulfide (1.96 g, 16 mmol) was added. The resulting mixture was stirred for 1 h, quenched with a saturated ammonium chloride solution (20 mL), extracted with ethyl acetate (2×100 mL), dried over anhydrous sodium sulfate, concentrated in vacuo. The residue was purified by flash column chromatography (Qingdao silica gel, 300 mesh, 10% dichloromethane/hexanes) to afford 1-(tert-butyl-dimethyl-silanyl)-5-ethylsulfanyl-2,3-dihydro-1H-pyrrolo[2,3-b]pyridine (2.2 g, 71%): LC/MS m/e calcd for $C_{15}H_{26}N_2SSi$ [M+H]$^+$ 295.54.

To a solution of 1-(tert-butyl-dimethyl-silanyl)-5-ethylsulfanyl-2,3-dihydro-1H-pyrrolo[2,3-b]pyridine (2.2 g, 7.6 mmol) in dichloromethane (50 mL) was added 2,3-dichloro-5,6-dicyano-1,4-benzoquinone (2.07 g, 9.1 mmol) at room temperature. After stirring for 12 h at room temperature, the mixture was concentrated. The residue. was purified by flash column chromatography (Qingdao silica gel, 300 mesh, 11% dichloromethane/hexanes) to afford 1-(tert-butyl-dimethyl-silanyl)-5-ethylsulfanyl-1H-pyrrolo[2,3-b]pyridine (0.5 g, 23%) as a yellow oil: LC/MS m/e calcd for $C_{15}H_{24}N_2SSi$ [M+H]$^+$ 292.52.

A mixture of 1-(tert-butyl-dimethyl-silanyl)-5-ethylsulfanyl-1H-pyrrolo[2,3-b]pyridine (2.5 g, 8.68 mmol) and a solution of tetrabutylammonium fluoride in tetrahydrofuran (1 M, 9.11 mL, 9.11 mmol) was stirred for 2 h at room temperature. The mixture was poured into brine (15 mL), extracted with ethyl acetate (2×50 mL), washed with a saturated aqueous ammonium chloride solution (3×20 mL), dried over anhydrous sodium sulfate and then concentrated in vacuo. Purification by flash column chromatography (Qingdao silica gel, 300 mesh, 20% ethyl acetate/hexanes) afforded 5-ethylsulfanyl-1H-pyrrolo[2,3-b]pyridine (600 mg, 48%) as a white solid which was used in the next step without purification: LC/MS m/e calcd for $C_9H_{10}N_2O$ [M+H]$^+$ 179.26, observed 179.2.

To a mixture of 5-ethylsulfanyl-1H-pyrrolo[2,3-b]pyridine (2.7 g, 15.2 mmol), sodium hydroxide (1.82 g, 45.6 mmol) and tetrabutylammonium bromide (150 mg, 0.46 mmol) in dichloromethane (30 mL) at 0° C. was added benzenesulfonyl chloride (4.0 g, 22.8 mmol) dropwise. After stirring for 12 h at room temperature, the mixture was washed with water (2×10 mL), dried over anhydrous sodium sulfate and concentrated in vacuo. The residue was purified by flash column chromatography (silica gel from QingDao, 200-300 mesh, 50% dichloromethane/hexanes) to afford 1-benzenesulfonyl-5-ethylsulfanyl-1H-pyrrolo[2,3-b]pyridine (2.68 g, 63%): LC/MS m/e calcd for $C_{15}H_{14}N_2O_2S_2$ [M+H]$^+$ 319.42, observed 319.1.

To a suspension of 1-benzenesulfonyl-5-ethylsulfanyl-1H-pyrrolo[2,3-b]pyridine (2.68 g, 8.43 mmol) in dry tetrahydrofuran (60 mL) at −78° C. was added a solution of n-butyllithium in n-hexane (1.6M, 6.85 mL, 10.96 mmol) dropwise. The mixture was stirred at −78° C. for 10 min and then treated with cyclopentanecarbaldehyde (1.42 g, 12.65 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (silica gel from QingDao, 200-300 mesh, 20% ethyl acetate/hexanes) afforded 1-(1-benzenesulfonyl-5-ethylsulfanyl-1H-pyrrolo[2,3-b]pyridin-2-yl)-

2-cyclopentyl-ethanol (3.0 g, 83%) as a white solid: LC/MS m/e calcd for $C_{22}H_{26}N_2O_3S_2$ [M+H]$^+$ 431.59, observed 431.1.

To a solution of 1-(1-benzenesulfonyl-5-ethylsulfanyl-1H-pyrrolo[2,3-b]pyridin-2-yl)-2-cyclopentyl-ethanol (3.0 g, 7.0 mmol) in dichloromethane (150 mL) was added Dess-Martin periodinane (7.4 g, 17.4 mmol) at 25° C. The reaction mixture was stirred at 25° C. for 1 h and then quenched with a saturated aqueous sodium bicarbonate solution (60 mL). The mixture was extracted with ethyl acetate (250 mL), washed with a saturated aqueous sodium bicarbonate solution (3×50 mL), brine, dried over anhydrous sodium sulfate and then concentrated in vacuo. The residue was purified by flash column chromatography (silica gel from QingDao, 200-300 mesh, 20% ethyl acetate/hexanes) to afford 1-(1-benzenesulfonyl-5-ethanesulfinyl-1H-pyrrolo[2,3-b]pyridin-2-yl)-2-cyclopentyl-ethanone (1.5 g, 48%) as a light yellow solid: LC/MS m/e calcd for $C_{22}H_{24}N_2O_4S_2$ [M+H]$^+$ 445.58, observed 444.9.

To a solution of 1-(1-benzenesulfonyl-5-ethanesulfinyl-1H-pyrrolo[2,3-b]pyridin-2-yl)-2-cyclopentyl-ethanone (130 mg, 0.29 mmol) in anhydrous tetrahydrofuran (30 mL) at −78° C. under a nitrogen atmosphere was added a solution of lithium bis(trimethylsilyl)amide in tetrahydrofuran (1 M, 0.44 mL, 0.44 mmol) dropwise. After stirring at −78° C. for 1 h, a solution of p-toluenesulfonic anhydride (170 mg, 0.52 mmol) in tetrahydrofuran (2 mL) was added dropwise. The resulting mixture was stirred at −78° C. for an additional 1.5 h. The reaction was quenched with water, extracted with ethyl acetate (20 mL), washed with brine, dried over anhydrous sodium sulfate and then concentrated in vacuo. Purification by flash column chromatography (silica gel from QingDao, 200-300 mesh, 25% ethyl acetate/hexanes) afforded toluene-4-sulfonic acid 1-(1-benzenesulfonyl-5-ethanesulfinyl-1H-pyrrolo[2,3-b]pyridin-2-yl)-2-cyclopentyl-vinyl ester (80 mg, 46%) as a light yellow solid: LC/MS m/e calcd for $C_{29}H_{30}N_2O_6S_3$ [M+H]$^+$ 599.76, observed 599.0.

To a mixture of toluene-4-sulfonic acid 1-(1-benzenesulfonyl-5-ethanesulfinyl-1H-pyrrolo[2,3-b]pyridin-2-yl)-2-cyclopentyl-vinyl ester (80 mg, 0.134 mmol), 4-methylsulfonyl phenylboronic acid (80 mg, 0.401 mmol) and dichlorobis(triphenylphosphine)palladium (II) (9.4 mg, 0.013 mmol) in dioxane (1 mL) was added an aqueous sodium carbonate solution (2 M, 0.2 mL, 0.4 mmol). The resulting mixture was subjected to microwave irradiation for 2 h at 100° C. The mixture was diluted with ethyl acetate (10 mL), washed with a saturated aqueous sodium bicarbonate solution (2×3 mL), brine, dried over anhydrous sodium sulfate and then concentrated in vacuo. Purification by flash column chromatography (silica gel from QingDao, 200-300 mesh, 25% ethyl acetate/hexanes) afforded 1-benzenesulfonyl-2-[2-cyclopentyl-1-(4-methanesulfonyl-phenyl)-vinyl]-5-ethanesulfinyl-1H-pyrrolo[2,3-b]pyridine (56 mg, 72%) as a light yellow solid: LC/MS m/e calcd for $C_{29}H_{30}N_2O_5S_3$ [M+H]$^+$ 583.76, observed 583.2.

A mixture of 1-benzenesulfonyl-2-[2-cyclopentyl-1-(4-methanesulfonyl-phenyl)-vinyl]-5-ethanesulfinyl-1H-pyrrolo[2,3-b]pyridine (56 mg, 0.096 mmol) and a solution of tetrabutylammonium fluoride in tetrahydrofuran (1 M, 3.85 mL, 3.85 mmol) was stirred for 12 h at room temperature. The mixture was poured into brine (5 mL), extracted with ethyl acetate (2×20 mL), washed with a saturated aqueous ammonium chloride solution (3×10 mL), dried over anhydrous sodium sulfate and then concentrated in vacuo to give 2-[2-cyclopentyl-1-(4-methanesulfonyl-phenyl)-vinyl]-5-ethanesulfinyl-1H-pyrrolo[2,3-b]pyridine (37 mg, 88%) as a solid which was used in the next step without purification: LC/MS m/e calcd for $C_{23}H_{26}N_2O_3S_2$ [M+H]$^+$ 443.6, observed 443.1.

A mixture of 2-[2-cyclopentyl-1-(4-methanesulfonyl-phenyl)-vinyl]-5-ethanesulfinyl-1H-pyrrolo[2,3-b]pyridine (37 mg, 0.084 mmol) and 10% palladium on activated carbon (40 mg) in methanol (50 mL) was heated at 50° C. under hydrogen (45 psi) for 5 h. After cooling to room temperature, the catalyst was removed by filtration and washed with ethyl acetate. The filtrate was concentrated in vacuo to give 2-[2-cyclopentyl-1-(4-methanesulfonyl-phenyl)-ethyl]-5-ethanesulfinyl-1H-pyrrolo[2,3-b]pyridine (37.3 mg, 100%) as a white solid: LC/MS m/e calcd for $C_{23}H_{28}N_2O_3S_2$ [M+H]$^+$ 445.62, observed 445.1.

To a solution of 2-[2-cyclopentyl-1-(4-methanesulfonyl-phenyl)-ethyl]-5-ethanesulfinyl-1H-pyrrolo[2,3-b]pyridine (37.3 mg, 0.84 mmol) in methanol (4 mL) at 0° C. was added a solution of potassium permanganate (13.3 mg, 0.084 mmol) in water (2 mL) dropwise. After stirring for 2 h at 0° C., the mixture was extracted with ethyl acetate, washed with brine, dried over anhydrous sodium sulfate, filtered through a short silica gel pad (QingDao silica gel, 200-300 mesh), and concentrated in vacuo to give the residue. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-[2-cyclopentyl-1-(4-methanesulfonyl-phenyl)-ethyl]-5-ethanesulfonyl-1H-pyrrolo[2,3-b]pyridine (8 mg, 21%): LC/MS m/e calcd for $C_{23}H_{28}N_2O_4S_2$ [M+H]$^+$ 461.62, observed 461.0; $^1$H NMR (400 MHz, CD$_3$OD) δ ppm 8.59 (d, J=2.0 Hz, 1H), 8.38 (d, J=2.0 Hz, 1H), 7.88-7.92 (m, J=8.3 Hz, 2H), 7.59-7.63 (m, J=8.3 Hz, 2H), 6.62 (s, 1H), 4.36 (t, J=8.0 Hz, 1H), 3.25 (q, J=7.4 Hz, 4H), 3.07-3.13 (m, 4H), 2.26-2.34 (m, 1H), 2.11-2.19 (m, 1H), 1.61-1.71 (m, 2H), 1.46-1.53 (m, 2H), 1.23 (t, J=7.3 Hz, 5H).

Example 126

2-[2-Cyclopentyl-1-(4-methanesulfonyl-phenyl)-ethyl]-5-trifluoromethyl-1H-pyrrolo[2,3-b]pyridine

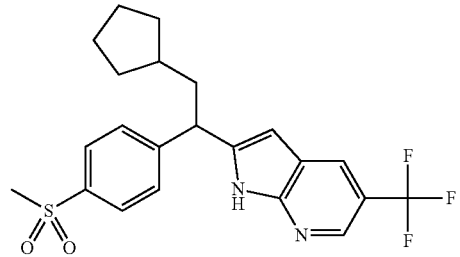

A mixture of 5-trifluoromethyl-pyridin-2-ylamine (32.4 g, 0.2 mol) and potassium iodate (17.12 g, 0.08 mol) in 2M sulfuric acid (400 mL) was heated at 100° C. and a solution of potassium iodide (33.2 g, 0.2 mol) in water (83 mL) was added dropwise over 1 h. The resulting mixture was heated to reflux for 12 h. After being cooled to room temperature, the mixture was adjusted to pH 7 with careful addition of solid sodium bicarbonate. The mixture was extracted with dichloromethane, washed with a saturated sodium thiosulfate solution, dried over anhydrous sodium sulfate and concentrated in vacuo to afford 3-iodo-5-trifluoromethyl-pyridin-2-ylamine (52.5 g, 91%) as yellow solid: LC/MS m/e calcd for $C_4H_3IN_2$ [M+H]$^+$ 289.01, observed 288.8.

3-Iodo-5-trifluoromethyl-pyridin-2-ylamine (52.5 g, 180 mmol) was dissolved in a mixture of triethylamine (76 mL) and tetrahydrofuran (300 mL) and the solution was degassed and purged with nitrogen. Trimethylsilyl acetylene (38 mL, 270 mmol), copper(I) iodide (0.7 g, 3.6 mmol) and bis(triphenylphosphino) palladium (II) chloride (2.53 g, 3.6 mmol) were added. The mixture was degassed and purged with nitrogen one more time. The mixture was stirred at ambient temperature for 16 h and a solution containing a white precipitate resulted. The precipitate was removed by filtration, and the filtrate was concentrated in vacuo. The residue was purified by flash column chromatography (silica gel from QingDao, 200-300 mesh, 15%-35% ethyl acetate in hexanes) to afford 5-trifluoromethyl-3-trimethylsilanylethynyl-pyridin-2-ylamine (43.8 g, 92%) as a yellow solid: LC/MS m/e calcd for $C_{11}H_{13}F_3N_2Si$ [M+H]$^+$ 259.32, observed 258.9.

5-Trifluoromethyl-3-trimethylsilanylethynyl-pyridin-2-ylamine (43.8 g, 170 mmol) and copper(I) iodide (6.5 g, 34 mmol) were dissolved in N-methylpyrrolidone (0.85 L). The mixture was stirred at 190° C. for 30 min. The mixture was evaporated to remove N-methylpyrrolidone in vacuo. The residue was purified by flash column chromatography (QingDao silical gel, 200-300 mesh, 40% ethyl acetate/hexanes) to afford 5-trifluoromethyl-1H-pyrrolo[2,3-b]pyridine (7.5 g, 24%) as a yellow solid: LC/MS m/e calcd for $C_8H_5F_3N_2$ [M+H]$^+$ 187.14, observed 187.0.

To a mixture of 5-trifluoromethyl-1H-pyrrolo[2,3-b]pyridine (7.5 g, 40.3 mmol), sodium hydroxide (4.84 g, 120.9 mmol) and tetrabutylammonium bromide (390 mg, 1.21 mmol) in dichloromethane (150 mL) at 0° C. was added benzenesulfonyl chloride (10.64 g, 60.45 mmol) dropwise. After stirring for 12 h at room temperature, washed with water (2×30 mL), dried over anhydrous sodium sulfate and concentrated in vacuo. The residue was purified by flash column chromatography (silica gel from QingDao, 200-300 mesh, 50% dichloromethane/hexanes) to afford 1-benzenesulfonyl-5-trifluoromethyl-1H-pyrrolo[2,3-b]pyridine (6.35 g, 48%): LC/MS m/e calcd for $C_{14}H_9F_3N_2O_2S$ [M+H]$^+$ 327.30, observed 326.8.

To a suspension of 1-benzenesulfonyl-5-trifluoromethyl-1H-pyrrolo[2,3-b]pyridine (1.0 g, 3.07 mmol) in dry tetrahydrofuran (50 mL) at −78° C. was added a solution of n-butyllithium in n-hexane (2.5 M, 1.5 mL, 3.68 mmol) dropwise. The mixture was stirred at −78° C. for 5 min and then treated with cyclopentanecarbaldehyde (0.52 g, 4.6 mmol) dropwise. The resulting mixture was stirred at −78° C. for 1 h and quenched with brine. The mixture was extracted with ethyl acetate (2×100 mL), washed with brine, dried over anhydrous sodium sulfate and concentrated in vacuo. Purification by flash column chromatography (QingDao silica gel, 200-300 mesh, 50% dichloromethane/hexanes) afforded 1-(1-benzenesulfonyl-5-trifluoromethyl-1H-pyrrolo[2,3-b]pyridin-2-yl)-2-cyclopentyl-ethanol (1.34 g, 100%): LC/MS m/e calcd for $C_{21}H_{21}F_3N_2O_3S$ [M+H]$^+$ 439.47, observed 438.7.

To a solution of 1-(1-benzenesulfonyl-5-trifluoromethyl-1H-pyrrolo[2,3-b]pyridin-2-yl)-2-cyclopentyl-ethanol (1.34 g, 3.07 mmol) in dichloromethane (50 ml) was added Dess-Martin periodinane (2.6 g, 6.14 mmol) at 25° C. The reaction mixture was stirred at 25° C. for 1 h and then quenched with a saturated aqueous sodium bicarbonate solution (20 mL). The mixture was extracted with ethyl acetate (100 mL), washed with a saturated aqueous sodium bicarbonate solution (3×20 mL), brine, dried over anhydrous sodium sulfate and then concentrated in vacuo. The residue was purified by flash column chromatography (silica gel from QingDao, 200-300 mesh, 50% dichloromethane/hexanes) to afford 1-(1-benzenesulfonyl-5-trifluoromethyl-1H-pyrrolo[2,3-b]pyridin-2-yl)-2-cyclopentyl-ethanone (1.33 g, 100%) as a light yellow solid: LC/MS m/e calcd for $C_{21}H_{19}F_3N_2O_3S$ [M+H]$^+$ 437.46, observed 436.8.

To a solution of 1-(1-benzenesulfonyl-5-trifluoromethyl-1H-pyrrolo[2,3-b]pyridin-2-yl)-2-cyclopentyl-ethanone (2.28 g, 5.23 mmol) in anhydrous tetrahydrofuran (140 mL) at −78° C. under nitrogen atmosphere was added a solution of lithium bis(trimethylsilyl)amide in tetrahydrofuran (1 M, 7.84 mL, 7.84 mmol) dropwise. After stirring at −78° C. for 1 h, a solution of p-toluenesulfonic anhydride (3.07 g, 9.41 mmol) in tetrahydrofuran (10 mL) was added dropwise. The resulting mixture was stirred for an additional 1.5 h at −78° C. The reaction was quenched with water, extracted with ethyl acetate (200 mL), washed with brine, dried over anhydrous sodium sulfate and then concentrated in vacuo. Purification by flash column chromatography (silica gel from QingDao, 200-300 mesh, 50% dichloromethane/hexanes) afforded toluene-4-sulfonic acid 1-(1-benzenesulfonyl-5-trifluoromethyl-1H-pyrrolo[2,3-b]pyridin-2-yl)-2-cyclopentyl-vinyl ester (0.85 g, 28%) as a light yellow solid: LC/MS m/e calcd for $C_{28}H_{25}F_3N_2O_5S_2$ [M+H]$^+$ 591.65, observed 590.6.

To a mixture of toluene-4-sulfonic acid 1-(1-benzenesulfonyl-5-trifluoromethyl-1H-pyrrolo[2,3-b]pyridin-2-yl)-2-cyclopentyl-vinyl ester (500 mg, 0.93 mmol), 4-methylsulfonyl phenylboronic acid (560 mg, 2.78 mmol) and dichlorobis (triphenylphosphine)palladium (II) (65.3 mg, 0.09 mmol) in dioxane (4 mL) was added an aqueous sodium carbonate solution (2 M, 1.40 mL, 2.8 mmol). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash column chromatography (silica gel from QingDao, 200-300 mesh, 35% ethyl acetate/hexanes) afforded 1-benzenesulfonyl-2-[2-cyclopentyl-1-(4-methanesulfonyl-phenyl)-vinyl]-5-trifluoromethyl-1H-pyrrolo[2,3-b]pyridine (270 mg, 93%) as a light yellow solid: LC/MS m/e calcd for $C_{28}H_{25}F_3N_2O_4S_2$ [M+H]$^+$ 575.65, observed 574.7.

A mixture of 1-benzenesulfonyl-2-[2-cyclopentyl-1-(4-methanesulfonyl-phenyl)-vinyl]-5-trifluoromethyl-1H-pyrrolo[2,3-b]pyridine (270 mg, 0.47 mmol) and a solution of tetrabutylammonium fluoride in tetrahydrofuran (1 M, 9.4 mL, 9.4 mmol) was stirred for 12 h at room temperature. The mixture was poured into brine (15 mL), extracted with ethyl acetate (2×50 mL), washed with a saturated aqueous ammonium chloride solution (3×20 mL), dried over anhydrous sodium sulfate and then concentrated in vacuo to afford 2-[2-cyclopentyl-1-(4-methanesulfonyl-phenyl)-vinyl]-5-trifluoromethyl-1H-pyrrolo[2,3-b]pyridine (190 mg, 93%) as a solid which was used in the next step without purification: LC/MS m/e calcd for $C_{22}H_{21}F_3N_2O_2S$ [M+H]$^+$ 435.48, observed 434.8.

A solution of 2-[2-cyclopentyl-1-(4-methanesulfonyl-phenyl)-vinyl]-5-trifluoromethyl-1H-pyrrolo[2,3-b]pyridine (190 mg, 0.44 mmol) in methanol (70 mL) was passed through a H-Cube reactor (10% palladium on activated carbon, 50° C., 50 bar of hydrogen pressure, 1 mL/minute). The reaction solution was concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-5-trifluoromethyl-1H-pyrrolo[2,3-b]pyridine (60 mg, 41%) as a white solid: LC/MS m/e calcd for $C_{22}H_{23}F_3N_2O_2S$ [M+H]$^+$ 437.50, observed 436.9; $^1$H NMR (400 MHz, CD$_3$OD) δ ppm 8.44 (s, 1H), 8.23 (s, 1H), 7.93-7.98 (m, J=8.3 Hz, 2H), 7.63-7.69 (m, J=8.3 Hz, 2H), 6.59 (s, 1H), 4.40 (t, J=7.8 Hz, 1H), 3.14 (s, 3H), 2.30-2.38 (m, 1H), 2.15-2.24 (m, 1H), 1.65-1.92 (m, 5H), 1.49-1.61 (m, 2H), 1.21-1.38 (m, 2H).

Example 127

2-[2-Cyclopentyl-1(R)-(4-methanesulfonyl-phenyl)-ethyl]-5-trifluoromethyl-1H-pyrrolo[2,3-b]pyridine

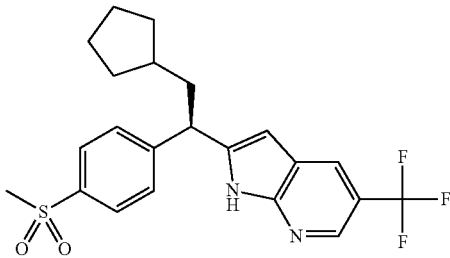

The 1:1 mixture of enantiomers of 2-[2-cyclopentyl-1-(4-methanesulfonyl-phenyl)-ethyl]-5-trifluoromethyl-1H-pyrrolo[2,3-b]pyridine (prepared as in Example 126) were separated by Agilent high performance liquid chromatography (chiral column: Daicel IA-H, 250 mm×20 mm i. d., 5 μm-particle size, temperature: 25° C., flow rate of 15 mL/min, 60% alcohol/hexanes as mobile phase and UV detection: 214 and 254 nm) to afford two pure enantiomers. The second peak, 2-[2-cyclopentyl-1(R)-(4-methanesulfonyl-phenyl)-ethyl]-5-trifluoromethyl-1H-pyrrolo[2,3-b]pyridine was isolated as white solid: LC/MS m/e calcd for $C_{22}H_{23}F_3N_2O_2S$ [M+H]$^+$ 437.50, observed 436.9; $^1$H NMR (400 MHz, CD$_3$OD) δ ppm 8.44 (s, 1H), 8.22-8.25 (m, 1H), 7.93-7.97 (m, J=8.3 Hz, 2H), 7.63-7.68 (m, J=8.3 Hz, 2H), 6.59 (s, 1H), 4.40 (t, J=8.0 Hz, 1H), 3.14 (s, 3H), 2.34 (dt, J=13.9, 7.2 Hz, 1H), 2.15-2.23 (m, 1H), 1.65-1.92 (m, 5H), 1.49-1.61 (m, 2H), 1.21-1.35 (m, 2H).

Example 128

2-[2-Cyclopentyl-1-(4-methanesulfonyl-phenyl)-ethyl]-5-methyl-1H-pyrrolo[2,3-b]pyridine

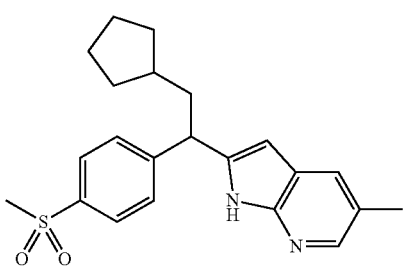

To a solution 5-bromo-1-(tert-butyl-dimethyl-silanyl)-1H-pyrrolo[2,3-b]pyridine (prepared as in Example 7, 10.0 g, 32.2 mmol) in anhydrous tetrahydrofuran (200 mL) at −78° C. was added a solution of n-butyllithium in n-hexane (2.5 M, 19.3 mL, 48.2 mmol) dropwise. After stirring for 20 min at −78° C., methyl iodide (13.72 g, 96.6 mmol) was added. The resulting mixture was stirred for 2 h, quenched with a saturated ammonium chloride solution (50 mL), extracted with ethyl acetate (2×200 mL), dried over anhydrous sodium sulfate, concentrated in vacuo to give 1-(tert-butyl-dimethyl-silanyl)-5-methyl-1H-pyrrolo[2,3-b]pyridine (7.92 g, 100%) which was used in the next step without purification: LC/MS m/e calcd for $C_{14}H_{22}N_2Si$ [M+H]$^+$ 247.43, observed 247.0.

A mixture of 1-(tert-butyl-dimethyl-silanyl)-5-methyl-1H-pyrrolo[2,3-b]pyridine (7.92 g, 32.2 mmol) and a solution tetrabutylammonium fluoride in tetrahydrofuran (1 M, 161 mL, 161 mmol) was stirred for 2 h at room temperature. The mixture was poured into brine (50 mL), extracted with ethyl acetate (2×200 mL), washed with a saturated aqueous ammonium chloride solution (3×60 mL), dried over anhydrous sodium sulfate and then concentrated in vacuo. Purification by a flash column chromatography (Qingdao silica gel, 300 mesh, 20% ethyl acetate/hexanes) afforded 5-methyl-1H-pyrrolo[2,3-b]pyridine (3.5 g, 82%) as a white solid: LC/MS m/e calcd for $C_8H_8N_2$ [M+H]$^+$ 133.17, observed 133.0.

To a mixture of 5-methyl-1H-pyrrolo[2,3-b]pyridine (3.5 g, 26.5 mmol), triethylamine (8.03 g, 79.5 mmol), and 4-dimethylaminopyridine (0.32 g, 2.65 mmol) in dichloromethane (100 mL) at 0° C. was added benzenesulfonyl chloride (7.0 g, 39.8 mmol). After stirring for 48 h at room temperature, the reaction was quenched with water (50 mL) and extracted with dichloromethane (2×120 mL). The organic layer was washed with a saturated sodium bicarbonate solution (2×30 mL), water (2×30 mL), brine (50 mL), dried over anhydrous sodium sulfate and concentrated in vacuo. The residue was purified by flash column chromatography (silica gel from QingDao, 200-300 mesh, 33% dichloromethane/hexanes) to afford 1-benzenesulfonyl-5-methyl-1H-pyrrolo[2,3-b]pyridine (4.6 g, 64%) as white solid: LC/MS m/e calcd for $C_{14}H_{12}N_2O_4S$ [M+H]$^+$ 273.33, observed 272.9.

To a suspension of 1-benzenesulfonyl-5-methyl-1H-pyrrolo[2,3-b]pyridine (4.2 g, 15.4 mmol) in dry tetrahydrofuran (200 mL) at −78° C. was added a solution of n-butyllithium in n-hexane (2.5 M, 9.3 mL, 23.2 mmol) dropwise. The mixture was stirred at −78° C. for 5 min and then treated with cyclopentanecarbaldehyde (3.45 g, 30.8 mmol) dropwise. The resulting mixture was stirred at −78° C. for 1 h and quenched with brine. The mixture was extracted with ethyl acetate (2×200 mL), washed with brine, dried over anhydrous sodium sulfate and concentrated in vacuo. Purification by flash column chromatography (QingDao silica gel, 200-300 mesh, 60% dichloromethane/hexanes) afforded 1-(1-benzenesulfonyl-5-methyl-1H-pyrrolo[2,3-b]pyridin-2-yl)-2-cyclopentyl-ethanol (3.13 g, 53%): LC/MS m/e calcd for $C_{21}H_{24}N_2O_3S$ [M+H]$^+$ 385.50, observed 384.9.

To a solution of 1-(1-benzenesulfonyl-5-methyl-1H-pyrrolo[2,3-b]pyridin-2-yl)-2-cyclopentyl-ethanol (3.13 g, 8.15 mmol) in dichloromethane (150 ml) was added Dess-Martin periodinane (5.18 g, 12.2 mmol) at 25° C. The reaction mixture was stirred at 25° C. for 1 h and then quenched with a saturated aqueous sodium bicarbonate solution (40 mL). The mixture was extracted with ethyl acetate (200 mL), washed with a saturated aqueous sodium bicarbonate solution (40 mL×3), brine, dried over anhydrous sodium sulfate and then concentrated in vacuo. The residue was purified by flash column chromatography (silica gel from QingDao, 200-300 mesh, 60% dichloromethane/hexanes) to afford 1-(1-benzenesulfonyl-5-methyl-1H-pyrrolo[2,3-b]pyridin-2-yl)-2-cyclopentyl-ethanone (2.8 g, 90%) as a light yellow solid: LC/MS m/e calcd for $C_{21}H_{22}N_2O_3S$ [M+H]$^+$ 383.49, observed 382.8.

To a solution of 1-(1-benzenesulfonyl-5-methyl-1H-pyrrolo[2,3-b]pyridin-2-yl)-2-cyclopentyl-ethanone (2.8 g, 7.33 mmol) in anhydrous tetrahydrofuran (140 mL) at −78° C. under nitrogen atmosphere was added a solution of lithium bis(trimethylsilyl)amide in tetrahydrofuran (1.0 M, 11 mL, 11 mmol) dropwise. After stirring at −78° C. for 1 h, a solution of p-toluenesulfonic anhydride (4.3 g, 13.2 mmol) in tetrahydrofuran (10 mL) was added dropwise. The resulting mixture was stirred for −78° C. for an additional 1.5 h. The reaction was quenched with water, extracted with ethyl acetate (200 mL), washed with brine, dried over anhydrous sodium sulfate and then concentrated in vacuo. Purification by flash column chromatography (silica gel from QingDao, 200-300 mesh, 100% dichloromethane) afforded toluene-4-sulfonic acid 1-(1-benzenesulfonyl-5-methyl-1H-pyrrolo[2,3-b]pyridin-2-yl)-2-cyclopentyl-vinyl ester (3.65 g, 93%) as a light yellow solid: LC/MS m/e calcd for $C_{28}H_{28}N_2O_5S_2$ [M+H]$^+$ 537.67, observed 536.7.

To a mixture of toluene-4-sulfonic acid 1-(1-benzenesulfonyl-5-methyl-1H-pyrrolo[2,3-b]pyridin-2-yl)-2-cyclopentyl-vinyl ester (500 mg, 0.93 mmol), 4-methylsulfonyl phenylboronic acid (560 mg, 2.8 mmol) and dichlorobis(triphenylphosphine)palladium (II) (65 mg, 0.093 mmol) in dioxane (5 mL) was added an aqueous sodium carbonate solution (2 M, 1.40 mL, 2.8 mmol). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash column chromatography (silica gel from QingDao, 200-300 mesh, 35% ethyl acetate/hexanes) afforded 1-benzenesulfonyl-2-[2-cyclopentyl-1-(4-methanesulfonyl-phenyl)-vinyl]-5-methyl-1H-pyrrolo[2,3-b]pyridine (390 mg, 81%) as a white solid: LC/MS m/e calcd for $C_{28}H_{28}N_2O_4S_2$ [M+H]$^+$ 521.67, observed 520.7.

A mixture of 1-benzenesulfonyl-2-[2-cyclopentyl-1-(4-methanesulfonyl-phenyl)-vinyl]-5-methyl-1H-pyrrolo[2,3-b]pyridine (390 mg, 0.75 mmol) and a solution of tetrabutylammonium fluoride in tetrahydrofuran (1 M, 15 mL, 15 mmol) was stirred for 12 h at room temperature. The mixture was poured into brine (15 mL), extracted with ethyl acetate (2×50 mL), washed with a saturated aqueous ammonium chloride solution (3×20 mL), dried over anhydrous sodium sulfate and then concentrated in vacuo to afford 2-[2-cyclopentyl-1-(4-methanesulfonyl-phenyl)-vinyl]-5-methyl-1H-pyrrolo[2,3-b]pyridine (240 mg, 84%) as a solid which was used in the next step without purification: LC/MS m/e calcd for $C_{22}H_{24}N_2O_2S$ [M+H]$^+$ 381.51, observed 380.9.

A mixture of 2-[2-cyclopentyl-1-(4-methanesulfonyl-phenyl)-vinyl]-5-methyl-1H-pyrrolo[2,3-b]pyridine (240 mg, 0.63 mmol) and 10% palladium on activated carbon (100 mg) in methanol (50 mL) was heated at 50° C. under hydrogen (50 psi) for 5 h. After cooling to room temperature, the catalyst was removed by filtration and washed with ethyl acetate. The filtrate was concentrated in vacuo. The residue was purified using a Waters automated flash system (column: Xterra 30 mm×100 mm, sample manager 2767, pump 2525, detector: ZQ mass and UV 2487, solvent system: acetonitrile and 0.1% ammonium hydroxide in water) to afford 2-[2-cyclopentyl-1-(4-methanesulfonyl-phenyl)-ethyl]-5-methyl-1H-pyrrolo[2,3-b]pyridine as a white solid (150 mg, 100%): LC/MS m/e calcd for $C_{22}H_{26}N_2O_2S$ [M+H]$^+$ 383.53, observed 382.9; $^1$H NMR (400 MHz, CD$_3$OD) δ ppm 8.21 (s, 1H), 8.06 (s, 1H), 7.87-7.91 (m, J=8.1 Hz, 2H), 7.56-7.61 (m, J=8.3 Hz, 2H), 6.61 (s, 1H), 4.34 (t, J=7.8 Hz, 1H), 2.99-3.10 (m, 3H), 2.48 (s, 3H), 2.22-2.30 (m, 1H), 2.10-2.18 (m, 1H), 1.58-1.86 (m, 5H), 1.43-1.54 (m, 2H), 1.16-1.30 (m, 2H).

Example 129

2-{4-[2-Cyclopentyl-1(R)-(5-methyl-1H-pyrrolo[2,3-b]pyridin-2-yl)-ethyl]-2-fluoro-phenyl}-propan-2-ol

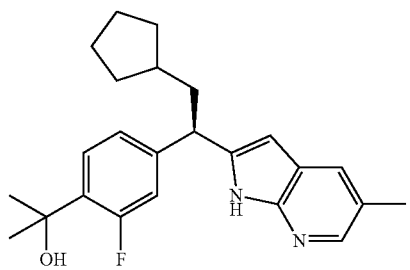

To a mixture of toluene-4-sulfonic acid 1-(1-benzenesulfonyl-5-methyl-1H-pyrrolo[2,3-b]pyridin-2-yl)-2-cyclopentyl-vinyl ester (prepared as in Example 128, 1.28 g, 2.4 mmol), 2-fluoro-4-(4,4,5,5-tetramethyl-[1,3,2]dioxaborolan-2-yl)-benzoic acid methyl ester (2.01 mg, 2.4 mmol) and dichlorobis(triphenylphosphine)palladium (II) (170 mg, 0.24 mmol) in dioxane (10 mL) was added an aqueous sodium carbonate solution (2 M, 3.6 mL, 7.2 mmol). The resulting mixture was subjected to microwave irradiation for 2 h at 100° C. The mixture was diluted with ethyl acetate (100 mL), washed with a saturated aqueous sodium bicarbonate solution (2×30 mL), brine, dried over anhydrous sodium sulfate and then concentrated in vacuo. Purification by flash column chromatography (silica gel from QingDao, 200-300 mesh, 25% ethyl acetate/hexanes) afforded 4-[1-(1-benzenesulfonyl-5-methyl-1H-pyrrolo[2,3-b]pyridin-2-yl)-2-cyclopentyl-vinyl]-2-fluoro-benzoic acid methyl ester (1.03 g, 83%) as a light yellow solid: LC/MS m/e calcd for $C_{29}H_{27}FN_2O_4S$ [M+H]$^+$ 519.61, observed 518.8.

A mixture of 4-[1-(1-benzenesulfonyl-5-methyl-1H-pyrrolo[2,3-b]pyridin-2-yl)-2-cyclopentyl-vinyl]-2-fluoro-benzoic acid methyl ester (470 mg, 1.99 mmol) and a solution of tetrabutylammonium fluoride in tetrahydrofuran (1 M, 39.8 mL, 39.8 mmol) was stirred for 12 h at room temperature. The mixture was poured into brine (15 mL), extracted with ethyl acetate (2×50 mL), washed with a saturated aqueous ammonium chloride solution (3×30 mL), dried over anhydrous sodium sulfate and then concentrated in vacuo to give 4-[2-cyclopentyl-1-(5-methyl-1H-pyrrolo[2,3-b]pyridin-2-yl)-vinyl]-2-fluoro-benzoic acid methyl ester (0.75 g, 100%) as a solid which was used in the next step without purification: LC/MS m/e calcd for $C_{23}H_{23}FN_2O_2$ [M+H]$^+$ 379.45, observed 378.9.

A mixture of 4-[2-cyclopentyl-1-(5-methyl-1H-pyrrolo[2,3-b]pyridin-2-yl)-vinyl]-2-fluoro-benzoic acid methyl ester (0.8 g, 2.1 mmol) and 10% palladium on activated carbon (600 mg) in methanol (100 mL) was heated at 50° C. under hydrogen (50 psi) for 5 h. After cooling to room temperature, the catalyst was removed by filtration and washed with ethyl acetate. The filtrate was concentrated in vacuo to give 4-[2-cyclopentyl-1-(5-methyl-1H-pyrrolo[2,3-b]pyridin-2-yl)-ethyl]-2-fluoro-benzoic acid methyl ester as a white solid (129 mg, 16%): LC/MS m/e calcd for $C_{23}H_{25}FN_2O_2$ [M+H]$^+$ 381.47, observed 381.0.

To a solution of 4-[2-cyclopentyl-1-(5-methyl-1H-pyrrolo[2,3-b]pyridin-2-yl)-ethyl]-2-fluoro-benzoic acid methyl ester (129 mg, 0.34 mmol) in anhydrous tetrahydrofuran (5 mL) at 0° C. was added a solution of methylmagnesium chloride in tetrahydrofuran (1 M, 2.0 ml, 2.0 mmol) dropwise. After stirring for 2 h at 0° C., the reaction mixture was poured into brine (15 mL), extracted with ethyl acetate (2×50 mL), dried over anhydrous sodium sulfate and then concentrated in vacuo. Purification using a Waters automated flash system (column: Xterra 30 mm×100 mm, sample manager 2767, pump 2525, detector: ZQ mass and UV 2487, solvent system: acetonitrile and 0.1% ammonium hydroxide in water) afforded 2-{4-[2-cyclopentyl-1-(5-methyl-1H-pyrrolo[2,3-b]pyridin-2-yl)-ethyl]-2-fluoro-phenyl}-propan-2-ol (100 mg, 77%): LC/MS m/e calcd for $C_{24}H_{29}FN_2O$ [M+H]$^+$ 381.51, observed 381.0.

The 1:1 mixture of enantiomers of 2-{4-[2-cyclopentyl-1-(5-methyl-1H-pyrrolo[2,3-b]pyridin-2-yl)-ethyl]-2-fluoro-phenyl}-propan-2-ol were separated by Agilent high performance liquid chromatography (chiral column: Daicel IA-H, 250 mm×20 mm i. d., 5 μm-particle size, temperature: 25° C., flow rate of 15 mL/min, 40% isopropyl alcohol/hexanes as mobile phase and UV detection: 214 and 254 nm) to afford two pure enantiomers. The second peak, 2-{4-[2-cyclopentyl-1(R)-(5-methyl-1H-pyrrolo[2,3-b]pyridin-2-yl)-ethyl]-2-fluoro-phenyl}-propan-2-ol was isolated as white solid: LC/MS m/e calcd for $C_{24}H_{29}FN_2O$ [M+H]$^+$ 381.51, observed 381.0; $^1$H NMR (400 MHz, CD$_3$OD) δ ppm 7.87 (s, 1H), 7.64 (s, 1H), 7.50 (t, J=8.3 Hz, 1H), 7.06 (d, J=8.1 Hz, 1H), 6.95 (d, J=13.1 Hz, 1H), 6.20 (s, 1H), 4.04-4.12 (m, 1H), 2.34 (s, 3H), 2.09-2.18 (m, 1H), 1.95-2.05 (m, 1H), 1.50-1.78 (m, 9H), 1.36-1.49 (m, 2H), 1.09-1.30 (m, 2H)

Example 130

2-(3-Methyl-1-m-tolyl-butyl)-1H-pyrrolo[2,3-b]pyridine

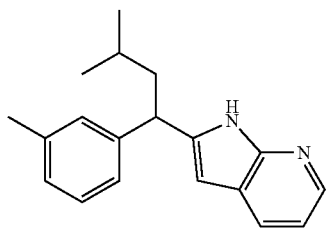

A mixture of 7-azaindole (10 g, 84.6 mmol) and tetrabutylammonium bromide (0.81 g, 2.53 mmol) in dichloromethane (211 mL, 0.4 M) at 0° C. was treated with powdered sodium hydroxide (10.15 g, 253.9 mmol). This solution was stirred at 0° C. for 10 min, it was then slowly treated with benzenesulfonyl chloride (16.3 mL, 126.9 mmol). The reaction was allowed to gradually warm to 25° C. and was stirred for 16 h. At this time, the resulting solids were removed by filtration and were washed with dichloromethane (2×50 mL). The filtrate was concentrated in vacuo to afford a yellow solid which was dried under high vacuum for 30 min. At this time, the solids were triturated with hexanes (3×50 mL) to afford 1-benzenesulfonyl-1H-pyrrolo[2,3-b]pyridine (19.5 g, 89.2%) as a light yellow solid: $^1$H NMR (400 MHz, d$_6$-DMSO) δ ppm 8.38 (dd, 1H, J$_1$=4.5 Hz, J$_2$=1.2 Hz), 8.12 (d, 2H, J=7.8 Hz), 8.05 (dd, 1H, J$_1$=7.8 Hz, J$_2$=1.8 Hz), 7.93 (d, 1H, J=3.9 Hz), 7.74-7.59 (m, 3H), 7.32-7.28 (m, 1H), 6.84 (d, 1H, J=3.9 Hz).

To a suspension of 1-benzenesulfonyl-1H-pyrrolo[2,3-b]pyridine (5.0 g, 19.3 mmol) in dry tetrahydrofuran (125 mL) at −78° C. was added lithium diisopropylamide (14.5 mL, 29 mmol) dropwise. The mixture was stirred at −78° C. for 10 min and then treated with 3-methylbutanal (3.9 g, 45 mmol) dropwise. The resulting mixture was stirred at −78° C. for 1.5 h. At this time, the reaction was quenched with a saturated aqueous sodium chloride solution. The resulting mixture was then extracted with ethyl acetate (3×150 mL). The combined organic layers were dried over anhydrous sodium sulfate, filtered and concentrated in vacuo. Silica gel column chromatography (10-15% ethyl acetate/petroleum ether) afforded 1-(1-benzenesulfonyl-1H-pyrrolo[2,3-b]pyridin-2-yl)-3-methyl-butan-1-ol (3.4 g, 51.8%) as a white solid: $^1$H NMR (300 MHz, d$_6$-DMSO): δ 8.29 (d, 1H, J=3.3 Hz), 8.10 (d, 2H, J=7.8 Hz), 7.96 (d, 1H, J=7.5 Hz), 7.72-7.59 (m, 3H), 7.28-7.24 (m, 1H), 6.81 (s, 1H), 5.55-5.46 (m, 2H), 2.05-1.90 (m, 1H), 1.81-1.73 (m, 1H), 1.04 (d, 3H, J=6.3 Hz), 0.97 (s, 3H), 0.95 (s, 3H).

A solution of Dess-Martin periodinane reagent (3.3 g, 7.8 mmol) in dichloromethane (50 mL) at 25° C. was treated with 1-(1-benzenesulfonyl-1H-pyrrolo[2,3-b]pyridin-2-yl)-3-methyl-butan-1-ol (1.4 g, 4.1 mmol). The reaction was stirred at 25° C. for 3 h. At this time, the reaction was quenched by the addition of a saturated aqueous sodium bicarbonate solution. The resulting solution was extracted with ethyl acetate (3×100 mL). The combined organic layers were dried over anhydrous sodium sulfate, filtered and concentrated in vacuo. Silica gel column chromatography (20% ethyl acetate/petroleum ether) afforded 1-(1-benzenesulfonyl-1H-pyrrolo[2,3-b]pyridin-2-yl)-3-methyl-butan-1-one as a white solid (1.2 g, 82.1%): $^1$H NMR (300 MHz, d$_6$-DMSO): δ ppm 8.54 (d, 1H, J=4.5 Hz), 8.27 (d, 2H, J=7.8 Hz), 8.17 (d, 1H, J=7.8 Hz), 7.76-7.66 (m, 3H), 7.58 (s, 1H), 7.42-7.38 (m, 1H), 2.91 (d, 2H, J=6.9 Hz), 2.23-2.18 (m, 1H), 1.01 (s, 3H), 0.99 (s, 3H).

A solution of 1-(1-benzenesulfonyl-1H-pyrrolo[2,3-b]pyridin-2-yl)-3-methyl-butan-1-one (1.1 g, 3.2 mmol) in tetrahydrofuran (40 mL) at −78° C. was treated with lithiumbis(trimethylsilyl)amide in tetrahydrofuran (1 M, 5.6 mL, 5.6 mmol). The reaction was then stirred at −78° C. for 1 h. At this time, the reaction was treated with a solution of p-toluenesulfonic anhydride (2.0 g, 5.9 mmol) in tetrahydrofuran (6 mL). The reaction was stirred at −78° C. for 2 h. At this time, the reaction was poured into water (200 mL) and then extracted with ethyl acetate (3×100 mL). The organics were dried over anhydrous sodium sulfate, filtered and concentrated in vacuo. Silica gel column chromatography (15% ethyl acetate/petroleum ether) afforded toluene-4-sulfonic acid-1-(1-benzenesulfonyl-1H-pyrrolo[2,3-b]pyridin-2-yl)-3-methyl-but-1-enyl ester as a white solid (1.1 g, 67.8%): $^1$H NMR (300 MHz, d$_6$-DMSO): δ ppm 8.38 (d, 1H, J=4.5 Hz), 8.04 (d, 2H, J=7.8 Hz), 7.72 (t, 1H, J=7.2 Hz), 7.63-7.58 (m, 2H), 7.33-7.27 (m, 3H), 7.00 (d, 2H, J=4.8 Hz), 6.72 (s, 1H), 5.78 (d, 2H, J=9.9 Hz), 2.81-2.75 (m, 1H), 2.11 (s, 3H), 1.01 (s, 3H), 0.99 (s, 3H).

A suspension of toluene-4-sulfonic acid-1-(1-benzenesulfonyl-1H-pyrrolo[2,3-b]pyridin-2-yl)-3-methyl-but-1-enyl ester (3.0 g, 6.04 mmol), m-tolylboronic acid (2.05 g, 15.1 mmol), bis(triphenylphosphine)palladium(II) dichloride (0.5 g, 0.71 mmol) in dioxane (30 mL) and an aqueous sodium carbonate solution (2N, 15 mL) was heated in a microwave at ~90° C. for 2 h. The reaction mixture was cooled to 25° C., diluted with ethyl acetate (300 mL), washed with a saturated aqueous sodium bicarbonate solution and saturated sodium chloride solution. The organic layer was dried over anhydrous sodium sulfate, filtered and concentrated in vacuo. Silica gel column chromatography (300-400 mesh, 9% ethyl acetate/petroleum ether) afforded 1-benzenesulfonyl-2-(3-methyl-1-m-tolyl-but-1-enyl)-1H-pyrrolo[2, 3-b]pyridine (2.99 g, crude) as a white solid, which was used in the next step without further purification: $^1$H NMR (300 MHz, CDCl$_3$) δ ppm 8.49 (dd, 1H, $J_1$=4.8 Hz, $J_2$=0.9 Hz), 7.89 (dd, 1H, $J_1$=7.8 Hz, $J_2$=1.5 Hz), 7.61 (dd, 2H, $J_1$=8.4 Hz, $J_2$=1.5 Hz), 7.43-7.01 (m, 7H), 6.89 (s, 1H), 6.52 (s, 1H), 6.11 (d, 1H, J=10.2 Hz), 2.73-2.60 (m, 1H), 2.17 (s, 3H), 1.12 (dd, 6H, $J_1$=9.3 Hz, $J_2$=6.6 Hz).

A solution of 1-benzenesulfonyl-2-(3-methyl-1-m-tolyl-but-1-enyl)-1H-pyrrolo[2,3-b]pyridine (2.99 g) in ethanol (50 mL) and tetrahydrofuran (100 mL) was treated with 10% aqueous sodium hydroxide solution (20 mL). The reaction was stirred at 85° C. for 14 h. The reaction mixture was cooled to 25° C. and concentrated in vacuo. Water (100 mL) was added to the residue, and the solution was extracted with ethyl acetate (2×100 mL). The organic layers were dried over anhydrous sodium sulfate, filtered and concentrated in vacuo. A light yellow solid was obtained and washed with ethanol (20 mL), then dried to afford 2-(3-methyl-1-m-tolylbut-1-enyl)-1H-pyrrolo[2,3-b]pyridine (1.30 g, 77.8%) as a white solid: $^1$H NMR (300 MHz, CDCl$_3$): δ ppm 9.50 (s, 1H), 7.98-7.89 (m, 2H), 7.23-7.01 (m, 5H), 6.50 (s, 1H), 5.64 (d, 1H, J=10.2 Hz), 2.98-2.90 (m, 1H), 2.32 (s, 3H), 1.12 (s, 3H), 1.10 (s, 3H).

A solution of 2-(3-methyl-1-m-tolylbut-1-enyl)-1H-pyrrolo[2,3-b]pyridine (1.30 g, 4.70 mmol) in tetrahydrofuran (20 mL) and methanol (40 mL) was treated with 10% palladium on carbon (260 mg). The reaction was stirred at 25° C. under hydrogen atmosphere for 2 d. The reaction mixture was filtered and washed with tetrahydrofuran (2×15 mL). The filtrate was concentrated in vacuo. Silica gel column chromatography (300-400 mesh, 11% ethyl acetate/petroleum ether) afforded 2-(3-methyl-1-m-tolylbutyl)-1H-pyrrolo[2,3-b]pyridine (1.07 g, 81.3%) as light oil: $^1$H NMR (300 MHz, d$_6$-DMSO): δ ppm 11.54 (s, 1H), 8.09 (d, 1H, J=3.6 Hz), 7.80 (d, 1H, J=7.5 Hz), 7.19-7.16 (m, 3H), 6.98-6.94 (m, 2H), 6.26 (d, 1H, J=1.5 Hz), 4.13 (t, 1H, J=8.1 Hz), 2.27 (s, 3H), 2.09-2.05 (m, 1H), 1.86-1.81 (m, 1H), 1.41-1.36 (m, 1H), 0.90 (s, 3H), 0.89 (s, 3H.

Example 131

2-(1-(3-Chloro-phenyl)-3-methyl-butyl)-1H-pyrrolo [2,3-b]pyridine

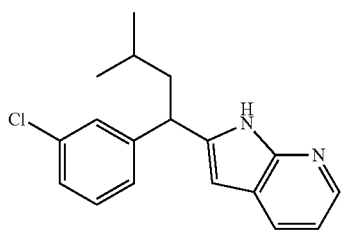

A suspension of toluene-4-sulfonic acid-1-(1-benzenesulfonyl-1H-pyrrolo[2,3-b]pyridin-2-yl)-3-methyl-but-1-enyl ester (prepared as in Example 130, 3.0 g, 6.0 mmol), 3-chloro-phenylboronic acid (2.35 g, 15 mmol), bis(triphenylphosphine)palladium(II) dichloride (0.42 g, 0.6 mmol) in dioxane (30 mL) and an aqueous sodium carbonate solution (2N, 15 mL) was heated in a microwave at 100° C. for 2 h. The reaction mixture was diluted with ethyl acetate (100 mL) and washed with a saturated sodium bicarbonate solution (2×50 mL). The organics were dried over anhydrous sodium sulfate, filtered and concentrated in vacuo. Silica gel column chromatography (30 g, 5% ethyl acetate/petroleum ether) afforded 2-(1-(3-chloro-phenyl)-3-methyl-but-1-enyl)-1-(phenylsulfonyl)-1H-pyrrolo[2,3-b]pyridine (2.5 g, 95.4%) as an off-white solid: $^1$H NMR (300 MHz, CDCl$_3$) δ ppm 8.51 (dd, 1H, $J_1$=4.8 Hz, $J_2$=1.8 Hz), 7.89 (dd, 1H, $J_1$=7.8 Hz, $J_2$=1.8 Hz), 7.68 (dd, 2H, $J_1$=8.7 Hz, $J_2$=1.5 Hz), 7.44 (m, 1H), 7.28-7.06 (m, 5H), 6.53 (s, 1H), 6.13 (d, 1H, J=10.2 Hz), 2.65 (m, 1H), 1.15-1.08 (m, 6H).

A solution of 2-(1-(3-chloro-phenyl)-3-methyl-but-1-enyl)-1-(phenylsulfonyl)-1H-pyrrolo[2,3-b]pyridine (2.5 g, 5.7 mmol) in ethanol (45 mL) and tetrahydrofuran (90 mL) was treated with a 10% aqueous sodium hydroxide solution (15 mL). The reaction was stirred at 70° C. for 16 h. The solvent was removed in vacuo and the obtained precipitate was filtered and washed with water (3×50 mL) and ethyl acetate (20 mL) to afford 2-(1-(3-chloro-phenyl)-3-methyl-but-1-enyl)-1H-pyrrolo[2,3-b]pyridine (1.3 g, 77%) as a white solid: $^1$H NMR (300 MHz, d$_6$-DMSO) δ ppm 11.57 (s, 1H), 8.17 (dd, 1H, $J_1$=4.5 Hz, $J_2$=1.5 Hz), 7.93 (dd, 1H, $J_1$=8.4 Hz, $J_2$=1.8 Hz), 7.31 (m, 2H), 7.21 (m, 1H), 7.15 (m, 1H), 7.05 (m, 1H), 6.40 (s, 1H), 6.21 (d, 1H, J=9.9 Hz), 2.57 (m, 1H), 1.03-1.01 (m, 6H).

A solution of 2-(1-(3-chloro-phenyl)-3-methyl-but-1-enyl)-1H-pyrrolo[2,3-b]pyridine (1.3 g, 4.4 mmol) in tetrahydrofuran (50 mL) was treated with platinum dioxide (200 mg). The reaction was stirred at 25° C. under hydrogen atmosphere for 3 d. At this time, the reaction mixture was filtered and the filtrate was concentrated in vacuo. HPLC purification afforded 2-(1-(3-chloro-phenyl)-3-methyl-butyl)-1H-pyrrolo[2,3-b]pyridine (280 mg, 21.4%) as a colorless oil: $^1$H NMR (300 MHz, d$_6$-DMSO): δ ppm 11.83 (s, 1H), 8.17 (d, 1H, J=4.8 Hz), 7.96 (d, 1H, J=7.2 Hz), 7.46 (s, 1H), 7.36-7.25 (m, 3H), 7.11 (m, 1H), 6.40 (s, 1H), 4.25 (t, 1H, J=7.8 Hz), 2.11-2.04 (m, 1H), 1.93-1.86 (m, 1H), 1.40-1.36 (m, 1H), 0.91 (s, 3H), 0.88 (s, 3H).

Example 132

2-(1-(3-Fluoro-phenyl)-3-methyl-butyl)-1H-pyrrolo [2,3-b]pyridine

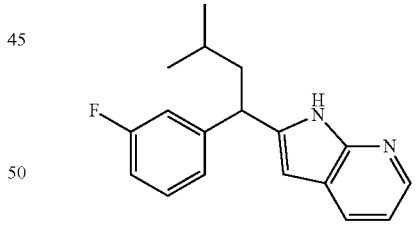

A suspension of toluene-4-sulfonic acid-1-(1-benzenesulfonyl-1H-pyrrolo[2,3-b]pyridin-2-yl)-3-methyl-but-1-enyl ester (prepared as in Example 130, 3.0 g, 6.05 mmol), 3-fluoro-phenylboronic acid (2.1 g, 15 mmol), bis(triphenylphosphine)palladium(II) dichloride (0.42 g, 0.6 mmol) in dioxane (30 mL) and an aqueous sodium carbonate solution (2N, 15 mL) was heated at 90° C. in a microwave for 2 h. The reaction mixture was diluted with ethyl acetate (200 mL) and washed with a saturated aqueous sodium bicarbonate solution (2×50 mL). The organics were dried over anhydrous sodium sulfate, filtered and concentrated in vacuo. Silica gel column chromatography (40 g, 17% ethyl acetate/petroleum ether) afforded 2-(1-(3-fluoro-phenyl)-3-methyl-but-1-enyl)-1-(phenylsulfonyl)-1H-pyrrolo[2,3-b]pyridine (2.6 g, 88%) as an off-white solid: ¹H NMR (300 MHz, CDCl₃) δ ppm 8.50 (dd, 1H, J₁=5.1 Hz, J₂=1.8 Hz), 7.89 (dd, 1H, J₁=7.5 Hz, J₂=1.5 Hz), 7.69 (dd, 2H, J₁=8.4 Hz, J₂=1.2 Hz), 7.46-7.40 (m, 1H), 7.27-7.13 (m, 5H), 7.01-6.89 (m, 2H), 6.85-6.80 (m, 1H), 6.53 (s, 1H), 6.14 (d, 1H J=10.2 Hz), 2.71-2.59 (m, 1H), 1.15-1.10 (m, 6H).

A solution of 2-(1-(3-fluoro-phenyl)-3-methyl-but-1-enyl)-1-(phenylsulfonyl)-1H-pyrrolo[2,3-b]pyridine (2.6 g, 6.2 mmol) in ethanol (8 mL) and tetrahydrofuran (15 mL) was treated with an aqueous sodium hydroxide solution (10%, 20 mL). The reaction was stirred at 80° C. for 16 h. At this time, the reaction mixture was cooled to 25° C. and the resulting precipitate was collected by filtration. The solids were washed with petroleum ether and diethyl ether and then dried under vacuum to afford 2-(1-(3-fluoro-phenyl)-3-methyl-but-1-enyl)-1H-pyrrolo[2,3-b]pyridine (1.2 g, 69%) as a white solid: ¹H NMR (300 MHz, CDCl₃) δ ppm 10.50 (s, 1H), 7.89 (dd, 1H, J₁=4.8 Hz, J₂=1.5 Hz), 7.84 (dd, 1H, J₁=5.1 Hz, J₂=1.5 Hz), 7.27-7.22 (m, 2H), 6.48 (d, 1H, J=2.1 Hz), 6.03 (d, 1H, J=10.5 Hz), 2.96-2.84 (m, 1H), 1.12 (s, 3H), 1.10 (s, 3H).

A solution of 2-(1-(3-fluoro-phenyl)-3-methyl-but-1-enyl)-1H-pyrrolo[2,3-b]pyridine (1.2 g, 4.28 mmol) in methanol (35 mL) was treated with 10% palladium on carbon (180 mg). The reaction was stirred at 25° C. under hydrogen atmosphere for 16 h. The reaction mixture was filtered and the filtrate was concentrated in vacuo to afford 2-(1-(3-fluoro-phenyl)-3-methyl-butyl)-1H-pyrrolo[2,3-b]pyridine (1.2 g, 99%) as an off-white solid: ¹H NMR (300 MHz, d₆-DMSO): δ ppm 11.59 (s, 1H), 8.08 (dd, 1H, J₁=4.8 Hz, J₂=1.5 Hz), 7.82-7.79 (m, 1H), 7.37-7.21 (m, 3H), 7.04-6.95 (m, 2H), 6.30 (s, 1H), 4.23 (t, 1H, J=8.1 Hz), 2.11-2.04 (m, 1H), 1.92-1.85 (m, 1H), 1.40-1.35 (m, 1H), 0.91 (s, 3H), 0.89 (s, 3H).

Example 133

2-(1-(3-Ethoxy-phenyl)-3-methyl-butyl)-1H-pyrrolo[2,3-b]pyridine

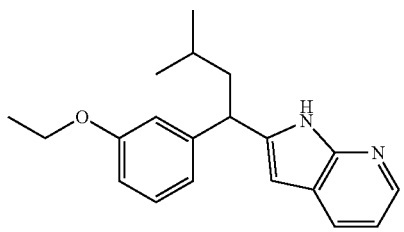

A suspension of toluene-4-sulfonic acid-1-(1-benzenesulfonyl-1H-pyrrolo[2,3-b]pyridin-2-yl)-3-methyl-but-1-enyl ester (prepared as in Example 130, 3.0 g, 6.04 mmol), 3-ethoxy-phenylboronic acid (2.51 g, 15.1 mmol), bis(triphenylphosphine)palladium(II) dichloride (420 mg, 0.60 mmol) in 1,4-dioxane (30 mL) and an aqueous sodium carbonate solution (2N, 15.4 mL) was heated in a microwave at 100° C. for 2 h under nitrogen. The reaction mixture was diluted with ethyl acetate (20 mL) and washed with a saturated aqueous sodium bicarbonate solution (2×40 mL). The organics were dried over anhydrous sodium sulfate, filtered and concentrated in vacuo. Silica gel column chromatography (40 g, 11% ethyl acetate/petroleum ether) afforded 2-(1-(3-ethoxy-phenyl)-3-methyl-but-1-enyl)-1-(phenylsulfonyl)-1H-pyrrolo[2,3-b]pyridine (2.2 g, 81%) as a yellow oil: ¹H NMR (300 MHz, CDCl₃) δ ppm 8.49 (d, 1H, J=4.5 Hz), 7.87 (d, 1H, J=8.4 Hz), 7.67 (d, 2H, J=4.8 Hz), 7.41 (t, 1H, J=7.5 Hz), 7.27-7.10 (m, 4H), 6.79 ((t, 2H, J=6.3 Hz), 6.52 (s, 1H), 6.14 (d, 1H, J=6.6 Hz), 3.94-3.85 (m, 2H), 2.71-2.64 (m, 1H), 1.33 (t, 3H, J=7.2 Hz), 1.14 (t, 6H, J=7.5 Hz).

A solution of 2-(1-(3-ethoxy-phenyl)-3-methyl-but-1-enyl)-1-(phenylsulfonyl)-1H-pyrrolo[2,3-b]pyridine (2.2 g, 4.9 mmol) in ethanol (58.5 mL) and tetrahydrofuran (117 mL) was treated with an aqueous sodium hydroxide solution (10%, 22 mL). The reaction was stirred at 70° C. for 18 h. After cooling to 25° C., the reaction mixture was diluted with water (200 mL) and extracted with ethyl acetate (2×150 mL). The organic extracts were dried over anhydrous sodium sulfate, filtered and concentrated in vacuo. Silica gel column chromatography (50 g, ethyl acetate/petroleum ether 1:15) afforded 2-(1-(3-ethoxy-phenyl)-3-methyl-but-1-enyl)-1H-pyrrolo[2,3-b]pyridine (1.3 g, 86%) as a yellow oil: ¹H NMR (300 MHz, d₆-DMSO) δ ppm 11.59 (s, 1H), 8.16 (d, 1H, J=4.5 Hz), 7.92 (d, 1H, J=7.5 Hz), 7.19 (t, 1H, J=7.8 Hz), 7.04 (q, 1H), 6.82 (t, 2H, J=2.1 Hz), 6.72 (s, 1H), 6.36 (d, 1H, J=1.8 Hz), 6.15 (d, 1H, J=9.9 Hz), 3.95 (q, 2H, J=13.8 Hz), 2.61-2.49 (m, 1H), 1.26 (t, 3H, J=6.9 Hz), 1.03 (s, 3H), 1.01 (s, 3H).

A solution of 2-(1-(3-ethoxy-phenyl)-3-methyl-but-1-enyl)-1H-pyrrolo[2,3-b]pyridine (1.3 g, 4.2 mmol) in methanol (30 mL) was treated with 10% palladium on carbon (130 mg). The reaction was stirred for 16 h at 25° C. under a balloon filled with hydrogen gas. The reaction mixture was filtered through a pad of celite and washed with methanol (2×20 mL). The filtrate was concentrated in vacuo. Silica gel column chromatography (30 g, ethyl acetate/petroleum ether: 1:10) afforded 2-(1-(3-ethoxy-phenyl)-3-methyl-butyl)-1H-pyrrolo[2,3-b]pyridine (800 mg, 62%) as a white solid: ¹H NMR (300 MHz, CDCl₃) δ ppm 9.37 (s, 1H), 8.15 (d, 1H, J=4.5 Hz), 7.83 (d, 1H, J=7.5 Hz), 7.20 (t, 1H, J=7.8 Hz), 7.01 (dd, 1H, J1=7.8 Hz, J2=4.8 Hz), 6.87-6.74 (m, 3H), 6.32 (s, 1H), 4.15 (t, 1H, J=8.1 Hz), 3.95 (q, 2H, J=6.9 Hz), 2.08-1.91 (m, 2H), 1.59-1.50 (m, 1H), 1.37 (t, 3H, J=6.9 Hz), 0.96 (s, 3H), 0.94 (s, 3H).

Example 134

2-(1-(3-Methoxy-phenyl)-3-methyl-butyl)-1H-pyrrolo[2,3-b]pyridine

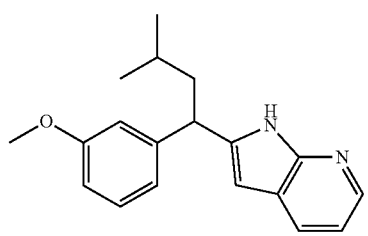

A suspension of toluene-4-sulfonic acid-1-(1-benzenesulfonyl-1H-pyrrolo[2,3-b]pyridin-2-yl)-3-methyl-but-1-enyl ester (prepared as in Example 130, 3.0 g, 6.04 mmol), 3-methoxy-phenylboronic acid (2.3 g, 15.1 mmol), bis(triphenylphosphine)palladium(II) dichloride (425 mg, 0.6 mmol) in 1,4-dioxane (30 mL) and an aqueous sodium carbonate solution (2N, 15.4 mL) was heated in a microwave at 100° C. for 2 h. The reaction mixture was diluted with ethyl acetate (20 mL) and washed with a saturated aqueous sodium bicarbonate solution (2×40 mL). The organics were dried over anhydrous sodium sulfate, filtered and concentrated in vacuo.

Silica gel column chromatography (30 g, petroleum ether/ethyl acetate 10:1) afforded 2-(1-(3-methoxy-phenyl)-3-methyl-but-1-enyl)-1-(phenylsulfonyl)-1H-pyrrolo[2,3-b]pyridine (2.3 g, 90%) as a white solid: $^1$H NMR (300 MHz, CDCl$_3$) δ ppm 8.50 (d, 1H, J=4.8 Hz), 7.90 (d, 1H, J=4.8 Hz), 7.67 (d, 2H, J=7.5 Hz), 7.42 (t, 1H, J=7.5 Hz), 7.27-7.18 (m, 3H), 6.82 ((t, 2H, J=9.0 Hz), 6.65 (s, 1H), 6.55-6.46 (m, 2H), 6.18-6.15 (d, 1H, J=10.2 Hz), 3.67 (s, 3H), 2.69-2.66 (m, 1H), 1.15 (s, 3H), 1.13 (s, 3H).

A solution of 2-(1-(3-methoxy-phenyl)-3-methyl-but-1-enyl)-1-(phenylsulfonyl)-1H-pyrrolo[2,3-b]pyridine (1.87 g, 4.3 mmol) in ethanol (38.7 mL) and tetrahydrofuran (77.4 mL) was treated with an aqueous sodium hydroxide solution (10%, 14.6 mL). The reaction was stirred at 70° C. for 18 h. After cooling to 25° C., the reaction mixture was diluted with water (70 mL) and extracted with ethyl acetate (3×60 mL). The organic extracts were dried over anhydrous sodium sulfate, filtered and concentrated in vacuo. Silica gel column chromatography (30 g, petroleum ether/ethyl acetate 10:1) afforded 2-(1-(3-methoxy-phenyl)-3-methyl-but-1-enyl)-1H-pyrrolo[2,3-b]pyridine (1.05 g, 90%) as a yellow oil: $^1$H NMR (300 MHz, CDCl$_3$) δ ppm 9.91 (s, 1H), 7.95 (dd, 1H, J$_1$=3.6 Hz, J$_2$=1.2 Hz), 7.89 (dd, 1H, J$_1$=7.8 Hz, J$_2$=1.2 Hz), 7.23 (t, 1H, J=7.8 Hz), 7.02 (s, 1H), 6.92-6.82 (m, 3H), 6.50 (s, 1H), 5.99 (d, 1H, J=9.9 Hz), 3.76 (s, 3H), 2.94-2.91 (m, 1H), 1.11 (s, 3H), 1.09 (s, 3H).

A solution of 2-(1-(3-methoxy-phenyl)-3-methyl-but-1-enyl)-1H-pyrrolo[2,3-b]pyridine (1.3 g, 4.5 mmol) in methanol (30 mL) was treated with 10% palladium on carbon (130 mg). The reaction was stirred for 16 h at 25° C. under a balloon filled with hydrogen gas. The reaction mixture was filtered through a pad of celite and washed with methanol (2×30 mL). The filtrate was concentrated in vacuo. Silica gel column chromatography (20 g, petroleum ether/ethyl acetate 15:1) afforded 2-(1-(3-methoxy-phenyl)-3-methyl-butyl)-1H-pyrrolo[2,3-b]pyridine (900 mg, 68%) as a yellow oil: $^1$H NMR (300 MHz, CDCl$_3$) δ ppm 10.54 (br. s., 1H), 8.16 (t, 1H, J=3.6 Hz), 7.83 (d, 1H, J=7.8 Hz), 7.24 (t, 1H, J=8.1 Hz), 7.02 (dd, 1H, J$_1$=7.8 Hz, J$_2$=4.8 Hz), 6.91-6.74 (m, 3H), 6.32 (s, 1H), 4.20 (t, 1H, J=7.5 Hz), 3.73 (s, 3H), 2.10-1.95 (m, 2H), 1.60-1.51 (m, 1H), 0.96 (d, 3H, J=4.2 Hz), 0.89 (s, 3H, J=4.2 Hz).

Example 135

1-{3-[3-Methyl-1-(1H-pyrrolo[2,3-b]pyridin-2-yl)-butyl]-phenyl}-ethanone

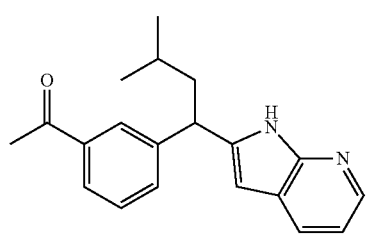

A suspension of toluene-4-sulfonic acid-1-(1-benzenesulfonyl-1H-pyrrolo[2,3-b]pyridin-2-yl)-3-methyl-but-1-enyl ester (prepared as in Example 130, 3.0 g, 6.0 mmol), 3-acetylphenylboronic acid (2.5 g, 15 mmol), bis(triphenylphosphine)palladium(II) dichloride (0.42 g, 0.6 mmol) in dioxane (30 mL) and an aqueous sodium carbonate solution (2N, 15 mL) was heated in a microwave at 100° C. for 2 h. The reaction mixture was diluted with ethyl acetate (100 mL) and washed with a saturated aqueous sodium bicarbonate solution (2×50 mL). The organics were dried over anhydrous sodium sulfate, filtered and concentrated in vacuo. Silica gel column chromatography (40 g, 10% ethyl acetate/petroleum ether) afforded 1-(3-(3-methyl-1-(1-(phenylsulfonyl)-1H-pyrrolo[2,3-b]pyridin-2-yl)but-1-enyl)phenyl)ethanone (1.5 g, 56.3%) as an off-white solid: $^1$H NMR (300 MHz, CDCl$_3$) δ ppm 8.49 (dd, 1H, J$_1$=4.8 Hz, J$_2$=1.8 Hz), 7.90 (dd, 1H, J$_1$=7.8 Hz, J$_2$=1.5 Hz), 7.81 (dd, 1H, J$_1$=8.1 Hz, J$_2$=1.8 Hz), 7.68-764 (m, 3H), 7.45-7.16 (m, 6H), 6.58 (s, 1H), 6.18 (d, 1H, J=10.2 Hz), 2.67-2.65 (m, 1H), 2.44 (s, 3H), 1.17-1.12 (m, 6H).

A solution of 1-(3-(3-methyl-1-(1-(phenylsulfonyl)-1H-pyrrolo[2,3-b]pyridin-2-yl)but-1-enyl)phenyl)ethanone (1.5 g, 3.4 mmol) in ethanol (30 mL) and tetrahydrofuran (60 mL) was treated with an aqueous sodium hydroxide solution (10%, 20 mL). The reaction was stirred at 80° C. for 16 h. Most of the solvent was removed in vacuo. The resulting precipitate was removed by filtration and washed with water (50 mL). The filtrate was concentrated in vacuo. Silica gel column chromatography (30 g, 200-300 mesh, 15% ethyl acetate/petroleum ether) afforded 1-(3-(3-methyl-1-(1H-pyrrolo[2,3-b]pyridin-2-yl)but-1-enyl)phenyl)ethanone (0.85 g, 82.2%) as an off-white solid: $^1$H NMR (300 MHz, d$_6$-DMSO) δ ppm 11.60 (s, 1H), 8.20 (dd, 1H, J$_1$=4.8 Hz, J$_2$=1.5 Hz), 7.96 (d, 1H, J=8.1 Hz), 7.90-7.87 (m, 1H), 7.78 (s, 1H), 7.48-7.46 (m, 2H), 7.09 (dd, 1H, J$_1$=7.5 Hz, J$_2$=5.1 Hz), 6.44 (d, 1H, J=1.8 Hz), 6.24 (d, 1H, J=9.9 Hz), 2.63-2.56 (m, 1H), 2.57 (s, 3H), 1.08-1.02 (m, 6H).

A solution of 1-(3-(3-methyl-1-(1H-pyrrolo[2,3-b]pyridin-2-yl)but-1-enyl)phenyl)ethanone (0.85 g, 2.8 mmol) in methanol (20 mL) and tetrahydrofuran (30 mL) was treated with 10% palladium on carbon (300 mg). The reaction was stirred for 16 h at 25° C. under hydrogen atmosphere. At this time, the reaction mixture was filtered. The filtrate was concentrated in vacuo. Silica gel column chromatography (20 g, 200-300 mesh, 10% ethyl acetate/petroleum ether) afforded 1-{3-[3-methyl-1-(1H-pyrrolo[2,3-b]pyridin-2-yl)-butyl]-phenyl}-ethanone (0.50 g, 58.3%) as an off-white solid: $^1$H NMR (300 MHz, d$_6$-DMSO) δ ppm 11.63 (s, 1H), 8.09 (d, 1H, J=3.6 Hz), 7.96 (s, 1H), 7.81 (d, 2H, J=7.5 Hz), 7.66 (d, 1H, J=7.5 Hz), 7.46 (t, 1H, J=7.5 Hz), 6.98 (dd, 1H, J$_1$=4.5 Hz, J2=8.1 Hz), 6.31 (s, 1H), 4.30 (t, 1H, J=8.1 Hz), 2.57 (s, 3H), 2.17-2.10 (m, 1H), 1.91-1.86 (m, 1H), 1.41-1.39 (m, 1H), 0.92 (s, 3H), 0.90 (s, 3H).

Example 136

N,N-Dimethyl-3-(3-methyl-1-(1H-pyrrolo[2,3-b]pyridine-2-yl)butyl)benzenamine

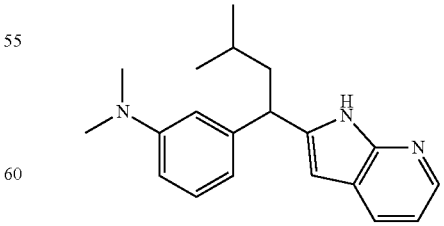

A suspension of toluene-4-sulfonic acid-1-(1-benzenesulfonyl-1H-pyrrolo[2,3-b]pyridin-2-yl)-3-methyl-but-1-enyl ester (prepared as in Example 130, 4.0 g, 8.0 mmol), 3-(dimethylamino)phenylboronic acid (3.3 g, 20 mmol), bis (triphenylphosphine)palladium(II) dichloride (567 mg, 0.8 mmol) in 1,4-dioxane (40 mL) and an aqueous sodium carbonate solution (2N, 21 mL) was heated in a microwave reactor to 100° C. for 3 h under nitrogen. At this time, the reaction was cooled to 25° C., diluted with ethyl acetate (50 mL) and then washed with a saturated aqueous sodium bicarbonate solution (2×50 mL). The organic layers were dried over anhydrous sodium sulfate, filtered and concentrated in vacuo. Silica gel column chromatography (60 g, petroleum ether/ethyl acetate 15:1) afforded N,N-dimethyl-3-(3-methyl-1-(1-(phenylsulfonyl)-1H-pyrrolo[2,3-b]pyridine-2-yl)but-1-enyl)benzenamine (3.0 g, 83%) as a yellow solid: $^1$H NMR (300 MHz, CDCl$_3$) δ ppm 8.48 (dd, 1H, J$_1$=4.5 Hz, J$_2$=3.6 Hz), 7.85 (dd, 1H, J$_1$=7.8 Hz, J$_2$=1.2 Hz), 7.65 (d, 2H, J=7.8 Hz), 7.38-7.36 (m, 1H), 7.31-7.14 (m, 4H), 7.06 (t, 1H, J=8.1 Hz), 6.65-6.48 (m, 3H), 6.14 (d, 1H, J=10.2 Hz), 2.77 (s, 6H), 2.72-2.64 (m, 1H), 1.14 (s, 3H), 1.12 (s, 3H).

A solution of N,N-dimethyl-3-(3-methyl-1-(1-(phenylsulfonyl)-1H-pyrrolo[2,3-b]pyridine-2-yl)but-1-enyl)benzenamine (3.0 g, 6.7 mmol) in ethanol (60 mL) and tetrahydrofuran (120 mL) was treated with an aqueous sodium hydroxide solution (10%, 23 mL). The reaction was stirred at 70° C. for 18 h. At this time, the reaction was cooled to 25° C., diluted with water (200 mL) and then extracted with ethyl acetate (2×100 mL). The organic extracts were dried over anhydrous sodium sulfate, filtered and concentrated in vacuo. Silica gel column chromatography (50 g, petroleum ether/ethyl acetate 10:1) afforded N,N-dimethyl-3-(3-methyl-1-(1H-pyrrolo[2,3-b]pyridin-2-yl)but-1-enyl)benzenamine (1.6 g, 76%) as a white solid: $^1$H NMR (300 MHz, CDCl$_3$) δ ppm 8.46 (dd, 1H, J$_1$=4.8 Hz, J$_2$=1.8 Hz), 7.86 (dd, 1H, J$_1$=7.8 Hz, J$_2$=1.8 Hz), 7.65 (d, 2H, J=7.8 Hz), 7.37 (d, 1H, J=7.5 Hz), 7.24-7.15 (m, 2H), 6.51 (s, 1H), 6.13 (d, 1H, J=10.2 Hz), 2.78 (s, 6H), 2.71-2.64 (m, 1H), 1.28 (s, 3H), 1.25 (s, 3H).

A solution of N,N-dimethyl-3-(3-methyl-1-(1H-pyrrolo[2,3-b]pyridin-2-yl)but-1-enyl)benzenamine (1.6 g, 5.2 mmol) in methanol (40 mL) and tetrahydrofuran (40 mL) was treated with 10% palladium on carbon (320 mg). The reaction was stirred for 16 h at 25° C. under a balloon filled with hydrogen gas. At this time, the reaction mixture was filtered through a pad of celite and washed with tetrahydrofuran (2×20 mL). The filtrate was concentrated in vacuo. Silica gel column chromatography (30 g, petroleum ether/ethyl acetate 8:1) afforded N,N-dimethyl-3-(3-methyl-1-(1H-pyrrolo[2,3-b]pyridin-2-yl)butyl)benzeneamine (1.2 g, 75%) as a yellow oil: $^1$H NMR (300 MHz, CDCl$_3$) δ ppm 9.54 (br. s., 1H), 8.14 (d, 1H, J=4.5 Hz), 7.78 (d, 1H, J=7.8 Hz), 7.15 (t, 1H, J=7.2 Hz), 7.03 (dd, 1H, J$_1$=7.8 Hz, J$_2$=4.8 Hz), 6.64-6.57 (m, 3H), 6.30 (s, 1H), 4.12 (t, 1H, J=8.1 Hz), 2.89 (s, 6H), 2.09-1.81 (m, 2H), 1.61-1.52 (m, 1H), 0.96 (s, 3H), 0.93 (s, 3H).

Example 137

2-(1-(3-(1H-Pyrazol-1-yl)phenyl)-3-methylbutyl)-1H-pyrrolo[2,3-b]pyridine

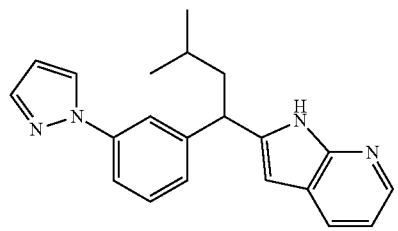

A suspension of toluene-4-sulfonic acid-1-(1-benzenesulfonyl-1H-pyrrolo[2,3-b]pyridin-2-yl)-3-methyl-but-1-enyl ester (prepared as in Example 130, 3.0 g, 6.04 mmol), 1-(3-(4,4,5,5-tetramethyl-1,3,2-dioxaborolan-2-yl)phenyl)-1H-pyrazole (4.08 g, 15.1 mmol), bis(triphenylphosphine)palladium(II) dichloride (0.5 g, 0.71 mmol) in dioxane (30 mL) and an aqueous sodium carbonate solution (2N, 15 mL) was heated at 100° C. in a microwave for 2 h. At this time, the reaction mixture was cooled to 25° C., diluted with ethyl acetate (350 mL) and washed with a saturated aqueous sodium carbonate solution (2×75 mL). The organic layer was dried over anhydrous sodium sulfate, filtered and concentrated in vacuo. Silica gel column chromatography (300-400 mesh, 50% ethyl acetate/petroleum ether) afforded 2-(1-(3-(1H-pyrazol-1-yl)phenyl)-3-methylbut-1-enyl)-1-(phenylsulfonyl)-1H-pyrrolo[2,3-b]pyridine (3.4 g, 60.1%) as a gray solid: $^1$H NMR (300 MHz, CDCl$_3$) δ ppm 8.49 (d, 1H, J=2.1 Hz), 8.40 (dd, 1H, J$_1$=4.8 Hz, J$_2$=1.8 Hz), 8.10 (dd, 2H, J$_1$=7.8 Hz, J$_2$=1.8 Hz), 7.44 (dd, 1H, J$_1$=7.8 Hz, J$_2$=1.2 Hz), 7.68-7.61 (m, 4H), 7.55 (t, 1H, J=8.1 Hz), 7.42-7.33 (m, 4H), 7.06 (d, 1H, J=7.8 Hz), 6.89 (s, 1H), 6.52 (t, 1H, J=1.8 Hz), 6.35 (d, 1H, J=9.6 Hz), 1.14 (d, 3H, J=5.1 Hz), 1.12 (d, 3H, J=4.8 Hz).

A solution of 2-(1-(3-(1H-pyrazol-1-yl)phenyl)-3-methylbut-1-enyl)-1-(phenylsulfonyl)-1H-pyrrolo[2,3-b]pyridine (3.4 g, 7.2 mmol) in ethanol (50 mL) and tetrahydrofuran (100 mL) was treated with an aqueous sodium hydroxide solution (10%, 20 mL). The reaction was stirred at 85° C. for 16 h. At this time, the reaction mixture was cooled to 25° C., concentrated in vacuo, diluted with water (100 mL) and then extracted with ethyl acetate (3×150 mL). The organic layers were washed with a saturated aqueous sodium chloride solution, dried over anhydrous sodium sulfate, filtered and concentrated in vacuo. The resulting solid was washed with ethanol (15 mL), and dried to afford 2-(1-(3-(1H-pyrazol-1-yl)phenyl)-3-methylbut-1-enyl)-1H-pyrrolo[2,3-b]pyridine (1.64 g, 68.9%) as a white solid: $^1$H NMR (300 MHz, CDCl$_3$) δ ppm 11.64 (s, 1H), 8.52 (d, 1H, J=2.1 Hz), 8.19 (dd, 1H, J$_1$=4.5 Hz, J$_2$=1.8 Hz), 7.95 (dd, 2H, J$_1$=7.8 Hz, J$_2$=1.2 Hz), 7.75-7.69 (m, 3H), 7.42 (t, 1H, J=8.1 Hz), 7.13-7.05 (m, 2H), 6.52 (t, 1H, J=2.1 Hz), 6.44 (d, 1H, J=1.8 Hz), 6.27 (d, 1H, J=9.9 Hz), 2.70-2.57 (m, 1H), 1.17 (s, 3H), 1.15 (s, 3H).

A solution of 2-(1-(3-(1H-pyrazol-1-yl)phenyl)-3-methylbut-1-enyl)-1H-pyrrolo[2,3-b]pyridine (1.4 g, 4.3 mmol) in tetrahydrofuran (20 mL) and methanol (40 mL) was treated with 10% palladium on carbon (285 mg). The reaction was stirred at 25° C. under hydrogen atmosphere for 3 d. At this time, the reaction mixture was filtered and was washed with tetrahydrofuran (2×15 mL). The filtrate was concentrated in vacuo. Silica gel column chromatography (300-400 mesh, 25% ethyl acetate/petroleum ether) afforded 2-(1-(3-(1H-pyrazol-1-yl)phenyl)-3-methylbutyl)-1H-pyrrolo[2,3-b]pyridine (1.03 g, 71.8%) as a white solid: $^1$H NMR (300 MHz, d$_6$-DMSO) δ ppm 11.62 (s, 1H), 8.48 (d, 1H, J=1.8 Hz), 8.10 (d, 1H, J=4.5 Hz), 7.89 (s, 1H), 7.81 (d, 1H, J=7.5 Hz), 7.73 (s, 1H), 7.65 (d, 1H, J=8.4 Hz), 7.41 (t, 1H, J=7.8 Hz), 7.31 (d, 1H, J=7.5 Hz), 6.97 (dd, 1H, J$_1$=7.8 Hz, J$_2$=4.8 Hz), 6.54 (s, 1H), 6.33 (s, 1H), 4.28 (t, 1H, J=8.1 Hz), 2.17-2.10 (m, 1H), 1.97-1.90 (m, 1H), 1.45-1.36 (m, 1H), 0.93 (d, 3H, J=2.4 Hz), 0.91 (d, 3H, J=2.7 Hz).

Example 138

2-[2-Cyclopentyl-1-(4-methanesulfonyl-phenyl)-ethyl]-1H-pyrrolo[2,3-b]pyridine

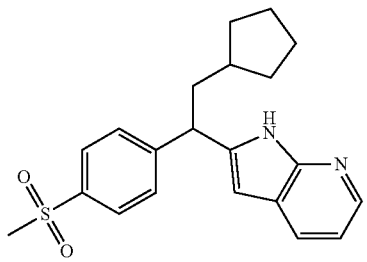

A solution of pentane (100 mL), diethyl ether (100 mL) and iodomethylcyclopentane (prepared as in PCT WO2004/052869A1 Example 1, 6.9 g, 32.85 mmol) was cooled to −78° C. and a solution of t-butyl lithium in pentane (1.7 M, 42.5 mL, 72.27 mmol) was added dropwise. The mixture was then stirred at −78° C. for 15 min and then the cooling bath was removed and it was stirred for 1 h and finally recooled to −78° C. To this mixture was then added a solution of 4-(methylthio)benzaldehyde (10.0 g, 65.7 mmol) in diethyl ether (20 mL) dropwise. The mixture was then stirred and warmed up to room temperature and stirred overnight. The mixture was then quenched by the addition of a saturated aqueous sodium bicarbonate solution (100 mL) and stirred overnight. The mixture was then diluted with ethyl acetate (150 mL) and water (150 mL). The aqueous layer was then washed with ethyl acetate (100 mL). The combined organic layers were then dried over magnesium sulfate, filtered and the filterate concentrated in vacuo. Flash chromatography (Merck Silica gel 60, 230-400 mesh, methylene chloride) afforded a mixture of 2-cyclopentyl-1-(4-methylsulfanyl-phenyl)-ethanone and 2-cyclopentyl-1-(4-methylsulfanyl-phenyl)-ethanol (6.3 g) as a yellow oil.

A solution of the mixture of 2-cyclopentyl-1-(4-methylsulfanyl-phenyl)-ethanone and 2-cyclopentyl-1-(4-methylsulfanyl-phenyl)-ethanol (6.3 g, ~26.65 mmol) in methylene chloride (150 mL) at room temperature was treated with pyridinium chlorochromate on basic alumina (~20%, 60 g). The mixture was stirred for 2 h at room temperature and then filtered through a plug of celite and then the celite was washed with additional methylene chloride. The filtrate was then dried over magnesium sulfate, filtered and the filterate concentrated in vacuo. The dark brown oil was then purified by flash chromatography (Merck Silica gel 60, 230-400 mesh, 10% ethyl acetate/hexanes) to afford 2-cyclopentyl-1-(4-methylsulfanyl-phenyl)-ethanone (5.91 g, ~95%) as a pale yellow solid.

A solution of sodium hydride (1.44 g, 60 mmol) in dimethyl formamide/dimethyl sulfoxide (5:1, 120 mL) cooled to 0° C. was treated with a solution of 7-azaindole (4.72 g, 40 mmol) in dimethyl formamide dropwise. The mixture was then stirred at 0° C. for 15 min, then room temperature for 30 min and then recooled to 0° C. After this time, 2-(trimethylsilyl)ethoxymethyl chloride (10.62 mL, 60 mmol) was added dropwise. The mixture was then stirred for 30 min at 0° C. and then warmed to room temperature and stirred for 2 h. The mixture was then poured into water (200 mL) slowly. The aqueous layer was extracted with diethyl ether (2×50 mL). The combined organic layers were then dried over magnesium sulfate, filtered and the filterate concentrated in vacuo. The orange oil was then purified by flash chromatography (Merck Silica gel 60, 230-400 mesh, 33% ethyl acetate/hexanes) to afford 1-(2-trimethylsilanyl-ethoxymethyl)-1H-pyrrolo[2,3-b]pyridine (10.02 g, 99%) as a pale yellow liquid.

A solution of 1-(2-trimethylsilanyl-ethoxymethyl)-1H-pyrrolo[2,3-b]pyridine (7.95 g, 32.0 mmol) in tetrahydrofuran (100 mL) was cooled to −78° C. and then treated with n-butyl lithium in hexanes (2.5 M, 12.80 mL, 32.0 mmol) dropwise. The cooling bath was then removed and the mixture stirred at room temperature for 45 min. The mixture was recooled to −78° C. and a solution of 2-cyclopentyl-1-(4-methylsulfanyl-phenyl)-ethanone (6.0 g, 25.6 mmol) in tetrahydrofuran (15 mL) was added dropwise. The resulting mixture was then stirred at −78° C. for 30 min and then warmed to room temperature and stirred for 5 h. After this time, the mixture was quenched by the addition of water (75 mL) and diluted with ethyl acetate (150 mL). The aqueous layer was separated and washed with ethyl acetate (2×75 mL). The combined organic layers were dried over magnesium sulfate, filtered and the filterate concentrated in vacuo. The resulting yellow oil was purified by flash chromatography (Merck Silica gel 60, 230-400 mesh, 10% ethyl acetate/hexanes) to afford a mixture of 2-cyclopentyl-1-(4-methylsulfanyl-phenyl)-1-[1-(2-trimethylsilanyl-ethoxymethyl)-1H-pyrrolo[2,3-b]pyridin-2-yl]-ethanol and 2-cyclopentyl-1-(4-methylsulfanyl-phenyl)-ethanone (1:4 mixture). The mixture was then treated in the same manner as the alkylation conditions above. A solution of 1-(2-trimethylsilanyl-ethoxymethyl)-1H-pyrrolo[2,3-b]pyridine (7.95 g, 32.0 mmol) in tetrahydrofuran (100 mL) was cooled to −78° C. and then treated with n-butyl lithium in hexane (2.5 M, 12.80 mL, 32.0 mmol) dropwise. The cooling bath was then removed and the mixtured stirred at room temperature for 45 min. The resulting mixture was recooled to −78° C. and a solution of the mixture of 2-cyclopentyl-1-(4-methylsulfanyl-phenyl)-ethanone and 2-cyclopentyl-1-(4-methylsulfanyl-phenyl)-1-[1-(2-trimethylsilanyl-ethoxymethyl)-1H-pyrrolo[2,3-b]pyridin-2-yl]-ethanol in tetrahydrofuran (15 mL) was added dropwise. The resulting mixture was then stirred at −78° C. for 30 min and then warmed to room temperature and stirred for 18 h. After this time, the mixture was quenched by the addition of water (75 mL) and diluted with ethyl acetate (150 mL). The aqueous layer was separated and washed with ethyl acetate (2×75 mL). The combined organic layers were dried over magnesium sulfate, filtered and the filterate concentrated in vacuo. Purification by flash chromatography (Merck Silica gel 60, 230-400 mesh, 10% ethyl acetate/hexanes) afforded 2-cyclopentyl-1-(4-methylsulfanyl-phenyl)-1-[1-(2-trimethylsilanyl-ethoxymethyl)-1H-pyrrolo[2,3-b]pyridin-2-yl]-ethanol (7.1 g, 57%) as a yellow oil.

A solution of 2-cyclopentyl-1-(4-methylsulfanyl-phenyl)-1-[1-(2-trimethylsilanyl-ethoxymethyl)-1H-pyrrolo[2,3-b]pyridin-2-yl]-ethanol (7.0 g, 14.5 mmol) and triethylsilane (9.26 mL, 58.0 mmol) in methylene chloride (125 mL) at room temperature was treated with boron trifluoride etherate (7.35 mL, 58.0 mmol). The resulting mixture was then warmed to 40° C. and stirred for 2.5 h. The mixture was then cooled to room temperature and quenched by the addition of a saturated aqueous sodium carbonate solution (10 mL). The mixture was further diluted with water (50 mL) and extracted with methylene chloride (2×50 mL). The combined organic layers were dried over magnesium sulfate, filtered and the filterate concentrated in vacuo. The resulting oil was then purified by flash chromatography (Merck Silica gel 60, 230-400 mesh, 25% ethyl acetate/hexanes) to afford a mixture of three compounds one of which is 2-[2-cyclopentyl-1-(4-methylsulfanyl-phenyl)-ethyl]-1H-pyrrolo[2,3-b]pyridine (3.93 g) as a yellow foam.

A solution of sodium periodate (3.20 g, 14.95 mmol) in water (20 mL) was treated with a solution of the mixture of compounds of which one was 2-[2-cyclopentyl-1-(4-methylsulfanyl-phenyl)-ethyl]-1H-pyrrolo[2,3-b]pyridine (from above, 2.5 g) in methanol (50 mL) and additional methanol (75 mL). The mixture was stirred at room temperature for 2 h. The mixture was concentrated and then partitioned between chloroform (100 mL) and water (100 mL). The organic layer was separated and dried over magnesium sulfate, filtered and the filterate concentrated in vacuo. The resulting oil was purified by Biotage flash chromatography (40 M column, 25% ethyl acetate/hexanes to 5% methanol/ethyl acetate) to afford a mixture of 2-[2-cyclopentyl-1-(4-methanesulfinyl-phenyl)-ethyl]-1H-pyrrolo[2,3-b]pyridine and 2-[2-cyclopentyl-1-(4-methanesulfinyl-phenyl)-vinyl]-1H-pyrrolo[2,3-b]pyridine (1.7 g) as a yellow solid.

A solution of the mixture of 2-[2-cyclopentyl-1-(4-methanesulfinyl-phenyl)-ethyl]-1H-pyrrolo[2,3-b]pyridine and 2-[2-cyclopentyl-1-(4-methanesulfinyl-phenyl)-vinyl]-1H-pyrrolo[2,3-b]pyridine (1.7 g) in methanol (50 mL) at 0° C. was treated dropwise with a solution of potassium permanganate (800 mg, 5.09 mmol) in water (15 mL). The resulting mixture was stirred to 1.5 h. The mixture was then partitioned between water (100 mL) and chloroform (100 mL). The aqueous layer was then extracted with ethyl acetate (2×100 mL). The combined organic layers were then dried over magnesium sulfate, filtered and the filterate concentrated in vacuo. Purification using a Biotage flash chromatography system (40 M column, 50% ethyl acetate/hexanes) afforded 2-[2-cyclopentyl-1-(4-methanesulfonyl-phenyl)-ethyl]-1H-pyrrolo[2,3-b]pyridine (420 mg, 23%) as a yellow foam which still contained some impurities. After standing overnight, a white solid had formed and this was then collected by filtration and the solids lightly washed with 10% ethyl acetate/hexanes to afford 2-[2-cyclopentyl-1-(4-methanesulfonyl-phenyl)-ethyl]-1H-pyrrolo[2,3-b]pyridine (300 mg) as a white solid: $^1$H NMR (300 MHz, CDCl$_3$) δ ppm 9.81 (br s, 1H), 8.18 (dd, J=4.8, 1.5 Hz, 1H), 7.86 (d, J=8.2 Hz, 2H), 7.81-7.90 (m, 1H), 7.48 (d, J=8.2 Hz, 2H), 7.05 (dd, J=7.7, 4.8 Hz, 1H), 6.37 (d, J=1.5 Hz, 1H), 4.25 (t, J=7.9 Hz, 1H), 3.02 (s, 3H), 2.19-2.31 (m, 1H), 2.05-2.17 (m, 1H), 1.61-1.88 (m, 5H), 1.41-1.54 (m, 2H), 1.08-1.24 (m, 2H).

Example 139

2-[2-Cyclopentyl-1-(3,4-dichloro-phenyl)-ethyl]-1H-pyrrolo[2,3-b]pyridine

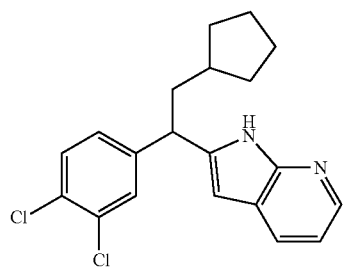

A solution of pentane (50 mL), diethyl ether (50 mL) and iodomethylcyclopentane (prepared as in PCT WO2004/052869 A1 Example 1, 3.9 g, 18.6 mmol) was cooled to −78° C. and a solution of t-butyl lithium in pentane (1.7 M, 18.5 mL, 31.5 mmol) was added dropwise. The mixture was then stirred at −78° C. for 30 min and then warmed to room temperature and stirred for 30 min and finally recooled to −78° C. To this mixture was then added a solution of 3,4-dichlorobenzaldehyde (5.0 g, 28.6 mmol) in diethyl ether (20 mL) dropwise. The mixture was then stirred at −78° C. for 1 h and then warmed up to room temperature and stirred overnight. The mixture was then quenched by the addition of a saturated aqueous ammonium chloride solution (50 mL). The organic layer was then separated and washed with a saturated brine solution (50 mL), dried over magnesium sulfate, filtered and the filterate concentrated in vacuo. Flash chromatography (Merck Silica gel 60, 230-400 mesh, 10% ethyl acetate/hexanes) afforded 2-cyclopentyl-1-(3,4-dichloro-phenyl)-ethanone (2.36 g, 50%) as a yellow solid.

A solution of n-butyl lithium in hexane (2.5 M, 4.5 mL, 11.2 mmol) was treated with N,N,N',N'-tetramethylethylenediamine (1.69 mL, 11.2 mmol) dropwise, which resulted in a slight exotherm. The resulting yellow mixture was then stirred at room temperature for 15 min. After this time, the mixture was treated with 1-(2-trimethylsilanyl-ethoxymethyl)-1H-pyrrolo[2,3-b]pyridine (prepared as in Example 138, 3.48 g, 14.0 mmol) dropwise. The resulting mixture was then stirred at room temperature for 30 min and then treated with a solution of 2-cyclopentyl-1-(3,4-dichloro-phenyl)-ethanone (1.8 g, 7.0 mmol) in tetrahydrofuran (8 mL) and then stirred at room temperature for 6 h. After this time, the reaction mixture was quenched by the addition of a saturated aqueous ammonium chloride solution (25 mL) and it was then stirred over the weekend. The reaction mixture was then extracted with ethyl acetate (2×100 mL) and the combined organic layers were then dried over magnesium sulfate, filtered and the filterate concentrated in vacuo. Flash chromatography (Merck Silica gel 60, 230-400 mesh, 10% ethyl acetate/hexanes) afforded 2-cyclopentyl-1-(3,4-dichloro-phenyl)-1-[1-(2-trimethylsilanyl-ethoxymethyl)-1H-pyrrolo[2,3-b]pyridin-2-yl]-ethanol (1.13 g, 32%) as a yellow oil.

A solution of 2-cyclopentyl-1-(3,4-dichloro-phenyl)-1-[1-(2-trimethylsilanyl-ethoxymethyl)-1H-pyrrolo[2,3-b]pyridin-2-yl]-ethanol (400 mg, 0.79 mmol) and triethylsilane (442 µL, 2.77 mmol) at room temperature was treated with boron trifluoride etherate (351 µL, 2.77 mmol). The resulting mixture was then heated at 40° C. for 2 h. After this time, the mixture was cooled to room temperature and quenched with a saturated aqueous solution of sodium carbonate (5 mL) and then water (10 mL). The mixture was then extracted with diethyl ether (2×30 mL). The combined organic extracts were dried over magnesium sulfate, filtered, and the filterate concentrated in vacuo. Purification by flash chromatography (Merck Silica gel 60, 230-400 mesh, 25% ethyl acetate/hexanes) afforded a mixture of compounds, 2-[2-cyclopentyl-1-(3,4-dichloro-phenyl)-ethyl]-1H-pyrrolo[2,3-b]pyridine and 2-[2-cyclopentyl-1-(3,4-dichloro-phenyl)-vinyl]-1H-pyrrolo[2,3-b]pyridine (185 mg) as a white foam.

A flask was charged with the mixture of 2-[2-cyclopentyl-1-(3,4-dichloro-phenyl)-ethyl]-1H-pyrrolo[2,3-b]pyridine and 2-[2-cyclopentyl-1-(3,4-dichloro-phenyl)-vinyl]-1H-pyrrolo[2,3-b]pyridine (185 mg), 10% palladium on activated carbon (100 mg) and methanol (5 mL). The flask was purged with hydrogen and then allowed to stir for 24 h under a balloon of hydrogen at room temperature. After this time, another portion of 10% palladium on activated carbon (50 mg) was added and again the reaction was purged with hydrogen and stirred at room temperature under a balloon of hydrogen for 24 h. The mixture was then filtered to remove the solids and the solids washed with methanol (10 mL). The filterate was concentrated in vacuo and the residue was purified by flash chromatography (Merck Silica gel 60, 230-400 mesh, 33% ethyl acetate/hexanes) to afford 2-[2-cyclopentyl-1-(3,4-dichloro-phenyl)-ethyl]-1H-pyrrolo[2,3-b]pyridine (77 mg) as a white foam: $^1$H NMR (400 MHz, CDCl$_3$) δ ppm 9.75 (br s, 1H), 8.18 (dd, J=4.8, 1.1 Hz, 2H), 7.88 (dd, J=7.9, 1.1 Hz, 2H), 7.37 (d, J=8.2 Hz, 1H), 7.37 (d, J=2.1 Hz, 1H), 7.12 (dd, J=8.2, 2.1 Hz, 1H), 7.07 (dd, J=7.9, 4.8 Hz, 1H), 6.34 (s, 1H), 4.11 (t, J=7.7 Hz, 1H), 2.19 (ddd, J=13.8, 7.3, 7.1 Hz, 1H), 2.00-2.12 (m, 1H), 1.56-1.97 (m, 5H), 1.41-1.57 (m, 2H), 1.08-1.25 (m, 2H).

Example 140

In Vitro Glucokinase Activity

The compounds of formula I which include the compounds set forth in the Examples activated glucokinase in vitro by the procedure of this Example. In this manner, they increase the flux of glucose metabolism which causes increased insulin secretion. Therefore, the compounds of formula I are glucokinase activators useful for increasing insulin secretion.

Glucokinase In Vitro Assay Protocol: Glucokinase (GK) was assayed by coupling the production of glucose-6-phosphate to the generation of NADH with glucose-6-phosphate dehydrogenase (G6PDH, 0.75-1 kunits/mg; Boehringer Mannheim, Indianapolis, Ind.) from *Leuconostoc mesenteroides* as the coupling enzyme (Scheme 2).

Scheme 2

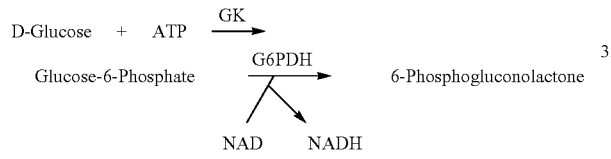

Recombinant human liver GK1 was expressed in *E. coli* as a glutathione S-transferase fusion protein (GST-GK) [Liang et al, 1995] and was purified by chromatography over a glutathione-Sepharose 4B affinity column using the procedure provided by the manufacturer (Amersham Pharmacia Biotech, Piscataway, N.J.). Previous studies have demonstrated that the enzymatic properties of native GK and GST-GK are essentially identical (Liang et al, 1995; Neet et al., 1990).

The assay was conducted at 30° C. in a flat bottom 96-well tissue culture plate from Costar (Cambridge, Mass.) with a final incubation volume of 120 μL. The incubation reaction contained the following: 25 mM Hepes buffer (pH 7.1), 25 mM KCl, 5 mM D-glucose, 1 mM ATP, 1.8 mM NAD, 2 mM MgCl$_2$, 1 μM sorbitol-6-phosphate, 1 mM dithiothreitol, test drug or 10% dimethylsulfoxide, ~7 units/ml G6PDH, and GK (see below). All organic reagents were >98% pure and were from Boehringer Mannheim with the exceptions of D-glucose and Hepes which were from Sigma Chemical Co, St Louis, Mo. Test compounds were dissolved in dimethylsulfoxide and were added to the incubation reaction minus GST-GK in a volume of 12 μL to yield a final dimethylsulfoxide concentration of 10%. This mix was pre-incubated in the temperature controlled chamber of a SPECTRAmax 250 microplate spectrophotometer (Molecular Devices Corporation, Sunnyvale, Calif.) for 10 minutes to allow temperature equilibrium and then the reaction was started by the addition of 20 μL GST-GK.

After addition of enzyme, the increase in optical density (OD) at 340 nm was monitored spectrophotometrically to determine the rate of change (OD$_{340}$ per min). The GK activity (OD$_{340}$/min) in control wells (10% dimethylsulfoxide minus GK activators) was compared with the activity in wells containing test GK activators, and the concentration of activator that produced a 50% increase in the activity of GK, i.e., the SC$_{1.5}$, was calculated.

The table below provides the in vitro glucokinase activity for the compounds in the Examples:

| Example | SC$_{1.5}$ |
|---|---|
| 1 | 19.0 μM |
| 2 | 11.3 μM |
| 3 | 1.9 μM |
| 4 | 10.5 μM |
| 5 | 1.9 μM |
| 6 | 1.0 μM |
| 7 | 25.6 μM |
| 8 | 3.4 μM |
| 9 | 10.9 μM |
| 10 | 0.218 μM |
| 11 | 7.3 μM |
| 12 | 0.18 μM |
| 13 | 2.0 μM |
| 14 | 0.742 μM |
| 15 | 0.451 μM |
| 16 | 0.21 μM |
| 17 | 3.1 μM |
| 18 | 0.719 μM |
| 19 | 0.414 μM |
| 20 | 0.693 μM |
| 21 | 0.821 μM |
| 22 | 2.5 μM |
| 23 | 21.9 μM |
| 24 | 2.0 μM |
| 25 | 22.0 μM |
| 26 | 2.3 μM |
| 27 | 13.5 μM |
| 28 | 2.8 μM |
| 29 | 1.1 μM |
| 30 | 0.8 μM |
| 31 | 1.9 μM |
| 32 | 1.1 μM |
| 33 | 3.0 μM |
| 34 | 0.958 μM |
| 35 | 1.4 fold at 30 μM |
| 36 | 3.4 μM |
| 37 | 4.4 μM |
| 38 | 9.8 μM |
| 39 | 9.1 μM |
| 40 | 9.0 μM |
| 41 | 2.8 μM |
| 42 | 0.903 μM |
| 43 | 1.4 μM |
| 44 | 4.3 μM |
| 45 | 14.9 μM |
| 46 | 0.028 μM |
| 47 | 0.415 μM |
| 48 | 0.654 μM |
| 49 | 0.354 μM |
| 50 | 0.603 μM |
| 51 | 0.343 μM |
| 52 | 0.37 μM |
| 53 | 0.144 μM |
| 54 | 1.2 μM |
| 55 | 0.512 μM |
| 56 | 3.4 μM |
| 57 | 22.3 μM |
| 58 | 9.5 μM |
| 59 | 5.5 μM |
| 60 | 0.451 μM |
| 61 | 3.0 μM |
| 62 | 6.0 μM |
| 63 | 3.5 μM |
| 64 | 2.2 μM |

-continued

| Example | SC$_{1.5}$ |
|---|---|
| 65 | 2.8 μM |
| 66 | 4.2 μM |
| 67 | 0.505 μM |
| 68 | 0.888 μM |
| 69 | 0.387 μM |
| 70 | 0.082 μM |
| 71 | 2.3 μM |
| 72 | 13.3 μM |
| 73 | 0.653 μM |
| 74 | 20.6 μM |
| 75 | 2.5 μM |
| 76 | 14.9 μM |
| 77 | 0.692 μM |
| 78 | 11.9 μM |
| 79 | 0.201 μM |
| 80 | 2.6 μM |
| 81 | 2.3 μM |
| 82 | 0.647 μM |
| 83 | 1.4 fold at 30 μM |
| 84 | 5.9 μM |
| 85 | 23.6 μM |
| 86 | 0.857 μM |
| 87 | 11.0 μM |
| 88 | 0.178 μM |
| 89 | 2.5 μM |
| 90 | 0.73 μM |
| 91 | 0.832 μM |
| 92 | 1.1 μM |
| 93 | 1.7 μM |
| 94 | 2.3 μM |
| 95 | 0.379 μM |
| 96 | 0.144 μM |
| 97 | 2.2 μM |
| 98 | 0.67 μM |
| 99 | 0.394 μM |
| 100 | 0.201 μM |
| 101 | 0.854 μM |
| 102 | 0.427 μM |
| 103 | 0.18 μM |
| 104 | 0.081 μM |
| 105 | 0.368 μM |
| 106 | 0.189 μM |
| 107 | 9.4 μM |
| 108 | 2.4 μM |
| 109 | 2.1 μM |
| 110 | 14.1 μM |
| 111 | 0.15 μM |
| 112 | 0.587 μM |
| 113 | 1.8 μM |
| 114 | 2.2 μM |
| 115 | 7.4 μM |
| 116 | 0.009 μM |
| 117 | 0.071 μM |
| 118 | 0.05 μM |
| 119 | 0.78 μM |
| 120 | 0.241 μM |
| 121 | 0.458 μM |
| 122 | 0.051 μM |
| 123 | 0.47 μM |
| 124 | 0.21 μM |
| 125 | 1.4 fold at 30 μM |
| 126 | 2.0 μM |
| 127 | 0.607 μM |
| 128 | 0.85 μM |
| 129 | 2.6 μM |
| 130 | 7.8 μM |
| 131 | 9.9 μM |
| 132 | 10.9 μM |
| 133 | 25.0 μM |
| 134 | 12.9 μM |
| 135 | 9.6 μM |
| 136 | 14.3 μM |
| 137 | 15.2 μM |
| 138 | 0.236 μM |
| 139 | 1.1 μM |

REFERENCES

Liang, Y., Kesavan, P., Wang, L., Niswender, K., Tanizawa, Y., Permut, M. A., Magnuson, M., and Matschinsky, F. M. Variable effects of maturity-onset-diabetes-of-youth (MODY)-associated glucokinase mutations on the substrate interactions and stability of the enzyme. Biochem. J. 309: 167-173, 1995.

Neet, K., Keenan, R. P., and Tippett, P. S. Observation of a kinetic slow transition in monomeric glucokinase. Biochemistry 29; 770-777, 1990.

Example 141

In Vivo Glucokinase Activity

Glucokinase Activator in vivo Screen Protocol in Lean and Diet Induced Obese Mice: Lean or Diet-Induced Obese (DIO) C57BL/6J mice were orally dosed via gavage with Glucokinase (GK) activator following a two hour fasting period. Blood glucose determinations were made at various (e.g. 0, 1, 2, 4 and 8 hours post-oral gavage) times during the study.

C57Bl/6J mice were obtained from Jackson Laboratory (Bar Harbor, Me.) and were maintained in a light-dark cycle with lights on from 0600-1800 hr. For studies in lean mice, the mice were received at age ten weeks and given ad libitum access to control diet (LabDiet 5001 chow, PMI Nutrition, Brentwood, Mo.), and were at least age 11 weeks at the time of study. For studies in the DIO model, the mice were received at age five weeks and given ad libitum access to Bio-Sery F3282 High Fat Diet (Frenchtown, N.J.), and were at least age 16 weeks at the time of study. The experiments were conducted during the light phase of the light-dark cycle. Mice (n=6) are weighed and fasted for a two hour period prior to oral treatment. GK activators are formulated in Gelucire vehicle (Ethanol:Gelucire44/14:PEG400q.s. 4:66:30 v/w/v. For studies in lean mice, the mice were dosed orally with 5.04 per gram of body weight (i.e. 5 ml/kg×10.0 mg/ml formulation to equal a 50 mg/kg dose). For studies in DIO mice, the mice were dosed orally with 5.04 per gram of body weight (i.e. 5.0 ml/kg×5 mg/ml formulation to equal a 25 mg/kg dose). Immediately prior to dosing, a pre-dose (time zero) blood glucose reading was acquired by snipping off a small portion of the animal's tail and collecting 154 blood into a heparinized capillary tube for analysis. Following GK activator administration, additional blood glucose readings were taken at various time points post dose from the same tail wound. Results were interpreted by comparing the mean blood glucose values of vehicle treated mice with GK activator treated mice over the study period. Preferred compounds were considered to be those that exhibited a statistically significant ($p \leq 0.05$) decrease in blood glucose compared to vehicle for two consecutive assay time points.

The Table below provides data for % glucose lowering of a representative number of compounds of the present invention vs control at 2 hours post 25 or 50 mg/kg dose in C57B6 mice:

| Example | % gluc lowering @ 2 H | Dose (mg/K) |
|---|---|---|
| 3 | −5.6 | 50 |
| 16 | −31.3 | 25 |
| 19 | −14.8 | 25 |
| 22 | −6.3 | 25 |
| 32 | −23.4 | 25 |

-continued

| Example | % gluc lowering @ 2 H | Dose (mg/K) |
|---|---|---|
| 34 | −10.7 | 25 |
| 42 | −10.3 | 25 |
| 60 | −29.9 | 25 |
| 67 | −43.6 | 25 |
| 69 | −40.3 | 50 |
| 82 | −42.7 | 25 |
| 95 | −49.4 | 50 |
| 109 | −31.6 | 50 |
| 118 | −48.4 | 25 |
| 120 | −52 | 25 |
| 122 | −59.4 | 25 |
| 124 | −35 | 25 |
| 138 | −50.4 | 50 |
| 139 | 25.4 | 50 |

It is to be understood that the invention is not limited to the particular embodiments of the invention described above, as variations of the particular embodiments may be made and still fall within the scope of the appended claims.

What is claimed is:
1. A compound of formula (I):

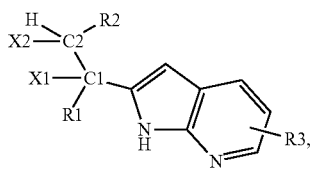

(I)

wherein:
R1 is -phenyl, unsubstituted or mono- or bi-substituted independently with halogen, -cyano, -lower alkyl, -alkoxy, —$SO_2CH_3$, —$CF_3$, —$C(CH_3)_2OH$, —$CH(CH_3)OH$, —$C(CH_3)(C(CH_3)_2)OH$, —$SO_2(CH_2)_2OH$, —$NH(SO_2CH_3)$, —$C(O)CH_3$, —$C(CH_2CH_3)_2OH$, —$N(CH_3)_2$, —$SO_2CH(CH_3)_2$, —$SO_2(CH_2)_2OCH_2CH_3$, —$SO_2(CH_2)_2N(CH_3)_2$, pyrazole or —$SO_2(CH_2)_2$-morpholine,
-heteroaryl, unsubstituted or substituted with lower alkyl, alkoxy or —$SO_2CH_3$, or
-2,3-dihydrobenzo[1,4]dioxin-6-yl;
R2 is -lower alkyl,
-heterocycloalkyl, or
-cycloalkyl, unsubstituted or substituted with (=O);
R3 is -hydrogen,
-halogen,
-an acyl group,
-cyano,
-lower alkyl, unsubstituted or mono-, bi- or tri-substituted independently with hydroxy, alkoxy, halogen, lower alkyl, cyano, (=O), or —$N(CH_3)_2$,
—$OCH_3$,
—$OCH_2C(O)N(CH_3)_2$,
—$O(CH_2)_2OCH_3$,
—$O(CH_2)_2N(CH_3)_2$,
—$OCH(CH_3)_2$,
—$OC(CH_3)_2CH_2OH$,
—$OCH_2CH_2OH$,
—$OC(CH_3)_2C(O)OCH_2CH_3$,
—$OC(CH_3)_2C(O)OH$,
—$CH_2OC(O)CH_2N(CH_3)_2$,
—$NHC(O)CH_2N(CH_3)_2$, or
—$SO_2$-lower alkyl;

the bond between $C_1$ and $C_2$ is a single or double bond;
X1 is -hydrogen,
-hydroxy,
-alkoxy, or
-absent if the bond between $C_1$ and $C_2$ is a double bond; and
X2 is -hydrogen, or
-absent if the bond between $C_1$ and $C_2$ is a double bond,
or a pharmaceutically acceptable salt thereof.

2. The compound according to claim 1, wherein:
R1 is -phenyl, unsubstituted or mono- or bi-substituted independently with halogen, -cyano, -lower alkyl, -alkoxy, —$SO_2CH_3$, —$CF_3$, —$C(CH_3)_2OH$, —$CH(CH_3)OH$, —$C(CH_3)(C(CH_3)_2)OH$, —$SO_2(CH_2)_2OH$, —$NH(SO_2CH_3)$, —$C(O)CH_3$, —$C(CH_2CH_3)_2OH$, —$N(CH_3)_2$, —$SO_2CH(CH_3)_2$, —$SO_2(CH_2)_2OCH_2CH_3$, —$SO_2(CH_2)_2N(CH_3)_2$, pyrazole or —$SO_2(CH_2)_2$-morpholine;
R2 is -lower alkyl;
R3 is -hydrogen,
-halogen,
-an acyl group,
-cyano, or
-lower alkyl, unsubstituted or mono-, bi- or tri-substituted independently with hydroxy, alkoxy, halogen, lower alkyl, cyano, (=O), or —$N(CH_3)_2$;
the bond between $C_1$ and $C_2$ is a single bond;
X1 is -hydrogen,
-hydroxy, or
-alkoxy; and
X2 is -hydrogen.

3. The compound according to claim 1, wherein:
R1 is -phenyl, unsubstituted or mono- or bi-substituted independently with halogen, -cyano, -lower alkyl, -alkoxy, —$SO_2CH_3$, —$CF_3$, —$C(CH_3)_2OH$, —$CH(CH_3)OH$, —$C(CH_3)(C(CH_3)_2)OH$, —$SO_2(CH_2)_2OH$, —$NH(SO_2CH_3)$, —$C(O)CH_3$, —$C(CH_2CH_3)_2OH$, —$N(CH_3)_2$, —$SO_2CH(CH_3)_2$, —$SO_2(CH_2)_2OCH_2CH_3$, —$SO_2(CH_2)_2N(CH_3)_2$, pyrazole or —$SO_2(CH_2)_2$-morpholine:
R2 is -lower alkyl;
R3 is —$OCH_3$,
—$OCH_2C(O)N(CH_3)_2$,
—$O(CH_2)_2OCH_3$,
—$O(CH_2)_2N(CH_3)_2$,
—$OCH(CH_3)_2$,
—$OC(CH_3)_2CH_2OH$,
—$OCH_2CH_2OH$,
—$OC(CH_3)_2C(O)OCH_2CH_3$,
—$OC(CH_3)_2C(O)OH$,
—$CH_2OC(O)CH_2N(CH_3)_2$,
—$NHC(O)CH_2N(CH_3)_2$, or
—$SO_2$-lower alkyl;
the bond between $C_1$ and $C_2$ is a single bond;
X1 is -hydrogen,
-hydroxy, or
-alkoxy; and
X2 is -hydrogen.

4. The compound according to claim 1, wherein:
R1 is -phenyl, unsubstituted or mono- or bi-substituted independently with halogen, -cyano, -lower alkyl, -alkoxy, —$SO_2CH_3$, —$CF_3$, —$C(CH_3)_2OH$, —$CH(CH_3)OH$, —$C(CH_3)(C(CH_3)_2)OH$, —$SO_2(CH_2)_2OH$, —$NH(SO_2CH_3)$, —$C(O)CH_3$, —$C(CH_2CH_3)_2OH$, —$N(CH_3)_2$, —$SO_2CH(CH_3)_2$, —$SO_2(CH_2)_2OCH_2CH_3$, —$SO_2(CH_2)_2N(CH_3)_2$, pyrazole or —$SO_2(CH_2)_2$-morpholine;

R2 is -heterocycloalkyl, or
-cycloalkyl, unsubstituted or substituted with (=O);
R3 is -hydrogen,
-halogen,
-an acyl group,
-cyano, or
-lower alkyl, unsubstituted or mono-, bi- or tri-substituted independently with hydroxy, alkoxy, halogen, lower alkyl, cyano, (=O), or —N(CH$_3$)$_2$;
the bond between C$_1$ and C$_2$ is a single bond;
X1 is -hydrogen,
-hydroxy,
-alkoxy; and
X2 is -hydrogen.

5. The compound according to claim 1, wherein:
R1 is -phenyl, unsubstituted or mono- or bi-substituted independently with halogen, -cyano, -lower alkyl, -alkoxy, —SO$_2$CH$_3$, —CF$_3$, —C(CH$_3$)$_2$OH, —CH(CH$_3$)OH, —C(CH$_3$)(C(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole or —SO$_2$(CH$_2$)$_2$-morpholine;
R2 is -heterocycloalkyl, or
-cycloalkyl, unsubstituted or substituted with (=O);
R3 is —OCH$_3$,
—OCH$_2$C(O)N(CH$_3$)$_2$,
—O(CH$_2$)$_2$OCH$_3$,
—O(CH$_2$)$_2$N(CH$_3$)$_2$,
—OCH(CH$_3$)$_2$,
—OC(CH$_3$)$_2$CH$_2$OH,
—OCH$_2$CH$_2$OH,
—OC(CH$_3$)$_2$C(O)OCH$_2$CH$_3$,
—OC(CH$_3$)$_2$C(O)OH,
—CH$_2$OC(O)CH$_2$N(CH$_3$)$_2$,
—NHC(O)CH$_2$N(CH$_3$)$_2$, or
—SO$_2$-lower alkyl;
the bond between C$_1$ and C$_2$ is a single bond;
X1 is -hydrogen,
-hydroxy, or
-alkoxy; and
X2 is -hydrogen.

6. The compound according to claim 1, wherein:
R1 is -heteroaryl, unsubstituted or substituted with lower alkyl, alkoxy or —SO$_2$CH$_3$;
R2 is -lower alkyl;
R3 is -hydrogen,
-halogen,
-an acyl group,
-cyano, or
-lower alkyl, unsubstituted or mono-, bi- or tri-substituted independently with hydroxy, alkoxy, halogen, lower alkyl, cyano, (=O), or —N(CH$_3$)$_2$;
the bond between C$_1$ and C$_2$ is a single bond;
X1 is -hydrogen,
-hydroxy, or
-alkoxy; and
X2 is -hydrogen.

7. The compound according to claim 1, wherein:
R1 is -heteroaryl, unsubstituted or substituted with lower alkyl, alkoxy or —SO$_2$CH$_3$;
R2 is -lower alkyl;
R3 is —OCH$_3$,
—OCH$_2$C(O)N(CH$_3$)$_2$,
—O(CH$_2$)$_2$OCH$_3$,
—O(CH$_2$)$_2$N(CH$_3$)$_2$,
—OCH(CH$_3$)$_2$,
—OC(CH$_3$)$_2$CH$_2$OH,
—OCH$_2$CH$_2$OH,
—OC(CH$_3$)$_2$C(O)OCH$_2$CH$_3$,
—OC(CH$_3$)$_2$C(O)OH,
—CH$_2$OC(O)CH$_2$N(CH$_3$)$_2$,
—NHC(O)CH$_2$N(CH$_3$)$_2$, or
—SO$_2$-lower alkyl;
the bond between C$_1$ and C$_2$ is a single bond;
X1 is -hydrogen,
-hydroxy, or
-alkoxy; and
X2 is -hydrogen.

8. The compound according to claim 1, wherein:
R1 is -heteroaryl, unsubstituted or substituted with lower alkyl, alkoxy or —SO$_2$CH$_3$, or
-2,3-dihydrobenzo[1,4]dioxin-6-yl;
R2 is -heterocycloalkyl, or
-cycloalkyl, unsubstituted or substituted with (=O);
R3 is -hydrogen,
-halogen,
-an acyl group,
-cyano, or
-lower alkyl, unsubstituted or mono-, bi- or tri-substituted independently with hydroxy, alkoxy, halogen, lower alkyl, cyano, (=O), or —N(CH$_3$)$_2$;
the bond between C$_1$ and C$_2$ is a single bond;
X1 is -hydrogen,
-hydroxy,
-alkoxy; and
X2 is -hydrogen.

9. The compound according to claim 1, wherein:
R1 is -heteroaryl, unsubstituted or substituted with lower alkyl, alkoxy or —SO$_2$CH$_3$, or
-2,3-dihydrobenzo[1,4]dioxin-6-yl;
R2 is -heterocycloalkyl, or
-cycloalkyl, unsubstituted or substituted with (=O);
R3 is —OCH$_3$,
—OCH$_2$C(O)N(CH$_3$)$_2$,
—O(CH$_2$)$_2$OCH$_3$,
—O(CH$_2$)$_2$N(CH$_3$)$_2$,
—OCH(CH$_3$)$_2$,
—OC(CH$_3$)$_2$CH$_2$OH,
—OCH$_2$CH$_2$OH,
—OC(CH$_3$)$_2$C(O)OCH$_2$CH$_3$,
—OC(CH$_3$)$_2$C(O)OH,
—CH$_2$C(O)CH$_2$N(CH$_3$)$_2$,
—NHC(O)CH$_2$N(CH$_3$)$_2$, or
—SO$_2$-lower alkyl;
the bond between C$_1$ and C$_2$ is a single bond;
X1 is -hydrogen,
-hydroxy,
-alkoxy; and
X2 is -hydrogen.

10. The compound according to claim 1, wherein R1 is phenyl, unsubstituted or mono- or bi-substituted independently with halogen, -cyano, -lower alkyl, -alkoxy, —SO$_2$CH$_3$, —CF$_3$, —C(CH$_3$)$_2$OH, —CH(CH$_3$)OH, —C(CH$_3$)(C(CH$_3$)$_2$)OH, —SO$_2$(CH$_2$)$_2$OH, —NH(SO$_2$CH$_3$), —C(O)CH$_3$, —C(CH$_2$CH$_3$)$_2$OH, —N(CH$_3$)$_2$, —SO$_2$CH(CH$_3$)$_2$, —SO$_2$(CH$_2$)$_2$OCH$_2$CH$_3$, —SO$_2$(CH$_2$)$_2$N(CH$_3$)$_2$, pyrazole or —SO$_2$(CH$_2$)$_2$-morpholine.

11. The compound according to claim 1, wherein R1 is heteroaryl, unsubstituted or substituted with lower alkyl, alkoxy or —SO$_2$CH$_3$, or -2,3-dihydrobenzo[1,4]dioxin-6-yl.

12. The compound according to claim 1, wherein R1 is 4-methanesulfonyl-3-trifluoromethyl-phenyl, 3-fluoro-4-(1-hydroxy-1-methyl-ethyl)-phenyl, 4-(1-hydroxy-1,2-dimethyl-propyl)-phenyl, 4-(1-ethyl-1-hydroxy-propyl)-phenyl, 4-(propane-2-sulfonyl)-phenyl, 4-(2-dimethylamino-ethanesulfonyl)-phenyl, 4-(2-morpholin-4-yl-ethanesulfonyl)-phenyl, 4-(2-hydroxy-ethanesulfonyl)-phenyl, 4-(2-ethoxy-ethanesulfonyl)-phenyl, 2-fluoro-4-(1-hydroxy-1-methyl-ethyl)-phenyl, 4-methanesulfonylamino-phenyl, 3-pyrazol-1-yl-phenyl, 2,3-dihydro-benzo[1,4]dioxin-6-yl, 3,4-dichloro-phenyl, 3,5-dimethyl-phenyl, 3-acetyl-phenyl, 3-chloro-phenyl, 3-dimethylamino-phenyl, 3-ethoxy-phenyl, 3-fluoro-phenyl, 3-methoxy-phenyl, 4-(1-hydroxy-1-methyl-ethyl)-phenyl, 4-(1-hydroxy-ethyl)-phenyl, 4-acetyl-phenyl, 4-cyano-phenyl, 4-dimethylamino-phenyl, 4-isopropyl-phenyl, 4-methanesulfonyl-phenyl, 4-trifluoromethyl-phenyl, 5-methanesulfonyl-pyridin-2-yl, 6-ethoxy-pyridin-3-yl, 6-methanesulfonyl-pyridin-3-yl, 6-methoxy-pyridin-3-yl, 6-methyl-pyridin-3-yl, m-tolyl or pyridin-3-yl.

13. The compound according to claim 1, wherein R2 is lower alkyl.

14. The compound according to claim 1, wherein R2 is heterocycloalkyl, or cycloalkyl, unsubstituted or substituted with (=O).

15. The compound according to claim 1, wherein R2 is cyclobutyl, cyclohexyl, cyclopentyl, isopropyl, tert-butyl, tetrahydro-furan-2-yl, tetrahydro-pyran-4-yl, tetrahydro-pyran-2-yl or 3-oxo-cyclopentyl.

16. The compound according to claim 1, wherein R3 is hydrogen, halogen, an acyl group, cyano, or lower alkyl, unsubstituted or mono-, bi- or tri-substituted independently with hydroxy, alkoxy, halogen, lower alkyl, cyano, (=O), or —N(CH$_3$)$_2$.

17. The compound according to claim 1, wherein R3 is hydrogen, 2-hydroxyethyl-carbamoyl, 1,2-dihydroxy-ethyl, methoxycarbonyl, 1-carboxy-1-methyl-ethoxy, 1-ethoxycarbonyl-1-methyl-ethoxy, 1-hydroxy-ethyl, 2,3-dihydroxy-propyl, 2-dimethylamino-acetoxymethyl, 2-dimethylamino-acetylamino, 2-dimethylamino-ethoxy, 2-dimethylamino-ethyl, 2-hydroxy-1,1-dimethyl-ethoxy, 2-hydroxy-ethoxy, 2-hydroxy-ethyl, 2-methoxy-ethoxy, 3-hydroxy-propyl, 3-methoxy-propyl, carboxy, chloro, cyano, cyanomethyl, dimethylcarbamoylmethoxy, dimethylcarbamoylmethyl, ethanesulfonyl, fluoro, hydroxymethyl, isopropoxy, isopropylcarbamoyl, methoxy, methoxymethyl, methyl, methylcarbamoyl, morpholine-4-carbonyl or trifluoromethyl.

18. The compound according to claim 1, wherein the bond between C$_1$ and C$_2$ is a single bond.

19. The compound according to claim 1, wherein the bond between C$_1$ and C$_2$ is a double bond.

20. The compound according to claim 1, wherein X1 is hydrogen, hydroxy or alkoxy.

21. The compound according to claim 1, wherein X2 is hydrogen.

22. The compound according to claim 1, wherein said compound is:
  2-[1-(4-Methanesulfonyl-phenyl)-3-methyl-butyl]-1H-pyrrolo[2,3-b]pyridin-5-carboxylic acid isopropylamide,
  2-[1-(4-Methanesulfonyl-phenyl)-3-methyl-butyl]-1H-pyrrolo[2,3-b]pyridin-5-carboxylic acid methylamide,
  2-[2-Cyclopentyl-1-(4-methanesulfonyl-phenyl)-ethyl]-1H-pyrrolo[2,3-b]pyridin-5-carboxylic acid isopropylamide,
  {2-[2-Cyclopentyl-1-(4-methanesulfonyl-phenyl)-ethyl]-1H-pyrrolo[2,3-b]pyridin-5-yl}-morpholin-4-yl-methanone,
  2-[2-Cyclopentyl-1-(4-methanesulfonyl-phenyl)-ethyl]-1H-pyrrolo[2,3-b]pyridin-5-carboxylic acid methylamide,
  2-[2-Cyclopentyl-1(R)-(4-methanesulfonyl-phenyl)-ethyl]-1H-pyrrolo[2,3-b]pyridin-5-carboxylic acid methylamide,
  1-{2-[2-Cyclopentyl-1-(4-methanesulfonyl-phenyl)-ethyl]-1H-pyrrolo[2,3-b]pyridin-5-yl}-ethane-1,2-diol,
  {2-[2-Cyclopentyl-1-(4-methanesulfonyl-phenyl)-ethyl]-1H-pyrrolo[2,3-b]pyridin-5-yl}-methanol,
  1-{2-[2-Cyclopentyl-1-(4-methanesulfonyl-phenyl)-ethyl]-1H-pyrrolo[2,3-b]pyridin-5-yl}-ethanol,
  2-[2-Cyclohexyl-1(R)-(4-methanesulfonyl-phenyl)-ethyl]-5-methoxy-1H-pyrrolo[2,3-b]pyridine,
  3-{2-[2-Cyclopentyl-1-(4-methanesulfonyl-phenyl)-ethyl]-1H-pyrrolo[2,3-b]pyridin-5-yl}-propane-1,2-diol,
  2-[2-Cyclopentyl-1-(4-methanesulfonyl-phenyl)-ethyl]-5-methoxy-1H-pyrrolo[2,3-b]pyridine,
  2-{2-[2-Cyclopentyl-1-(4-methanesulfonyl-phenyl)-ethyl]-1H-pyrrolo[2,3-b]pyridin-5-yloxy}-N,N-dimethyl-acetamide,
  2-{2-[2-Cyclopentyl-1(R)-(4-methanesulfonyl-phenyl)-ethyl]-1H-pyrrolo[2,3-b]pyridin-5-yloxy}-N,N-dimethyl-acetamide, or
  2-[2-Cyclopentyl-1-(4-methanesulfonyl-phenyl)-ethyl]-5-(2-methoxy-ethoxy)-1H-pyrrolo[2,3-b]pyridine.

23. The compound according to claim 1, wherein said compound is:
  2-[2-Cyclopentyl-1(R)-(4-methanesulfonyl-phenyl)-ethyl]-5-(2-methoxy-ethoxy)-1H-pyrrolo[2,3-b]pyridine,
  (2-{2-[2-Cyclopentyl-1-(4-methanesulfonyl-phenyl)-ethyl]-1H-pyrrolo[2,3-b]pyridin-5-yloxy}-ethyl)-dimethyl-amine,
  2-[2-Cyclopentyl-1-(4-methanesulfonyl-phenyl)-ethyl]-5-isopropoxy-1H-pyrrolo[2,3-b]pyridine,
  2-[2-Cyclopentyl-1(R)-(4-methanesulfonyl-phenyl)-ethyl]-5-isopropoxy-1H-pyrrolo[2,3-b]pyridine,
  2-[2-Cyclopentyl-1-(4-trifluoromethyl-phenyl)-ethyl]-5-methoxy-1H-pyrrolo[2,3b]pyridine,
  2-[(E)-1-(4-Methanesulfonyl-phenyl)-2-(tetrahydro-furan-2-yl)-vinyl]-5-methoxy-1H-pyrrolo[2,3-b]pyridine,
  2-[1-(4-Methanesulfonyl-phenyl)-2-(tetrahydro-furan-2-yl)-ethyl]-5-methoxy-1H-pyrrolo[2,3-b]pyridine,
  2-[1-(4-Methanesulfonyl-phenyl)-2-(tetrahydro-furan-2-yl)-ethyl]-5-methoxy-1H-pyrrolo[2,3-b]pyridine,
  2-[1-(4-Methanesulfonyl-phenyl)-2-(tetrahydro-furan-2-yl)-ethyl]-5-methoxy-1H-pyrrolo[2,3-b]pyridine,
  2-[1-(4-Methanesulfonyl-phenyl)-2-(tetrahydro-furan-2-yl)-ethyl]-5-methoxy-1H-pyrrolo[2,3-b]pyridine, diastereomer 4,
  2-{2-[2-Cyclopentyl-1-(4-methanesulfonyl-phenyl)-ethyl]-1H-pyrrolo[2,3-b]pyridin-5-yloxy}-2-methyl-propionic acid ethyl ester,
  2-{2-[2-Cyclopentyl-1-(4-methanesulfonyl-phenyl)-ethyl]-1H-pyrrolo[2,3-b]pyridin-5-yloxy}-2-methyl-propionic acid,
  2-{2-[2-Cyclopentyl-1-(4-methanesulfonyl-phenyl)-ethyl]-1H-pyrrolo[2,3-b]pyridin-5-yloxy}-2-methyl-propan-1-ol,
  2-{2-[2-Cyclopentyl-1(R)-(4-methanesulfonyl-phenyl)-ethyl]-1H-pyrrolo[2,3-b]pyridin-5-yloxy}-2-methyl-propan-1-ol, or
  2-{2-[2-Cyclopentyl-1-(4-methanesulfonyl-phenyl)-ethyl]-1H-pyrrolo[2,3-b]pyridin-5-yloxy}-ethanol.

24. The compound according to claim 1, wherein said compound is:

2-[1-(4-Methanesulfonyl-phenyl)-2-(tetrahydro-pyran-4-yl)-5-methoxy-1H-pyrrolo[2,3-b]pyridine, 2-1(R)-(4-Methanesulfonyl-phenyl)-2-(tetrahydro-pyran-4-yl)-5-methoxy-1H-pyrrolo[2,3-b]pyridine, 5-Methoxy-2-[2-(tetrahydro-pyran-4-yl)-1-(4-trifluoromethyl-phenyl)-ethyl]-1H-pyrrolo[2,3-b]pyridine, 5-Methoxy-2-[2-(tetrahydro-pyran-4-yl)-1(R)-(4-trifluoromethyl-phenyl)-ethyl]-1H-pyrrolo[2,3-b]pyridine, 2-{4-[2-Cyclopentyl-1-(5-methoxy-1H-pyrrolo[2,3-b]pyridin-2-yl)-ethyl]-phenyl}-propan-2-ol, 2-{2-[2-Cyclopentyl-1-(4-methanesulfonyl-phenyl)-ethyl]-1H-pyrrolo[2,3-b]pyridin-5-yl}-ethanol, Dimethylamino-acetic acid 2-[2-cyclopentyl-1-(4-methanesulfonyl-phenyl)-ethyl]-1H-pyrrolo[2,3-b]pyridin-5-ylmethyl-ester, {2-[2-Cyclopentyl-1-(4-methanesulfonyl-phenyl)-ethyl]-1H-pyrrolo[2,3-b]pyridin-5-yl}-acetonitrile, 2-{2-[2-Cyclopentyl-1-(4-methanesulfonyl-phenyl)-ethyl]-1H-pyrrolo[2,3-b]pyridin-5-yl}-N,N-dimethyl-acetamide, (2-{2-[2-Cyclopentyl-1-(4-methanesulfonyl-phenyl)-ethyl]-1H-pyrrolo[2,3-b]pyridin-5-yl}-ethyl)-dimethyl-amine, 2-[2-Cyclopentyl-1-(4-methanesulfonyl-phenyl)-ethyl]-5-methoxymethyl-1H-pyrrolo[2,3-b]pyridine, 2-[2-Cyclopentyl-1(R)-(4-methanesulfonyl-phenyl)-ethyl]-5-methoxymethyl-1H-pyrrolo[2,3-b]pyridine, 4-[2-Cyclopentyl-1-(1H-pyrrolo[2,3-b]pyridin-2-yl)-ethyl]-benzonitrile, 2-[2-Cyclopentyl-1-(4-methanesulfonyl-phenyl)-ethyl]-5-(3-methoxy-propyl)-1H-pyrrolo[2,3-b]pyridine, 3-{2-[2-Cyclopentyl-1-(4-methanesulfonyl-phenyl)-ethyl]-1H-pyrrolo[2,3-b]pyridin-5-yl}-propan-1-ol, or 2-[(E)-2-Cyclobutyl-1-(4-methanesulfonyl-phenyl)-vinyl]-5-fluoro-1H-pyrrolo[2,3-b]pyridine.

25. The compound according to claim 1, wherein said compound is:

2-[2-Cyclobutyl-1-(4-methanesulfonyl-phenyl)-ethyl]-5-fluoro-1H-pyrrolo[2,3-b]pyridine, 2-Cyclopentyl-1-(5-fluoro-1H-pyrrolo[2,3-b]pyridin-2-yl)-1-(4-methanesulfonyl-phenyl)-ethanol, 2-Cyclopentyl-1-(5-fluoro-1H-pyrrolo[2,3-b]pyridin-2-yl)-1-(4-methanesulfonyl-phenyl)-ethanol, 4-[2-Cyclopentyl-1-(5-fluoro-1H-pyrrolo[2,3-b]pyridin-2-yl)-ethyl]-benzonitrile, 4-[2-Cyclopentyl-1(R)-(5-fluoro-1H-pyrrolo[2,3-b]pyridin-2-yl)-ethyl]-benzonitrile, 2-[2-Cyclopentyl-1-(4-methanesulfonyl-phenyl)-ethyl]-1H-pyrrolo[2,3-b]pyridin-5-carbonitrile, 2-[2-Cyclopentyl-1(R)-(4-methanesulfonyl-phenyl)-ethyl]-1H-pyrrolo[2,3-b]pyridin-5-carbonitrile, 2-[2-Cyclopentyl-1-(4-methanesulfonyl-phenyl)-ethyl]-1H-pyrrolo[2,3-b]pyridin-5-carboxylic acid methyl Ester, 2-[2-Cyclopentyl-1(R)-(4-methanesulfonyl-phenyl)-ethyl]-1H-pyrrolo[2,3-b]pyridin-5-carboxylic acid methyl ester, 2-[2-Cyclopentyl-1(R)-(4-methanesulfonyl-phenyl)-ethyl]-1H-pyrrolo[2,3-b]pyridin-5-carboxylic acid, 2-{2-Cyclopentyl-1-[3-fluoro-4-(1-hydroxy-1-methyl-ethyl)-phenyl]-ethyl}-1H-pyrrolo[2,3-b]pyridin-5-carboxylic acid, 2-{2-Cyclopentyl-1(R)-[3-fluoro-4-(1-hydroxy-1-methyl-ethyl)-phenyl]-ethyl}-1H-pyrrolo[2,3-b]pyridin-5-carboxylic acid, 2-[2-Cyclopentyl-1-(6-methanesulfonyl-pyridin-3-yl)-ethyl]-1H-pyrrolo[2,3-b]pyridin-5-carboxylic acid(2-hydroxy-ethyl)-amide, 2-[1-(4-Methanesulfonyl-phenyl)-2-(tetrahydro-pyran-2-yl)-ethyl]-1H-pyrrolo[2,3-b]pyridine, 2-[2-Cyclopentyl-1-(6-methoxy-pyridin-3-yl))-ethyl]-1H-pyrrolo[2,3-b]pyridine, 2-[2-Cyclopentyl-1-(2,3-dihydro-benzo[1,4]dioxin-6-yl)-ethyl]-1H-pyrrolo[2,3-b]pyridine, 2-[2-Cyclopentyl-1-(6-methyl-pyridin-3-yl))-ethyl]-1H-pyrrolo[2,3-b]pyridine or 1-{4-[2-Cyclopentyl-1-(1H-pyrrolo[2,3-b]pyridin-2-yl)-ethyl]-phenyl}-ethanol.

26. The compound according to claim 1, wherein said compound is:

{4-[2-Cyclopentyl-1-(1H-pyrrolo[2,3-b]pyridin-2-yl)-ethyl]-phenyl}-dimethyl-amine, 2-[2-Cyclopentyl-1-(3.5-dimethyl-phenyl)-ethyl]-1H-pyrrolo[2,3-b]pyridine, 2-[1(R)-(4-Methanesulfonyl-phenyl)-2-(tetrahydro-pyran-4-yl)-ethyl]-1H-pyrrolo[2,3-b]pyridine, 2-[2-(Tetrahydro-pyran-4-yl)-1-(4-trifluoromethyl-phenyl)-ethyl]-1H-pyrrolo[2,3-b]pyridine, 2-[2-Cyclopentyl-1-[4-(propane-2-sulfonyl-phenyl)-ethyl]-1H-pyrrolo[2,3-b]pyridine, (E)-2-[1-(4-Methanesulfonyl-phenyl)-2-(tetrahydro-furan-2-yl)-vinyl]-1H-pyrrolo[2,3-b]pyridine, 2-[1-(4-Methanesulfonyl-phenyl)-2-(tetrahydro-furan-2-yl)-ethyl]-1H-pyrrolo[2,3-b]pyridine, 2-Cyclobutyl-1-(4-methanesulfonyl-3-trifluoromethyl-phenyl)-1-(5-methoxy-1H-pyrrolo[2,3-b]pyridin-2-yl)-ethanol, 2-[(E)-1-(4-Methanesulfonyl-phenyl)-3,3-dimethyl-but-1-enyl]-1H-pyrrolo[2,3-b]pyridine, 2-[1-(4-Methanesulfonyl-phenyl)-3,3-dimethyl-butyl]-1H-pyrrolo[2,3-b]pyridine, N-{4-[2-Cyclopentyl-1-(1H-pyrrolo[2,3-b]pyridin-2-yl)-ethyl]-phenyl}-methanesulfonamide, 2-Cyclobutyl-1-(4-methanesulfonyl-3-trifluoromethyl-phenyl)-1-(1H-pyrrolo[2,3-b]pyridin-2-yl)-ethanol, 2-[2-Cyclobutyl-1-(4-methanesulfonyl-3-trifluoromethyl-phenyl)-ethyl]-1H-pyrrolo[2,3-b]pyridine, 3-[2-(4-Methanesulfonyl-phenyl)-2-(1H-pyrrolo[2,3-b]pyridin-2-yl)-ethyl]-cyclopentanone, 3-[2-(4-Methanesulfonyl-phenyl)-2-(1H-pyrrolo[2,3-b]pyridin-2-yl)-ethyl]-cyclopentanone, 1-{4-[2-Cyclopentyl-1-(1H-pyrrolo[2,3-b]pyridin-2-yl)-ethyl]-phenyl}-ethanone, 2-{4-[2-Cyclopentyl-1-(1H-pyrrolo[2,3-b]pyridin-2-yl)-ethyl]-phenyl}-propan-2-ol, 2-{4-[2-Cyclopentyl-1(R)-(1H-pyrrolo[2,3-b]pyridin-2-yl)-ethyl]-phenyl}-propan-2-ol, 3-{4-[2-Cyclopentyl-1-(1H-pyrrolo[2,3-b]pyridin-2-yl)-ethyl]-phenyl}-pentan-3-ol, or 3-{4-[2-Cyclopentyl-1(R)-(1H-pyrrolo[2,3-b]pyridin-2-yl)-ethyl]-phenyl}-pentan-3-ol.

27. The compound according to claim 1, wherein said compound is:

2-{4-[2-Cyclopentyl-1-(1H-pyrrolo[2,3-b]pyridin-2-yl)-ethyl]-phenyl}-3-methyl-butan-2-ol, 2-Cyclopentyl-1-(4-methanesulfonyl-phenyl)-1-(1H-pyrrolo[2,3-b]pyridin-2-yl)-ethanol, 2-[2-Cyclopentyl-1-ethoxy-1-(4-methanesulfonyl-phenyl)-ethyl]-1H-pyrrolo[2,3-b]pyridine, 2-{4-[2-Cyclopentyl-1-(5-fluoro-1H-pyrrolo[2,3-b]pyridin-2-yl)-ethyl]-benzenesulfonyl}-ethanol, (2-{4-[1-(5-Fluoro-1H-pyrrolo[2,3-b]pyridin-2-yl)-2-(tetrahydro-pyran-4-yl)-ethyl]-benzenesulfonyl}-ethanol,
2-{2-Cyclopentyl-1-[4-(2-ethoxy-ethanesulfonyl)-phenyl]-ethyl}-1H-pyrrolo[2,3-b]pyridine,
(2-{4-[2-Cyclopentyl-1-(1H-pyrrolo[2,3-b]pyridin-2-yl)-ethyl]-benzenesulfonyl}-ethanol,
(2-{4-[2-Cyclopentyl-1-(1H-pyrrolo[2,3-b]pyridin-2-yl)-ethyl]-benzenesulfonyl}-ethyl)-dimethyl-amine,
2-{2-Cyclopentyl-1-[4-(2-morpholin-4-yl-ethanesulfonyl)-phenyl]-ethyl}-1H-pyrrolo[2,3-b]pyridine,
2-{4-[2-Cyclopentyl-1-(1H-pyrrolo[2,3-b]pyridin-2-yl)-ethyl]-3-fluoro-phenyl}-propan-2-ol,
2-{4-[2-Cyclopentyl-1-(1H-pyrrolo[2,3-b]pyridin-2-yl)-ethyl]-2-fluoro-phenyl}-propan-2-ol,
2-{4-[2-Cyclopentyl-1(R)-(1H-pyrrolo[2,3-b]pyridin-2-yl)-ethyl]-2-fluoro-phenyl}-propan-2-ol,
2-{2-Fluoro-4-[1-(5-fluoro-1H-pyrrolo[2,3-b]pyridin-2-yl)-2-(tetrahydro-pyran-4-yl)-ethyl]-phenyl}-propan-2-ol,
2-{2-Fluoro-4-[1(R)-(5-fluoro-1H-pyrrolo[2,3-b]pyridin-2-yl)-2-(tetrahydro-pyran-4-yl)-ethyl]-phenyl}-propan-2-ol,
5-Fluoro-2-[1-(4-methanesulfonyl-phenyl)-3-methyl-butyl]-1H-pyrrolo[2,3-b]pyridine,
5-Fluoro-2-[1(R)-(4-methanesulfonyl-phenyl)-3-methyl-butyl]-1H-pyrrolo[2,3-b]pyridine, or
(2-{4-[1-(5-Fluoro-(1H-pyrrolo[2,3-b]pyridin-2-yl)-3-methyl-butyl]-benzenesulfonyl}-ethanol.

28. The compound according to claim 1, wherein said compound is:
(2-{4-[1(R)-(5-Fluoro-(1H-pyrrolo[2,3-b]pyridin-2-yl)-3-methyl-butyl]-benzenesulfonyl}-ethanol,
2-{4-[2-Cyclopentyl-1-(5-fluoro-1H-pyrrolo[2,3-b]pyridin-2-yl)-ethyl]-2-fluoro-phenyl}-propan-2-ol,
2-{4-[2-Cyclopentyl-1(R)-(5-fluoro-1H-pyrrolo[2,3-b]pyridin-2-yl)-ethyl]-2-fluoro-phenyl}-propan-2-ol,
2-{2-Fluoro-4-[1-(5-fluoro-1H-pyrrolo[2,3-b]pyridin-2-yl)-3-methyl-butyl]-phenyl}-propan-2-ol,
2-{2-Fluoro-4-[1(R)-(5-fluoro-1H-pyrrolo[2,3-b]pyridin-2-yl)-3-methyl-butyl]-phenyl}-propan-2-ol,
N-{2-[2-Cyclopentyl-1-(4-methanesulfonyl-phenyl)-ethyl]-1H-pyrrolo[2,3-b]pyridin-5-yl}-2-dimethylamino-acetamide,
2-[2-Cyclopentyl-1-(6-ethoxy-pyridin-3-yl)-ethyl]-1H-pyrrolo[2,3-b]pyridine,
2-[2-Cyclopentyl-1-(6-methanesulfonyl-pyridin-3-yl)-ethyl]-1H-pyrrolo[2,3-b]pyridine,
2-(2-Cyclopentyl-1-pyridin-3-yl-ethyl)-1H-pyrrolo[2,3-b]pyridine,
5-Chloro-2-[2-cyclopentyl-1-(4-methanesulfonyl-phenyl)-ethyl]-1H-pyrrolo[2,3-b]pyridine,
2-[2-Cyclopentyl-1-(5-methanesulfonyl-pyridin-2-yl)-ethyl]-1H-pyrrolo[2,3-b]pyridine,
2-[2-Cyclopentyl-1-(4-methanesulfonyl-phenyl)-ethyl]-6-methoxy-1H-pyrrolo[2,3-b]pyridine,
5-Chloro-2-[1-(4-methanesulfonyl-phenyl)-2-(tetrahydro-pyran-4-yl)-ethyl]-1H-pyrrolo[2,3-b]pyridine,
2-Cyclobutyl-1-(4-methanesulfonyl-phenyl)-1-(1H-pyrrolo[2,3-]pyridin-2-yl)-ethanol,
2-[(E)-2-cyclopentyl-1-(4-methanesulfonyl-phenyl)-vinyl]-5-fluoro-1H-pyrrolo[2,3-b]pyridine,
2-[2-Cyclopentyl-1-(4-methanesulfonyl-phenyl)-ethyl]-5-fluoro-1H-pyrrolo[2,3-b]pyridine,
2-[2-Cyclopentyl-1(R)-(4-methanesulfonyl-phenyl)-ethyl]-5-fluoro-1H-pyrrolo[2,3-b]pyridine, or
2-{4-[2-Cyclopentyl-1-(5-fluoro-1H-pyrrolo[2,3-b]pyridin-2-yl)-ethyl]-phenyl}-propan-2-ol.

29. The compound according to claim 1, wherein said compound is:
2-{4-[2-Cyclopentyl-1(R)-(5-fluoro-1H-pyrrolo[2,3-b]pyridin-2-yl)-ethyl]-phenyl}-propan-2-ol,
2-[2-Cyclopentyl-1-(4-isopropyl-phenyl)-ethyl]-5-fluoro-1H-pyrrolo[2,3-b]pyridine,
5-Fluoro-2-[(E)-1-(4-methanesulfonyl-phenyl)-2-(tetrahydro-pyran-4-yl)-vinyl]-1H-pyrrolo[2,3-b]pyridine,
5-Fluoro-2-[1-(4-methanesulfonyl-phenyl)-2-(tetrahydro-pyran-4-yl)-ethyl]-1H-pyrrolo[2,3-b]pyridine,
5-Fluoro-2-[1(R)-(4-methanesulfonyl-phenyl)-2-(tetrahydro-pyran-4-yl)-ethyl]-1H-pyrrolo[2,3-b]pyridine,
2-[2-Cyclopentyl-1-(4-methanesulfonyl-phenyl)-ethyl]-5-ethanesulfonyl-1H-pyrrolo[2,3-b]pyridine,
2-[2-Cyclopentyl-1-(4-methanesulfonyl-phenyl)-ethyl]-5-trifluoromethyl-1H-pyrrolo[2,3-b]pyridine,
2-[2-Cyclopentyl-1(R)-(4-methanesulfonyl-phenyl)-ethyl]-5-trifluoromethyl-1H-pyrrolo[2,3-b]pyridine,
2-[2-Cyclopentyl-1-(4-methanesulfonyl-phenyl)-ethyl]-5-methyl-1H-pyrrolo[2,3-b]pyridine,
2-{4-[2-Cyclopentyl-1(R)-(5-methyl-1H-pyrrolo[2,3-b]pyridin-2-yl)-ethyl]-2-fluoro-phenyl}-propan-2-ol,
2-(3-Methyl-1-m-tolyl-butyl)-1H-pyrrolo[2,3-b]pyridine,
2-(1-(3-Chloro-phenyl)-3-methyl-butyl)-1H-pyrrolo[2,3-b]pyridine,
2-(1-(3-Fluoro-phenyl)-3-methyl-butyl)-1H-pyrrolo[2,3-b]pyridine,
2-(1-(3-Ethoxy-phenyl)-3-methyl-butyl)-1H-pyrrolo[2,3-b]pyridine,
2-(1-(3-Methoxy-phenyl)-3-methyl-butyl)-1H-pyrrolo[2,3-b]pyridine,
1-{3-[3-Methyl-1-(1H-pyrrolo[2,3-b]pyridin-2-yl)-butyl]-phenyl}-ethanone,
N,N-Dimethyl-3-(3-methyl-1-(1H-pyrrolo[2,3-b]pyridine-2-yl)butyl)benzenamine,
2-(1-(3-(1H-Pyrazol-1-yl)phenyl)-3-methylbutyl)-1H-pyrrolo[2,3-b]pyridine,
2-[2-Cyclopentyl-1-(4-methanesulfonyl-phenyl)-ethyl]-1H-pyrrolo[2,3-b]pyridine, or
2-[2-Cyclopentyl-1-(3,4-dichloro-phenyl)-ethyl]-1H-pyrrolo[2,3-b]pyridine.

30. A pharmaceutical composition, comprising a therapeutically effective amount of a compound according to claim 1 and a pharmaceutically acceptable carrier and/or adjuvant.

* * * * *